(12) United States Patent
Scharenberg et al.

(10) Patent No.: US 12,385,070 B2
(45) Date of Patent: Aug. 12, 2025

(54) HOMOLOGY DIRECTED REPAIR COMPOSITIONS FOR THE TREATMENT OF HEMOGLOBINOPATHIES

(71) Applicants: Seattle Children's Hospital, Seattle, WA (US); Fred Hutchinson Cancer Center, Seattle, WA (US)

(72) Inventors: Andrew Scharenberg, Seattle, WA (US); Kyle Jacoby, Seattle, WA (US); Hans-Peter Kiem, Seattle, WA (US); David J. Rawlings, Seattle, WA (US); Christopher Lux, Bremerton, WA (US); Sowmya Pattabhi, Bellevue, WA (US); Olivier M. Humbert, Seattle, WA (US)

(73) Assignees: Seattle Children's Hospital, Seattle, WA (US); Fred Hutchinson Cancer Center, Seattle, WA (US)

( * ) Notice: Subject to any disclaimer, the term of this patent is extended or adjusted under 35 U.S.C. 154(b) by 46 days.

(21) Appl. No.: 18/344,732

(22) Filed: Jun. 29, 2023

(65) Prior Publication Data

US 2024/0124896 A1 Apr. 18, 2024

Related U.S. Application Data

(63) Continuation of application No. 16/608,182, filed as application No. PCT/US2018/029235 on Apr. 24, 2018, now Pat. No. 12,110,499.

(60) Provisional application No. 62/488,927, filed on Apr. 24, 2017.

(51) Int. Cl.
| | |
|---|---|
| *C12N 15/90* | (2006.01) |
| *A61K 35/28* | (2015.01) |
| *A61P 9/00* | (2006.01) |
| *C07K 14/805* | (2006.01) |
| *C12N 15/11* | (2006.01) |
| *C12N 15/86* | (2006.01) |

(52) U.S. Cl.
CPC ............ *C12N 15/907* (2013.01); *A61K 35/28* (2013.01); *A61P 9/00* (2018.01); *C07K 14/805* (2013.01); *C12N 15/11* (2013.01); *C12N 15/86* (2013.01); *C12N 2310/20* (2017.05); *C12N 2750/14143* (2013.01); *C12N 2800/80* (2013.01)

(58) Field of Classification Search
CPC ...... C12N 15/907; C12N 15/11; C12N 15/86; C12N 2310/20; C12N 2750/14143; C12N 2800/80; C12N 15/102; C12N 15/10; A61K 35/28; A61K 48/00; A61P 9/00; C07K 14/805
See application file for complete search history.

(56) References Cited

U.S. PATENT DOCUMENTS

| | | | |
|---|---|---|---|
| 6,051,402 | A | 4/2000 | LeBoulch et al. |
| 7,901,671 | B2 | 3/2011 | Leboulch et al. |
| 9,017,967 | B2 | 4/2015 | Bonas et al. |
| 9,068,199 | B2 | 6/2015 | Leboulch et al. |
| 2014/0080216 | A1 | 3/2014 | Cost et al. |
| 2015/0133528 | A1 | 5/2015 | Krieg et al. |
| 2015/0166969 | A1 | 6/2015 | Takeuchi et al. |
| 2020/0255857 | A1 | 8/2020 | Gori et al. |

FOREIGN PATENT DOCUMENTS

| | | |
|---|---|---|
| WO | WO2014036219 A2 | 3/2014 |
| WO | WO2017115268 A1 | 7/2017 |
| WO | WO2017218948 A2 | 12/2017 |
| WO | WO2002088346 A2 | 11/2022 |

OTHER PUBLICATIONS

Office Action for European Application No. 18789938.0, Dated May 21, 2024, 4 pages.
Balazs and Godbey, "Liposomes for use in gene delivery," J. Drug Deliv., vol. 2011, No. 326497, 2011, 12 pages.
Choi, et al., "Optimization of AAV expression cassettes to improve packaging capacity and transgene expression on neurons", Molecular brain, vol. 7, No. 17, 2014, 10 pages.
Cong, et al., "Multiplex genome engineering using CRISPR/Cas systems," Science, vol. 339, No. 6121, 2013, pp. 819-823.
Dever, et al., "CRISPR/Cas9 β-globin gene targeting in human haematopoietic stem cells," Nature, vol. 539, No. 7629, 2016, pp. 384-389.
Office Action Dated Dec. 20, 2021 for European Application No. 18789938, 5 pages.
European Office Action mailed Feb. 2, 2023, for European Patent Application No. 18789938, a foreign counterpart to U.S. Appl. No. 16/608,182, 6 pages.
Finotti, et al., "Recent trends in the gene therapy of B-thalassemia", J. Blood Med., vol. 6, 2015, pp. 69-85.
Gilman, et al., "Distal CCAAT box deletion in the A gamma globin gene of two black adolescents with elevated fetal A gamma globin," Nucleic Acids Res., vol. 16, No. 22, 1988, pp. 10635-10642.
Hoban, et al., "Correction of the sickle cell disease mutation in human hematopoietic stem/progenitor cells," Blood, vol. 125, No. 17, 2015, pp. 2597-29604.

(Continued)

*Primary Examiner* — Fereydoun G Sajjadi
*Assistant Examiner* — Alexander W Nicol
(74) *Attorney, Agent, or Firm* — C. Rachal Winger; Chrystal Quisenberry; Lee & Hayes PC

(57) ABSTRACT

The present disclosure provides improved compositions for the homology directed repair of the human globin locus for the prevention, treatment, or amelioration of at least one symptom of a hemoglobinopathy.

27 Claims, 98 Drawing Sheets
Specification includes a Sequence Listing.

(56) References Cited

OTHER PUBLICATIONS

Huang and Yen, "Role of the hepatitis B virus posttranscriptional regulatory element in export of intronless transcripts," Mol. Cell. Biol., vol. 15, No. 7, 1995, pp. 3864-3869.

Jinek, et al., "A programmable dual-RNA-guided DNA endonuclease in adaptive bacterial immunity," Science, vol. 337, No. 6096, 2012, pp. 816-821.

Jinek, et al., "RNA-programmed genome editing in human cells," eLife 2:e00471, 2013, 9 pages.

Kiem, et al., Abstract "Novel Gene Editing Approaches for Hemoglobinopathies," National Institutes of Health Grant No. HL 136135 (Funding Start Date Jan. 17, 2017).

Liu and Mertz, "HnRNP L binds a cis-acting RNA sequence element that enables intron-dependent gene expression," Genes Dev., vol. 9, No. 14, 1995, pp. 1766.

Liu, et al., "Poly(cationic lipid)-mediated in vivo gene delivery to mouse liver," Gene Therapy., vol. 10, No. 2, 2003, pp. 180-187.

Mali, et al., "RNA-guided human genome engineering via Cas9," Science, vol. 339, No. 6121, 2013, pp. 823-826.

Manca, et al., "Disorders of the Synthesis of Human Fetal Hemoglobin," IUBMB Life, vol. 60, No. 2, 2008, pp. 94-111.

Office Action Dated Aug. 8, 2022 for U.S. Appl. No. 16/608,182, 13 Pages.

Pattabhi, et al., "In Vivo Outcome of Homology-Directed Repair at the HBB Gene in HSC Using Alternative Donor Template Delivery Methods," Mol. Ther. Nucleic Acids, vol. 17, 2019, pp. 277-288.

Qi, et al., "Repurposing CRISPR as an RNA-guided platform for sequence-specific control of gene expression," Cell, vol. 152, No. 5, 2013, pp. 1173-1183.

Ran, et al., "Genome engineering using the CRISPR-Cas9 system," Nature Protocols, vol. 8, No. 11, 2013, pp. 2281-2308.

Segal, "Bacteria herald a new era of gene editing," eLife 2:e00563, 2013, 3 pages.

Search Report and Written Opinion Dated Oct. 2, 2018 in International Application No. PCT/US2018/029235, 12 pages.

Wall, et al., "The human B-globin gene 3' enhanver contains multiple binding sites for an erythroid-specific protein," Gen. Dev., vol. 2, 1988, 1089-1100.

Zetsche, et al., "Cpf1 is a single RNA-guided endonuclease of a class 2 CRISPR-Cas system," Cell, vol. 163, No. 3, 2015, pp. 759-771.

Zufferey, et al., "Woodchuck hepatitis virus posttranscriptional regulatory element enhances expression of transgenes delivered by retroviral vectors," J. Virol., vol. 73, No. 4, 1999, pp. 2886-2892.

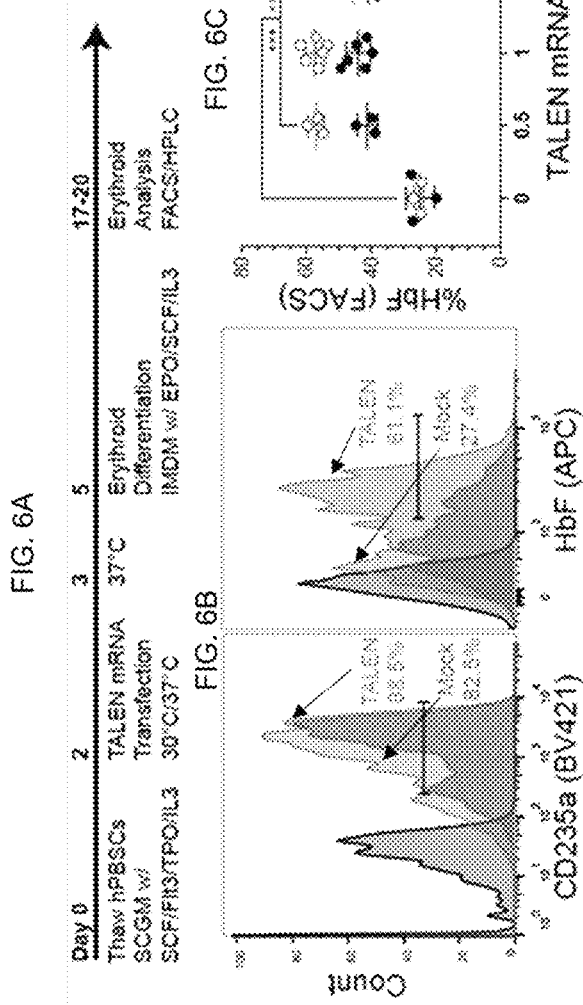

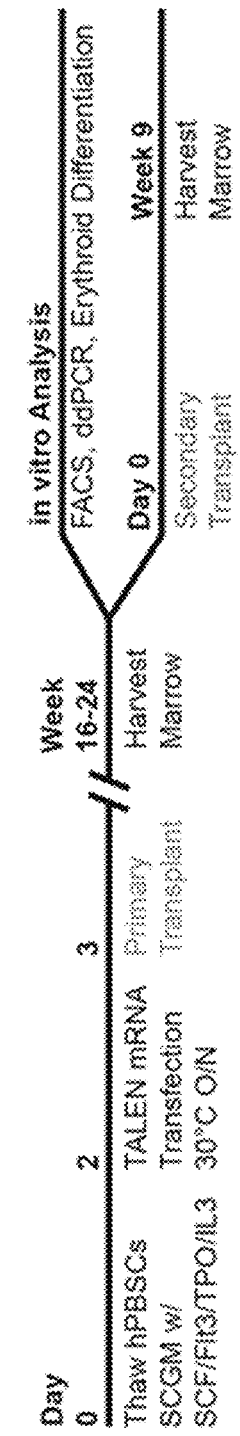
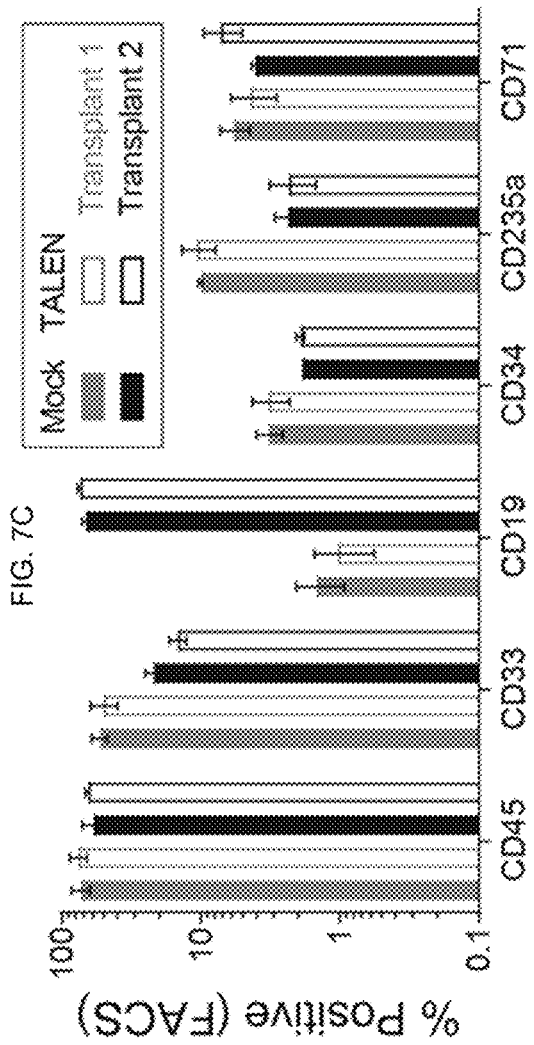
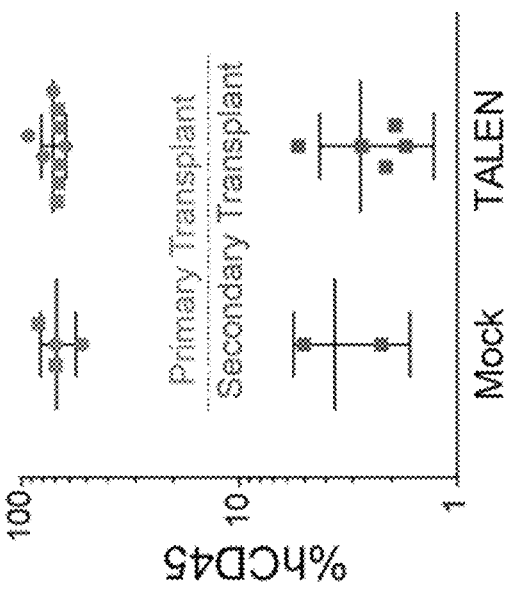

3.5kb, 1.3kb HPFH deletion repair templates
- Generate a large deletion to drive fetal hemoglobin expression d3.5kb  1240  pAAV d3.5kb(600) MND>GFP.wPRE-O.BGHpA
        1241  pAAV d3.5kb(600) HPFH-2.MND>GFP.wPRE-O.BGHpA d1.3kb  1255  pAAV HBG1d-1.3kb,-382(600) MND>GFP.wPRE3.SV40USE.pA
        1256  pAAV HBG1d-1.3kb,-1(600) MND>GFP.wPRE3.SV40USE.pA;HBBp>

FIG. 9

HBG1 Round 1 Repair Templates
- V1&3 – uses the d13 HBG1 promoter to drive T87Q globin expression
- V4 – uses HBB promoter in the HBG1 locus to drive T87Q globin expression HBG1 Round 2 Repair Templates
- New versions based on data from V1

| | | |
|---|---|---|
| HBG1 Round1 | V1E1 | pAAV HBG1.d-667,-1(600) MND>GFP.wPRE0.BGHpA;HBBp> (Upstream) |
| | V1E4 | pAAV HBG1(200-600).d13&dATG,stop>HBB(T87Q).3'enh;MND>GFP *200-600bp HA |
| | V1E5/1303 | pAAV HBG1(400).d13min>HBB(T87Q).3'enh;MND>GFP.SV40pA |
| | V3E5 | pAAV HBG1(200-600).d13>HBB(T87Q).3'enhCore;MND>GFP::T2A::Ex2 *200-600bp HA |
| | V3E6/1260 | V3E5 (400) corrected polyA |
| | V3E7/1292 | pAAV HBG1(600).d13min>HBB(T87Q).3'enhCore;MND>GFP.SV40pA |
| | V4E4 | pAAV HBG1d-247(200-600).HBBp>HBB(T87Q).3'enh;MND>MGMT::T2A::Ex2 *200-600bp HA |
| | V4E5/1304 | pAAV HBG1(400).d-141,-1 HBBp>HBB(T87Q).3'enh;MND>GFP.SV40pA |
| | 1238 | pAAV HBG1(400).d13>HBBopt(T87Q).wPRE-O.BGHpA;HPFH2.MND>GFP::P2A:Ex2 * |
| HBG1 Round2 | 1239 | pAAV HBG1(400).d13>HBBopt(T87Q).wPRE-O.BGHpA;HPFH2.MND>GFP::P2A:Ex2 * |
| | 1291 | HBG1(400).d13min>HBBopt(T87Q).wPRE-O.BGHpA;HPFH2.MND>GFP.SV40pA (like 1238) |
| 1324 | | HBG1(1k,900).d13 [MND>GFP.SV40pA];HPFH2.HS40.HBG1d13p>    Alt-HR Version |
| 1325 | | HBG1(1k,900).d13 [MND>GFP.SV40pA];HPFH2.HS40.HBG1d13p>    deletional variant of 1324 |
| 1323 | | HBG1d-141,-1(459,600) [MND>GFP.wPRE3.SV40USE.pA];HPFH-2.HS40.HBBp>    like 1293 GFP inverted |

FIG. 10

HBG1 Round 3 Repair Templates
- Improved 3rd generation based on previous HBG1 templates
- Drives T87Q Expression with HBG1 promoter

| HBG1 Round3 | 1343 | HBG1(650).d0 HBBp>HBB(T87Q).core3'enh;PGK>MGMT(P140K).SV40pA |
| | 1344 | HBG1(500).d0 HBBp>HBB(T87Q).core3'enh;PGK>MGMT(P140K).wPRE3.SV40pA |
| | 1345 | HBG1(650).d0 HBBp>HBB(T87Q).core3'enh;MND>GFP.SV40pA |
| | 1346 | HBG1(650).d0 HBG1d13>HBB(T87Q).core3'enh;PGK>MGMT(P140K).SV40pA |
| | 1333 | HBG1d-141,-1(459,600) MND>MGMT.wPRE3.SV40USE.pA;HPFH-2.HS40.HBBp> |
| | 1334 | HBG1d-141,-1(459,600) hPGK>MGMT.wPRE3.SV40USE.pA;HPFH-2.HS40.HBBp> |
| | 1336 | HBG1(600).d-114,488 HG1d13>HBB(T87Q).core3'enh;PGK>MGMT.T2A.Ex2 |

Simple repair template with 2kb homology arms flanking a 13bp deletion

| d13 Repair | 1315 | pAAV HBG1(2.2kb)d13 repair only |

FIG. 11

Rhesus Repair Templates

| | |
|---|---|
| Rhesus 1268 V3E6(400) in AAV (corrected polyA) | RHESUS V3E6 |
| 1308 HBG1d-141,-1(900,1kb)<br>MND>GFP.wPRE3.SV40USE.pA;HBBp><br>HBG1(650).d0 | RHESUS 1295 |
| 1347 HBBp>HBB(T87Q).core3'enh;PGK>MGMT(P140K).SV40pA | RHESUS 1343 'ideal' |
| 1348 HBG1(650).d0<br>HBBp>HBB(T87Q).core3'enh;MND>GFP.SV40pA | RHESUS 1345 |

FIG. 12

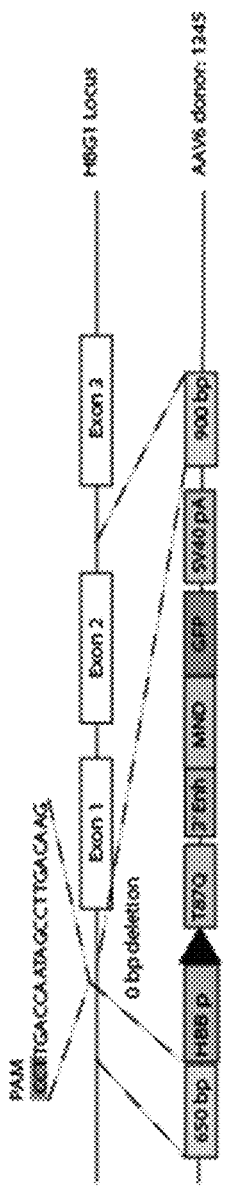
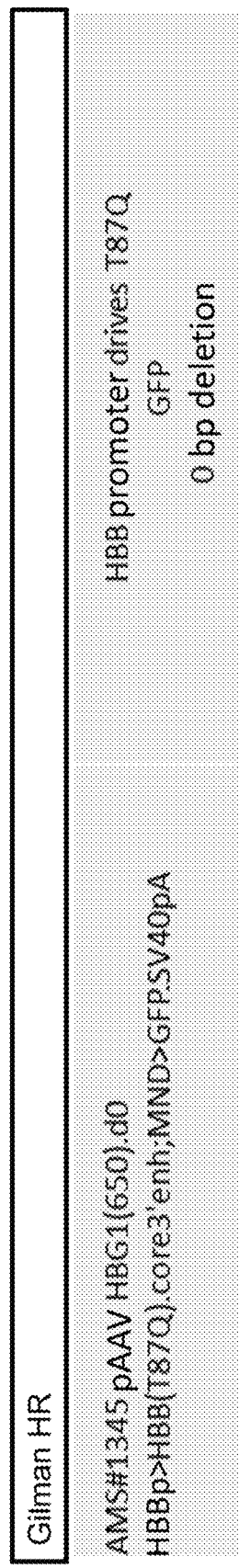
FIG. 27

MGMT Cassettes (Human)

| Construct | Details |
|---|---|
| AMS#1346 pAAV HBG1(650).d0 HBG1d13>HBB(T87Q).core3'enh;PGK>MGMT(P140K).SV40pA | HBG1>T87Q, has direct repeat, MGMT, 281 bp deletion |
| AMS#1343 pAAV HBG1(650).d0 HBBp>HBB(T87Q).core3'enh;PGK>MGMT(P140K).SV40pA | HBB>T87Q, MGMT, 0 bp deletion |

FIG. 30

| Animal ID | A7417 | A7414 | A7412 | A7416 | A7415 | A7413 |
|---|---|---|---|---|---|---|
| Target cells | CD34+ | CD34+ | CD34+ | CD90+ | CD90+ | CD90+ |
| Date of infusion | 7/14/17 | 8/4/17 | 2/8/18 | 9/28/17 | 11/17/17 | 3/23/18 |
| Animal Weight [kg] | 5 | 4.9 | 7.3 | 5.25 | 4.5 | 4.55 |
| Cell-sorting parameters | | | | | | |
| # of cells before sort | 95.2E+06 | 90.0E+06 | 144E+06 | 287E+06 | 290E+06 | 155E+06 |
| # of CD90- sorted | - | - | - | 10.0E+06 | 11.3E+06 | 14.0E+06 |
| # of CD90+ sorted | - | - | - | 125E+06 | 199E+06 | 103E+06 |
| Infusion product parameters | | | | | | |
| # in CD34 fraction | 125E+06 | 83.5E+06 | 204E+06 | - | - | - |
| # in CD90+ fraction | - | - | - | 15.0E+06 | 8.65E+06 | 5.15E+06 |
| # in CD90- fraction | - | - | - | 266E+06 | 213E+06 | 50.0E+06 |
| Total cells infused | 125E+06 | 83.5E+06 | 204E+06 | 281E+06 | 221E+06 | 55.2E+06 |
| Calculated number of cells infused | | | | | | |
| # of CD34+ cells | 53.0E+06 | 33.5E+06 | 148E+06 | 64.6E+06 | 77.4E+06 | 15.7E+06 |
| # of CD90+ cells | 3,537,500 | 3,582,150 | 4,998,000 | 5,223,540 | 3,053,730 | 1,639,000 |
| # of CD34+ cells/kg | 10.6E+06 | 6.84E+06 | 20.3E+06 | 12.3E+06 | 17.2E+06 | 3.45E+06 |
| # of CD90+ cells/kg | 707,500 | 731,051 | 684,657 | 994,960 | 678,606 | 360,219 |

FIG. 46

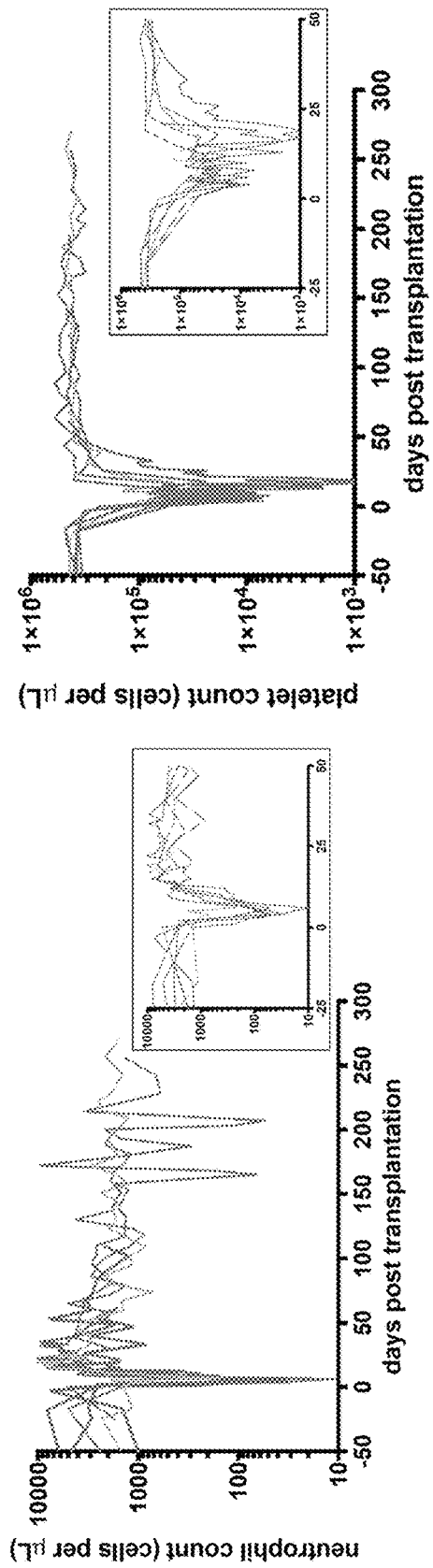
FIG. 48A
FIG. 48B
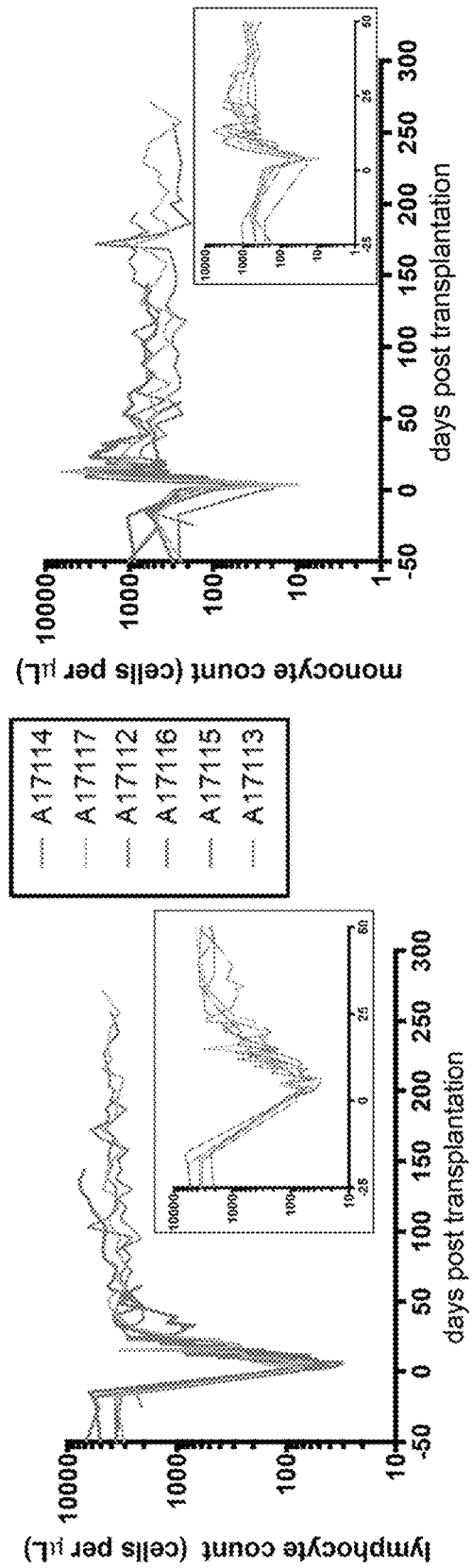
FIG. 48C
FIG. 48D

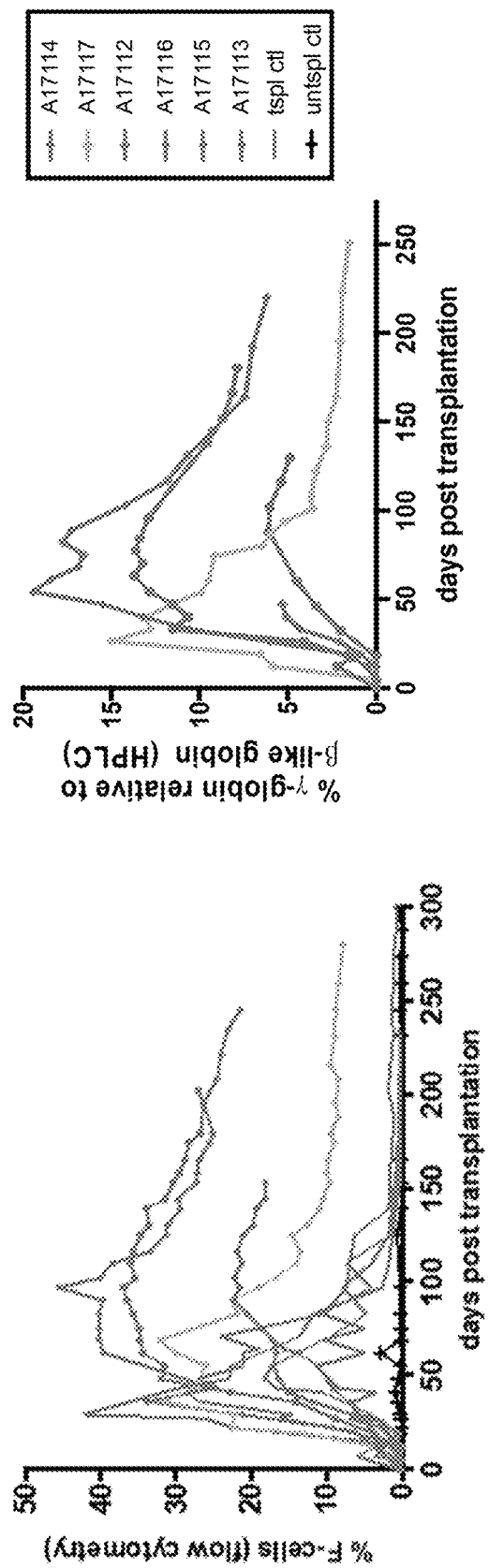
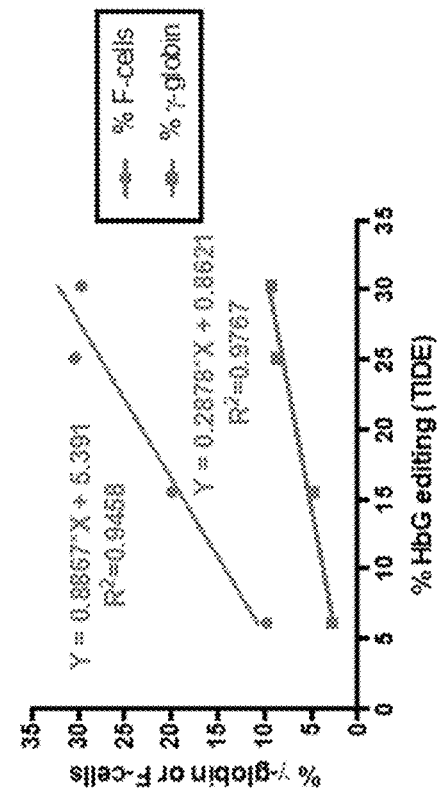
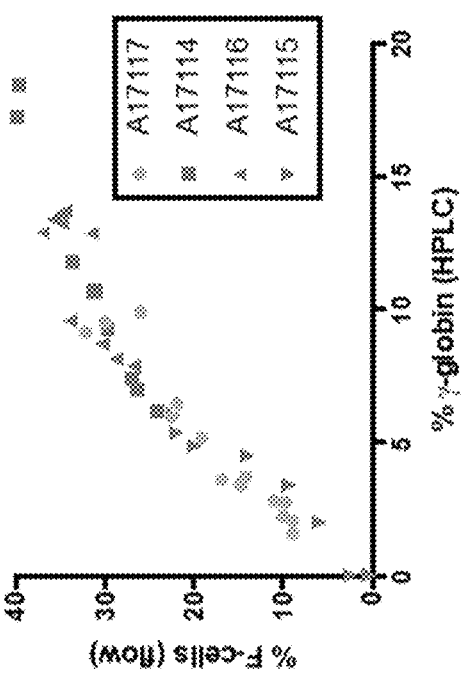
FIG. 50A
FIG. 50B
FIG. 50C
FIG. 50D

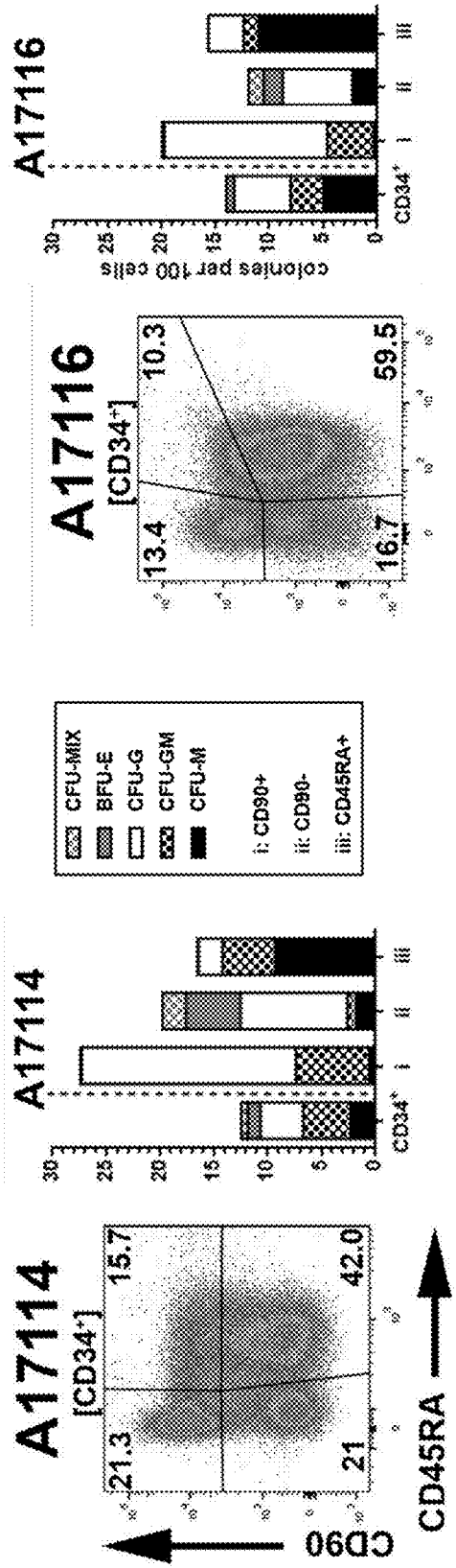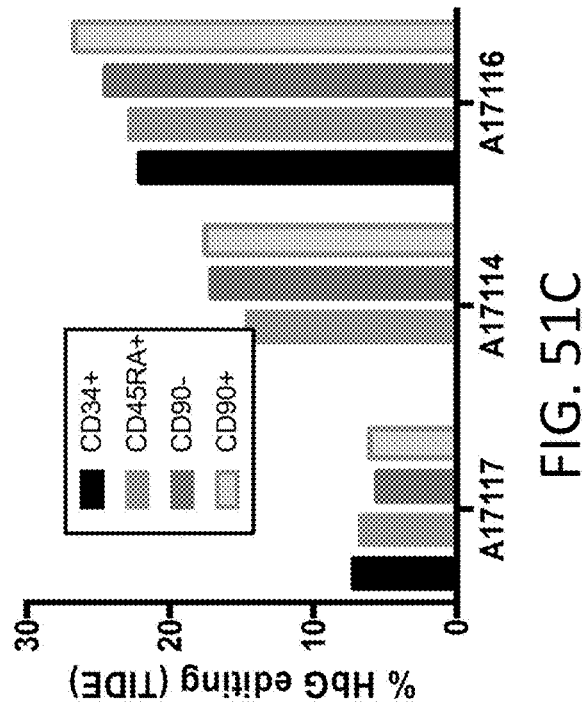
FIG. 51A
FIG. 51B
FIG. 51C

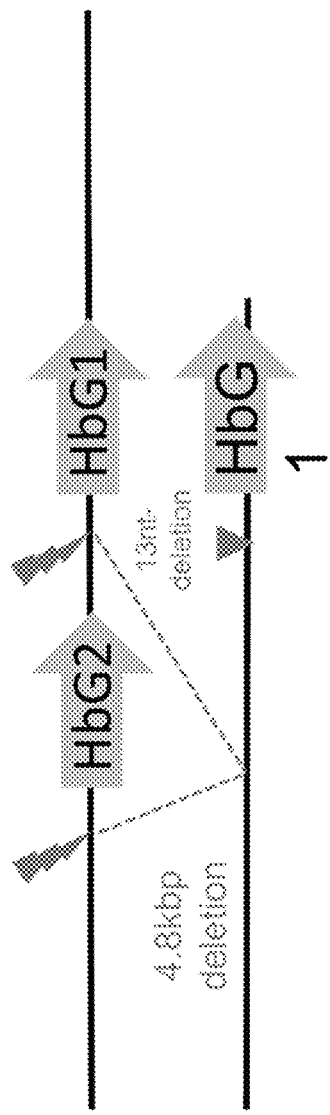
FIG. 52
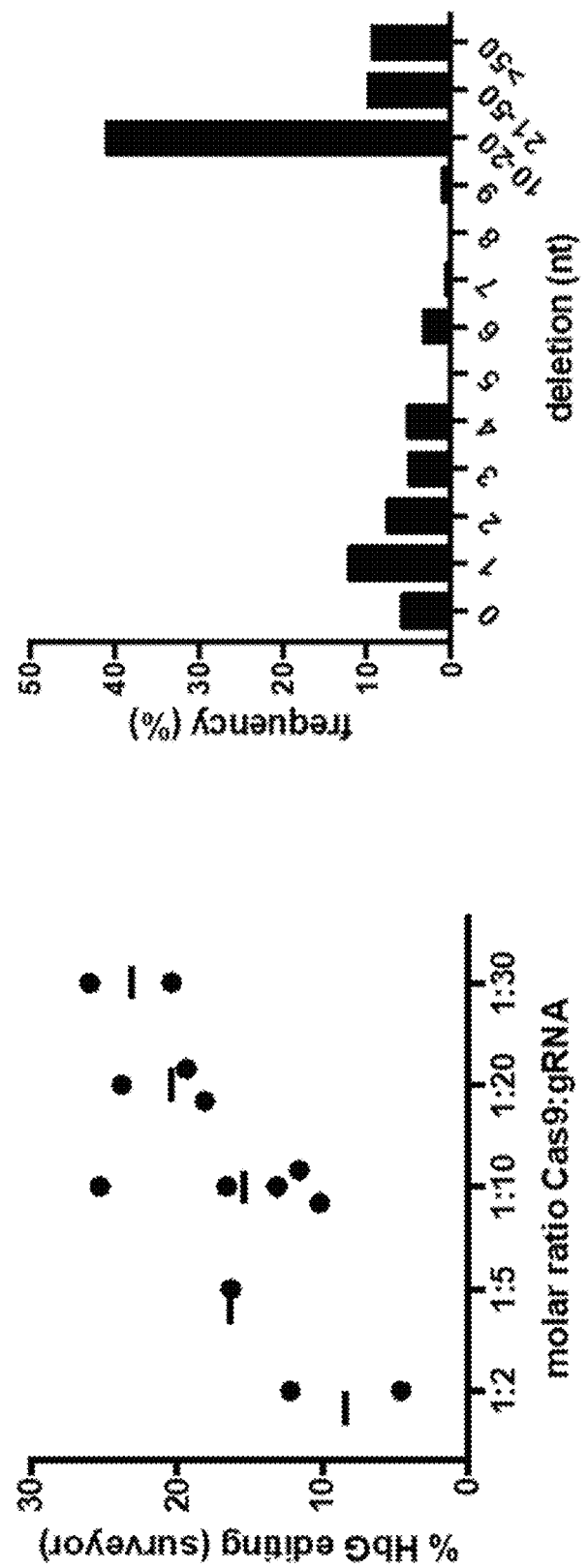
FIG. 53B
FIG. 53A

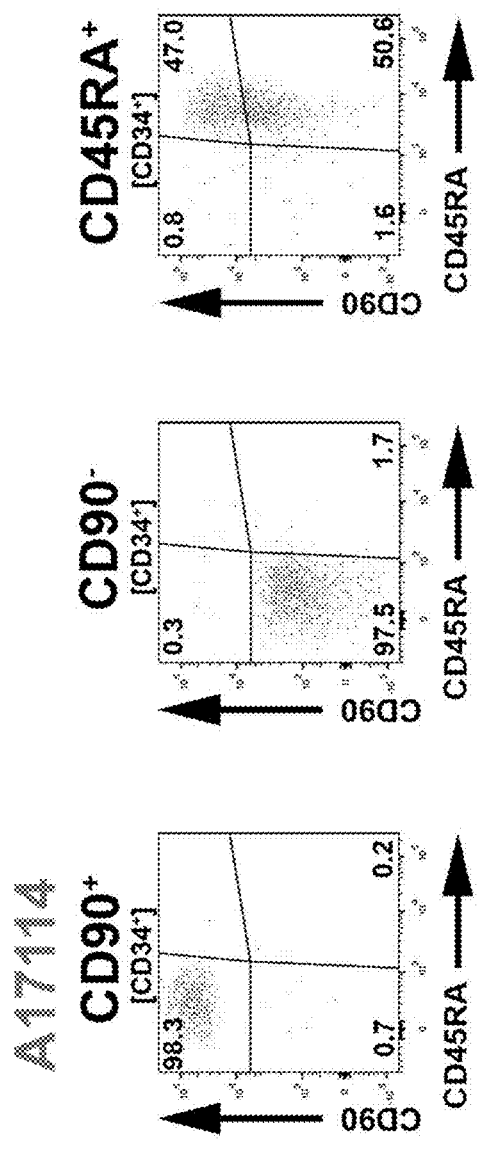
FIG. 53C
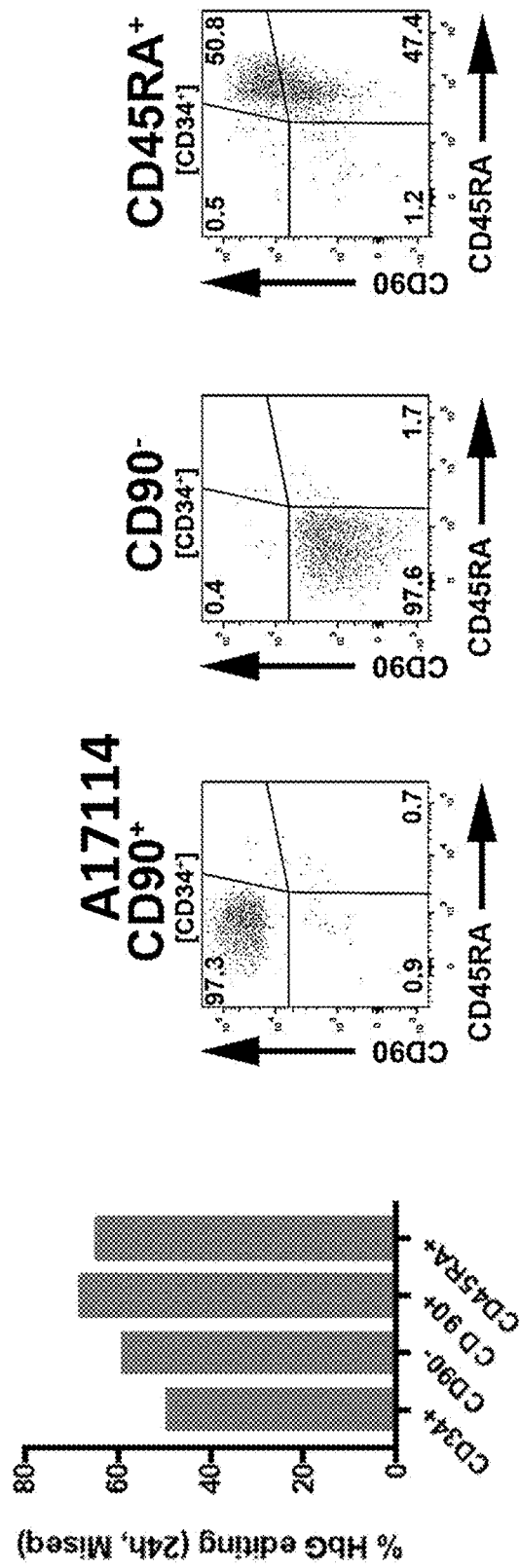
FIG. 53E
FIG. 53D

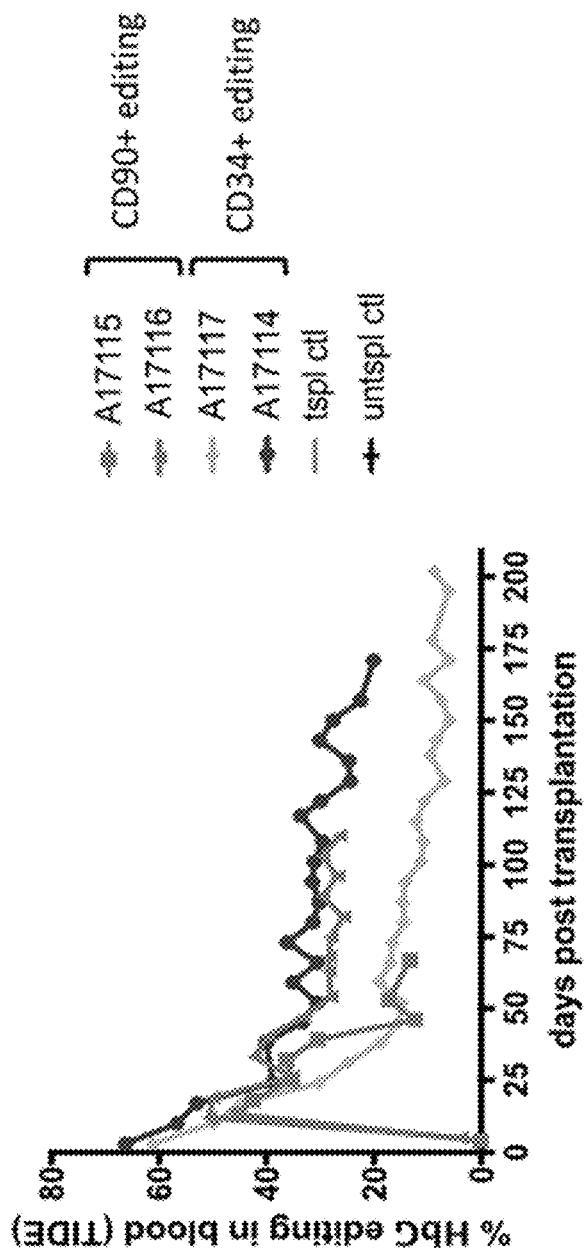
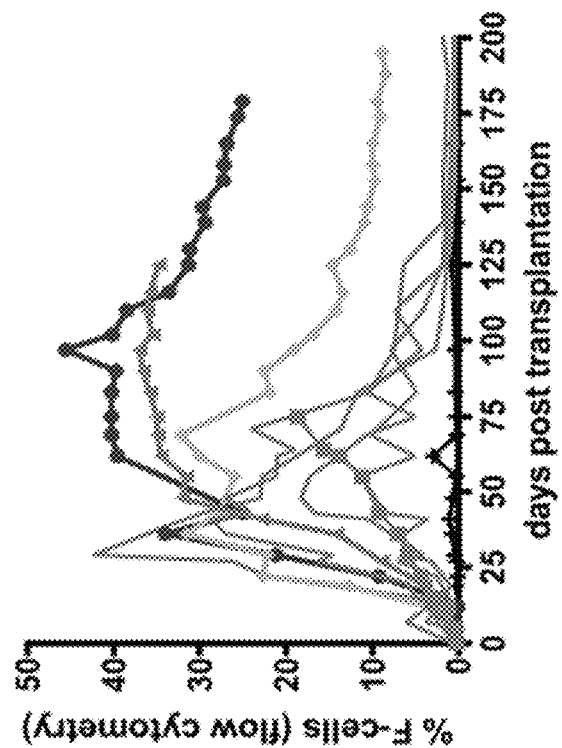
FIG. 61A
FIG. 61B

AAV5 donor construct 1348:
HBG1(650).d0 HBBp>HBB(T87Q).core3'enh;MND>GFP.SV40pA

```
                            SEQUENCE LISTING

Sequence total quantity: 84
SEQ ID NO: 1            moltype = DNA  length = 21
FEATURE                 Location/Qualifiers
source                  1..21
                        mol_type = genomic DNA
                        organism = Homo sapiens
SEQUENCE: 1
cttgaccaat agccttgaca a                                                    21

SEQ ID NO: 2            moltype = DNA  length = 16
FEATURE                 Location/Qualifiers
source                  1..16
                        mol_type = genomic DNA
                        organism = Homo sapiens
SEQUENCE: 2
gaccaatagc cttgac                                                          16

SEQ ID NO: 3            moltype = DNA  length = 13
FEATURE                 Location/Qualifiers
source                  1..13
                        mol_type = genomic DNA
                        organism = Homo sapiens
SEQUENCE: 3
caatagcctt gac                                                             13

SEQ ID NO: 4            moltype = DNA  length = 10
FEATURE                 Location/Qualifiers
source                  1..10
                        mol_type = genomic DNA
                        organism = Homo sapiens
SEQUENCE: 4
gaccaatagc                                                                 10
```

| SEQ ID NO: 5 | moltype = length = |
|---|---|
| SEQUENCE: 5 | |
| 000 | |

| SEQ ID NO: 6 | moltype = length = |
|---|---|
| SEQUENCE: 6 | |
| 000 | |

| SEQ ID NO: 7 | moltype = DNA length = 2835 |
|---|---|
| FEATURE | Location/Qualifiers |
| source | 1..2835 |
| | mol_type = genomic DNA |
| | organism = Homo sapiens |

SEQUENCE: 7

```
ctcaggatcc acatgcagct tgtcacagtg cagttcactc agctgggcaa aggtgccctt    60
gagatcatcc aggtgctttg tggcatctcc aaggaagtc agcaccttct tgccatgtgc    120
cttgactttg gggttgccca tgatggcaga ggcagaggac aggttgccaa agctgtcaaa    180
gaacctctgg gtccatgggt agacaaccag gagcctgtga gattgacaag aacagtttga    240
cagtcagaag gtgccacaaa tcctgagaag cgacctggac ttttgccagg cacagggtcc    300
ttccttccct cccttgtcct ggtcaccaga gcctaccttc ccaggttttc tcctccagca    360
tcttccacat tcaccttgcc ccacaggctt gtgatagtag cctgtcctc ctctgtgaaa    420
tgacccatgg cgtctggact aggagctat tgataacctc agacgttcca gaagcgagtg    480
tgtggaactg ctgaagggtg cttcctttta ttcttcatcc ctagccagcc gccggccccct   540
ggcctcactg gatactctaa gactattggt caagtttgcc ttgtcaaggc tattggtcaa    600
ggcaaggctg gccaacccat gggtggagtt tagccaggca ccgtttcaga cagatatttg    660
cattagagata gtgtgtgggaa ggggccccca agaggatact gctaattttt tttatagcct   720
ttgcctttgtt ccgattcagt cattccagtt tttctctaat ttattcttcc ctttagctag   780
tttccttctc ccatcataga ggataccagg acttcttttg tcagccgttt tttaccttct    840
tgtctctagc tccagtgagg cctgtagttt aaagctaaag catgtaccaa tttttgaaaa    900
gttcagggat tgtgaaatgt gttttaggca taggtccagg attttttgacg ggacaaatct    960
tagtctcttt cagttagcag tggtttctaa ggaaaaagtg ctatacttct ttttgaatat   1020
actctttgtg acttttgcca ttatctctta atttctcaat agtgcagtga aaacaatttc   1080
tataaagcca cagtttcagc gcagtaaatag attagtgtta cataatataa gacctaatgc   1140
ttacctcaat atctacttat ccgtacctat ttgaaataaa tcatgactgt ttcatcttag   1200
aaaaatattt gattccatat tcaggtatgt atgtatacac cagatgatgt gtatttacca   1260
ctggataagt gtgtgtgctg gctgatgacc caggttttg gcgtagctct tctatgctca    1320
gtaaagatga tggtagaatg ttcttttggca ggtactgtgg attagaatta attatcttgt   1380
ataaatgcta ggttcacttc tcagggaatc ttactctaag acataagatg tgcgtgtaca    1440
tggaaaacaa ctctaaagag gcaagggttg tttttattga ctaatagtcc acacactatt   1500
ataactcgaa tattagtgta ctttagacag ctttatttct aacacagtgc tgtttctgac   1560
atattggacc attaacaggg taggaagtat ttatggtggt ttttggttc tgtttttgctt   1620
tttggttagtt tgttttttgtt tttctctgaa agtgatccat gatctctaac cttgctagat   1680
tataatgcca gaagctctgg aattctggct tatcggaggc aagctgtatc ttcaaattag   1740
ttttatcccct aagctatcag gttgattgaa attattataa tattggtgaa attctttcat   1800
ccttcatgat cctgtgtaaa gctttatctct gctcattgat acagatggct aaaaggccag   1860
aaagacacac atttacccat gtaacaagcc tgcacatcct gcacatgtac cttcgaaatt   1920
aaaatgaaat gaaataaaat taaaggaaa aaaatgccat ggcaacatca ggaagttatc   1980
ttttatggtc taaaaatggg cagcataaat aatctacccc ttgtttagca tactattgaa   2040
aaataacaat aaaaatcggc aaccagtagc ccttgcgtct actctgccta tgaagtagcc   2100
attcatttat tccttcaatt tttttataaac ttgttttact aaaaaaaaaa aggacaaaaa   2160
aagaaagtgc gaattgtgaa atggtagtga gtgatggcat ttgaagtggg tcctttatga   2220
tttgatggag ccaggcagaa gacgtttgga gaaagaagtt cctgaaagta ggaagggcat   2280
gtggaaaact ctgaggctga ggaaaaaaaa gaaagaaaga aatataaaga agaacttgaa   2340
catttcactg tatataaaca cattacaagc ctaaagtaag ttgaagaaaa aatagaattc   2400
aaagttagac agaagggctc aggcttacta tttgcatctt acagatgaga gtagtagagt   2460
tggtattttta ttctgaaaca cagaggacaa gtggagattt gtaaacctga gataaacatg   2520
gtttctaatc cactgaacac cgaagcttat ttttttctct tcttcatct gccttactta   2580
gtgcaaggtg ctataacaaa atagcataga ctgggtgact tcaacaacag gattttttct   2640
cacttttctg ctggttcctg gtcagggctc tcttcctggg ttgcaggtgg ctgacttccc   2700
actgtgtcct caccagaagg aagagaaatg ctaatctct ctgcttctga tgaggaaaat   2760
aattctatga tggggatctg ctctcatgag ctcctctaaa cctgattact tttccaaagc   2820
ctcccccaca aatgg                                                   2835
```

| SEQ ID NO: 8 | moltype = DNA length = 2835 |
|---|---|
| FEATURE | Location/Qualifiers |
| source | 1..2835 |
| | mol_type = genomic DNA |
| | organism = Homo sapiens |

SEQUENCE: 8

```
ccatttgtgg gggaggcttt ggaaaagtaa tcaggtttag aggagctcat gagagcagat    60
ccccatcata gaattatttt cctcatcaga agcagagaga ttagccattt ctcttccttc   120
tggtgaggac acagtgggaa gtcagccacc tgcaacccag gaagagagcc ctgaccagga   180
accagcagaa aagtgagaaa aaatcctgtt gttgaagtca cccagtctat gctattttgt   240
tatagcaccct tgcactaagt aaggcagatg aagaaagaa aaaaaataag cttcggtgtt   300
cagtggatta gaaccatgt ttatctcagg tttacaaatc tccacttgtc ctctgtgttt   360
cagaataaaa taccaactct actactctca tctgtaagat gcaaatagta agcctgagcc   420
cttctgtcta actttgaatt ctatttttc ttcaacgtac tttaggcttg taatgtgttt    480
atatacagtg aaatgtcaag ttcttttcttt atattcttt ctttctttttt tttcctcagc   540
```

```
ctcagagttt tccacatgcc cttcctactt tcaggaactt cttttctcca acgtcttctg    600
cctggctcca tcaaatcata aaggacccac ttcaaatgcc atcactcact accatttcac    660
aattcgcact ttctttcttt gtccttttt tttttagtaa aacaagttta taaaaaattg     720
aaggaataaa tgaatggcta cttcataggc agagtagacg caagggctac tggttgccga    780
tttttattgt tattttcaa tagtatgcta aacaaggagt agattattta tgctgcccat    840
ttttagacca taaagataa cttcctgatg ttgccatggc atttttttcc ttttaatttt    900
atttcatttc attttaattt cgaaggtaca tgtgcaggat gtgcaggctt gttacatggg    960
taaatgtgtg tctttctggc cttttagcca tctgtatcaa tgagcagata taagctttac   1020
acaggatcat gaaggatgaa agaatttcac caatattata ataatttaaa tcaacctgat   1080
agcttagggg ataaactaat ttgaagatac agcttgcctc cgataagcca gaattccaga   1140
gcttctggca ttataatcta gcaaggttag agatcatgga tcactttcag agaaaaacaa   1200
aaacaaacta accaaaagca aaacagaacc aaaaaccac cataaatact tcctaccctg    1260
ttaatggtcc aatatgtcag aaacagcact gtgttagaaa taaagctgtc taaagtacac   1320
taatattcga gttataatag tgtgtggact attagtcaat aaaaacaacc cttgcctctt   1380
tagagttgtt ttccatgtac acgcacatct tatgtcttag agtaagattc cctgagaagt    1440
gaacctagca tttatacaag ataattaatt ctaatccaca gtacctgcca agaacattc     1500
taccatcatc tttactgagc atagaagagc tacgccaaaa ccctgggtca tcagccagca    1560
cacacactta tccagtggta aatacacatc atctggtgta tacatacata cctgaatatg   1620
gaatcaaata tttttctaag atgaaacagt catgatttat ttcaaatagg tacggataag   1680
tagatattga ggtaagcatt aggtcttata ttatgtaaca ctaatctatt actgcgctga    1740
aactgtggct ttatagaaat tgttttcact gcactattga gaaattaaga gataatggca    1800
aaagtcacaa agagtatatt caaaaagaag tatgcactt tttccttaga aaccactgct   1860
aactgaaaga gactaagatt tgtcccgtca aaaatcctgg acctatgcct aaaacacatt    1920
tcacaatccc tgaacttttc aaaaattggt acatgcttta gctttaaact acaggcctca    1980
ctggagctag agacaagaag gtaaaaacg gctgacaaaa gaagtcctgg tatcctctat    2040
gatgggagaa ggaaactagc taaagggaag aataaattag agaaaaactg gaatgactga    2100
atcggaacaa ggcaaaggct ataaaaaaa ttagcagtat cctcttgggg gcccttccc     2160
cacactatct caatgcaaat atctgtctga acggtccct ggctaaactc cacccatggg    2220
ttggccagcc ttgccttgac caatagcctt gacaaggcaa acttgaccaa tagtcttaga    2280
gtatccagtg aggccagggg ccggcggctg gctagggatg aagaataaaa ggaagcaccc    2340
ttcagcagtt ccacacactc gcttctggaa cgtctgaggt tatcaataag ctcctagtcc    2400
agacgccatg ggtcatttca cagaggagga caaggctact atcacaagcc tgtggggcaa    2460
ggtgaatgtg gaagatgctg gaggagaaac cctgggaagg taggctctgg tgaccaggac   2520
aaggaggga aggaaggacc ctgtgcctgg caaaagtcca ggtcgcttct caggatttgt    2580
ggcacctttct gactgtcaaa ctgttcttgt caatctcaca ggctcctggt tgtctaccca    2640
tggacccaga ggttctttga cagctttggc aacctgtcct ctgcctctgc catcatgggc    2700
aacccccaaag tcaaggcaca tggcaagaag gtgctgactt ccttgggaga tgccacaaag    2760
cacctggatg atctcaaggg cacctttgcc cagctgagtg aactgcactg tgacaagctg    2820
catgtggatc ctgag                                                     2835

SEQ ID NO: 9              moltype = DNA  length = 1000
FEATURE                   Location/Qualifiers
source                    1..1000
                          mol_type = genomic DNA
                          organism = Homo sapiens
SEQUENCE: 9
gtcaataaaa acaacccttg cctctttaga gttgttttcc atgtacacgc acatcttatg      60
tcttagagta agattccctg agaagtgaac ctagcattta acaagataa ttaattctaa     120
tccacagtac ctgccaaaga acattctacc atcatcttta ctgagcatag aagagctacg    180
ccaaaaccct gggtcatcag ccagcacaca cacttatcca gtggtaaata cacatcatct    240
ggtgtataca tacacctgaa tatggaat caaatattt ctaagatgaa acagtcatg       300
atttatttca aataggtacg gataagtaga tattgaggta agcattaggt cttatattat    360
gtaacactaa tctattactg cgctgaaact gtggctttat agaaattgtt ttcactgcac    420
tattgagaaa ttaagagata tggcaaaag tcacaaagag tatattcaaa aagaagtata    480
gcacttttc cttagaaacc actgctaact gaaagagact aagattgtc ccgtcaaaaa    540
tcctggacct atgcctaaaa cacatttcac aatccctgaa cttttcaaaa attggtacat    600
gctttagctt taaactacag gcctcactgg agctagagac aagaaggtaa aaacggctg    660
acaaaagaag tcctggtatc ctctatgatg ggagaaggaa actagctaaa gggaagaata    720
aattagagaa aaactggaat gactgaatcg gaacaaggcaa aagctataa aaaaattag    780
cagtatcctc ttgggggccc cttcccaca ctatctcaat gcaaatatct gtctgaaacg    840
gtccctggct aaactccacc catgggtgg ccagccttgc cttgaccaat agccttgaca    900
aggcaaactt gaccaatagt cttagagtat ccagtgaggc caggggccgg cggctggcta    960
gggatgaaga ataaaaggaa gcacccttca gcagttccac                         1000

SEQ ID NO: 10             moltype = DNA  length = 7210
FEATURE                   Location/Qualifiers
source                    1..7210
                          mol_type = other DNA
                          organism = Synthetic construct
SEQUENCE: 10
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc    120
actaggggtt ccttgtagtt aatgattaac cgccatgct acttatctac acgcgtcata    180
aatacttcct accctgttaa tggtcaata tgtcagaaac agcactgtgt tagaaataaa    240
gctgtctaaa gtacactaat attcgagtta taatagtgtg tggactatta gtcaataaaa    300
acaacccttg cctctttaga gttgttttcc atgtacacgc acatcttatg tcttagta     360
agattccctg agaagtgaac ctagcattta acaagataa ttaattctaa tccacagtac    420
ctgccaaaga acattctacc atcatcttta ctgagcatag aagagctacg ccaaaaccct    480
gggtcatcag ccagcacaca cacttatcca gtggtaaata cacatcatct ggtgtataca    540
```

```
tacatacctg aatatggaat caaatatttt tctaagatga aacagtcatg atttatttca   600
aataggtacg gataagtaga tattgaggta agcattaggt cttatattat gtaacactaa   660
tctattactg cgctgaaact gtggctttat agaaattgtt ttcactgcac tattgagaaa   720
ttaagagata atggcaaaag tcacaaagag tatattcaaa agaagtata gcacttttc    780
cttagaaacc actgctaact gaaagagact aagatttgtc ccgtcaaaaa tcctggacct   840
atgcctaaaa cacatttcac aatccctgaa cttttcaaaa attggtacat gctttagctt   900
taaactacag gcctcactgg agctagagac aagaaggtaa aaaacggctg acaaaagaag   960
tcctggtatc ctctatgatg ggagaaggaa actagctaaa gggaagaata aattagagaa  1020
aaactggaat gactgaatcg gaacaaggca aaggctataa aaaaaattaa gcagcagtat  1080
cctcttgggg gcccctttcc cacactatct caatgcaaat atctgtctga aacggtcct   1140
ggctaaactc cacccatggg ttggccagcc ttgccttgac gaacagagaa acaggagaat  1200
atgggccaaa caggatatct gtggtaagca gttcctgccc cggctcaggg ccaagaacag  1260
ttggaacagc agaatatggg ccaaacagga tatctgtggt aagcagttcc tgccccggct  1320
cagggccaag aacagatggt ccccagatgc ggtcccgccc tcagcagttt ctagagaacc  1380
atcagatgtt tccagggtgc cccaaggacc tgaaatgacc ctgtgcctta tttgaactaa  1440
ccaatcagtt cgcttctcgc ttctgttcgc gcgcttctgc tccccgagct ctatataagc  1500
agagctcgtt tagtgaaccg tcagatcgcc tggagacgcc atccacgctg ttttgacttc  1560
catagaagga tctcgaggcc accatggtga gcaagggcga ggagctgttc accggggtgg  1620
tgcccatcct ggtcgagctg gacggcgacg taaacggcca aagttcagc gtgtccggcg   1680
agggcgaggg cgatgccacc tacggcaagc tgaccctgaa gttcatctgc accaccggca  1740
agctgcccgt gccctggccc accctcgtga ccaccctgac ctacggcgtg cagtgcttca  1800
gccgctaccc cgaccacatg aagcagcacg acttcttcaa gtccgccatg cccgaaggct  1860
acgtccagga gcgcaccatc ttcttcaagg acgacggcaa ctacaagacc cgcgccgagg  1920
tgaagttcga gggcgacacc ctggtgaacc gcatcgagct gaagggcatc gacttcaagg  1980
aggacggcaa catcctgggg cacaagctgg agtacaacta caacagccac aacgtctata  2040
tcatggccga caagcagaag aacggcatca aggtgaactt caagatccgc cacaacatcg  2100
aggacggcag cgtgcagctc gccgaccact accagcagaa cacccccatc ggcgacggcc  2160
ccgtgctgct gcccgacaac cactacctga gcacccagtc cgccctgagc aaagaccccca 2220
acgagaagcg cgatcacatg gtcctgctgg agttcgtgac cgccgccggg atcactctcg  2280
gcatggacga gctgtacaag taaactagtg tcgactgctt tatttgtgaa atttgtgatg  2340
ctattgcttt atttgtaacc attataagct gcaataaaca agttaacaac aacaattgca  2400
ttcatttat gtttcaggtt caggggagg tgtgggaggt ttttaaaca atagccttga    2460
caaggcaaac ttgaccaata gtcttagagt atccagtgag gccaggggcc ggcggctggc  2520
tagggatgaa gaataaaagg aagcacccct cagcagttcc acacactcgc ttctggaacg  2580
tctgaggtta tcaataagct cctagtccag acgccatggg tcatttcaca gaggaggaca  2640
aggctactat cacaagcctg tggggcaagg tgaatgtgga agatgctgga ggagaaaccc  2700
tgggaaggta ggctctggtg accaggacaa gggagggaag gaaggaccct gtgcctggca  2760
aaagtccagg tcgcttctca ggatttgtgg caccttctga ctgtcaaaact gttcttgtca  2820
atctcacagg ctccggtttg tctacccatg gacccagagg ttctttgaca gctttggcaa  2880
cctgtcctct gcctctgcca tcatgggcaa ccccaaagtc aaggcacatg gcaagaaggt  2940
gctgacttcc ttgggagatg ccacaaagca cctggatgat ctcaagggca cctttgccca  3000
gctgagtgaa ctgcactgtg acaagctgca tgtggatcct gagaacttca aggtgagtcc  3060
aggagatgtt tcagccctgt tgccttagt tcgcaggcaa cttagacaac tgagtattga   3120
tctgagcaca gcagggtgtg agctgtttga agatactggg gttggggggtg aagaaactgc 3180
agaggactaa ctgggctgag acccagtggt aatgttttag ggcctaagga gcgcctctaa  3240
aaatctagat ggacaatttt gactttgaga aaagagaggt ggaaatgagg aaaatgactt   3300
ttcttatta gattccagta gaaagaactt tcatctttcc ctcatttttg ttgttttaaa   3360
acatctatct ggaggcagga caagtatggt cgttaaaaag atgcaggcag aaggcatata   3420
ttggctcagt caaagtgggg aactttgggc tagagtagat aagtagcatg gcgggttaat   3480
cattaactac aaggaacccc tagtgatgga gttggccact ccctctctgc gcgctcgctc   3540
gctcactgag gccgggcgac caaaggtcgc ccgacgcccg ggctttgccc gggcggcctc   3600
agtgagcgag cgagcgcgcc agctggcgta atagcgaaga ggcccgcacc gatcgccctt   3660
cccaacagtt gcgcagcctg aatggcgaat ggcgattccg ttgcaatggc tggcggtaat   3720
attgttctgg atattaccag caaggccgat agtttgagtt cttctactca ggcaagtgat   3780
gttattacta atcaaagaag tattgcgaca acggttaatt tgcgtgatgg acagactctt   3840
ttactcggtg gcctcactga ttataaaaac acttctcagg attctggcgt accgttcctg   3900
tctaaaatcc ctttaatcgg cctcctgttt agctcccgct ctgattctaa cgaggaaagc   3960
acgttatacg tgctcgtcaa agcaaccata gtacgcgccc tgtagcggcg cattaagcgc   4020
ggcgggtgtg gtgttacgc gcagcgtgac cgctacactt gccagcgccc tagcgcccgc   4080
tcctttcgct ttcttccctt cctttctcgc cacgttcgcc ggctttcccc gtcaagctct   4140
aaatcggggg ctccctttag ggttccgatt tagtgcttta cggcacctcg accccaaaaa   4200
acttgattag ggtgatggtt cacgtagtgg gccatcgccc tgatagacgg ttttcgccc    4260
tttgacgttg gagtccacgt tctttaatag tggactcttg ttccaaactg gaacaacact   4320
caaccctatc tcggtctatt cttttgattt ataaggaatt tgccgattt cggcctattg     4380
gttaaaaaat gagctgattt aacaaaaatt taacgcgaat tttaacaaaa tattaacgtt   4440
tacaatttaa atatttgctt atacaatctt cctgttttg gggcttttct gattatcaac   4500
cggggtacat atgattgaca tgctagtttt acgattaccg ttcatcgatt ctcttgtttg   4560
ctccagactc tcaggcaatg acctgatagc cttttgtagag accctcaaa aatagctacc   4620
ctctccggca tgaatttatc agctagaacg gttgaatatc atattgatgg tgatttgact   4680
gtctccggcc tttctcaccc gtttgaatct ttacctacac attactcagg cattgcattt   4740
aaaatatatg agggttctaa aaattttat ccttgcgttg aaataaaggc ttctcccgca   4800
aaagtattac agggtcataa tgtttttggt acaaccgatt tagctttatg ctctgaggct   4860
ttattgctta attttgctaa ttctttgcct tgcctgtatg atttattgga tgttggaatc   4920
gcctgatgcg gtattttctc cttacgcatc tgtgcggtat tcacaccgc atatggtgca   4980
ctctcagtac aatctgctct gatgccgcat agttaagcca gccccgacac ccgccaaac   5040
ccgctgacgc gccctgacgg gcttgtctgc tcccggcatc cgcttacaga caagctgtga   5100
ccgtctccgg gagctgcatg tgtcagaggt tttcaccgtc atcaccgaaa cgcgcgagac   5160
gaaagggcct cgtgatacgc ctattttat aggttaatgt catgataata atggtttctt    5220
agacgtcagg tggcacttt cggggaaatg tgcgcggaac ccctatttgt ttattttct    5280
```

```
aaatacattc aaatatgtat ccgctcatga gacaataacc ctgataaatg cttcaataat    5340
attgaaaaag gaagagtatg agtattcaac atttccgtgt cgcccttatt cccttttttg    5400
cggcattttg ccttcctgtt tttgctcacc cagaaacgct ggtgaaagta aaagatgctg    5460
aagatcagtt gggtgcacga gtgggttaca tcgaactgga tctcaacagc ggtaagatcc    5520
ttgagagttt tcgccccgaa gaacgttttc caatgatgag cacttttaaa gttctgctat    5580
gtggcgcggt attatcccgt attgacgccg ggcaagagca actcggtcgc cgcatacact    5640
attctcagaa tgacttggtt gagtactcac cagtcacaga aaagcatctt acggatggca    5700
tgacagtaag agaattatgc agtgctgcca taaccatgag tgataacact gcggccaact    5760
tacttctgac aacgatcgga ggaccgaagg agctaaccgc ttttttgcac aacatggggg    5820
atcatgtaac tcgccttgat cgttgggaac cggagctgaa tgaagccata ccaaacgacg    5880
agcgtgacac cacgatgcct gtagcaatgg caacaacgtt gcgcaaacta ttaactggcg    5940
aactacttac tctagcttcc cggcaacaat taatagactg gatggaggcg gataaagttg    6000
caggaccact tctgcgctcg gcccttccgg ctggctggtt tattgctgat aaatctggag    6060
ccggtgagcg tgggtctcgc ggtatcattg cagcactggg gccagatggt aagccctccc    6120
gtatcgtagt tatctacacg acggggagtc aggcaactat ggatgaacga atagacagat    6180
cgctgagat aggtgcctca ctgattaagc attggtaact gtcagaccaa gtttactcat    6240
atatacttta gattgattta aaacttcatt tttaatttaa aaggatctag gtgaagatcc    6300
tttttgataa tctcatgacc aaaatccctt aacgtgagtt ttcgttccac tgagcgtcag    6360
accccgtaga aaagatcaaa ggatcttctt gagatccttt ttttctgcgc gtaatctgct    6420
gcttgcaaac aaaaaaacca ccgctaccag cggtggtttg tttgccggat caagagctac    6480
caactctttt tccgaaggta actggcttca gcagagcgca gataccaaat actgtccttc    6540
tagtgtagcc gtagttaggc caccacttca agaactctgt agcaccgcct acatacctcg    6600
ctctgctaat cctgttacca gtggctgctg ccagtggcga taagtcgtgt cttaccgggt    6660
tggactcaag acgatagtta ccggataagg cgcagcggtc gggctgaacg gggggttcgt    6720
gcacacagcc cagcttggag cgaacgacct acaccgaact gagataccta cagcgtgagc    6780
tatgagaaag cgccacgctt cccgaaggga gaaaggcgga caggtatccg gtaagcggca    6840
gggtcggaac aggagagcgc acgagggagc ttccaggggg aaacgcctgg tatctttata    6900
gtcctgtcgg gtttcgccac ctctgacttg agcgtcgatt tttgtgatgc tcgtcagggg    6960
ggcggagcct atggaaaaac gccagcaacg cggccttttt acggttcctg gccttttgct    7020
ggccttttgc tcacatgttc tttcctgcgt tatccctga ttctgtggat aaccgtatta    7080
ccgcctttga gtgagctgat accgctcgcc gcagccgaac gaccgagcgc agcgagtcag    7140
tgagcgagga gcggaagag cgcccaatac gcaaaccgcc tctccccgcg cgttggccga    7200
ttcattaatg                                                          7210

SEQ ID NO: 11         moltype = DNA   length = 7204
FEATURE               Location/Qualifiers
source                1..7204
                      mol_type = other DNA
                      organism = Synthetic construct
SEQUENCE: 11
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc    120
actaggggtt ccttgtagtt aatgattaac ccgccatgct acttatctac acgcgcataa    180
atacttccta ccctgttaat ggtccaatat gtcagaaaca gcactgtgtt agaaataaag    240
ctgtctaaag tacactaata ttcgagttat aatagtgtgt ggactattag tcaataaaaa    300
caaccccttg ctctttagag ttgttttcca tgtacacgca catcttatgt cttagagtaa    360
gattccctga gaagtgaacc tagcatttat acaagataat taattctaat ccacagtacc    420
tgccaaagaa cattctacca tcatctttac tgagcataga agagctacgc caaaaccctg    480
ggtcatcagc cagcacacac acttatccag tggtaaatac acatcatctg gtgtatacat    540
acatacctga atatggaatc aaatatttt ctaagatgaa acagtcatga tttatttcaa    600
ataggtacgg ataagtagat attgaggtaa gcattaggtc ttatattatg taacactaat    660
ctattactgc gctgaaactg tggcttata gaaattgttt tcactgcact attgagaaat    720
taagagataa tggcaaaagt cacaaagagt atattcaaaa agaagtatag cacttttcc    780
ttagaaaacca ctgctaactg aaagagacta agatttgtcc cgtcaaaaat cctggaccta    840
tgcctaaaac acatttcaca atccctgaac ttttcaaaaa ttggtacatg cttttagcttt    900
aaactacagg cctcactgga gctagagaca agaaggtaaa aacggctgaa caaaagaagt    960
cctggtatcc tctatgatgg gagaaggaaa ctagctaaag ggaagaataa attagagaaa    1020
aactggaatg actgaatcgg aacaaggcaa aggctataaa aaaaattaag cagcagtatc    1080
ctcttggggg cccttcccc cacactatctc aatgcaaata tctgtctgaa acggtccctg    1140
gctaaactcc acccatgggt tggccagcct tgccttgacg aacagagaaa caggagata    1200
tgggccaaac aggatatctg tggtaagcag ttcctgcccc ggctcaggc caagaacagt    1260
tggaacagca gaatatgggc caaacaggat atctgtggta agcagttcct gccccggctc    1320
agggccaaga acagatggtc cccagatgcg gtcccgccct cagcagtttc tagagaacca    1380
tcagatgttt ccagggtgcc ccaaggacct gaaatgacc tgtgccttat ttgaactaac    1440
caatcagttc gcttctcgct tctgttcgcg cgcttctgct ccccgagctc tatataagca    1500
gagctcgttt agtgaaccgt cagatcgcct ggagacgcca tccacgctgt tttgacttcc    1560
atagaaggat ctcgaggcca ccatggtgag caagggcgag gagctgttca ccggggtggt    1620
gcccatcctg gtcgagctgg acggcgacgt aaacggccac aagttcagcg tgtccggcga    1680
gggcgagggc gatgccacct acggcaagct gaccctgaag ttcatctgca ccaccggcaa    1740
gctgcccgtg ccctgcccca cctcgtgac caccctgacc tacggcgtgc agtgcttcag    1800
ccgctacccc gaccacatga agcagcacga cttcttcaag tccgccatgc ccgaaggcta    1860
cgtccaggag cgcaccatct tcttcaagga cgacggcaac tacaagaccc gcgccgaggt    1920
gaagttcgag ggcgacaccc tggtgaaccg catcgagctg aagggcatcg acttcaagga    1980
ggacggcaac atctgggggc acaagctgga gtacaactac aacagccaca acgtctatat    2040
catggccgac aagcagaaga cggcatcaa ggtgaacttc aagatccgcc acaacatcga    2100
ggacggcagc gtgcagctcg ccgaccacta ccagcagaac ccccatcgc gcgacggccc    2160
cgtgctgctg cccgacaacc actacctgag cacccagtcc gccctgagca agaccccaa    2220
cgagaagcgc gatcacatgg tcctgctgga gttcgtgacc gccgcggga tcactctcgg    2280
catggacgag ctgtacaagt aaactagtgt cgactgcttt atttgtgaaa tttgtgatgc    2340
```

```
tattgcttta tttgtaacca ttataagctg caataaacaa gttaacaaca acaattgcat  2400
tcattttatg tttcaggttc aggggaggt gtgggaggtt ttttaaaaac ttcaaggtga  2460
gtccaggaga tgtttcagcc ctgttgcctt tagtctcgag gcaacttaga caactgagta  2520
ttgatctgag cacagcaggg tgtgagctgt ttgaagatac tggggttggg ggtgaagaaa  2580
ctgcagagga ctaactgggc tgagacccag tggtaatgtt ttagggccta aggagcgcct  2640
ctaaaaatct agatggacaa ttttgacttt gagaaaagag aggtggaaat gaggaaaatg  2700
acttttatta gattccagta gaaagaactt tcatctttcc ctcattttg ttgttttaaa  2760
acatctatct ggaggcagga caagtatggt cgttaaaaag atgcaggcag aaggcatata  2820
ttggctcagt caaagtgggg aactttggtg gccaaacata cattgctaag gctattccta  2880
tatcagctgg acacatataa aatgctgcta atgcttcatt acaaacttat atcctttaat  2940
tccagatggg ggcaaagtat gtccagggt gaggaacaat tgaaacattt gggctggagt  3000
agattttgaa agtcagctct gtgtgtgtgt gtgtgtgcgc gcgcgcgtgt gtgtgtgtgt  3060
gtgtcagcgt gtgtttcttt taacgtcttc agcctacaac atacagggtt catggtggca  3120
agaagatagc aagatttaaa ttatggccag tgactagtgc ttgaagggga acaactacct  3180
gcatttaatg ggaaggcaaa atctcaggct ttgagggaag ttaacatagg cttgattctg  3240
ggtagaagct gggtgtgtag ttatctggag gccaggctgg agctctcagc tcactatggg  3300
ttcatccttta ttgtctcctt tcatctcaac agctcctggg aaatgtgctg gtgaccgttt  3360
tggcaatcca tttcggcaaa gaattcaccc ctgaggtgca ggcttcctgg cagaagatgg  3420
tgactgcagt ggccagtgcc ctgctagagt agataagtag catggcgggt taatcattaa  3480
ctacaaggaa cccctagtga tggagttggc cactccctct ctgcgcgctc gctcgctcac  3540
tgaggccggg cgaccaaagg tcgcccgacg cccgggcttt gccgggcgg cctcagtgag  3600
cgagcgagcg cgcagctgg cgtaatagcg aagaggcccg caccgatcgc ccttcccaac  3660
agttgcgcag cctgaatggc gaatggcgat tccgttgcaa tggctggcgg taatattgtt  3720
ctggatatta ccagcaaggc cgatagtttg agttcttcta ctcaggcaag tgatgttatt  3780
actaatcaaa gaagtattgc gacaacggtt aatttgcgtg atggacagac tcttttactc  3840
ggtgcctca ctgattataa aaacacttct caggattctg gcgtaccgtt cctgtctaaa  3900
atccctttaa tcggcctcct gtttagctcc cgctctgatt ctaacgagga aagcacgtta  3960
tacgtgctcg tcaaagcaac catagtacgc gccctagc ggcgcattaa gcgcggcggg  4020
tgtggtggtt acgcgcagcg tgaccgctac acttgccagc gccctagcgc ccgctccttt  4080
cgctttcttc ccttccttc tcgccacgtt cgccggctttc ccccgtcaag ctctaaatcg  4140
ggggctccct ttagggttcc gatttagtgc tttacggcac ctcgacccca aaaaacttga  4200
ttagggtgat ggttcacgta gtgggccatc gccctgatag acggttttc gccctttgac  4260
gttggagtcc acgttcttta atagtggact cttgttccaa actggaacaa cactcaaccc  4320
tatctcggtc tattctttg atttataagg gattttcggc ctattggttaaa  4380
aaatgagctg atttaacaaa aatttaacgc gaattttaac aaaatattaa cgtttacaat  4440
ttaaatattt gcttatacaa tcttcctgtt tttgggctt ttctgattat caaccggggt  4500
acatatgatt gacatgctag ttttacgatt accgttcatc gattctctg tttgctccag  4560
actctcaggc aatgacctga tagcctttgt agagacctc caaaaatagc taccctctcc  4620
ggcatgaatt tatcagctag aacggttgaa tatcatattg atggtgattt gactgtctcc  4680
ggcctttctc acccgtttga atctttaccct acacattact caggcattgc atttaaaata  4740
tatgagggtc ctaaaaattt ttatccttgc gttgaaataa aggcttctcc cgcaaaagta  4800
ttacagggtc ataatgtttt tggtacaacc gatttagctt tatgctctga ggctttattg  4860
cttaattttg ctaattcttt gccttgcctg tatgatttat tggatgttgg aatcgcctga  4920
tgcggtattt tctccttacg catctgtgcg gtatttcaca ccgcatatgg tgcactctca  4980
gtacaatctg ctctgatgcc gcatagttaa gccagccccg acaccgcca cacccgctg  5040
acgcgccctg acgggcttgt ctgctcccgg catccgctta cagacaagct gtgaccgtct  5100
ccgggagctg catgtgtcag aggttttcac cgtcatcacc gaaacgcgcg agacgaaagg  5160
gcctcgtgat acgcctattt ttataggtta atgtcatgat aataatggtt tcttagacgt  5220
caggtggcac ttttcgggga atgtgcgcg gaacccctat ttgtttattt ttctaaatac  5280
attcaaatat gtatccgctc atgagacaat aaccctgata aatgcttcaa taatattgaa  5340
aaaggaagag tatgagtatt caacatttcc gtgtcgccct tattccctt tttgcggcat  5400
tttgccttcc tgttttgct cacccagaaa cgctggtgaa agtaaaagat gctgaagatc  5460
agttgggtgc acgagtgggt tacatcgaac tggatctcaa cagcggtaag atccttgaga  5520
gttttcgccc cgaagaacgt tttccaatga tgagcacttt taaagttctg ctatgtggcg  5580
cggtattatc ccgtattgac gccgggcaag agcaactcgg tcgccgcata cactattctc  5640
agaatgactt ggttgagtac tcaccagtca cagaaaagca tcttacggat ggcatgacag  5700
taagagaatt atgcagtgct gccataacca tgagtgataa cactgcggcc aacttacttc  5760
tgacaacgat cggaggaccg aaggagctaa ccgcttttt gcacaacatg gggatcatg  5820
taactcgcct tgatcgttgg gaaccggagc tgaatgaagc cataccaaac gacgagcgtg  5880
acaccacgat gcctgtagca atggcaacaa cgttgcgcaa actattaact ggcgaactac  5940
ttactctagc ttcccggcaa caattaatag actggatgga ggcggataaa gttgcaggac  6000
cacttctgcg ctcggccctt ccggctggct ggtttattgc tgataaatct ggagccggtg  6060
agcgtgggtc tcgcggtatc attgcagcac tggggccaga tggtaagccc tcccgtatcg  6120
tagttatcta cacgacgggg agtcaggcaa ctatggatga acgaaataga cagatcgctg  6180
agataggtgc ctcactgatt aagcattggt aactgtcaga ccaagtttac tcatatatac  6240
tttagattga tttaaaactt catttttaat ttaaaaggat ctaggtgaag atccttttg  6300
ataatctcat gaccaaaatc ccttaacgtg agttttcgtt ccactgagcg tcagaccccg  6360
tagaaaagat caaaggatct cttgagatc cttttttct gcgcgtaatc tgctgcttgc  6420
aaacaaaaaa accaccgcta ccagcggtgg tttgtttgcc ggatcaagag ctaccaactc  6480
tttttccgaa ggtaactggc ttcagcagag cgcagatacc aaatactgtc cttctagtgt  6540
agccgtagtt aggccaccac ttcaagaact ctgtagcacc gcctacatac ctcgctctgc  6600
taatcctgtt accagtggct gctgccagtg gcgataagtc gtgtcttacc gggttggact  6660
caagacgata gttaccggat aaggcgcagc ggtcgggctg aacggggggt tcgtgcacac  6720
agcccagctt ggagcgaacg acctacaccg aactgagata cctacagcgt gagctatgag  6780
aaagcgccac gcttcccgaa gggagaaagg cggacaggta tccggtaagc ggcagggtcg  6840
gaacaggaga gcgcacgagg gagcttccag gggaaacgc ctggtatctt tatagtcctg  6900
tcgggtttcg ccacctctga cttgagcgtc gatttttgtg atgctcgtca ggggggcgga  6960
gcctatggaa aaacgccagc aacgcggcct ttttacggtt cctggccttt tgctggcctt  7020
ttgctcacat gttctttcct gcgttatccc ctgattctgt ggataaccgt attaccgcct  7080
```

```
ttgagtgagc tgataccgct cgccgcagcc gaacgaccga gcgcagcgag tcagtgagcg    7140
aggaagcgga agagcgccca atacgcaaac cgcctctccc cgcgcgttgg ccgattcatt    7200
aatg                                                                 7204

SEQ ID NO: 12           moltype = DNA   length = 8236
FEATURE                 Location/Qualifiers
source                  1..8236
                        mol_type = other DNA
                        organism = Synthetic construct
SEQUENCE: 12
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt cctacgcgta gatcttaccc tgttaatggt ccaatatgtc agaaacagca     180
ctgtgttaga aataaagctg tctaaagtac actaatattc gagttataat agtgtgtgga     240
ctattagtca ataaaaacaa cccttgcctc tttagagttg ttttccatgt acacgcacat     300
cttatgtctt agagtaagat tccctgagaa gtgaacctag catttataca agataattaa     360
ttctaatcca cagtacctgc caaagaacat tctaccatca tctttactga gcatagaaga     420
gctacgccaa aaccctgggt catcagccag cacacacact tatccagtgg taaatacaca     480
tcatctggtg tatacataca tacctgaata tggaatcaaa tatttttcta agatgaaaca     540
gtcatgattt atttcaaata ggtacggata agtagatatt gaggtaagca ttaggtctta     600
tattatgtaa cactaatcta ttactgcgct gaaactgtgg ctttatagaa attgttttca     660
ctgcactatt gagaaattaa gagataatgg caaaagtcac aaagagtata ttcaaaaaga     720
agtatagcac tttttcctta gaaccactgc taactgaaa gagactaaga tttgtcccgt     780
caaaaatcct ggacctatgc ctaaaacaca tttcacaatc cctgaacttt tcaaaaattg     840
gtacatgctt tagctttaaa ctacaggcct cactggagct agagacaaga aggtaaaaaa     900
cggctgacaa aagaagtcct ggtatcctct atgatgggag aaggaaacta gctaaaggga     960
agaataaaatt agagaaaaac tggaatgact gaatcggaac aaggcaaagg ctataaaaaa    1020
aattagcagt atcctcttgg gggcccttc cccacactat ctcaatgcaa atatctgtct     1080
gaaacggtcc ctggctaaac tccacccatg ggttggccag ccttgccttg accaatagcc    1140
ttgacgaatt cgctttaaaa aacctcccac atctccccct gaacctgaaa cataaaatga    1200
atgcaattgt tgttgttaac ttgtttattg cagcttataa tggttacaaa taaagcaata    1260
gcatcacaaa tttcacaaat aaagcttact tgtacagctc gtccatgccg agagtgatcc    1320
cggcggcggt cacgaactcc agcaggacca tgtgatcgcg cttctcgttg ggtcttttgc    1380
tcagggcgga ctgggtgctc aggtagtggt tgtcgggcag cagcacgggg ccgtcgccga    1440
tgggggtgtt ctgctggtag tggtcggcga gctgcacgct gccgtcctcg atgttgtggc    1500
ggatcttgaa gttcaccttg atgccgttct tctgcttgtc ggccatgata tagacgttgt    1560
ggctgttgta gttgtactcc agcttgtgcc ccaggatgtt gccgtcctcc ttgaagtcga    1620
tgcccttcag ctcgatgcgg ttcaccaggg tgtcgccctc gaacttcacc tcggcgcggg    1680
tcttgtagtt gccgtcgtcc ttgaagaaga tggtgcgctc ggacgtag ccttcgggca    1740
tggcggactt gaagaagtcg tgctgcttca tgtggtcggg gtagcggctg aagcactgca    1800
cgccgtaggt caggggtggtc acgagggtgg gccagggcac gggcagcttg ccggtggtgc    1860
agatgaactt cagggtcagc ttgccgtagg tggcatcgcc ctcgccctcg ccggacacgc    1920
tgaacttgtg gccgtttacg tcgccgtcca gctcgaccag gatgggcacc accccggtga    1980
acagctcctc gcccttgctc accatggtgg cggcgcggcc gcgatctgac ggttcactaa    2040
acgagctctg cttatataga gctcggggag cagaagcgcg cgaacagaag cgagaagcga    2100
actgattggt tagttcaaat aaggcacagg gtcatttcag gtccttgggg caccctgaa    2160
acatctgatg gttctctaga aactgctgag ggcgggacg catctgggga ccatctgttc    2220
ttggccctga gccggggcag gaactgctta ccacagatat cctgtttggc ccatattctg    2280
ctgttccaac tgttcttggc cctgagccgg ggcaggaact gcttaccaca gatatcctgt    2340
ttgcccata ttctcctgtt tctctgttcc cgcggcgaga tcgagaccat cctgctaac    2400
acagtgaaac cccgtctcta ctaaaaaaat acaaaaatt agccgggctt ggtggcgcat    2460
gcctgtagtc ccagctacta tggaggctga ggcgggagaa tggcgtgaac gcggggggcg    2520
gagcttgcag tgagcagaga tcaggggcca ctgcactcca gcctgggcga cagagagaga    2580
ctctgtctca aaaaaagaa aaaaaaatt tagtagacta gctaaaaaaa tccagagata    2640
gttattgatg catatgtaaa agtcttccaa tatttacaag tacaatgaaa aaaaaaataac    2700
cttgaattaa gtgtagaact cattgacaat gtttcaaagg atgtgaggga taaactaaaa    2760
tttgggcagt acatgctgtt cctgtgtact tggaacagag ggagaaaatc tgggctggaa    2820
atattgttat aggagttagc acatgaaggt gacaactaaa ttatttggag tagatggagt    2880
caccagcaca tgtgaatagt tttagaatga aatgacccaa gatagaactt tggagagccc    2940
ccaaatttaa ataaaatcag tataagagaa gaggaagaaa ccaaatggta tactagtcta    3000
aattgtttct tagtgacaaa agaataacct gaatattaga ttagctgcct atatgctctc    3060
tgaatcaatt tcattcaaca tgcaacagtt ctggaaccta tcaggaccca cagtcagcca    3120
ggcaagcaca tctgcccaag ccaagggtgg aggcatgcag ctgtggggt ctgtgaaaac    3180
acttgaggga gcagataact gggccaacca tgactcagtg cttctggagg ccaacaggac    3240
tgctgagtca tcctgtgggg gtggaggtgg gacaaggaa aggggtgaat ggtactgctg    3300
attacaacct ctggtgctgc ctcccccctcc tgtttatctg agagaggcct cactggagct    3360
agagacaaga aggtaaaaaa cggctgacaa aagaagtcct ggtatcctct atgatgggag    3420
aaggaaacta gctaaaggga agaataaaatt agagaaaaac tggaatgact gaatcggaac    3480
aaggcaaagg ctataaaaaa aattagcagt atcctcttgg gggcccttc cccacactat    3540
ctcaatgcaa atatctgtct gaaacggtcc ctggctaaac tccacccatg ggttggccag    3600
ccttgccttg acaaggcaaa cttgaccaat agtcttagag tatccagtga ggcaggggc    3660
cggcggctgg ctaggatgaa gaataaaag gaagcaccct tcagcagttc cacacactcg    3720
cttctggaac gtctgaggtt atcaataagc tcctagtcca gacgcatgg gtcatttcac    3780
agaggaggac aagtcacta tcacaagcct gtggggcaga gtgaatgtgg aagatgctgg    3840
aggagaaacc ctgggaaggt aggctctggt gaccaggaca aggggaggaa ggaaggaccc    3900
tgtgcctggc aaagtccag gtcgcttctc aggatttgtg gcaccttctg actgtcaaac    3960
tgttcttgtc aatctcacag gctcctggtt gtctacccat ggacccagag gttctttgac    4020
agctttggca acctgtcctc tgcctctgcc atcatgggca acccaaagt caaggcacat    4080
ggcaagaagg tgctgacttc cttgggagat gccacaaagc acctggatga tctcaagggc    4140
```

```
acctttgccc agctgagtga actgcactgt gacaagctgc atgtggatcc tgagaacttc  4200
aaggtgagtc caggagatgt ttcagccctg ttgcctttag tctcgaggca acttagacaa  4260
cggagtattg atctgagcac agcagggtgt gagctgtttg aagatactgg ggttgggggt  4320
gaagaaactg cagaggacta actgggctga acccagtgg taatgtttta gggcctaagg  4380
agtgcctcta aaaatctaga tggacaattt tgactttgaa aaagagagg tggaaatgaa  4440
gaaaatgact tttctttatt agattccagt agaaagaact ttcatctttc cctcattttt  4500
gttgttttaa aagtcgacag gaaccccctag tgatggagtt ggccactccc tctctgcgcg  4560
ctcgctcgct cactgaggcc gggcgaccaa aggtcgcccg acgcccgggc tttgcccggg  4620
cggcctcagt gagcgagcga gcgcgcagct ggcgtaatag cgaagaggcc cgcaccgatc  4680
gcccttccca acagttgcgc agcctgaatg gcgaatgggcg attccgttgc aatggctggc  4740
ggtaatattg ttctggatat taccagcaag gccgatagtt tgagttcttc tactcaggca  4800
agtgatgtta ttactaatca aagaagtatt gcgacaacgg ttaatttgcg tgatggacag  4860
actcttttac tcggtggcct cactgattat aaaaacactt ctcaggattc tggcgtaccg  4920
ttcctgtcta aaatcccttt aatcggcctc ctgtttagct cccgctctga ttctaacgag  4980
gaaagcacgt tatacgtgct cgtcaaagca accatagtac gcgccctgta gcggcgcatt  5040
aagcgcggcg ggtgtggtgg ttacgcgcag cgtgaccgct acacttgcca gcgccctagc  5100
gcccgctcct ttcgctttct tcccttcctt tctcgccacg ttcgccggct ttccccgtca  5160
agctctaaat cggggctcc ctttagggtt ccgatttagt gctttacggc acctcgaccc  5220
caaaaactt gattagggtg atggttcacg tagtgggcca tcgccctgat agacggtttt  5280
tcgccctttg acgttggagt ccacgttctt aatagtgga ctcttgttcc aaactggaac  5340
aacactcaac cctatctcgg tctattcttt tgatttataa gggattttgc cgatttcggc  5400
ctattggtta aaaaatgagc tgatttaaca aaaatttaac gcgaatttta acaaaatatt  5460
aacgtttaca atttaaatat ttgcttatac aatcttcctg ttttgggc ttttctgatt  5520
atcaaccggg gtacatatga ttgacatgct agttttacga ttaccgttca tcgattctct  5580
tgtttgctcc agactctcag gcaatgacct gatagccttt gtagagacct ctcaaaaata  5640
gctaccctct ccggcatgaa tttatcagct agaacggttg aatatcatat tgatggtgat  5700
ttgactgtct ccggcctttc tcacccgttt gaatctttac ctacacatta ctcaggcatt  5760
gcatttaaaa tatatgaggg ttctaaaaat ttttatcctt gcgttgaaat aaaggcttct  5820
cccgcaaaag tattacaggg tcataatgtt tttggtacaa ccgatttagc tttatgctct  5880
gaggctttat tgcttaattt tgctaattct ttgccttgcc tgtatgattt attggatgtt  5940
ggaatcgcct gatgcggtat tttctcctta cgcatctgtg cggtatttca caccgcatat  6000
ggtgcactct cagtacaatc tgctctgatg ccgcatagtt aagccagccc gacacccgc  6060
caacacccgc tgacgcgccc tgacgggctt gtctgctccc ggcatccgct tacagacaag  6120
ctgtgaccgt ctccgggagc tgcatgtgtc agaggttttc accgtcatca ccgaaacgcg  6180
cgagacgaaa gggcctcgtg atacgcctat ttttataggt taatgtcatg ataataatgg  6240
tttcttagac gtcaggtggc acttttcggg gaaatgtgcg cggaacccct atttgtttat  6300
ttttctaaat acattcaaat atgtatccgc tcatgagaca ataaccctga taatgcttc  6360
aataatattg aaaaaggaag agtatgagta ttcaacattt ccgtgtcgcc cttattccct  6420
tttttgcggc attttgcctt cctgttttg ctcacccaga acgctggtg aaagtaaaag  6480
atgctgaaga tcagttgggt gcacgagtgg gttacatcga actggatctc aacagcggta  6540
agatccttga gagttttcgc cccgaagaac gttttccaat gatgagcact tttaaagttc  6600
tgctatgtgg cgcggtatta tcccgtattg acgccggca agagcaactc ggtcgccgca  6660
tacactattc tcagaatgac ttggttgagt actcaccagt cacagaaaag catcttacgg  6720
atggcatgac agtaagagaa ttatgcagtg ctgccataac catgagtgat aacactgcgg  6780
ccaacttact tctgacaacg atcggaggac cgaaggagct aaccgctttt ttgcacaaca  6840
tgggggatca tgtaactcgc cttgatcgtt gggaaccgga gctgaatgaa gccataccaa  6900
acgacgagcg tgacaccacg atgcctgtag caatggcaac aacgttgcgc aaactattaa  6960
ctggcgaact acttactcta gcttcccggc aacaattaat agactggatg gaggcggata  7020
aagttgcagg accacttctg cgctcggccc ttccggctgg ctggtttatt gctgataaat  7080
ctggagccgg tgagcgtggg tctcgcggta tcattgcagc actggggcca gatggtaagc  7140
cctcccgtat cgtagttatc tacacgacgg ggagtcaggc aactatggat gaacgaaata  7200
gacagatcgc tgagataggt gcctcactga ttaagcattg gtaactgtca gaccaagttt  7260
actcatatat actttagatt gatttaaaac ttcattttta atttaaaagg atctaggtga  7320
agatcctttt tgataatctc atgaccaaaa tcccttaacg tgagttttcg ttccactgag  7380
cgtcagaccc cgtagaaaag atcaaaggat cttcttgaga tcctttttt ctgcgcgtaa  7440
tctgctgctt gcaaacaaaa aaaccaccgc taccagcggt ggtttgtttg ccggatcaag  7500
agctaccaac tctttttccg aaggtaactg gcttcagcag agcgcagata ccaaatactg  7560
tccttctagt gtagccgtag ttaggccacc acttcaagaa ctctgtagca ccgcctacat  7620
acctcgctct gctaatcctg ttaccagtgg ctgctgccaa tggcgataag tcgtgtctta  7680
ccgggttgga ctcaagacga tagttaccgg ataaggcgca gcggtcgggc tgaacggggg  7740
gttcgtgcac acagcccagc ttggagcgaa cgacctacac cgaactgaga tacctacagc  7800
gtgagctatg agaaagcgcc acgcttcccg aagggagaaa ggcggacagg tatccggtaa  7860
gcggcagggt cggaacagga gagcgcacga gggagcttcc agggggaaac gcctggtatc  7920
tttatagtcc tgtcgggttt cgccacctct gacttgagcg tcgatttttg tgatgctcgt  7980
caggggggcg gagcctatgg aaaaacgcca gcaacgcggc cttttacgg ttcctggcct  8040
tttgctggcc ttttgctcac atgttctttc ctgcgttatc ccctgattct gtggataacc  8100
gtattaccgc ctttgagtga gctgataccg ctcgccgcag ccgaacgacc gagcgcagcg  8160
agtcagtgag cgaggaagcg gaagagcgcc caatacgcaa accgcctctc cccgcgcgtt  8220
ggccgattca ttaatg                                                  8236

SEQ ID NO: 13          moltype = DNA   length = 7955
FEATURE                Location/Qualifiers
source                 1..7955
                       mol_type = other DNA
                       organism = Synthetic construct
SEQUENCE: 13
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt cctacgcgta gatcttaccc tgttaatggt ccaatatgtc agaaacagca  180
```

```
ctgtgttaga aataaagctg tctaaagtac actaatattc gagttataat agtgtgtgga   240
ctattagtca ataaaaacaa cccttgcctc tttagagttg ttttccatgt acacgcacat   300
cttatgtctt agagtaagat tccctgagaa gtgaacctag catttataca agataattaa   360
ttctaatcca cagtacctgc caaagaacat tctaccatca tctttactga gcatagaaga   420
gctacgccaa aaccctgggt catcagccag cacacacact tatccagtgg taaatacaca   480
tcatctggtg tatacataca tacctgaata tggaatcaaa tattttttcta agatgaaaca   540
gtcatgattt atttcaaata ggtacggata agtagatatt gaggtaagca ttaggtctta   600
tattatgtaa cactaatcta ttactgcgct gaaactgtgg ctttatagaa attgttttca   660
ctgcactatt gagaaattaa gagataatgg caaaagtcac aaaagagtata ttcaaaaaga   720
agtatagcac ttttttcctta gaaaccactg ctaactgaaa gagactaaga tttgtcccgt   780
caaaaatcct ggacctatgc ctaaaacaca tttcacaatc cctgaacttt tcaaaaattg   840
gtacatgctt tagctttaaa ctacgaattc gctttaaaaa acctcccaca tctcccctg    900
aacctgaaac ataaaatgaa tgcaattgtt gttgttaact tgtttattgc agcttataat   960
ggttacaaat aaagcaatag catcacaaat ttcacaaata aagcttactt gtacagctcg  1020
tccatgccga gagtgatccc ggcggcggtc acgaactcca gcaggaccat gtgatcgcgc  1080
ttctcgttgg ggtctttgct cagggcggac tgggtgctca ggtagtggtt gtcgggcagc  1140
agcacggggc cgtcgccgat gggggtgttc tgctggtagt ggtcggcgag ctgcacgctg  1200
ccgtcctcga tgttgtggcg gatcttgaag ttcaccttga tgccgttctt ctgccttgcg  1260
gccatgatat agacgttgtg gctgttgtag ttgtactcca gcttgtgccc caggatgttg  1320
ccgtcctcct tgaagtcgat gcccttcagc tcgatgcggt tcaccagggt gtcgccctcg  1380
aacttcacct cggcgcgggt cttgtagttg ccgtcgtcct tgaagaagat ggtgcgctcc  1440
tggacgtagc cttcgggcat ggcggacttg aagaagtcgt gctgcttcat gtggtcgggg  1500
tagcggctga agcactgcac gccgtaggtc agggtggtca cgagggtggg ccagggcacg  1560
ggcagcttgc cggtggtgca gatgaacttc agggtcagct tgccgtaggt ggcatcgccc  1620
tcgccctcgc cggacacgct gaacttgtgg ccgtttacgt cgccgtccag ctcgaccagg  1680
atgggcacca ccccggtgaa cagctcctcg cccttgctca ccatggtggc ggcgcggccg  1740
cgatctgacg gttcactaaa cgagctctgc ttatatagag ctcggggagc agaagcgcgc  1800
gaacagaagc gagaagcgaa ctgattggtt agttcaaata aggcacaggg tcatttcagg  1860
tccttggggc accctggaaa catctgatgg ttctctagaa actgctgagg gcgggaccgc  1920
atctggggac catctgttct tggccctgag ccggggcagg aactgcttac cacagatatc  1980
ctgtttggcc catattctgc tgttccaact gttcttggcc ctgagccggg gcaggaactg  2040
cttaccacag atatcctgtt tggcccatat tctcctgttt ctctgttccc gcggcgagat  2100
cgagaccatc ctggctaaca cagtgaaacc ccgtctctac taaaaaaata caaaaaatta  2160
gccgggcttg gtggcgggtg cctgtagtcc cagctactat ggaggctgag gcgggagaat  2220
ggcgtgaacg cggggggcgg agcttgcagt cagcagagat caggggccac tgcactccag  2280
cctgggcgac agagagagac tctgtctcaa aaaaagaaa aaaaaattt agtagactag   2340
ctaaaaaaat ccagagatag ttattgatgc atatgtaaaa gtcttccaat atttacaagt  2400
acaatgaaaa aaaaataacc ttgaattaag tgtagaactc attgacaatg tttcaaagga  2460
tgtgagggat aaactaaaat ttgggcagta catgctgttc ctgtgtactt ggaacagagg  2520
gagaaaatct gggctggaaa tattgttata ggagttagca catgaaggtg acaactaaat  2580
tatttggagt agatggagtc accagcacat gtgaatagtt ttagaatgaa atgacccaag  2640
atagaacttt ggagagcccc caatttaaa taaaatcagt ataagagaag aggaagaaac   2700
caaatgtat actagtctaa attgtttctt agtgacaaaa gaataacctg aatattagat   2760
tagctgccta tatgctctct gaatcaattt cattcaacat gcaacagttc tggaacctat  2820
cagggaccac agtcagccag gcaagcacat ctgcccaagc caagggtgga ggcatgcagc  2880
tgtgggggtc tgtgaaaaca cttgagggag cagataactg ggccaaccat gactcagtgc  2940
ttctggaggc caacaggact gctgagtcat cctgtgggtg tggaggtggg acaagggaaa  3000
ggggtgaatg gtactgctga ttacaacctc tggtgctgcc tccccctcct gtttatctga  3060
gagaggcctc actggagcta gagacaagaa ggtaaaaaac ggctgacaaa agaagtcctg  3120
gtatcctcta tgatgggaga aggaaactag ctaaaggaa gaataaatta gagaaaaact   3180
ggaatgactg aatcggaaca aggcaaagc tataaaaaaa attagcagta tcctcttggg   3240
ggccccttcc ccacactatc tcaatgcaaa tatctgtctg aaacggtccc tggctaaact  3300
ccacccatgg gttggccagc cttgccttga caaggcaaac ttgaccaata gtcttagagt  3360
atccagtgag gccaggggcc ggcggctggc tagggatgaa gaataaaagg aagcacccctt  3420
cagcagttcc acacactcgc ttctggaacg tctgaggtta tcaataagct cctagtccag  3480
acgccatggg tcatttcaca gaggaggaca aggctactat cacaagcctg tggggcaagg  3540
tgaatgtgga agatgctgga ggagaaaccc tgggaaggta ggctctggtg accaggacaa  3600
gggagggaag gaaggaccct gtgcctggca aaagtccagg tcgcttctca ggatttgtgg  3660
caccttctga ctgtcaaact gttcttgtca atctcacagg ctcctggttg tctaccccatg 3720
gacccagagg ttctttgaca gctttggcaa cctgtcctct gcctctgcca tcatgggcaa  3780
ccccaaagtc aaggcacatg gcaagaaggt gctgacttcc ttgggagatg ccacaaagca  3840
cctggatgat ctcaagggca cctttgccca gctgagtgaa ctgcactgtg acaagctgca  3900
tgtggatcct gagaacttca aggtgagtcc aggagatgtt tcagccctgt gcctttagt   3960
ctcgaggcaa cttagacaac ggagtattga tctgagcaa agctgttgga                4020
agatactggg gttggggtg aagaaactgc agaggactaa ctgggctgag acccagtggt   4080
aatgttttag ggcctaagga gtgcctctaa aaatctagat ggacaatttt gactttgaga   4140
aaagagaggt ggaaatgagg aaaatgactt tctttatta gattccagta gaaagaactt   4200
tcatctttcc ctcatttttg ttgttttaaa agtgacagg aaccctagt gatggagttg    4260
gccactccct ctctgcgcgc tcgctcgctc actgaggccg ggcgaccaaa ggtcgcccga   4320
cgcccgggct tgcccggggc ggcctcagtg agcgagcgag cgcgcagctg cgtaatagcg   4380
gaagaggccc gcaccgatcg cccttcccaa cagttgcgca gcctgaatgg cgaatgcga   4440
ttccgttgca atggctggcg gtaatattgt tctggatatt accagcaagg ccgatagttt   4500
gagttcttct actcaggcaa gtgatgttat tactaatcaa agaagtattg cgacaacggt   4560
taattcgt gatggacaga ctcttttact cggtgcctc actgattata aaaacttc     4620
tcaggattct ggcgtaccgt tcctgtctaa aatccctta atcggcctcc tgtttagctc   4680
ccgctctgat tctaacgagg aaagcacgtt atacgtgctc gtcaaagcaa ccatagtacg   4740
cgccctgtag cggcgcatta gcgcggcgg gtgtggtggt tacgcgcagc gtgaccgcta   4800
cacttgccag cgccctagcg cccgctcctt tcgctttctt cccttccttt ctcgccacgt   4860
tcgccggctt tccccgtcaa gctctaaatc ggggggctccc tttagggttc cgatttagtg   4920
```

```
ctttacggca cctcgacccc aaaaaacttg attagggtga tggttcacgt agtgggccat  4980
cgccctgata gacggttttt cgcccttga cgttggagtc cacgttcttt aatagtggac  5040
tcttgttcca aactggaaca acactcaacc ctatctcggt ctattctttt gatttataag  5100
ggattttgcc gatttcggcc tattggttaa aaaatgagct gatttaacaa aaatttaacg  5160
cgaattttaa caaaatatta acgttacaa tttaaatatt tgcttataca atcttcctgt  5220
ttttggggct tttctgatta tcaaccgggg tacatatgat tgacatgcta gttttacgat  5280
taccgttcat cgattctctt gtttgctcca gactctcagg caatgacctg atagcctttg  5340
tagagacctc tcaaaaatag ctaccctctc cggcatgaat ttatcagcta gaacggttga  5400
atatcatatt gatggtgatt tgactgtctc cggcctttct cacccgtttg aatctttacc  5460
tacacattac tcaggcattg catttaaaat atatgagggt tctaaaaatt tttatccttg  5520
cgttgaaata aaggcttctc ccgcaaaagt attacagggt cataatgttt ttggtacaac  5580
cgatttagct ttatgctctg aggctttatt gcttaatttt gctaattctt tgccttgcct  5640
gtatgattta ttggatgttg aatcgcctg atgcggtatt ttctccttac gcatctgtgc  5700
ggtatttcac accgcatatg gtgcactctc agtacaatct gctctgatgc cgcatagtta  5760
agccagcccc gacacccgcc aacacccgct gacgcgccct gacgggcttg tctgctcccg  5820
gcatccgctt acagacaagc tgtgaccgtc tccgggagct gcatgtgtca gaggttttca  5880
ccgtcatcac cgaaacgcgc gagacgaaag ggcctcgtga tacgcctatt tttataggtt  5940
aatgtcatga taataatggt ttcttagacg tcaggtggca cttttcgggg aaatgtgcgc  6000
ggaaccccta tttgtttatt tttctaaata cattcaaata tgtatccgct catgagacaa  6060
taaccctgat aaatgcttca ataatattga aaaaggaaga gtatgagtat tcaacatttc  6120
cgtgtcgccc ttattccctt ttttgcggca ttttgccttc ctgtttttgc tcacccagaa  6180
acgctggtga agtaaaaga tgctgaagat cagttgggtg cacgagtggg ttacatcgaa  6240
ctggatctca acagcggtaa gatccttgag agttttcgcc ccgaagaacg ttttccaatg  6300
atgagcactt ttaaagttct gctatgtggc gcggtattat cccgtattga cgccgggcaa  6360
gagcaactcg gtcgccgcat acactattct cagaatgact tggttgagta ctcaccagtc  6420
acagaaaagc atcttacgga tggcatgaca gtaagagaat tatgcagtgc tgccataacc  6480
atgagtgata acactgcggc caacttactt ctgacaacga tcggaggacc gaaggagcta  6540
accgcttttt tgcacaacat gggggatcat gtaactcgcc ttgatcgttg ggaaccggag  6600
ctgaatgaag ccataccaaa cgacgagcgt gacaccacga tgcctgtagc aatggcaaca  6660
acgttgcgca aactattaac tggcgaacta cttactctag cttcccggca acaattaata  6720
gactggatgg aggcggataa agttgcagga ccacttctgc gctcggccct tccggctggc  6780
tggtttattg ctgataaatc tggagccggt gagcgtgggt ctcgcggtat cattgcagca  6840
ctggggccag atggtaagcc ctcccgtatc gtagttatct acacgacggg gagtcaggca  6900
actatggatg aacgaaatag acagatcgct gagataggtg cctcactgat taagcattgg  6960
taactgtcag accaagttta ctcatatata ctttagattg atttaaaact tcattttaa  7020
tttaaaagga tctaggtgaa gatcctttt gataatctca tgaccaaaat cccttaacgt  7080
gagttttcgt tccactgagc gtcagacccc gtagaaaaga tcaaaggatc ttcttgagat  7140
ccttttttc tgcgcgtaat ctgctgcttg caaacaaaaa aaccaccgct accagcggtg  7200
gtttgtttgc cggatcaaga gctaccaact cttttccga aggtaactgg cttcagcaga  7260
gcgcagatac caaatactgt ccttctagtg tagccgtagt taggccacca cttcaagaac  7320
tctgtagcac cgcctacata cctcgctctg ctaatcctgt taccagtggc tgctgccagt  7380
ggcgataagt cgtgtcttac cgggttggac tcaagacgat agttaccgga taaggcgcag  7440
cggtcgggct gaacggggggg ttcgtgcaca gcccagct tggagcgaac gacctacacc  7500
gaactgagat acctacagcg tgagctatga gaaagcgcca cgcttcccga agggagaaag  7560
gcggacaggt atccggtaag cggcagggtc ggaacaggag agcgcacgag ggagcttcca  7620
gggggaaacg cctggtatct ttatagtcct gtcgggttc gccacctctg acttgagcgt  7680
cgatttttgt gatgctcgtc aggggggcgg agcctatgga aaaacgccag caacgcggcc  7740
tttttacggt tcctggcctt tgctggcct tttgctcaca tgttctttcc tgcgttatcc  7800
cctgattctg tggataaccg tattaccgcc tttgagtgag ctgataccgc tcgccgcagc  7860
cgaacgaccg agcgcagcga gtcagtgagc gaggaagcgg aagagcgccc aatacgcaaa  7920
ccgcctctcc ccgcgcgttg gccgattcat taatg                            7955
```

SEQ ID NO: 14        moltype = DNA   length = 8222
FEATURE              Location/Qualifiers
source               1..8222
                      mol_type = other DNA
                      organism = Synthetic construct
SEQUENCE: 14

```
cagctgcgcg ctcgctcgct cactgaggcc gcccgggcaa agcccggcg tcgggcgacc   60
tttggtcgcc cggcctcagt gagcgagcga gcgcgcagag agggagtggc caactccatc  120
actaggggtt cctacgcgta gatctggtgt atacatacat acctgaatat ggaatcaaat  180
attttttctaa gatgaaacag tcatgattta tttcaaatag gtacggataa gtagatattg  240
aggtaagcat taggtcttat attatgtaac actaatctat tactgcgctg aaactgtggc  300
tttatagaaa ttgttttcac tgcactattg agaaattaag agataatgac aaaagtcaca  360
aagagtatat tcaaaagaa gtatagcact ttttccttag aaaccactgc taactgaaag  420
agactaagat ttgtcccgtc aaaaatcctg gacctatgcc taaaacacat tcacaatcc   480
ctgaactttt caaaaattgg tacatgcttt agctttaaac tacaggcctc actgagcta   540
gagacaagaa ggtaaaaaac ggctgacaaa agaagtcctg gtatcctcta tgatgggaga  600
aggaaactag ctaaagggaa gaataaatta gagaaaaact ggaatgactg aatcggaaca  660
aggcaaaggc tataaaaaaa attaagcagc agtatcctct tggggccccc ttccccacac  720
tatctcaatg caaatatctg tctgaaacgg tccctggcta aactccaccc atgggttggc  780
cagccttgcc ttgacgctag cgtaaataca cttgcaaagg aggatgtttt tagtagcaat  840
ttgtactgat ggtatgggc caagagatat atcttagagg gagggctgag ggtttgaagt  900
ccaactccta agccagtgcc agaagagcca aggacagca cggctgtcat cacttagacc  960
tcaccctgtg gagccacacc ctaggggtgg ccaatctact cccaggagca ggagggcag  1020
gagccagggc tgggcataaa agtcagggca gagccatcta ttgcttacat ttgcttctga  1080
cacaactgtg ttcactagca acctcaaaca gacaccatgg tgcacctgac tcctgaggag  1140
aagtctgccg ttactgccct gtggggcaag gtgaacgtgg atgaagttgg tggtgaggcc  1200
ctgggcaggt tggtatcaag gttacaagac aggtttaagg agaccaatag aaactgggca  1260
```

```
tgtggagaca gagaagactc ttgggttct gataggcact gactctctct gcctattggt   1320
ctattttccc acccttaggc tgctggtggt ctaccctttgg acccagaggt tctttgagtc   1380
ctttggggat ctgtccactc ctgatgctgt tatgggcaac cctaaggtga aggctcatgg   1440
caagaaagtg ctcggtgcct ttagtgatgg cctggctcac ctggacaacc tcaagggcac   1500
ctttgcccag ctgagtgagc tgcactgtga caagctgcag gtggatcctg agaacttcag   1560
ggtgagtcta tgggacccct gatgttttct ttcccttct tttctatggt taagttcatg   1620
tcataggaag gggagaagta acagggtaca catattgacc aaatcagggt aattttgcat   1680
ttgtaatttt aaaaaatgct ttcttcttt aatatactt tttgtttatc ttatttctaa   1740
tactttccct aatctcttt tttcagggca ataatgatac aatgtatcat gcctctttgt   1800
accattctaa agaataacag tgataatttc tgggttaagg caatagcaat atttctgcat   1860
ataaatattt ctgcatataa attgtaactg atgtaagagg tttcatattg ctaatagcag   1920
ctacaatcca gctaccattc tgctttatt ttatggttgg gataaggctg gattattctg   1980
agtccaagct aggcccttt gctaatcatg ttcatacctc ttatcttcct cccacagctc   2040
ctgggcaacg tgctggtctg tgtgctggcc catcactttg gcaaagaatt caccccacca   2100
gtgcaggctg cctatcagaa agtggtggct ggtgtggcta atgccctggc ccacaagtat   2160
cactaagctc gctttcttgc tgtccaattt ctattaaagg ttcctttgtt ccctaagtcc   2220
aactactaaa ctgggggata ttatgaaggg ccttgagcat ctggattctg cctaataaaa   2280
aacattttatt ttcattgcaa tgatgtattt aaattattc tgaatatttt actaaaaagg   2340
gaatgtggga ggttgcagtg ctagtctccc ggaactatca ctctttcaca gtctgctttg   2400
gaaggactgg gcttagtatg aaagttagg actgagaaga atttgaaagg gggctttttg   2460
tagcttgata ttcactactg tcttattacc ctatcatagg cccacccccaa atggaagtcc   2520
cattcttcct caggatgttt aagattagca ttcaggaaga gatcagaggt ctgctggctc   2580
ccttatcatg tcccttatgg tgcttctggc tctgcaccgc gggaacagag aaacaggaga   2640
atatgggcca aacaggatat ctgtggtaag cagttcctgc cccggctcag ggccaagaac   2700
agttggaaca gcagaaatatg ggccaaacag gatatctgtg gtaagcagtt cctgccccgg   2760
ctcagggcca agaacagatg ccccccagat gcggtcccgc cctcagcagt ttctagagaa   2820
ccatcagatg ttccagggt gccccaagga cctgaaatga ccctgtgcct tatttgaact   2880
aaccaatcag ttcgcttctc gcttctgttc gcgcgcttct gctccccgag ctctatataa   2940
gcagagctcg tttagtgaac cgtcagatcg cggccgcgcc gccaccatgg tgagcaaggg   3000
cgaggagctg ttcaccgggg tggtgcccat cctggtcgag ctggacggcg acgtaaacgg   3060
ccacaagttc agcgtgtccg gcgagggcga gggcgatgcc acctacggca agctgaccct   3120
gaagttcatc tgcaccaccg gcaagctgcc cgtgccctgg cccaccctcg tgaccaccct   3180
gacctacggc gtgcagtgct tcagccgcta ccccgaccac atgaagcagc acgacttctt   3240
caagtccgcc atgcccgaag gctacgtcca ggagcgcacc atcttcttca aggacgacgg   3300
caactacaag acccgcgccg aggtgaagtt cgagggcgac accctggtga accgcatcga   3360
gctgaagggc atcgacttca aggaggacgg caacatcctg gggcacaagc tggagtacaa   3420
ctacaacagc cacaacgtct atatcatggc cgacaagcag aagaacggca tcaaggtgaa   3480
cttcaagatc cgccacaaca tcgaggacgg cagcgtgcag ctcgccgacc actaccagca   3540
gaacacccc atcggcgacg gccccgtgct gctgcccgac aaccactact gagcaccca   3600
gtccccctg agcaaagacc caacgagaa gcgcgatcac atggtcctgc tggagttcgt   3660
gaccgccgcc gggatcactc tcggcatgga cgagctgtac aagtaagctt tatttgtgaa   3720
atttgtgatg ctattgcttt atttgtaacc attataagct gcaataaaca agttaacaac   3780
aacaattgca ttcattttat gtttcaggtt cagggggagg tgtgggaggt tttttaaagc   3840
cctgcaggca atagccttga caaggcaaac ttgaccaata gtcttagagt atccagtgag   3900
gccaggggcc ggcggctggc tagggatgaa gaataaaagg aagcacctt cagcagttcc   3960
acacactcgc ttctggaacg tctgaggtta tcaataagct cctagtccag acgccatggg   4020
tcatttcaca gaggaggaca aggctactat cacaagcctg tggccaagg tgaatgtgaa   4080
agatgctgga ggagaaaccc tgggaaggta ggctctggtg accaggacaa gggagggaag   4140
gaaggacccct gtgcctggca aaagtccagg tcgcttctca ggatttgtgg cacctttctga   4200
ctgtcaaact gttcttgtca atctcacagg ctcctggtta tctacccatg gacccagagg   4260
ttctttgaca gcttttggcaa cctgtcctct gcctctgcca tcatgggcaa ccccaaagtc   4320
aaggcacatg gcaagaaggt gctgacttcc ttgggagatg ccacaaagca cctggatgat   4380
ctcaagggca ccttgcccca gctgagtgaa ctgcactgtg acaagctgca tgtggatcct   4440
gagaacttca aggtgagtcc aggagatgtt tcagccctgt tgcctttagt ctcgaggcgt   4500
cgacaggaac ccctagtgat ggagttggcc actccctcg tgcgcgctcg ctcgctcact   4560
gaggccgggc gaccaaaggt cgcccgacgc ccgggctttg cccgggcggc ctcagtgagc   4620
gagcgagcgc gcagctggcg taatagcgaa gaggcccgca ccgatcgccc ttcccaacag   4680
ttgcgcagcc tgaatggcga atggcgattc cgttgcaatg gctggcggta atattgttct   4740
ggatattacc agcaaggccg atagttgag ttcttctact caggcaagtg atgttattac   4800
taatcaaaga agtattgcga caacggttaa tttgcgtgat ggacagactc ttttactcgg   4860
tggcctcact gattataaaa acacttctca ggattctggc gtaccgttcc tgtctaaaat   4920
ccctttaatc ggcctcctgt ttagctcccg ctctgattct aacgaggaaa gcacgttata   4980
cgtgctcgtc aaagcaacca tagtacgcgc cctgtagcgg cgcattaagc gcggcgggtg   5040
tggtggttac gcgcagcgtg accgctacac ttgccagcgc cctagcgccc gctcgtttcg   5100
ctttcttccc ttcctttctc gccacgttcg ccggctttcc ccgtcaagct ctaaatcggg   5160
ggctccctt agggttccga tttagtgctt tacggcacct cgaccccaaa aaacttgatt   5220
agggtgatgg ttcacgtagt gggccatcgc cctgatagac ggttttttcgc cctttgacgt   5280
tggagtccac gttctttaat agtggactct tgttccaaac tggaacaaca ctcaaccta   5340
tctcggtcta ttcttttgat ttataaggga ttttgccgat ttcggcctat tggttaaaaa   5400
atgagctgat ttaacaaaaa tttaacgcga atttaacaa atattaacg tttacaattt   5460
aaatatttgc ttatacaatc ttcctgttt tggggctttt ctgattatca accggggtac   5520
atatgattga catgctagtt ttacgattac cgttcatcga ttctcttgtt tgctccagac   5580
tctcaggcaa tgacctgata gcctttgtag agacctctca aaaatagcta ccctctccgg   5640
catgaattta tcagctagaa cggttgaata tcatattgat ggtgatttga ctgtctccgg   5700
cctttctcac ccgtttgaat ctttacctac acattactga ggcattgcat taaaatata   5760
tgagggttct aaaaattttt atccttgcgt tgaaataaag gcttctcccg caaaagtatt   5820
acagggtcat aatgtttttg gtacaaccga tttagcttta tgctctgagg ctttattgct   5880
taattttgct aattctttgc cttgcctgta tgatttattg gatgttggaa tcgcctgatg   5940
cggtatttttc tccttacgca tctgtgcggt atttcacacc gcatatggtg cactctcagt   6000
```

```
acaatctgct ctgatgccgc atagttaagc cagccccgac acccgccaac acccgctgac 6060
gcgccctgac gggcttgtct gctcccggca tccgcttaca gacaagctgt gaccgtctcc 6120
gggagctgca tgtgtcagag gttttcaccg tcatcaccga aacgcgcgag acgaaagggc 6180
ctcgtgatac gcctattttt ataggttaat gtcatgataa taatggtttc ttagacgtca 6240
ggtggcactt ttcggggaaa tgtgcgcgga accccctattt gtttattttt ctaaatacat 6300
tcaaatatgt atccgctcat gagacaataa ccctgataaa tgcttcaata atattgaaaa 6360
aggaagagta tgagtattca acatttccgt gtcgcccta ttcccttttt tgcggcattt 6420
tgccttcctg ttttgctca cccagaaacg ctggtgaaag taaaagatgc tgaagatcag 6480
ttgggtgcac gagtgggtta catcgaactg gatctcaaca gcggtaagat ccttgagagt 6540
tttcgccccg aagaacgttt tccaatgatg agcacttttta aagttctgct atgtggcgcg 6600
gtattatccc gtattgacgc cgggcaagag caactcggtc gccgcataca ctattctcag 6660
aatgacttgg ttgagtactc accagtcaca gaaaagcatc ttacgatgg catgacagta 6720
agagaattat gcagtgctgc cataaccatg agtgataaca ctgcggccaa cttacttctg 6780
acaacgatcg gaggaccgaa ggagctaacc gcttttttta caacaatgga ggatcatga 6840
actcgccttg atcgttggga accggagctg aatgaagcca taccaaacga cgagcgtgac 6900
accacgatgc ctgtagcaat ggcaacaacg ttgcgcaaac tattaactgg cgaactactt 6960
actctagctt cccggcaaca attaatagac tggatgagg cggataaagt tgcaggacca 7020
cttctgcgct cggcccttcc ggctggctgg tttattgctg ataaatctgg agccggtgag 7080
cgtgggtctc gcggtatcat tgcagcactg gggccagatg gtaagccctc ccgtatcgta 7140
gttatctaca cgacgggag tcaggcaact atggatgaac gaaatagaca gatcgctgag 7200
ataggtgcct cactgattaa gcattggtaa ctgtcagacc aagtttactc atatatactt 7260
tagattgatt taaaacttca ttttaattt aaaaggatct aggtgaagat cctttttgat 7320
aatctcatga ccaaaatccc ttaacgtgag ttttcgttcc actgagcgtc agaccccgta 7380
gaaaagatca aaggatcttc ttgagatcct ttttttctgc gcgtaatctg ctgcttgcaa 7440
acaaaaaaac caccgctacc agcggtggtt tgtttgccgg atcaagagct accaactctt 7500
tttccgaagg taactggctt cagcagagcg cagataccaa atactgtcct tctagtgtag 7560
ccgtagttag gccaccactt caagaactct gtagcaccgc ctacatacct cgctctgcta 7620
atcctgttac cagtggctgc tgccagtggc gataagtcgt gtcttaccgg gttggactca 7680
agacgatagt taccggataa ggcgcagcgg tcgggctgaa cggggggttc gtgcacacag 7740
cccagcttgg agcgaacgac ctacaccgaa ctgagatacc tacagcgtga gctatgagaa 7800
agcgccacgc ttcccgaagg gagaaaggcg gacaggtatc cggtaagcgg cagggtcgga 7860
acaggagagc gcacgaggga gcttccaggg gaaacgcct ggtatcttta tagtcctgtc 7920
gggtttcgcc acctctgact tgagcgtcga ttttgtgat gctcgtcagg ggggcggagc 7980
ctatggaaaa acgccagcaa cgcggccttt ttacggttcc tggccttttg ctggccttt 8040
gctcacatgt tctttcctgc gttatcccct gattctgtgg ataaccgtat taccgccttt 8100
gagtgagctg ataccgctcg ccgcagccga acgaccgagc gcagcgagtc agtgagcgag 8160
gaagcggaag agcgcccaat acgcaaaccg cctctccccg cgcgttggcc gattcattaa 8220
tg                                                                 8222
```

SEQ ID NO: 15          moltype = DNA   length = 8214
FEATURE                Location/Qualifiers
source                 1..8214
                       mol_type = other DNA
                       organism = Synthetic construct SEQUENCE: 15
```
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgc ctacatacat acctgaataa gaaaaaaaaa 180
tacctttgct gagatgaaac acacatgatt tatttcaaat aggtacagag aagtagatac 240
tgaagtaagg attaagtatt atattatatt acataacatt aatctattcc tgcactgaaa 300
ccgttgcttt atatgatttt tttttcact acactaatga gaacttaaga gataatgacc 360
taaaaccaca gagagtattt tcaaagataa gtatagcaca atgcttacta atgagacta 420
agacttgtcc catcgaaaat cctgaccta tgcctaaaac acgtgtcaca atcccccgaac 480
tttttcaaaaa ttggtacatg ctttaacttt aatctccagg cctcactgga gctagagaca 540
agaaggtaaa aaaaggctga caaaagaagt cctggtatct tctatggtgg gagaaggaaa 600
ctagctaaag gaagaataa attagagaaa aattggaatg attgaatcgg aacaaggcaa 660
aggctataaa aaaattaagc agcagtatcc tcttgggggc ccttccca cactatctca 720
atgcaaatat ctgtctgaaa cggtccctgg ctaaactcca cccatgggtt ggccagtctt 780
gccttgacgc tagcgtaaat acacttgcaa aggaggatgt ttttagtagc aatttgtact 840
gatggtatgg ggccaagaga tatatcttag agggagggct gagggtttga agtccaactc 900
ctaagccagt gccagaagag ccaaggacag gtacggctgt catcacttag acctcaccct 960
gtggagccac accctagggt tggccaatct actcccagga gcaggaggg caggagccag 1020
ggctgggcat aaaagtcagg gcagagccat ctattgctta catttgcttc tgacacaact 1080
gtgttcacta gcaacctcaa acagacacca tggtgcacct gactcctgag gagaagtctg 1140
ccgttactgc cctgtgggc aaggtgaacg tggatgaagt tggtggtgag gccctgggca 1200
ggttggtatc aaggttacaa gacaggttta aggagaccaa tagaaactgg gcatgtggag 1260
acagagaaga ctcttgggtt tctgataggc actgactctc tctgcctatt ggtctatttt 1320
cccacccta ggctgctggt ggtctaccct tgggcccaga ggttcttga gtcctttggg 1380
gatctgtcca ctcctgatgc tgttatgggc aaccctaagg tgaaggctca tggcaagaaa 1440
gtgctcggtg ccttagtga tggcctggct caccttggaca acctcaaggg cacctttgcc 1500
cagctgagtg agctgcactg tgacaagctg cacgtggatc ctgagaactt cagggtgagt 1560
ctatgggacc cttgatgttt tctttcccct tcttttctat ggttaagttc atgtcatagg 1620
aaggggagaa gtaacagggt acacatattg accaaatcag ggtaatttg catttgtaat 1680
tttaaaaat gcttcttct tttaatatac tttttagttc atcttatttc taatacttc 1740
cctaatctct ttcttccagg gcaataatga tacaatgtat catgcctctt tgcaccattc 1800
taaagaataa cagtgataat ttctgggtta aggcaatagc aatatttctg catataaata 1860
tttctgcata taaattgtaa ctgatgtaag aggtttcata ttgctaatag cagctacaat 1920
ccagctacca ttctgctttt attttatggt tgggataagg ctggattatt ctgagtccaa 1980
gctaggccct tttgctaatc atgttcatac ctcttatctt cctcccacag ctcctgggca 2040
```

```
acgtgctggt ctgtgtgctg gcccatcact ttggcaaaga attcaccaca ccagtgcagg   2100
ctgcctatca gaaagtggtg gctggtgtgg ctaatgccct ggcccacaag tatcactaag   2160
ctcgcttcct tgctgtccaa tttctattaa aggttccttt gttccctaag tccaactact   2220
aaactggggg atattatgaa gggccttgag catctggatt ctgcctaata aaaacatttt   2280
attttcattg caatgatgta tttaaattat ttctgaatat tttactaaaa agggaatgtg   2340
ggaggttgca gtgctagtct cccggaacta tcactctttc acagtctgct ttggaaggac   2400
tgggcttagt atgaaaagtt aggactgaga agaatttgaa aggggctttt tgtagcttg   2460
atattcacta ctgtcttatt accctatcat aggcccaccc caaatggaag tcccattctt   2520
cctcaggatg tttaagatta gcattcagga agagatcaga ggtctgctgg ctcccttatc   2580
atgtcccctta tggtgcttct ggctctgcac cgcgggaaca gagaaacagg agaatatggt   2640
ccaaacagga tatctgtggt aagcagttcc tgccccggct cagggccaag aacagttgga   2700
acagcagaat atgggccaaa caggatatct gtggtaagca gttcctgccc cggctcaggg   2760
ccaagaacag atggtcccca gatgcggtcc cgccctcagc agtttctaga aaccatcag   2820
atgtttccag ggtgccccaa ggacctgaaa tgaccctgtg cctatttga actaaccaat   2880
cagttcgctt ctcgcttctg ttcgcgcgct tctgctcccc gagctctata taagcagagc   2940
tcgtttagtg aaccgtcaga tcgcggccgc gccgccacca tggtgagcaa gggcgaggag   3000
ctgttcaccg ggtggtgcc catcctggtc gagctggacg gcgacgtaaa cggccacaag   3060
ttcagcgtgt ccggcgaggg cgagggcgat gccacctacg gcaagctgac cctgaagttc   3120
atctgcacca ccggcaagct gcccgtgccc tggcccaccc tcgtgaccac cctgacctac   3180
ggcgtgcagt gcttcagccg ctaccccgac cacatgaagc agcacgactt cttcaagtcc   3240
gccatgcccg aaggctacgt ccaggagcgc accatcttct tcaaggacga cggcaactac   3300
aagacccgcg ccgaggtgaa gttcgagggc gacacccgg tgaaccgcat cgagctgaag   3360
ggcatcgact tcaaggagga cggcaacatc ctggggcaca agctggagta caactacaac   3420
agccacaacg tctatatcat ggccgacaag cagaagaacg gcatcaaggt gaacttcaag   3480
atccgccaca acatcgagga cggcagcgtg cagctcgccg accactacca gcagaacacc   3540
cccatcggcg acggccccgt gctgctgccc gacaaccact acctgagcac ccagtccgcc   3600
ctgagcaaag accccaacga aagcgcgat cacatggtcc tgctggagtt cgtgaccgcc   3660
gccgggatca ctctcggcat ggacgagctg tacaagtaag ctttatttgt gaaatttgtg   3720
atgctattgc tttatttgta accattataa gctgcaataa acaagttaac aacaacaatt   3780
gcattcattt tatgttcag gttcaggggg agatgtggga ggttttttaa agccctgcag   3840
gcaatagcct tgacaaggca accttgacca atagtcttag agtatcaggt gaggccaggg   3900
gccggcggct ggctagggat gaagaataaa aggaagcacc ctccagcagt tccacacact   3960
cgcttctgga acggctgaga ttatcaataa gctcctagtc cagacgccat gggtcatttc   4020
acagaggagg acaaggctac tatcacaagc ctgtgggca aggtgaatgt ggaagatgct   4080
ggaggagaaa ccctgggaag gtaggcctg gtgaccagga caaggaaggg aaggaaggac   4140
cctgtgcctg gcaaaagtcc aggccacttc tcaggatttg tggcactttc tgactgtcaa   4200
actgctcttg ttcaatctca caggctcctg gttgtctacc catggaccca gaggttcttt   4260
gacagctttg gcaacctgtc ctctgcctct gccatcatgg gcaaccccaa ggtcaaggca   4320
cacggcaaga aggtgctgac ttccttggga gatgccataa aagaacctgg tgatctcaaa   4380
ggcacctttg cccagctgag tgagctgcac tgtgacaagc tgcatgtgga tcctgagaac   4440
ttcagggtga gtccaggagt ttcagcagtt tcagagttca gtctcaaggc gtcgacagga   4500
accccctagtg atggagttgg ccactccctc tctgcgcgct cgctcgctca ctgaggccgg   4560
gcgaccaaag gtcgcccgac gcccgggctt gcccgggcg gcctcagtga gcgagcgagc   4620
gcgcagctgg cgtaatagcg aagaggcccg caccgatcgc ccttcccaac agttgcgcag   4680
cctgaatggc gaatgcgat tccgttgcaa tggctggcgg taatattgtt ctggatatta   4740
ccagcaaggc cgatagtttg agttcttcta ctcaggcaag tgatgttatt actaatcaaa   4800
gaagtattgc gacaacggtt aatttgcgtg atggacaagc tcttttactc ggtggcctca   4860
ctgattataa aaacacttct caggattctg gcgtaccgtt cctgtctaaa atccctttaa   4920
tcggcctcct gtttagctcc cgctctgatt ctaacgagga aagcacgtta tacgtgctcg   4980
tcaaagcaac catagtacgc gccctgtagc ggcgcattaa gcgcggcggg tgtggtggt   5040
acgcgcagcg tgaccgctac acttgccagc gccctagcgc ccgctccttt cgctttcttc   5100
ccttcctttc tcgccacgtt cgccggcttt cccgtcaag ctctaaatcg ggggctccct   5160
ttagggttcc gatttagtgc tttacggcac ctcgaccccca aaaaacttga ttagggtgat   5220
ggttcacgta gtgggccatc gccctgatag acggtttttc gccctttgac gttggagtcc   5280
acgttcttta atagtggact cttgttccaa actggaacaa cactcaaccc tatctcggtc   5340
tattctttg atttataagg gattttgccg atttcggcct attggttaaa aatgactgc   5400
atttaacaaa aatttaacgc gaattttaac aaaatattaa cgtttacaat ttaaatattt   5460
gcttatacaa tcttcctgtt tttgggcttt tctgattat caaccggggt acatatgatt   5520
gacatgctag ttttacgatt accgttcatc gattctcttg tttgctccag actctcaggc   5580
aatgacctga tagcctttgt agagaccctct caaaaatagc taccctctcc ggcatgaatt   5640
tatcagctag aacggttgaa tatcatattg atggtgattt gactgtctcc ggcctttctc   5700
acccgtttga atctttacct acacattact caggcattgc atttaaaata tatgagggtt   5760
ctaaaaattt ttatccttgc gttgaaataa aggcttctcc cgcaaagta ttacagggtc   5820
ataatgtttt tggtacaacc gatttagctt tatgctctga ggcttttattg cttaattttg   5880
ctaattcttt gccttgcctg tatgatttat tggatgttgg aatcgcctga tgcggtattt   5940
tctccttacg catctgtgcg gtatttcaca ccgcatatgg tgcactctca gtacaatctg   6000
ctctgatgcc gcatagttaa gccagccccg acacccgcca cacccgctg acgcgccctg   6060
acgggcttgt ctgctcccgg catccgctta cagacaagct gtgaccgtct ccgggagctg   6120
catgtgtcag aggttttcac cgtcatcacc gaaacgcgcg agaacgaagg gcctcgtgat   6180
acgcctattt ttataggtta atgtcatgat aataatggtt tcttagacgt caggtggcac   6240
ttttcgggga aatgtgcgcg gaaccctat ttgtttattt tctaaatac attcaaatat   6300
gtatccgctc atgagacaat aaccctgata aatgcttcaa taatattgaa aaaggaagag   6360
tatgagtatt caacatttcc gtgtcgccct tattccctt tttgcggcat tttgccttcc   6420
tgtttttgct cacccagaaa cgctggtgaa agtaaaagat gctgaagatc agttgggtgc   6480
acgagtgggt tacatcgaac tggatctcaa cagcggtaag atccttgaga gttttcgccc   6540
cgaagaacgt tttccaatga tgagcacttt taaagttctg ctatgtggcg cggtattatc   6600
ccgtattgac gccgggcaag agcaactcgg tcgccgcata cactattctc agaatgactt   6660
ggttgagtac tcaccagtca cagaaaagca tcttacggat ggcatgacag taagagaatt   6720
atgcagtgct gccataacca tgagtgataa cactgcggcc aacttacttc tgacaacgat   6780
```

```
cggaggaccg aaggagctaa ccgctttttt gcacaacatg ggggatcatg taactcgcct 6840
tgatcgttgg gaaccggagc tgaatgaagc cataccaaac gacgagcgtg acaccacgat 6900
gcctgtagca atggcaacaa cgttgcgcaa actattaact ggcgaactac ttactctagc 6960
ttcccggcaa caattaatag actggatgga ggcggataaa gttgcaggac cacttctgcg 7020
ctcggccctt ccggctggct ggtttattgc tgataaatct ggagccggtg agcgtgggtc 7080
tcgcggtatc attgcagcac tggggccaga tggtaagccc tcccgtatcg tagttatcta 7140
cacgacgggg agtcaggcaa ctatggatga acgaaataga cagatcgctg agataggtgc 7200
ctcactgatt aagcattggt aactgtcaga ccaagtttac tcatatatac tttagattga 7260
tttaaaactt cattttaat ttaaaaggat ctaggtgaag atccttttg ataatctcat 7320
gaccaaaatc ccttaacgtg agttttcgtt ccactgagcg tcagacccg tagaaaagat 7380
caaaggatct tcttgagatc cttttttct gcgcgtaatc tgctgcttgc aaacaaaaaa 7440
accaccgcta ccagcggtgg tttgtttgcc ggatcaagag ctaccaactc ttttccgaa 7500
ggtaactggc ttcagcagag cgcagatacc aaatactgtc cttctagtgt agccgtagtt 7560
aggccaccac ttcaagaact ctgtagcacc gcctacatac ctcgctctgc taatcctgtt 7620
accagtggct gctgccagtg gcgataagtc gtgtcttacc gggttggact caagacgata 7680
gttaccggat aaggcgcagc ggtcgggctg aacggggggt tcgtgcacac agcccagctt 7740
ggagcgaacg acctacaccg aactgagata cctacagcgt gagctatgag aaagcgccac 7800
gcttcccgaa gggagaaagg cggacaggta tccggtaagc ggcagggtcg gaacaggaga 7860
gcgcacgagg gagcttccag ggggaaacgc ctggtatctt tatagtcctg tcgggtttcg 7920
ccacctctga cttgagcgtc gatttttgtg atgctcgtca gggggcgga gcctatggaa 7980
aaacgccagc aacgcggcct ttttacggtt cctggccttt tgctggcctt ttgctcacat 8040
gttctttcct gcgttatccc ctgattctgt ggataaccgt attaccgcct ttgagtgagc 8100
tgataccgct cgccgcagcc gaacgaccga gcgcagcgag tcagtgagcg aggaagcgga 8160
agagcgccca atacgcaaac cgcctctccc gcgcgttgg ccgattcatt aatg 8214

SEQ ID NO: 16         moltype = DNA  length = 7712
FEATURE               Location/Qualifiers
source                1..7712
                      mol_type = other DNA
                      organism = Synthetic construct
SEQUENCE: 16
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actagggtt ccttgtagtt aatgattaac ccgccatgct acttatctac acgcgtagat 180
ctagtgcatc aacttcttat ttgtgtaata agaaaattgg gaaaacgatc ttcaatatgc 240
ttaccaagct gtgattccaa atattacgta aatacacttg caaaggagga tgttttttagt 300
agcaatttgt actgatggta tggggccaag agatatatct tagagggagg ctgagggtt 360
tgaagtccaa ctcctaagcc agtgccgaaa gagccaagga caggtacggc tgtcatcact 420
tagacctcac cctgtggagc cacaccctag ggttggccaa tctactccca ggagcaggga 480
gggcaggagc cagggctggg cataaaagtc agggcagagc catctattgc ttacatttgc 540
ttctgacaca actgtgttca ctagcaacct caaacagaca ccaggtgagt taaacccatg 600
agagagaata acagaactgc gagtgatggg ccagttaagc gtagatggct aattagttca 660
gacaaatgta aaatgccaac accgtctgta aagaaaccta actgatcctc ttccttttgca 720
ctgtcttctt cacaggccgc caccatggtc catcttacac cggaggagaa gtccgctgta 780
acggcactgt gggggaaagt taatgtcgat gaagtcggcg gtgaagcact cggcaggttg 840
ctggtagtgt accccgtggac acaacgattc tttgaaagtt tcggggacct gtccacaccc 900
gatgctgtga tgggtaatcc aaaagtaaaa gcacacggca agaaagtcct cggcgcgttt 960
agtgatggtc tggcccattt ggataacttg aagggtacat tcgcgcagct ttccgaactc 1020
cactgtgaca agttgcacgt agatccagaa aactccggc ttctgggcaa tgtgcttgta 1080
tgcgttctgc tcaccattt tgggaaggag tttaccccac ccgtgcaagc ggcttaccaa 1140
aaagtggtcg caggagtggc taatgcccct gcacataaat atcactaagg taccgataat 1200
caacctctgg attacaaaat ttgtgaaaga ttgactggta ttcttaacta tgttgctcct 1260
tttacgctat gtggatacgc tgctttaatg cctttgtatc atgctattgc ttcccgtatg 1320
gctttcattt tctcctcctt gtataaatcc tggttagttc ttgccacggc ggaactcatc 1380
gccgcctgcc ttgccctgc ctggacaggg gctcggctgt tgggcactga caattccgtg 1440
gtgtttattt gtgaaatttg tgatgctatt gctttatttg taaccattat aagctgcaat 1500
gtgaaatttg tgatgctatt gctttatttg taaccattat aagctgcaat aaacaagtta 1560
acaacaacaa ttgcattcat tttatgtttc aggttcaggg ggagatgtgg gaggtttttt 1620
aaagcttaat taacgagatc gagaccatcc tggctaacac agtgaaaccc cgtctctact 1680
aaaaaaatac aaaaaattag ccgggcttgg tggcgggtgc ctgtagtccc agctactatg 1740
gaggctgagg cgggagaatg gcgtgaacgc gggggcggga gcttgcagtg agcagagatc 1800
aggggccact gcactccagc ctgggcgaca gagagagact ctgtctcaaa aaaagaaaa 1860
aaaaaattta gtagactagc taaaaaaatc cagagatagt tattgatgca tatgtaaaag 1920
tcttccaata tttacaagta caatgaaaaa aaataaccct taaagt gtagaactca 1980
ttgacaatgt ttcaaaggat gtgagggata aactaaaatt tggcagtac atgctgttcc 2040
tgtgtacttg gaacagaggg agaaaatctg gctggaaaat attgttatag gagttagcac 2100
atgaaggtga caactaaatt atttggagta gatgagtca ccagcacatg tgaatagttt 2160
tagaatgaaa tgacccaaga tagaactttg gagagccccc aaatttaaat aaaatcagta 2220
taagagaaga ggaagaaacc tagtgtata ctagtctaaa ttgtttctta gtgacaaaag 2280
aataaccctga atattagatt agctgcctat atgctctctg aatcaatttc attcaacatg 2340
caacagtccg cggggaacaga gaaacaggag aatatgggcc aaacaggata tctgtggtaa 2400
gcagttcctg ccccggctca gggccaagaa cagttggaac agcagaatat gggccaaaca 2460
ggatatctgt ggtaagcagt tcctgccccg gctcagggcc aagaacagat ggtccccaga 2520
tgcggtcccg ccctcagcag tttctagaga accatcaggt gtttccaggg tgccccaagg 2580
acctgaaatg accctgtgcc ttatttgaac taaccaatca gttcgcttct cgcttctgtt 2640
cgcgcgcttc tgctccccga gctctatata gcagagctc gtttagtgaa ccgtcagatc 2700
gcctggagac gccatccacg ctgttttgac ttccatagaa ggcggccgcg ccgccaccat 2760
ggtgagcaag ggcgaggagc tgttcaccgg ggtggtgccc atcctggtcg agctggacgg 2820
cgacgtaaac ggccacaagt tcagcgtgtc cggcgagggc gagggcgatg ccacctacgg 2880
```

```
caagctgacc ctgaagttca tctgcaccac cggcaagctg cccgtgccct ggcccaccct   2940
cgtgaccacc ctgacctacg gcgtgcagtg cttcagccgc taccccgacc acatgaagca   3000
gcacgacttc ttcaagtccg ccatgcccga aggctacgtc caggagcgca ccatcttctt   3060
caaggacgac ggcaactaca agacccgcgc cgaggtgaag ttcgagggcg acaccctggt   3120
gaaccgcatc gagctgaagg gcatcgactt caaggaggac ggcaacatcc tggggcacaa   3180
gctggagtac aactacaaca gccacaacgt ctatatcatg gccgacaagc agaagaacgg   3240
catcaaggtg aacttcaaga tccgccacaa catcgaggac ggcagcgtgc agctcgccga   3300
ccactaccag cagaacaccc ccatcggcga cggccccgtg ctgctgcccg acaaccacta   3360
cctgagcacc cagtccgccc tgagcaaaga ccccaacgag aagcgcgatc acatggtcct   3420
gctggagttc gtgaccgccg ccgggatcac tctcggcatg gacgagctgt acaagggaag   3480
cggagctact aacttcagcc tgctgaagca ggctggagac gtggaggaga accctggacc   3540
tacctgcagg cctgagaact tcagggtgag tctatgggac gcttgatgtt ttctttcccc   3600
ttcttttcta tggttaagtt catgtcatag gaaggggata agtaacaggg tacagtttag   3660
aatgggaaac agacgaatga ttgcatcagt gtggaagtct caggatcgtt ttagtttctt   3720
ttatttgctg ttcataacaa ttgtttcttt tgtttaatt cttgcttct ttttttct   3780
tctccgcaat tttactatt atacttaatg ccttaacatt gtgtataaca aaaggaaata   3840
tctctgagat acattaagta acttaaaaaa aaactttaca cagtctgcct agtacattac   3900
tatttggaat atatgtgtgc ttatttgcat attcataatc tccctacttt gtcgacgtag   3960
ataagtagca tggcgggtta atcattaact acaaggaacc cctagtgatg gagttggcca   4020
ctccctctct gcgcgctcgc tcgctcactg aggccgggcg accaaaggtc gcccgacgcc   4080
cgggctttgc ccgggcggcc tcagtgagcg agcgagcgcg ccagctggcg taatagcgaa   4140
gaggcccgca ccgatcgccc ttcccaacag ttgcgcagca tgaatggcga atggcgattc   4200
cgttgcaatg gctggcggta atattgttct ggatattacc agcaaggccg atagtttgag   4260
ttcttctact caggcaagtg atgttattac taatcaaaga agtattgcga caacggttaa   4320
tttgcgtgat ggacagactc ttttactcgg tggcctcact gattataaaa acacttctca   4380
ggattctggc gtaccgttcc tgtctaaaat ccctttaatg ggcctcctgt ttagctcccg   4440
ctctgattct aacgaggaaa gcacgttata cgtgctcgtc aaagcaacca tagtacgcgc   4500
cctgtagcgg cgcattaagc gcggcgggtg tggtggttac gcgcagcgtg accgctacac   4560
ttgccagcgc cctagcgccc gctcctttcg ctttcttccc ttcctttctc gccacgttcg   4620
ccggctttcc ccgtcaagct ctaaatcggg ggctccctt agggttccga tttagtgctt   4680
tacggcacct cgaccccaaa aaacttgatt agggtgatgg ttcacgtagt gggccatcgc   4740
cctgatagac ggttttttcgc cctttgacgt tggagtccac gttctttaat agtggactct   4800
tgttccaaac tggaacaaca ctcaacccta tctcggtcta ttcttttgat ttataaggga   4860
ttttgccgat ttcggcctat tggttaaaaa atgagctgat ttaacaaaaa tttaacgcga   4920
attttaacaa aatattaacg tttacaattt aaatatttgc ttatacaatc ttcctgtttt   4980
tggggctttt ctgattatca accggggtac atatgattga catgctagtt ttacgattac   5040
cgttcatcga ttctcttgtt tgctccagac tctcaggcaa tgacctgata gcctttgtag   5100
agacctctca aaaatagcta ccctctccgg catgaattta tcagctagaa cggttgaata   5160
tcatattgat ggtgatttga ctgtctccgg cctttctcac ccgtttgaat ctttacctac   5220
acattactca ggcattgcat ttaaaatata tgagggttct aaaaattttt atccttgcgt   5280
tgaaataaag gcttctcccg caaaagtatt acagggtcat aatgtttttg gtacaaccga   5340
tttagcttta tgctctgagg ctttattgct taattttgct aattctttgc cttgcctgta   5400
tgatttattg gatgttggaa tcgcctgatg cggtattttc tccttacgca tctgtgcggt   5460
atttcacacc gcatatggtg cactctcagt acaatctgct ctgatgccgc atagttaagc   5520
cagccccgac acccgccaac acccgctgac gcgccctgac gggcttgtct gctcccggca   5580
tccgcttaca gacaagctgt gaccgtctcc gggagctgca tgtgtcagag gttttcaccg   5640
tcatcaccga aacgcgcgag acgaaagggc ctcgtgatac ccctattttt ataggttaat   5700
gtcatgataa taatggtttc ttagacgtca ggtggcactt ttcggggaaa tgtgcgcgga   5760
acccctattt gtttatttt ctaaatacat tcaaatatgt atccgctcat gagacaataa   5820
ccctgataaa tgcttcaata atattgaaaa aggaagagta tgagtattca catttccgt   5880
gtcgccctta ttcccttttt tgcggcattt tgccttcctg ttttgctca cccagaaacg   5940
ctggtgaaag taaaagatgc tgaagatcag ttgggtgcac gagtgggtta catcgaactg   6000
gatctcaaca gcggtaagat ccttgagagt tttcgccccg aagaacgttt tccaatgatg   6060
agcacttta aagttctgct atgtggcgcg gtattatccc gtattgacgc cgggcaagag   6120
caactcggtc gccgcataca ctattctcag aatgacttgg ttgagtactc accagtcaca   6180
gaaaagcatc ttacggatgg catgacagta agagaattat gcagtgctgc cataaccatg   6240
agtgataaca ctgcggccaa cttacttctg acaacgatcg gaggaccgaa ggagctaacc   6300
gcttttttgc acaacatggg ggatcatgta actcgccttg atcgttggga accggagctg   6360
aatgaagcca taccaaacga cgagcgtgac accacgatgc ctgtagcaat ggcaacaacg   6420
ttgcgcaaac tattaactgg cgaactactt actctagctt cccggcaaca attaatagac   6480
tggatggagg cggataaagt tgcaggacca cttctgcgct cggcccttcc ggctggctgg   6540
tttattgctg ataaatctgg agccggtgag cgtgggtctc gcggtatcat tgcagcactg   6600
gggccagatg gtaagccctc ccgtatcgta gttatctaca cgacggggag tcaggcaact   6660
atggatgaac gaaatagaca gatcgctgag ataggtgcct cactgattaa gcattggtaa   6720
ctgtcagacc aagtttactc atatatactt tagattgatt taaaacttca ttttaatttt   6780
aaaaggatct aggtgaagat ccttttttga atctcatga ccaaaatccc ttaacgtgag   6840
ttttcgttcc actgagcgtc agaccccgta gaaaagatca aggatcttc ttgagatcct   6900
ttttttctgc gcgtaatctg ctgcttgcaa acaaaaaaac caccgctacc agcggtggtt   6960
tgtttgccgg atcaagagct accaactctt tttccgaagg taactggctt cagcagagcg   7020
cagataccaa atactgtcct tctagtgtag ccgtagttag gccaccactt caagaactct   7080
gtagcaccgc ctacatacct cgctctgcta atcctgttac cagtggctgc tgccagtggc   7140
gataagtcgt gtcttaccgg gttggactca agacgatagt taccggataa ggcgcagcgg   7200
tcgggctgaa cggggggttc gtgcacacag cccagcttgg agcgaacgac ctacaccgaa   7260
ctgagatacc tacagcgtga gctatgagaa agcgccacgc ttcccgaagg gagaaaggcg   7320
gacaggtatc cggtaagcgg cagggtcgga acaggagagc gcacgaggga gcttccaggg   7380
ggaaacgcct ggtatcttta tagtcctgtc gggtttcgcc acctctgact tgagcgtcga   7440
tttttgtgat gctcgtcagg ggggcggagc ctatggaaaa acgccagcaa cgcggccttt   7500
ttacggttcc tggccttttg ctggcctttt gctcacatgt tctttcctgc gttatcccct   7560
gattctgtgg ataaccgtat taccgccttt gagtgagctg ataccgctcg ccgcagccga   7620
```

```
acgaccgagc gcagcgagtc agtgagcgag gaagcggaag agcgcccaat acgcaaaccg     7680
cctctccccg cgcgttggcc gattcattaa tg                                   7712

SEQ ID NO: 17           moltype = DNA   length = 8293
FEATURE                 Location/Qualifiers
source                  1..8293
                        mol_type = other DNA
                        organism = Synthetic construct
SEQUENCE: 17
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt cctacgcgta gatctggtgt atacatacat acctgaatat ggaatcaaat    180
atttttctaa gatgaaacag tcatgattta tttcaaatag gtacggataa gtagatattg    240
aggtaagcat taggtcttat attatgtaac actaatctat tactgcgctg aaactgtggc    300
tttatagaaa ttgttttcac tgcactattg agaaattaag agataatggc aaaagtcaca    360
aagagtatat tcaaaaagaa gtatagcact ttttccttag aaaccactgc taactgaaag    420
agactaagat ttgtcccgtc aaaaatcctg gacctatgcc taaaacacat ttcacaatcc    480
ctgaactttt caaaaattgg tacatgcttt agctttaaac tacaggcctc actggagcta    540
gagacaagaa ggtaaaaaac ggctgacaaa agaagtcctg gtatcctcta tgatgggaga    600
aggaaactag ctaaagggaa gaataaaatta gagaaaaact ggaatgactg aatcggaaca    660
aggcaaaggc tataaaaaaa attaagcagc agtatcctct tgggggcccc ttccccacac    720
tatctcaatg caaatatctg tctgaaacgg tccctgactg aactccaccc atgggttggc    780
cagccttgcc ttgacgctag cgtaaataca cttgcaaagg aggatgtttt tagtagcaat    840
ttgtactgat ggtatggggc caagagatat atcttagagg gagggctgag ggtttgaagt    900
ccaactccta agccagtgcc agaagagcca aggacaggta cggctgtcat cacttagacc    960
tcaccctgtg gagccacacc ctaggggttgg ccaatctact cccaggagca gggagggcag   1020
gagccagggc tgggcataaa agtcagggca gagccatcta ttgcttacat ttgcttctga   1080
cacaactgtg ttcactagca acctcaaaca gacaccatgg tgcacctgac tcctgaggag   1140
aagtctgccg ttactgccct gtggggcaag gtgaacgtgg atgaagttgg tggtgaggcc   1200
ctgggcaggt tggtatcaag gttacaagac aggtttaagg agaccaatag aaactgggca   1260
tgtggagaca gagaagactc ttgggttttct gataggcact gactctctct gcctattggt   1320
ctatttttccc acccttaggc tgctggtggt ctacccttgg acccagaggt tctttgagtc   1380
ctttggggat ctgtccactc ctgatgctgt tatgggcaac cctaaggtga aggctcatgg   1440
caagaaagtg ctcggtgcct ttagtgatgg cctggctgac ctcaagggca cctttgccac   1500
actgagtgag tgcactgtga caagctgcac gtggatcctg agaacttcag   1560
ggtgagtcta tgggaccctt gatgttttct ttccccttct tttctatggt taagttcatg   1620
tcataggaag gggagaagta acagggtaca catattgacc aaatcagggt aattttgcat   1680
ttgtaattttt aaaaaatgct ttcttctttt aatatacttt tttgtttatc ttatttctaa   1740
tactttccct aatctctttc tttcagggca ataatgatac aatgtatcat gcctcttttg   1800
accattctaa agaataacag tgataaattttc tgggttaagg caatagcaat atttctgcat   1860
ataaatatttt ctgcatataa attgtaactg atgtaagagg tttcatattg ctaatagcag   1920
ctacaatcca gctaccattc tgcttttatt ttatggttgg gataaggctg gattattctg   1980
agtccaagct aggcccctttt gctaatcatg ttcatacctc ttatcttcct cccacagctc   2040
ctgggcaacg tgctggtctg tgtgctggcc catcactttg gcaaagaatt caccccacca   2100
gtgcaggctg cctatcagaa agtggtggct ggtgtggcta atgccctggc ccacaagtat   2160
cactaagctc gcttcttgc tgtccaattt ctattaaagg ttccttttgtt ccctaagtcc   2220
aactactaaa ctgggggata ttatgaaggg ccttgagcat ctggattctg cctaataaaa   2280
aacatttatt ttcattgcaa tgatgtattt aaattatttc tgaatatttt actaaaaaggg   2340
gaatgtggga ggtcagtg ctagtctccc ggaactatca ctctttcaca gtctgctttg    2400
gaaggactgg gcttagtatg aaaagttagg actgagaaga atttgaaagg gggcttttttg   2460
tagcttgata ttcactactg tcttattacc ctatcatagg cccaccccaa atggaagtcc   2520
cattcttcct caggatgttt aagattagca ttcaggaaga gatcagaggt ctgctggctc   2580
ccttatcatg tcccttatgg tgctctggc tctgcaccgc ggccacgggg ttgggggttgc   2640
gccttttcca aggcagccct gggtttgcgc agggacgcgg ctgctctggg cgtggttccg   2700
ggaacgcag cggcgccgac cctgggtctc gcacattctt cacgtccgtt cgcagcgtca   2760
cccggatctt cgccgctacc cttgtgggcc cccggcgca gcttcctgct ccgcccctaa    2820
gtcgggaagg ttccttgcgg ttcgcggcgt gccggacgtg acaaacgaa gccgcacgtc   2880
tcactagtac cctcgcagac ggacagcgcc agggagcaat gcagcgcgc cgaccgcgat    2940
gggctgtggc caatagcggc tgctcagcgg ggcgcgccga gagcagcggc cggaagggg    3000
cggtgcggga ggcggggtgt gggcggtag tgtgggcct gttcctgccc gcgcggtgtt    3060
ccgcattctg caagcctccg gagcgcacgt cggcagtcgg ctccctcgtt gaccgaatca    3120
ccgacctctc tccccagcgg ccgcgccgcc accatggaca aggattgtga atgaaacgc    3180
accacactgg acagcccttt ggggaagctg gagctgtctg gttgtgagca gggtctgcac    3240
gaaataaagc tcctgggcaa ggggacgtct gcagctgatg ccgtggaggt cccagccgc    3300
gctgcggttc tcgaggtcc ggagcccctg atgcagtgca cagcctggct gaatgccttat   3360
ttccaccagc ccgaggctat cgaagagttc ccgtgccgg ctcttcacca tccgttttcc    3420
cagcaagagt cgttcaccag acaggtgtta tggaagctgc tgaaggttgt gaaattcgga    3480
gaagtgattt cttaccagca attagcagcc ctggcaggca accccaaagc cgcgcgagca    3540
gtgggaggag caatgagagg caatcctgtc aaaatcctgca cagagtgtc                3600
tgcagcagcg gagccgtggg caactactcc ggaggactgg ccgtgaagga atggcttctg    3660
gcccatgaag gccaccggtt ggggaagcca ggctgggag ggagctcagg tctgcaggg     3720
gcctggctca agggagcggg agctacctcg ggctccccgc ctgctggccg aaactaagct    3780
ttatttgtga aatttgtgat gctattgctt tatttgtaac cattataagc tgcaataaac    3840
aagttaacaa caacaattgc attcatttta tgtttcaggt tcagggggag atgtgggagg    3900
ttttttaaag ccctgcaggc aatagccttg acaaggcaaa cttgaccaat agtcttagag    3960
tatccagtga ggcagggc cggcggctgg ctagggatga agaataaaag gaagcaccct    4020
tcagcagttc cacacactcg cttctggaac gtctgaggtt atcaataagc tcctagtcca    4080
gacgccatgg gtcattttcac agaggaggac aaggctacta tcaacaagcct gtgggcaag    4140
gtgaatgtgg aagatgctgg aggagaaacc ctgggaaggt aggctctggt gaccaggaca    4200
```

```
agggagggaa ggaaggaccc tgtgcctggc aaaagtccag gtcgcttctc aggatttgtg   4260
gcaccttctg actgtcaaac tgttcttgtc aatctcacag gctcctggtt gtctacccat   4320
ggacccagag gttctttgac agctttggca acctgtcctc tgcctctgcc atcatgggca   4380
accccaaagt caaggcacat ggcaagaagg tgctgacttc cttgggagat gccacaaagc   4440
acctggatga tctcaagggc acctttgccc agctgagtga actgcactgt gacaagctgc   4500
atgtggatcc tgagaacttc aaggtgagtc caggagatgt ttcagccctg ttgcctttag   4560
tctcgaggcg tcgacaggaa cccctagtga tggagttggc cactccctct ctgcgcgctc   4620
gctcgctcac tgaggccggg cgaccaaagg tcgcccgacg cccgggcttt gcccgggcgg   4680
cctcagtgag cgagcgagcg cgcagctggc gtaatagcga agaggcccgc accgatcgcc   4740
cttcccaaca gttgcgcagc ctgaatggcg aatggcgatt ccgttgcaat ggctggcggt   4800
aatattgttc tggatattac cagcaaggcc gatagtttga gttcttctac tcaggcaagt   4860
gatgttatta ctaatcaaag aagtattgcg acaacggtta atttgcgtga tggacagact   4920
cttttactcg gtggcctcac tgattataaa aacacttctc aggattctgg cgtaccggtc   4980
ctgtctaaaa tccctttaat cggcctcctg tttagctctc gctctgattc taacgaggaa   5040
agcacgttat acgtgctcgt caaagcaacc atagtacgcg ccctgtagcg gcgcattaag   5100
cgcggcgggt gtggtggtta cgcgcagcgt gaccgctaca cttgccagcg ccctagcgcc   5160
cgctcctttc gctttcttcc cttcctttct cgccacgttc gccggctttc cccgtcaagc   5220
tctaaatcgg gggctccctt tagggttccg atttagtgct ttacggcacc tcgaccccaa   5280
aaaacttgat tagggtgatg gttcacgtag tgggccatcg ccctgataga cggttttttcg   5340
ccctttgacg ttggagtcca cgttctttaa tagtggactc ttgttccaaa ctggaacaac   5400
actcaaccct atctcggtct attctttga tttataaggg attttgccga tttcggccta   5460
ttggttaaaa aatgagctga tttaacaaaa atttaacggg aattttaaca aaatattaac   5520
gtttacaatt taaatatttg cttatacaat cttcctgttt ttggggcttt tctgattatc   5580
aaccgggta catatgattg acatgctagt tttacgatta ccgttcatcg attctcttgt   5640
ttgctccaga ctctcaggca atgacctgat agcctttgta gagacctctc aaaaatagct   5700
accctctccg gcatgaattt atcagctaga acggttgaat atcatattga tggtgatttg   5760
actgtctccg gcctttctca cccgtttgaa tctttaccta cacattactc aggcattgca   5820
tttaaaatat atgagggttc taaaaatttt tatccttgcg ttgaaataaa ggcttctccc   5880
gcaaaagtat tacagggtca taatgttttt ggtacaaccg atttagcttt atgctctgag   5940
gctttattgc ttaattttgc taattctttg ccttgcctgt atgatttatt ggatgttgga   6000
atcgcctgat gcggtatttt ctccttacgc atctgtgcgg tatttcacac cgcatatggt   6060
gcactctcag tacaatctgc tctgatgccg catagttaag ccagccccga cacccgccaa   6120
cacccgctga cgcgccctga cgggcttgtc tgctcccggc atccgcttac agacaagctg   6180
tgaccgtctc cgggagctgc atgtgtcaga ggttttcacc gtcatcaccg aaacgcgcga   6240
gacgaaaggg cctcgtgata cgcctatttt tataggttaa tgtcatgata ataatggttt   6300
cttagacgtc aggtggcact tttcggggaa atgtgcgcgg aacccctatt tgtttatttt   6360
tctaaataca ttcaaatatg tatccgctca tgagacaata accctgataa atgcttcaat   6420
aatattgaaa aaggaagagt atgagtattc aacatttccg tgtcgccctt attcccttt   6480
ttgcgcatt ttgccttcct gtttttgctc acccagaaac gctggtgaaa gtaaaagatg   6540
ctgaagatca gttgggtgca cgagtgggtt acatcgaact ggatctcaac agcggtaaga   6600
tccttgagag ttttcgcccc gaagaacgtt ttccaatgat gagcactttt aaagttctgc   6660
tatgtggcgc ggtattatcc cgtattgacg ccgggcaaga gcaactcggt cgccgcatac   6720
actattctca gaatgacttg gttgagtact caccagtcac agaaaagcat cttacgatg   6780
gcatgacagt aagagaatta tgcagtgctg ccataaccat gagtgataac actgcggcca   6840
acttacttct gacaacgatc ggaggaccga aggagctaac cgcttttttg cacaacatgg   6900
gggatcatgt aactcgcctt gatcgttggg aaccggagct gaatgaagcc ataccaaacg   6960
acgagcgtga caccacgatg cctgtagcaa tggcaacaac gttgcgcaaa ctattaactg   7020
gcgaactact tactctagct tcccggcaac aattaataga ctggatggag gcggataaag   7080
ttgcaggacc acttctgcgc tcggcccttc cggctggctg gtttattgct gataaatctg   7140
gagccggtga gcgtgggtct cgcggtatca ttgcagcact ggggccagat ggtaagccct   7200
cccgtatcgt agttatctac acgacgggga gtcaggcaac tatggatgaa cgaaatagac   7260
agatcgctga gataggtgcc tcactgatta gcattggta actgtcagac caagtttact   7320
catatatact ttagattgat ttaaaacttc attttttaatt taaaaggatc taggtgaaga   7380
tccttttga taatctcatg accaaaatcc cttaacgtga gttttcgttc cactgagcgt   7440
cagaccccgt agaaaagatc aaaggatctt cttgagatcc ttttttttctg cgcgtaatct   7500
gctgcttgca aacaaaaaaa ccaccgctac cagcggtggt ttgtttgccg gatcaagagc   7560
taccaactct ttttccgaag gtaactggct tcagcagagc gcagatacca aatactgtcc   7620
ttctagtgta gccgtagtta ggccaccact tcaagaactc tgtagcaccg cctacatacc   7680
tcgctctgct aatcctgtta ccagtggctg ctgccagtgg cgataagtcg tgtcttaccg   7740
ggttggactc aagacgatag ttaccggata aggcgcagcg gtcgggctga acggggggt   7800
cgtgcacaca gcccagcttg gagcgaacga cctacaccga actgagatac ctacagcgtg   7860
agctatgaga aagcgccacg cttcccgaag ggagaaaggc ggacaggtat ccggtaagcg   7920
gcagggtcgg aacaggagag cgcacgaggg agcttccagg gggaaacgcc tggtatcttt   7980
atagtcctgt cgggtttcgc cacctctgac ttgagcgtcg atttttgtga tgctcgtcag   8040
gggggcggag cctatggaaa aacgccagca acgcggcctt tttacggttc ctggccttt   8100
gctggccttt tgctcacatg ttctttcctg cgttatcccc tgattctgtg ataaccgta   8160
ttaccgcctt tgagtgagct gataccgctc gccgcagccg aacgaccgag cgcagcgagt   8220
cagtgagcga ggaagcggaa gagcgcccaa tacgcaaacc gcctctcccc gcgcgttggc   8280
cgattcatta atg                                                     8293
```

SEQ ID NO: 18        moltype = DNA  length = 8126
FEATURE               Location/Qualifiers
source                1..8126
                        mol_type = other DNA
                        organism = Synthetic construct
SEQUENCE: 18

```
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc   120
actaggggtt cctacgcgta gatctggtgt atacatacat acctgaatat ggaatcaaat   180
```

```
attttttctaa gatgaaacag tcatgattta tttcaaatag gtacggataa gtagatattg  240
aggtaagcat taggtcttat attatgtaac actaatctat tactgcgctg aaactgtggc  300
tttatagaaa ttgttttcac tgcactattg agaaattaag agataatggc aaaagtcaca  360
aagagtatat tcaaaagaa gtatagcact ttttccttag aaaccactgc taactgaaag  420
agactaagat ttgtcccgtc aaaaatcctg gacctatgcc taaaacacat ttcacaatcc  480
ctgaacttt caaaaattgg tacatgcttt agctttaaac tacaggcctc actggagcta  540
gagacaagaa ggtaaaaac ggctgacaaa agaagtcctg gtatcctcta tgatgggaga  600
aggaaactag ctaaagggaa gaataaatta gagaaaaact ggaatgactg aatcggaaca  660
aggcaaaggc tataaaaaaa attaagcagc agtatcctct tggggggccc ttccccacac  720
tatctcaatg caaatatctg tctgaaacgg tccctggcta aactccaccc atgggttggc  780
cagccttgcc ttgacaaggc aaacttgacc aatagtctta gagtatccag tgaggccagg  840
ggccggcggc tggctaggga tgaagaataa aaggaagcac ccttcagcag ttccacacac  900
tcgcttctgg aacgtctgag gttatcaata agctcctagt ccagacgcca tggtgcacct  960
gactcctgag gagaagtctg ccgttactgc cctgtggggc aaggtgaacg tggatgaagt 1020
tggtggtgag gccctgggca ggttggtatc aaggttacaa gacaggttta aggagaccaa 1080
tagaaactgg gcatgtggag acagagaaga ctcttgggtt tctgataggc actgactctc 1140
tctgcctatt ggtctatttt cccacccta ggctgctggt ggtctaccct tggacccaga 1200
ggttctttga gtcctttggg gatctgtcca ctcctgatgc tgttatgggc aaccctaagg 1260
tgaaggctca tggcaagaaa gtgctcggtg cctttagtga tggcctggct cacctggaca 1320
acctcaaggg cacctttgcc cagctgagtg agctgcactg tgacaagctg cacgtggatc 1380
ctgagaactt cagggtgagt ctatgggacc cttgatgttt tcttccct tcttttctat 1440
ggttaagttc atgtcatagg aagggagaa gtaacaggt acacatattg accaaatcag 1500
ggtaattttg catttgtaat tttaaaaat gcttcttct tttaatatac ttttttgttt 1560
atcttatttc taatactttc cctaatctct ttctttcagg gcaataatga tacaatgtat 1620
catgcctctt tgcaccattc taaagaataa cagtgataat ttctgggtta aggcaatagc 1680
aatatttctg catataaata tttctgcata taaattgtaa ctgatgtaag aggtttcata 1740
ttgctaatag cagctacaat ccagctacca ttctgctttt attttatggt tgggataagg 1800
ctggattatt ctgagtccaa gctaggccct tttgctaatc atgttcatac ctcttatctt 1860
cctcccacag ctcctgggca acgtgctggt ctgtgtgctg gcccatcact ttggcaaaga 1920
attcacccca ccagtgcagg ctgcctatca gaaagtggtg gctggtgtgg ctaatgccct 1980
ggcccacaag tatcactaag ctcgctttct tgctgtccaa tttctattaa aggttccttt 2040
gttccctaag tccaactact aaactggggg atattatgaa gggccttgag catctggatt 2100
ctgcctaata aaaacatt attttcattg caatgatgta tttaaattat ttctgaatat 2160
tttactaaaa agggaatgtg ggaggttgca gtgctagtct cccggaacta tcactctttc 2220
acagtctgct ttggaaggac tgggcttagt atgaaaagtt aggactgaga agaattgaa 2280
aggggctt ttgtagcttg atattcacta ctgtctattt accctatcat aggcccaccc 2340
caaatggaag tccattctt cctcaggatg tttaagatta gcattcagga agagatcaga 2400
ggtctgctgg ctcccttatc atgtccctta tggtgcttct ggctctgcac cgcggccacg 2460
gggttgggt tgcgccttt ccaaggcagc cctgggttg cgcagggacg cggctgctct 2520
gggcgtggtt ccgggaaacg cagcggcgcc gaccctgggt ctcgcacatt cttcacgtcc 2580
gttcgcagcg tcacccggat cttccgcgct acccttgtgg gcccccggc gacgcttcct 2640
gctccgcccc taagtcggga aggttccttg cggttcgcgg cgtgccggac gtgacaaacg 2700
gaagccgcac gtctcactag taccctcgca gacggacagc gcagggagc aatggcaggg 2760
cgccgaccgc gatgggctgt ggccaatagc ggctgctcag cggggcgcgc cgagagcagc 2820
ggccgggaag gggcggtgcg ggaggcgggg tgtggggcgg tagtgtgggc cctgttcctg 2880
cccgcgcggt gttccgcatt ctgcaagcct ccggagcgca cgtcggcagt cggctccctc 2940
gttgaccgaa tcaccgacct ctctcccag cggccgcgcc gccaccatgg acaaggattg 3000
tgaaatgaaa cgcaccacac tggacagccc tttggggaag ctggagctgt ctggttgtga 3060
gcagggtctg cacgaaataa agctcctggg caaggggacg tctgcagctg atgccgtgga 3120
ggtcccagcc cccgctgcgg ttctcggagg tccgagccc ctgatgcagt gcacagcctg 3180
gctgaatgcc tatttccacc agcccgaggc tatcgaaag ttccccgtgc cggctcttca 3240
ccatcccgtt ttccagcaag agtcgttcac cagacaggtg ttatgaagc tgctgaaggt 3300
tgtgaaattc ggagaagtga tttcttacca gcaattagca gccctggcag gcaaccccaa 3360
agccgcgcga gcagtgggag gagcaatgag aggcaatcct gtcaaaatcc tcatcccgtg 3420
ccacagagtg gtctgcagca gcggagccgt gggcaactac tccggaggac tggccgtgaa 3480
ggaatggctt ctggcccatg aaggccaccg gttggggaag ccaggcttgg gagggagctc 3540
aggtctggca ggggcctggc tcaagggagc gggagctacc tcgggctccc cgcctgctgg 3600
ccgaaactaa gctttatttg tgaaatttgt gatgctattg cttatttgt aaccattata 3660
agctgcaata aacaagttaa caacaacaat tgcattcatt ttatgtttca ggttcagggg 3720
gagatgtggg aggttttta aagccctgca ggcaatagc ttgacaaggc aaacttgacc 3780
aatagtctta gagtatccag tgaggccagg ggccggcggc tggctaggga tgaagaataa 3840
aaggaagcac ccttcagcag ttccacacac tcgcttctgg aacgtctgag gttatcaata 3900
agctcctagt ccagacgcca tggtcattt cacagaggag gacaaggcta ctatcacaag 3960
cctgtgggc aaggtgaatg tggaggagaa accctgggaa ggtaggctg 4020
ggtgaccagg acaagggagg gaaggaagga cccgtgcct ggcaaagtc caggtcgctt 4080
ctcaggattt gtggcaccttt ctgactgtca aactgttctt gtcaatctca caggctcctg 4140
gttgtctacc catggaccca gaggtctttt gacagctttg caacctgtc ctctgcctct 4200
gccatcatgg gcaaccccaa gtcaaggca catggcaaga aggtgctgac ttccttggga 4260
gatgccacaa agcaccttg tgatctcaag ggacctgag tgaactgcac 4320
tgtgacaagc tgcatgtgga tcctgagaac ttcaaggtga gtccaggaga tgtttcagcc 4380
ctgttgcctt tagtctcgag gcgtcgacag gaaccctag tgatggagtt ggccactccc 4440
tctctgcgcg ctcgctcgct cactgaggcc gggcgaccaa aggtcgcccg acgcccgggc 4500
tttgcccggg cggcctcagt gagcgagcga gcgcgcagct ggcgtaatag cgaagaggcc 4560
cgcaccgatc gcccttccca acagttgcgc agcctgaatg gcgaatgggc attccgttgc 4620
aatggctggc ggtaatattg ttctggatat taccagcaag gccgatagtt tgagttcttc 4680
tactcaggca agtgatgtta ttactaatca agaagtatt gcgacaacgg ttaatttgcg 4740
tgatggacag actcttttac tcggtggcct cactgattat aaaaacactt ctcaggattc 4800
tggcgtaccg ttcctgtcta aaatccctt aatcggcctc ctgttagct cccgctctga 4860
ttctaacgag gaaagcacgt tatacgtgct cgtcaaagca accatagtac gcgccctgta 4920
```

```
gcggcgcatt aagcgcggcg ggtgtggtgg ttacgcgcag cgtgaccgct acacttgcca      4980
gcgccctagc gcccgctcct ttcgctttct tcccttcctt tctcgccacg ttcgccggct      5040
ttccccgtca agctctaaat cggggctcc ctttagggtt ccgatttagt gctttacggc      5100
acctcgaccc caaaaaactt gattagggtg atggttcacg tagtgggcca tcgcctgat      5160
agacggtttt tcgcccttg acgttggagt ccacgttctt taatagtgga ctcttgttcc      5220
aaactggaac aacactcaac cctatctcgg tctattcttt tgatttataa gggattttgc      5280
cgatttcggc ctattggtta aaaaatgagc tgatttaaca aaaatttaac gcgaatttta      5340
acaaatatt aacgtttaca atttaaatat ttgcttatac aatcttcctg ttttggggc      5400
ttttctgatt atcaaccggg gtacatatga ttgacatgct agttttacga ttaccgttca      5460
tcgattctct tgtttgctcc agactctcag gcaatgacct gatagccttt gtagagacct      5520
ctcaaaaata gctaccctct ccggcatgaa tttatcagct agaacggttg aatatcatat      5580
tgatggtgat ttgactgtct ccggcctttc tcacccgttt gaatcttac ctacacatta      5640
ctcaggcatt gcatttaaaa tatatgaggg ttctaaaaat ttttatcctt gcgttgaaat      5700
aaaggcttct cccgcaaaag tattacaggg tcataatgtt tttggtacaa ccgatttagc      5760
tttatgctct gaggctttat tgcttaattt tgctaattct ttgccttgcc tgtatgattt      5820
attggatgtt ggaatcgcct gatgcggtat tttctcctta cgcatctgtg cggtatttca      5880
caccgcatat ggtgcactct cagtacaatc tgctctgatg ccgcatagtt aagccagccc      5940
cgacacccgc caacacccgc tgacgcgccc tgacgggctt gtctgctccc ggcatccgct      6000
tacagacaag ctgtgaccgt ctccgggagc tgcatgtgtc agaggttttc accgtcatca      6060
ccgaaacgcg cgagacgaaa gggcctcgtg atacgcctat ttttataggt taatgtcatg      6120
ataataatgg tttcttagac gtcaggtggc acttttcggg gaaatgtgcg cggaacccct      6180
atttgtttat ttttctaaat acattcaaat atgtatccgc tcatgagaca ataaccctga      6240
taaatgcttc aataatattg aaaaaggaag agtatgagta ttcaacattt ccgtgtcgcc      6300
cttattccct tttttgcggc attttgcctt cctgtttttg ctcacccaga aacgctggtg      6360
aaagtaaaag atgctgaaga tcagttgggt gcacgagtgg gttacatcga actggatctc      6420
aacagcggta agatcttga gagttttcgc cccgaagaac gttttccaat gatgagcact      6480
tttaaagttc tgctatgtgg cgcggtatta tcccgtattg acgccgggca agagcaactc      6540
ggtcgccgca tacactattc tcagaatgac ttggttgagt actcaccagt cacagaaaag      6600
catcttacgg atggcatgac agtaagagaa ttatgcagtg ctgccataac catgagtgat      6660
aacactgcgg ccaacttact tctgacaacg atcggaggac cgaaggagct aaccgctttt      6720
ttgcacaaca tgggggatca tgtaactcgc cttgatcgtt gggaaccgga gctgaatgaa      6780
gccataccaa acgacgagcg tgacaccacg atgcctgtag caatggcaac aacgttgcgc      6840
aaactattaa ctggcgaact acttactcta gcttcccggc aacaattaat agactggatg      6900
gaggcggata aagttgcagg accacttctg cgctcggccc ttccggctgg ctggtttatt      6960
gctgataaat ctggagccgg tgagcgtggg tctcgcggta tcattgcagc actggggcca      7020
gatggtaagc cctcccgtat cgtagttatc tacacgacgg ggagtcaggc aactatggat      7080
gaacgaaata gacagatcgc tgagataggt gcctcactga ttaagcattg gtaactgtca      7140
gaccaagttt actcatatat actttagatt gatttaaaac ttcattttta atttaaaagg      7200
atctaggtga agatcctttt tgataatctc atgaccaaaa tcccttaacg tgagttttcg      7260
ttccactgag cgtcagaccc cgtagaaaag atcaaaggat cttcttgaga tcctttttt      7320
ctgcgcgtaa tctgctgctt gcaaacaaaa aaaccaccgc taccagcggt ggtttgtttg      7380
ccggatcaag agctaccaac tctttttccg aaggtaactg gcttcagcag agcgcagata      7440
ccaaatactg tccttctagt gtagccgtag ttaggccacc acttcaagaa ctctgtagca      7500
ccgcctacat acctcgctct gctaatcctg ttaccagtgg ctgctgccag tggcgataag      7560
tcgtgtctta ccgggttgga ctcaagacga tagttaccgg ataaggcgca gcggtcgggc      7620
tgaacggggg gttcgtgcac acagcccagc ttggagcgaa cgacctacac cgaactgaga      7680
tacctacagc gtgagctatg agaaagcgcc acgcttcccg aagggagaaa ggcggacagg      7740
tatccggtaa gcggcagggt cggaacagga gagcgcacga gggagcttcc agggggaaac      7800
gcctggtatc tttatagtcc tgtcgggttt cgccacctct gacttgagcg tcgatttttg      7860
tgatgctcgt caggggggcg gagcctatgg aaaaacgcca gcaacgcggc cttttacgg      7920
ttcctggcct tttgctggcc ttttgctcac atgttcttc ctgcgttatc ccctgattct      7980
gtggataacc gtattaccgc ctttgagtga gctgataccg ctcgccgcag ccgaacgacc      8040
gagcgcagcg agtcagtgag cgaggaagcg gaagagcgcc caatacgcaa accgcctctc      8100
cccgcgcgtt ggccgattca ttaatg                                          8126

SEQ ID NO: 19          moltype = DNA  length = 8024
FEATURE                Location/Qualifiers
source                 1..8024
                       mol_type = other DNA
                       organism = Synthetic construct
SEQUENCE: 19
cagctgcgcg ctcgctcgct cactgaggcc gcccgggcaa agcccgggcg tcgggcgacc        60
tttggtcgcc cggcctcagt gagcgagcga gcgcgcagag agggagtggc caactccatc       120
actaggggtt ccttgtagtt aatgattaac ccgccatgct acttatctac acgcgtagat       180
cttgaaacag tcatgattta tttcaaatag gtacgcgata agtagatattg aggtaagcat      240
taggtcttat attatgtaac actaatctat tactgcgctg aaactgtggc tttatagaaa       300
ttgttttcac tgcactattg agaaattaag agataatggc aaaagtcaca aagagtatat       360
tcaaaaagaa gtatagcact ttttccttag aaaccactgc taactgaaag agactaagat       420
ttgtcccgtc aaaaatcctg gacctatgcc taaaacacat ttcacaatcc ctgaacttta       480
caaaaattgg tacatgcttt agctttaaac tacaggcctc actgagcta gagacaagaa        540
ggtaaaaaac ggctgacaaa agaagtcctg gtatcctcta tgatgggaga aggaaactag       600
ctaaaggaa gaataaatta gagaaaaact ggaatgactg aatcggaaca aggcaaaggc        660
tataaaaaa attagcagta tcctcttggg ggccccttcc ccacactatc tcaatgcaaa       720
tatctgtctg aaacgtccc tggctaaact ccaccatgg gtggccagc cttgccttga         780
caaggcaaac ttgaccaata gtcttagagt atccagtgag gccaggggcc ggcggctggc       840
tagggatgaa gaataaaagg aagcacctt cagcagttcc acacactcgc ttctggaacg       900
tctgaggtta tcaataagct cctagtccag acgccatggt gcacctgact cctgaggaga       960
agtctgccgt tactgccctg tggggcaagg tgaacgtgga tgaagttggt ggtgaggccc      1020
tgggcaggtt ggtatcaagg ttacaagaca ggtttaagga gaccaataga aactgggcat      1080
```

```
gtggagacag agaagactct tgggtttctg ataggcactg actctctctg cctattggtc   1140
tattttccca cccttaggct gctggtggtc taccccttgga cccagaggtt ctttgagtcc   1200
tttggggatc tgtccactcc tgatgctgtt atgggcaacc ctaaggtgaa ggctcatggc   1260
aagaaagtgc tcggtgcctt tagtgatggc ctggctcacc tggacaacct caagggcacc   1320
tttgcccagc tgagtgagct gcactgtgac aagctgcacg tggatcctga gaacttcagg   1380
gtgagtctat gggacccttg atgttttctt tcccctttctt ttctatggtt aagttcatgt   1440
cataggaagg ggagaagtaa cagggtacac atattgacca aatcagggta attttgcatt   1500
tgtaatttta aaaaatgctt tcttcttttta atatactttt ttgtttatct tatttctaat   1560
actttcccta atctctttct ttcagggcaa taatgataca atgtatcatg cctctttgca   1620
ccattctaaa gaataacagt gataattctc gggttaaggc aatagcaata tttctgcata   1680
taaatatttc tgcatataaa ttgtaactga tgtaagaggt ttcatattgc taatagcagc   1740
tacaatccag ctaccattct gcttttattt tatggttggg ataaggctgg attattctga   1800
gtccaagcta ggccctttgg ctaatcatgt tcatacctct tatcttcctc ccacagctcc   1860
tgggcaacgt gctggtctgt gtgctggccc atcacttctg caaagaattc accccaccag   1920
tgcaggctgc ctatcagaaa gtggtggctg gtgtggctaa tgccctggcc cacaagtatc   1980
actaagctcg ctttcttgct gtccaatttc tattaaaggt tcctttgttc cctaagtcca   2040
actactaaac tgggggatat tatgaagggc cttgagcatc tggattctgc ctaataaaaa   2100
acatttattt tcattgcaat gatgtattta aattatttct gaatattta ctaaaaaggg   2160
aatgtgggag gttgcagtgc tagtctcccg gaactatcac tctttcacag tctgctttgg   2220
aaggactggg cttagtatga aaagttagga ctgagaagaa tttgaaaggg ggcttttttgt   2280
agcttgatat tcactactgt cttattaccc tatcataggc ccacccccaaa tggaagtccc   2340
attccttcctc aggatgttta agattagcat tcaggaagag atcagaggtc tgctggctcc   2400
cttatcatgt cccttatggt gcttctggct ctgcaccgcg gccacggggt tggggttgcg   2460
ccttttccaa ggcagccctg ggtttgcgca gggacgcggc tgctctgggc gtggttccgg   2520
gaaacgcagc ggcgccgacc ctgggtctcg cacattcttc acgtccgttc gcagcgtcac   2580
ccggatcttc gccgctaccc ttgtgggccc cccggcgacg cttcctgctc cgccccctaag   2640
tcggaaggt tccttgcggt tcgcggcgtg ccggacgtga caaacggaag ccgcacgtct   2700
cactagtacc ctcgcagacg gacagcgcca gggagcaatg gcagcgcgcc gaccgcgatg   2760
ggctgtggcc aatagcggct gctcagcggg gcgcgccgag agcagcggcc gggaagggggc   2820
ggtgcgggag gcggggtgtg gggcggtagt gtgggccctg ttcctgcccg cgcggtgttc   2880
cgcattctgc aagcctccgg agcgcacgtc ggcagtcggc tccctcgttg accgaatcac   2940
cgacctctct ccccagcggc cgcgccgcca ccatggacaa ggattgtgaa atgaaacgca   3000
ccacactgga cagccctttg gggaagctgg agctgtctgg ttgtgagcag ggtctgcacg   3060
aaataaagct cctgggcaag gggacgtctg cagctgatgc cgtggaggtc ccagccccccg   3120
ctgcggttct cggaggtccg gagccccctga tgcagtgcac agctcggctg aatgcctatt   3180
tccaccagcc cgaggctatc gaagagttcc ccgtgccggc tcttcaccat cccgttttcc   3240
agcaagagtc gttcaccaga caggtgttat ggaagctgct gaaggttgtg aaattcggag   3300
aagtgatttc ttaccagcaa ttagcagccc tggcaggcaa ccccaaagcc gcgcgagcag   3360
tgggagagc aatgagaggc aatcctgtca aaatcctcat cccgtgccac agagtggtct   3420
gcagcagcgg agccgtgggc aactactccg gaggactgcc cgtgaaggaa tggcttctgt   3480
cccatgaagg ccaccggttg gggaagccag gcttgggagg gagctcaggt ctggcagggg   3540
cctggctcaa gggagcggga gctacctcgg gctcccgcc tgctggccga aacgagggca   3600
gaggaagtct tctaacatgc ggtgacgtgg aggagaatcc gaggaactt   3660
caaggtgagt ccaggagatg tttcagcccct gttgccttta gtctcgaggc aacttagaca   3720
acggagtatt gatctgagca cagcagggtg tgagctgttt gaagatactg ggggttgggggg   3780
tgaagaaact gcagaggact aactgggctg agacccagtg gtaatgtttt agggcctaag   3840
gagtgcctct aaaaagctag atggacaatt ttgactttga gaaaagaagg gtggaaaatga   3900
ggaaaatgac ttttctttat tagattccag tagaaagaac tttcatcttt ccctcatttt   3960
tgttgttta aacatctat ctggaggcag acaagtatg tcgttaaaaa agatgcaggc   4020
agaaggcata tattggctca gtcaaagtgg ggaactttgg tggccaaaca tacattgcta   4080
aggctattcc tatatcagct ggacacatat aaaatgctgc taatgcttca ttacaaactt   4140
atatcctta attccagatg ggggcaaagt atgtccaggg gtgaggaaca attgaaacat   4200
ttgggctgga gtagattttg aaagtcagct ctgtgtgtgt gtgtgtgtgt gcgcgcgcgc   4260
gtgtcgacgt agataagtag catggcgggt taatcattaa ctacaaggaa ccctagtga   4320
tggagttggc cactccctct ctgcgcgctc gctcgctcaa tgaggccggg cgaccaaagg   4380
tcgcccgacg cccgggcttt gcccgggcgg cctcagtgac cgagcgagcg cgccagctgg   4440
cgtaatagcg aagaggcccg caccgatcgc ccttcccaac agttgcgcag cctgaatggc   4500
gaatggcgat tccgttgcaa tggctggcgg taatattgtt ctggatatta ccagcaaggc   4560
cgatagtttg agttcttcta ctcaggcaag tgatgttatt actaatcaaa gaagtattgc   4620
gacaacggtt aatttgcgtg atgacagac tcttttactc ggtggcctca ctgattataa   4680
aaacacttct caggattctg gcgtaccgtt cctgtctaaa atcccttaa tcggcctcct   4740
gtttagctcc cgctctgatt ctaacgagga aagcacgtta tacgtgctcg tcaaagcaac   4800
catagtacgc gccctgtagc ggcgcattaa gcgcggcggg tgtggtggtt acgcgcagcg   4860
tgaccgctac acttgccagc gccctagcgc ccgctccttc cttcctttc tcgccacgtt   4920
cgccgctttt cccgtcaag ctctaaatcg ggctccct ttagggttcc   4980
gatttagtgc tttacggcac ctcgacccca aaaaacttga ttagggtgat ggttcacgta   5040
gtgggccatc gccctgatag acggtttttc gccctttgac gttggagtcc acgttcttta   5100
atagtggact cttgttccaa actggaacaa cactcaaacc tatctcggtc tattcttttg   5160
atttataagg gattttgccg atttcggcct attggttaaa aaatgagctg atttaacaaa   5220
aatttaacgc gaattttaac aaaatattaa cgtttacaat ttaaatattt gcttatacaa   5280
tcttcctgtt tttggggctt ttctgattat caaccgggt acatatgatt gacatgctag   5340
ttttacgatt accgttcatc gattctcttg tttgctccag actctcaggc aatgacctga   5400
tagcctttgt agagacctct caaaaatagc taccctctcc ggcatgaatt tatcagctag   5460
aacggttgaa tatcatattg atggtgattt gactgtttcc gcctttctc acccgtttga   5520
atctttacct acacattact caggcattgc atttaaaata tatgagggtt ctaaaaattt   5580
ttatccttgc gttgaaataa aggcttctcc cgcaaaagta ttacagggtc ataatgtttt   5640
tggtacaacc gatttagctt tatgctctga ggctttattg cttaatttgt ctaattcttt   5700
gccttgcctg tatgattat tggatgttgg aatcgcctga tgcggtattt tctccttacg   5760
catctgtgcg gtatttcaca ccgcatatgg tgcactctca gtacaatctg ctctgatgcc   5820
```

```
gcatagttaa gccagcccg acacccgcca acaccgctg acgcgccctg acgggcttgt    5880
ctgctcccgg catccgctta cagacaagct gtgaccgtct ccgggagctg catgtgtcag    5940
aggttttcac cgtcatcacc gaaacgcgcg agacgaaagg gcctcgtgat acgcctattt    6000
ttataggtta atgtcatgat aataatggtt tcttagacgt caggtggcac ttttcgggga    6060
aatgtgcgcg gaaccctat ttgtttattt ttctaaatac attcaaatat gtatccgctc    6120
atgagacaat aaccctgata aatgcttcaa taatattgaa aaaggaagag tatgagtatt    6180
caacatttcc gtgtcgccct tattccctt tttgcggcat tttgccttcc tgttttgct    6240
cacccagaaa cgctggtgaa agtaaaagat gctgaagatc agttgggtgc acgagtgggt    6300
tacatcgaac tggatctcaa cagcggtaag atccttgaga gttttcgccc cgaagaacgt    6360
tttccaatga tgagcacttt taaagttctg ctatgtggcg cggtattatc ccgtattgac    6420
gccgggcaag agcaactcgg tcgccgcata cactattctc agaatgactt ggttgagtac    6480
tcaccagtca cagaaaagca tcttacggat ggcatgacag taagagaatt atgcagtgct    6540
gccataacca tgagtgataa cactgcggcc aacttacttc tgacaacgat cggaggaccg    6600
aaggagctaa ccgcttttt gcacaacatg gggatcatg taactcgcct tgatcgttga    6660
gaaccggagc tgaatgaagc cataccaaac gacgagcgtg acaccacgag gcctgtagca    6720
atggcaacaa cgttgcgcaa actattaact ggcgaactac ttactctagc ttcccggcaa    6780
caattaatag actggatgga ggcggataaa gttgcaggac cacttctgcg ctcggccctt    6840
ccggctggct ggtttattgc tgataaatct ggagccggtg agcgtgggtc tcgcggtatc    6900
attgcagcac tggggccaga tggtaagccc tcccgtatcg tagttatcta cacgacgggg    6960
agtcaggcaa ctatggatga acgaaataga cagatcgctg agataggtgc ctcactgatt    7020
aagcattggt aactgtcaga ccaagtttac tcatatatac tttagattga tttaaaactt    7080
catttttaat ttaaaaggat ctaggtgaag atccttttg ataatctcat gaccaaaatc    7140
ccttaacgtg agttttcgtt ccactgagcg tcagaccccg tagaaaagat caaaggatc    7200
tcttgagatc ctttttttct gcgcgtaatc tgctgcttgc aaacaaaaaa accaccgcta    7260
ccagcggtgg tttgtttgcc ggatcaagag ctaccaactc ttttccgaa ggtaactggc    7320
ttcagcagag cgcagatacc aaatactgtc cttctagtgt agccgtagtt aggccaccac    7380
ttcaagaact ctgtagcacc gcctacatac ctcgctctgc taatcctgtt accagtggct    7440
gctgccagtg gcgataagtc gtgtcttacc gggttggact caagacgata gttaccggat    7500
aaggcgcagc ggtcgggctg aacggggggt tcgtgcacac agcccagctt ggagcgaacg    7560
acctacaccg aactgagata cctacagcgt gagctatgag aaagcgccac gcttcccgaa    7620
gggagaaagg cggacaggta tccggtaagc ggcagggtcg gaacaggaga gcgcacgagg    7680
gagcttccag ggggaaacgc ctggtatctt tatagtcctg tcgggtttcg ccacctctga    7740
cttgagcgtc gatttttgtg atgctcgtca gggggggcgga gcctatgaa aaacgccagc    7800
aacgcggcct ttttacggtt cctggccttt tgctggcctt ttgctcacat gttctttcct    7860
gcgttatccc ctgattctgt ggataaccgt attaccgcct ttgagtgagc tgataccgct    7920
cgccgcagcc gaacgaccga gcgcagcgag tcagtgagcg aggaagcgga agagcgccca    7980
atacgcaaac cgcctctccc cgcgcgttgg ccgattcatt aatg                    8024

SEQ ID NO: 20          moltype = DNA  length = 7729
FEATURE                Location/Qualifiers
source                 1..7729
                       mol_type = other DNA
                       organism = Synthetic construct
SEQUENCE: 20
cagctgcgcg ctcgctcgct cactgaggcc gccgggcaa agcccgggcg tcgggcgacc      60
tttggtcgcc cggcctcagt gagcgagcga gcgcgcagag agggagtggc caactccatc    120
actaggggtt ccttgtagtt aatgattaac ccgccatgct acttatctac acgcgtagat    180
ctagaaattg ttttcactgc actattgaga aattaagaga taatggcaaa agtcacaaag    240
agtatattca aaaagaagta tagcactttt tccttagaaa ccactgctaa ctgaaagaga    300
ctaagatttg tcccgtcaaa aatcctggac ctatgcctaa aacacatttc acaatccctg    360
aactttttcaa aaattggtac atgctttagc tttaaactac aggcctcact ggagctgaca    420
acaagaaggt aaaaaacggc tgacaaaaga agtcctggta tcctctatga tgggagaagg    480
aaactagcta aagggaagaa taaattagag aaaaactgga atgactgaat cggaacaagg    540
caaaggctat aaaaaaaatt agcagtatcc tcttgggggc cccttcccca cactatctca    600
atgcaaatat ctgtctgaaa cggtccctgg ctaaactccc cccgcgggaa cagagaaaca    660
ggagaatatg gccaaacag gatatctgtg gtaagcagtt cctgcccgg ctcagggcca    720
agaacagttg gaacagcaga atatgggcca acaggatat ctgtggtaag cagttcctgc    780
cccggctcag ggccaagaac agatggtccc cagatgcggt cccgccctca gcagtttcta    840
gagaaccatc agatgtttcc agggtgcccc aaggacctga aatgaccctg tgccttattt    900
gaactaacca atcagttcgc ttctcgcttc tgttcgcgcg cttctgctcc ccgagctcta    960
tataagcaga gctcgtttag tgaaccgtca gatcgcctgg agacgccatc cacgctgttt   1020
tgacttccat agaaggcggc gcgccgcca ccatggacaa ggattgtgaa atgaaacgca   1080
ccacactgga cagcccttg gggaagctgg agctgtctg ttgtgagcag ggtctgcacg   1140
aaataaagct cctgggcaag gggacgtctg cagctgatgc cgtggaggtc ccagcccccg   1200
ctgcggttct cggaggtccg gagccctga tgcagtgcac agcctggctg aatgccatt   1260
tccaccagcc cgaggctatc gaagagttcc ccgtgccggc tcttcaccat cccgttttcc   1320
agcaagagtc gttcaccaga caggtgttat ggaagctgct gaaggttgtg aaattcggag   1380
aagtgatttc ttaccagcaa ttagcagccc tggcaggcaa ccccaaagcc gcgcgagcag   1440
tgggaggagc aatgagaggc aatcctgtca aaatcctcat ccgtgccac agagtggtct   1500
gcagcagcgg agccgtgggc aactactccg gaggactgcc cgtgaaggaa tggcttctgg   1560
cccatgaagg ccaccggttg gggaagccag gcttgggagg gagctcaggt ctggcagggg   1620
cctggctcaa gggagcggga gctacctcgg gctcccgcc tgctggccga actaacctg   1680
cagggataat caacctctgg attacaaaat ttgtgaaaga ttgactggta ttcttaacta   1740
tgttgctcct tttacgctat gtggatacgc tgctttaatg cctttgtatc atgctattgc   1800
ttcccgtatg gctttcattt tctcctcctt gtataaatcc tggttagttc ttgccacggc   1860
ggaactcatc gccgcctgcc ttgcccgctg ctggacaggg ctcggctgt gggcactga   1920
caattccgtg gtgtttattt gtgaaatttg tgatgctatt gctttatttg taaccattct   1980
agcttttattt gtgaaatttg tgatgctatt gctttatttg taaccattat aagctgcaat   2040
aaacaagtta acaacaacaa ttgcattcat tttatgtttc aggttcaggg ggagatgtgg   2100
```

```
gaggtttttt aaagcgaatt ccgagatcga gaccatcctg gctaacacag tgaaacccccg   2160
tctctactaa aaaaatacaa aaaattagcc gggcttggtg gcgggtgcct gtagtcccag   2220
ctactatgga ggctgaggcg ggagaatggc gtgaacgcgg gggcggagc ttgcagtgag    2280
cagagatcag gggccactgc actccagcct gggcgacaga gagagactct gtctcaaaaa   2340
aaagaaaaaa aaaatttagt agactagcta aaaaaatcca gagatagtta ttgatgcata   2400
tgtaaaagtc ttccaatatt tacaagtaca atgaaaaaaa aataaccttg aattaagtgt   2460
agaactcatt gacaatgttt caaaggatgt gagggataaa ctaaaatttg ggcagtacat   2520
gctgttcctg tgtacttgga acagagggag aaaatctggg ctggaaatat tgttatagga   2580
gttagcacat gaaggtgaca actaaattat ttggagtaga tggagtcacc agcacatggt   2640
aatagtttta gaatgaaatg acccaagata gaactttgga gagccccccaa atttaaataa   2700
aatcagtata agagaagagg aagaaaccaa atggtatact agtctaaatt gtttcttagt   2760
gacaaaagaa taacctgaat attagattag ctgcctatat gctctctgaa tcaatttcat   2820
tcaacatgca acagttctgg aacctatcag ggaccacagt cagccaggca agcacatctg   2880
cccaagccaa gggtggaggc atgcagctgt gggggtctgt gaaaacactt gagggagcag   2940
ataactgggc caaccatgac tcagtgcttc tggaggccaa caggactgct gagtcatcct   3000
gtgggggtgg aagtgggaca agggaaaggg gtgaatggta ctgctgatta caacctctgg   3060
tgctgcctcc ccctcctgtt tatctgagag gctagcgtaa atacacttgc aaaggaggat   3120
gtttttagta gcaatttgta ctgatgtat ggggccaaga gatatatctt agagggaggg   3180
ctgagggttt gaagtccaac tcctaagcca gtgccagaag agccaaggac aggtacggct   3240
gtcatcactt agacctcacc ctgtggagcc acacccctagg gttggccaat ctactcccag   3300
gagcagggag ggcaggagcc agggctgggc ataaaagtca gggcagagcc atctattgct   3360
tacactcgct tctggaacgt ctgaggttat caataagctc ctagtccaga cccatgggt    3420
catttcacag aggaggacaa ggctactatc acaagcctgt ggggcaaggt gaatgtggaa   3480
gatgctggag gagaaaccct gggaaggtag gctctggtga ccaggacaag ggagggaagg   3540
aaggaccctg tgcctggcaa aagtccaggt cgcttctcag gatttgtggc accttctgac   3600
tgtcaaactg ttcttgtcaa tctcacagge cctggttgt ctacccatgg acccagaggt    3660
tctttgacaa ctttggcaac cgtcctctg cctctgccat catgggcaac cccaaagtca    3720
aggcacatgg caagaaggtg ctgacttcct gggagatgc cacaaagcac ctggatgatc    3780
tcaagggcac ctttgcccag ctgagtgaac tgcactgtga caagctgcat gtggatcctg   3840
agaacttcaa ggtgagtcca ggagatgttt cagccctgtt gcctttagtc tcgaggcaac   3900
ttagacaacg gagtattgat ctgagcacag cagggtgtga gctgtttgaa gatactgggg   3960
tctcgaggtc gacgtagata agtagcatgg cgggttaatc attaactaca aggaaccccct  4020
agtgatggag ttggccactc cctctctgcg cgctcgctcg ctcactgagg ccgggcgacc   4080
aaaggtcgcc cgacgcccgg gctttgcccg ggcggcctca gtgacgcagc gagcgcgcca   4140
gctggcgtaa tagcgaagag gcccgcaccg atcgcccttc ccaacagttg cgcagcctga   4200
atggcgaatg gcgattccgt tgcaatggct ggcggtaata ttgttctgga tattaccagc   4260
aaggccgata gtttgagttc ttctactcag gcaagtgatg ttattactaa tcaaagaagt   4320
attgcgacaa cggttaattt gcgtgatgga cagactcttt tactcggtgg cctcactgat   4380
tataaaaaca cttctcagga ttctggcgta ccgttcctgt ctaaaatccc tttaatcggc   4440
ctcctgtttta gctcccgctc tgattctaac gaggaaagca cgttatacgt gctcgtcaaa   4500
gcaaccatag tacgcgccct gtagcggcgc attaagcgcg gcgggtgtgg tggttacgcg   4560
cagcgtgacc gctacacttg ccagcgccct agcgccccgct cctttcgctt tcttccctttc  4620
ctttctcgcc acgttcgccg gctttccccg tcaagctcta aatcggggggc tccctttagg   4680
gttccgattt agtgctttac ggcacctcga ccccaaaaaa cttgattagg gtgatggttc   4740
acgtagtggg ccatcgccct gatagacggt ttttcgccct ttgacgttgg agtccacgtt   4800
ctttaatagt ggactcttgt tccaaactgg aacaacactc aacccctatct cggtctattc   4860
ttttgattta taagggattt tgccgatttc ggcctattgg ttaaaaaatg agctgatttta  4920
acaaaaattt aacgcgaatt ttaacaaaat attaacgttt acaatttaaa tatttgctta   4980
tacaatcttc ctgttttttgg ggcttttctt attatcaacc ggggtacata tgattgacat   5040
gctagtttta cgattaccgt tcatcgattc tcttgtttgc tccagactct caggcaatga   5100
cctgatagcc tttgtagaga cctctcaaaa atagctaccc tctccggcat gaatttatca   5160
gctagaacgg ttgaatatca tattgatggt gatttgactg tctccggcct ttctcacccg   5220
tttgaatctt tacctacaca ttactcaggc attgcattta aaatatatga gggttctaaa   5280
aatttttatc cttgcgttga aataaaggct tctcccgcaa aagtattaca gggtcataat   5340
gtttttggta caaccgattt agctttatgc tctgaggctt tattgcttaa ttttgctaat   5400
tctttgcctt gcctgtatga tttattggat gttggaatcg cctgatgcgg tatttttctcc   5460
ttacgcatct gtgcggtatt tcacaccgca tatggtgcac tctcagtaca atctgctctg   5520
atgccgcata gttaagccag ccccgacacc cgccaacacc cgctgacgcg ccctgacggg   5580
cttgtctgct cccggcatcc gcttacagac aagctgtgac cgtctccggg agctgcatgt   5640
gtcagaggtt ttcaccgtca tcaccgaaac gcgcgagacg aaagggcctc gtgatacgcc   5700
tatttttata ggttaatgtc atgataataa tggtttctta gacgtcaggt ggcacttttc   5760
ggggaaatgt gcgcggaacc cctatttgtt tatttttcta aatacattca aatatgtatc   5820
cgctcatgag acaataaccc tgataaatgc ttcaataata ttgaaaaagg aagagtatga   5880
gtattcaaca tttccgtgtc gcccttattc ccttttttgc ggcattttgc cttcctgttt   5940
ttgctcaccc agaaacgctg gtgaaagtaa aagatgctga agatcagttg ggtgcacgag   6000
tgggttacat cgaactggat ctcaacagcg gtaagatcct tgagagtttt cgccccgaag   6060
aacgttttcc aatgatgagc acttttaaag ttctgctatg tggcgcggta ttatcccgta   6120
ttgacgccgg gcaagagcaa ctcggtcgcc gcatacacta ttctcagaat gacttggttg   6180
agtactcacc agtcacagaa aagcatctta cggatggcat gacagtaaga gaattatgca   6240
gtgctgccat aaccatgagt gataacactg cggccaactt acttctgaca acgatcggag   6300
gaccgaagga gctaaccgct tttttgcaca acatggggga tcatgtaact cgccttgatc   6360
gttgggaacc ggagctgaat gaagccatac caaacgacga gcgtgacacc acgatgcctg   6420
tagcaatggc aacaacgttg cgcaaactat taactggcga actacttact ctagcttccc   6480
ggcaacaatt aatagactgg atggaggcgg ataaagttgc aggaccactt ctgcgctcgg   6540
cccttccggc tggctggttt attgctgata aatctggagc cggtgagcgt gggtctcgcg   6600
gtatcattgc agcactgggg ccagatggta agccctcccg tatcgtagtt atctacacga   6660
cggggagtca ggcaactatg gatgaacgaa atagacagat cgctgagata ggtgcctcac   6720
tgattaagca ttggtaactg tcagaccaag tttactcata tatactttag attgatttaa   6780
aacttcatttt ttaatttaaa aggatctagg tgaagatcct ttttgataat ctcatgacca   6840
```

```
aaatccctta acgtgagttt tcgttccact gagcgtcaga ccccgtagaa aagatcaaag    6900
gatcttcttg agatccttt tttctgcgcg taatctgctg cttgcaaaca aaaaaaccac     6960
cgctaccagc ggtggtttgt ttgccggatc aagagctacc aactcttttt ccgaaggtaa    7020
ctggcttcag cagagcgcag ataccaaata ctgtccttct agtgtagccg tagttaggcc    7080
accacttcaa gaactctgta gcaccgccta catacctcgc tctgctaatc ctgttaccag    7140
tggctgctgc cagtggcgat aagtcgtgtc ttaccgggtt ggactcaaga cgatagttac    7200
cggataaggc gcagcggtcg ggctgaacgg ggggttcgtg cacacagccc agcttggagc    7260
gaacgaccta caccgaactg agatacctac agcgtgagct atgagaaagc gccacgcttc    7320
ccgaagggag aaaggcggac aggtatccgg taagcggcag ggtcggaaca ggagagcgca    7380
cgagggagct tccaggggga aacgcctggt atctttatag tcctgtcggg tttcgccacc    7440
tctgacttga gcgtcgattt ttgtgatgct cgtcaggggg gcggagccta tggaaaaacg    7500
ccagcaacgc ggcctttta cggttcctgg ccttttgctg gccttttgct cacatgttct     7560
ttcctgcgtt atccctgat tctgtggata accgtattac cgcctttgag tgagctgata     7620
ccgctcgccg cagccgaacg accgagcgca gcgagtcagt gagcgaggaa gcggaagagc    7680
gcccaatacg caaaccgcct ctccccgcgc gttggccgat tcattaatg                7729

SEQ ID NO: 21        moltype = DNA  length = 8285
FEATURE              Location/Qualifiers
source               1..8285
                     mol_type = other DNA
                     organism = Synthetic construct
SEQUENCE: 21
cagctgcgcg ctcgctcgct cactgaggcc gcccggcaa agcccgggcg tcggcgacc       60
tttggtcgcc cggcctcagt gagcgagcga gcgcgcagag agggagtggc caactccatc    120
actagggggt cctacgcgta gatctggtgc ctacatacat acctgaataa gaaaaaaaaa    180
tacctttgct gagatgaaac acacatgatt tatttcaaat aggtacagag aagtagatac    240
tgaagtaagg attaagtatt atattatatt acataacatt aatctattcc tgcactgaaa    300
ccgttgcttt atatgatttt ttttttcact cactaatga gaacttaaga gataatggcc      360
taaaaccaca gagagtattt tcaaagataa gtatagcaca atgcttacta aatgagacta    420
agacttgtcc catcgaaaat cctgaccta tgcctaaaac acgtgtcaca atccccgaac      480
ttttcaaaaa ttggtacatg ctttaacttt aatctccagg cctcactgga gctagagtca    540
agaaggtaaa aaaaggctga caaaagaagt cctggtatct tctatggtgg gagaaggaaa    600
ctagctaaag ggaagaataa attagagaaa aattggaatg attgaatcgg aacaaggcaa    660
aggctataaa aaaattaagc agcagtatcc tcttgggggc cccttcccca cactatctca    720
atgcaaatat ctgtctgaaa cggtcctgg ctaaactcca cccatgggtt ggccagtctt      780
gccttgacgc tagcgtaaat acacttgcaa aggaggatgt tttagtagc aatttgtact      840
gatggtatgg ggcaagaga tatatcttag agggagggct gagggtttga agtccaactc      900
ctaagccagt gccagaagag ccaaggacag gtacggctgt catcacttag acctcaccct    960
gtggagccac accctagggt tggccaatct actcccagga gcaggagggg caggagccag    1020
ggctgggcat aaaagtcagg gcagagccat ctattgctta catttgcttc tgacacaact    1080
gtgttcacta gcaacctcaa acagacacca tggtgcacct gactcctgag gagaagtctg    1140
ccgttactgc cctgtgggc aaggtgaacg tggatgaagt tggtggtgag gccctgggca      1200
ggttggtaca aagttacaa gacaggttta aggagaccaa tagaaactgg gcatgtggag      1260
acagagaaga ctcttgggtt tctgataggc actgactctc tctgcctatt ggtctatttt    1320
cccaccctta ggctgctggt ggtctaccct tggacccaga ggttcttga gtcctttggg      1380
gatctgtcca ctcctgatgc tgttatgggc aaccctaagg tgaaggctca tggcaagaaa    1440
gtgctcggtg cctttagtga tggcctggct cacctggaca acctcaaggg caccttttgc    1500
cagctgagtg agctgcactg tgacaagctg cacgtggatc ctgagaactt caggggtagt    1560
ctatgggacc cttgatgttt tcttccct tcttttctat ggttaagttc atgtcatagg       1620
aaggggagaa gtaacagggt acacatattg accaaatcag ggtaattttg catttgtaat    1680
tttaaaaaat gcttcttct tttaatatac tttttgttt atcttattc taatactttc        1740
cctaatctct ttctttcagg gcaataatga tacaatgtat catgcctctt tgcaccattc    1800
taaagaataa cagtgataat ttctgggtta aggcaatagc aatatttctg catataaata    1860
tttctgcata taaattgtaa ctgatgtaag aggtttcata ttgctaatag cagctacaat    1920
ccagctacca ttctgctttt atttatggt tgggataagg ctggattatt ctgagtccaa      1980
gctaggccct tttgctaatc atgttcatac ctcttatctt cctcccacag ctcctgggca    2040
acgtgctggt ctgtgtgctg gcccatcact tggcaaaga attcacccca ccagtggcagg    2100
ctgcctatca gaaagtggtg gctggtgtgg ctaatgccct ggcccacaag tatcactaag    2160
ctcgctttct tgctgtccaa tttctattaa aggttccttt gttccctaag tccaactact    2220
aaactgggga tattatgaa gggccttgag catctggatt ctgcctaata aaaaacattt      2280
attttcattg caatgatgta tttaaattat ttctgaatat tttactaaaa agggaatgtg    2340
ggaggttgca gtgctagtct cccggaacta tcactctttc acagtctgct ttggaaggac    2400
tgggcttagt atgaaaagtt aggactgaga agaatttgaa aggggcttt ttgtagcttg      2460
atattcacta ctgtcttatt accctatcat aggcccaacc caaatggaag tcccattctt    2520
cctcaggatg tttaagatta gcattcagga agagatcaga ggtctgctgg ctcccttatc    2580
atgtccctta tggtgcttct ggctctgcac gcgcggcacg gggttggggt tgcgcctttt    2640
ccaaggcagc cctgggttg cgcagggacg cggctgctct gggcgtggtt ccgggaaacg      2700
cagcggcgcc gaccctgggt ctcgcacatt tttcacgtcc gttccgcagcg tcacccggat    2760
cttcgcgct acccttgtgg gccccccggc gacgcttcct gctccgcccc taagtcggga    2820
aggttccttg cggttcgcgg cgtgccggac gtgacaaacg gaagccgcac gtctcactag    2880
taccctcgca gacggacagc gccagggagc aatggcagcg cgccgaccgc gatgggctgt    2940
ggccaatagc ggctgctcag cggggcgcgc cgagagcagc ggccgggaag gggcggtgcg    3000
ggaggcgggg tgtggggcgg tagtgtgggc cctgttcctg cccgcgcggt gttccgcatt    3060
ctgcaagcct ccggagcgca cgtcggcagt cggctccccg gttgaccgaa tcaccgacct    3120
ctctccccag cggccgcgcc gccaccatga caaggattg tgaaatgaaa cgcaccacac      3180
tggacagccc tttgggaag ctggagctgt ctggttgtga gcagggtctg cacgaaataa      3240
agctcctggg caaggggacg tctgcagctg atgccgtgga ggtccagcc ccgctgcgg       3300
ttctcggagg tccggagccc ctgatgcagt gcacagcctg gctgaatgcc tatttccacc    3360
agcccgaggc tatcgaagag ttcccccgtgc cggctcttca ccatcccgtt ttcagcaag    3420
```

```
agtcgttcac cagacaggtg ttatggaagc tgctgaaggt tgtgaaattc ggagaagtga  3480
tttcttacca gcaattagca gccctggcag gcaaccccaa agccgcgcga gcagtgggag  3540
gagcaatgag aggcaatcct gtcaaaatcc tcatcccgtg ccacagagtg gtctgcagca  3600
gcggagccgt gggcaactac tccggaggac tggccgtgaa ggaatggctt ctggcccatg  3660
aaggccaccg gttggggaag ccaggcttgg gagggagctc aggtctggca ggggcctggc  3720
tcaagggagc gggagctacc tcgggctccc cgcctgctgg ccgaaactaa gctttatttg  3780
tgaaatttgt gatgctattg ctttatttgt aaccattata agctgcaata aacaagttaa  3840
caacaacaat tgcattcatt ttatgtttca ggttcagggg gagatgtggg aggttttta  3900
aagccctgca ggcaataagcc ttgacaaggc aaccttgacc aatagtctta gagtatcagg  3960
tgaggccagg ggccggcggc tggctaggga tgaagaataa aaggaagcac cctccagcag  4020
ttccacacac tcgcttctgg aacggctgag attatcaata agctcctagt ccagacgcca  4080
tgggtcattt cacagaggag gacaaggcta ctatcacaag cctgtgggc aaggtgaatg  4140
tggaagatgc tggaggagaa accctgggaa ggtaggctct ggtgaccagg acaaggaagg  4200
gaaggaagga ccctgtgcct ggcaaaagtc caggccactt ctcaggattt gtggcacttt  4260
ctgactgtca aactgctctt gttcaatctc acaggctcct ggttgtctac ccatgaccc  4320
agaggttctt tgacagcttt ggcaacctgt cctctgcctc tgccatcatg ggcaacccca  4380
aggtcaaggc acacggcaag aaggtgctga cttccttggg agatgccata agaacctgg  4440
atgatctcaa gggcaccttt gcccagctga gtgagctgca ctgtgacaag ctgcatgtgg  4500
atcctgagaa cttcagggtg agtccaggag tttcagcagt tcagagttc agtctcaagg  4560
cgtcgacagg aaccctagt gatggagttg gccactccct ctgcgcgc tgctcgctc  4620
actgaggccg ggcgaccaaa ggtcgcccga cgcccgggct ttgcccggc ggcctcagtg  4680
agcgaggcag cgcgcagctg gcgtaatagc gaagaggccc gcaccgatcg cccttcccaa  4740
cagttgcgca gcctgaatgg cgaatgggcga ttccgttgca atggctggcg gtaatattgt  4800
tctggatatt accagcaagg ccgatagttt gagttcttct actcaggcaa gtgatgttat  4860
tactaatcaa agaagtattg cgacaacggt taatttgcgt gatggacaga ctcttttact  4920
cggtgcctc actgattata aaaacacttc tcaggattc ggcgtaccgt tcctgtctaa  4980
aatcccttta atcggcctcc tgtttagctc ccgctctgat tctaacgagg aaagcacgtt  5040
atacgtgctc gtcaaagcaa ccatagtacg cgccctgtag cggcgcatta agcgcggcgg  5100
gtgtggtggt tacgcgcagc gtgaccgcta cacttgccag cgccctagcg cccgctcctt  5160
tcgctttctt cccttccttt ctcgccacgt tcgccgggct tccccgtcaa gctctaaatc  5220
ggggctccc tttagggttc cgatttagtg ctttacggca cctcgacccc aaaaaacttg  5280
attagggtga tggttcacgt agtgggccat cgccctgata dacggttttt cgcccttga  5340
cgttggagtc cacgttcttt aatagtgac tcttgttcca aactgaaca acactcaacc  5400
ctatctcggt ctattcttt gatttataag ggattttgcc gatttcggcc tattggttaa  5460
aaaatgagct gatttaacaa aaatttaacg cgaattttaa caaatatta acgtttacaa  5520
tttaaatatt tgcttataca atcttcctgt ttttggggct tttctgatta tcaaccgggg  5580
tacatatgat tgacatgcta gttttacgat taccgttcat cgattctctt gtttgctcca  5640
gactctcagg caatgacctg atagcctttg tagagacctc tcaaaaatag ctaccctctc  5700
cggcatgaat ttatcagcta gaacggttga atatcatatt gatggtgatt tgactgtctc  5760
cggcctttct cacccgtttg aatctttacc tacacattac tcaggcattg catttaaaat  5820
atatgagggt tctaaaaatt ttttatccttg cgttgaaata aaggcttctc ccgcaaaagt  5880
attacagggt cataatgttt ttggtacaac cgatttagct ttatgctctg aggctttatt  5940
gcttaatttt gctaattctt tgccttgcct gtatgatttta ttggatgttg gaatcgcctg  6000
atgcggtatt ttctccttac gcatctgtgc ggtatttcac accgcatatg gtgcactctc  6060
agtacaatct gctctgatgc cgcatagtta agccagcccc gacacccgcc aacacccgct  6120
gacgcgccct gacgggcttg tctgctcccg gcatccgctt acagacaagc tgtgaccgtc  6180
tccgggagct gcatgtgtca gaggttttca ccgtcatcac cgaaacgcgc gagacgaaag  6240
ggcctcgtga tacgcctatt tttataggtt aatgtcatga taataatggt tcttagacgt  6300
tcaggtggca cttttcgggg aaatgtgcgc ggaaccccta tttgtttatt tttctaaata  6360
cattcaaata tgtatccgct catgagacaa taaccctgat aaatgcttca ataatattga  6420
aaaaggaaga gtatgagtat tcaacatttc cgtgtcgccc ttattccctt ttttgcggca  6480
ttttgccttc ctgtttttgc tcacccagaa acgctggtga agtaaaaga tgctgaagat  6540
cagttgggtg cacgagtggg ttacatcgaa ctggatctca acagcggtaa gatccttgag  6600
agttttcgcc ccgaagaacg ttttccaatg atgagcactt ttaaagttct gctatgtggc  6660
gcggtattat cccgtattga cgccgggcaa gagcaactcg gtcgccgcat acactattct  6720
cagaatgact tggttgagta ctcaccagtc acagaaaagc atcttacgga tggcatgaca  6780
gtaagagaat tatgcagtgc tgccataacc atgagtgata acactgcggc caacttactt  6840
ctgacaacga tcggaggacc gaaggagcta accgcttttt tgcacaacat ggggatcat  6900
gtaactcgcc ttgatcgttg ggaaccggag ctgaatgaag ccataccaaa cgacgagcgt  6960
gacaccacga tgcctgtagc aatggcaaca acgttgcgca aactattaac tggcgaacta  7020
cttactctag cttcccggca acaattaata gactggatgg aggcggataa agttgcagga  7080
ccacttctgc gctcggccct tccggctggc tggtttattg ctgataaatc tggagccggt  7140
gagcgtgggt ctcgcggtat cattgcagca ctggggccag atggtaagcc ctcccgtatc  7200
gtagttatct acacgacggg gagtcaggca actatggatg acgatatcc  7260
gagataggtg cctcactgat taagcattgg taactgtcag accaagttta ctcatatata  7320
ctttagattg atttaaaact tcattttaa tttaaaagga tctaggtgaa gatccttttt  7380
gataatctca tgaccaaaat cccttaacgt gagttttcgt tccactgagc gtcagacccc  7440
gtagaaaaga tcaaaggatc ttcttgagat ccttttttc tgcgcgtaat ctgctgcttg  7500
caaacaaaaa aaccaccgct accagcggtg gtttgtttgc cggatcaaga gctaccaact  7560
cttttccga aggtaactgg cttcagcaga gcgcagatac caaatactgt ccttctagtg  7620
tagccgtagt taggccacca cttcaagaac tctgtagcac cgcctacata cctcgctctg  7680
ctaatcctgt taccagtggc tgctgccagt ggcgataagt cgtgtcttac cgggttggac  7740
tcaagacgat agttaccgga taaggcgcag cggtcgggct gaacgggggg ttcgtgcaca  7800
cagcccagct tggagcgaac gacctacacc gaactgagat acctacagcg tgagctatga  7860
gaaagcgcca cgcttcccga agggagaaag gcggacaggt atccggtaag cggcagggtc  7920
ggaacaggag agcgcacgag ggagcttcca ggggaaacg cctggtatct ttatagtcct  7980
gtcgggtttc gccacctctg acttgagcgt cgatttttgt gatgctcgtc aggggggcgg  8040
agcctatgga aaaacgccag caacgcggcc tttttacggt tcctggcctt ttgctggcct  8100
tttgctcaca tgttctttcc tgcgttatcc cctgattctg tggataaccg tattaccgcc  8160
```

```
tttgagtgag ctgataccgc tcgccgcagc cgaacgaccg agcgcagcga gtcagtgagc   8220
gaggaagcgg aagagcgccc aatacgcaaa ccgcctctcc ccgcgcgttg gccgattcat   8280
taatg                                                              8285

SEQ ID NO: 22           moltype = DNA   length = 7095
FEATURE                 Location/Qualifiers
source                  1..7095
                        mol_type = other DNA
                        organism = Synthetic construct
SEQUENCE: 22
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actagggggtt ccttgtagtt aatgattaac cgccatgct acttatctac acgcgtagat    180
ctagccagtg tttaccattg cagaatgtac atgcgactga aagggtgagg aaacctggga    240
aatgtcagtt cctcaaatac agagaacact gagggaagga tgagaaataa atgtgaaagc    300
agacatgaat ggtaattgac agaaggaaac taggatgtgt ccagtaaatg aataattaca    360
gtgtgcagtg attattgcaa tgattaatgt atgataagat aatatgaaaa cacagaattc    420
aaacagcagt gaactgagat tagaattgtg gagagcactg gcatttaaga atgtcacact    480
tagaatgtgt ctctaggcat tgttctgtgc atatatcatc tcaatattca ttatctgaaa    540
attatgaatt aggtacaaag ctcaaataat ttatttttc aggttagcaa gaactttttt     600
ttttttttc tgagatagag cattgctatg gttgcccagg ctggagtgca atggcatgat     660
ccaggctcac tgcaacatct gcctcccagg ttcaagcgat tctcctgcct cagcctccca    720
agtagctggc actacaggca tgtgccacca ccatgcctgg ctaattttct atttttagta    780
gaccgcggga acagagaaac aggagaatat gggccaaaca ggatatctgt ggtaagcagt    840
tcctgccccg gctcagggcc aagaacagtt ggaacagcag aatatgggcc aaacaggata    900
tctgtggtaa gcagttcctg ccccggctca gggccaagaa cagtggtcc ccagatgcgg     960
tcccgccctc agcagtttct agagaaccat cagatgtttc cagggtgccc caaggacctg   1020
aaatgaccct gtgccttatt tgaactaacc aatcagttcg cttctcgctt ctgttcgcgc   1080
gcttctgctc cccgagctct atataagcag agctcgttta gtgaaccgtc agatcgcctg   1140
gagacgccat ccacgctgtt ttgacttcca tagaaggcgg ccgcgccgcc accatggtta   1200
gcaagggcga ggagctgttc accggggtgg tgcccatcct ggtcgagctg gacggcgacg   1260
taaacggcca aagttcagc gtgtccggcg agggcgaggg cgatgccacc tacggcaagc    1320
tgaccctgaa gttcatctgc accaccggca agctgcccgt gccctggccc accctcgtga   1380
ccacccctgac ctacggcgtg cagtgcttca gccgctaccc cgaccacatg aagcagcacg   1440
acttcttcaa gtccgccatg cccgaaggct acgtccagga gcgcaccatc ttcttcaagg   1500
acgacggcaa ctacaagacc cgcgccgagg tgaagttcga gggcgacacc ctggtgaacc   1560
gcatcgagct gaagggcatc gacttcaagg aggacggcaa catcctgggg cacaagctgg   1620
agtacaacta caacagccac aacgtctata tcatggccga caagcagaag aacggcatca   1680
aggtgaactt caagatccgc cacaacatcg aggacggcag cgtgcagctc gccgaccact   1740
accagcagaa cacccccatc ggcgacggcc ccgtgctgct gcccgacaac cactacctga   1800
gcacccagtc cgccctgagc aaagacccca acgagaagcg cgatcacatg gtcctgctgg   1860
agttcgtgac cgccgccggg atcactctcg gcatggacga gctgtacaag taacctgcag   1920
ggagcatctt accgccattt attccatat ttgttctgatt tttcttgatt tgggtataca    1980
tttaaatgtt aataaaacaa aatggtgggg caatcattta catttttagg gatatgtaat   2040
tactagttca ggtgtattgc cacaagacaa acatgttaag aaactttccc gttatttacg   2100
ctctgttcct gttaatcaac ctctggatta caaaattgt gaaagattga ctgatattct   2160
taactatgtt gctccttta cgctgtgtgg atatgctgct ttatagcctc tgtatctagc    2220
tattgcttcc cgtacggctt tcgttttctc ctccttgtat aaatcctggt tgctgtctct   2280
tttagaggag ttgtggcccg ttgtccgtca acgtggcgtg gtgtgctctg tgtttgctga   2340
cgcaaccccc actggctggg gcattgccac cacctgtcaa ctccttttctg gactttcgc    2400
tttccccctc ccgatcgcca cggcagaact catcgccgcc tgccttgccc gctgctggac   2460
aggggctagg ttgctgggca ctgataattc cgtggtgttg tctgtgcctt ctagttgcca   2520
gccatctgtt gtttgcccct ccccgtgcc ttccttgacc ctggaaggtg ccactcccac    2580
tgtcctttcc taataaaatg aggaaattgc atcgcattgt ctgagtaggt gtcattctat   2640
tctgggggt ggggtggggc aggacagcaa ggggaggat tgggaagaca atagcaggca    2700
tgctggggat gcggtgggct ctatggcagg gcaagttaag ggaatagtgg aatgaaggtt   2760
cattttcat tctcacaaac taatgaaacc ctgcttatct taaaccaacc tgctcactgg    2820
agcagggagg acaggaccag cataaaaggc agggcagagt cgactgttgc ttacactttc   2880
ttctgacata acagtgttca ctagcaacct caaacagaca catggtgca tctgactcct    2940
gaggagaaga ctgctgtcaa tgccctgtgg ggcaaagtga acgtggatgc agttggtggt   3000
gaggccctgg gcaggttggt atcaaggtta taagagaggc tcaaggaggc aaatggaaac   3060
tgggcatgtg tagacagaga agactcttgg gtttctgata ggcactgact ctctgtccct   3120
tgggctgttt tcctaccctc agattactgg tggtctaccc ttggacccag aggttctttg   3180
agtccttttgg ggatctgtcc tctcctgatg ctgttatggg caaccctaag gtgaaggctc   3240
atggcaagaa ggtgctaggt gcctttagtg atgcctggc tcacctggac aacctcaagg   3300
gcacttttc tcagctgagt gagctgcctc gaggtcgacg tagataagta gcatggcggg   3360
ttaatcatta actacaagga acccctagtg atggagttgg ccactccctc tctgcgcgct   3420
cgctcgctca ctgaggccgg gcgaccaaag gtcgcccgac gcccgggctt tgcccgggcg   3480
gcctcagtga gcgagcgagc gcgcagctg gcgtaatagc gaagaggccc gcaccgatcg   3540
cccttcccaa cagttgcgca gcctgaatgg cgaatggcga ttccgttgca atggctggc    3600
gtaatattgt tctggatatt accagcaagg ccgatagttt gagttcttct actcaggcaa   3660
gtgatgttat tactaatcaa agaagtattg cgacaacggt taatttgcgt gatggacaga   3720
ctcttttact cggtggcctc actgattata aaaacacttc tcaggattct ggcgtaccgt   3780
tcctgtctaa aatccctta atcggcctcc tgtttagctc ccgctctgat tctaacgagg   3840
aaagcacgtt atacgtgctc gtcaaagcaa ccatagtacg cgccctgtag cggcgcatta   3900
agcgcggcgg gtgtggtggt tacgcgcagc gtgaccgcta cacttgccag cgccctagcg   3960
cccgctcctt tcgctttctt cccttccttt ctcgccacgt tcgccggctt tccccgtcaa   4020
gctctaaatc gggggctccc tttagggttc cgatttagtg ctttacgca cctcgacccc    4080
aaaaaacttg attagggtga tggttcacgt agtgggccat cgccctgata gacggttttt   4140
```

```
cgcccttga cgttggagtc cacgttcttt aatagtggac tcttgttcca aactggaaca   4200
acactcaacc ctatctcggt ctattctttt gatttataag ggattttgcc gatttcggcc   4260
tattggttaa aaaatgagct gatttaacaa aaatttaacg cgaattttaa caaaatatta   4320
acgtttacaa tttaaatatt tgcttataca atcttcctgt ttttgggget tttctgatta   4380
tcaaccgggg tacatatgat tgacatgcta gtttacgat taccgttcat cgattctctt   4440
gtttgctcca gactctcagg caatgacctg atagcctttg tagagacctc tcaaaaatag   4500
ctaccctctc cggcatgaat ttatcagcta gaacggttga atatcatatt gatggtgatt   4560
tgactgtctc cggcctttct cacccgtttg aatctttacc tacacattac tcaggcattg   4620
catttaaaat atatgagggt tctaaaaatt tttatccttg cgttgaaata aaggcttctc   4680
ccgcaaaagt attacagggt cataatgttt ttggtacaac cgatttagct ttatgctctg   4740
aggctttatt gcttaatttt gctaattctt tgccttgcct gtatgattta ttggatgttg   4800
gaatcgcctg atgcggtatt ttctccttac gcatctgtgc ggtatttcac accgcatatg   4860
gtgcactctc agtacaatct gctctgatgc cgcatagtta agccagcccc gacacccgcc   4920
aacacccgct gacgcgccct gacgggcttg tctgctcccg gcatccgctt acagacaagc   4980
tgtgaccgtc tccgggagct gcatgtgtca gaggttttca ccgtcatcac cgaaacgcgc   5040
gagacgaaag ggcctcgtga tacgcctatt tttataggtt aatgtcatga taataatggt   5100
ttcttagacg tcaggtggca cttttcgggg aaatgtgcgc ggaaccccta tttgtttatt   5160
tttctaaata cattcaaata tgtatccgct catgagacaa taaccctgat aaatgcttca   5220
ataatattga aaaaggaaga gtatgagtat tcaacatttc cgtgtcgccc ttattccctt   5280
ttttgcgca ttttgccttc ctgtttttgc tcacccagaa acgctggtga agtaaaaga   5340
tgctgaagat cagttgggtg cacgagtggg ttacatcgaa ctggatctca acagcggtaa   5400
gatccttgag agttttcgcc ccgaagaacg ttttccatg atgagcactt ttaaagttct   5460
gctatgtggc gcggtattat cccgtattga cgccgggcaa gagcaactcg gtcgccgcat   5520
acactattct cagaatgact tggttgagta ctcaccagtc acagaaaagc atcttacgga   5580
tggcatgaca gtaagagaat tatgcagtgc tgccataacc atgagtgata acactgcggc   5640
caacttactt ctgacaacga tcggaggacc gaaggagctaa accgcttttt tgcacaacat   5700
gggggatcat gtaactcgcc ttgatcgttg gaaccggag ctgaatgaag ccataccaaa   5760
cgacgagcgt gacaccacga tgcctgtagc aatggcaaca acgttgcgca aactattaac   5820
tggcgaacta cttactctag cttcccggca caattaata gactggatgg aggcggataa   5880
agttgcagga ccacttctgc gctcggccct tccggctggc tggtttattg ctgataaatc   5940
tggagccggt gagcgtgggt ctcgcggtat cattgcagca ctggggccag atggtaagcc   6000
ctcccgtatc gtagttatct acacgacggg gagtcaggca actatggatg aacgaaatag   6060
acagatcgct gagataggtg cctcactgat taagcattgg taactgtcag accaagttta   6120
ctcatatata ctttagattg atttaaaact tcattttta tttaaaagga tctaggtgaa   6180
gatcctttt gataatctca tgaccaaaat cccttaacgt gagttttcgt tccactgagc   6240
gtcagacccc gtagaaaaga tcaaaggatc ttcttgagat cctttttttc tgcgcgtaat   6300
ctgctgcttg caaacaaaaa aaccaccgct accagcggtg gtttgtttgc cggatcaaga   6360
gctaccaact ctttttccga aggtaactgg cttcagcaga gcgcagatac caaatactgt   6420
ccttctagtg tagccgtagt taggccacca cttcaagaac tctgtagcac cgcctacata   6480
cctcgctctg ctaatcctgt taccagtggc tgctgccagt ggcgataagt cgtgtcttac   6540
cgggttggac tcaagacgat agttaccgga taaggcgcag cggtcgggct gaacgggggg   6600
ttcgtgcaca cagcccagct tggagcgaac gacctacacc gaactgagat acctacagcg   6660
tgagctatga gaaagcgcca cgcttcccga agggagaaag gcggacaggt atccggtaag   6720
cggcagggtc ggaacaggag agcgcacgag ggagcttcca gggggaaacg cctggtatct   6780
ttatagtcct gtcgggtttc gccacctctg acttgagcgt cgatttttgt gatgctcgtc   6840
aggggggcgg agcctatgga aaaacgccag caacgcggcc tttttacggt tcctggcctt   6900
ttgctggcct tttgctcaca tgttctttcc tgcgttatcc cctgattctg tggataaccg   6960
tattaccgcc tttgagtgag ctgataccgc tcgccgcagc cgaacgaccg agcgcagcga   7020
gtcagtgagc gaggaagcgg aagagcgccc aatacgcaaa ccgcctctcc ccgcgcgttg   7080
gccgattcat taatg                                                   7095

SEQ ID NO: 23           moltype = DNA   length = 7809
FEATURE                 Location/Qualifiers
source                  1..7809
                        mol_type = other DNA
                        organism = Synthetic construct
SEQUENCE: 23
cagctgcgcg ctcgctcgct cactgaggcc gcccgggcaa agcccgggcg tcgggcgacc   60
tttggtcgcc cggcctcagt gagcgagcga gcgcgcagag agggagttgg caactccatc   120
actaggggtt ccttgtagtt aatgattaac ccgccatgct acttatctac acgcgtagat   180
ctagccagtg tttaccattg cagaatgtac atgcgactga aagggtgagg aaacctggga   240
aatgtcagtt cctcaaatac agagaacact gagggaagga tgagaaataa atgtgaaagc   300
agacatgaat ggtaattgac agaaggaaac taggatgtgt ccagtaaatg aataattaca   360
gtgtgcagtg attattgcaa tgattaatgt atgataagat aatatgaaaa cacagaattc   420
aaacagcagt gaactgagat tagaattgtg gagagcactg gcatttaaga atgtcacact   480
tagaatgtgt ctctaggcat tgttctgtgc atatatcatc tcaatattca ttatctgaaa   540
attatgaatt aggtacaaag ctcaaataat ttattttttc aggttagcaa gaactttttt   600
ttttttttc tgagatagag cattgctatg gttgcccagg ctggagtgca atggcatgat   660
ccaggctcac tgcaacatct gcctcccagg ttcaagcgat tctcctgcct cagcctccca   720
agtagctggc actacaggca tgtgccacca ccatgcctgg ctaattttct atttttagta   780
gacgagatcg agaccatcct ggctaacaca gtgaaacccc gtctctacta aaaaaataca   840
aaaaattagc cgggcttggt ggcgggtgcc tgtagtccca gctactatgg aggctgaggc   900
gggagaatgg cgtgaacgcg gggggcggag cttgcagtga gcagagatca ggggccactg   960
cactccgagg tgggcgaaca gagagactc tgtctcaaaa aaagaaaaa aaaattag      1020
tagactagct aaaaaaaatc cagagatagt attgatgcat atgtaaaagt cttccaatat   1080
ttacaagtac aatgaaaaaa aaataacctt gaattaagtg tagaactcat tgacaatgtt   1140
tcaaaggatg tgagggataa actaaaattt ggcagtaca tgctgttcct gtgtacttgg   1200
aacagaggga gaaatctggg ctggaaata ttgttatagg agttagcaca tgaaggtgac   1260
aactaaaatta tttggagtag atggagtcac cagcacatgt gaatagtttt agaatgaaat   1320
```

```
gacccaagat agaactttgg agagccccca aatttaaata aaatcagtat aagagaagag   1380
gaagaaacca aatggtatac tagtctaaat tgtttcttag tgacaaaaga ataacctgaa   1440
tattagatta gctgcctata tgctctctga atcaatttca ttcaacatgc aacagtccgc   1500
gggaacagag aaacaggaga atatgggcca aacaggatat ctgtggtaag cagttcctgc   1560
cccggctcag ggccaagaac agttggaaca gcagaatatg ggccaaacag gatatctgtg   1620
gtaagcagtt cctgccccgg ctcagggcca agaacagatg gtccccagat gcggtcccgc   1680
cctcagcagt ttctagagaa ccatcagatg tttccagggt gccccaagga cctgaaatga   1740
ccctgtgcct tatttgaact aaccaatcag ttcgcttctc gcttctgttc gcgcgcttct   1800
gctccccgag ctctatataa gcagagctcg tttagtgaac cgtcagatcg cctggagacg   1860
ccatccacgc tgttttgact tccatagaag gcggccgcgc cgccaccatg gtgagcaagg   1920
gcgaggagct gttcaccggg gtggtgccca tcctggtcga gctggacggc gacgtaaacg   1980
gccacaagtt cagcgtgtcc ggcgagggcg agggcgatgc cacctacggc aagctgaccc   2040
tgaagttcat ctgcaccacc ggcaagctgc ccgtgccctg gcccaccctc gtgaccaccc   2100
tgacctacgg cgtgcagtgc ttcagccgct accccgacca catgaagcag cacgacttct   2160
tcaagtccgc catgcccgaa ggctacgtcc aggagcgcac catcttcttc aaggacgacg   2220
gcaactacaa gacccgcgcc gaggtgaagt tcgagggcga caccctggtg aaccgcatcg   2280
agctgaaggg catcgacttc aaggaggacg gcaacatcct ggggcacaag ctggagtaca   2340
actacaacag ccacaacgtc tatatcatgg ccgacaagca gaagaacggc atcaaggtga   2400
acttcaagat ccgccacaac atcgaggacg gcagcgtgca gctcgccgac cactaccagc   2460
agaacacccc catcggcgac ggccccgtgc tgctgcccga caaccactac ctgagcaccc   2520
agtccgccct gagcaaagac cccaacgaga gcgcgatca catggtcctg ctggagttcg   2580
tgaccgccgc cgggatcact ctcggcatgg acgagctgta caagtaacct gcagggagca   2640
tcttaccgcc atttattccc atatttgttc tgttttctt gatttgggta tacatttaaa   2700
tgttaataaa acaaaatggt ggggcaatca tttacatttt tagggatatg taattactag   2760
ttcaggtgta ttgccacaag acaaacatgt taagaaactt tcccgttatt tacgctctgt   2820
tcctgttaat caacctctgg attacaaaat ttgtgaaaga ttgactgata ttcttaacta   2880
tgttgctcct tttacgctgt gtggatatgc tgctttatag cctctgtatc tagctattgc   2940
ttcccgtacg gctttcgttt tctcctcctt gtataaatcc tggttgctgt ctcttttaga   3000
ggagttgtgg cccgttgtcc gtcaacgtgg cgtggtgtgc tctgtgtttg ctgacgcaac   3060
ccccactggc tggggcattg ccaccacctg tcaactcactg tcgggactt tcgctttccc   3120
cctcccgatc gccacggcag aactcatcgc cgcctgcctt gcccgctgct ggacaggggc   3180
taggttgctg ggcactgata attccgtggt gttgtctgtg ccttctagtt gccagccatc   3240
tgttgtttgc ccctcccccg tgccttcctt gaccctggaa ggtgccactc ccactgtcct   3300
ttcctaataa aatgaggaaa ttgcatcgca ttgtctgagt aggtgtcatt ctattctggg   3360
gggtggggtg gggcaggaca gcaaggggga ggattgggaa gacaatagca ggcatgctggg   3420
ggatgcggtg ggctctatgg cagggcaagt taagggaata gtgaatgaa ggttcatttt   3480
tcattctcac aaactaatga aaccctgctt atcttaaacc aacctgctca ctggagcagg   3540
gaggacagga ccagcataaa aggcagggca gagtcgactg ttgcttacac tttcttctga   3600
cataacagtg ttcactagca acctcaaaca gacaccatgg tgcatctgac tcctgaggag   3660
aagactgctg tcaatgccct gtggggcaaa gtgaacgtgg atgcagttgg tggtgaggcc   3720
ctgggcaggt tggtatcaag gttataagag aggctcaagg aggcaaatgg aaactgggca   3780
tgtgtagaca gagaagactc ttgggtttct gataggcact gactctctgt cccttgggct   3840
gttttcctac cctcagatta ctggtggtct acccttggac tcagaggttc tttgagtcct   3900
ttggggatct gtcctctcct gatgctgtta tgggcaaccc taaggtgaag gctcatggca   3960
agaaggtgct aggtgccttt agtgatggcc tggctcacct ggacaacctc aagggcactt   4020
tttctcagct gagtgagctg cctcgaggtc gacgtagata agtagcatgg cggttaatc   4080
attaactaca aggaaccct agtgatggga ttggccactc cctctctgcg ctgctcgtcg   4140
ctcactgagg ccgggcgacc aaaggtcgcc cgacgcccgg gctttgcccg gcggcctca   4200
gtgagcgagc gagcgcgcca gctggcgtaa tagcgaagag gcccgcaccg atcgcccttc   4260
ccaacagttg cgcagcctga atggcgaatg gcgattccgt tgcaatggct ggcggtaata   4320
ttgttctgga tattaccagc aaggccgata gtttgagttc ttctactcag gcaagtgatg   4380
ttattactaa tcaaagaagt attgcgacaa cggttaattt gcgtgatgga cagactcttt   4440
tactcggtgg cctcactgat tataaaaaca cttctcagga ttctggcgta ccgttcctgt   4500
ctaaaatccc tttaatcggc ctcctgttta gctcccgctc tgattctaac gaggaaagca   4560
cgttatacgt gctcgtcaaa gcaaccatag tacgcgcctc gtagcggcgc attaagcgcg   4620
gcgggtgtgg tggttacgcg cagcgtgacc gctacacttg ccagcgccct agcgcccgct   4680
cctttcgctt tcttcccttc ctttctcgcc acgttcgccg gctttccccg tcaagctcta   4740
aatcggggg ccctttagg gttccgattt agtgctttac ggcacctcga cccaaaaaaa   4800
cttgattagg gtgatggttc acgtagtggg ccatcgccct gatagacgtt ttttcgccct   4860
ttgacgttgg agtccacgtt ctttaatagt ggactcttgt tccaaactgg aacaacactc   4920
aaccctatct cggtctattc ttttgattta aagggattt tgccgatttc ggcctattgg   4980
ttaaaaatg agctgattta acaaaaattt aacgcgaatt ttaacaaaat attaacgttt   5040
acaatttaaa tatttgctta tacaatcttc ctgtttttgg ggcttttctg attatcaacc   5100
ggggtacata tgattgacat gctagtttta cgattaccgt tcatcgattc tcttgtttgc   5160
tccagactct caggcaatga cctgatagcc tttgtagaga cctctcaaaa atagctaccc   5220
tctccggcat gaatttatca gctagaacgg ttgaatatca tattgatggt gatttgactg   5280
tctccggcct ttctcacccg tttgaatctt tacctacaca ttactcaggc attgcattta   5340
aaatatatga gggttctaaa aatttttatc cttgcgttga aataaaggct tctcccgcaa   5400
aagtattaca gggtcataat gttttttggta caaccgattt agctttatgc tctgaggctt   5460
tattgcttaa ttttgctaat tctttgcctt gcctgtatga tttattggat gttggaatcg   5520
cctgatgcgg tattttctcc ttacgcatct gtgcggtatt tcacaccgca tatggtgcac   5580
tctcagtaca atctgctctg atgccgcata gttaagccag ccccgacacc cgccaacacc   5640
cgctgacgcg ccctgacggg cttgtctgct cccggcatcc gcttacagac aagctgtgac   5700
cgtctccggg agctgcatgt gtcagaggtt ttcaccgtca tcaccgaaac gcgcgagacg   5760
aaagggcctc gtgatacgcc tatttttata ggttaatgtc atgataataa tggtttctta   5820
gacgtcaggt ggcactttc ggggaaatgt gcgcggaacc cctatttgtt tatttttcta   5880
aatacattca aatatgtatc cgctcatgag acaataaccc tgataaatgc ttcaataata   5940
ttgaaaaagg aagagtatga gtattcaaca tttccgtgtc gcccttattc ccttttttgc   6000
ggcatttgc cttcctgttt ttgctcaccc agaaacgctg gtgaaagtaa aagatgctga   6060
```

```
agatcagttg ggtgcacgag tgggttacat cgaactggat ctcaacagcg gtaagatcct   6120
tgagagtttt cgccccgaag aacgttttcc aatgatgagc acttttaaag ttctgctatg   6180
tggcgcggta ttatcccgta ttgacgccgg gcaagagcaa ctcggtcgcc gcatacacta   6240
ttctcagaat gacttggttg agtactcacc agtcacagaa aagcatctta cggatggcat   6300
gacagtaaga gaattatgca gtgctgccat aaccatgagt gataacactg cggccaactt   6360
acttctgaca acgatcggag gaccgaagga gctaaccgct tttttgcaca acatggggga   6420
tcatgtaact cgccttgatc gttgggaacc ggagctgaat gaagccatac caaacgacga   6480
gcgtgacacc acgatgcctg tagcaatggc aacaacgttg cgcaaactat taactggcga   6540
actacttact ctagcttccc ggcaacaatt aatagactgg atggaggcgg ataaagttgc   6600
aggaccactt ctgcgctcgg cccttccggc tggctggttt attgctgata aatctggagc   6660
cggtgagcgt gggtctcgcg gtatcattgc agcactgggg ccagatggta agccctcccg   6720
tatcgtagtt atctacacga cggggagtca ggcaactatg gatgaacgaa atagacagat   6780
cgctgagata ggtgcctcac tgattaagca ttggtaactg tcagaccaag tttactcata   6840
tatactttag attgatttaa aacttcattt ttaatttaaa aggatctagg tgaagatcct   6900
ttttgataat ctcatgacca aaatcccttta acgtgagttt tcgttccact gagcgtcaga   6960
ccccgtagaa aagatcaaag gatcttcttg agatcctttt tttctgcgcg taatctgctg   7020
cttgcaaaca aaaaaaccac cgctaccagc ggtggtttgt ttgccggatc aagagctacc   7080
aactcttttt ccgaaggtaa ctggcttcag cagagcgcag ataccaaata ctgtccttct   7140
agtgtagccg tagttaggcc accacttcaa gaactctgta gcaccgccta catacctcgc   7200
tctgctaatc ctgttaccag tggctgctgc cagtggcgat aagtcgtgtc ttaccgggtt   7260
ggactcaaga cgatagttac cggataaggc gcagcggtcg ggctgaacgg ggggttcgtg   7320
cacacagccc agcttggagc gaacgaccta ccgaactg agataccta gcgtgagctt   7380
atgagaaagc gccacgcttc ccgaagggag aaaggcggac aggtatccgg taagcggcag   7440
ggtcggaaca ggagagcgca cgagggagct tccaggggga aacgcctggt atctttatag   7500
tcctgtcggg tttcgccacc tctgacttga gcgtcgattt ttgtgatgct cgtcagggg   7560
gcggagccta tggaaaaacg ccagcaacgc ggcctttta cggttcctgg ccttttgctg   7620
gccttttgct cacatgttct ttcctgcgtt atcccctgat tctgtggata accgtattac   7680
cgcctttgag tgagctgata ccgctcgccg cagccgaacg accgagcgca gcgagtcagt   7740
gagcgaggaa gcggaagagc gcccaatacg caaaccgcct ctccccgcgc gttggccgat   7800
tcattaatg                                                          7809

SEQ ID NO: 24             moltype = DNA  length = 6726
FEATURE                   Location/Qualifiers
source                    1..6726
                          mol_type = other DNA
                          organism = Synthetic construct
SEQUENCE: 24
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc   120
actaggggtt ccttgtagtt aatgattaac cgccatgct acttatctac acgcgtagat   180
ctacgtactt taggctgtat atgtgtttat atacagtgaa atgtcaagtt ctttctttat   240
atttcttct ttctttttt tcctcagcct cagagtttc cacatgccct tcctactttc   300
aggaacttct ttctccaaac gtcttctgcc tggctccatc aaatcataaa gacccactt   360
caaatgccat cactcactac catttcacaa ttcgcacttt cttctttgt cctttttttt   420
tttagtaaaa caagtttata aaaaattgaa ggaataaatg aatggctact tcataggcag   480
agtagacgca agggctactg gttgccgatt tttattgtta tttttcaata gtatgctaaa   540
caagggtag attatttatg ctgcccattt ttagaccata aaagataact tcctgatgtt   600
gccatggcat ttttttcctt taatttttat ttcattttcat tttaatttcg aaggtacatg   660
tgcaggatgt gcaggcttgt tacatgggta atgtgtgtc tttctggcct tttagccatc   720
tgtatcaatg agcagatata agcttacac aggatcatga aggatgaaag aatttcacca   780
atccgcggga acagagaaac aggagaatat gggccaaaca ggatatctgt ggtaagcagt   840
tcctgccccg gctcagggcc aagaacagtt ggaacagcag aatatgggcc aaacaggata   900
tctgtggtaa gcagttcctg cccccggctca gggccaagaa cagatggtcc ccagatgcgg   960
tcccgccctc agcagtttct agagaaccat cagatgtttc caggggtgccc caaggacctg   1020
aaatgctctc gtgcctatt tgaactaacc aatcagttcg cttctcgctt ctgttcgcgc   1080
gcttctgctc cccgagctct atataagcag agctcgttta gtgaaccgtc agatcgcctg   1140
gagacgccat ccacgctgtt ttgacttcca tagaaggcgg ccgcgccgcc accatggtga   1200
gcaagggcga ggagctgttc accggggtgg tgcccatcct ggtcgagctg gacggcgacg   1260
taaacggcca caagttcagc gtgtccggcg agggcgaggg cgatgccacc tacggcaagc   1320
tgaccctgaa gttcatctgc accaccggca agctgcccgt gcccctggcc accctcgtga   1380
ccaccctgac ctacggcgtg cagtgcttca gccgctaccc cgaccacatg aagcagcacg   1440
acttcttcaa gtccgccatg cccgaaggct acgtccagga gcgcaccatc ttcttcaagg   1500
acgacggcaa ctacaagacc cgcgccgagg tgaagttcga gggcgacacc ctggtgaacc   1560
gcatcgagct gaagggcatc gacttcaagg aggacggcaa catcctgggg cacaagctgg   1620
agtacaacta caacagccac aacgtctata tcatggccga caagcagaag aacggcatca   1680
aggtgaactt caagatccgc cacaacatcg aggacggcag cgtgcagctc gccgaccact   1740
accagcagaa caccccatc ggcgacggcc ccgtgctgct gcccgacaac cactacctga   1800
gcacccagtc cgccctgagc aaagacccca acgagaagcg cgatcacatg gtcctgctgg   1860
agttcgtgac cgccgccggg atcactctcg gcatgacga gctgtacaag taacctgcag   1920
ggataatcaa cctctggatt acaaaatttg tgaaagattg actggtattc ttaactatgt   1980
tgctcctttt acgctatgtg gatacgctgc tttaatgcct ttgtatcatg ctattgcttc   2040
ccgtatggct ttcattttct cctccttgta taaatcctgg ttagttcttg ccacggcgga   2100
actcatcgcc gcctgccttg cccgctgctg acagggct cggctgttgg cactgacaa   2160
ttccgtggtg ttgtcgggga aattgtga tgctattgct ttatttgtaa ccattataag   2220
ctgcaataaa caagttaaca caacaattg cattcatttt atgtttcagg ttcaggggga   2280
gtgtgggag gttttttaaa gcgaattcag gcctcactgg agctagagac aagaaggtaa   2340
aaacgctg acaaaagaag tcctggtatc ctctatgatg ggagaaggaa actagctaaa   2400
gggaagaata aattagagaa aaactggaat gactgaatcg gaacaaggca aaggctataa   2460
aaaaaattag                                                          2520
```

```
cagtatcctc ttgggggccc cttccccaca ctatctcaat gcaaatatct gtctgaaacg    2580
gtccctggct aaactccacc catgggttgg ccagccttgc cttgaccaat agccttgaca    2640
aggcaaactt gaccaatagt cttagagtat ccagtgaggc caggggccgg cggctggcta    2700
gggatgaaga ataaaaggaa gcacccttca gcagttccac acactcgctt ctggaacgtc    2760
tgaggttatc aataagctcc tagtccagac gccatgggct atttcacaga ggaggacaag    2820
gctactatca caagcctgtg gggcaaggtg aatgtggaag atgctggagg agaaaccctg    2880
ggaaggtagg ctctggtgac caggacaagg gagggaagga aggaccctgt gcctggcaaa    2940
agtccaggtc gcttctcact cgaggtcgac gtagataagt agcatggcgg gttaatcatt    3000
aactacaagg aaccccctagt gatggagttg gccactccct ctctgcgcgc tcgctcgctc    3060
actgaggccg ggcgaccaaa ggtcgcccga cgcccgggct ttgcccgggc ggcctcagtg    3120
agcgagcgag cgcgccagct ggcgtaatag cgaagaggcc cgcaccgatc gcccttccca    3180
acagttgcgc agcctgaatg gcgaatgcgc attccgttgc aatggctggc ggtaatattg    3240
ttctggatat taccagcaag gccgatagtt tgagttcttc tactcaggca agtgatgtta    3300
ttactaatca aagaagtatt gcgacaacgg ttaatttgcg tgatggacag actcttttac    3360
tcggtggcct cactgattat aaaaacactt ctcaggattc tggcgtaccg ttcctgtcta    3420
aaatcccttt aatcggcctc ctgtttagct cccgctctga ttctaacgag gaaagcacgt    3480
tatacgtgct cgtcaaagca accatagtac gcgccctgta gcggcgcatt aagcgcggcg    3540
ggtgtggtgg ttacgcgcag cgtgaccgct acacttgcca gcgccctagc gcccgctcct    3600
ttcgctttct tcccttcctt tctcgccacg ttcgccggct ttccccgtca gctctaaat    3660
cggggggctcc ctttagggtt ccgatttagt gctttacggc acctcgaccc caaaaaactt    3720
gattaggtg atggttcacg tagtgggcca tcgccctgat agacggtttt tcgccctttg    3780
acgttggagt ccacgttctt taatagtgga ctcttgttcc aaactggaac aacactcaac    3840
cctatctcgg tctattcttt tgatttataa gggattttgc cgatttcggc ctattggtta    3900
aaaaatgagc tgatttaaca aaaatttaac gcgaatttta acaaaatatt aacgtttaca    3960
atttaaatat ttgcttatac aatcttcctg ttttggggct ttttctgatt atcaaccggg    4020
gtacatatga ttgacatgct agttttacga ttaccgttct tcgattctct tgtttgtcc    4080
agactctcag gcaatgacct gatagccttt gtagagaccct ctcaaaaata gctaccctca    4140
ccggcatgaa tttatcagct agaacggttg aatatcatat tgatggtgat ttgactgtct    4200
ccggcctttc tcacccgttt gaatctttac ctacacatta tcaggcatt gcatttaaaa    4260
tatatgaggg ttctaaaaat ttttatcctt gcgttgaaat aaaggcttc cccgcaaaag    4320
tattacaggg tcataatgtt tttggtacaa ccgatttagc tttatgctct gaggctttat    4380
tgcttaattt tgctaattct ttgccttgcc tgtatgattt attggatgtt ggaatcgcct    4440
gatgcggtat tttctcctta cgcatctgtg cggtatttca caccgcatat ggtgcactct    4500
cagtacaatc tgctctgatg ccgcatagtt aagccagccc cgacacccgc caacacccgc    4560
tgacgcgccc tgacgggctt gtctgctccc ggcatccgct tacagacaag ctgtgaccgt    4620
ctccgggagc tgcatgtgtc agaggttttc accgtcatca ccgaaacgcg cgagacgaaa    4680
gggcctcgtg atacgcctat ttttataggt taatgtcatg ataataatgg tttcttagac    4740
gtcaggtggc acttttcggg gaaatgtgcg cggaaccccct atttgtttat ttttctaaat    4800
acattcaaat atgtatccgc tcatgagaca ataaccctga taaatgcttc aataatattg    4860
aaaaaggaag agtatgagta ttcaacattt ccgtgtcgcc cttattccct tttttgcggc    4920
attttgcctt cctgtttttg ctcacccaga aacgctggtg aaagtaaaag atgctgaaga    4980
tcagttgggt gcacgagtgg gttacatcga actggatctc aacagcggta agatccttga    5040
gagttttcgc cccgaagaac gttttccaat gatgagcact tttaaagttc tgctatgtgg    5100
cgcggtatta tcccgtattg acgccgggca agagcaactc ggtcgccgca tacactattc    5160
tcagaatgac ttggttgagt actcaccagt cacagaaaag catcttacgg atggcatgac    5220
agtaagagaa ttatgcagtg ctgccataac catgagtgat aacactgcgg ccaacttact    5280
tctgacaacg atcggaggac cgaaggagct aaccgctttt ttgcacaaca tgggggatca    5340
tgtaactcgc cttgatcgtt gggaaccgga gctgaatgaa gccataccaa acgacgagcg    5400
tgacaccacg atgcctgtag caatggcaac aacgttgcgc aaactattaa ctggcgaact    5460
acttactcta gcttcccggc aacaattaat agactggatg gaggcggata agttgcagg    5520
accacttctg cgctcggccc ttccggctgg ctggtttatt gctgataaat ctggagccgg    5580
tgagcgtggg tctcgcggta tcattgcagc actggggcca gatggtaagc cctcccgtat    5640
cgtagttatc tacacgacgg ggagtcaggc aactatggat gaacgaaata gacagatcgc    5700
tgagataggt gcctcactga ttaagcattg gtaactgtca gaccaagttt actcatatat    5760
actttagatt gatttaaaac ttcatttttta atttaaaagg atctaggtga agatcctttt    5820
tgataatctc atgaccaaaa tcccttaacg tgagttttcg ttccactgag cgtcagaccc    5880
cgtagaaaag atcaaaggat cttcttgaga tccttttttt ctgcgcgtaa tctgctgctt    5940
gcaaacaaaa aaaccaccgc taccagcggt ggtttgtttg ccggatcaag agctaccaac    6000
tctttttccg aaggtaactg gcttcagcag agcgcagata ccaaatactg tccttctagt    6060
gtagccgtag ttaggccacc acttcaagaa ctctgtagca ccgcctacat acctcgctct    6120
gctaatcctg ttaccagtgg ctgctgccag tggcgataag tcgtgtctta ccgggttgga    6180
ctcaagacga tagttaccgg ataaggcgca gcggtcgggc tgaacggggg gttcgtgcac    6240
acagcccagc ttggagcgaa cgacctacac cgaactgaga tacctacagc gtgagctatg    6300
agaaagcgcc acgcttcccg aagggagaaa ggcggacagg tatccggtaa ggcgcagcgg    6360
cggaacagga gcgcacgagg gagcttccag ggggaaacg cctggtatc tttatagtcc    6420
tgtcgggttt cgccacctct gacttgagcg tcgatttttg tgatgctcgt caggggggcg    6480
gagcctatga aaaacgcca gcaacgcggc ctttttacgg ttcctggcct tttgctggcc    6540
ttttgctcac atgttctttc ctgcgttatc ccctgattct gtggataacc gtattaccgc    6600
ctttgagtga gctgataccg ctcgccgcag ccgaacgacc gagcgcagcg agtcagtgag    6660
cgaggaagcg gaagagcgcc caatacgcaa accgcctctc ccgcgcgtt ggccgattca    6720
ttaatg                                                                6726
```

SEQ ID NO: 25          moltype = DNA length = 6991
FEATURE               Location/Qualifiers
source                1..6991
                       mol_type = other DNA
                       organism = Synthetic construct
SEQUENCE: 25
cagctgcgcg ctcgctcgct cactgaggcc gcccgggcaa agcccgggcg tcgggcgacc    60

-continued

```
tttggtcgcc cggcctcagt gagcgagcga gcgcgcagag agggagtggc caactccatc   120
actaggggtt ccttgtagtt aatgattaac ccgccatgct acttatctac acgcgtagat   180
ctacgtactt taggcttgta atgtgtttat atacagtgaa atgtcaagtt ctttctttat   240
atttctttct ttctttttttt tcctcagcct cagagttttc cacatgccct tcctactttc   300
aggaacttct ttctccaaac gtcttctgcc tggctccatc aaatcataaa ggacccactt   360
caaatgccat cactcactac catttcacaa ttcgcacttt cttctttggt ccttttttt   420
tttagtaaaa caagtttata aaaaattgaa ggaataaatg aatggctact tcataggcag   480
agtagacgca agggctactg gttgccgatt tttattgtta tttttcaata gtatgctaaa   540
caaggggtag attatttatg ctgcccattt ttagaccata aaagataact tcctgatgtt   600
gccatggcat ttttttcctt ttaattttat ttcattttcat tttaatttcg aaggtacatg   660
tgcaggatgt gcaggcttgt tacatgggta aatgtgtgtc tttctggcct tttagccatc   720
tgtatcaatg agcagatata agctttacac aggatcatga aggatgaaag aatttcacca   780
atccgcggga acagagaaac aggagaatat gggccaaaca ggatatctgt ggtaagcagt   840
tcctgcccg gctcagggcc aagaacagtt ggaacagcag aatatgggcc aaacaggata   900
tctgtggtaa gcagttcctg ccccggctca gggccaagaa cagatggtcc ccagatgcgg   960
tcccgccctc agcagtttct agagaaccat cagatgtttc cagggtgccc caaggacctg  1020
aaatgaccct gtgccttatt tgaactaacc aatcagttcg cttctcgctt ctgttcgcgc  1080
gcttctgctc cccgagctct atataagcag agctcgttta gtgaaccgtc agatcgcctg  1140
gagacgccat ccacgctgtt ttgacttcca tagaaggcgg ccgcgccgcc accatggtga  1200
gcaagggcga ggagctgttc accggggtgg tgcccatcct ggtcgagctg gacggcgacg  1260
taaacgcca caagttcagc gtgtccggcg agggcgaggg cgatgccacc tacggcaagc  1320
tgaccctgaa gttcatctgc accaccggca agctgcccgt gccctggccc acctctgtg   1380
ccacctgac ctacgcgtg cagtgcttca gccgctaccc cgaccacatg aagcagcacg  1440
acttcttcaa gtccgccatg cccgaaggct acgtccagga gcgcaccatc ttcttcaagg  1500
acgacggcaa ctacaagacc cgcgccgagg tgaagttcga gggcgacacc ctggtgaacc  1560
gcatcgagct gaagggcatc gacttcaagg aggacggcaa catcctgggg cacaagctgg  1620
agtacaacta caacagccac aacgtctata tcatggccga caagcagaag aacggcatca  1680
aggtgaactt caagatccgc cacaacatcg aggacggcag cgtgcagctc gccgaccact  1740
accagcagaa cacccccatc ggcgacggcc ccgtgctgct gcccgacaac cactacctga  1800
gcacccagtc cgccctgagc aaagaccca acgagaagcg cgatcactgg gtcctgctg   1860
agttcgtgac cgccgccggg atcactctcg gcatggacga gctgtacaag taacctgcag  1920
ggataatcaa cctctggatt acaaaatttg tgaaagattg actggtattc ttaactatgt  1980
tgctcctttt acgctatgtg gatacgctgc tttaatgcct ttgtatcatg ctattgcttc  2040
ccgtatggct ttcatttct cctccttgta taaatcctgg ttagttcttg ccacggcgga  2100
actcatcgcc gctgccttg cccgctgctg gacaggggct cggctgttgg gcactgacaa  2160
ttccgtggtg tttattgtg aaatttgtga tgctattgct ttatttgtaa ccattctagc  2220
tttatttgtg aaatttgtga tgctattgct ttatttgtaa ccattataag ctgcaataaa  2280
caagttaaca acaacaattg cattcattt atgtttcagg ttcaggggga gatgtgggag  2340
gttttttaaa gcgaattcgt aaatacactt gcaaaggagg atgtttttag tagcaattg   2400
tactgatggt atgggccaa gagatatatc ttagaggag ggctgagggt ttgaagtcca   2460
actcctaagc cagtgccaga agagccaagg acaggtacgg ctgtcatcac ttagacctca  2520
ccctgtggag ccacacccta gggttggcca atctactccc aggagcaggg agggcaggag  2580
ccaggggctgg gcataaaagt caggggcagag ccatctatttg cttacactcg cttctggaac  2640
gtctgaggtt atcaataagc tcctagtcca gacgccatgg gtcatttcac agaggaggac  2700
aaggctacta tcacaagcct gtggggcaag gtgaatgtgg aagatgctgg aggagaaacc  2760
ctgggaaggt aggctctggt gaccaggaca agggagggaa ggaaggaccc tgtgcctggc  2820
aaaagtccag gtcgcttctc aggatttgtg gcaccttctg actgtcaaac tgttcttgtc  2880
aatctcacag gctcctggtt gtctacccat ggacccagag gttctttgac agctttggca  2940
acctgtcctc tgcctctgcc atcatgggca acccccaaagt caaggcacat ggcaagaagg  3000
tgctgacttc cttgggagat gccacaaagc acctggatga tctcaagggc accttttgccc  3060
agctagtgga actgcactgt gacaagctgc atgtggatcc tgagaacttc aaggtgagtc  3120
caggagatgt ttcagccctg ttgccttag tctcgaggca acttagacaa cggagtattg  3180
atctgagcac agcagggtgt gagctgtttg aagatactgg ggtctcgagg tcgacgtaga  3240
taagtagcat ggcgggttaa tcattaacta caaggaaccc ctagtgatgg agttggccac  3300
tccctctctg cgcgctcgct cgctcactga ggccgggcga ccaaaggtcg cccgacgccc  3360
gggctttgcc cgggcggcct cagtgagcga gcgagcgcgc cagctggcgt aatagcgaag  3420
aggcccgcac cgatcgccct tcccaacagt tgcgcagcct gaatggcgaa tggcgattcc  3480
gttgcaatgg ctggcggtaa tattgttctg gatattacca gcaaggccga tagtttgagt  3540
tcttctactc aggcaagtga tgttattact aatcaaagaa gtattgcgac aacggttaat  3600
ttgcgtgatg gacagactct tttactcggt ggcctcactg attataaaaa cacttctcag  3660
gattctggcg taccgttcct gtctaaaatc ccttttaatcg gcctcctgtt tagctcccgc  3720
tctgattcta acgaggaaag cacgttatac gtgctcgtca agcaaccat agtacgcgcc  3780
ctgtagcggc gcattaagcg cggcgggtgt ggtggttacg cgcagcgtga ccgctacact  3840
tgccagcgcc ctagcgcccg ctcctttcgc tttcttccct tcctttctcg ccacgttcgc  3900
cggctttccc cgtcaagctc taaatcgggg ctcccctta gggttccgat ttagtgcttt  3960
acggcacctc gaccccaaaa aacttgatta gggtgatggt tcacgtagtg gccatcgcc   4020
ctgatagacg gtttttcgcc ctttgacgtt ggagtccacg ttctttaata gtggactctt  4080
gttccaaact ggaacaacac tcaacctat ctcggtctat tctttgatt tataagggat   4140
tttgccgatt tcggcctatt ggttaaaaaa tgagcgtaat taacaaaaa ttaacgcgaa   4200
ttttaacaaa atattaacgt ttacaattta aatatttgct tatacaatct tcctgttttt  4260
ggggcttttc tgattatcaa ccggggtaca tatgattgac atgctagttt tacgattacc  4320
gttcatcgat tctcttgttt gctccagact ctcaggcaat gacctgatag cctttgtaga  4380
gacctctcaa aaatagctac cctctccggc atgaattat cagctagaac ggttgaatat   4440
catattgatg gtgatttgac tgtctccggc ctttctcacc cgtttgaatc ttacctaca   4500
cattactcag gcattgcatt taaaatatat gagggttcta aaaattttta tccttgcgtt  4560
gaaataaagg cttctcccgc aaaagtatta cagggtcata atgttttgg tacaaccgat   4620
ttagctttat gctctgaggc tttattgctt aattttgcta attctttgcc ttgcctgtat   4680
gatttattgg atgttggaat cgcctgatgc ggtattttct ccttacgcat ctgtgcggta  4740
tttcacaccg catatggtgc actctcagta caatctgctc tgatgccgca tagttaagcc  4800
```

-continued

```
agccccgaca cccgccaaca cccgctgacg cgccctgacg ggcttgtctg ctcccggcat 4860
ccgcttacag acaagctgtg accgtctccg ggagctgcat gtgtcagagg ttttcaccgt 4920
catcaccgaa acgcgcgaga cgaaagggcc tcgtgatacg cctatttta taggttaatg 4980
tcatgataat aatggtttct tagacgtcag gtggcactt tcggggaaat gtgcgcggaa 5040
cccctatttg tttatttttc taaatacatt caaatatgta tccgctcatg agacaataac 5100
cctgataaat gcttcaataa tattgaaaaa ggaagagtat gagtattcaa catttccgtg 5160
tcgcccttat tcccttttt gcggcatttt gccttcctgt ttttgctcac ccagaaacgc 5220
tggtgaaagt aaaagatgct gaagatcagt tgggtgcacg agtgggttac atcgaactgg 5280
atctcaacag cggtaagatc cttgagagtt ttcgccccga agaacgtttt ccaatgatga 5340
gcacttttaa agttctgcta tgtggcgcgg tattatcccg tattgacgcc gggcaagagc 5400
aactcggtcg ccgcatacac tattctcaga atgacttggt tgagtactca ccagtcacag 5460
aaaagcatct tacggatggc atgacagtaa gagaattatg cagtgctgcc ataaccatga 5520
gtgataaac tgcggccaac ttacttctga caacgatcgg aggaccgaag gagctaaccg 5580
cttttttgca caacatgggg gatcatgtaa ctcgccttga tcgttgggaa ccggagctga 5640
atgaagccat accaaacgac gagcgtgaca ccacgatgcc tgtagcaatg gcaacaacgt 5700
tgcgcaaact attaactggc gaactactta ctctagcttc ccggcaacaa ttaatagact 5760
ggatggaggc ggataaagtt gcaggaccac ttctgcgctc ggcccttccg gctggctggt 5820
ttattgctga taaatctgga gccggtgagc gtgggtctcg cggtatcatt gcagcactgg 5880
ggccagatgg taagccctcc cgtatcgtag ttatctacac gacggggagt caggcaacta 5940
tggatgaacg aaatagacag atcgctgaga taggtgcctc actgattaag cattggtaac 6000
tgtcagacca agtttactca tatatacttt agattgattt aaaacttcat ttttaattta 6060
aaaggatcta ggtgaagatc ctttttgata atctcatgac caaatccct taacgtgagt 6120
tttcgttcca ctgagcgtca gaccccgtag aaaagatcaa aggatcttct tgagatcctt 6180
ttttttctgcg cgtaatctgc tgcttgcaaa caaaaaaacc accgctacca gcggtggttt 6240
gtttgccgga tcaagagcta ccaactcttt ttccgaaggt aactggcttc agcagagcgc 6300
agataccaaa tactgtcctt ctagtgtagc cgtagttagg ccaccacttc aagaactctg 6360
tagcaccgcc tacatacctc gctctgctaa tcctgttacc agtggctgct gccagtggcg 6420
ataagtcgtg tcttaccggg ttggactcaa gacgatagtt accggataag gcgcagcggt 6480
cgggctgaac ggggggttcg tgcacacagc ccagcttgga gcgaacgacc tacaccgaac 6540
tgagatacct acagcgtgag ctatgagaaa gcgccacgct tcccgaaggg agaaaggcgg 6600
acaggtatcc ggtaagcggc agggtcgaa caggagagcg cacgagggag cttccagggg 6660
gaaacgcctg gtatctttat agtcctgtcg ggtttcgcca cctctgactt gagcgtcgat 6720
ttttgtgatg ctcgtcaggg gggcggagcc tatggaaaaa cgccagcaac gcggcctttt 6780
tacggttcct ggccttttgc tggccttttg ctcacatgtt ctttcctgcg ttatccctg 6840
attctgtgga taaccgtatt accgcctttg agtgagctga taccgctcgc cgcagccgaa 6900
cgaccgagcg cagcgagtca gtgagcgagg aagcggaaga gcgcccaata cgcaaaccgc 6960
ctctccccgc gcgttggccg attcattaat g 6991
```

SEQ ID NO: 26   moltype = DNA length = 7724
FEATURE     Location/Qualifiers
source      1..7724
        mol_type = other DNA
        organism = Synthetic construct
SEQUENCE: 26

```
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actagggtt ccttgtagtt aatgattaac ccgccatgct acttatctac gtagccatgc 180
tctagcggcc tcggcctctg cataaataaa aaaaattagt cagccatgag cttggacgug 240
tagatctcac tttcagagaa aaacaaaaac aaactaacca aaagcaaaac agaaccaaaa 300
aaccaccata aatacttcct accctgttaa tggtccaata tgtcagaaac agcactgtgt 360
tagaaataaa gctgtctaaa gtacactaat attcgagtta taatagtgtg tggactatta 420
gtcaataaaa acaacccttg cctctttaga gttgttttcc atgtacacgc acatcttatg 480
tcttagagta agattccctg agaagtgaac ctagcattta acaagataa ttaattctaa 540
tccacagtac ctgccaaaga acattctacc atcatcttta ctgagcatag aagagctacg 600
ccaaaaccct gggtcatcag ccagcacaca cacttatcca gtggtaaata cacatcatct 660
ggtgtataca tacataccg aatatggaat caaatatttt tctaagatga aacagtcatg 720
atttatttca aataggtacg gataagtaga tatgaacaga gaaacaggag aatatgggcc 780
aaacaggata tctgtggtaa gcagttcctg ccccggctca gggccaagaa cagttggaac 840
agcagaatat gggccaaaca ggatatctgt ggtaagcagt tcctgccccg gctcagggcc 900
aagaacagat ggtccccaga tgcggtcccg ccctcagcag tttctagaga accatcagat 960
gtttccaggg tgccccaagg acctgaaatg accctgtgcc ttatttgaac taaccaatca 1020
gttcgcttct cgcttctgtt cgcgcgcttc tgctccccga gctctatata gcagagctc 1080
gtttagtgaa ccgtcagatc gcggccgcgc cgccaccatg gtgagcaagg gcgaggagct 1140
gttcaccggg gtggtgccca tcctggtcga gctggacggc gacgtaaacg gccacaagtt 1200
cagcgtgtcc ggcgagggcg agggcgatgc cacctacggc aagctgaccc tgaagttcat 1260
ctgcaccacc ggcaagctgc ccgtgccctg gcccaccctc gtgaccaccc tgacctacgg 1320
cgtgcagtgc ttcagccgct accccgacca catgaagcag cacgacttct tcaagtccgc 1380
catgcccgaa ggctacgtcc aggagcgcac catcttcttc aaggacgacg gcaactacaa 1440
gacccgcgcc gaggtgaagt tcgagggcga caccctggtg aaccgcatcg agctgaaggg 1500
catcgacttc aaggaggacg gcaacatcct ggggcacaag ctggagtaca actacaacag 1560
ccacaacgtc tatatcatgg ccgacaagca gaagaacggc atcaaggtga acttcaagat 1620
ccgccacaac atcgaggacg gcagcgtgca gctcgccgac cactaccagc agaacacccc 1680
catcggcgac ggccccgtgc tgctgcccga caaccactac ctgagcaccc agtccgccct 1740
gagcaaagac cccaacgaga agcgcgatca catggtcctg ctggagttcg tgaccgccgc 1800
cgggatcact ctcggcatgg acgagctgta caagtaggac catcttaccg ccatttattc 1860
ccatatttgt tctgttttc ttgatttggg tatacattta aatgtaaata aaacaaaatg 1920
gtggggcaat catttacatt tttagggata tgtaattact agttcaggtg tattgccaca 1980
agacaaacat gttaagaaac tttccgtta tttacgctct gttcctgtta atcaacctct 2040
ggattacaaa atttgtgaaa gattgactga tattcttaac tatgttgctc cttttacgct 2100
```

```
gtgtggatat gctgctttat agcctctgta tctagctatt gcttcccgta cggctttcgt  2160
tttctcctcc ttgtataaat cctggttgct gtctctttta gaggagttgt ggcccgttgt  2220
ccgtcaacgt ggcgtggtgt gctctgtgtt tgctgacgca accccactg gctgggcat   2280
tgccaccacc tgtcaactcc tttctgggac tttcgctttc ccctcccga tcgccacggc   2340
agaactcatc gccgcctgcc ttgcccgctg ctggacaggg gctaggttgc tgggcactga  2400
taattccgtg gtgttgtctg tgccttctag ttgccagcca tctgttgttt gccctcccc   2460
cgtgccttcc ttgaccctgg aaggtgccac tcccactgtc ctttcctaat aaaatgagga  2520
aattgcatcg cattgtctga gtaggtgtca ttctattctg gggggtgggg tggggcagga  2580
cagcaagggg gaggattggg aagacaatag caggcatgct gggggatgcg gtgggctctat 2640
ggctagatgt ccccagttaa cctcctattt gacaccactg attaccccat tgatagtcac  2700
actttgggtt gtaagtgact tttatttat ttgtattttt gactgcatta agaggtctct   2760
agttttttat ctcttgtttc ccaaaaccta ataagtaact aatgcacaga gcacattgat  2820
ttgtatttat tctattttta gacataattt attagcatgc atgagcaaat taagaaaaac  2880
aacaacaaat gaatgcatat atatgtatat gtatgtgtgt atatatacac acatatatat  2940
atatattttt tcttttctta ccagaaggtt ttaatccaaa taaggagaag atatgcttag  3000
aaccgaggta gagttttcat ccattctgtc ctgtaagtat tttgcatatt ctggagacgc  3060
aggaagagat ccatctacat atcccaaagc tgaattatgg tagacaaaac tcttccactt  3120
ttagtgcatc aacttcttat ttgtgtaata agaaaattgg gaaaacgatc ttcaatatgc  3180
ttaccaagct gtgattccaa atattacgta aatacacttg caaaggagga tgttttttagt 3240
agcaatttgt actgatggta tggggccaag agatatatct tagagggagg ctgagggtt   3300
tgaagtccaa ctcctaagcc agtgccagaa gagccaagga caggtacggc tgtcatcact  3360
tagacctcac cctgtggagc cacaccctag ggttggccaa tctactccca ggagcaggga  3420
gggcaggagc cagggctggg cataaaagtc agggcagagc catctattgc ttacactcgc  3480
ttctggaacg tctgaggtta tcaataagct cctagtccag acgccatggg tcatttcaca  3540
gaggaggaca aggctactat cacaagcctg tgggcaaggt gaatgtgga agatgctgga   3600
ggagaaaccc tgggaaggta ggctctggtg accaggacaa gggaggggag gaaggaccct   3660
gtgcctggca aaagtccagg tcgcttctca ggatttgtgg caccttctga ctgtcaaact  3720
gttcttgtca atctcacagg ctcctggttg tctacccatg gacccagagg ttctttgaca  3780
gctttggcaa cctgtcctct gcctctgcca tcatgggcaa ccccaaagtc aaggcacatg  3840
gcaagaaggt gctgacttcc ttgggagatg ccacaaagca cctggatgat ctcaagggca  3900
cctttgccca gctgagtgaa ctgcactgtg acaagctgca tgtggatcct gagaacttca  3960
aggtcgacgt agataagtag catggcgggt taatcattaa ctacaaggaa ccctagtga   4020
tggagttggc cactccctct ctgcgcgctc gctcgctcac tgaggccggg cgaccaaagg  4080
tcgcccgacg cccgggcttt gcccgggcgg cctcagtgag cgagcgagcg cgcagctgg   4140
cgtaatagcg aagaggcccg caccgatcgc ccttcccaac agttgcgcag cctgaatggc  4200
gaatggcgat tccgttgcaa tggctggcgg taatattgtt ctggatatta ccagcaaggc  4260
cgatagtttg agttcttcta ctcaggcaag tgatgttatt actaatcaaa gaagtattgc  4320
gacaacggtt aatttgcgtg atggacgac tcttttactc ggtggcctca ctgattataa   4380
aaacacttct caggattctg gcgtaccgtt cctgtctaaa atcccttta tcggcctcct   4440
gtttagctcc cgctctgatt ctaacgagga aagcacgtta tacgtgctcg tcaaagcaac  4500
catagtacgc gccctgtagc ggcgcattaa gcgcggcggg tgtggtggtt acgcgcagcg  4560
tgaccgctac acttgccagc gccctagcgc ccgctccttt cgctttcttc ccttcctttc  4620
tcgccacgtt cgccggcttt ccccgtcaag ctctaaatcg ggggctccct ttagggttcc  4680
gatttagtgc tttacggcac ctcgacccca aaaaacttga ttagggtgat ggttcacgta  4740
gtgggccatc gccctgatag acggtttttc gccctttgac gttggagtcc acgttcttta  4800
atagtggact cttgttccaa actggaacaa cactcaaccc tatctcggtc tattcttttg  4860
atttataagg gattttgccg atttcggcct attggttaaa aaatgagctg atttaacaaa  4920
aatttaacgc gaattttaac aaaatattaa cgtttacaat ttaaatattt gcttatacaa  4980
tcttcctgtt tttggggctt ttctgattat caaccgggt acatatgatt gacatgctag  5040
ttttacgatt accgttcatc gattctcttg tttgctccag actctcaggc aatgacctga  5100
tagccttttgt agagacctct caaaaatagc taccctctcc ggcatgaatt tatcagctag  5160
aacggttgaa tatcatattg atggtgattt gactgtctcc ggcctttctc acccgtttga  5220
atctttacct acacattact caggcattgc atttaaaata tatgagggtt ctaaaaattt  5280
ttatccttgc gttgaaataa aggcttctcc cgcaaaagta ttacagggtc ataatgtttt  5340
tggtacaacc gatttagctt tatgctctga ggctttattg cttaattttt ctaattcttt  5400
gccttgcctg tatgatttat tggatgttgg aatcgcctga tgcggtattt tctccttacg  5460
catctgtgcg gtatttcaca ccgcatatgg tgcactctca gtacaatctg ctctgatgcc  5520
gcatagttaa gccagccccg acacccgcca cacccgctg acgcgccctg acgggcttgt   5580
ctgctcccgg catccgctta cagacaagct gtgaccgtct ccgggagctg catgtgtcag  5640
aggttttcac cgtcatcacc gaaacgcgcg agacgaaagg gcctcgtgat acgcctattt  5700
ttataggtta atgtcatgat aataatggtt tcttagacgt caggtggcac ttttcgggga  5760
aatgtgcgcg gaaccctat ttgttttattt ttctaaatac attcaaatat gtatccgctc  5820
atgagacaat aaccctgata aatgcttcaa taatattgaa aaaggaagag tatgagtatt  5880
caacatttcc gtgtcgccct tattcccttt ttgcggcat tttgccttcc tgttttgct   5940
cacccagaaa cgctggtgaa agtaaaagat gctgaagatc agttgggtgc acgagtgggt  6000
tacatcgaac tggatctcaa cagcggtaag atccttgaga gttttcgccc cgaagaacgt  6060
tttccaatga tgagcacttt taagttctg ctatgtggcg cggtattatc ccgtattgac   6120
gccgggcaag agcaactcgg tcgccgcata cactattctc agaatgactt ggttgagtac  6180
tcaccagtca cagaaaagca tcttacggat ggcatgacag taagagaatt atgcagtgct  6240
gccataacca tgagtgataa cactgcggcc aacttacttc tgacaacgat cggaggaccg  6300
aaggagctaa ccgcttttt gcacaacatg gggatcatg taactcgcct tgatcgttgg  6360
gaaccggagc tgaatgaagc cataccaaac gacgagcgtg acaccacgat gcctgtagca  6420
atggcaacaa cgttgcgcaa actattaact ggcgaactac ttactctagc ttcccggcaa  6480
caattaatag actggatgga ggcggataaa gttgcaggac cacttctgcg ctcggccctt  6540
ccggctggct ggtttattgc tgataaatct ggagccggtg agcgtgggtc tcgcggtatc  6600
attgcagcac tggggccaga tggtaagccc tcccgtatcg tagttatcta cacgacgggg  6660
agtcaggcaa ctatggatga acgaaataga cagatcgctg agataggtgc ctcactgatt  6720
aagcattggt aactgtcaga ccaagtttac tcatatatac tttagattga tttaaaactt  6780
catttttaat ttaaaaggat ctaggtgaag atcctttttg ataatctcat gaccaaaatc  6840
```

```
ccttaacgtg agttttcgtt ccactgagcg tcagacgccg tagaaaagat caaaggatct  6900
tcttgagatc cttttttttct gcgcgtaatc tgctgcttgc aaacaaaaaa accaccgcta  6960
ccagcggtgg tttgtttgcc ggatcaagag ctaccaactc ttttttccgaa ggtaactggc  7020
ttcagcagag cgcagatacc aaatactgtc cttctagtgt agccgtagtt aggccaccac  7080
ttcaagaact ctgtagcacc gcctacatac ctcgctctgc taatcctgtt accagtggct  7140
gctgccagtg gcgataagtc gtgtcttacc gggttggact caagacgata gttaccggat  7200
aaggcgcagc ggtcgggctg aacggggggt tcgtgcacac agcccagctt ggagcgaacg  7260
acctacaccg aactgagata cctacagcgt gagctatgag aaagcgccac gcttcccgaa  7320
gggagaaagg cggacaggta tccggtaagc ggcagggtcg gaacaggaga gcgcacgagg  7380
gagcttccag ggggaaacgc ctggtatctt tatagtcctg tcgggtttcg ccacctctga  7440
cttgagcgtc gatttttgtg atgctcgtca gggggggcgga gcctatggaa aaacgccagc  7500
aacgcggcct ttttacggtt cctggccttt tgctggcctt ttgctcacat gttctttcct  7560
gcgttatccc ctgattctgt ggataaccgt attaccgcct ttgagtgagc tgataccgct  7620
cgccgcagcc gaacgaccga gcgcagcgag tcagtgagcg aggaagcgga agagcgccca  7680
atacgcaaac cgcctctccc cgcgcgttgg ccgattcatt aatg              7724

SEQ ID NO: 27      moltype = DNA  length = 8525
FEATURE            Location/Qualifiers
source             1..8525
                   mol_type = other DNA
                   organism = Synthetic construct
SEQUENCE: 27
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc   120
actgggggtt ccttgtagtt aatgattaac ccgccatgct acttatctac gtagccatgc   180
tctagcgcc tcggcctctg cataaataaa aaaaattagt cagccatgag cttggacgcg    240
tagatctaga tgaaacagtc atgatttatt tcaaataggt acggataagt agatattgag   300
gtaagcatta ggtcttatat tatgtaacac taatctatta ctgcgctgaa actgtggctt   360
tatagaaatt gttttcactg cactattgag aaattaagag ataatggcaa aagtcacaaa   420
gagtatattc aaaaagaagt atagcacttt ttccttagaa accactgcta actgaaagag   480
actaagattt gtcccgtcaa aaatcctgga cctatgccta aaacacattt cacaatccct   540
gaactttttca aaaattggta catgctttag ctttaaacta caggcctcac tggagctaga   600
gacaagaagg taaaaacgg ctgacaaaag aagtcctggt atcctctatg atgggagaag   660
gaaactagct aaagggaaga aataattaga gaaaaactgg aatgactgaa tcggaacaag   720
gcaaaggcta taaaaaaaat tagcagtatc ctcttgggcg cccttcccc acactatctg   780
aatgcaaata tctgtctgaa acggtccctg gctaaactcc acccatgggt tggccagcct   840
tgccttgaca aggcaaactt gaccaatagt cttagagtat ccagtgaggc caggggccgg   900
cggctggcta gggatgaaga ataaaaggaa gcaccccttca gcagttccac acactcgctt   960
ctgaacgtc tgaggttatc aataagctcc tagtccagac gccatggtgc acctgactcc  1020
tgaggagaag tctgccgtta ctgccctgtg gggcaaggtg aacgtggatg aagttggtgg  1080
tgaggccctg ggcaggttgg tatcaagttt acaagcagg tttaaggaga ccaatagaaa  1140
ctgggcatgt ggagacagag aagactcttg ggtttctgat aggcactgac tctctctgcc  1200
tattgtcta tttttcccacc cttaggctgc tggtggtcta ccctggacag cagaggttct  1260
ttgagtcctt tggggatctg tccactcctg atgctgttat gggcaaccct aaggtgaagg  1320
ctcatggcaa gaaagtgctc ggtgccttta gtgatggcct ggctcacctg gacaacctca  1380
agggcacctt tgcccagctg agtgagctgc actgtgacaa gctgcacgtg gatcctgaga  1440
acttcagggt gagtctatgg gacccttgat gttttctttc cccttcttt ctatggttaa   1500
gttcatgtca taggaagggg agaagtaaca gggtacacat attgaccaaa tcagggtaat  1560
tttgcatttg taattttaaa aaatgctttc ttcttttaat atactttttt gtttatctta  1620
tttctaatac tttccctaat ctcttttctt cagggcaata atgatacaat gtatcatgcc  1680
tcttgaccc atttctaaaga ataacagtga taatttctgg gttaaggcaa tagcaatatt  1740
tctgcatata aatatttctg catataaatt gtaactgatg taagaggttt catattgcta  1800
atagcagcta caatccagct accattctgc ttttattttta tggttgggat aaggctggat  1860
tattctgagt ccaagctagg ccctttttgct aatcatgttc atacctctta tcttcctccc  1920
acagctcctg ggcaacgtgc tggtctgtgt gctggcccat cactttggca aagaattcac  1980
cccaccagtg caggctgcct atcagaaagt ggtggctggt gtggctaatg ccctggccca  2040
caagtatcac taagctcgct ttcttgctgt ccaatttcta ttaaaggttc ctttgttccc  2100
taagtccaac tactaaactg ggggatatta tgaagggcct tgagcatctg gattctgcct  2160
aataaaaaac attttatttc attgcaatga tgtatttaaa ttatttctga atattttact  2220
aaaaagggaa tgtgggaggt cagtgcattt aaaacataaa gaaatgaaga gctagttcaa  2280
accttggaa aatacactat atcttaaact ccatgaaaga aggtgaggct gcaaacagct  2340
aatgcacatt ggcaacagcc cctgatgcct atgccttatt catccctcag aaaaggattc  2400
aagtagaggc ttgatttgga ggttaaagtt ttgctatgct gtattttaca ttacttattg  2460
ttttagctgt cctcatgaat gtctttttcac tacccattg cttatcctgc atctctcagc  2520
cttgactcca ctcagttctc ttgcttagag ataccacctt tcccctgaag tgttccttcc  2580
atgttttacg gcgagatggt ttctcctcgc ctggccactc agccttagtt gtctctgttg  2640
tcttatagag gtcacttga agaaggaaaa acagggggca tggtttgact gtcctgtgag  2700
cccttcttcc ctgcctcccc cactcacagt gacccggaat ctgcagtcgt agtctcccgg  2760
aactatcact cttttcacagt ctgctttgga aggactgggc tagtatgaa aagttaggac  2820
tgagaagaat ttgaaagggg ctttttgta gcttgatatt cactactgtc ttattaccct  2880
atcataggcc caccccaaat ggaagtccca ttcttcctca ggatgttaa gattagcatt  2940
caggaagaga tcagaggtct gctggctccc ttatcatgtc ccttatgtg cttctggctc  3000
tgcagttatt agcatagtgt taccatcaac caccttaact tcattttttct tattcaatac  3060
ctagccgcgg gaacagaaa acaggagaat atgggccaaa caggatatct gtggtaagca  3120
gttcctgccc cggctcaggg ccaagaacag ttgaacagc agaatatggg ccaaacagga  3180
tatctgtggt aagcagttcc tgccccggct caggcaag aacagatggt ccccagatgc  3240
ggtccccgccc tcagcagttt ctagagaacc atcagatgtt ccagggtgc cccaggacc  3300
tgaaatgacc ctgtgcctta tttgaactaa ccaatcagtt cgcttctcgc ttctgttcgc  3360
gcgcttctgc tcccccgagct ctatataagc agagctcgtt tagtgaaccg tcagatcgcg  3420
```

```
gccgcgccgc caccatggtg agcaagggcg aggagctgtt caccggggtg gtgcccatcc    3480
tggtcgagct ggacggcgac gtaaacggcc acaagttcag cgtgtccggc gagggcgagg    3540
gcgatgccac ctacggcaag ctgaccctga agttcatctg caccaccggc aagctgcccg    3600
tgcccctggc caccctcgtg accacccgga cctacggcgt gcagtgcttc agccgctacc    3660
ccgaccacat gaagcagcac gacttcttca gtccgccac gcccgaaggc tacgtccagg    3720
agcgcaccat cttcttcaag gacgacggca actacaagac ccgcgccgag gtgaagttcg    3780
agggcgacac cctggtgaac cgcatcgagc tgaagggcat cgacttcaag gaggacggca    3840
acatcctggg gcacaagctg gagtacaact acaacagcca caacgtctat atcatggccg    3900
acaagcagaa gaacggcatc aaggtgaact tcaagatccg ccacaacatc gaggacggca    3960
gcgtgcagct cgccgaccac taccagcaga cacccccat cggcgacggc cccgtgctgc    4020
tgcccgacaa ccactacctg agcacccagt ccgccctgag caaagacccc aacgagaagc    4080
gcgatcacat ggtcctgctg gagttcgtga ccgccgccgg gatcactctc ggcatggacg    4140
agctgtacaa gtaacctgca gggctcactg cccatgattc agagctttca aggataggct    4200
ttattctgca agcaatacaa ataataaatc tattctgctg agagatcaca catgattttc    4260
ttcagctctt tttttacat cttttaaat atatgagcca caaagggttt atattgaggg    4320
aagtgtgtat gtgtatttct gcatgcctgt tgtgtttgt ggtgtgtgca tgctcctcat    4380
ttattttat atgagatgtg cattttgatg agcaaataaa agcagtaaag acacttgtac    4440
acgggagttc tgcaagtggg agtaaatggt gtaggagaaa tccggtggga agaaagacct    4500
ctataggaca ggacttctca gaaacagatg ttttggaaga gatgggaaaa ggttcagtga    4560
agacctgggg gctggattga ttgcagctga gtagcaagga tggttcttaa ggaagggaaa    4620
gtgttccaag ctttaggaat tcaaggttta gtcaggtgta gcaattctat tttattagga    4680
ggaatactat ttctaatggc acttagcttt tcacagccct tgtggatgcc taagaaagtg    4740
aaattaatcc catgccctca agtgtcgacg tagataagta gcatggcggg ttaatcatta    4800
actacaagga accctagtg atggagttgg ccactccctc tctgcgcgct cgctcgctca    4860
ctgaggccgg gcgaccaaag gtcgcccgac gcccgggctt gcccgggcg gcctcagtga    4920
gcgagcgagc gcgccagctg gcgtaatagc gaagaggccc gcaccgatcg cccttcccaa    4980
cagttgcgca gcctgaatgg cgaatgcgca ttccgttgca atggctggcg gtaatattgt    5040
tctggatatt accagcaagg ccgatagttt gagttcttct actcaggcaa gtgatgttat    5100
tactaatcaa agaagtattg cgacaacggt taatttgcgt gatggacaga ctcttttact    5160
cggtgcctc actgattata aaaacacttc tcaggattct ggcgtaccgt tcctgtctaa    5220
aatccctta atcggcctcc tgtttagctc ccgctctgat tctaacgagg aaagcacgtt    5280
atacgtgctc gtcaaagcaa ccatagtacg cgccctgtag cggcgcatta agcgcggcgg    5340
gtgtggtggt tacgcgcagc gtgaccgcta cacttgccag cgccctagcg cccgctcctt    5400
tcgctttctt cccttccttt ctcgccacgt tcgccggctt tccccgtcaa gctctaaatc    5460
ggggctccc tttagggttc cgatttagtg ctttacggca cctcgacccc aaaaaacttg    5520
attagggtga tggttcacgt agtgggccat cgccctgata acggttttt cgccctttga    5580
cgttggagtc cacgttcttt aatagtggac tcttgttcca aactggaaca acactcaacc    5640
ctatctcggt ctattctttt gatttataag ggattttgcc gatttcggcc tattggttaa    5700
aaaatgagct gatttaacaa aaatttaacg cgaattttaa caaaatatta acgtttacaa    5760
tttaaatatt gcttataca atcttcctgt ttttggggct tttctgatta tcaaccgggg    5820
tacatatgat tgacatgcta gttttacgat taccgttcat cgattctctt gtttgctcca    5880
gactctcagg caatgacctg atagcctttg tagagacctc tcaaaaatag ctaccctctc    5940
cggcatgaat ttatcagcta gaacggttga atatcatatt gatggtgatt tgactgtctc    6000
cggcctttct caccgtttg aatctttacc tacacattac tcaggcattg catttaaaat    6060
atatgagggt tctaaaaatt tttatccttg cgttgaaata aaggcttctc ccgcaaaagt    6120
attacagggt cataatgttt ttggtacaac cgatttagct ttatgctctg aggctttatt    6180
gcttaatttt gctaattctt tgccttgcct gtatgattta ttggatgttg gaatcgcctg    6240
atgcggtatt ttctccttac gcatctgtgc ggtatttcac accgcatatg gtgcactctc    6300
agtacaatct gctctgatgc cgcatagtta agccagcccc gacacccgcc aacacccgct    6360
gacgcgccct gacgggcttg tctgctcccg gcatccgctt acagacaagc tgtgaccgtc    6420
tccgggagct gcatgtgtca gaggttttca ccgtcatcac cgaaacgcgc gagacgaaag    6480
ggcctcgtga tacgcctatt tttataggtt aatgtcatga taataatggt ttcttagacg    6540
tcaggtggca cttttcgggg aaatgtgcgc ggaacccta tttgtttatt tttctaaata    6600
cattcaaata tgtatccgct catgagacaa taaccctgat aaatgcttca ataatattga    6660
aaaaggaaga gtatgagtat tcaacatttc cgtgtcgccc ttattccctt ttttgcggca    6720
ttttgccttc ctgtttttgc tcacccagaa acgctggtga agtaaaaga tgctgaagat    6780
cagttgggtg cacgagtggg ttacatcgaa ctggatctca acagcggtaa gatccttgag    6840
agttttcgcc ccgaagaacg ttttccaatg atgagcactt taaagttct gctatgtggc    6900
gcggtattat cccgtattga cgccgggcaa gagcaactcg gtcgccgcat acactattct    6960
cagaatgact tggttgagta ctcaccagtc acagaaaagc atcttacgga tggcatgaca    7020
gtaagagaat tatgcagtgc tgccataacc atgagtgata acactgcggc caacttactt    7080
ctgacaacga tcgaggacc gaaggagcta accgcttttt tgcacaacat ggggatcat    7140
gtaactcgcc ttgatcgttg gaaccggag ctgaatgaag ccataccaaa cgacgagcgt    7200
gacaccacga tgcctgtagc aatggcaaca acgttgcgca aactattaac tggcgaacta    7260
cttactctag cttcccggca acaattaata gactggatgg aggcggataa agttgcagga    7320
ccacttctgc gctcggccct tccggctggc tggtttattg ctgataaatc tggagccggt    7380
gagcgtgggt ctcgcggtat cattgcagca ctggggccag atggtaagcc ctcccgtatc    7440
gtagttatct acacgacggg gagtcaggca actatgatg aacgaaatag acagatcgct    7500
gagataggtg cctcactgat taagcattgg taactgtcag accaagttta ctcatatata    7560
ctttagattg atttaaaact tcatttttaa tttaaaagga tctaggtgaa gatcctttt    7620
gataatctca tgaccaaaat cccttaacgt gagttttcgt tccactgagc gtcagacccc    7680
gtagaaaaga tcaaaggatc ttcttgagat ccttttttc tgcgcgtaat ctgctgcttg    7740
caaacaaaaa aaccaccgct accagcggtg gtttgtttgc cggatcaaga gctaccaact    7800
ctttttccga aggtaactgg cttcagcaga gcgcagatac caaatactgt ccttctagtg    7860
tagccgtagt taggccacca cttcaagaac tctgtagcac cgcctacata cctcgctctg    7920
ctaatcctgt taccagtggc tgctgccagt ggcgataagt cgtgtcttac cgggttggac    7980
tcaagacgat agttaccgga taaggcgcag cggtcgggct gaacgggggg ttcgtgcaca    8040
cagcccagct tggagcgaac gacctacacc gaactgagat acctacagcg tgagctatga    8100
gaaagcgcca cgcttcccga agggagaaag gcggacaggt atccggtaag cggcagggtc    8160
```

```
ggaacaggag agcgcacgag ggagcttcca gggggaaacg cctggtatct ttatagtcct   8220
gtcgggtttc gccacctctg acttgagcgt cgatttttgt gatgctcgtc aggggggcgg   8280
agcctatgga aaaacgccag caacgcggcc ttttacggt tcctggcctt ttgctggcct    8340
tttgctcaca tgttctttcc tgcgttatcc cctgattctg tggataaccg tattaccgcc   8400
tttgagtgag ctgataccgc tcgccgcagc cgaacgaccg agcgcagcga gtcagtgagc   8460
gaggaagcgg aagagcgccc aatacgcaaa ccgcctctcc ccgcgcgttg gccgattcat   8520
taatg                                                               8525

SEQ ID NO: 28          moltype = DNA   length = 8118
FEATURE                Location/Qualifiers
source                 1..8118
                       mol_type = other DNA
                       organism = Synthetic construct
SEQUENCE: 28
cagctgcgcg ctcgctcgct cactgaggcc gccgggcaa agcccgggcg tcgggcgacc    60
tttggtcgcc cggcctcagt gagcgagcga gcgcgcagag agggagtggc caactccatc   120
actaggggtt cctacgcgta gatcttttt ccttagaaac cactgctaac tgaaagagac    180
taagatttgt cccgtcaaaa atcctggacc tatgcctaaa acacatttca caatccctga   240
acttttcaaa aattggtaca tgctttagct ttaaactaca ggcctcactg gagctagaga   300
caagaaggta aaaacggct gacaaaagaa gtcctggtat cctctatgat gggagaagga    360
aactagctaa agggaagaat aaattagaga aaaactggaa tgactgaatc ggaacaaggc   420
aaaggctata aaaaaatta gcagtatcct cttgggggag ccttcccac actatctcaa    480
tgcaaatatc tgtctgaaac ggtccctggc taaactccac ccatgggttg gccagccttg   540
ccttgacaag gcaaacttga ccaatagtct tagagtatcc agtgaggcca ggggccggcg   600
gctggctagg gatgaagaat aaaaggaagc acccttcagc agttccacac actcgcttct   660
ggaacgtctg aggttatcaa taagctccta gtccagacgc catgtgcat ctgactcctg    720
aggagaagtc tgccgttact gccctgtggg gcaaggtgaa cgtggatgaa gttggtggtg   780
aggccctggg caggttggta tcaaggttac aagacaggtt taaggagacc aatagaaact   840
gggcatgtgg agacagagaa gactcttggg tttctgatag gcactgactc tctctgccta   900
ttggtctatt ttcccaccct taggctgctg gtggtctacc cttggaccca gaggttcttt   960
gagtcctttg gggatctgtc cactcctgat gctgttatgg gcaaccctaa ggtgaaggct   1020
catggcaaga aagtgctcgg tgcctttagt gatggcctgg ctcacctgga caacctcaag   1080
ggcacctttg cccagctgag tgagctgcac tgtgacaagc tgcacgtgga tcctgagaac   1140
ttcagggtga gtctatggga cccttgatgt tttcttccc cttctttct atggttaagt     1200
tcatgtcata ggaaggggag aagtaacagg gtacacatat tgaccaaatc agggtaattt   1260
tgcatttgta attttaaaaa atgctttctt ctttaatat actttttgt ttatcttatt     1320
tctaatactt tccctaatct ctttcttttca gggcaataat gatacaatgt atcatgcctc   1380
tttgcaccat tctaaagaat aacagtgata atttctgggt taaggcaata gcaatatttc   1440
tgcatataaa tattctgca tataaattgt aactgatgta agaggtttca tattgctaat    1500
agcagctaca atccagctac cattctgctt ttattttatg gttgggataa ggctggatta   1560
ttctgagtcc aagctaggcc cttttgctaa tcatgttcat acctcttatc ttcctcccac   1620
agctcctggg caacgtgctg gtctgtgtgc tggcccatca ctttggcaaa gaattcaccc   1680
caccagtgca ggctgcctat cagaaagtgg tggctggtgt ggctaatgcc ctggcccaca   1740
agtatcacta agctcgcttt cttgctgtcc aatttctatt aaaggttcct tgttcccta    1800
agtccaacta ctaaactggg ggatatattg aagggccttg agcatctgga ttctgcctaa   1860
taaaaaacat ttattttcat tgcaatgatg tatttaaatt atttctgaat attttactaa   1920
aaagggaatg tgggaggtca gtgcatttaa aactaaaaga aatgaagagc tagttcaaac   1980
cttgggaaaa tacactatat cttaaactcc atgaaagaag gtgaggctgc aaacagctaa   2040
tgcacattgg caacagcccc tgatgcctat gccttattca tccctcagaa aaggattcaa   2100
gtagaggctt gatttggagg ttaaagtttt gctatgctgt attttacatt acttattgtt   2160
ttagctgtcc tcatgaatgt cttttcacta cccatttgct tatcctgact ctctcagcct   2220
tgactccact cagttctctt gcttagagat accacctttc ccctgaagtg ttccttccat   2280
gttttacggc gagatggttt ctcctcgcct ggccactcag ccttagttgt ctctgttgtc   2340
ttatagaggt ctacttgaag aaggaaaaac aggggcatg gtttgactgt cctgtgagcc    2400
cttcttccct gcctccccca ctcacagtga cccggaatct gcagtgctag tctcccggaa   2460
ctatcactct ttcacagtct gctttggaag gactgggctt agtatgaaaa gttaggactg   2520
agaagaattt gaaggggggc ttttttgtagc ttgatattca ctactgtctt attaccctat   2580
cataggccca ccccaaatgg aagtcccatt cttcctcagg atgtttaaga ttagcattca   2640
ggaagagatc agaggtctgc tggctccctt atcatgtccc ttatggtgct tctggctctg   2700
cagttattag catagtgtta ccatcaacca ccttaacttc atttttctta ttcaatacct   2760
agccgcggga acagagaaac aggagaatat gggccaaaca ggatatcgt ggtaagcagt    2820
tcctgccccg gctcagggcc aagaacagtt ggaacagcag aatatgggcc aaacaggata   2880
tctgtggtaa gcagttcctg ccccggctca gggccaagaa cagatggtcc ccagatgcgg   2940
tcccgccctc agcagtttct agagaaccat cagatgttcc caaggacctg                3000
aaatgaccct gtgccttatt tgaactaacc aatcagttcg cttctcgctt ctgttcgcgc   3060
gcttctgctc cccgagctct atataagcag agctcgttta gtgaaccgtc agatcgcggc   3120
cgcgccgcca ccatggtgag caagggcgag gagctgttca ccggggtggt gcccatcctg   3180
gtcgagctgg acggcgacgt aaacggccac aagttcagcg tgtccggcga gggcgagggc   3240
gatgccacct acggcaagct gaccctgaag ttcatctgca ccaccggcaa gctgcccgtg   3300
ccctggccca cccctcgtgac cacccctgacc tacggcgtgc agtgcttcag ccgctacccc   3360
gaccacatga gcagcacga cttcttcaag tccgccatgc ccgaaggcta cgtccaggag   3420
cgcaccatct cttcaagga cgacggcaac tacaagaccc gcgccgaggt gaagttcgag   3480
ggcgacaccc tggtgaaccg catcgagctg aagggcatcg acttcaagga ggacggcaac   3540
atcctggggc acaagctgga gtacaactac aacagccacg aggtcaagag cccaacatcg   3600
aagcagaaga acggcatcaa ggtgaacttc aagatccgcc acaacatcga ggacggcagc   3660
gtgcagctcg ccgaccacta ccagcagaac ccccatcg cgacggccc cgtgctgctg      3720
cccgacaacc actacctgag cacccagtcc gccctgagca agacccaa cgagaagcgc     3780
gatcacatgg tcctgctgga gttcgtgacc gccgcggga tcactctcgg catggacgag    3840
ctgtacaagt aagcttttatt tgtgaaattt gtgatgctat tgctttattt gtaaccatta   3900
```

```
taagctgcaa taaacaagtt aacaacaaca attgcattca tttttatgttt caggttcagg   3960
gggagatgtg ggaggttttt taaagccctg caggatgggt catttcacag aggaggacaa   4020
ggctactatc acaagcctgt ggggcaaggt gaatgtggaa gatgctggag gagaaaccct   4080
gggaaggtag gctctggtga ccaggacaag ggagggaagg aaggaccctg tgcctggcaa   4140
aagtccaggt cgcttctcag gatttgtggc accttctgac tgtcaaactg ttctttgtcaa  4200
tctcacaggc tcctggttgt ctacccatgg acccagaggt tctttgacag ctttggcaac   4260
ctgtcctctg cctctgccat catgggcaac cccaaagtca aggcacatgg caagaaggtg   4320
ctgacttcct tgggagatgc cacaaagcac ctggatgatc tcaagggcac ctttgcccag   4380
ctgagtgaac tgcagtcgac aggaacccct agtgatggag ttggccactc cctctctgcg   4440
cgctcgctcg ctcactgagg ccgggcgacc aaaggtcgcc cgacgcccgg gctttgcccg   4500
ggcggcctca gtgagcgagc gagcgcgcag ctggcgtaat agcgaagagg cccgcaccga   4560
tcgcccttcc caacagttgc gcagcctgaa tggcgaatgg cgattccgtt gcaatggctg   4620
gcggtaatat tgttctggat attaccagca aggccgatag tttgagttct tctactcagg   4680
caagtgatgt tattactaat caaagaagta ttgcgacaac ggttaatttg cgtgatggac   4740
agactctttt actcggtggc ctcactgatt ataaaaacac ttctcaggat tctggcgtac   4800
cgttcctgtc taaaatccct ttaatcggcc tcctgtttag ctcccgctct gattctaacg   4860
aggaaagcac gttatacgtg ctcgtcaaag caaccatagt acgcgccctg tagcggcgca   4920
ttaagcgcgg cgggtgtggt ggttacgcgc agcgtgaccg ctacacttgc cagcgcccta   4980
gcgcccgctc ctttcgcttt cttcccttcc tttctcgcca cgttcgccgg ctttccccgt   5040
caagctctaa atcgggggct ccctttaggg ttccgattta gtgctttacg cacctcgac   5100
cccaaaaaac ttgattaggg tgatggttca cgtagtgggc catcgccctg atagacggtt   5160
tttcgccctt tgacgttgga gtccacgttc tttaatagtg gactctttgt ccaaactgga   5220
acaacactca accctatctc ggtctattct tttgatttat aagggatttt gccgatttcg   5280
gcctattggt taaaaaatga gctgatttaa caaaaattta cgcgaattt taacaaaata   5340
ttaacgttta caatttaaat atttgcttat acaatcttcc tgttttttggg gcttttctga   5400
ttatcaaccg gggtacatat gattgacatg ctagttttac gattaccgtt catcgattct   5460
cttgtttgct ccagactctc aggcaatgac ctgatagcct ttgtagagac ctctcaaaaa   5520
tagctaccct ctccggcatg aatttatcag ctagaacggt tgaatatcat attgatggtg   5580
atttgactgt ctccggcctt tctcacccgt ttgaatcttt acctacacat tactcaggca   5640
ttgcatttaa aatatatgag ggttctaaaa attttatcc ttcgttgaa ataaaggctt    5700
ctcccgcaaa agtattacag ggtcataatg tttttggtac aaccgattta gctttatgct   5760
ctgaggcttt attgcttaat tttgctaatt ctttgccttg cctgtatgat ttattggatg   5820
ttggaatcgc ctgatgcggt attttctcct tacgcatctg tgcggtattt cacaccgcat   5880
atggtgcact ctcagtacaa tctgctctga tgccgcatag ttaagccagc cccgacaccc   5940
gccaacaccc gctgacgcgc cctgacgggc ttgtctgctc ccggcatccg cttacagaca   6000
agctgtgacc gtctccggga gctgcatgtg tcagaggttt tcaccgtcat caccgaaacg   6060
cgcgagacga aagggcctcg tgatacgcct atttttatag gttaatgtca tgataataat   6120
ggtttcttag acgtcaggtg gcacttttcg gggaaatgtg cgcggaaccc ctatttgttt   6180
atttttctaa atacattcaa atatgtatcc gctcatgaga caataaccct gataaatgct   6240
tcaataatat tgaaaaagga agagtatgag tattcaacat ttccgtgtcg cccttattcc   6300
cttttttgcg gcattttgcc ttcctgtttt tgctcaccca gaaacgctgg tgaaagtaaa   6360
agatgctgaa gatcagttgg gtgcacgagt gggttacatc gaactggatc tcaacagcgg   6420
taagatcctt gagagttttc gccccgaaga acgttttcca atgatgagca cttttaaagt   6480
tctgctatgt ggcgcggtat tatcccgtat tgacgccggg caagagcaac tcggtcgccg   6540
catacactat tctcagaatg acttggttga gtactcacca gtcacagaaa agcatcttac   6600
ggatggcatg acagtaagag aattatgcag tgctgccata accatgagtg ataacactgc   6660
ggccaactta cttctgacaa cgatcggagg accgaaggag ctaaccgctt ttttgcacaa   6720
catgggggat catgtaactc gccttgatcg ttgggaaccg gagctgaatg aagccatacc   6780
aaacgacgag cgtgacacca cgatgcctgt agcaatggca acaacgttgc gcaaactatt   6840
aactggcgaa ctacttactc tagcttcccg gcaacaatta atagactgga tggaggcgga   6900
taaagttgca ggaccacttc tgcgctcggc ccttccggct ggctggttta ttgctgataa   6960
atctggagcc ggtgagcgtg ggtctcgcgg tatcattgca gcactggggc cagatggtaa   7020
gccctcccgt atcgtagtta tctacacgac ggggagtcag gcaactatgg atgaacgaaa   7080
tagacagatc gctgagatag gtgcctcact gattaagcat tggtaactgt cagaccaagt   7140
ttactcatat atactttaga ttgatttaaa acttcattt taatttaaaa ggatctaggt   7200
gaagatcctt tttgataatc tcatgaccaa aatcccttaa cgtgagtttt cgttccactg   7260
agcgtcagac cccgtagaaa agatcaaagg atcttcttga tccttttttt tctgcgcgt   7320
aatctgctgc ttgcaaacaa aaaaaccacc gctaccagcg gtggtttgtt tgccggatca   7380
agagctacca actcttttc cgaaggtaac tggcttcagc agagcgcaga taccaaatac   7440
tgtccttcta gtgtagccgt agttaggcca ccacttcaag aactctgtag caccgcctac   7500
atacctcgct ctgctaatcc tgttaccagt ggctgctgcc agtggcgata agtcgtgtct   7560
taccgggttg gactcaagac gatagttacc ggataaggcg cagcggtcgg gctgaacggg   7620
gggttcgtgc acacagccca gcttggagcg aacgacctac accgaactga gatacctaca   7680
gcgtgagcta tgagaaagcg ccacgcttcc cgaagggaga aaggcggaca ggtatccggt   7740
aagcggcagg gtcggaacag gagagcgcac gagggagctt ccagggggaa acgcctggta   7800
tctttatagt cctgtcgggt ttcgccacct ctgacttgag cgtcgatttt tgtgatgctc   7860
gtcagggggg cggagcctat ggaaaaacgc cagcaacgcg gcctttttac ggttcctggc   7920
cttttgctgg ccttttgctc acatgttctt cctgcgtta tccccgatt ctgtggataa   7980
ccgtattacc gcctttgagt gagctgatac cgctcgccgc agccgaacga ccgagcgcag   8040
cgagtcagtg agcgaggaag cggaagagcg cccaatacgc aaaccgcctc tccccgcgcg   8100
ttggccgatt cattaatg                                                  8118
```

SEQ ID NO: 29          moltype = DNA  length = 7963
FEATURE                Location/Qualifiers
source                 1..7963
                       mol_type = other DNA
                       organism = Synthetic construct
SEQUENCE: 29
cagctgcgcg ctcgctcgct cactgaggcc gcccgggcaa agcccgggcg tcgggcgacc   60

```
tttggtcgcc cggcctcagt gagcgagcga gcgcgcagag agggagtggc caactccatc   120
actaggggtt ccttgtagtt aatgattaac ccgccatgct acttatctac gtagccatgc   180
tctagcggcc tcggcctctg cataaataaa aaaaattagt cagccatgag cttggacgcg   240
tagatcttga aacagtcatg atttatttca aataggtacg gataagtaga tattgaggta   300
agcattaggt cttatattat gtaacactaa tctattactg cgctgaaact gtggctttat   360
agaaattgtt ttcactgcac tattgagaaa ttaagagata atggcaaaag tcacaaagag   420
tatattcaaa aagaagtata gcacttttt ccttagaaacc actgctaact gaaagagact   480
aagatttgtc ccgtcaaaaa tcctggacct atgcctaaaa cacatttcac aatccctgaa   540
cttttcaaaa attggtacat gctttagctt taaactacag gcctcactgg agctagagac   600
aagaaggtaa aaaacggctg acaaaagaag tcctgtatc ctctatgatg ggagaaggaa   660
actagctaaa gggaagaata aattagagaa aaactggaat gactgaatcg gaacaaggca   720
aaggctataa aaaaaattag cagtatcctc ttgggggccc cttccccaca ctatctcaat   780
gcaaatatct gtctgaaacg gtccctggct aaactccacc catgggttgg ccagccttgc   840
cttgacaagg caaacttgac caatagtctt agagtatcca gtgaggccag gggccggcgg   900
ctggctaggg atgaagaata aaaggaagca cccttcagca gttccacaca ctcgcttctg   960
gaacgtctga ggtatcaat aagctcctag tccagacgcc atggtgcacc tgactcctga  1020
ggagaagtct gccgttactg ccctgtgggg caaggtgaac gtggatgaag ttggtggtga  1080
ggccctgggc aggttggtat caaggttaca agacaggttt aaggagacca atagaaactg  1140
ggcatgtgga gacagagaag actcttgggt ttctgatagg cactgactct ctctgcctat  1200
tggtctattt tcccacccctt aggctgctgg tggtctaccc ttgacccag aggttctttg  1260
agtccttttgg ggatctgtcc actcctgatg ctgttatggg caaccctaag gtgaaggctc  1320
atggcaagaa agtgctcggt gccttagtg atggcctggc tcacctggac aacctcaagg  1380
gcacctttgc ccagctgagt gagctgcact gtgacaagct gcacgtggat cctgagaact  1440
tcagggtgag tctatgggac ccttgatgtt ttctttcccc ttcttttcta tggttaagtt  1500
catgtccatg gaaggggaga agtaacaggg tacacatatt gaccaaatca gggtaatttt  1560
gcatttgtaa tttttaaaaaa tgcttctttc ttttaatata cttttttgtt tatcttattt  1620
ctaatacttt ccctaatctc tttctttcag ggcaataatg atacaatgta tcatgcctct  1680
ttgcaccatt ctaagaata acagtgataa tttctgggtt aaggcaatag caatatttct  1740
gcatataaat atttctgcat ataaattgta actgatgtaa gaggtttcat attgctaata  1800
gcagctacaa tccagctacc atttctgctt tatttttatgg ttgggataag gctggattat  1860
tctgagtcca agctaggccc ttttgctaat catgttcata cctcttatct tcctcccaca  1920
gctcctgggc aacgtgctgg tctgtgtgct ggcccatcac tttggcaaag aattcacccc  1980
accagtgcag gctgcctatc agaaagtggt ggctggtgtg gctaatgccc tggcccacaa  2040
gtatcactaa gctcgctttc ttgctgtcca atttctatta aaggttcctt tgttccctaa  2100
gtccaactac taaactgggg gatattatga agggccttga gcatctggat tctgcctaat  2160
aaaaaacatt tattttcatt gctgcagtgc tagtctcccg gaactatcac tcttttcacag  2220
tctgctttgg aaggactggg cttagtatga aagttagga ctgagaagaa tttgaaaggg  2280
ggcttttttgt agcttgatat tcactactgt cttattaccc tatcataggc ccaccccaaa  2340
tggaagtccc attcttcctc aggatgttta agattagcat tcaggaagag atcagagttc  2400
tgctggctcc cttatcatgt cccttatggt gcttctggct ctgcaccgcg gaacagaga  2460
aacaggagaa tatgggccaa acaggatatc tgtggtaagc agttcctgcc ccggctcagg  2520
gccaagaaca gttggaacag cagaatatgg gccaaacagg atatctgtgg taagcagttc  2580
ctgccccggc tcagggccaa gaacagatgg tcccccagatg cggtccccgcc ctcagcagtt  2640
tctagagaac catcagatgt ttccaggggtg ccccaaggac ctgaaatgac cctgtgcctt  2700
atttgaacta accaatcagt tcgcttctcg ctttctgttcg cgcgcttctg ctccccgagc  2760
tctatataag cagagctcgt ttagtgaacc gtcagatcgc ggccgcgcgg ccaccatggt  2820
gagcaagggc gaggagctgt tcaccggggt ggtgcccatc ctggtcgagc tggacggcga  2880
cgtaaacggc cacaagttca gcgtgtccgg cgagggcgag ggcgatgcca cctacggcaa  2940
gctgaccctg aagttcatct gcaccaccgg caagctgccc gtgccctggc ccaccctcgt  3000
gaccaccctg acctacggcg tgcagtgctt cagccgctac cccgaccaca tgaagcagca  3060
cgacttcttc aagtccgcca tgcccgaagg ctacgtccag gagcgcacca tcttcttcaa  3120
ggacgacggc aactacaaga cccgcgccga ggtgaagttc gagggcgaca cccctggtgaa  3180
ccgcatcgag ctgaagggca tcgacttcaa ggaggacggc aacatcctgg ggcacaagct  3240
ggagtacaac tacaacagcc acaacgtcta tatcatggcc gacaagcaga gaacggcat  3300
caaggtgaac ttcaagatcc gccacaacat cgaggacggc agcgtgcagc tcgccgacca  3360
ctaccagcag aacacccca tcggcgacgg ccccgtgctg ctgcccgaca ccactacct  3420
gagcacccag tccgccctga gcaaagaccc caacgagaag cgcgatcaca tggtcctgct  3480
ggagttcgtg accgccgccg ggatcactct cggcatggac gagctgtaca aggagggcag  3540
aggaagtctt ctaacatgcg gtgacgtgga ggagaatccg gccccccctg caggaacttc  3600
aaggtgagtc caggagatgt ttcagccctg ttgctttag tctcgaggca acttagacaa  3660
cggagtattg atctgagcac agcagggtgt gagctgtttg aagatactgg ggttggggggt  3720
gaagaaactg cagaggacta actgggctga acccagtgg taatgtttta gggcctaagg  3780
agtgcctcta aaaatctaga tggacaattt tgactttgag aaaagagagg tggaaatgag  3840
gaaaatgact tttctttatt agattccagt agaaagaact ttcatctttc cctcattttt  3900
gttgttttaa aacatctatc tggaggcagg acaagtatgg tcgttaaaaa gatgcaggca  3960
gaaggcatat attggctcag tcaaagtggg gaactttggt ggccaaacat acattgctaa  4020
ggctattcct atatcagctg gacacatata aaatgctgct aatgcttcat acaaacttaa  4080
tatcctttaa ttccagatgg gggcaaagta tgtccagggg tgaggaacaa ttgaaacatt  4140
tgggctggag tagatttttga aagtcagctc tgtgtgtgtg tgtgtgtgtg cgcgcgcgcg  4200
tgtcgacgta gataagtagc atggcgggtt aatcattaac tacaaggaac ccctagtgat  4260
ggagttggcc actccctctc tgcgcgctcg ctcgctcact gaggccgggc gaccaaaggt  4320
cgcccgacgc ccgggctttg cccggcggc tcagtgagc gagcgagcgc gcagctggc  4380
gtaatagcga agaggcccgc accgatcgcc cttcccaaca gttgcgcagc ctgaatggcg  4440
aatgggacgatt ccgttgcaat ggctggcggt taattattgc tggatattac cagcaaggcc  4500
gatagtttga gttcttctac tcaggcaagt gatgttatta caatcaaag aagtattgcg  4560
acaacggtta atttgcgtga tggacagact cttttactcg gtggcctcac tgattataaa  4620
aacacttctc aggattctgg cgtaccgttc ctgtctaaaa tccctttaat cggcctcctg  4680
tttagctccc gctctgattc taacgaggaa agcacggtta cgtgctcgt caaagcaacc  4740
atagtacgcg ccctgtagcg gcgcattaag cgcggcgggt gtggtggtta cgcgcagcgt  4800
```

```
gaccgctaca cttgccagcg ccctagcgcc cgctccttc gctttcttcc cttcctttct 4860
cgccacgttc gccggctttc cccgtcaagc tctaaatcgg gggctcccctt tagggttccg 4920
atttagtgct ttacggcacc tcgaccccaa aaaacttgat tagggtgatg gttcacgtag 4980
tgggccatcg ccctgataga cggttttcg ccctttgacg ttggagtcca cgttcttaa 5040
tagtggactc ttgttccaaa ctggaacaac actcaaccct atctcggtct attcttttga 5100
tttataaggg attttgccga tttcggccta ttggttaaaa aatgagctga tttaacaaaa 5160
atttaacgcg aattttaaca aaatattaac gtttacaatt taaatatttg cttatacaat 5220
cttcctgttt ttggggcttt tctgattatc aaccggggta catatgattg acatgctagt 5280
tttacgatta ccgttcatcg attctcttgt ttgctccaga ctctcaggca atgacctgat 5340
agcctttgta gagacctctc aaaaatagct accctctccg gcatgaattt atcagctaga 5400
acggttgaat atcatattga tggtgatttg actgtctccg gcctttctca cccgtttgaa 5460
tctttaccta cacattactc aggcattgca tttaaaatat atgagggttc taaaaatttt 5520
tatccttgcg ttgaaataaa ggcttctccc gcaaaagtat tacagggtca taatgttttt 5580
ggtacaaccg atttagcttt atgctctgag gctttattgc ttaattttgc taattctttg 5640
ccttgcctgt atgatttatt ggatgttgga atcgcctgat gcggtatttt ctccttacgc 5700
atctgtgcg tatttcacac cgcatatggt gcactctcag tacaatctgc tctgatgccg 5760
catagttaag ccagccccga caccgccaa cacccgctga cgcgccctga cgggcttgtc 5820
tgctcccggc atccgcttac agacaagctg tgaccgtctc cgggagctgc atgtgtcaga 5880
ggttttcacc gtcatcaccg aaacgcgcga gacgaaaggg cctcgtgata cgcctatttt 5940
tataggttaa tgtcatgata ataatggttt cttagacgtc aggtggcact tttcggggaa 6000
atgtgcgcgg aaccccatat tgtttatttt tctaaataca ttcaaatatg tatccgctca 6060
tgagacaata accctgataa atgcttcaat aatattgaaa aaggaagagt atgagtattc 6120
aacatttccg tgtcgccctt attccctttt ttgcggcatt ttgccttcct gtttttgctc 6180
acccagaaac gctggtgaaa gtaaaagatg ctgaagatca gttgggtgca cgagtgggtt 6240
acatcgaact ggatctcaac agcggtaaga tccttgagag ttttcgcccc gaagaacgtt 6300
ttccaatgat gagcactttt aaagtctgtc tatgtggcgc ggtattatcc cgtattgacg 6360
ccgggcaaga gcaactcggt cgccgcatac actattctca gaatgacttg gttgagtact 6420
caccagtcac agaaaagcat cttacggatg gcatgacagt aagagaatta tgcagtgctg 6480
ccataaccat gagtgataac actgcggcca acttacttct gacaacgatc ggaggaccga 6540
aggagctaac cgcttttttg cacaacatgg gggatcatgt aactcgcctt gatcgttggg 6600
aaccggagct gaatgaagcc ataccaaacg acgagcgtga caccacgatg cctgtagcaa 6660
tggcaacaac gttgcgcaaa ctattaactg gcgaactact tactctagct tcccggcaac 6720
aattaataga ctggatggag gcggataaag ttgcaggacc acttctgcgc tcggcccttc 6780
cggctggctg gtttattgct gataaatctg gagccggtga gcgtgggtct cgcggtatca 6840
ttgcagcact ggggccagat ggtaagccct cccgtatcgt agttatctac acgacgggga 6900
gtcaggcaac tatgcatgaa cgaaatagac agatcgctga gataggtgcc tcactgatta 6960
agcattggta actgtcagac caagtttact catatatact ttagattgat ttaaaacttc 7020
attttttaatt taaaaggatc taggtgaaga tcctttttga taatctcatg accaaaatcc 7080
cttaacgtga gttttcgttc cactgagcgt cagaccccgt agaaaagatc aaaggatctc 7140
cttgagatcc ttttttttctg cgcgtaatct gctgcttgca aacaaaaaa ccaccgctac 7200
cagcggtggt ttgtttgccg gatcaagagc taccaactct ttttccgaag gtaactggct 7260
tcagcagagc gcagatacca aatactgtcc ttctagtgta gccgtagtta ggccaccact 7320
tcaagaactc tgtagcaccg cctacatacc tcgctctgct aatcctgtta ccagtggctg 7380
ctgccagtgg cgataagtcg tgtcttaccg ggttggactc aagacgatag ttaccggata 7440
aggcgcagcg gtcgggctga acggggggttc gtgcacaca gcccagcttg gagcgaacga 7500
cctacaccga actgagatac ctacagcgtg agctatgaga aagcgccacg cttcccgaag 7560
ggagaaaggc ggacaggtat ccggtaagcg gcagggtcgg aacaggagag cgcacgaggg 7620
agcttccagg gggaaacgcc tggtatcttt atagtcctgt cgggtttcgc cacctctgac 7680
ttgagcgtcg attttttgtga tgctcgtcag ggggggcggag cctatggaaa aacgccagca 7740
acgcggcctt tttacggttc ctggcctttt gctggccttt tgctcacatg ttctttcctg 7800
cgttatcccc tgattctgtg gataaccgta ttaccgcctt tgagtgagct gataccgctc 7860
gccgcagccg aacgaccgag cgcagcgagt cagtgagcga ggaagcggaa gagcgcccaa 7920
tacgcaaacc gcctctcccc gcgcgttggc cgattcatta atg 7963

SEQ ID NO: 30          moltype = DNA   length = 7553
FEATURE                Location/Qualifiers
source                 1..7553
                       mol_type = other DNA
                       organism = Synthetic construct
SEQUENCE: 30
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac acgcgtagat 180
cttccttaga aaccactgct aactgaaaga gactaagatt tgtcccgtca aaatcctgg 240
acctatgcct aaaacacatt tcacaatccc tgaactttc aaaaattggt acatgcttta 300
gctttaaact acaggcctca ctggagctag agacaagaag gtaaaaaacg ctgacaaaa 360
gaagtcctgg tatcctctat gatgggagaa ggaaactagc taaagggaag aataaattag 420
agaaaaactg gaatgactga atcggaacaa ggcaaaggct ataaaaaaaa ttagcagtat 480
cctcttgggg gccccttccc cacactatct caatgcaaat atctgtctga aacggtcct 540
ggctaaactc cacccatggg ttggccagcc ttgccttgac aaggcaaact tgaccaatag 600
tcttagagta tccagtgagg ccaggggccg gcggctggct agggatgaag aataaaagga 660
agcacccttc agcagttcca cacactcgct tctggaacgt ctgaggttat caataagctc 720
ctagtccaga cgccatggtg cacctgactc ctgaggagaa gtctgccgtt actgccctgt 780
ggggcaaggt gaacgtggat gaagttggtg gtgaggccct gggcagg 840
tacaagacag gtttaaggag accaataaga actgggcatg tggagacaga gaagactctt 900
gggtttctga taggcactga ctctctctgc ctattggtct attttccac ccttaggctg 960
ctggtggtct acccttggac ccagaggttc tttgagtcct ttgggatct gtccactcct 1020
gatgctgtta tgggcaaccc taaggtgaag gctcatggca agaaagtgct cggtgccttt 1080
agtgatggcc tggctcacct ggacaacctc aagggcacct ttgcccagct gagtgagctg 1140
```

```
cactgtgaca agctgcacgt ggatcctgag aacttcaggg tgagtctatg ggacccttga   1200
tgttttcttt cccctcttt tctatggtta agttcatgtc ataggaaggg gagaagtaac   1260
agggtacaca tattgaccaa atcagggtaa ttttgcattt gtaattttaa aaaatgcttt   1320
cttcttttaa tatactttt tgtttatctt atttctaata ctttccctaa tctctttctt   1380
tcagggcaat aatgatacaa tgtatcatgc ctctttgac cattctaaag aataacagtg   1440
ataatttctg ggttaaggca atagcaatat ttctgcatat aaatatttct gcatataaat   1500
tgtaactgat gtaagaggtt tcatattgct aatagcagct acaatccagc taccattctg   1560
cttttatttt atggttggga taaggctgga ttattctgag tccaagctag gccctttgc   1620
taatcatgtt catacctctt atcttcctcc cacagctcct gggcaacgtg ctggtctgtg   1680
tgctggccca tcactttggc aaagaattca ccccaccagt gcaggctgcc tatcagaaag   1740
tggtggctgg tgtggctaat gccctggccc acaagtatca ctaagctcgc tttcttgctg   1800
tccaatttct attaaaggtt cctttgttcc ctaagtccaa ctactaaact gggggatatt   1860
atgaagggcc ttgagcatct ggattctgcc taataaaaaa catttatttt cattgcaatg   1920
atgtatttaa attatttctg aatattttac taaaaagggga atgtgggagg ttgcagtgtt   1980
agtctcccgg aactatcact ctttcacagt ctgctttgga aggactgggc ttagtatgaa   2040
aagttaggac tgagaagaat ttgaaagggg gcttttttgta gcttgatatt cactactgtc   2100
ttattaccct atcataggcc caccccaaat ggaagtccca ttcttcctca ggatgtttaa   2160
gattagcatt caggaagaga tcagaagtct gctggctccc ttatcatgtc ccttatggtg   2220
cttctggctc tgcaccgcgg aacagagaaa acaggagaat atgggccaaa caggatatct   2280
gtggtaagca gttcctgccc cggctcaggg ccaagaacag ttggaacagc agaatatggg   2340
ccaaacagga tatctgtggt aagcagttcc tgccccggct cagggccaag aacagatggt   2400
cccagatgc ggtcccgccc tcagcagttt ctagagaacc atcagatgtt tccagggtgc   2460
cccaaggacc tgaaatgacc ctgtgcctta tttgaactaa ccaatcagtt cgcttctcgc   2520
ttctgttcgc gcgcttctgc tccccgagct ctatataagc agagctcgtt tagtgaaccg   2580
tcagatcgcg gccgcgccgc caccatggtg agcaagggcg aggagctgtt caccggggtg   2640
gtgcccatcc tggtcgagct ggacggcgac gtaaacggcc acaagttcag cgtgtccggc   2700
gagggcgagg gcgatgccac ctacggcaag ctgaccctga agttcatctg caccaccggc   2760
aagctgcccg tgccctggcc caccctcgtg accaccctga cctacggcgt gcagtgcttc   2820
agccgctacc ccgaccacat gaagcagcac gacttcttca agtccgccat gcccgaaggc   2880
tacgtccagg agcgcaccat cttcttcaag gacgacggca actacaagac ccgcgccgag   2940
gtgaagttcg agggcgacac cctggtgaac cgcatcgagc tgaagggcat cgacttcaag   3000
gaggacggca acatcctggg gcacaagctg gagtacaact acaacagcca caacgtctat   3060
atcatggccg acaagcagaa gaacggcatc aaggtgaact tcaagatccg ccacaacatc   3120
gaggacggca gcgtgcagct cgccgaccac taccagcaga acacccccat cggcgacggc   3180
cccgtgctgc tgcccgacaa ccactacctg agcacccagt ccgccctgag caaagacccc   3240
aacgagaagc gcgatcacat ggtcctgctg gagttcgtga ccgccgccgg gatcactctc   3300
ggcatggacg agctgtacaa ggagggcaga ggaagtcttc taacatgcgg tgacgtggag   3360
gagaatccgg gcccccctgc aggaacttca aggtgagtcc aggagatgtt tcagccctgt   3420
tgccttagt ctcgaggcaa cttagacaac ggagtattga tctgagcaca gcagggtgtg   3480
agctgtttga agatactggg gttggggggtg aagaaactgc agaggactaa ctgggctgag   3540
acccagtggt aatgttttag ggcctaagga gtgcctctaa aaatctagat ggacaatttt   3600
gactttgaga aaagagaggt ggaaatgagg aaaatgactt ttcttttatta gattccagta   3660
gaaagaactt tcatctttcc ctcattttg tgtttttaaa acatctatct ggaggcgaga   3720
caagtatggt cgttaaaaaag atgcaggcag aaggcatata ttggctcagt caaagtgggg   3780
aactttggtg ggtcgacgta gataagtagc atggcgggtt aatcattaac tacaaggaac   3840
ccctagtgat ggagttggcc actccctctc tgcgcgctcg ctcgctcact gaggccgggc   3900
gaccaaaggt cgcccgacgc ccgggcttg ccgggcgcg ctcagtgagc gagcgagcgc   3960
gccagctggc gtaatagcga agaggcccgc accgatcgcc cttcccaaca gttgcgcagc   4020
ctgaatggcg aatggcgatt ccgttgcaat ggctggcggt aatatttgttc tggatattac   4080
cagcaaggcc gatagtttga gttcttctac tcaggcaagt gatgttatta ctaatcaaag   4140
aagtattgcg acaacggtta atttgcgtga tggacagatt ctttttactcg gtggcctca   4200
tgattataaa aacacttctc aggattctgg cgtaccgttc ctgtctaaaa tccctttaat   4260
cggcctcctg tttagctccc gctctgattc taacgaggaa agcacgttat acgtgctcgt   4320
caaagcaacc atagtacgcg ccctgtagcg gcgcattaag cgcggcgggt gtggtggtta   4380
cgcgcagcgt gaccgctaca cttgccagcg ccctagcgcc cgctcctttc gctttcttcc   4440
cttcctttct cgccacgttc gccggctttc cccgtcaagc tctaaatcgg gggctccctt   4500
tagggttccg atttagtgct ttacggcacc tcgaccccaa aaaacttgat tagggtgatg   4560
gttcacgtag tgggccatcg ccctgataga cggttttttcg ccctttgacg ttggagtcca   4620
cgttctttaa tagtggactc ttgttccaaa ctggaacaac actcaaccct atctcggtct   4680
attctttga tttataaggg attttgccga tttcggccta ttggttaaaa aatgagctga   4740
tttaacaaaa atttaacgcg aattttaaca aaatattaac gtttacaatt taaatatttg   4800
cttatacaat cttcctgttt tgggcgcttt tctgattatc aaccgggta catatgattg   4860
acatgctagt tttacgatta ccgttcatcg attctcttgt ttgctccaga ctctcaggca   4920
atgacctgat agctttgta gagacctctc aaaaatagct acctctccg gcatgaattt   4980
atcagctaga acggttgaat atcatattga tggtgatttg actgtctccg gcctttctca   5040
cccgtttgaa tctttaccta cacattactc aggcattgca tttaaaatat atgagggttc   5100
taaaaatttt tatcccttgcg ttgaaataaa ggcttctccc gcaaaagtat tacagggtca   5160
taatgttttt ggtacaaccg atttagcttt atgctctgag gctttattgc ttaattttg   5220
taattctttg ccttgcctgt atgatttatt ggatgttgga atcgcctgat ggtgatttg   5280
ctccttacgc atctgtgcgg tatttcacac cgcatatggt gcactctcag tacaatctgc   5340
tctgatgccg catagttaag ccagccccga cacccgccaa cacccgctga cgcgccctga   5400
cgggcttgtc tgctccccgg atccgcttac agacaagctg tgaccgtctc cgggagctgc   5460
atgtgtcaga ggttttcacc gtcatcaccg aaacgcgcga cgaaaggg cctcgtgata   5520
cgcctattt tataggttaa tgtcatgata ataatggttt cttagacgtc aggtggcact   5580
tttcggggaa atgtgcgcgg aaccctatt tgtttatttt tctaaataca ttcaaatatg   5640
tatccgctca tgagacaata accctgataa atgcttcaat aatattgaaa aaggaagagt   5700
atgagtattc aacatttccg tgtcgccctt attccctttt tgcggcatt tgccttcct   5760
gttttgctc acccagaaac gctggtgaaa gtaaaagatg ctgaagatca gttgggtgca   5820
cgagtgggtt acatcgaact ggatctcaac agcggtaaga tccttgagag ttttcgcccc   5880
```

```
gaagaacgtt ttccaatgat gagcacttt aaagttctgc tatgtggcgc ggtattatcc   5940
cgtattgacg ccgggcaaga gcaactcggt cgccgcatac actattctca gaatgacttg   6000
gttgagtact caccagtcac agaaaagcat cttacggatg gcatgacagt aagagaatta   6060
tgcagtgctg ccataaccat gagtgataac actgcggcca acttacttct gacaacgatc   6120
ggaggaccga aggagctaac cgctttttg cacaacatgg gggatcatgt aactcgcctt   6180
gatcgttggg aaccggagct gaatgaagcc ataccaaacg acgagcgtga caccacgatg   6240
cctgtagcaa tggcaacaac gttgcgcaaa ctattaactg gcgaactact tactctagct   6300
tcccggcaac aattaataga ctggatggag gcggataaag ttgcaggacc acttctgcgc   6360
tcggcccttc cggctggctg gtttattgct gataaatctg gagccggtga gcgtgggtct   6420
cgcggtatca ttgcagcact ggggccagat ggtaagccct cccgtatcgt agttatctac   6480
acgacgggga gtcaggcaac tatggatgaa cgaaatagac agatcgctga gataggtgcc   6540
tcactgatta agcattggta actgtcagac caagtttact catatatact ttagattgat   6600
ttaaaacttc atttttaatt taaaaggatc taggtgaaga tcctttttga taatctcatg   6660
accaaaatcc cttaacgtga gttttcgttc cactgagcgt cagaccccgt agaaaagatc   6720
aaaggatctt cttgagatcc ttttttctg cgcgtaatct gctgcttgca aacaaaaaaa   6780
ccaccgctac cagcggtggt ttgtttgccg gatcaagagc taccaactct ttttccgaag   6840
gtaactggct tcagcagagc gcagatacca atactgtcc ttctagtgta gccgtagtta   6900
ggccaccact tcaagaactc tgtagcaccg cctacatacc tcgctctgct aatcctgtta   6960
ccagtggctg ctgccagtgg cgataagtcg tgtcttaccg ggttggactc aagacgatag   7020
ttaccggata aggcgcagcg tcgggctga acggggggtt cgtgcacaca gcccagcttg   7080
gagcgaacga cctacaccga actgagatac ctacagcgtg agctatgaga aagcgccacg   7140
cttcccgaag ggagaaaggc ggacaggtat ccggtaagcg gcagggtcgg aacaggagag   7200
cgcacgaggg agcttccagg gggaaacgcc tggtatcttt atagtcctgt cgggtttcgc   7260
cacctctgac ttgagcgtcg attttttgtga tgctcgtcag gggggcggag cctatggaaa   7320
aacgccagca acgcggcctt tttacggttc ctggcctttt gctggccttt tgctcacatg   7380
ttctttcctg cgttatcccc tgattctgtg gataaccgta taaccgcctt tgagtgagct   7440
gataccgctc gccgcagccg aacgaccgag cgcagcgagt cagtgagcga ggaagcggaa   7500
gagcgcccaa tacgcaaacc gcctctcccc gcgcgttggc cgattcatta atg          7553

SEQ ID NO: 31        moltype = DNA  length = 8029
FEATURE              Location/Qualifiers
source               1..8029
                     mol_type = other DNA
                     organism = Synthetic construct
SEQUENCE: 31
cagctgcgcg ctcgctcgct cactgaggcc gccgggcaa agcccgggcg tcggcgacc       60
tttggtcgcc cggcctcagt gagcgagcga gcgcgcagag agggagtggc caactccatc   120
actaggggtt ccttgtagtt aatgattaac ccgccatgct acttatctac acgcgtagat   180
cttgaaacag tcatgattta tttcaaatag gtacggataa gtagatattg aggtaagcat   240
taggtcttat attatgtaac actaatctat tactgcgctg aaactgtggc tttatagaaa   300
ttgttttcac tgcactattg agaaattaag agataatggc aaaagtcaca aagagtatat   360
tcaaaaagaa gtatagcact ttttccttag aaaccactgc taactgaaag agactaagat   420
ttgtcccgtc aaaaatcctg gacctatgcc taaaacacat ttcacaatcc ctgaacttt    480
caaaaattgg tacatgcttt agcttaaac tacaggcctc actgagcta gagacaagaa    540
ggtaaaaaac ggctgacaaa agaagtcctg gtatcctcta tgatgggaga aggaaactag   600
ctaaagggaa gaataaatta gagaaaaact ggaatgactg aatcggaaca aggcaaaggc   660
tataaaaaaa attagcagta tcctcttggg ggcccctttcc ccacactatc tcaatgcaaa   720
tatctgtctg aaacggtccc tggctaaact ccaccatgg gttggccagc cttgccttga   780
caaggcaaac ttgaccaata gtcttagagt atccagtgag gccaggggcc ggcggctggc   840
tagggatgaa gaataaaagg aagcacccctt cagcagttcc acacactcgc ttctggaacg   900
tctgaggtta tcaataagct cctagtccaa acgccatggt gacctgact cctgaggaga    960
agtctgccgt tactgccctg tggggcaagg tgaacgtgga tgaagttggt ggtgaggccc   1020
tgggcaggtt ggtatcaagg ttacaagaca ggtttaagga gaccaataga aactgggcat   1080
gtggagacag agaagactct tgggtttctg ataggcactg actctctctg cctattggtc   1140
tattttccca cccttaggct gctggtggtc taccctttgga cccagaggtt cttttgagtcc   1200
tttggggatc tgtccactcc tgatgctgtt atgggcaacc ctaaggtgaa ggctcatggc   1260
aagaaagtgc tcggtgcctt tagtgatggc ctggctcacc tggacaacct caagggcacc   1320
tttgcccagc tgagtgagct gcactgtgac aagctgcacg tggatcctga aacttcagg    1380
gtgagtctat gggacccttg atgttttctt tccccttctt ttctatgtt aagttcatgt   1440
cataggaagg ggagaagtaa caggggtacac atattgacca aatcaggta atttttgcatt   1500
tgtaatttta aaaatgcttt tcttctttta atatactttt tgttatct tatttctaat      1560
actttcccta atctctttct ttcagggcaa taatgataca atgtatcatg cctctttgca   1620
ccattctaaa gaataacagt gataatttct gggttaaggc aatagcaata tttctgcata   1680
taaatatttc tgcatataaa ttgtaactga tgtaagaggt ttcatattgc taatagcagc   1740
tacaatccag ctaccattct gcttttattt tatggttggg ataaggctgg attattctga   1800
gtccaagcta ggcccttttg ctaatcatgt tcatacctct tatcttcctc ccacagctcc   1860
tgggcaacgt gctggtctgt gtgctggccc atcactttgg caaagaattc accccaccag   1920
tgcaggctgc ctatcagaaa gtggtggctg gtgtggctaa tgccctggcc cacaagtatc   1980
actaagctcg ctttcttgct gtccaatttc tattaaaggt tccttttgtct cctaagtcca   2040
actactaaac tggggatat tatgaaggc cttgagcatc tggattctgc ctaataaaaa     2100
acatttattt tcattgcaat gatgtattta aattattcct gaatatttta ctaaaaaggg   2160
aatgtgggag gttgcagtgc tagtctcccg gaactatcac tctttcacag tctgctttgg   2220
aaggactggg cttagtatga aaagttagga ctgagaagaa tttgaaggg gcttttttgt    2280
agcttgatat tcactactgt tcttattaccc tcataggccc caccccaaa tggaagtcca   2340
attcttcctc aggatgttta agattagcat tcaggaagaa atcagaggtc tgctggctca   2400
cttatcatgt cccttatggt gcttctggct ctgaccgcg gaacagaga aacaggagaa     2460
tatgggccaa acaggatatc tgtggtaagc agttcctgcc ccggctcagg gccaagaaca   2520
gttgaacag cagaatatgg gccaaacagg atatctgtgg taagcagttc ctgccccggc   2580
tcagggccaa gaacagatgg tcccagatgc ggtcccgcc ctcagcagtt ctagagaac     2640
```

```
catcagatgt ttccaggggtg ccccaaggac ctgaaatgac cctgtgcctt atttgaacta   2700
accaatcagt tcgcttctcg cttctgttcg cgcgcttctg ctccccgagc tctatataag   2760
cagagctcgt ttagtgaacc gtcagatcgc ggccgcgccg ccaccatggt gagcaagggc   2820
gaggagctgt tcaccggggt ggtgcccatc ctggtcgagc tggacggcga cgtaaacggc   2880
cacaagttca gcgtgtccgg cgagggcgag ggcgatgcca cctacggcaa gctgaccctg   2940
aagttcatct gcaccaccgg caagctgccc gtgccctggc ccaccctcgt gaccaccctg   3000
acctacggcg tgcagtgctt cagccgctac cccgaccaca tgaagcagca cgacttcttc   3060
aagtccgcca tgcccgaagg ctacgtccag gagcgcacca tcttcttcaa ggacgacggc   3120
aactacaaga cccgcgccga ggtgaagttc gagggcgact ccctggtgaa ccgcatcgag   3180
ctgaagggca tcgacttcaa ggaggacggc aacatcctgg ggcacaagct ggagtacaac   3240
tacaacagcc acaacgtcta tatcatggcc gacaagcaga agaacggcat caaggtgaac   3300
ttcaagatcc gccacaacat cgaggacggc agcgtgcagc tcgccgacca ctaccagcag   3360
aacacccccca tcggcgacgg ccccgtgctg ctgcccgaca accactacct gagcacccag   3420
tccgccctga gcaaagaccc caacgagaag cgcgatcaca tggtcctgct ggagttcgtg   3480
accgccgccg ggatcactct cggcatggac gagctgtaca agtaagcttt atttgtgaaa   3540
tttgtgatgc tattgcttta tttgtaacca ttataagctg caataaacaa gttaacaaca   3600
acaattgcat tcattttatg tttcaggttc agggggagat gtgggaggtt ttttaaagcc   3660
ctgcaggatg ggtcatttca cagaggagga caaggctact atcacaagcc tgtggggcaa   3720
ggtgaatgtg gaagatgctg gaggagaaac cctgggaagg taggctctgg tgaccaggac   3780
aagggaggga aggaaggacc ctgtgcctgg caaaagtcca ggtcgcttct caggatttgt   3840
ggcaccttct gactgtcaaa ctgttcttgt caatctcaca ggctcctggt tgtctaccca   3900
tggaccccaga ggttctttga cagctttggc aacctgtcct ctgcctctgc catcatgggc   3960
aaccccaaag tcaaggcaca tggcaagaag gtgctgactt ccttgggaga tgccacaaag   4020
cacctggatg atctcaaggg cacctttgcc cagctgagtg aactgcactg tgacaagctg   4080
catgtggatc ctgagaactt caaggtgagt ccaggagatg tttcagccct gttgccttta   4140
gtctcgaggc aacttagaca acggagtatt gatctgagca cagcagggtg tgagctgttt   4200
gaagatactg gggttggggg tgaagaaact gcagaggact aactgggctg agcccagtg   4260
gtaatgtgtc gacgtagata agtagcatgg cgggttaatc attaactaca aggaacccct   4320
agtgatggag ttggccactc cctctctgcg cgctcgctcg ctcactgagg ccgggcgacc   4380
aaaggtcgcc cgacgcccgg gctttgcccg ggcggcctca gtgagcgagc gagcgcgcca   4440
gctggcgtaa tagcgaagag gcccgcaccg atcgcccttc ccaacagttg cgcagcctga   4500
atggcgaatg gcgattccgt tgcaatggct ggcggtaata ttgttctgga tattaccagc   4560
aaggccgata gtttgagttc ttctactcag gcaagtgatg ttattactaa tcaaagaagt   4620
attgcgacaa cggttaattt gcgtgatgga cagactcttt tactcggtgg cctcactgat   4680
tataaaaaca cttctcagga ttctggcgta ccgttcctgt ctaaaatccc tttaatcggc   4740
ctcctgttta gctcccgctc tgattctaac gaggaaagca cgttatacgt gctcgtcaaa   4800
gcaaccatag tacgcgccct gtagcggcgc attaagcgcg gcgggtgtgg tggttacgcg   4860
cagcgtgacc gctacacttg ccagcgccct agcgcccgct cctttcgctt tcttcccttc   4920
ctttctcgcc acgttcgccg gctttccccg tcaagctcta aatcggggc tccctttagg   4980
gttccgattt agtgctttac ggcacctcga ccccaaaaaa cttgattagg gtgatggttc   5040
acgtagtggg ccatcgccct gatagacggt ttttcgccct ttgacgttgg agtccacgtt   5100
ctttaatagt ggactcttgt tccaaactgg aacaacactc aacccctatct cggtctattc   5160
ttttgattta taagggattt tgccgatttc ggcctattgg ttaaaaaatg agctgattta   5220
acaaaaattt aacgcgaatt ttaacaaaat attaacgttt acaatttaaa tatttgctta   5280
tacaatcttc ctgttttggg gcttttctg attatcaacc ggggtacata tgattgacat   5340
gctagtttta cgattaccgt tcatcgattc tcttgtttgc tccagactct caggcaatga   5400
cctgatagcc tttgtagaga cctctcaaaa atagctacct ctccggcat gaatttatca   5460
gctagaacgg ttgaatatca tattgatggt gatttgactg tctccggcct ttctcacccg   5520
tttgaatctt tacctacaca ttactcaggc attgcattta aaatatatga gggttctaaa   5580
aatttttatc cttgcgttga aataaaggct tctcccgcaa aagtattaca gggtcataat   5640
gtttttggta caaccgattt agctttatgc tctgaggctt tattgcttaa ttttgctaat   5700
tctttgcctt gcctgtatga tttattggat gttggaatcg cctgatgcgg tatttttctcc   5760
ttacgcatct gtgcggtatt tcacaccgca tatggtgcac tctcagtaca atctgctctg   5820
atgccgcata gttaagccag ccccgacacc cgccaacacc cgctgacgcg ccctgacggg   5880
cttgtctgct cccggcatcc gcttacagac aagctgtgac cgtctccggg agctgcatgt   5940
gtcagaggtt ttcaccgtca tcaccgaaac gcgcgagacg aaagggcctc gtgatacgcc   6000
tatttttata ggttaatgtc atgataataa tggtttctta cgtcaggt ggcacttttc   6060
ggggaaatgt gcgcggaacc cctatttgtt tatttttcta aatacattca aatatgtatc   6120
cgctcatgag acaataaccc tgataaatgc ttcaataata ttgaaaaagg aagagtatga   6180
gtattcaaca tttccgtgtc gcccttattc cctttttgc ggcattttgc cttcctgttt   6240
ttgctcaccc agaaacgctg gtgaaagtaa aagatgctga agatcagttg ggtgcacgag   6300
tgggttacat cgaactggat ctcaacagcg gtaagatcct tgagagtttt cgccccgaag   6360
aacgttttcc aatgatgagc acttttaaag ttctgctatg tggcgcggta ttatcccgta   6420
ttgacgccgg caagagcaa ctcggtcgcc gcatacacta ttctcagaat gacttggttg   6480
agtactcacc agtcacagaa aagcatctta cggatggcat gacagtaaga gaattatgca   6540
gtgctgccat aaccatgagt gataacactg cggccaactt acttctgaca acgatcggag   6600
gaccgaagga gctaaccgct ttttgcaca acatggggga tcatgtaact cgccttgatc   6660
gttgggaacc ggagctgaat gaagccatac caaacgacga gcgtgacacc acgatgcctg   6720
tagcaatggc aacaacgttg cgcaaactat taactggcga actacttact ctagcttccc   6780
ggcaacaatt aatagactgg atggaggcgg ataaagttgc aggaccactt ctgcgctcgg   6840
cccttccggc tggctggttt attgctgata aatctggagc cggtgagcgt gggtctcgcg   6900
gtatcattgc agcactgggg ccagatggta agccctcccg tatcgtagtt atctacacga   6960
cggggagtca ggcaactatg gatgaacgaa atagacagat cgctgagata ggtgcctcac   7020
tgattaagca ttggtaactg tcagaccaag tttactcata tatactttag attgatttaa   7080
aacttcattt ttaatttaaa aggatctagg tgaagatcct ttttgataat ctcatgacca   7140
aaatccctta acgtgagttt tcgttccact gagcgtcaga ccccgtagaa aagatcaaag   7200
gatcttcttg agatccttt tttctgcgcg taatctgctg cttgcaaaca aaaaaaccac   7260
cgctaccagc ggtggtttgt ttgccggatc aagagctacc aactctttt ccgaaggtaa   7320
ctggcttcag cagagcgcag ataccaaata ctgtccttct agtgtagccg tagttaggcc   7380
```

```
accacttcaa gaactctgta gcaccgccta catacctcgc tctgctaatc ctgttaccag  7440
tggctgctgc cagtggcgat aagtcgtgtc ttaccgggtt ggactcaaga cgatagttac  7500
cggataaggc gcagcggtcg ggctgaacgg ggggttcgtg cacacagccc agcttggagc  7560
gaacgaccta caccgaactg agatacctac agcgtgagct atgagaaagc gccacgcttc  7620
ccgaagggag aaaggcggac aggtatccgg taagcggcag ggtcggaaca ggagagcgca  7680
cgagggagct tccaggggga aacgcctggt atctttatag tcctgtcggg tttcgccacc  7740
tctgacttga gcgtcgattt ttgtgatgct cgtcaggggg gcggagccta tggaaaaacg  7800
ccagcaacgc ggccttttta cggttcctgg ccttttgctg gccttttgct cacatgttct  7860
ttcctgcgtt atcccctgat tctgtggata accgtattac cgcctttgag tgagctgata  7920
ccgctcgccg cagccgaacg accgagcgca gcgagtcagt gagcgaggaa gcggaagagc  7980
gcccaatacg caaaccgcct ctccccgcgc gttggccgat tcattaatg              8029

SEQ ID NO: 32           moltype = DNA   length = 8466
FEATURE                 Location/Qualifiers
source                  1..8466
                        mol_type = other DNA
                        organism = Synthetic construct
SEQUENCE: 32
cagctgcgcg ctcgctcgct cactgaggcc gcccggcaa agcccgggcg tcgggcgacc    60
tttggtcgcc cggcctcagt gagcgagcga gcgcgcagag agggagtggc caactccatc   120
actagggggt ccttgtagtt aatgattaac ccgccatgct acttatctac gtagccatgc   180
tctagcggcc tcggcctctg cataaataaa aaaaattagt cagccatggg cttggacgcg   240
tagatctcat ctttactgag catagaagag ctacgccaaa accctgggtc atcagccagc   300
acacacactt atccagtggt aaatacacat catctggtgt atacatacat acctgaatat   360
ggaatcaaat atttttctaa gatgaaacag tcatgattta tttcaaatag gtacggataa   420
gtagatattg aggtaagcat taggtcttat attatgtaac taatctat tactgcgctg     480
aaactgtggc tttatagaaa ttgttttcac tgcactattg agaaattaag agataatggc   540
aaaagtcaca aagagtatat tcaaaaagaa gtatagcact ttttccttag aaaccactgc   600
taactgaaag agactaagat ttgtcccgtc aaaaatcctg gacctatgcc taaaacacat   660
ttcacaatcc ctgaactttt caaaaattgg tacatgcttt agcttttaaac tacaggcctc  720
actggagcta gagacaagaa ggtaaaaaac ggctgacaaa agaagtcctg gtatcctcta   780
tgatgggaga aggaaactag ctaaagggaa gaataaatta gagaaaaact ggaatgactg   840
aatcggaagt aaatacactt gcaaggagg atgttttag tagcaatttg tactgatggt     900
atggggcaa gagatatatc ttagaggag ggctgagggt ttgaagtcca actcctaagc     960
cagtgccaga agagccaagg acaggtacgg ctgtcatcac ttagacctca ccctgtggag  1020
ccacaccta gggttggcca atctactccc aggagcaggg agggcaggag ccagggctgg   1080
gcataaaagt caggggcagag ccatctattg cttatggtgc acctgactcc tgaggagaag  1140
tctgccgtta ctgccctgtg gggcaaggtg aacgtggatg aagttggtgg tgaggccctg  1200
ggcaggctgc tggtggtcta cccttggacc cagaggttct ttgagtcctt tggggatctg  1260
tccactcctg atgctgttat gggcaaccct aaggtgaagg ctcatggcaa gaaagtgctc  1320
ggtgcctta gtgatggcct ggctcacctg gacaacctca agggcacctt tgcccagctg   1380
agtgagctgc actgtgacaa gctgcacgtg gatcctgaga acttcagggt gagtctatgg  1440
gacccttgat gtttctttc cccttctttt ctatggtgaa agttcatgtca taggaagggg   1500
agaagtaaca gggtacacat attgaccaaa tcagggtaat tttgcatttg taattttaaa  1560
aaatgctttc ttcttttaat atacttttttt gtttatctta tttctaatac ttcccttaat  1620
ctcttttcttt cagggcaata atgatacaat gtatcatgcc tctttgcacc attctaaaga  1680
ataacagtga taatttctgg gttaaggcaa tagcaatatt tctgcatata aatatttctg  1740
catataaatt gtaactgatg taagaggttt catattgcta atagcagcta caatccagct  1800
accattctgc ttttatttta tggttgggat aaggctggat tattctgagt ccaagctagg  1860
cccttttgct aatcatgttc atacctctta tcttcctccc acagctcctg ggcaacgtgc  1920
tggtctgtgt gctggcccat cacttttggca aagaattcac cccaccagtg caggctgcct  1980
atcagaaagt ggtggctggt gtggctaatg ccctggccca caagtatcac taagctcgct  2040
ttcttgctgt ccaatttcta ttaaaggttc ctttgttccc taagtccaac tactaaactg  2100
ggggatatta tgaagggcct tgagcatctg gattctgcct aataaaaaac attattttc   2160
attgcaatga tgtatttaaa ttatttctga atattttact aaaaagggaa tgtgggaggt  2220
cagtgcattt aaaacataaa gaaatgaaga gctagttcaa accttgggaa aatacactat  2280
atcttaaact ccatgaaaga aggtgaggct gcaaacagct aatgcacatt ggcaacagcc  2340
cctgatgcct atgccttatt catccctcag aaaaggattc aagtagaggc ttgatttgga  2400
ggtaaagtt ttgctatgct gtattttaca ttacttattg ttttagctgt cctcatgaat    2460
gtcttttcac tacccatttg cttatcctgc atctctcagc cttgactcca ctcagttctc  2520
ttgcttagag ataccacctt tcccctgaag tgttccttcc atgttttacg gcgagatggt  2580
ttctcctcgc ctgccactc agcttagtt gtctctgttg tcttatagag gtctacttga    2640
agaaggaaaa acaggggca tggtttgact gtcctgtgag cccttcttcc ctgcctccc    2700
cactcacagt gacccggaat ctgcagtgct agtctccgca aactatcact ctttcacagt  2760
ctgctttgga aggactgggc ttagtatgaa aagttaggac tgagaagaat ttgaaggggg  2820
gcttttgta gcttgatatt cactactgtc ttattaccct atcataggcc cacccccaaat  2880
ggaagtccca ttcttcctca ggatgtttaa gattagcatt caggaagaga tcagaggtct  2940
gctgggctcc ttatcatgtc ccttatggtg cttctggctc tgcagttatt agcatagtgt  3000
taccatcaac caccttaact tcatttttct tattcaatac ctagccgcgg gaacagaa    3060
acaggagaat atgggccaaa caggatatct gtggtaagca gttcctgccc cggctcaggg  3120
ccaagaacag ttggaacagc agaatatggg ccaaacagga tatctgtggt aagcagttcc  3180
tgccccggct caggggcaag aacagatggt ccccagatgc ggtcccgccc tcagcagttt  3240
ctagagaacc atcagatgtt tccagggtgc ccaaggacc tgaaatgacc ctgtgcctta   3300
tttgaactaa ccaatcagtt cgcttctcgc ttctgttccgc ttctgctgctc ccccgagct  3360
ctatataagc agagctcgtt tagtgaaccg tcagatcgcg ccgcgcgc caccatggac    3420
aaggattgtg aaatgaaacg caccacactg acagccctt ggggaagct ggagctgtct    3480
ggttgtgagc agggtctgca cgaaataaag ctcctgggca aggggacgtc tgcagctgat  3540
gccgtggagg tcccagcccc cgctgcggtt ctcgaggtc cggagcccct gatgcagtgc  3600
acagcctggc tgaatgccta tttccaccag cccgaggcta tcgaagagtt cccgtgccg   3660
```

```
gctcttcacc atcccgtttt ccagcaagag tcgttcacca gacaggtgtt atggaagctg   3720
ctgaaggttg tgaaattcgg agaagtgatt tcttaccagc aattagcagc cctggcaggc   3780
aaccccaaag ccgcgcgagc agtgggagga gcaatgagag gcaatcctgt caaaatcctc   3840
atcccgtgcc acagagtggt ctgcagcagc ggagccgtgg gcaactactc cggaggactg   3900
gccgtgaagg aatggcttct ggcccatgaa ggccaccggt tggggaagcc aggcttggga   3960
gggagctcag gtctggcagg ggcctggctc aagggagcgg gagctacctc gggctccccg   4020
cctgctggcc gaaacgaggg cagaggaagt cttctaacat gcggtgacgt ggaggagaat   4080
ccgggccccc ctgcaggaac ttcaaggtga gtccaggaga tgtttcagcc ctgttgcctt   4140
tagtctcgag gcaacttaga caacgagta ttgatctgag cacagcaggg tgtgagctgt   4200
ttgaagatac tggggttggg ggtgaagaaa ctgcagaaga ctaactgggc tgagacccag   4260
tggtaatgtt ttagggccta aggagtgcct ctaaaaatct agatgdacaa ttttgacttt   4320
gagaaaagag aggtggaaat gaggaaaatg acttttcttt attagattcc agtagaaaga   4380
actttcatct ttccctcatt tttgttgttt taaaacatct atctgtggc aggacagaa    4440
tggtcgttaa aaagatgcag gcagaaggca tatattggct cagtcaaagt ggggaacttt   4500
ggtggccaaa catacattgc taaggctatt cctatatcag ctggacacat ataaaatgct   4560
gctaatgctt cattacaaac ttatatcctt taattccaga tggggggcaaa gtatgtccag   4620
gggtgaggaa caattgaaac atttgggctg gagtagattt tgaaagtcag ctctgtgtgt   4680
gtgtgtgt gtgcgcgcgc gcgtgtcgac gtagataagt agcatggcgg gttaatcatt    4740
aactacaagg aaccctagt gatggagttg gccactccct ctctgcgcgc tcgctcgctc    4800
actgaggccg ggcgaccaaa ggtcgcccga cgcccggggct ttgcccgggc ggcctcagtg   4860
agcgagcgag cgcgccagct ggcgtaatag cgaagaggcc cgcaccgatc gcccttccca   4920
acagttgcgc agcctgaatg gcgaatggcc attccgttgc aatggctggc ggtaatattg   4980
ttctggatat taccagcaag gccgatagtt tgagttcttc tactcaggca agtgatgtta   5040
ttactaatca aagaagtatt gcgacaacgg ttaaattgcg tgatggacag actcttttac   5100
tcggtggcct cactgattat aaaaacactt ctcaggattc tggcgtaccg ttcctgtcta   5160
aaatcccttt aatcggcctc ctgtttagct cccgctctga ttctaacgag gaaagcacgt   5220
tatacgtgct cgtcaaagca accatagtac gcgccctgta gcggcgcatt aagcgcggcg   5280
ggtgtggtgg ttacgcgcag cgtgaccgct acacttgcca gcgccctagc gcccgctcct   5340
ttcgctttct tcccttcctt tctcgccacg ttcgccggct ttccccgtca agctctaaat   5400
cgggggctcc ctttagggtt ccgatttagt gctttacggc acctcgaccc caaaaaactt   5460
gattagggtg atggttcacg tagtgggcca tcgccctgat agacggtttt tcgccctttg   5520
acgttggagt ccacgttctt taatagtgga ctcttgttcc aaactggaac aacactcaac   5580
cctatctcgg tctattcttt tgatttataa gggattttgc cgatttcggc ctattggtta   5640
aaaaatgagc tgatttaaca aaaatttaac gcgaatttta acaaaatatt aacgtttaca   5700
atttaaatat ttgcttatac aatcttcctg ttttttgggggc ttttctgatt atcaaccggg   5760
gtacatatga ttgacatgct agttttacga ttaccgttca tcgattctct tgtttgctcc   5820
agactctcag gcaatgacct gatagccttt gtagagacct ctcaaaaata gctaccctct   5880
ccggcatgaa tttatcagct agaacggttg aatatcatat tgatggtgat ttgactgtct   5940
ccggccttt tcacccgttt gaatctttac ctacacatta ctcaggcatt gcatttaaaa   6000
tatatgaggg ttctaaaaat ttttatcctt gcgttgaaat aaaggcttct cccgcaaaag   6060
tattacaggg tcataatgtt tttggtacaa ccgatttagc tttatgctct gaggctttat   6120
tgcttaattt tgctaattct ttgccttgcc tgtatgattt attggatgtt ggaatcgcct   6180
gatgcggtat tttctcctta cgcatctgtg cggtatttca caccgcatat ggtgcactct   6240
cagtacaatc tgctctgatg ccgcatagtt aagccagccc cgacacccgc caacacccgc   6300
tgacgcgccc tgacgggctt gtctgctccc ggcatccgct tacagacaag ctgtgaccgt   6360
ctccgggagc tgcatgtgtc agaggttttc accgtcatca ccgaaacgcg cgagacgaaa   6420
gggcctcgtg atacgcctat ttttatagt taatgtcatg ataataatgg tttcttagac   6480
gtcaggtggc acttttcggg gaaatgtgcg cggaacccct atttgtttat ttttctaaat   6540
acattcaaat atgtatccgc tcatgagaca ataaccctga taaatgcttc aataatattg   6600
aaaaaggaag agtatgagta ttcaacattt ccgtgtcgcc cttattccct ttttttgcggc   6660
attttgcctt cctgtttttg ctcacccaga aacgctgtg aaagtaaaag atgctgaaga   6720
tcagttgggt gcacgagtgg gttacatcga actggatctc aacagcggta agatccttga   6780
gagttttcgc cccgaagaac gttttccaat gatgagcact tttaaagttc tgctatgtgg   6840
cgcggtatta tcccgtattg acgccgggca agagcaactc ggtcgccgca tacactattc   6900
tcagaatgac ttggttgagt actcaccagt cacagaaaag catcttacgg atggcatgac   6960
agtaagagaa ttatgcagtg ctgccataac catgagtgat aacactgcgg ccaacttact   7020
tctgacaacg atcggaggac cgaaggagct aaccgctttt ttgcacaaca tgggggatca   7080
tgtaactcgc cttgatcgtt gggaaccgga gctgaatgaa gccataccaa acgacgagcg   7140
tgacaccacg atgcctgtag caatggcaac aacgttgcgc aaactattaa ctggcgaact   7200
acttactcta gcttcccggc aacaattaat agactggatg gaggcggata aagttgcagg   7260
accacttctg cgctcggccc ttccggctgg ctggtttatt gctgataaat ctggagccgg   7320
tgagcgtggg tctcgcggta tcattgcagc actggggcca gatggtaagc cctcccgtat   7380
cgtagttatc tacacgacgg ggagtcaggc aactatggat gaacgaaata gacagatcgc   7440
tgagataggt gcctcactga ttaagcattg gtaactgtca gaccaagttt actcatatat   7500
actttagatt gatttaaaac ttcatttta atttaaaagg atctaggtga agatcctttt   7560
tgataatctc atgaccaaaa tcccttaacg tgagttttcg ttccactgag cgtcagaccc   7620
cgtagaaaag atcaaaggat cttcttgaga tcctttttt ctgcgcgtaa tctgctgctt   7680
gcaaacaaaa aaaccaccgc taccagcggt ggtttgtttg ccggatcaag agctaccaac   7740
tcttttccg aaggtaactg gcttcagcag agcgcagata ccaaatactg tccttctagt    7800
gtagccgtag ttaggccacc acttcaagaa ctctgtagca ccgcctacat acctcgctct   7860
gctaatcctg ttaccagtgg ctgctgccag tggcgataag tcgtgtctta ccgggttgga   7920
ctcaagacga tagttaccgg ataaggcgca gcggtcgggc tgaacggggg gttcgtgcac   7980
acagcccagc ttggagcgaa cgacctacac cgaactgaga tacctacagc gtgagctatg   8040
agaaagcgcc acgcttcccg aagggagaaa ggcggacagg tatccggtaa gcggcagggt   8100
cggaacagga gagcgcacga gggagcttcc agggggaaac gcctggtatc tttatagtcc   8160
tgtcgggttt cgccacctct gacttgagcg tcgatttttg tgatgctcgt caggggggcg   8220
gagcctatgg aaaaacgcca gcaacgcggc ctttttacgg ttcctggcct tttgctggcc   8280
ttttgctcac atgttctttc ctgcgttatc ccctgattct gtggataacc gtattaccgc   8340
ctttgagtga gctgataccg ctcgccgcag ccgaacgacc gagcgcagcg agtcagtgag   8400
```

```
cgaggaagcg gaagagcgcc caatacgcaa accgcctctc cccgcgcgtt ggccgattca    8460
ttaatg                                                               8466

SEQ ID NO: 33          moltype = DNA   length = 8252
FEATURE                Location/Qualifiers
source                 1..8252
                       mol_type = other DNA
                       organism = Synthetic construct
SEQUENCE: 33
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt cctacgcgta gatcttttt ccttagaaac cactgctaac tgaaagagac     180
taagatttgt cccgtcaaaa atcctggacc tatgcctaaa acacatttca caatccctga     240
acttttcaaa aattggtaca tgctttagct ttaaactaca ggcctcactg gagctagaga     300
caagaaggta aaaaacggct gacaaaagaa gtcctggtat cctctatgat gggagaagga     360
aactagctaa agggaagaat aaattagaga aaaactggaa tgactgaatc ggaacaaggc     420
aaaggctata aaaaaaatta gcagtatcct cttgggggcc ccttccccac actatctcaa     480
tgcaaaatatc tgtctgaaac ggtccctggc taaactccac gtaaatacac ttgcaaagga     540
ggatgttttt agtagcaatt tgtactgatg gtatggggcc aagagatata tcttagaggg     600
agggctgagg gtttgaagtc caactcctaa gccagtgcca gaagagccaa ggacaggtac     660
ggctgtcatc acttagacct cacccctgtgg agccacaccc taggggttgg caatctactc     720
ccaggagcag ggagggcagg agccaggggct gggcataaaa gtcagggcag agccatctat     780
tgcttacatt tgcttctgac acaactgtgt tcactagcaa cctcaaacag acaccatggt     840
gcacctgact cctgaggaga agtctgccgt tactgccctg tggggcaagg tgaacgtgga     900
tgaagttggt ggtgaggccc tgggcaggtt ggtatcaagg ttacaagaca ggtttaagga     960
gaccaataga aactgggcat gtggagacag agaagactct tgggtttctg ataggcactg    1020
actctctctg cctattggtc tatttttccca cccttaggct gctggtggtc tacccttgga    1080
cccagaggtt ctttgagtcc tttggggatc tgtccactcc tgatgctgtt atgggcaacc    1140
ctaaggtgaa ggctcatggc aagaaagtgc tcggtgcctt tagtgatggc ctggctcacc    1200
tggacaacct caagggcacc tttgcccagc tgagtgagct gcactgtgac aagctgcacg    1260
tggatcctga aaacttcagg gtgagtctat gggacccttg atgttttctt tccccttctt    1320
ttctatggtt aagttcatgt cataggaagg ggagaagtaa cagggtacac atattgacca    1380
aatcagggta attttgcatt tgtaatttta aaaaatgctt tcttcttta atatactttt     1440
ttgtttatct tatttctaat actttcccta atctcttttct ttcagggcaa taatgataca    1500
atgtatcatg cctctctttgca ccattctaaa gaataacagt gataatttct gggttaaggc    1560
aatagcaata tttctgcata taaatatttc tgcatataaa ttgtaactga tgtaagaggt    1620
ttcatattgc taatagcagc tacaatccag ctaccattct gcttttattt tatggttggg    1680
ataaggctga attattctga gtccaagcta ggccctttg ctaatcatgt tcatacctct    1740
tatcttcctc ccacagctcc tgggcaacgt gctggtctgt gtgctggccc atcacttttgg    1800
caaagaattc accccaccag tgcaggctgc ctatcagaaa gtggtggctg gtgtggctaa    1860
tgcccctggcc cacaagtatc actaagctcg ctttcttgct gtccaatttc tattaaaggt    1920
tcctttgttc cctaagtcca actactaaac tgggggatat tatgaagggc cttgagcatc    1980
tggattctgc ctaataaaaa acatttattt tcattgcaat gatgtattta aattatttct    2040
gaatatttta ctaaaagggg aatgtgggag gtcagtgcat ttaaaacata agaaatgaa     2100
gagctagttc aaaccttggg aaaatacact atatcttaaa ctccatgaaa gaaggtgagg    2160
ctgcaaacag ctaatgcaca ttggcaacag cccctgatgc ctatgcctta ttcatccctc    2220
agaaaaggat tcaagtagag gcttgatttg gaggttaaag ttttgctatg ctgtattta    2280
cattacttat tgttttagct gtcctcatga atgtcttttc actacccatt tgcttatcct    2340
gcatctctca gccttgactc cactcagttc tcttgcttag agataccacc tttcccctga    2400
agtgttcctt ccatgtttta cggcgagatg gtttctcctc gcctgccac tcagccttag    2460
ttgtctctgt tgtcttatag aggtctactt gaagaaggaa aaacaggggg catggtttga    2520
ctgtcctgtg agcccttctt ccctgcctcc cccactcaca gtgacccgga atctgcagtg    2580
ctagtctccc ggaactatca ctcttttcaca gtctgctttg gaaggactgg gcttagtatg    2640
aaaagttagg actgagaaga atttgaaagg gggcttttttg tagcttgata ttcactactg    2700
tcttattacc ctatcatagg cccaccccaa atggaagtc cattcttcct caggatgttt    2760
aagattagca ttcaggaaga gatcagaggt ctgctggctc ccttatcatg tcccttatgg    2820
tgcttctggc tctgcagtta ttagcatagt gttaccatca accaccttaa cttcatttt     2880
cttattcaat acctagccgc gggaacagag aaacaggaga atatgggcca aacaggatat    2940
ctgtggtaag cagttcctgc cccggctcag gccaagaac agttggaaca gcagaatatg    3000
ggccaaacag gatatctgtg gtaagcagtt cctgccccgg ctcagggcca agaacagatg    3060
gtccccagat gcggtccgc cctcagcagt ttctagagaa ccatcagatg tttccagggt    3120
gccccaagga cctgaaatga ccctgtgcct tatttgaact aaccaatcag ttcgcttctc    3180
gcttctgttc gcgcgcttct gctccccgag ctctatataa gcagagctcg tttagtgaac    3240
cgtcagatcg cggccgccgc gccaccatgg tgagcaaggg cgaggagctg ttcaccgggg    3300
tggtgcccat cctggtcgag ctggacggcg acgtaaacgg ccacaagttc agcgtgtccg    3360
gcgagggcga gggcgatgcc acctacggca agctgaccct gaagttcatc tgcaccaccg    3420
gcaagctgcc cgtgccctgg cccaccctcg tgaccaccct gacctacggc gtgcagtgct    3480
tcagccgcta ccccgaccac atgaagcagc acgacttctt caagtccgcc atgcccgaag    3540
gctacgtcca ggagcgcacc atcttcttca aggacgacgg caactacaag acccgcgccg    3600
aggtgaagtt cgagggcgac accctggtga accgcatcga gctgaagggc atcgacttca    3660
aggaggacgg caacatcctg gggcacaagc tggagtacaa ctacaacagc cacaacgtct    3720
atatcatggc cgacaagcag aagaacggca tcaaggtgaa cttcaagatc cgccacaaca    3780
tcgaggacgg cagcgtgcag ctcgccgacc actaccagca gaacaccccc atcggcgacg    3840
gccccgtgct gctgcccgac aaccactacc tgagcaccca gtccgccctg agcaaagacc    3900
ccaacgagaa gcgcgatcac atggtcctgc tggagttcgt gaccgccgcc gggatcactc    3960
tcggcatgga cgagctgtac aagtaagctt tatttgtgaa atttgtgatg ctattgcttt    4020
atttgtaacc attataagct gcaataaaca agttaacaac aacaattgca ttcattttat    4080
gtttcaggtt cagggggaga tgtgggaggt tttttaaagc cctgcaggat gggtcatttc    4140
acagaggagg acaaggctac tatcacaagc ctgtgggca aggtgaatgt ggaagatgct    4200
```

```
ggaggagaaa ccctgggaag gtaggctctg gtgaccagga caagggaggg aaggaaggac  4260
cctgtgcctg gcaaaagtcc aggtcgcttc tcaggatttg tggcaccttc tgactgtcaa  4320
actgttcttg tcaatctcac aggctcctgg ttgtctaccc atggacccag aggttctttg  4380
acagctttgg caacctgtcc tctgcctctg ccatcatggg caaccccaaa gtcaaggcac  4440
atggcaagaa ggtgctgact tccttgggag atgccacaaa gcacctggat gatctcaagg  4500
gcacctttgc ccagctgagt gaactgcagt cgacaggaac ccctagtgat ggagttggcc  4560
actccctctc tgcgcgctcg ctcgctcact gaggccgggc gaccaaaggt cgcccgacgc  4620
ccgggctttc cccgggcggc ctcagtgagc gagcgagcgc gcagctggcg taatagcgaa  4680
gaggcccgca ccgatcgccc ttcccaacag ttgcgcagcc tgaatggcga atggcgattc  4740
cgttgcaatg gctggcggta atattgttct ggatattacc agcaaggccg atagtttgag  4800
ttcttctact caggcaagtg atgttattac taatcaaaga agtattgcga caacggttaa  4860
tttgcgtgat ggacagactc ttttactcgg tggcctcact gattataaaa acacttctca  4920
ggattctggc gtaccgttcc tgtctaaaat ccctttaatc ggcctcctgt ttagctcccg  4980
ctctgattct aacgaggaaa gcacgttata cgtgctcgtc aaagcaacca tagtacgcgc  5040
cctgtagcgg cgcattaagc gcggcgggtg tggtggttac gcgcagcgtg accgctacac  5100
ttgccagcgc cctagcgccc gctcctttcg ctttcttccc ttcctttctc gccacgttcg  5160
ccggctttcc ccgtcaagct ctaaatcggg gctccctttag ggttccga tttagtgctt  5220
tacggcacct cgaccccaaa aaacttgatt agggtgatgg ttcacgtagt gggccatcgc  5280
cctgatagac ggtttttcgc cctttgacgt tggagtccac gttctttaat agtggactct  5340
tgttccaaac tggaacaaca ctcaaccctatctcggtcta ttcttttgat ttataaggga  5400
ttttgccgat ttcggcctat tggttaaaaa atgagctgat ttaacaaaaa tttaacgcga  5460
attttaacaa aatattaacg tttacaattt aaatatttgc ttatacaatc ttcctgtttt  5520
tggggctttt ctgattatca accggggtac atatgattga catgctagtt ttacgattac  5580
cgttcatcga ttctcttgtt tgctccagac tctcaggcaa tgacctgata gcctttgtag  5640
agacctctca aaaatagcta ccctctccgg catgaattta tcagctagaa cggttgaata  5700
tcatattgat ggtgatttga ctgtctccgg cctttctcac ccgtttgaat ctttacctac  5760
acattactca ggcattgcat ttaaaatata tgagggttct aaaaattttt atccttgcgt  5820
tgaaataaag gcttctcccg caaaagtatt acagggtcat aatgttttg gtacaaccga  5880
tttagcttta tgctctgagg ctttattgct taattttgct aattctttgc cttgcctgta  5940
tgatttattg gatgttgaa tcgcctgatg cggtattttc tccttacgca tctgtgcggt  6000
atttcacacc gcatatggtg cactctcagt acaatctgct ctgatgccgc atagttaagc  6060
cagccccgac acccgccaac acccgctgac gcgccctgac gggcttgtct gctcccggca  6120
tccgcttaca gacaagctgt gaccgtctcc gggagctgca tgtgtcagag gttttcaccg  6180
tcatcaccga aacgcgcgag acgaaagggc ctcgtgatac gcctatttttat aggttaat  6240
gtcatgataa taatggtttc ttagacgtca ggtggcactt tcggggaaa tgtgcgcgga  6300
accctatttt gtttattttt ctaaatacat tcaaatatgt atccgctcat gagacaataa  6360
ccctgataaa tgcttcaata atattgaaaa aggaagagta tgagtattca acatttccgt  6420
gtcgccctta ttccctttttt tgcggcattt tgccttcctg ttttgctca cccagaaacg  6480
ctggtgaaag taaaagatgc tgaagatcag ttgggtgcac gagtgggtta catcgaactg  6540
gatctcaaca gcggtaagat ccttgagagt tttcgccccg aagaacgttt tccaatgatg  6600
agcactttta aagttctgct atgtggcgcg gtattatccc gtattgacgc cgggcaagag  6660
caactcggtc gccgcataca ctattctcag aatgacttgg ttgagtactc accagtcaca  6720
gaaaagcatc ttacggatgg catgacagta agagaattat gcagtgctgc cataaccatg  6780
agtgataaca ctgcggccaa cttacttctg acaacgatcg gaggaccgaa ggagctaacc  6840
gcttttttgc acaacatggg ggatcatgta actcgccttg atcgttggga accggagctg  6900
aatgaagcca taccaaacga cgagcgtgac accacgatgc ctgtagcaat ggcaacaacg  6960
ttgcgcaaac tattaactgg cgaactactt actctagctt cccggcaaca attaatagac  7020
tggatggagg cggataaagt tgcaggacca cttctgcgct cggcccttcc ggctggctgg  7080
tttattgctg ataaatctgg agccggtgag cgtgggtctc gcggtatcat tgcagcactg  7140
gggccagatg gtaagccctc ccgtatcgta gttatctaca cgacggggag tcaggcaact  7200
atggatgaac gaaatagaca gatcgctgag ataggtgcct cactgattaa gcattggtaa  7260
ctgtcagacc aagtttactc atatatactt tagattgatt taaaacttca ttttttaatttt  7320
aaaaggatct aggtgaagat cctttttgat aatctcatga ccaaaatccc ttaacgtgag  7380
ttttcgttcc actgagcgtc agaccccgta gaaaagatca aaggatcttc ttgagatcct  7440
ttttttctgc gcgtaatctg ctgcttgcaa acaaaaaaac caccgctacc agcggtggtt  7500
tgtttgccgg atcaagagct accaactctt tttccgaagg taactggctt cagcagagcg  7560
cagataccaa atactgtcct tctagtgtag ccgtagttag gccaccactt caagaactct  7620
gtagcaccgc ctacatacct cgctctgcta atcctgttac cagtggctgc tgccagtggc  7680
gataagtcgt gtcttaccgg gttggactca agacgatagt taccggataa ggcgcagcgg  7740
tcgggctgaa cggggggttc gtgcacacag cccagcttgg agcgaacgac ctacaccgaa  7800
ctgagatacc tacagcgtga gctatgagaa agcgccacgc ttcccgaagg gagaaaggcg  7860
gacaggtatc cggtaagcgg cagggtcgga acaggagagc gcacgaggga gcttccaggg  7920
ggaaacgcct ggtatcttta tagtcctgtc gggtttcgcc acctctgact tgagcgtcga  7980
tttttgtgat gctcgtcagg gggcggagc ctatggaaa acgccagcaa cgcggccttt  8040
ttacggttcc tggccttttg ctggcctttt gctcacatgt tctttcctgc gttatcccct  8100
gattctgtgg ataaccgtat taccgccttt gagtgagctg ataccgctcg ccgcagccga  8160
acgaccgagc gcagcgagtc agtgagcgag gaagcggaag agcgcccaat acgcaaaccg  8220
cctctccccg cgcgttggcc gattcattaa tg  8252

SEQ ID NO: 34        moltype = DNA  length = 7375
FEATURE              Location/Qualifiers
source               1..7375
                     mol_type = other DNA
                     organism = Synthetic construct
SEQUENCE: 34
cagctgcgcg ctcgctcgct cactgaggcc gcccggcaa agcccgggcg tcgggcgacc    60
tttggtcgcc cggcctcagt gagcgagcga gcgcgcagag agggagtggc caactccatc   120
actaggggtt ccttgtagtt aatgattaac cgccatgct acttatctac acgcgtagat   180
cttttttcct tagaaaccac tgctaactga aagagactaa gatttgtccc gtcaaaaatc   240
```

```
ctggacctat gcctaaaaca catttcacaa tccctgaact tttcaaaaat tggtacatgc  300
tttagcttta aactcaggc ctcactggag ctagagacaa gaaggtaaaa aacggctgac  360
aaaagaagtc ctggtatcct ctatgatggg agaaggaaac tagctaaagg gaagaataaa  420
ttagagaaaa actggaatga ctgaatcgga acaaggcaaa ggctataaaa aaaattagca  480
gtatcctctt ggggggcccct tccccacact atctcaatgc aaatatctgt ctgaaacggt  540
ccctggctaa actccaccca tgggttggcc agccttgcct tgacaaggca aacttgacca  600
atagtcttag agtatccagt gaggccaggg ccggcggct ggctagggat gaagaataaa  660
aggaagcacc cttcagcagt tccacacact cgcttctgga acgtctgagg ttatcaataa  720
gctcctagtc cagacgccgc cgccaccatg gtccatctta caccggagga gaagtccgct  780
gtaacggcac tgtgggggaa agttaatgtc gatgaagtcg gcggtgaagc actcggcagg  840
ttgctggtag tgtacccgtg gacacaacga ttctttgaaa gtttcgggga cctgtccaca  900
cccgatgctg tgatgggtaa tccaaaagta aaagcacacg gcaagaaagt cctcggcgcg  960
tttagtgatg gtctggccca tttggataac ttgaagggta cattcgcca gctttccgaa 1020
ctccactgtg acaagttgca cgtagatcca gaaaacttcc ggcttctggg caatgtgctt 1080
gtatgcgttc tggctcacca ttttgggaag gagtttaccc cacccgtgca agcggcttac 1140
caaaaagtgg tcgcaggagt ggctaatgcc cttgcacata aatatcacta aggtaccgag 1200
catcttaccg ccatttattc ccatatttgt tctgttttc ttgatttggg tatacattta 1260
aatgttaata aaacaaaatg gtggggcaat catttacatt tttagggata tgtaattact 1320
agttcaggtg tattgccaca agacaaacat gttaagaaac tttcccgtta tttacgctct 1380
gttcctgtta atcaacctct ggattacaaa atttgtgaaa gattgactga tattcttaac 1440
tatgttgctc cttttacgct gtgtggatat gctgctttat agcctctgta tctagctatt 1500
gcttcccgta cggctttcgt tttctcctcc ttgtataaat cctggttgct gtctctttta 1560
gaggagttgt ggcccgttgt ccgtcaacgt ggcgtggtgt gctctgtgtt tgctgacgca 1620
accccccactg gctggggcat tgccaccacc tgtcaactcc tttctgggac tttcgctttc 1680
cccctcccga tcgccacggc agaactcatc gccgcctgcc ttgcccgctg ctggacaggg 1740
gctaggttgc tgggcactga taattccgtg gtgttgttca ggcttctag ttgccagcca 1800
tctgttgttt gcccctcccc cgtgccttcc ttgaccctgg aaggtgccac tcccactgtc 1860
cttcctaat aaaatgagga aattgcatcg cattgtctga gtaggtgtca ttctattctg 1920
ggggggtgggg tggggcagga cagcaagggg gaggattggg aagacaatag caggcatgct 1980
ggggatcggg tgggctctat ggcccgcggg aacagagaaa caggagaata tgggccaaac 2040
aggatatctg tggtaagcag ttcctgcccc ggctcagggc caagaacagt tggaacagca 2100
gaatatgggc caaacaggat atctgtggta agcagttcct gccccggctc agggccaaga 2160
acagatggtc cccagatgcg gtcccgcct cagcagtttc tagagaacca tcagatgttt 2220
ccagggtgcc ccaaggacct gaaatgaccc tgtgcctat ttgaactaac caatcagttc 2280
gcttctgct tctgttccgc cgcttctgct ccccgagctc tatataagca gagctcgttt 2340
agtgaaccgt cagatcgcct ggagacgcca tccacgctgt tttgacttcc atagaaggcg 2400
gccgcgccgc caccatggtg agcaaggcg aggagctgtt caccggggtg gtgcccatcc 2460
tggtcgagct ggacggcgac gtaaacggcc acaagttcag cgtgtccggc gagggcgagg 2520
gcgatgccac ctacggcaag ctgaccctga agttcatctg caccaccggc aagctgcccg 2580
tgccctggcc caccctcgtg accaccctga cctacggcgt gcagtgcttc agccgctacc 2640
ccgaccacat gaagcagcac gacttcttca gtccgccat gcccgaaggc tacgtccagg 2700
agcgcaccat cttcttcaag gacgacggca actacaagac ccgcgccgag gtgaagttcg 2760
agggcgacac cctggtgaac cgcatcgagc tgaagggcat cgacttcaag gaggacggca 2820
acatcctggg gcacaagctg gagtacaact acaacagcca caacgtctat atcatgccg 2880
acaagcagaa gaacggcatc aaggtgaact tcaagatccg ccacaacatc gaggacggca 2940
gcgtgcagct cgccgaccac taccagcaga caccccccat cggcgacggc cccgtgctgc 3000
tgcccgacaa ccactacctg agcacccagt ccgccctgag caaagacccc aacgagaagc 3060
gcgatcacat ggtcctgctg gagttcgtga ccgccgccgg gatcactctc ggcatgacg 3120
agctgtacaa gggaagcgga gctactaact tcagcctgct gaagcaggct ggagacgtgg 3180
aggagaaccc tggacctcct gcaggaactt caaggtgagt ccaggagatg tttcagccct 3240
gttgcttta gtctcgaggc aacttagaca acggagtatt gatctgagca cagcagggtg 3300
tgagctgttt gaagatactg gggttggggg tgaagaaact gcagaggact aactgggctg 3360
agaccagtg gtaatgttt agggcctaag gagtgcctct aaaatctag atggacaatt 3420
ttgactttga gaaagagag gtggaaatga ggaaaatgac ttttctttat tagattccag 3480
tagaaagaac tttcatcttt ccctcattt tgttgttta aaacatcat ctggaggcag 3540
gacaagtatg tcgttaaaa agatgcaggc agaaggcata tattggctca gtcaaagtgg 3600
ggaactttgg tgggtcgacg tagataagta gcatggcggg ttaatcatta actacaagga 3660
acccctagtg atggagttgg ccactccctc tctgcgcgct cgctcgctca ctgaggccgg 3720
gcgaccaaag gtcgcccgac gcccgggctt tgcccgggcg gcctcagtga gcgagcgagc 3780
gcgccagctg gcgtaatagc gaagaggccc gcaccgatcg cccttcccaa cagttgcgca 3840
gcctgaatgg cgaatggcga ttccgttgca atgctggcg gtaatattgt tctggatatt 3900
accagcaagg ccgatagttt gagttcttct actcaggcaa gtgatgttat tactaatcaa 3960
agaagtattg cgacaacggt taatttgcgt gatggacaga ctcttttact cggtggcctc 4020
actgattata aaaacacttc tcaggattct ggcgtaccgt tcctgtctaa aatccctta 4080
atcggcctcc tgtttagctc ccgctctgat tctaacgagg aaagcacgtt atacgtgctc 4140
gtcaaagcaa ccatagtacg cgccctgtag cggcgcatta agcgcggcgg gtgtggtggt 4200
tacgcgcagc gtgaccgcta cacttgccag cgccctagcg cccgctcctt tcgctttctt 4260
cccttccttt ctcgccacgt tcgccggctt tccccgtcaa gctctaaatc ggggggctccc 4320
tttagggttc cgatttagtg ctttacggca cctcgacccc aaaaaacttg attagggtga 4380
tggttcacgt agtgggccat cgccctgata caggttttt cgccctttga cgttggagtc 4440
cacgttcttt aatagtggac tcttgttcca aactggaaca acactcaacc ctatctcggt 4500
ctattctttt gatttataag gattttgcc gatttcggcc tattggttaa aaatgagct 4560
gatttaacaa aaatttaacg cgaattttaa caaaatatta acgtttacaa tttaaatatt 4620
tgcttataca atcttcctgt ttttggggct tttctgatta tcaaccgggg tacatatgat 4680
tgacatgcta gttttacgat taccgttcat cgattctctt gtttgctcca gactctcagg 4740
caatgacctg atagcctttg tagagacctc tcaaaaatag ctaccctctc cgcatgaat 4800
ttatcagcta gaacggttga atatcatatt gatggtgatt tgactgtctc cggcctttct 4860
cacccgtttg aatctttacc tacacattac tcaggcattg catttaaaat atgagggt 4920
tctaaaaatt tttatccttg cgttgaaata aaggcttctc ccgcaaaagt attacagggt 4980
```

```
cataatgttt ttggtacaac cgatttagct ttatgctctg aggctttatt gcttaatttt  5040
gctaattctt tgccttgcct gtatgattta ttggatgttg gaatcgcctg atgcggtatt  5100
ttctccttac gcatctgtgc ggtatttcac accgcatatg gtgcactctc agtacaatct  5160
gctctgatgc cgcatagtta agccagcccc gacacccgcc aacacccgct gacgcgccct  5220
gacgggcttg tctgctcccg gcatccgctt acagacaagc tgtgaccgtc tccgggagct  5280
gcatgtgtca gaggttttca ccgtcatcac cgaaacgcgc gagacgaaag ggcctcgtga  5340
tacgcctatt tttataggtt aatgtcatga taataatggt ttcttagacg tcaggtggca  5400
cttttcgggg aaatgtgcgc ggaacccctc tttgtttatt tttctaaata cattcaaata  5460
tgtatccgct catgagacaa taaccctgat aaatgcttca ataatattga aaaaggaaga  5520
gtatgagtat tcaacatttc cgtgtcgccc ttattccctt ttttgcggca ttttgccttc  5580
ctgtttttgc tcacccagaa acgctggtga agtaaaaga tgctgaagat cagttgggtg  5640
cacgagtggg ttacatcgaa ctggatctca acagcggtaa gatccttgag agttttcgcc  5700
ccgaagaacg ttttccaatg atgagcactt ttaaagttct gctatgtggc gcggtattat  5760
cccgtattga cgccgggcaa gagcaactcg gtcgccgcat acactattct cagaatgact  5820
tggttgagta ctcaccagtc acagaaaagc atcttacgga tggcatgaca gtaagagaat  5880
tatgcagtgc tgccataacc atgagtgata acactgcggc caacttactt ctgacaacga  5940
tcggaggacc gaaggagcta accgcttttt tgcacaacat ggggdatcat gtaactcgcc  6000
ttgatcgttg ggaaccggag ctgaatgaag ccataccaaa cgacgagcgt gacaccacga  6060
tgcctgtagc aatggcaaca acgttgcgca aactattaac tggcgaacta cttactctag  6120
cttcccggca acaattaata gactggatgg aggcggataa agttgcagga ccacttctgc  6180
gctcggccct tccggctggc tggtttattg ctgataaatc tggagccggt gagcgtgggt  6240
ctcgcggtat cattgcagca ctggggccag atggtaagcc ctcccgtatc gtagttatct  6300
acacgacggg gagtcaggca actatggatg aacgaaatag acagatcgct gagataggtg  6360
cctcactgat taagcattgg taactgtcag accaagttta ctcatatata ctttagattg  6420
atttaaaact tcatttttaa tttaaaagga tctaggtgaa gatcctttt gataatctca  6480
tgaccaaaat cccttaacgt gagttttcgt tccactgagc gtcagacccc gtagaaaaga  6540
tcaaaggatc ttcttgagat cctttttttc tgcgcgtaat ctgctgcttg caaacaaaaa  6600
aaccaccgct accagcggtg gtttgtttgc cggatcaaga gctaccaact cttttttccga  6660
aggtaactgg cttcagcaga gcgcagatac caaatactgt ccttctagtg tagccgtagt  6720
taggccacca cttcaagaac tctgtagcac cgcctacata cctcgctctg ctaatcctgt  6780
taccagtggc tgctgccagt ggcgataagt cgtgtcttac cgggttggac tcaagacgat  6840
agttaccgga taaggcgcag cggtcgggct gaacggggg ttcgtgcaca cagcccagct  6900
tggagcgaac gacctacacc gaactgagat acctacagcg tgagctatga aaagcgcca  6960
cgcttcccga agggagaaag gcggacaggt atccggtaag cggcagggtc ggaacaggag  7020
agcgcacgag ggagcttcca gggggaaacg cctggtatct ttatagtcct gtcgggttc  7080
gccacctctg acttgagcgt cgatttttgt gatgctcgtc agggggggcg agcctatgga  7140
aaaacgccag caacgcggcc ttttacggt tcctggcctt ttgctggcct tttgctcaca  7200
tgttctttcc tgcgttatcc cctgattctg tggataaccg tattaccgcc tttgagtgag  7260
ctgataccgc tcgccgcagc cgaacgaccg agcgcagcga gtcagtgagc gaggaagcgg  7320
aagagcgccc aatacgcaaa ccgcctctcc ccgcgcgttg gccgattcat taatg         7375
```

| SEQ ID NO: 35 | moltype = DNA length = 8089 |
|---|---|
| FEATURE | Location/Qualifiers |
| source | 1..8089 |
| | mol_type = other DNA |
| | organism = Synthetic construct |

SEQUENCE: 35

```
cagctgcgcg ctcgctcgct cactgaggcc gcccgggcaa agcccgggcg tcggcgacc   60
tttggtcgcc cggcctcagt gagcgagcga gcgcgcagag agggagtggc caactccatc  120
actagggggt ccttgtagtt aatgattaac ccgccatgct acttatctac acgcgtagat  180
cttttttcct tagaaaccac tgctaactga aagagactaa gattgtccc gtcaaaaatc   240
ctggacctat gcctaaaaca cattcacaa tccctgaact tttcaaaaat tggtacatgc   300
tttagcttta aactcagggc ctcactggag ctagagacaa gaaggtaaaa aacggctgac   360
aaaagaagtc ctggtatcct ctatgatggg agaaggaaac tagctaaagg gaagaataaa   420
ttagagaaaa actggaatga ctgaatcgga acaaggcaaa ggctataaaa aaaattagca   480
gtatcctctt gggggccct tccccacact atctcaatgc aaatatctgt ctgaaacggt   540
ccctggctaa actccaccca tgggttggcc agccttgcct tgacaaggca aacttgacca   600
atagtcttag agtatccagt gaggccaggg ccggcggct ggctaggggat gaagaataaa   660
aggaagcacc cttcagcagt tccacacact cgcttctgga acgtctgagg ttatcaataa   720
gctcctagtc cagacgccgc cgccaccatg gtccatctta caccggagga gaagtccgct   780
gtaacggcac tgtggggaa agttaatgtc gatgaagtcg gcggtgaagc actcggcagg   840
ttgctggtag tgtaccgtg gacacaacga ttctttgaaa gtttcgggga cctgtccaca   900
cccgatgctg tgatgggtaa tccaaagta aagcacacg gcaagaaagt cctcggcgcg   960
tttagtgatg gtctggccca tttgataac ttgaaggta cattcgcgca gctttcgaaa  1020
ctccactgtg acaagttgca cgtagatcca gaaaacttcc ggcttctggg caatgtgctt  1080
gtatgcgttc tggctcacca tttttgggaag gagtttaccc caccccgtgca agcggcttac  1140
caaaagtggt cgcaggagt ggctaatgcc cttgcacata aatatcacta aggtaccgag  1200
catcttaccg ccattttttc ccatattgt tctgttttc ttgatttggg tatacattta  1260
aatgttaata aaacaaaatg gtgggggcaat catttacatt tttaggata tgtaattact  1320
agttcagtg tattgccaca agacaaacat gttaagaaac tttcccgtta tttacgctct  1380
gttcctgtta atcaacctct ggattacaaa atttgtgaaa gattgactga tattcttaac  1440
tatgttgctc cttttacgct gtgtggatat gctgcttat agcctctgta tctagctatt  1500
gcttcccgta cggctttcgt ttctcctcc ttgtataaat cctggttgct gtctcttttta  1560
gaggagttgt ggcccgttgt ccgtcaacgt ggcgtggtgt gctctgacgca  1620
accccccactg gctggggcat tgccaccacc tgtcaactcc tttctgggac tttcgctttc  1680
ccctcccga tcgccacggc agaactcatc gccgcctgcc ttgcccgctg ctggacaggg  1740
gctaggttgc tgggcactga taattccgtg tgttgtctg tgccttctag ttgccagcca  1800
tctgttgttt gcccctcccc cgtgccttcc ttgaccctgg aaggtgccac tcccactgtc  1860
ctttcctaat aaaatgagga aattgcatcg cattgtctga gtaggtgtca ttctattctg  1920
```

```
gggggtgggg tgggcagga cagcaagggg gaggattggg aagacaatag caggcatgct   1980
ggggatgcgg tgggctctat ggccgagatc gagaccatcc tggctaacac agtgaaaccc   2040
cgtctctact aaaaaaatac aaaaaattag ccgggcttgg tggcgggtgc ctgtagtccc   2100
agctactatg gaggctgagg cgggagaatg gcgtgaacgc gggggcgga gcttgcagtg    2160
agcagagatc aggggccact gcactccagc ctgggcgaca gagagagact ctgtctcaaa   2220
aaaaagaaaa aaaaaattta gtagactagc taaaaaaatc cagagatagt tattgatgca   2280
tatgtaaaag tcttccaata tttacaagta caatgaaaaa aaaataacct tgaattaagt   2340
gtagaactca ttgacaatgt ttcaaaggat gtgagggata aactaaaatt tgggcagtac   2400
atgctgttcc tgtgtacttg gaacagaggg agaaaatctg ggctggaaat attgttatag   2460
gagttagcac atgaaggtga caactaaatt atttggagta gatggagtca ccagcacatg   2520
tgaatagttt tagaatgaaa tgacccaaga tagaactttg gagagccccc aaattttaaat  2580
aaaatcagta taagagaaga ggaagaaacc aaatggtata ctagtctaaa ttgtttctta   2640
gtgacaaaag aataacctga atattagatt agctgcctat atgctctctg aatcaatttc   2700
attcaacatg caacagtccg cgggaacaga gaaacaggaa aatatgggcc aaacaggata   2760
tctgtggtaa gcagttcctg cccccggctca gggccaagaa cagttggaac agcagaatat   2820
gggccaaaca ggatatctgt ggtaagcagt tcctgccccg gctcagggcc aagaacagat   2880
ggtccccaga tgcggtcccg ccctcagcag tttctagaga accatcagat gtttccaggg   2940
tgccccaagg acctgaaatg accctgtgcc ttatttgaac taaccaatca gttcgcttct   3000
cgcttctgtt cgcgcgcttc tgctcccga gctctatata agcagagctc gtttagtgaa    3060
ccgtcagatc gcctcgagac gccatccacg ctgtttgac ttccatagaa ggcggccgcg    3120
ccgccaccat ggtgagcaag ggcgaggagc tgttcaccgg ggtggtgccc atcctggtcg    3180
agctgacgg cgacgtaaac ggccacaagt tcagcgtgtc cggcgaggc gagggcgatg      3240
ccacctacgg caagctgacc ctgaagttca tctgcaccac cggcaagctg cccgtgcct    3300
ggcccaccct cgtgaccacc ctgacctacg gcgtgcagtg cttcagccgc tacccccgacc  3360
acatgaagca gcacgacttc ttcaagtccg ccatgcccga aggctacgtc caggagcgca   3420
ccatcttctt caaggacgac ggcaactaca agacccgcgc cgaggtgaag ttcgagggcg   3480
acaccctggt gaaccgcatc gagctgaagg gcatcgactt caaggaggac ggcaacatcc   3540
tggggcacaa gctggagtac aactacaaca gccacaacgt ctatatcatg gccgacaagc   3600
agaagaacgg catcaaggtg aacttcaaga tccgccacaa catcgaggac ggcagcgtgc   3660
agctcgccga ccactaccag cagaacaccc ccatcggcga cggccccgtg ctgctgcccg   3720
acaaccacta cctgagcacc cagtccgccc tgagcaaaga ccccaacgaa agcgcgatc    3780
acatggtcct gctggagttc gtgaccgccg ccgggatcac tctcggcatg gacgagctgt   3840
acaagggaag cggagctact aacttcagcc tgctgaagca ggctggagac gtggaggaga    3900
accctggacc tcctgcagga acttcaaggt gagtccagga gatgtttcag ccctgttgcc   3960
tttagtctcg aggcaactta gacaacggag tattgatctg agcacagcag ggtgtgagct   4020
gtttgaagat actgggggttg ggggtgaaga aactgcagag gactaactgg gctgagaccc  4080
agtggtaatg tttagggcc taaggagtgc ctctaaaat ctagatggac aattttgact     4140
ttgagaaaag agaggtggaa atgaggaaaa tgacttttct ttattagatt ccagtagaaa   4200
gaacttcatc ctttccctca ttttttgtgt tttaaaacat ctatctggag gcaggacaag   4260
tatggtcgtt aaaagatgc aggcagaagg catatattgg ctcagtcaaa gtggggaact    4320
ttggtgggtc gacgtagata agtagcatgg cgggttaatc attaactaca aggaaccct    4380
agtgatggag ttggccactc cctctctgcg cgctcgctcg ctcactgagg ccgggcgacc   4440
aaaggtcgcc cgacgcccgg gctttgcccg ggcggcgtca gtgagcgagc gagcgcgcca  4500
gctggcgtaa tagcgaagag gcccgcaccg atcgccttc caacagttg cgcagcctga     4560
atggcgaatg gcgattccgt tgcaatggct ggcggtaata ttgttctgga tattaccagc   4620
aaggccgata gtttgagttc ttctactcag gcaagtgatg ttattactaa tcaaagaagt   4680
attgcgacaa cggttaattt gcgtgatgga cagactcttt tactcggtgg cctcactgat   4740
tataaaaaca cttctcagga ttctggcgta ccgttcctgt ctaaaatccc tttaatcggc   4800
ctcctgttta gctcccgctc tgattctaac gaggaaagca cgttatacgt gctcgtcaaa   4860
gcaaccatag tacgcgccct gtagcggcgc attaagcgcg gcgggtgtgg tggttacgcg   4920
cagcgtgacc gctacacttg ccagcgccct agcgcccgct cctttcgctt tcttcccttc   4980
ctttctcgcc acgttcgccg gctttccccg tcaagctcta aatcgggggc tccctttag    5040
gttccgattt agtgctttac ggcacctcga ccccaaaaaa cttgattagg gtgatggttc    5100
acgtagtggg ccatcgccct gatagacggt ttttcgccct tgacgttgg agtccacgtt    5160
ctttaatagt ggactcttgt tccaaactgg aacaacactc aacctatct cggtctattc     5220
ttttgattta aaggattt tgccgatttc ggcctattgg ttaaaaaatg agctgattta     5280
acaaaaattt aacgcgaatt ttaacaaaat attaacgttt acaatttaaa tatttgctta   5340
tacaatcttc ctgttttgg ggcttttctg attatcaacc ggggtacata tgattgacat    5400
gctagtttta cgattaccgt tcatcgattc tcttgtttgc tccagactct caggcaatga   5460
cctgatagcc tttgtagaga cctctcaaaa atagctaccc tctccggcat gaatttatca   5520
gctagaacgg ttgaatatca tattgatggt gatttgactg tctccggcct ttctcacccg   5580
tttgaatctt tacctacaca ttactcaggc attgcattta aaatatatga gggttctaaa   5640
aattttttatc cttgcgttga aataaaggct tctcccgcaa aagtattaca gggtcataat   5700
gtttttggta caaccgattt agctttatgc tctgaggctt tattgcttaa ttttgctaat   5760
tctttgcctt gcctgtatga tttattggat gttggaatcg cctgatgcgg tattttctcc   5820
ttacgcatct gtgcggtatt tcacaccgca tatggtgcac tctcagtaca atctgctctg   5880
atgccgcata gttaagccag ccccgacacc cgccaacacc cgctgacgcg ccctgacggg   5940
cttgtctgct cccggcatcc gcttacagac aagctgtgac cgtctccggg agctgcatgt   6000
gtcagaggtt ttcaccgtca tcaccgaaac gcgcgagacg aaagggcctc gtgatacgcc   6060
tatttttata ggttaatgtc atgataataa tggtttctta gacgtcaggt ggcacttttc   6120
ggggaaatgt gcgcggaacc cctatttgtt tatttttcta aatacattca aatatgtatc   6180
cgctcatgag acaataaccc tgataaatgc ttcaataata ttgaaaaagg aagagtatga   6240
gtattcaaca tttccgtgtc gcccttattc cttttttgc ggcattttgc cttcctgttt   6300
ttgctcaccc agaaacgctg gtgaaagtaa aagatgctga agatcagttg ggtgcacgag   6360
tgggttacat cgaactggat ctcaacagcg gtaagatcct tgagagtttt cgccccgaag   6420
aacgttttcc aatgatgagc acttttaaag ttctgctatg tggcgcggta ttatcccgta   6480
ttgacgccgg gcaagagcaa ctcggtcgcc gcatacacta ttctcagaat gacttggttg   6540
agtactcacc agtcacagaa aagcatctta cggatggcat gacagtaaga gaattatgca   6600
gtgctgccat aaccatgagt gataacactg cggccaactt acttctgaca acgatcggag   6660
```

```
gaccgaagga gctaaccgct tttttgcaca acatggggga tcatgtaact cgccttgatc    6720
gttgggaacc ggagctgaat gaagccatac caaacgacga gcgtgacacc acgatgcctg    6780
tagcaatggc aacaacgttg cgcaaactat taactggcga actacttact ctagcttccc    6840
ggcaacaatt aatagactgg atggaggcgg ataaagttgc aggaccactt ctgcgctcgg    6900
cccttccggc tggctggttt attgctgata atctggagc cggtgagcgt gggtctcgcg    6960
gtatcattgc agcactgggg ccagatggta agccctcccg tatcgtagtt atctacacga    7020
cggggagtca ggcaactatg gatgaacgaa atagacagat cgctgagata ggtgcctcac    7080
tgattaagca ttggtaactg tcagaccaag tttactcata tatactttag attgatttaa    7140
aacttcattt ttaatttaaa aggatctagg tgaagatcct ttttgataat ctcatgacca    7200
aaatcccta acgtgagttt tcgttccact gagcgtcaga ccccgtagaa aagatcaaag    7260
gatcttcttg agatcctttt tttctgcgcg taatctgctg cttgcaaaca aaaaaaccac    7320
cgctaccagc ggtggtttgt ttgccggatc aagagctacc aactctttt ccgaaggtaa    7380
ctggcttcag cagagcgcag ataccaaata ctgtccttct agtgtagccg tagttaggcc    7440
accacttcaa gaactctgta gcaccgccta catacctcgc tctgctaatc ctgttaccag    7500
tggctgctgc cagtggcgat aagtcgtgtc ttaccgggtt ggactcaaga cgatagttac    7560
cggataaggc gcagcggtcg ggctgaacgg ggggttcgtg cacacagccc agcttggagc    7620
gaacgaccta caccgaactg agatacctac agcgtgagct atgagaaagc gccacgcttc    7680
ccgaagggag aaaggcggac aggtatccgg taagcggcag ggtcggaaca ggagagcgca    7740
cgagggagct tccagggga aacgcctggt atctttatag tcctgtcggg tttcgccacc    7800
tctgacttga gcgtcgattt ttgtgatgct cgtcagggg gcggagccta tggaaaaacg    7860
ccagcaacgc ggccttttta cggttcctgg ccttttgctg ccttttgct cacatgttct    7920
ttcctgcgtt atccctgat tctgtggata accgtattac cgcctttgag tgagctgata    7980
ccgctcgccg cagccgaacg accgagcgca gcgagtcagt gagcgaggaa gcggaagagc    8040
gcccaatacg caaaccgcct ctccccgcgc gttggccgat tcattaatg              8089

SEQ ID NO: 36         moltype = DNA   length = 8152
FEATURE               Location/Qualifiers
source                1..8152
                      mol_type = other DNA
                      organism = Synthetic construct
SEQUENCE: 36
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actagggggt tcctgtagtt aatgattaac ccgcatgct acttatctac acgcgtagat    180
cttttttcct tagaaaccac tgctaactga aagagactaa gatttgtccc gtcaaaaatc    240
ctggacctat gcctaaaaca catttccaaa tccctgaact tttcaaaat tggtacatgc    300
tttagcttta aactacaggc ctcactggag ctagagacaa gaaggtaaaa aacggctgac    360
aaaagaagtc ctggtatcct ctatgatggg agaaggaaac tagctaaagg gaagaataaa    420
ttagagaaaa actggaatga ctgaatcgga acaaggcaaa ggctataaaa aaattagca    480
gtatcctctt gggggcccct tccccacact atctcaatgc aaatatctgt ctgaaacggt    540
ccctggctaa actccaccca tgggttggcc agccttgcct tgacaaggca aacttgacca    600
atagtcttag agtatccagt gaggccaggg gccggcggct ggctaggat gaagaataaa    660
aggaagcacc cttcagcagt tccacacact cgcttctgga acgtctgagg ttatcaataa    720
gctcctagtc cagacgccgc cgccaccatg gtccatctta caccggagga gaagtccgct    780
gtaacggcac tgtgggggaa agttaatgtc gatgaagtcg gcggtgaagc actcggcagg    840
ttgctggtag tgtaccccgtg gacacaacga ttctttgaaa gttcgggga cctgtccaca    900
cccgatgctg tgatgggtaa tccaaaagta aaagcacacg gcaagaaagt cctcggcgcg    960
tttagtgatg gtctgcccca tttggataac ttgaaggta cattcgcgca gctttccgaa    1020
ctccactgtg acaagttgca cgtagatcca gaaaacttcc ggcttctggg caatgtgctt    1080
gtatgcgttc tggctcacca ttttggaag gagtttaccc cacccgtgca agcggcttac    1140
caaaagtgg tcgcaggagt ggctaatgcc cttgcacata aatatcacta aggtaccgag    1200
catcttaccg ccatttattc ccatatttgt tctgttttc ttgatttggg tatacattta    1260
aatgttaata aaacaaaatg gtgggcaat catttacatt tttagggata tgtaattact    1320
agttcaggtg tattgccaca agacaaacat gttaagaaac tttcccgtta tttacgctct    1380
gttcctgtta atcaacctct ggattacaaa attttgtgaaa gattgactga tattcttaac    1440
tatgttgctc ctttacgct gtgtggatat gctgctttat agcctctgta tctagctatt    1500
gcttcccgta cggctttcgt tttctcctcc ttgtataaat cctggttgct gtctcttta    1560
gaggagttgt ggcccgttgt ccgtcaacgt ggcgtggtgt gctctgtgtt tgctgacgca    1620
accccactg gctggggcat tgccaccacc tgtcaactcc tttctgggac tttcgcttc    1680
ccctcccga tcgccacggc agaactcatc gccgcctgcc ttgcccgctg ctggacaggg    1740
gctaggttgc tgggcactga taattccgtg gtgttgtctg tgcttctag ttgccagcca    1800
tctgttgttt gcccctcccc cgtgccttcc ttgaccctgg aaggtgccac tcccactgtc    1860
ctttcctaat aaaatgagga attgcatcg cattgtctga gtaggtgtca ttctattctg    1920
gggggtgggg tggggcagga cagcaagggg gaggattggg aagacaatag caggcatgct    1980
ggggatgcgg tgggctctat ggccgagatc gagaccatcc tggctaacac agtgaaaccc    2040
cgtctctact aaaaaatac aaaaaattag ccgggcttgg tggcgggtgc ctgtagtccc    2100
agctactatg gaggctgagg cgggagaatg gcgtgaacgc gggggggcgga gcttgcagtg    2160
agcagagatc aggggccact gcactccagc ctgggcgaca gagagagact ctgtctcaaa    2220
aaaaagaaaa aaaaattta gtagactagc taaaaaatc cagagatagt tattgatgca    2280
tatgtaaaag tcttccaata tttcaagta caatgaaaaa aaataacct tgaattaagt    2340
gtagaactca ttgacaatgt ttcaaggat gtgagggata aactaaatt tgggcagtac    2400
atgctgttcc tgtgtacttg aacagaggg agaaaatctg gctgaaaat attgttatag    2460
gagttagcac atgaaggtga caactaaatt atttggagta gatggagtca ccagcacatg    2520
tgaatagttt tagaatgaaa tgacccaaga tagaacctgg cagggcccc aaatttaaat    2580
aaaatcagta taagaagaa ggaagaaacc aaatgtata ctagtctaaa ttgtttctta    2640
gtgacaaaag aataacctga atattagatt agctgcctat atgctctctg aatcaatttc    2700
attcaacatg caacagtccg cgggaacaga gaaacaggag aatatgggcc aaacaggata    2760
tctgtggtaa gcagttcctg ccccggctca gggccaagaa cagttggaac agcagaatat    2820
gggccaaaca ggatatctgt ggtaagcagt tcctgccccg gctcagggcc aagaacagat    2880
```

```
ggtccccaga tgcggtcccg ccctcagcag tttctagaga accatcagat gtttccaggg  2940
tgccccaagg acctgaaatg accctgtgcc ttatttgaac taaccaatca gttcgcttct  3000
cgcttctgtt cgcgcgcttc tgctcccega gctctatata agcagagctc gtttagtgaa  3060
ccgtcagatc gcctggagac gccatccacg ctgtttgac ttccatagaa ggcggccgcg  3120
ccgccaccat ggtgagcaag ggcgaggagc tgttcaccgg ggtggtgccc atcctggtcg  3180
agctggacgg cgacgtaaac ggccacaagt tcagcgtgtc cggcgagggc gagggcgatg  3240
ccacctacgg caagctgacc ctgaagttca tctgcaccac cggcaagctg cccgtgccct  3300
ggcccaccct cgtgaccacc ctgacctacg gcgtgcagtg cttcagccgc taccccgacc  3360
acatgaagca gcacgacttc ttcaagtccg ccatgcccga aggctacgtc caggagcgca  3420
ccatcttctt caaggacgac ggcaactaca agacccgcgc cgaggtgaag ttcgagggga  3480
acaccctggt gaaccgcatc gagctgaagg gcatcgactt caaggaggac ggcaacatcc  3540
tggggcacaa gctggagtac aactacaaca gccacaacgt ctatatcatg gccgacaagc  3600
agaagaacgg catcaaggtg aacttcaaga tccgccacaa catcgaggac ggcagcgtgc  3660
agctcgccga ccactaccag cagaacaccc ccatcggcga cggccccgtg ctgctgcccg  3720
acaaccacta cctgagcacc cagtccgccc tgagcaaaga ccccaacgaa aagcgcgatc  3780
acatggtcct gctggagttc gtgaccgccg ccgggatcac tctcggcatg gacgagctgt  3840
acaagtaagc tttatttgtg aaatttgtga tgctattgct ttatttgtaa ccattataag  3900
ctgcaataaa caagttaaca acaacaattg cattcatttt atgtttcagg ttcaggggga  3960
gatgtgggag gttttttaaa gccctgcagg atgggtcatt tcacagagga ggacaaggct  4020
actatcacaa gcctgtgggg caaggtgaat gtggaagatg ctggaggaga aaccctggga  4080
aggtaggctc tggtgaccag gacaagggag ggaaggaagg accctgtgcc tggcaaaagt  4140
ccaggtcgct tctcaggatt tgtggcacct tctgactgtc aaactgttct tgtcaatctc  4200
acaggctcct ggttgtctac ccatggaccc agaggttctt tgacagcttt ggcaacctgt  4260
cctctgcctc tgccatcatg ggcaaccca aagtcaaggc acatggcaag aaggtgctga  4320
cttccttggg agatgccaca aagcacctgg atgatctcaa gggcaccttt gcccagctga  4380
gtgaactgca gtcgacgtag ataagtagca tggcgggta atcattaact caaggaacc  4440
cctagtgatg gagttggcca ctccctctct gcgcgctcgc tcgctcactg aggccgggca  4500
accaaaggtc gcccgacgcc cgggcttgc ccggcggcc tcagtgagcg agcgagcgcg  4560
ccagctggcg taatagcgaa gaggcccgca ccgatcgccc ttcccaacag ttgcgcagcc  4620
tgaatggcga atggcgattc cgttgcaatg gctggcggta atattgttct ggatattacc  4680
agcaaggccg atagttgag ttcttctact caggcaagtg atgttattac taatcaaaga  4740
agtattgcga caacgtaa tttgcgtgat ggacagactc ttttactcgg tggcctcact  4800
gattataaaa acacttctca ggattctggc gtaccgttcc tgtctaaaat cccttaatc  4860
ggcctcctgt ttagctcccg ctctgattct aacgaggaaa gcacgttata cgtgctcgtc  4920
aaagcaacca tagtacgcgc cctgtagcgc cgcattaagc gcggcgggtg tggtggttac  4980
gcgcagcgtg accgctacac ttgccagcgc cctagcgccc gctccttcg ctttcttccc  5040
ttcctttctc gccacgttcg ccggctttcc ccgtcaagct ctaaatcggg ggctcccttt  5100
agggttccga tttagtgctt tacggcacct cgaccccaaa aaacttgatt agggtgatgg  5160
ttcacgtagt gggccatcgc cctgatagac ggtttttcgc cctttgacgt tggagtccac  5220
gttctttaat agtggactct tgttccaaac tggaacaaca ctcaaccta tctcggtcta  5280
ttcttttgat ttataaggga ttttgccgat ttcggcctat tggttaaaaa atgagctgat  5340
ttaacaaaaa tttaacgcga attttaacaa aatattaacg tttacaattt aaatatttgc  5400
ttatacaatc ttcctgtttt tgggcttttt ctgattatca accgggtac atatgattga  5460
catgctagtt ttacgattac cgttcatcga ttctcttgtt tgctccagac tctcaggcaa  5520
tgacctgata gcctttgtag agacctctca aaaatagcta ccctctccgg catgaattta  5580
tcagctagaa cggttgaata tcatattgat ggtgatttga ctgtctccgg cctttctcac  5640
ccgttgaat cttaccta acattactca ggcattgcat ttaaaatata tgagggttct  5700
aaaaattttt atccttgcgt tgaaataaag gcttctcccg caaaagtatt acagggtcat  5760
aatgtttttg gtacaaccga tttagcttta tgctctgagg cttattgct taattttgct  5820
aattctttgc cttgcctgta tgatttattg gatgttggaa tcgcctgatg cggtattttc  5880
tccttacgca tctgtgcggt attttcacacc gcatatggtg cactctcagt acaatctgct  5940
ctgatgccgc atagttaagc cagccccgac acccgccaac acccgctgac gcgccctgac  6000
gggcttgtct gctcccggca tccgcttaca gacaagctgt gaccgtctcc gggagctgca  6060
tgtgtcagag gttttcaccg tcatcaccga aacgcgcgag acgaaaggc ctcgtgatac  6120
gcctattttt ataggttaat gtcatgataa taatggtttc ttagacgtca ggtggcactt  6180
ttcggggaaa tgtgcgcgga acccctattt gtttattttt ctaaatacat tcaaatatgt  6240
atccgctcat gagacaataa ccctgataaa tgcttcaata atattgaaaa aggaagagta  6300
tgagtattca acatttccgt gtcgccctta ttccctttt tgcggcattt tgccttcctg  6360
ttttgctca cccagaaacg ctggtgaaag taaaagatgc tgaagatcag ttgggtgcac  6420
gagtgggtta catcgaactg gatctcaaca gcggtaagat ccttgagagt tttcgccccg  6480
aagaacgttt tccaatgatg agcacttta aagttctgct atgtggcgcg gtattatccc  6540
gtattgacgc cgggcaagag caactcggtc gccgcataca ctattctcag aatgacttgg  6600
ttgagtactc accagtcaca gaaaagcatc ttacggatgg catgacagta agagaattat  6660
gcagtgctgc cataaccatg agtgataaca ctgcggccaa cttacttctg acaacgatcg  6720
gaggaccgaa ggagctaacc gcttttttgc acaacatggg ggatcatgta actcgccttg  6780
atcgttggga accggagctg aatgaagcca taccaaacga cgagcgtgac accacgatgc  6840
ctgtagcaat ggcaacaacg ttgcgcaaac tattaactgg cgaactactt actctagctt  6900
cccggcaaca attaatagac tggatggagg cggataaagt tgcaggacca cttctgcgct  6960
cggcccttcc ggctggctgg tttattgctg ataaatctgg agccggtgag cgtgggtctc  7020
gcggtatcat tgcagcactg gggccagatg gtaagccctc ccgtatcgta gttatctaca  7080
cgacgggag tcaggcaact atggatgaac gaaatagaca gatcgctgag ataggtgcct  7140
cactgattaa gcattggtaa ctgtcagacc aagtttactc atatatactt tagattgatt  7200
taaaacttca tttttaattt aaaaggatct aggtgaagat cctttttgat aatctcatga  7260
ccaaaatccc ttaacgtgag ttttcgttcc actgagcgtc agaccccgta gaaagatca  7320
aaggatcttc ttgagatcct ttttttctgc gcgtaatctg ctgcttgcaa acaaaaaaac  7380
caccgctacc agcggtggtt tgtttgccgg atcaagagct accaactctt tttccgaagg  7440
taactggctt cagcagagcg cagataccaa atactgtcct tctagtgtag ccgtagttag  7500
gccaccactt caagaactct gtagcaccgc ctacatacct cgctctgcta atcctgttac  7560
cagtggctgc tgccagtggc gataagtcgt gtcttaccgg gttggactca agacgatagt  7620
```

```
taccggataa ggcgcagcgg tcgggctgaa cggggggttc gtgcacacag cccagcttgg   7680
agcgaacgac ctacaccgaa ctgagatacc tacagcgtga gctatgaaga agcgccacgc   7740
ttcccgaagg gagaaaggcg gacaggtatc cggtaagcgg cagggtcgga acaggagagc   7800
gcacgaggga gcttccaggg ggaaacgcct ggtatcttta tagtcctgtc gggtttcgcc   7860
acctctgact tgagcgtcga tttttgtgat gctcgtcagg gggcggagc ctatggaaaa   7920
acgccagcaa cgcggccttt ttacggttcc tggccttttg ctggccttttt gctcacatgt   7980
tctttcctgc gttatcccct gattctgtgg ataaccgtat taccgccttt gagtgagctg   8040
ataccgctcg ccgcagccga acgaccgagc gcagcgagtc agtgagcgag gaagcggaag   8100
agcgcccaat acgcaaaccg cctctccccg cgcgttggcc gattcattaa tg           8152

SEQ ID NO: 37           moltype = DNA   length = 8236
FEATURE                 Location/Qualifiers
source                  1..8236
                        mol_type = other DNA
                        organism = Synthetic construct
SEQUENCE: 37
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt cctacgcgta gatcttaccc tgttaatggt ccaatatgtc agaaacagca    180
ctgtgttaga aataaagctg tctaaagtac actaatattc gagttataat agtgtgtgga    240
ctattagtca ataaaaacaa cccttgcctc tttagagttg ttttccatgt acacgcacat    300
cttatgtctt agagtaagat tccctgagaa gtgaacctag catttataca agataattaa    360
ttctaatcca cagtacctgc caaagaacat tctaccatca tctttactga gcatagaaga    420
gctacgccaa aaccctgggt catcagccag cacacacact tatccagtgg taaatacaca    480
tcatctggtg tatacataca tacctgaata tggaatcaaa tattttttcta agatgaaaca    540
gtcatgatttt atttcaaata ggtacggata agtagatatt gaggtaagca ttaggtctta    600
tattatgtaa cactaatcta ttactgcgct gaaactgtgg ctttatagaa attgtttttca    660
ctgcactatt gagaaattaa agataatgg caaaagtcac aaagagtata ttcaaaaaga    720
agtatagcac ttttttcctta gaaaccactg ctaactgaaa gagactaaga tttgtcccgt    780
caaaaatcct ggacctatgc ctaaaacaca tttcacaatc cctgaacttt tcaaaaattg    840
gtacatgctt tagctttaaa ctacaggcct cactggagct agagacaaga aggtaaaaaa    900
cggctgacaa aagaagtcct ggtatcctct atgatgggag aaggaaacta gctaaaggga    960
agaataaatt agagaaaaac tggaatgact gaatcggaac aaggcaaagg ctataaaaaa   1020
aattagcagt atcctcttgg gggcccccttc cccacactat ctcaatgcaa atatctgtct   1080
gaaacggtcc ctggctaaac tccacccatg ggttggccag ccttgccttg accaatagcc   1140
ttgacgaatt cgctttaaaa aacctccacc atctcccct gaacctgaaa cataaaatga   1200
atgcaattgt tgttgttaac ttgtttattg cagcttataa tggttacaaa taaagcaata   1260
gcatcacaaa ttttcacaaat aaagcttact tgtacagctc gtccatgccg agagtgatcc   1320
cggcggcggt cacgaactcc agcaggacca tgtgatccgc cttctcgttg gggtctttgc   1380
tcagggcgga ctgggtgctc aggtagtggt tgtcgggcag cagcacgggg ccgtcgccga   1440
tgggggtgtt ctgctggtag tggtcggcga gctgcacgct gccgtcctcg atgttgtggc   1500
ggatcttgaa gttcaccttg atgccgttct tctgcttgtc ggccatgata tagacgttgt   1560
ggctgttgta gttgtactcc agcttgtgcc ccaggatgtt gccgtcctcc ttgaagtcga   1620
tgcccttcag ctcgatgcgg ttcaccaggg tgtcgccctc gaacttcacc tcggcgcggg   1680
tcttgtagtt gccgtcgtcc ttgaagaaga tggtgcgctc ctggacgtag ccttcgggca   1740
tggcggactt gaagaagtcg tgctgcttca tgtggtcggg gtagcggctg aagcactgca   1800
cgccgtaggt cagggtggtc acgagggtgg gccagggcac gggcagcttg ccggtggtgc   1860
agatgaactt cagggtcagc ttgccgtagg tggcatcgcc ctcgccctcg ccggacacgc   1920
tgaacttgtg gccgtttacg tcgccgtcca gctcgaccag gatgggcacc accccggtga   1980
acagctcctc gcccttgctc accatggtgg cggcgcggcc gcgatctgac ggttcactaa   2040
acgagctctg cttatataga gctcggggag cagaagcgcg cgaacagaag cgagaagcga   2100
actgattggt tagttcaaat aaggcacagg gtcatttcag gtccttgggg caccctggaa   2160
acatctgatg gttctctaga aactgctgag ggcgggaccg catctgggga ccatctgttc   2220
ttggccctga gccggggcag gaactgctta ccacagatat cctgtttggc ccatattctg   2280
ctgttccaac tgttcttggc cctgagccgg ggcaggaact gttaccaca gatatcctg   2340
ttggcccata ttctcctgtt tctctgttcc cgcggcgaga tcgagaccat cctggctaac   2400
acagtgaaac cccgtctcta ctaaaaaaat acaaaaaatt agccgggctt ggtggcgggt   2460
gcctgtagtc ccagctacta tggaggctga ggcgggagaa tggcgtgaac gcgggggggcg   2520
gagcttgcag tgagcagaga tcaggggcca ctgcactcca gcctgggcga cagagagaga   2580
ctctgtctca aaaaaagaaa aaaaaaaatt tagtagacta gctaaaaaaa tccagagata   2640
gttattgatg catatgtaaa agtccttcaa tatttacaag tacaatgaaa aaaaaataac   2700
cttgaattaa gtgtagaact cattgacaat gtttcaaagg atgtgaggga taaactaaaa   2760
tttgggcagt acatgctgtt cctgtgtact tggaacagag ggagaaaatc tgggctggaa   2820
atattgttat aggagttagc acatgaaggt gacaactaaa ttatttggag tagatggat   2880
caccagcaca tgtgaatagt tttagaatga aatgacccaa gatagaactt tggagagccc   2940
ccaaatttaa ataaaatcag tataagaaaa gaggaagaaa ccaaatggta tactagtcta   3000
aattgttttct tagtgacaaa agaataacct gaatattaga ttagctgcct atatgctctc   3060
tgaatcaatt tcattcaaca tgcaacagtt ctggaaccta tcagggacca cagtcagcca   3120
ggcaagcaca tctgcccaag ccaagggtgg aggcatgcag ctgtgggggt ctgtgaaaac   3180
acttgaggga gcagataact gggccaacca tgactcagtg cttctggagg ccaacaggac   3240
tgctgagtca tcctgtgggg gtggaggtgg gacaagggaa aggggtgaat ggtactgctg   3300
attacaacct ctggtgctgc ctcccccctcc tgtttatctg agagaggcct cactggagct   3360
agagacaaga aggtaaaaaa cggctgacaa aagaagtcct ggtatcctct atgatgggag   3420
aaggaaacta gctaaaggga agaataaatt agagaaaaac tggaatgact gaatcggaac   3480
aaggcaaagg ctataaaaaa aattagcagt atcctcttgg gggcccccttc cccacactat   3540
ctcaatgcaa atatctgtct gaaacggtcc ctggctaaac tccacccatg ggttggccag   3600
ccttgccttg acaaggcaaa cttgaccaat agtcttagag tatccagtga ggccagggc   3660
cggcggctgc taggatgaga agaataaaag gaagcaccct tcagcagttc cacacactcg   3720
cttctggaac gtctgaggtt atcaataagc tcctagtcca gacgccatgg gtcatttcac   3780
```

```
agaggaggac aaggctacta tcacaagcct gtggggcaag gtgaatgtgg aagatgctgg    3840
aggagaaacc ctgggaaggt aggctctggt gaccaggaca agggagggaa ggaaggaccc    3900
tgtgcctggc aaaagtccag gtcgcttctc aggatttgtg gcaccttctg actgtcaaac    3960
tgttcttgtc aatctcacag gctcctggtt gtctacccat ggaccagag gttctttgac     4020
agctttggca acctgtcctc tgcctctgcc atcatgggca accccaaagt caaggcacat    4080
ggcaagaagg tgctgacttc cttgggagat gccacaaagc acctggatga tctcaagggc    4140
acctttgccc agctgagtga actgcactgt gacaagctgc atgtggatcc tgagaacttc    4200
aaggtgagtc caggagatgt ttcagccctg ttgcctttag tctcgaggca acttagacaa    4260
cggagtattg atctgagcac agcagggtgt gagctgtttg aagatactgg ggttggggggt   4320
gaagaaactg cagaggacta actgggctga gacccagtgg taatgttttta gggcctaagg   4380
agtgcctcta aaaatctaga tggacaattt tgactttgag aaaagagagg tggaaatgag    4440
gaaaatgact tttctttatt agattccagt agaaagaact ttcatctttc cctcattttt    4500
gttgttttaa aagtcgacag gaaccctag tgatggagtt ggccactccc tctctgcgcg     4560
ctcgctcgct cactgaggcc gggcgaccaa aggtcgcccg acgcccggc tttgcccggg     4620
cggcctcagt gagcgagcga gcgcgcagct ggcgtaatag cgaagaggcc cgcaccgatc    4680
gcccttccca acagttgcgc agcctgaatg gcgaatggcg attccgttgc aatggctggc    4740
ggtaatattg ttctggatat taccagcaag gccgatagtt tgagttcttc tactcaggca    4800
agtgatgtta ttactaatca aagaagtatt gcgacaacgg ttaatttgcg tgatggacag    4860
actcttttac tcggtggcct cactgattat aaaaacactt ctcaggattc tggcgtaccg    4920
ttcctgtcta aaatcccttt aatcggcctc ctgtttagct cccgctctga ttctaacgag    4980
gaaagcacgt tatacgtgct cgtcaaagca accatagtac gcgccctgta gcggcgcatt    5040
aagcgcggcg ggtgtggtgg ttacgcgcag cgtgaccgct acacttgcca gcgccctagc    5100
gcccgctcct ttcgctttct tcccttcctt tctcgccacg ttcgccggct ttccccgtca    5160
agctctaaat cggggctcc ctttagggtt ccgatttagt gctttacggc acctcgaccc     5220
caaaaaactt gattagggtg atggttcacg tagtgggcca tcgccctgat agacggtttt    5280
tcgccctttg acgttggagt ccacgttctt taatagtgga ctcttgttcc aaactggaac    5340
aacactcaac cctatctcgg tctattcttt tgatttataa gggattttgc cgatttcggc    5400
ctattggtta aaaaatgagc tgatttaaca aaaatttaac gcgaatttta acaaaatatt    5460
aacgtttaca atttaaatat ttgcttatac aatcttcctg ttttttgggc ttttctgatt    5520
atcaaccggg gtacatatga ttgacatgct agttttacga ttaccgttca tcgattctct    5580
tgtttgctcc agactctcag gcaatgacct gatagccttt gtagagacct ctcaaaaata    5640
gctaccctct ccggcatgaa tttatcagct agaacggttg aatatcatat tgatggtgat    5700
ttgactgtct ccggcctttc tcacccgttt gaatctttac ctacacatta ctcaggcatt    5760
gcatttaaaa tatatgaggg ttctaaaaat ttttatcctt gcgttgaaat aaaggcttct    5820
cccgcaaaag tattacaggg tcataatgtt tttggtacaa ccgatttagc tttatgctct    5880
gaggctttat tgcttaattt tgctaattct ttgccttgcc tgtatgattt attggatgtt    5940
ggaatcgcct gatgcggtat tttctcctta cgcatctgtg cggtatttca caccgcatat    6000
ggtgcactct cagtacaatc tgctctgatg ccgcatagtt aagccagccc cgacacccgc    6060
caacacccgc tgacgcgccc tgacgggctt gtctgctccc ggcatccgct tacagacaag    6120
ctgtgaccgt ctccgggagc tgcatgtgtc agaggttttc accgtcatca ccgaaacgcg    6180
cgagacgaaa gggcctcgtg atacgcctat ttttataggt taatgtcatg ataataatgg    6240
tttcttagac gtcaggtggc acttttcggg gaaatgtgcg cggaacccct atttgtttat    6300
ttttctaaat acattcaaat atgtatccgc tcatgagaca taaccctgat aaatgcttca    6360
aataatattg aaaaaggaag agtatgagta ttcaacattt ccgtgtcgcc cttattccct    6420
tttttgcggc attttgcctt cctgtttttg ctcacccaga aacgctggtg aaagtaaaag    6480
atgctgaaga tcagttgggt gcacgagtgg gttacatcga actggatctc aacagcggta    6540
agatccttga gagttttcgc cccgaagaac gttttccaat gatgagcact tttaaagttc    6600
tgctatgtgg cgcggtatta cccgtattg acgccgggca agagcaactc ggtcgccgca    6660
tacactattc tcagaatgac ttggttgagt actcaccagt cacagaaaag catcttacgg    6720
atggcatgac agtaagagaa ttatgcagtg ctgccataac catgagtgat aacactgcgg    6780
ccaacttact tctgacaacg atcggaggac cgaaggagct aaccgctttt ttgcacaaca    6840
tgggggatca tgtaactcgc cttgatcgtt gggaaccgga gctgaatgaa gccataccaa    6900
acgacgagcg tgacaccacg atgcctgtag caatggcaac aacgttgcgc aaactattaa    6960
ctggcgaact acttactcta gcttcccggc aacaattaat agactggatg gaggcggata    7020
aagttgcagg accacttctg cgctcggccc ttccggctgg ctggtttatt gctgataaat    7080
ctggagccgg tgagcgtggg tctcgcggta tcattgcagc actggggcca gatggtaagc    7140
cctcccgtat cgtagttatc tacacgacgg gagtcaggc aactatggat gaacgaaata    7200
gacagatcgc tgagataggt gcctcactga ttaagcattg gtaactgtca gaccaagttt    7260
actcatatat actttagatt gatttaaaac ttcattttta atttaaaagg atctaggtga    7320
agatcctttt tgataatctc atgaccaaaa tcccttaacg tgagttttcg ttccactgag    7380
cgtcagaccc cgtagaaaag atcaaggat cttcttgaga tccttttttt ctgcgcgtaa     7440
tctgctgctt gcaaacaaaa aaccaccgc taccagcggt ggtttgtttg ccggatcaag     7500
agctaccaac tctttttccg aaggtaactg gcttcagcag agcgcagata ccaaatactg    7560
tccttctagt gtagccgtag ttaggccacc acttcaagaa ctctgtagca ccgcctacat    7620
acctcgctct gctaatcctg ttaccagtgg ctgctgccaa tggcgataag tcgtgtctta    7680
ccgggttgga ctcaagacga tagttaccgg ataaggcgca gcggtcgggc tgaacggggg    7740
gttcgtgcac acagcccagc ttggagcgaa cgacctacac cgaactgaga tacctacagc    7800
gtgagctatg agaaagcgcc acgcttcccg aagggagaaa ggcggacagg tatccggtaa    7860
gcggcagggt cggaacagga gagcgcacga gggagcttcc agggggaaac gcctggtatc    7920
tttatagtcc tgtcgggttt cgccacctct gacttgagcg tcgatttttg tgatgctcgt    7980
cagggggggcg gagcctatgg aaaaacgcca gcaacgcggc cttttacgg ttcctggcct     8040
tttgctggcc ttttgctcac atgttctttc ctgcgttatc ccctgattct gtggataacc    8100
gtattaccgc ctttgagtga gctgataccg ctcgccgcag ccgaacgacc gagcgcagcg    8160
agtcagtgag cgaggaagcg gaagagcgcc caatacgcaa accgcctctc cccgcgcgtt    8220
ggccgattca ttaatg                                                    8236

SEQ ID NO: 38        moltype = DNA  length = 7955
FEATURE              Location/Qualifiers
source               1..7955
``` mol_type = other DNA
organism = Synthetic construct

SEQUENCE: 38

```
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt cctacgcgta gatcttaccc tgttaatggt ccaatatgtc agaaacagca  180
ctgtgttaga aataaagctg tctaaagtac actaatattc gagttataat agtgtgtgga  240
ctattagtca ataaaaacaa cccttgcctc tttagagttg ttttccatgt acacgcacat  300
cttatgtctt agagtaagat tccctgagaa gtgaacctag catttataca agataattaa  360
ttctaatcca cagtacctgc caaagaacat tctaccatca tctttactga gcatagaaga  420
gctacgccaa aaccctgggt catcagccag cacacacact tatccagtgg taaatacaca  480
tcatctggtg tatacataca tacctgaata tggaatcaaa tattttttcta agatgaaaca  540
gtcatgattt atttcaaata ggtacggata agtagatatt gaggtaagca ttaggtctta  600
tattatgtaa cactaatcta ttactgcgct gaaactgtgg ctttatagaa attgttttta  660
ctgcactatt gagaaattaa gagataatgg caaaagtcac aaagagtata ttcaaaaaga  720
agtatagcac tttttcctta gaaccactg ctaactgaaa gagactaaga tttgtcccgt  780
caaaaatcct ggacctatgc ctaaaacaca tttcacaatc cctgaacttt tcaaaaattg  840
gtacatgctt tagcttttaaa ctacgaattc gctttaaaaa acctcccaca tctccccctg  900
aacctgaaac ataaaatgaa tgcaattgtt gttgttaact tgtttattgc agcttataat  960
ggttacaaat aaagcaatag catcacaaat ttcacaaata aagcttactt gtacagctcg 1020
tccatgccga gagtgatccc ggcggcggtc acgaactcca gcaggaccat gtgatcgcgc 1080
ttctcgttgg ggtctttgct cagggcggac tgggtgctca ggtagtggtt gtcgggcagc 1140
agcacgggc cgtcgccgat gggggtgttc tgctggtagt ggtcggcgag ctgcacgctg 1200
ccgtcctcga tgttgtggcg gatcttgaag ttcaccttga tgccgttctt ctgcttgtcg 1260
gccatgatat agacgttgtg gctgttgtag ttgtactcca gcttgtgccc caggatgttg 1320
ccgtcctcct tgaagtcgat gcccttcagc tcgatgcggt tcaccaggt gtcgcctcg 1380
aacttcacct cggcgcgggt cttgtagttg ccgtcgtcct tgaagaagat ggtgcgctcc 1440
tggacgtagc cttcgggcat ggcggacttg aagaagtcgt gctgcttcat gtggtcgggg 1500
tagcggctga agcactgcac gccgtaggtc agggtggtca cgaggtggg ccagggcacg 1560
ggcagcttgc cggtggtgca gatgaacttc agggtcagct tgccgtaggt ggcatcgccc 1620
tcgccctcgc cggacacgct gaacttgtgg ccgtttacgt cgccgtccag ctcgaccagg 1680
atgggcacca ccccggtgaa cagctcctcg cccttgctca ccatggtggc ggcgcggccg 1740
cgatctgacg gttcactaaa cgagctctgc ttatatagag ctcggggagc agaagcgcgc 1800
gaacagaagc gagaagcgaa ctgattggtt agttcaaata aggcacaggg tcatttcagg 1860
tccttgggc accctggaaa catctgatgg ttctctagaa actgctgagg gcgggaccgc 1920
atctggggac catctgttct tggccctgag ccggggcagg aactgcttac cacagatatc 1980
ctgtttggcc catattctgc tgttccaact gttcttggcc ctgagccggg gcaggaactg 2040
cttaccacag atatcctgtt tggcccatat tctcctgttt ctctgttccc gcggcgagat 2100
cgagaccatc ctggctaaca cagtgaaacc ccgtctctac taaaaaaaata caaaaaatta 2160
gccgggcttg gtggcgggtg cctgtagtcc cagctactat ggaggctgag gcgggagaat 2220
ggcgtgaacg cggggggcgg agcttgcagt gagcagagat caggggccac tgcactccag 2280
cctgggcgac agagagagac tctgtctcaa aaaaagaaa aaaaaattt agtagactag 2340
ctaaaaaaat ccagagatag ttattgatgc atatgtaaaa gtctttccaat atttacaagt 2400
acaatgaaaa aaaaataacc ttgaattaag tgtagaactc attgacaatg tttcaaagga 2460
tgtgagggat aaactaaaat ttgggcagta catgctgttc ctgtgtactt ggaacagagg 2520
gagaaaatct gggctggaaa tattgttata ggagttagca catgaaggtg acaactaaat 2580
tattggagt agatggagtc accagcacat gtgaatagtt ttagaatgaa atgacccaag 2640
ataaacttt ggagagcccc caaatttaaa taaaatcagt ataagagaag aggaagaaac 2700
caaatggtat actagtctaa attgtttctt agtgacaaaa gaataacctg aatattgat 2760
tagctgccta tatgctctct gaatcaattt cattcaacat gcaacagttc tggaacctat 2820
cagggaccac agtcagccag gcaagcacat ctgcccaagc caagggtgga ggcatgcagg 2880
tgtggggggtc tgtgaaaaca cttgagggag cagataactg gccaaccat gactcagtgc 2940
ttctggaggc caacaggact gctgagtcat cctgtggggg tggaggtggg acaagggaaa 3000
gggtgaatg gtactgctga ttacaacctc tggtgctgcc tccccctcct gtttatctga 3060
gagaggcctc actggagcta gagacaagaa ggtaaaaaac ggctgacaaa agaagtcctg 3120
gtatcctcta tgatgggaga aggaaactag ctaaagggaa gaataaatta gagaaaaact 3180
ggaatgactg aatcggaaca aggcaaaggc tataaaaaaa attagcagta tcctcttggg 3240
ggccccttcc ccacactatc tcaatgcaaa tatctgtctg aaacggtccc tggctaaact 3300
ccacccatgg gttggccagc cttgccttga caaggcaaac ttgaccaata gtcttagatt 3360
atccagtgag gccaggggcc ggcggctggc tagggatgaa gaataaaagg aagcaccctt 3420
cagcagttcc acacactcgc ttctggaacg tctgaggtta tcaataagct cctagtccag 3480
acgccatggg tcatttcaca gaggaggaca aggctactat cacaagcctg tggggcaagg 3540
tgaatgtgga agatgctgga ggagaaaccc tgggaaggta ggctctggtg accaggacaa 3600
gggagggaag gaaggaccct gtgcctggca aaagtccagg tcgcttctca ggattttgtag 3660
caccttctga ctgtcaaact gttccttgtca atctcacagg ctcctggttg tctacccatg 3720
gacccagagg ttctttgaca gctttggcaa cctgtcctct gcctctgcca tcatgggcaa 3780
cccccaaagtc aaggcacatg gcaagaaggt gctgacttcc ttgggagatg ccacaaagca 3840
cctggatgat ctcaagggca cctttgccca gctgagtgaa ctgcactgtg acaagctgca 3900
tgtggatcct gagaacttca aggtgagtcc aggagatgtt tcagccctgt tgcctttagt 3960
ctcgaggcaa cttagacaac ggagtattga tctgagcaca gcagggtgtg agctgtttga 4020
agatactggg gttggggtg aagaaactgc agaggactaa ctgggctgag acccagtggt 4080
aatgttttag ggcctaagga gtgcctctaa aaatctagat ggacaatttt gactttgaga 4140
aaagagaggt ggaaatgagg aaaatgactt ttctttatta gattccagta gaaagaactt 4200
tcatctttcc ctcatttttg ttgttttaaa agtcgacagg aaccctagt gatggagttg 4260
gccactccc ctctgcgcgc tcgctcgctc actgaggccg ggcgaccaaa ggtcgcccga 4320
cgcccgggct tgcccgggc ggcctcagtg agcgagcag cgcgcagctg gcgtaatagc 4380
gaagaggccc gcaccgatcg cccttcccaa cagttgcgca gcctgaatgg cgaatggcga 4440
ttccgttgca atggctggcg gtaatattgt tctgatatat accagcaagg ccgatagttt 4500
gagttcttct actcaggcaa gtgatgttat tactaatcaa agaagtattg cgacaacggt 4560
```

```
taatttgcgt gatggacaga ctcttttact cggtggcctc actgattata aaaacacttc   4620
tcaggattct ggcgtaccgt tcctgtctaa aatccettta atcggcctcc tgtttagctc   4680
ccgctctgat tctaacgagg aaagcacgtt atacgtgctc gtcaaagcaa ccatagtacg   4740
cgccctgtag cggcgcatta agcgcggcgg gtgtggtggt tacgcgcagc gtgaccgcta   4800
cacttgccag cgccctagcg cccgctcctt tcgctttctt cccttccttt ctcgccacgt   4860
tcgccggctt tccccgtcaa gctctaaatc gggggctccc tttagggttc cgatttagtg   4920
ctttacggca cctcgacccc aaaaaacttg attagggtga tggttcacgt agtgggccat   4980
cgccctgata gacggttttt cgccctttga cgttggagtc cacgttcttt aatagtggac   5040
tcttgttcca aactggaaca acactcaacc ctatctcggt ctattctttt gatttataag   5100
ggattttgcc gatttcggcc tattggttaa aaaatgagct gatttaacaa aaatttaacg   5160
cgaattttaa caaaatatta acgtttacaa tttaaatatt tgcttataca atcttcctgt   5220
ttttgggget tttctgatta tcaaccgggg tacatatgat tgacatgcta gttttacgat   5280
taccgttcat cgattctctt gtttgctcca gactctcagg caatgacctg atagcctttg   5340
tagagacctc tcaaaaatag ctaccctctc cggcatgaat ttatcagcta gaacggttga   5400
atatcatatt gatggtgatt tgactgtctc cggcctttct cacccgtttg aatctttacc   5460
tacacattac tcaggcattg catttaaaat atatgagggt tctaaaaatt tttatccttg   5520
cgttgaaata aaggcttctc ccgcaaaagt attacagggt cataatgttt ttggtacaac   5580
cgatttagct ttatgctctg aggctttatt gcttaatttt gctaattctt tgccttgcct   5640
gtatgattta ttggatgttg aatcgcctga tgcggtatt ttctccttac gcatctgtgc   5700
ggtatttcac accgcatatg gtgcactctc agtacaatct gctctgatgc cgcatagtta   5760
agccagcccc gacacccgcc aacacccgct gacgcgccct gacgggcttg tctgctcccg   5820
gcatccgctt acagacaagc tgtgaccgtc tccgggaacg catgtgtca gaggttttca   5880
ccgtcatcac cgaaacgcgc gagacgaaag gcctcgtga tacgcctatt tttataggtt   5940
aatgtcatga taataatggt ttcttagacg tcaggtggca cttttcgggg aaatgtgcgc   6000
ggaacccta tttgtttatt tttctaaata cattcaaata tgtatccgct catgagacaa   6060
taaccctgat aaatgcttca ataatattga aaaaggaaga gtatgagtat tcaacatttc   6120
cgtgtcgccc ttattccctt ttttgcggca ttttgccttc ctgtttttgc tcacccagaa   6180
acgctggtga aagtaaaaga tgctgaagat cagttgggtg cacgagtggg ttacatcgaa   6240
ctggatctca acagcggtaa gatccttgag agttttcgcc ccgaagaacg ttttccaatg   6300
atgagcactt ttaaagttct gctatgtggc gcggtattat cccgtattga cgccgggcaa   6360
gagcaactcg gtcgccgcat acactattct cagaatgact tggttgagta ctcaccagtc   6420
acagaaaagc atcttacgga tggcatgaca gtaagagaat tatgcagtgc tgccataacc   6480
atgagtgata acactgcggc caacttactt ctgacaacga tcggaggacc gaaggagcta   6540
accgcttttt tgcacaacat gggggatcat gtaactcgcc ttgatcgttg ggaaccggag   6600
ctgaatgaag ccataccaaa cgacgagcgt gacaccacga tgcctgtagc aatggcaaca   6660
acgttgcgca aactattaac tggcgaacta cttactctag cttcccggca caattaata   6720
gactggatga aggcggataa agttgcagga ccacttctgc gctcggccct tccggctggc   6780
tggttttattg ctgataaatc tggagccggt gagcgtgggt ctcgcggtat cattgcagca   6840
ctggggccag atggtaagcc ctcccgtatc gtagttatct acacgacggg gagtcaggca   6900
actatggatg aacgaaatag acagatcgct gagataggtg cctcactgat taagcattgg   6960
taactgtcag accaagttta ctcatatata ctttagattg atttaaaact tcattttta   7020
tttaaaagga tctaggtgaa gatcctttt gataatctca tgaccaaaat cccttaacgt   7080
gagttttcgt tccactgagc gtcagacccc gtagaaaaga tcaaaggatc ttcttgagat   7140
cctttttttc tgcgcgtaat ctgctgcttg caaacaaaaa aaccaccgct accagcggtg   7200
gtttgtttgc cggatcaaga gctaccaact cttttccga aggtaactgg cttcagcaga   7260
gcgcagatac caaatactgt ccttctagtg tagccgtagt taggccacca cttcaagaac   7320
tctgtagcac cgcctacata cctcgctctg ctaatcctgt taccagtggc tgctgccagt   7380
ggcgataagt cgtgtcttac cgggttggac tcaagacgat agttaccgga taaggcgcag   7440
cggtcgggct gaacggggggg ttcgtgcaca cagcccagct tggagcgaac gacctacacc   7500
gaactgagat acctacagcg tgagctatga gaaagcgcca cgcttcccga agggagaaag   7560
gcggacaggt atccggtaag cggcagggtc ggaacaggag agcgcacgag ggagcttcca   7620
gggggaaacg cctggtatct ttatagtcct gtcgggtttc gccacctctg acttgagcgt   7680
cgattttgt gatgctcgtc aggggggcgg agcctatgga aaaacgccag caacgcggcc   7740
tttttacggt tcctggcctt ttgctggcct tttgctcaca tgttctttcc tgcgttatcc   7800
cctgattctg tggataaccg tattaccgcc tttgagtgag ctgataccgc tcgccgcagc   7860
cgaacgaccg agcgcagcga gtcagtgagc gaggaagcgg aagagcgccc aatacgcaaa   7920
ccgcctctcc ccgcgcgttg gccgattcat taatg                             7955

SEQ ID NO: 39           moltype = DNA   length = 7825
FEATURE                 Location/Qualifiers
source                  1..7825
                        mol_type = other DNA
                        organism = Synthetic construct
SEQUENCE: 39
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc   120
actaggggtt ccttgtagtt aatgattaac cgccatgct acttatctac acgcgtagat   180
ctagaaattg ttttcactgc actattgaga aattaagaa taatggcaaa agtcacaaag   240
agtatattca aaagaagta tagcacttt tcctagaaa ccactgctaa ctgaaagaga   300
ctaagatttg tcccgtcaaa aatcctggac ctatgcctaa aacacatttc acaatccctg   360
aacttttcaa aaattggtac atgctttagc tttaaactac aggcctcact ggagctagag   420
acaagaaggt aaaaaacggc tgacaaaaga agtcctggta tcctctatga tgggagaagg   480
aaactagcta aaggaagaa taattagag aaaaactgga atgactgaat cggaacaagg   540
caaaggctat aaaaaaaatt agcagtatcc tcttgggggt cccttcccca cactatctca   600
atgcaaatat ctgtctgaaa cggtcccctgg ctaaactcca cccgcgggct taaaaaaacc   660
tcccacatct cccctgaac ctgaaacata aaatgaatgc aattgttgtt gttaacttgt   720
ttattgcagc ttataatggt tacaaataaa gcaatagcat cacaaatttc acaaataaag   780
ctagaatggt tacaaataaa gcaatagcat cacaaatttc acaaataaac accacggaat   840
tgtcagtgcc aacagccga gccctgtcc agcagcgggc aaggcaggcg gcgatgagtt   900
```

```
ccgccgtggc aagaactaac caggatttat acaaggagga gaaaatgaaa gccatacggg    960
aagcaatagc atgatacaaa ggcattaaag cagcgtatcc acatagcgta aaaggagcaa   1020
catagttaag aataccagtc aatctttcac aaatttttgta atccagaggt tgattatccc  1080
tgcaggttac ttgtacagct cgtccatgcc gagagtgatc ccggcggcgg tcacgaactc   1140
cagcaggacc atgtgatcgc gcttctcgtt ggggtctttg ctcagggcgg actgggtgct   1200
caggtagtgg ttgtcgggca gcagcacggg gccgtcgccg atgggggtgt tctgctggta   1260
gtggtcggcg agctgcacgc tgccgtcctc gatgttgtgg cggatcttga agttcacctt   1320
gatgccgttc ttctgcttgt cggccatgat atagacgttg tggctgttgt agttgtactc   1380
cagcttgtgc cccaggatgt tgccgtcctc cttgaagtcg atgcccttca gctcgatgcg   1440
gttcaccagg gtgtcgccct cgaacttcac ctcggcgcgg tgcttgtagt tgccgtcgtc   1500
cttgaagaag atggtgcgct cctggacgta gccttcgggc atggcggact tgaagaagtc   1560
gtgctgcttc atgtggtcgg ggtagcggct gaagcactgc acgccgtagg tcagggtggt   1620
cacgagggtg ggcagggca cgggcagctt gccggtggtg cagatgaact tcagggtcag   1680
cttgccgtag gtggcatcgc cctcgccctc gccggacacg ctgaacttgg ggccgtttac   1740
gtcgccgtcc agctcgacca ggatgggcac caccccggtg aacagctcct cgcccttgct   1800
caccatggtg gcggcgcggc cgccttctat ggaagtcaaa acagcgtgga tggcgtctcc   1860
aggcgatctg acggttcact aaacgagctc tgcttatata gagctcgggg agcagaagcg   1920
cgcgaacaga agcgagaagc gaactgattg gttagttcaa ataaggcaca gggtcatttc   1980
aggtccttgg ggcaccctgg aaacatctga tggttctcta gaaactgctg agggcgggac   2040
cgcatctggg gaccatctgt tcttggccct gagccgggc aggaactgct taccacagat    2100
atcctgtttg gcccatattc tgctgttcca actgttcttg gccctgagcc ggggcaggaa   2160
ctgcttacca cagatatcct gtttggccca tattctcctg tttctctgtt cgaattccga   2220
gatcgagacc atcctggcta acacagtgaa acccgtctc tactaaaaaa atacaaaaaa    2280
ttagccgggc ttggtggcgg gtgcctgtag tcccagctac tatggaggct gaggcgggag   2340
aatgcgtgaa acgcggggg cggagcttgc agtgagcaga atcagggc cactgcactc      2400
cagcctgggc gacagagaga gactctgtct caaaaaaaag aaaaaaaaaa tttagtagac   2460
tagctaaaaa aatccagaga tagttattga tgcatatgta aaagtcttcc aatatttaca   2520
agtacaatga aaaaaaaata accttgaatt aagtgtagaa ctcattgaca atgtttcaaa   2580
ggatgtgagg gataaactaa aatttgggca gtacatgctg ttcctgtgta cttgaacag    2640
agggagaaaa tctgggctgg aaatattgtt ataggagtta gcacatgaag gtgacaacta   2700
aattatttgg agtagatgga gtcaccagca catgtgaata gtttttagaat gaaatgaccc   2760
aagatagaac tttggagagc ccccaaattt aaataaaatc agtataagag aagaggaaga   2820
aaccaaatgt tatactagtc taaattgttt cttagtgaca aagaataac ctgaatatta    2880
gattagctgc ctatatgctc tctgaatcaa tttcattcaa catgcaacag ttctggaacc   2940
tatcagggac cacagtcagc caggcaagca catctgccca agccaagggt ggaggcatgc   3000
agctgtgggg gtctgtgaaa acacttgagg gagcagataa ctgggccaac catgactcag   3060
tgcttctgga ggccaacagg actgctgagt catcctgtgg gggtggaggt gggacaaggg   3120
aaaggggtga atggtactgc tgattacaac ctctggtgct gcctccccct cctgtttatc   3180
tgagaggcta gcgtaaatac acttgcaaag gaggatgttt ttagtagcaa tttgtactga   3240
tggtatgggg ccaagagata tatcttagag ggagggctga gggtttgaag tccaactcct   3300
aagccagtgc cagaagagcc aaggacaggt acgctgtca tcacttagac ctcaccctgt    3360
ggagccacac cctaggtttg gccaatctac tcccaggagc agggagggca ggagccaggg   3420
ctgggcataa aagtcagggc agagccatct attgcttaca ctcgcttctg gaacgtctga   3480
ggttatcaat aagctcctag tccagacgcc atggtgcatt tcacagagga ggacaaggct   3540
actatcacaa gcctgtgggg caaggtgaat gtggaagatg ctggaggaga accctgggaa   3600
aggtaggctc tggtgaccag gacaagggag ggaaggaagg accctgtgcc tggcaaaagt   3660
ccaggtcgct tctcaggatt tgtggccct tctgactgtc aaactgttct tgtcaatctc    3720
acaggctcct ggttgtctac ccatggaccc agaggttctt tgacagcttt ggcaacctgt   3780
cctctgcctc tgccatcatg ggcaacccca aagtcaaggc acatggcaag aaggtgctga   3840
cttccttggg agatgccaca aagcacctgg atgatctcaa gggcaccttt gcccagctga   3900
gtgaactgca ctgtgacaag ctgcatgtgg atcctgaaa cttcaaggtg agtccaggag    3960
atgtttcagc cctgttgcct ttagtctcga ggcaacttag acaacggagt attgatctga   4020
gcacagcagg gtgtgagctg tttgaagata ctggggctc gaggtcgacg tagataagta    4080
gcatggcggg ttaatcatta actacaagga accctagtg atggagttgg ccactccctc    4140
tctgcgcgct cgctcgctca ctgaggccgg gcgaccaaag gtcgcccgac gcccgggctt   4200
tgccgggcg gcctcagtga gcgagcgagc gcgccagctg gcgtaatagc gaagaggccc    4260
gcaccgatcg cccttcccaa cagttgcgca gcctgaatgg cgaatggcga ttccgttgca   4320
atggctggcg gtaatattgt tctggatatt accagcaagg ccgatagttt gagttcttct   4380
actcaggcaa gtgatgttat tactaatcaa agaagtattg cgacaacggt taatttgcgt   4440
gatgacagag ctcttttact cggtggcctc actgattata aaaacacttc tcaggattcc   4500
ggcgtaccgt tcctgtctaa aatcccttta atcggcctcc tgtttagctc ccgctctgat   4560
tctaacgagg aaagcacgtt atacgtgctc gtcaaagcaa ccatagtacg cgccctgtag   4620
cggcgcatta agcgcggcgg gtgtggtggt tacgcgcagc gtgaccgcta cacttgccag   4680
cgccctagcg cccgctcctt tcgctttctt cccttccttt ctcgccacgt tcgccggctt   4740
tccccgtcaa gctctaaatc gggggctccc tttagggttc cgatttagtg ctttacggca   4800
cctcgacccc aaaaaacttg attagggtga tggttcacgt agtgggccat cgccctgata   4860
gacggttttt cgccctttga cgttggagtc acgttctttt aatagtggac tcttgttcca   4920
aactggaaca cactcaacc ctatctcggt ctattcttt gatttataag gattttgcc     4980
gatttcggcc tattggttaa aaaatgagct gatttaacaa aaatttaacg cgaatttta    5040
caaaatatta acgtttacaa tttaaatatt tgcttataca atcttcctgt ttttgggct    5100
tttctgatta tcaaccgggg tacatatgat tgacatgcta gttttacgat taccgttcat   5160
cgattctctt gtttgctcca gactctcagg caatgacctg atagcctttg tagagacctc   5220
tcaaaaatag ctacccctc cggcatgaat ttatcagcta gaacggttga atatcatatt    5280
gatggtgatt tgactgtctc cggcctttct cacccgtttg aatctttacc tacacattac   5340
tcaggcattg catttaaaat atatgagggt tctaaaaatt tttatcctg cgttgaaata    5400
aaggcttctc ccgcaaaagt attacagggt cataatgttt ttggtacaac cgatttagct   5460
ttatgctctg aggctttatt gcttaatttt gctaattctt tgccttgcct gtatgattta   5520
ttggatgttg gaatcgcctg atgcggtatt ttctccttac gcatctgtgc ggtatttcac   5580
accgcatatg gtgcactctc agtacaatct gctctgatgc cgcatagtta agccagcccc   5640
```

```
gacacccgcc aacacccgct gacgcgccct gacgggcttg tctgctcccg gcatccgctt    5700
acagacaagc tgtgaccgtc tccgggagct gcatgtgtca gaggttttca ccgtcatcac    5760
cgaaacgcgc gagacgaaag ggcctcgtga tacgccuatt tttataggtt aatgtcatga    5820
taataatggt ttcttagacg tcaggtggca cttttcgggg aaatgtgcgc ggaacccata    5880
tttgtttatt tttctaaata cattcaaata tgtatccgct catgagacaa taaccctgat    5940
aaatgcttca ataatattga aaaggaaga gtatgagtat tcaacatttc cgtgtcgccc     6000
ttattccctt ttttgcggca ttttgccttc ctgttttgc tcacccagaa acgctggtga     6060
aagtaaaaga tgctgaagat cagttgggtg cacgagtggg ttacatcgaa ctggatctca    6120
acagcggtaa gatccttgag agttttcgcc ccgaagaacg ttttccaatg atgagcactt    6180
ttaaagttct gctatgtggc gcggtattat cccgtattga cgccgggcaa gagcaactcg    6240
gtcgccgcat acactattct cagaatgact tggttgagta ctcaccagtc acagaaaagc    6300
atcttacgga tggcatgaca gtaagagaat tatgcagtgc tgccataacc atgagtgata    6360
acactgcggc caacttactt ctgacaacga tcggaggacc gaaggagcta accgcttttt    6420
tgcacaacat gggggatcat gtaactcgcc ttgatcgttg ggaaccggag ctgaatgaag    6480
ccataccaaa cgacgagcgt gacaccacga tgcctgtagc aatggcaaca acgttgcgca    6540
aactattaac tggcgaacta cttactctag cttcccggca acaattaata gactggatgg    6600
aggcggataa agttgcagga ccacttctgc gctcggccct tccggctggc tggtttattg    6660
ctgataaatc tggagccggt gagcgtgggt ctcgcggtat cattgcagca ctggggccag    6720
atggtaagcc ctcccgtatc gtagttatct acacgacggg gagtcaggca actatggatg    6780
aacgaaatag acagatcgct gagataggtg cctcactgat taagcattgg taactgtcag    6840
accaagttta ctcatatata ctttagattg atttaaaact tcatttttaa tttaaaagga    6900
tctaggtgaa gatcctttt gataatctca tgaccaaaat cccttaacgt gagttttcgt     6960
tccactgagc gtcagacccc gtagaaaaga tcaaaggatc ttcttgagat cctttttttc    7020
tgcgcgtaat ctgctgcttg caaacaaaaa aaccaccgct accagcggtg gtttgtttgc    7080
cggatcaaga gctaccaact ctttttccga aggtaactgg cttcagcaga gcgcagatac    7140
caaatactgt ccttctagtg tagccgtagt taggccacca cttcaagaac tctgtagcac    7200
cgcctacata cctcgctctg ctaatcctgt taccagtggc tgctgccagt ggcgataagt    7260
cgtgtcttac cgggttggac tcaagacgat agttaccgga taaggcgcag cggtcgggct    7320
gaacgggggg ttcgtgcaca gcccagct tggagcgaac gacctacacc gaactgagat      7380
acctacagcg tgagctatga aaagcgcca gcttcccgaa agggagaaag gcggacaggt     7440
atccggtaag cggcagggtc ggaacaggag agcgcacgag ggagcttcca gggggaaacg    7500
cctggtatct ttatagtcct gtcgggtttc gccacctctg acttgagcgt cgattttgt     7560
gatgctcgtc agggggggcgg agccatgga aaacgccag caacgcggcc tttttacggt     7620
tcctggcctt ttgctggcct tttgctcaca tgttctttcc tgcgttatcc cctgattctg    7680
tggataaccg tattaccgcc tttgagtgag ctgataccgc tcgccgcagc cgaacgaccg    7740
agcgcagcga gtcagtgagc gaggaagcgg aagagcgccc aatacgcaaa ccgcctctcc    7800
ccgcgcgttg gccgattcat taatg                                         7825

SEQ ID NO: 40         moltype = DNA  length = 7729
FEATURE               Location/Qualifiers
source                1..7729
                      mol_type = other DNA
                      organism = Synthetic construct
SEQUENCE: 40
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actagggggtt ccttgtagtt aatgattaac ccgccatgct acttatctac acgcgtagat    180
ctagaaattg ttttcactgc actattgaga aattaagaga taatggcaaa agtcacaaag    240
agtatattca aaagaagta tagcactttt tccttagaaa ccactgctaa ctgaaagaga    300
ctaagatttg tcccgtcaaa aatcctggac ctatgcctaa aacacatttc acaatccctg    360
aactttttcaa aaattggtac atgctttagc tttaaactac aggcctcact ggagctgaag    420
acaagaaggt aaaaaacggc tgacaaaaga agtcctggta tcctctatga tgggagaagg    480
aaactagcta aagggaagaa taaattagag aaaaactgga atgactgaat cggaacaagg    540
caaaggctat aaaaaaaatt agcagtatcc tcttgggggc ccttccccca cactatctca    600
atgcaaatat ctgtctgaaa cggtcccgg ctaaactccc cccgcgggaa cagagaaaca     660
ggagaatatg ggccaaacag gatatctgtg gtaagcagtt cctgccccgg ctcagggcca    720
agaacagttg gaacagcaga atatgggcca acaggatat ctgtggtaag cagttcctgc     780
cccggctcag ggcaagaac agatggtccc cagatgcggt cccgccctca gcagtttcta    840
gagaaccatc agatgttttcc agggtgcccc aaggacctga aatgaccctg tgccttattt    900
gaactaacca atcagttcgc ttctcgcttc tgttcgcgcg cttctgctcc ccgagctcta    960
tataagcaga gctcgtttag tgaaccgtca gatcgcctgg agacgccatc cacgctgttt   1020
tgacttccat agaaggcggc gcgccgcca ccatggacaa ggattgtgaa atgaaacgca     1080
ccacactgga cagcccttg gggaagctgg agctgtctgt tgtgagcag ggtctgcacg      1140
aaataaagct cctgggcaag gggacgtctg cagctgatgc cgtggaggtc ccagccccgg   1200
ctgcggttct cggaggtccg gagccctga tgcagtgcac agcctggctg aatgccatt      1260
tccaccagcc cgaggctatc gaagagttcc ccgtgccggc tcttcaccat cccgttttcc   1320
agcaagagtc gttcaccaga caggtgttat ggaagctgct gaaggttgtg aaattcggag   1380
aagtgattc ttaccagcaa ttagcagccc tggcaggcaa cccaaagcc gcgcgagcag     1440
tggggaggagc aatgagaggc aatcctgtca aaatcctcat ccgtgccaca agagtggtct   1500
gcagcagcgg agccgtgggc aactactccg gaggactgc cgtcaaggaa tggcttctgg    1560
cccatgaagg ccaccggttg gggaagccaa gcttgggagg gagctcaggt ctggcagggg   1620
cctggctcaa gggagcggga gctacctcgg gctcccgcc tgctggccga actaacctg     1680
cagggataat caacctctgg attacaaaat tgtgaaaga ttgactggta ttcttaacta    1740
tgttgctcct tttacgctat gtggatacgc tgctttaatg cctttgtatc atgctattgc   1800
ttcccgtatg gctttcattt tctcctcctt gtataaatcc tggttagttc ttgccacggc   1860
ggaactcatc gccgcctgcc ttgcccgctg ctggacaggg gctcggctgt tgggcactga   1920
caattccgtg gtgtttattt tgaaatttg tgatgctatt gctttatttg taaccattct    1980
agcttttt gtgaaatttg tgatgctatt gctttatttg taaccattat aagctgcaat    2040
aaacaagtta acaacaacaa ttgcattcat tttatgtttc aggttcaggg ggagatgtgg   2100
```

```
gaggttttt  aaagcgaatt  ccgagatcga  gaccatcctg  gctaacacag  tgaaaccccg   2160
tctctactaa  aaaaatacaa  aaaattagcc  gggcttggtg  gcgggtgcct  gtagtcccag   2220
ctactatgga  ggctgaggcg  ggagaatggc  gtgaacgcgg  ggggcggagc  ttgcagtgag   2280
cagagatcag  gggccactgc  actccagcct  gggcgacaga  gagagactct  gtctcaaaaa   2340
aaagaaaaaa  aaaatttagt  agactagcta  aaaaaatcca  gagatagtta  ttgatgcata   2400
tgtaaaagtc  ttccaatatt  tacaagtaca  atgaaaaaaa  aataaccttg  aattaagtgt   2460
agaactcatt  gacaatgttt  caaaggatgt  gagggataaa  ctaaaatttg  ggcagtacat   2520
gctgttcctg  tgtacttgga  acagagggag  aaaatctggg  ctggaaatat  tgttatagga   2580
gttagcacat  gaaggtgaca  actaaattat  ttggagtaga  tggagtcacc  agcacatggt   2640
aatagtttta  gaatgaaatg  acccaagata  gaactttgga  gagccccaa   atttaaataa   2700
aatcagtata  agaagagg    aagaaaccaa  atggtatact  agtctaaatt  gtttcttagt   2760
gacaaaagaa  taacctgaat  attagattag  ctgcctatat  gctctctgaa  tcaatttcat   2820
tcaacatgca  acagttctgg  aacctatcag  ggaccacagt  cagccaggca  agcacatctg   2880
cccaagccaa  gggtggaggc  atgcagctgt  ggggtctgt   gaaaacactt  gagggagcag   2940
ataactgggc  caaccatgac  tcagtgcttc  tggaggccaa  caggactgct  gagtcatcct   3000
gtgggggtgg  aggtgggaca  agggaaaggg  gtgaatggta  ctgctgatta  caacctctgg   3060
tgctgcctcc  ccctcctgtt  tatctgagag  gctagcgtaa  atacacttgc  aaaggaggat   3120
gttttagta   gcaatttgta  ctgatggtat  ggggccaaga  gatatatctt  agagggaggg   3180
ctgagggttt  gaagtccaac  tcctaagcca  gtgccagaag  agccaaggac  aggtacggct   3240
gtcatcactt  agacctcacc  ctgtggagcc  acacccctagg gttggccaat  ctactcccag   3300
gagcagggag  ggcaggagcc  agggctgggc  ataaaagtca  gggcagagcc  atctattgct   3360
tacactcgct  tctggaacgt  ctgaggttat  caataagcct  ctagtccaga  cccatgggt    3420
catttcacag  aggaggacaa  ggctactatc  acaagcctgt  ggggcaaggt  gaatgtggaa   3480
gatgctggag  gagaaaccct  gggaaggtag  gctctggtga  ccaggacaag  ggagggaagg   3540
aaggaccctg  tgcctggcaa  aagtccaggt  cgcttctcag  gatttgtggc  accttctgac   3600
tgtcaaactg  ttcttgtcaa  tctcacaggc  tcctggttgt  ctacccatgg  acccagaggt   3660
tctttgacag  ctttggcaac  ctgtcctctg  cctctgccat  catgggcaac  cccaaagtca   3720
aggcacatgg  caagaaggtg  ctgacttcct  tgggagatgc  cacaaagcac  ctggatgatc   3780
tcaagggcac  ctttgcccag  ctgagtgaac  tgcactgtga  caagctgcat  gtggatcctg   3840
agaacttcaa  ggtgagtcca  ggagatgttt  cagccctgct  gcctttagtc  tcgaggcaac   3900
ttagacaacg  gagtattgat  ctgagcacag  cagggtgtga  gctgtttgaa  gatactgggg   3960
tctcgaggtc  gacgtagata  agtagcatgg  cgggttaatc  attaactaca  aggaacccct   4020
agtgatggag  ttggccactc  cctctctgcg  cgctcgctcg  ctcactgagg  ccgggcgacc   4080
aaaggtcgcc  cgacgcccgg  gctttgcccg  ggcggcctca  gtgacgcagc  gagcgcgcca   4140
gctggcgtaa  tagcgaagag  gcccgcaccg  atcgccctc   ccaacagttg  cgcagccctga  4200
atggcgaatg  gcgattccgt  tgcaatggct  ggcggtaata  ttgttctgga  tattaccagc   4260
aaggccgata  gtttgagttc  ttctactcag  gcaagtgatg  ttattactaa  tcaaagaagt   4320
attgcgacaa  cggttaattt  gcgtgatgga  cagactcttt  tactcggtgg  cctcactgat   4380
tataaaaaca  cttctcagga  ttctggcgta  ccgttcctgt  ctaaaatccc  tttaatcggc   4440
ctcctgtttta gctcccgctc  tgattctaac  gaggaaagca  cgttatacgt  gctcgtcaaa   4500
gcaaccatag  tacgcgccct  gtagcggcgc  attaagcgcg  gcgggtgtgg  tggttacgcg   4560
cagcgtgacc  gctacacttg  ccagcgccct  agcgcccgct  cctttcgctt  tcttcccttc   4620
ctttctcgcc  acgttcgccg  gcttcccccg  tcaagctcta  aatcggggc   tcccttttagg  4680
gttccgattt  agtgctttac  ggcacctcga  ccccaaaaa   cttgattagg  gtgatggttc   4740
acgtagtggg  ccatcgccct  gatagacggt  ttttcgccct  ttgacgttgg  agtccacgtt   4800
ctttaatagt  ggactcttgt  tccaaactgg  aacaacactc  aacccctatct  cggtctattc   4860
ttttgattta  taagggatt   tgccgatttc  ggcctattgg  ttaaaaaatg  agctgattta   4920
acaaaaattt  aacgcgaatt  ttaacaaaat  attaacgttt  acaatttaaa  tatttgctta   4980
tacaatcttc  ctgttttgg   ggcttttctg  attatcaacc  ggggtacata  tgattgacat   5040
gctagtttta  cgattaccgt  tcatcgattc  tcttgtttgc  tccagactct  caggcaatga   5100
cctgatagcc  tttgtagaga  cctctcaaaa  atagctaccc  tctccggcat  gaatttatca   5160
gctagaacgg  ttgaatatca  tattgatggt  gatttgactg  tctccggcct  ttctcacccg   5220
tttgaatctt  tacctacaca  ttactcaggc  attgcattta  aaatatatga  gggttctaaa   5280
aatttttatc  cttgcgttga  aataaaggct  tctcccgcaa  aagtattaca  gggtcataat   5340
gttttggta   caaccgattt  agctttatgc  tctgaggctt  tattgcttaa  tttgctaat   5400
tctttgcctt  gcctgtatga  tttattggat  gttggaatcg  cctgatgcgg  tatttctcc    5460
ttacgcatct  gtgcggtatt  tcacaccgca  tatggtgcac  tctcagtaca  atctgctctg   5520
atgccgcata  gttaagccag  ccccgacacc  cgccaacacc  cgctgacgcg  ccctgacggg   5580
cttgtctgct  cccggcatcc  gcttacagac  aagctgtgac  cgtctccggg  agctgcatgt   5640
gtcagaggtt  ttcaccgtca  tcaccgaaac  gcgcgagacg  aaagggcctc  gtgatacgcc   5700
tatttttata  ggttaatgtc  atgataataa  tggtttctta  gacgtcaggt  ggcacttttc   5760
ggggaaatgt  gcgcggaacc  cctatttgtt  tatttttcta  aatacattca  aatatgtatc   5820
cgctcatgag  acaataaccc  tgataaatgc  ttcaataata  ttgaaaaagg  aagagtatga   5880
gtattcaaca  tttccgtgtc  gcccttattc  ccttttttgc  ggcattttgc  cttcctgttt   5940
ttgctcaccc  agaaacgctg  gtgaaagtaa  aagatgctga  agatcagttg  ggtgcacgag   6000
tgggttacat  cgaactggat  ctcaacagcg  gtaagatcct  tgagagtttt  cgccccgaag   6060
aacgttttcc  aatgatgagc  acttttaaag  ttctgctatg  tggcgcggta  ttatcccgta   6120
ttgacgccgg  gcaagagcaa  ctcggtcgcc  gcatacacta  ttctcagaat  gacttggttg   6180
agtactcacc  agtcacagaa  aagcatctta  cggatggcat  gacagtaaga  gaattatgca   6240
gtgctgccat  aaccatgagt  gataacactg  cggccaactt  acttctgaca  acgatcggag   6300
gaccgaagga  gctaaccgct  ttttttgcaca  acatggggga  tcatgtaact  cgccttgatc   6360
gttgggaacc  ggagctgaat  gaagccatac  caaacgacga  gcgtgacacc  acgatgcctg   6420
tagcaatggc  aacaacgttg  cgcaaactat  taactggcga  actacttact  ctagcttccc   6480
ggcaacaatt  aatagactgg  atggaggcgg  ataaagttgc  aggaccactt  ctgcgctcgg   6540
cccttccggc  tggctggttt  attgctgata  aatctggagc  cggtgagcgt  gggtctcgcg   6600
gtatcattgc  agcactgggg  ccagatggta  agccctcccg  tatcgtagtt  atctacacga   6660
cggggagtca  ggcaactatg  gatgaacgaa  atagacagat  cgctgagata  ggtgcctcac   6720
tgattaagca  ttggtaactg  tcagaccaag  tttactcata  tatactttag  attgatttaa   6780
aacttcatt   ttaatttaaa  aggatctagg  tgaagatcct  ttttgataat  ctcatgacca   6840
```

-continued

```
aaatcccttaacgtgagttttcgttccactgagcgtcagaccccgtagaaaagatcaaag  6900
gatcttcttgagatccttttttttctgcgcgtaatctgctgcttgcaaacaaaaaaccac  6960
cgctaccagcggtggtttgtttgccggatcaagagctaccaactcttttccgaaggtaa  7020
ctggcttcagcagagcgcagataccaaatactgtccttctagtgtagccgtagttaggc  7080
accacttcaagaactctgtagcaccgcctacatcctcgctctgctaatcctgttaccag  7140
tggctgctgccagtggcgataagtcgtgtcttaccgggttggactcaagacgatagttac  7200
cggataaggcgcagcggtcgggctaacgggggttcgtgcacacagcccagcttggagc  7260
gaacgacctacaccgaactgagataccctacagcgtgagctatgagaaagccacgcttc  7320
ccgaagggagaaaggcggacaggtatccggtaagcggcagggtcggaacaggagagcgca  7380
cgagggagcttccaggggggaaacgcctggtatctttatagtcctgtcgggtttcgccacc  7440
tctgacttgagcgtcgatttttgtgatgctcgtcaggggggcggagcctatggaaaaacg  7500
ccagcaacgcggccttttttacggttcctggccttttgctgccttttgctcacatgttct  7560
ttcctgcgttatccctgatctgtggataaccgtattcagccttttgagtgagctgata  7620
ccgctcgccgcagccgaacgaccgagcgcagcgagtcagtgagcgaggaagcggaagagc  7680
gcccaatacgcaaaccgcctctccccgcgcgttggccgatctcattaatg             7729

SEQ ID NO: 41                moltype = DNA    length = 7855
FEATURE                      Location/Qualifiers
source                       1..7855
                             mol_type = other DNA
                             organism = Synthetic construct
SEQUENCE: 41
cagctgcgcgctcgctcgctcactgaggccgcccgggcaaagcccgggcgtcggcgacc     60
tttggtcgccccggcctcagtgagcgagcgagcgcgcagagagggagtggccaactccatc  120
actagggggtccttgtagttaatgattaaccgccatgctacttatctacacgcgtagat   180
ctagaaattgttttcactgcactattgagaaattaagagataatggcaaaagtcacaaag   240
agtatattcaaaaagaagtatagcactttttccttagaaaccactgctaactgaaagaga  300
ctaagattttgtcccgtcaaaaatcctggacctatgcctaaaacacatttcacaatccctg  360
aacttttcaaaaaattggtacatgctttagctttaaactacaggcctcactggagctagag  420
acaagaaggtaaaaaacggctgacaaaagaagtcctggtatcctctatgatgggagaagg  480
aaactagctaaagggaagaataaattagagaaaaactgagaatgactgaatcggaacaagg  540
caaaggctataaaaaaaattagcagtatcctcttgggggccccttccccacactatctca  600
atgcaaatatctgtctgaaacggtccctggctaaactccacccgcggccacggggttggg  660
gttgcgccttttccaaggcagccctgggtttgcgcagggacgcggctgctctgggcgtgg  720
ttccgggaaacgcagccggcgccgacccgtggtctcgcacattcttcacgtccgttccgcag 780
cgtcacccggatcttcgccgctaccccttgtgggccccccgcgcgacgcttcctgctccgcc  840
cctaagtcggaagggttcctgtgcggttcgcggcgtgccggacgtgacaaacggaagccgc  900
acgtctcactagtaccctcgcagacggacagcgccagggagcaatggcagcgcgccgacc   960
gcgatgggctgtggccaatagcgctgctcagcggggcgccgagagcagcggccgggga  1020
aggggcggtgcgggaggcgggtgtgggggcggtagtgtgggccctgttcctgcccgcgcg  1080
gtgttccgcattctgcaagcctccggagcgcacgtcggcagtcggctcctcgttgaccg   1140
aatcaccgactctctccccagcggccgcgccgccaccatggacaaggatgtgaaatga    1200
aacgcaccacactggacagcccttttgggaagctggagctgtcggttgtgagcagggtc   1260
tgcacgaaataaaagctcctggcaaggggacgtctgcagctgatgccgtggaggtcccag  1320
ccccccgctgcggttctcggaggtccggagccctgatgcagtgcacagcctggctgaatg  1380
cctatttccaccagcccgagctatcgaagagttccccgtgccggctcttcaccatccgg  1440
ttttccagcaagagtcgttcaccagacaggtgttatggaatgctgaaggttgtgaaat  1500
tcggagaagtgatttcttacagcaattagcagcctggcaggcaaccccaaagccgcgc   1560
gagcagtggggaggagcaatgagaggcaatcctgtcaaaatcctcatcccctgccacagag  1620
tggtctgcagcagcggagccgtgggcaactactccggaggactggccgtgaaggaatggc  1680
ttctgcccatgaaggccaccggttggggaagcaggctgggagggagctcaggtctgg    1740
caggggcctggctcaagggagcgggagctacctcgggctccccgcctgctggccgaaact  1800
aacctgcaggataatcaacctctggattacaaaatttgtgaaagattgactggtattct  1860
taactatgttgctccttttacgctatgtggatacgctgcttaatgccttgtatcatgc   1920
tattgcttcccgtatggcttcattttctcctccttgtataaatctggttagttcttgc   1980
cacggcggaactcatcgccgcctgccttgccgctgctggacagggctcggctgttggg   2040
cactgacaatccgtggtgtttatttgtgaaatttgtgatgctattgctttatttgtaac  2100
cattctagctttatttgtgaaatttgtgatgctattgctttattgtaaccattataagc  2160
tgcaataaaccaagttaacaacaacaattgcattcatttttgttcaggttcaggggggag  2220
atgtgggaggtttttttaaagcgaattccgagatcgagaccatcctggctaacacagtgaa  2280
accccgtctctactaaaaaaatacaaaaaattagccgggcttggtggcggtgcctgtag  2340
tcccagctactatggaggctgaggcggagaatggcgtgaacgcggggggcggagcttgc  2400
agtgagcagagatcagggcactgcactccagcctgggcgacagagagactctgtctg   2460
caaaaaaaagaaaaaaaaatttagtagcactagctaaaatcagaatagttattga   2520
tgcatatgtaaaagtcttccaatatttacaagtacaatgaaaaaaaataaccttgaatt  2580
aagtgtagaactcattgacaatgtttcaaaggatgtgaggataaaactaaaatttgggca  2640
gtacatgctgttcctgtgtacttggaacagagggagaaaatctgggctggaaatattgtt  2700
ataggagttagcacatgaaggtgacaactaaatttattggagtagatggagtcaccagca  2760
catgtgaatagttttagaatgaaatgacccagtaagtttggagaccccaaattt       2820
aaataaatcagtataagaggaaggaagaaaccaaatggtatactagtcaaattgttt   2880
cttagtgacaaagaataactgaaaatataattagctgcctatatgctctgaatcaa   2940
tttcattcaacatgcaacagttctggaacctatcagggaccacagtcagcagcaagca   3000
catctgcccaagcaagggtggaggcatgcagctgtgggtctgaaaacacttgagg        3060
gagcagataactgggccaaccatgactcagtgcttctggaggccaacaggactgctgagt  3120
catcctgtggggtggaggtggggacaagggaaaggggtgaatggtactgctgattacaac  3180
ctctggtgctgcctccccctcctgttatcgagagagggctagcgtaaatacactgcaaag  3240
gaggatgttttagtagcaatttgtactgataggtatggggccaagagatatatcttgag   3300
ggaggctgagggtttgaagtccaactcctaagccagtcagaagagccaaggacaggt   3360
acggctgtcatcacttagactctcaccctgtggagccacaccctaggggttgccaatctac  3420
```

```
tcccaggagc agggagggca ggagccaggg ctgggcataa aagtcagggc agagccatct    3480
attgcttaca ctcgcttctg gaacgtctga ggttatcaat aagctcctag tccagacgcc    3540
atgggtcatt tcacagagga ggacaaggct actatcacaa gcctgtgggg caaggtgaat    3600
gtggaagatg ctggaggaga aaccctggga aggtaggctc tggtgaccag gacaagggag    3660
ggaaggaagg accctgtgcc tggcaaaagt ccaggtcgct tctcaggatt tgtggcacct    3720
tctgactgtc aaactgttct tgtcaatctc acaggctcct ggttgtctac ccatggaccc    3780
agaggttctt tgacagcttt ggcaacctgt cctctgcctc tgccatcatg ggcaacccca    3840
aagtcaaggc acatggcaag aaggtgctga cttccttggg agatgccaca aagcacctgg    3900
atgatctcaa gggcaccttt gcccagctga gtgaactgca ctgtgacaag ctgcatgtgg    3960
atcctgagaa cttcaaggtg agtccaggag atgtttcagc cctgttgcct ttagtctcga    4020
ggcaacttag acaacggagt attgatctga gcacagcagg gtgtgagctg tttgaagata    4080
ctggggtctc gaggtcgacg tagataagta gcatggcggg ttaatcatta actacaagga    4140
accccctagtg atggagttgg ccactccctc tctgcgcgct cgctcgctca ctgaggccgg    4200
gcgaccaaag gtcgcccgac gcccgggctt gcccgggcgg cctcagtga gcgagcgagc    4260
gcgcagctg gcgtaatagc gaagaggccc gcaccgatcg cccttcccaa cagttgcgca    4320
gcctgaatgc gcaatggcga ttccgttgca atggctggcg gtaatattgt tctggatatt    4380
accagcaagg ccgatagttt gagttcttct actcaggcag tgatgttat tactaatcaa    4440
agaagtattg cgacaacggt taatttgcgt gatggacaga ctcttttact cggtggcctc    4500
actgattata aaaacacttc tcaggattct ggcgtaccgt tcctgtctaa aatcccttta    4560
atcggcctcc tgtttagctc ccggtctgat tctaacgagg aaagcacgtt atacgtgctc    4620
gtcaaagcaa ccatagtacg cgccctgtag cggcgcatta agcgcggcgg gtgtggtggt    4680
tacgcgcagc gtgaccgcta cacttgccag cgccctagcg cccgctcctt tcgctttctt    4740
cccttcctt ctcgccacgt tcgccggctt tccccgtcaa gctctaaatc ggggggctccc    4800
tttagggttc cgatttagtg ctttacggca cctcgacccc aaaaaacttg attagggtga    4860
tggttcacgt agtgggccat cgccctgata dacggttttt cgccctttga cgttggagtc    4920
cacgttcttt aatagtggac tcttgttcca aactggaaca acactcaacc ctatctcgg    4980
ctattctttt gatttataag ggattttgcc gatttcggcc tattggttaa aaaatgagct    5040
gatttaacaa aaatttaacg cgaattttaa caaaatatta acgtttacaa tttaaatatt    5100
tgcttataca atcttcctgt ttttgggggct tttctgatta tcaaccgggg tacatatgat    5160
tgacatgcta gttttacgat taccgttcat cgattctctt gtttgctcca gactctcagg    5220
caatgacctg atagcctttg tagagacctc tcaaaaatag ctaccctctc cggcatgaat    5280
ttatcagcta gaacggttga atatcatatt gatggtgatt tgactgtctc cggcctttct    5340
cacccgtttg aatcttacc tacacattac tcaggcattg catttaaaat atatgagggt    5400
tctaaaaatt tttatccttg cgttgaaata aaggcttcct ccgcaaaagt attacaggggt    5460
cataatgttt ttggtacaac cgatttagct ttatgctctg aggctttatt gcttaatttt    5520
gctaattctt tgccttgcct gtatgattta ttggatgttg gaatcgcctg atgcggtatt    5580
ttctccttac gcatctgtgc ggtatttcac accgcatatg gtgcactctc agtacaatct    5640
gctctgatgc cgcatagtta agccagcccc gacacccgcc aacaccgct gacgcgccct    5700
gacgggcttg tctgctcccg gcatccgctt acagacaagc tgtgaccgtc tccgggagct    5760
gcatgtgtca gaggttttca ccgtcatcac cgaaacgcgc gagacgaaag gcctcgtga    5820
tacgcctatt tttataggtt aatgtcatga taataatggt ttcttagacg tcaggtggca    5880
cttttcgggg aaatgtgcgc ggaacccta tttgtttatt tttctaaata cattcaaata    5940
tgtatccgct catgagacaa taaccctgat aaatgcttca ataatattga aaaaggaaga    6000
gtatgagtat tcaacatttc cgtgtcgccc ttattccctt ttttgcggca ttttgccttc    6060
ctgtttttgc tcacccagaa acgctggtga agtaaaaga tgctgaagat cagttgggtg    6120
cacgagtggg ttacatcgaa ctggatctca acagcggtaa gatccttgag agttttcgcc    6180
ccgaagaacg ttttccaatg atgagcactt taaagttctc gctatgtggcg gcggtattat    6240
cccgtattga cgccgggcaa gagcaactcg gtcgccgcat acactattct cagaatgact    6300
tggttgagta ctcaccagtc acagaaaagc atcttacgga tggcatgaca gtaagagaat    6360
tatgcagtgc tgccataacc atgagtgata acactgcggc caacttactt ctgacaacga    6420
tcggaggacc gaaggagcta accgcttttt tgcacaacat ggggatcat gtaactcgcc    6480
ttgatcgttg ggaaccggag ctgaatgaag ccataccaaa cgacgagcgt gacaccacga    6540
tgcctgtagc aatggcaaca acgttgcgca aactattaac tggcgaacta cttactctag    6600
cttcccggca acaattaata gactggatgg aggcggataa agttgcagga ccacttctgc    6660
gctcggccct tccggctggc tggttttatt ctgataaatc tggagccggt gagcgtgggt    6720
ctcgcggtat cattgcagca ctggggccag atggtaagcc ctcccgtatc gtagttatct    6780
acacgacggg gagtcaggca actatggatg aacgaaatag acagatcgct gagataggtg    6840
cctcactgat taagcattgg taactgtcag accaagttta ctcatatata ctttagattg    6900
atttaaaact tcatttttaa tttaaaagga tctaggtgaa gatccttttt gataatctca    6960
tgaccaaaat cccttaacgt gagttttcgt tccactgagc gtcagacccc gtagaaaaga    7020
tcaaaggatc ttcttgagat cctttttttc tgcgcgtaat ctgctgcttg caaacaaaaa    7080
aaccaccgct accagcggtg gtttgtttgc cggatcaaga gctaccaact ctttttccga    7140
aggtaactgg cttcagcaga gcgcagatac caaatactgt ccttctagtg tagccgtagt    7200
taggccacca cttcaagaac tctgtagcac cgcctacata cctcgctctg ctaatcctgt    7260
taccagtggc tgctgccagt ggcgataagt cgtgtcttac cgggttggac tcaagacgat    7320
agttaccgga taaggcgcag cggtcgggct gaacggggg ttcgtgcaca gcccagct    7380
tggagcgaac gacctacacc gaactgagat acctacagcg tgagctatga gaaagcgcca    7440
cgcttcccga agggagaaag gcggacaggt atccggtaag cggcagggtc ggaacaggag    7500
agcgcacgag ggagcttcca gggggaaacg cctggtatct ttatagtcct gtcgggtttc    7560
gccacctctg acttgagcgt cgatttttgt gatgctcgtc aggggggcgg agcctatgga    7620
aaaacgccag caacgcggcc tttttacggt tcctggcctt ttgctggcct tttgctcaca    7680
tgttctttcc tgcgttatcc cctgattctg tggataaccg tattaccgcc tttgagtgag    7740
ctgataccgc tcgccgcagc cgaacgaccg agcgcagcga gtcagtgagc gaggaagcgg    7800
aagagcgccc aatacgcaaa ccgcctctcc ccgcgcgttg gccgattcat taatg         7855
```

| SEQ ID NO: 42 | moltype = DNA length = 8024 |
|---|---|
| FEATURE | Location/Qualifiers |
| source | 1..8024 |
| | mol_type = other DNA | organism = Synthetic construct
SEQUENCE: 42

```
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt ccttgtagtt aatgattaac ccgccatgct acttatctac acgcgtagat  180
cttgaaacag tcatgattta tttcaaatag gtacggataa gtagatattg aggtaagcat  240
taggtcttat attatgtaac actaatctat tactgcgctg aaactgtggc tttatagaaa  300
ttgttttcac tgcactattg agaaattaag agataatggc aaaagtcaca aagagtatat  360
tcaaaaagaa gtatagcact ttttccttag aaaccactgc taactgaaag agactaagat  420
ttgtcccgtc aaaaatcctg gacctatgcc taaaacacat ttcacaatcc ctgaactttt  480
caaaaattgg tacatgcttt agctttaaac tacaggcctc actgagcta  gagacaagaa  540
ggtaaaaaac ggctgacaaa agaagtcctg gtatcctcta tgatgggaga aggaaactag  600
ctaaagggaa gaataaatta gagaaaaact ggaatgactg aatcggaaca aggcaaaggc  660
tataaaaaaa attagcagta tcctcttggg ggccccttcc ccacactatc tcaatgcaaa  720
tatctgtctg aaacggtccc tggctaaact ccacccatgg gttggccagc cttgccttga  780
caaggcaaac ttgaccaata gtcttagagt atccagtgag gccagggggcc ggcggctggc  840
tagggatgaa gaataaaagg aagcacccct cagcagttcc acacactcgc ttctggaacg  900
tctgaggtta tcaataagct cctagtccaa acgccatggt gcacctgact cctgaggaga  960
agtctgccgt tactgccctg tggggcaagg tgaacggtgga tgaagttggt ggtgaggccc 1020
tgggcaggtt ggtatcaagg ttacaagaca ggtttaagga gaccaataga aactgggcat 1080
gtggagacag agaagactct tgggtttctg ataggcactg actctctctg cctattggtc 1140
tattttccca cccttaggct gctggtggtc taccccttgga ccagaggtt ctttgagtcc 1200
tttggggatc tgtccactcc tgatgctgtt atgggcaacc ctaaggtgaa ggctcatggc 1260
aagaaagtgc tcggtgcctt tagtgatggc ctggctcacc tggacaacct caagggcacc 1320
tttgcccagc tgagtgagct gcactgtgac aagctgcacg tggatcctga aacttcagg  1380
gtgagtctat gggacccttg atgttttctt tccccttctt ttctatggtt aagttcatgt 1440
cataggaagg ggagaagtaa cagggtacac atattgacca aatcagggta attttgcatt 1500
tgtaatttta aaaaatgctt tcttctttta atatactttt ttgtttatct tatttctaat 1560
actttcccta atctctttct ttcagggcaa taatgataca atgtatcatg cctctttgca 1620
ccattctaaa gaataacagt gataatttct gggttaaggc aatagcaata tttctgcata 1680
taaatatttc tgcatataaa ttgtaactga tgtaagaggt ttcatattgc taatagcagc 1740
tacaatccag ctaccattct gcttttattt tatggttggg ataaggctgg attattctga 1800
gtccaagcta ggcccttttg ctaatcatgt tcatacctct tatcttcctc ccacagctcc 1860
tgggcaacgt gctggtctgt gtgctggctc atcactttgg caaagaattc acccaccag 1920
tgcaggctgc ctatcagaaa gtggtggctg gtgtggctaa tgccctggcc cacaagtatc 1980
actaagctcg ctttcttgct gtccaatttc tattaaaggt tcctttgttc cctaagtcca 2040
actactaaac tgggggatat tatgaagggc cttgagcatc tggattctgc ctaataaaaa 2100
acatttattt tcattgcaat gatgtattta aattatttct gaatattttta ctaaaaaggg 2160
aatgtgggag gttgcagtgc tagtctcccg gaactatcac tctttcacag tctgctttgg 2220
aaggactggg cttagtatga aaagttagga ctgagaagaa tttgaaaggg gcttttttgt 2280
agcttgatat tcactactgt cttattaccc tatcataggc caccccaaa tggaagtccc 2340
attcttcctc aggatgttta agattagcat tcaggaagag atcagaggtc tgctggctcc 2400
cttatcatgt ccccttatggt gcttctggct ctgcaccgcg gcacggggt tggggttgcg 2460
ccttttccaa ggcagccctg ggtttgcgca gggacgcgcg tgctctgggc gtggttccgg 2520
gaaacgcagc ggcgccgacc ctgggtctcg cacattcttc acgtccgttc gcagcgtcac 2580
ccggatcttc gccgctaccc ttgtgggccc cccgcgacg cttcctgctc cgcccctaag 2640
tcgggaaggt tccttgcggt tcgcggcgtg ccggacgtga caaacggaag ccgcacgtct 2700
cactagtacc ctcgcagacg gacagcgcca gggagcaatg gcagcgcgcc gaccgcgatg 2760
ggctgtggcc aatagcggct gctcagcggg gcgcgccgag agcagcggcc gggaagggggc 2820
ggtgcgggag gcgggggtgtg gggcggtagt gtgggccctg ttcctgcccg cgcggtgttc 2880
cgcattctgc aagcctccgg agcgcacgtc ggcagtcgc tccctcgttg accgaatcac 2940
cgacctctct ccccagcggc cgcgccgcca ccatgacaa ggattgtgaa atgaaacgaa 3000
ccacactgga cagccctttg gggaagctgg agctgtctgg ttgtgagcag ggtctgcacg 3060
aaaataaagct cctgggcaag gggacgtctg cagctgatgc cgtggaggtc ccagcccccg 3120
ctgcggttct cggaggtccg gagccctga tgcagtgcac agcctggctg aatgcctatt 3180
tccaccagcc cgaggctatc gaagagttcc ccgtgccggc tcttcaccat cccgttttcc 3240
agcaagagtc gttcaccaga caggtgttat ggaagctgct gaaggttgtg aaattcggag 3300
aagtgatttc ttaccagcaa ttagcagccc tggcaggcaa cccaaagcc gcgcgagcag 3360
tgggaggagc aatgagaggc aatcctgtca aaatcctcat cccgtgccaa cagatggtct 3420
gcagcagcga agccgtgggc aactactccg gaggactgcc cgtgaaggaa tggctttctgg 3480
cccatgaagg ccaccggttg gggaagcagg cttgggagg gagctcaggt ctggcagggg 3540
cctggctcaa gggagcggga gctacctcgg gctcccgcc tgctggccga aacgagggca 3600
gaggaagtct tctaacatgc ggtgacgtgg aggagaatcc gggcccccct gcaggaactt 3660
caaggtgagt ccaggagatg tttcagctcct gttgccttta gtctcgagge aacttagaca 3720
acggagtatt gatctgagca cagcagggt tgagctgttt gaagatactg gggttggggg 3780
tgaagaaact gcagaggact aactgggctg agacccagtg gtaatgtttt agggcctaag 3840
gagtgcctct aaaaatctag atggacaatt tgacttttga gaaagagag gtgaaatgaa 3900
ggaaaatgac ttttctttat tagattccag tagaaagaac tttcatcttt ccctcattt  3960
tgttgtttta aaacatctat ctggaggcag gacaagtatg tcgttaaaa agatgcaggc 4020
agaaggcata tattgctca gtcaaagtgg ggaactttgg tggccaaaca tacattgcta 4080
aggctattcc tatatcagct ggacacatat aaaatgctgc taatgcttca ttacaaactt 4140
atatccttta attccagatg ggggcaaagt atgtccaggg gtgaggaaca attgaaacat 4200
ttgggctgga gtagattttg aaagtcagct ctgtgtgtgt gtgtgtgtgt gcgcgcgcgc 4260
gtgtcgagt agataagtag catgcgggt taatcattaa ctacaaggaa ccctctagtga 4320
tggagttggc cactccctct ctgcgcgctc gctcgctcac tgaggccggg cgaccaaagg 4380
tcgcccgacg cccgggcttt gcccgggcgg cctcagtgag cgagcgagcg cgcagctgg  4440
cgtaatagcg aagaggcccg caccgatcgc ccttcccaac agttgcgcag cctgaatggc 4500
gaatggcgat tccgttgcaa tggctggcgg taatattgtt ctggatatta ccagcaaggc 4560
cgatagtttg agttcttcta ctcaggcaag tgatgttatt actaatcaaa gaagtattgc 4620
```

```
gacaacggtt aatttgcgtg atggacagac tcttttactc ggtggcctca ctgattataa    4680
aaacacttct caggattctg gcgtaccgtt cctgtctaaa atcccttaa tcggcctcct     4740
gtttagctcc cgctctgatt ctaacgagga agcacgtta tacgtgctcg tcaaagcaac     4800
catagtacgc gccctgtagc ggcgcattaa gcgcggcggg tgtggtggtt acgcgcagcg    4860
tgaccgctac acttgccagc gccctagcgc ccgctcctt cgctttcttc ccttcctttc     4920
tcgccacgtt cgccggcttt ccccgtcaag ctctaaatcg ggggctccct ttagggttcc    4980
gatttagtgc tttacggcac ctcgacccca aaaaacttga ttagggtgat ggttcacgta    5040
gtgggccatc gccctgatag acggttttc gcccttgac gttggagtcc acgttctta     5100
atagtggact cttgttccaa actggaacaa cactcaaccc tatctcggtc tattcttta    5160
atttataagg gattttgccg atttcggcct attggttaaa aaatgagctg atttaacaaa   5220
aatttaacgc gaattttaac aaaattattaa cgtttacaat ttaaatattt gcttatacaa  5280
tcttcctgtt tttggggctt ttctgattat caaccgggt acatatgatt gacatgctag    5340
tttacgatt accgttcatc gattctcttg tttgctccag actctcaggc aatgacctga    5400
tagccttgt agagacctct caaaaatagc taccctctcg gcgatgaatt tatcagctag    5460
aacggttgaa tatcatattg atggtgattt gactgtctcc ggcctttctc acccgtttga   5520
atctttacct acacattact caggcattgc atttaaaaata tatgagggtt ctaaaaattt   5580
ttatccttgc gttgaaataa aggcttctcc cgcaaaagta ttacagggtc ataatgtttt   5640
tggtacaacc gattagctt tatgctctga ggctttattg cttaattttg ctaattcttt    5700
gccttgcctg tatgatttat tggatgttgg aatcgcctga tgcggtattt tctccttacg   5760
catctgtgcg gtatttcaca ccgcatatgg tgcactctca gtacaatctg ctctgatgcc   5820
gcatagttaa gccagcccg acaccgcca caccccgctg acgcgccctg acgggcttgt     5880
ctgctcccgg catccgctta cagacaagct gtgaccgtct cagggagctg catgtgtcag   5940
aggttttcac cgtcatcacc gaaacgcgcg acgaaagg gcctcgtgat acgcctattt     6000
ttataggtta atgtcatgat aataatggtt tcttagacgt caggtggcac ttttcgggga   6060
aatgtgcgcg gaaccctat ttgtttattt ttctaaatac attcaaatat gtatccgctc    6120
atgagacaat aaccctgata aatgcttcaa taatattgaa aaaggaagag tatgagtatt   6180
caacatttcc gtgtcgccct tattccttt tttgcggcat tttgccttcc tgttttgct    6240
cacccagaaa cgctggtgaa agtaaaagat gctgaagatc agttgggtgc acgagtgggt   6300
tacatcgaac tggatctcaa cagcggtaag atccttgaga gttttcgccc cgaagaacgt   6360
tttccaatga tgagcactt taaagttctg ctatgtggcg cggtattatc ccgtattgac   6420
gccgggcaag agcaactcgg tcgccgcata cactattctc agaatgactt ggttgagtac   6480
tcaccagtca cagaaaagca tcttacggat ggcatgacag taagagaatt atgcagtgct   6540
gccataacca tgagtgataa cactgcggcc aacttactc tgacaacgat cggaggaccg   6600
aaggagctaa ccgctttttt gcacaacatg ggggatcatg taactcgcct tgatcgttgg   6660
gaaccggagc tgaatgaagc cataccaaac gacgagcgtg acaccacgat gcctgtagca   6720
atggcaacaa cgttgcgcaa actattaact ggcgaactac ttactctagc ttcccggcaa   6780
caattaatag actggatgga ggcggataaa gttgcaggac cacttctgcg ctcggccctt   6840
ccggctggct ggtttattgc tgataaatct ggagccggtg agcgtgggtc tcgcggtatc   6900
attgcagcac tggggccaga tggtaagcc tcccgtacta tagttatcta cacgacgggg    6960
agtcaggcaa ctatggatga acgaaataga cagatcgctg agataggtgc ctcactgatt   7020
aagcattggt aactgtcaga ccaagtttac tcatatatac tttagattga tttaaaactt   7080
cattttaat ttaaaggat ctaggtgaag atccttttg ataatctcat gaccaaaatc      7140
ccttaacgtg agttttcgtt ccactgagcg tcagaccccg tagaaaagat caaaggatct   7200
tcttgagatc cttttttct gcgcgtaatc tgctgcttgc aaacaaaaaa accaccgcta    7260
ccagcggtgg tttgtttgcc ggatcaagag ctaccaactc tttttccgaa ggtaactggc   7320
ttcagcagag cgcagatacc aaatactgtc cttctagtgt agccgtagtt aggccaccac   7380
ttcaagaact ctgtagcacc gcctacatac ctcgctctgc taatcctgtt accagtggct   7440
gctgccagtg gcgataagtc gtgtcttacc gggttggact caagacgata gttaccggat   7500
aaggcgcagc ggtcgggctg aacggggggt tcgtgcacac agcccagctt ggagcgaacg   7560
acctacaccg aactgagata cctacagcgt gagctatgag aaagcgccac gcttcccgaa   7620
gggagaaagg cggacaggta tccggtaagc ggcagggtcg gaacaggaga gcgcacgagg   7680
gagcttccag ggggaaacgc ctggtatctt tatagtcctg tcgggtttcg ccacctctga   7740
cttgagcgtc gatttttgtg atgctcgtca gggggcgga gcctatgaa aaacgccagc     7800
aacgcggcct ttttacggtt cctggccttt tgctggcctt ttgctcacat gttctttcct   7860
gcgttatccc ctgattctgt ggataaccgt attaccgcct ttgagtgagc tgataccgct   7920
cgccgcagcc gaacgaccga gcgcagcgag tcagtgagcg aggaagcgga agagcgccca   7980
atacgcaaac cgcctctccc cgcgcgttgg ccgattcatt aatg                    8024

SEQ ID NO: 43              moltype = DNA   length = 7953
FEATURE                    Location/Qualifiers
source                     1..7953
                           mol_type = other DNA
                           organism = Synthetic construct
SEQUENCE: 43
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actagggggt ccttgtagtt aatgattaac ccgccatgct acttatctac acgcgtagat    180
cttgaaacag tcatgattta tttcaaatag gtacggataa gtagatattg aggtaagcat    240
taggtcttat attatgtaac actaatctat tactgcgctg aaactgtggc tttataagaa    300
ttgttttcac tgcactattg agaaattaag agataatggc aaaagtcaca aagagtatat    360
tcaaaaagaa gtatagcact ttttccttag aaaccactgc taactgaaag agactaagat    420
ttgtcccgtc aaaaatcctg gacctatgcc taaaacacat tcacaatcc ctgaacttt      480
caaaaattgg tacatgcttt agctttaaac tacaggcctc actggagcta gagacaagaa   540
ggtaaaaaac ggctgacaaa agaagtcctg gtatcctcta tgatgggaga aggaaactag   600
ctaaagggaa gaataaatta gagaaaaact ggaatgactg aatcgggaca aggcaaaggc   660
tataaaaaaa attagcagta tcctcttggg ggcccttcc ccacactatc tcaatgcaaa    720
tatctgtctg aaacggtccc tggctaaact ccacccatgg gttggccagc cttgccttga   780
caaggcaaac ttgaccaata gtcttagagt atccagtgag gccaggggcc ggcggctggc   840
tagggatgaa gaataaaagg aagcacccctt cagcagttcc acacactcgc ttctggaacg   900
```

```
tctgaggtta tcaataagct cctagtccag acgccatggt gcacctgact cctgaggaga    960
agtctgccgt tactgccctg tggggcaagg tgaacgtgga tgaagttggt ggtgaggccc   1020
tgggcaggtt ggtatcaagg ttacaagaca ggtttaagga gaccaataga aactgggcat   1080
gtggagacag agaagactct tgggtttctg ataggcactg actctctctg cctattggtc   1140
tattttccca cccttaggct gctggtggtc taccsttgga cccagaggtt cttt gagtcc   1200
tttggggatc tgtccactcc tgatgctgtt atgggcaacc ctaaggtgaa ggctcatggc   1260
aagaaagtgc tcggtgcctt tagtgatggc ctggctcacc tggacaacct caagggcacc   1320
tttgcccagc tgagtgagct gcactgtgac aagctgcacg tggatcctga aacttcagg    1380
gtgagtctat gggacccttg atgttttctt tccccttctt ttctatggtt aagttcatgt   1440
cataggaagg ggagaagtaa cagggtacac atattgacca aatcagggta attttgcatt   1500
tgtaatttta aaaaatgctt tcttcttttta atatactttt ttgtttatct tatttctaat   1560
actttcccta atctctttct ttcagggcaa taatgataca atgtatcatg cctctttgca   1620
ccattctaaa gaataacagt gataaattct gggttaaggc aatagcaata tttctgcata   1680
taaatatttc tgcatataaa ttgtaactga tgtaagaggt ttcatattgc taatagcagc   1740
tacaatccag ctaccattct gcttttattt tatggttggg ataaggctgg attattctga   1800
gtccaagcta ggccctttg ctaatcatgt tcatacctct tatcttcctc ccacagctcc   1860
tgggcaacgt gctggtctgt gtgctggccc atcactttgg caaagaattc accccaccag   1920
tgcaggctgc ctatcagaaa gtggtggctg gtgtggctaa tgccctggcc cacaagtatc   1980
actaagctcg ctttcttgct gtccaatttc tattaaaggt tccttttgtc cctaagtcca   2040
actactaaac tgggggatat tatgaagggg cttgagcatc tggattctgc ctaataaaaa   2100
acatttattt tcattgcaat gatgtattta aattatttct gaatatttta ctaaaagggg   2160
aatgtgggag gttgcagtgc tagtctcccg gaactatcac tctttcacag tctgcttttgg  2220
aaggactggg cttagtatga aaagttagga ctgagaagaa tttgaaaggg ggcttttttgt  2280
agcttgatat tcactactgt cttattaccc tatcataggc caccccaaa tggaagtccc    2340
attcttcctc aggatgtta agattagcat tcaggaagag atcagaggtc tgctggctcc   2400
cttatcatgt cccttatggt gcttctggct ctgcaccgcg ggaacagaga aacaggagaa   2460
tatgggccaa acaggatatc tgtggtaagc agttcctgcc ccggctcagg gccaagaaca   2520
gttggaacag cagaatatgg gccaaacagg atatctgtgg taagcagttc ctgcccccggc  2580
tcagggccaa gaacagatgg tccccagatg cggtcccgcc ctcagcagtt tctagagaac   2640
catcagatgt ttccagggtg ccccaaggac ctgaaatgac cctgtgcctt atttgaacta    2700
accaatcagt tcgcttctcg cttctgttcg cgcgcttctg ctcccccgagc tctatataag    2760
cagagctcgt ttagtgaacc gtcagatcgc ggccgcgccg ccaccatggt gagcaagggc    2820
gaggagctgt tcaccggggt ggtgcccatc ctggtcgagc tggacggcga cgtaaacggc    2880
cacaagttca gcgtgtccgg cgagggcgag ggcgatgcca cctacggcaa gctgaccctg    2940
aagttcatct gcaccaccgg caagctgccc gtgccctggc ccaccctcgt gaccaccctg    3000
acctacggcg tgcagtgctt cagccgctac cccgaccaca tgaagcagca cgacttcttc    3060
aagtccgcca tgcccgaagg ctacgtccag gagcgcacca tcttcttcaa ggacgacggc    3120
aactacaaga cccgcgccga ggtgaagttc gagggcgaca ccctggtgaa ccgcatcgag    3180
ctgaagggca tcgacttcaa ggaggacggc aacatcctgg ggcacaagct ggagtacaac    3240
tacaacagcc acaacgtcta tatcatggcc gacaagcaga agaacggcat caaggtgaac    3300
ttcaagatcc gccacaacat cgaggacggc agcgtgcagc tcgccgacca ctaccagcag    3360
aacaccccca tcggcgacgg ccccgtgctg ctgcccgaca ccactacct gagcacccag    3420
tccgccctga gcaaagaccc caacgagaag cgcgatcaca tggtcctgct ggagttcgtg    3480
accgccgccg ggatcactct cggcatggac gagctgtaca agggagcag aggaagtctt    3540
ctaacatgcg gtgacgtgga ggagaatccg ggccccctg caggaacttc aaggtgagtc    3600
caggagatgt ttcagcctg ttgcctttag tctcgaggca acttagacaa cggagtattg    3660
atctgagcac agcaggqtgt gagctgtttg aagatactgg ggttggggt gaagaaactg    3720
cagaggacta actgggctga gacccagtgg taatgttta gggcctaagg agtgcctcta    3780
aaaatctaga tggacaattt tgactttgag aaaagagagg tggaaatgag gaaaatgact    3840
tttctttatt agattccagt agaaagaact ttcatctttc cctcatttt gttgttttaa    3900
aacatctatc tggaggcagg acaagtatgg tcgttaaaaa gatgcaggca gaagcatat    3960
attggctcag tcaaagtggg gaactttggt ggccaaacat acattgctaa ggctattcct    4020
atatcagctg gacacatata aaatgctgct aatgcttcat tacaaactta tatcctttaa    4080
ttccagatgt gggcaaagta tgtccagggg tgaggaacaa ttgaaacatt tgggctggag    4140
tagattttga aagtcagctc tgtgtgtgtg tgtgtgtgtg cgcgcgcgcg tgtcgacgta    4200
gataagtagc atggcgggtt aatcattaac tacaaggaac ccctagtgat ggagttggcc    4260
actccctctc tgcgcgctcg ctcgctcact gaggccgggc gaccaaaggt cgcccgacgc    4320
ccgggctttg cccgggcggc ctcagtgagc gagcgagcgc gccagctggc gtaatagcga    4380
agaggcccgc accgatcgcc cttcccaaca gttgcgcagc ctgaatggcg aatgcgatt    4440
ccgttgcaat ggctggcggt aatattgttc tggatattac cagcaaggcc gatagtttga    4500
gttcttctac tcaggcaagt gatgttatta ctaatcaaag aagtattgcg acaacggtta    4560
atttgcgtga tggacagact cttttactcg gtggcctcac tgattataaa aacacttctc    4620
aggattctgg cgtaccgttc ctgtctaaaa tcccttaat cggcctcctg tttagctccc    4680
gctctgattc taacgaggaa aagcacgtat acgtgctgga atagtacgcg    4740
ccctgtagcg gcgcattaag cgcggcgggt gtggtggtta cgcgcagcgt gaccgctaca    4800
cttgccagcg ccctagcgcc cgctcctttc gctttcttcc cttcctttct cgccacgttc    4860
gccggctttc cccgtcaagc tctaaatcgg ggctccctt tagggttccg atttagtgct    4920
ttacggcacc tcgaccccaa aaaacttgat tagggtgatg gttcacgtag tgggccatcg    4980
ccctgatagg cggttttcg cccttgacg ttggagtcca cgttctttaa tagtgactc     5040
ttgttccaaa ctggaacaac actcaaccct atctcggtct attcttttga tttataaggg    5100
atttgccgat ttcggccta ttggttaaaa atgagctga tttaacaaaa atttaacgcg     5160
aattttaaca aaatattaac gtttacaatt taaatatttg cttatacaat cttcctgttt    5220
ttggggcttt tctgattatc aaccgggggta catatgattg acatgctagt tttacgatta    5280
ccgttcatcg attctcttgt ttgctccaga ctctcaggca atgacctgat agcctttgta    5340
gagacctctc aaaaatagct accctctccg gcatgaattt atcactaga acggttgaat    5400
atcatattga tggtgatttg actgtctccg gcctttctca cccgtttgaa tctttaccta    5460
cacattactc aggcattgca tttaaaaatat atgagggttc taaaaatttt tatccttgcg    5520
ttgaaataaa ggcttctccc gcaaaagtat tacagggtca taatgttttt ggtacaaccg    5580
atttagcttt atgctctgag gctttattgc ttaatttttc taattcttg ccttgcctgt     5640
```

```
atgattatt ggatgttgga atcgcctgat gcggtatttt ctccttacgc atctgtgcgg    5700
tatttcacac cgcatatggt gcactctcag tacaatctgc tctgatgccg catagttaag    5760
ccagccccga cacccgccaa cacccgctga cgcgccctga cgggcttgtc tgctcccggc    5820
atccgcttac agacaagctg tgaccgtctc cgggagctgc atgtgtcaga ggttttcacc    5880
gtcatcaccg aaacgcgcga gacgaaaggg cctcgtgata cgcctatttt tataggttaa    5940
tgtcatgata ataatggttt cttagacgtc aggtggcact tttcggggaa atgtgcgcgg    6000
aaccccctatt tgtttatttt tctaaataca ttcaaatatg tatccgctca tgagacaata    6060
accctgataa atgcttcaat aatattgaaa aggaagagt atgagtattc aacatttccg      6120
tgtcgccctt attccctttt ttgcggcatt ttgccttcct gttttgctc acccagaaac      6180
gctggtgaaa gtaaaagatg ctgaagatca gttgggtgca cgagtgggtt acatcgaact    6240
ggatctcaac agcggtaaga tccttgagag ttttcgcccc gaagaacgtt ttccaatgat    6300
gagcactttt aaagttctgc tatgtggcgc ggtattatcc cgtattgacg ccgggcaaga    6360
gcaactcggt cgccgcatac actattctca gaatgacttg gttgagtact caccagtcac    6420
agaaaagcat cttacggatg gcatgacagt aagagaatta tgcagtgctg ccataaccat    6480
gagtgataac actgcggcca acttacttct gacaacgatc ggaggaccga aggagctaac    6540
cgcttttttg cacaacatgg gggatcatgt aactcgcctt gatcgttggg aaccggagct    6600
gaatgaagcc ataccaaacg acgagcgtga caccacgatg cctgtagcaa tggcaacaac    6660
gttgcgcaaa ctattaactg gcgaactact tactctagct tcccggcaac aattaataga    6720
ctggatggag gcggataaag ttgcaggacc acttctgcgc tcggcccttc cggctggctg    6780
gtttattgct gataaatctg gagccggtga gcgtgggtct cgcggtatca ttgcagcact    6840
ggggccagat ggtaagccct cccgtatcgt agttatctac acgacgggga gtcaggcaac    6900
tatggatgaa cgaaatagac agatcgctga gataggtgcc tcactgatta agcattggta    6960
actgtcagac caagtttact catatatact ttagattgat ttaaaacttc atttttaatt    7020
taaaaggatc taggtgaaga tcctttttga taatctcatg accaaaatcc cttaacgtga    7080
gttttcgttc cactgagcgt cagacccccgt agaaaagatc aaaggatctt cttgagatcc    7140
ttttttctg cgcgtaaatct gctgcttgca aacaaaaaaa ccaccgctac cagcggtcc     7200
ttgtttgccg gatcaagagc taccaactct ttttccgaag gtaactggct tcagcagagc    7260
gcagatacca aatactgtcc ttctagtgta gccgtagtta ggccaccact tcaagaactc    7320
tgtagcaccg cctacatacc tcgctctgct aatcctgtta ccagtggctg ctgccagtgg    7380
cgataagtcg tgtcttaccg ggttggactc aagacgatag ttaccggata aggcgcagcg    7440
gtcgggctga acggggggtt cgtgcacaca gcccagcttg gagcgaacga cctacaccga    7500
actgagatac ctacagcgtg agctatgaga aagcgccacg cttcccgaag ggagaaaggc    7560
ggacaggtat ccggtaagcg gcagggtcgg aacaggagag cgcacgaggg agcttccagg    7620
gggaaacgcc tggtatcttt atagtcctgt cgggtttcgc cacctctgac ttgagcgtcg    7680
atttttgtga tgctcgtcag ggggggcgga gcctatggaaa aacgccagca acgcggcctt    7740
tttacggttc ctggcctttt gctggccttt tgctcacatg ttctttcctg cgttatcccc    7800
tgattctgtg gataaccgta ttaccgcctt tgagtgagct gataccgctc gccgcagccg    7860
aacgaccgag cgcagcgagt cagtgagcga ggaagcggaa gagcgcccaa tacgcaaacc    7920
gcctctcccc gcgcgttggc cgattcatta atg                                7953
```

SEQ ID NO: 44          moltype = DNA   length = 7553
FEATURE                Location/Qualifiers
source                 1..7553
                       mol_type = other DNA
                       organism = Synthetic construct
SEQUENCE: 44

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtagat    180
cttccttaga aaccactgct aactgaaaga gactaagatt tgtcccgtca aaaatcctgg    240
acctatgcct aaaacacatt tcacaatccc tgaactttc aaaaattggt acatgcttta     300
gctttaaact acaggcctca ctggagctag agacaagaag gtaaaaaacg gctgacaaaa    360
gaagtcctgg tatcctctat gatgggagaa ggaaactagc taaagggaag aataaattag    420
agaaaaactg gaatgactga atcggaacaa ggcaaaggct ataaaaaaaa ttagcagtat    480
cctcttgggg gccccttccc cacactatct caatgcaaat atctgtctga aacggtccct    540
ggctaaactc cacccatggg ttggccagcc ttgccttgac aaggcaaact tgaccaatag    600
tcttagagta tccagtgagg ccaggggccg gcggctggca agggatgaag aataaaagga    660
agcacccttc agcagttcca cacactgctt ctggaacgt ctgaggttat caataagctc      720
ctagtccaga cgccatggtg cacctgactc ctgaggagaa gtctgccgtt actgccctgt    780
ggggcaaggt gaacgtggat gaagttggtg gtgaggccct gggcaggttg gtatccaagt    840
tacaagacag gtttaaggag accaataaga ctgggcatg tggagacaga gaagactctt       900
gggtttctga taggcactga ctctctctgc ctattggtct attttcccac ccttaggctg     960
ctggtggtct acccttggac ccagaggttc tttgagtcct ttggggatct gtccactcct    1020
gatgctgtta tgggcaaccc taaggtgaag gctcatggca agaaagtgct cggtgcctct    1080
agtgatggcc tggctcacct ggacaacctc aagggcacct tgcccagct gagtgagctg      1140
cactgtgaca agctgcacgt ggatcctgag aacttcaggg tgagtctatg gaccccctga    1200
tgttttcttt cccttcttt tctatggtta agttcatgtc ataggaaggg gagaagtaac      1260
agggtacaca tattgaccaa atcagggtaa ttttgcattt gtaattttaa aaaatgcttt    1320
cttcttttaa tatacttttt tgtttatctt atttctaata cttttcctaa tctctttctt    1380
tcagggcaat aatgatacaa tgtatcatgc ctctttgcac cattctaaag aataacagtg    1440
ataattctg ggttaaggca atagcaatat ttctgcatat aaatattct gcatataaat        1500
tgtaactgat gtaagaggtt tcatattgct aatagcagct acaatccagc taccattctg    1560
ctttattttt atggttggga taaggctgga ttattctgag tccaagctag gccccttttgc    1620
taatcatgtt catacctctt atcttcctcc cacagctgcg caacaacgtg ctggtgctgt    1680
tgctggccca tcactttggc aaagaattca cccaccaggt gcaggctgcc tatcagaaag    1740
tggtggctgg tgtggctaat gcctggcc acaagtatca ctaagctcgc tttcttgctg      1800
tccaatttct attaaaggtt cctttgttcc ctaagtccaa ctactaaact gggggatatt    1860
atgaagggcc ttgagcatct ggattctgcc taataaaaaa catttatttt cattgcaatg    1920
atgtatttaa attatttctg aatatttac taaaaaggga atgtgggagg ttgcagtgct    1980
```

-continued

```
agtctcccgg aactatcact cttcacagt ctgctttgga aggactgggc ttagtatgaa  2040
aagttaggac tgagaagaat ttgaaagggg gcttttttgta gcttgatatt cactactgtc  2100
ttattaccct atcataggcc caccccaaat ggaagtccca ttcttcctca ggatgtttaa  2160
gattagcatt caggaagaga tcagaggtct gctggctccc ttatcatgtc ccttatggtg  2220
cttctggctc tgcaccgcgg gaacagagaa acaggagaat atgggccaaa caggatatct  2280
gtggtaagca gttcctgccc cggctcaggg ccaagaacag ttggaacagc agaatatggg  2340
ccaaacagga tatctgtggt aagcagttcc tgcccggct cagggccaag aacgatggt  2400
ccccagatgc ggtcccgccc tcagcagttt ctagagaacc atcagatgtt tccagggtgc  2460
cccaaggacc tgaaatgacc ctgtgccta tttgaactaa ccaatcagtt cgcttcgtgc  2520
ttctgttcgc gcgcttctgc tccccgagct ctatataagc agagctcgtt tagtgaaccg  2580
tcagatcgcg gccgcgccgc caccatggtg agcaagggcg aggagctgtt caccggggtg  2640
gtgcccatcc tggtcgagct ggacggcgac gtaaacggcc acaagttcag cgtgtccggc  2700
gagggcgagg gcgatgccac ctacggcaag ctgaccctga agttcatctg caccaccggc  2760
aagctgcccg tgccctggcc caccctcgtg accaccctga cctacggcgt gcagtgcttc  2820
agccgctacc ccgaccacat gaagcagcac gacttcttca agtccgccat gcccgaaggc  2880
tacgtccagg agcgcaccat cttcttcaag gacgacggca actacaagac ccgcgccgag  2940
gtgaagttcg agggcgacac cctggtgaac cgcatcgagc tgaagggcat cgacttcaag  3000
gaggacggca acatcctggg gcacaagctg gagtacaact acaacagcca caacgtctat  3060
atcatggccg acaagcagaa gaacggcatc aaggtgaact tcaagatccg ccacaacatc  3120
gaggacggca gcgtgcagct cgccgaccac taccagcaga cacccccat cggcgacggc  3180
cccgtgctgc tgcccgacaa ccactacctg agcacccagt ccgccctgag caaagacccc  3240
aacgagaagc gcgatcacat ggtcctgctg gagttcgtga ccgccgccgg gatcactctc  3300
ggcatggacg agctgtacaa ggagggcaga ggaagtcttc taacatgcgg tgacgtggag  3360
gagaatccgg gccccctgc aggaacttca aggtgagtcc aggagatgtt tcagcccgtg  3420
tgcctttagt ctcgaggcaa cttagacaac ggagtattga tctgagcaca gcagggtgtg  3480
agctgtttga agatactggg gttggggggtg aagaaactga agaggactaa ctgggctgag  3540
acccagtggg aatgttttag ggcctaagga gtgcctctaa aaatctagat ggacaatttt  3600
gactttgaga aagagaggt ggaaatgagg aaaatgactt ttctttatta gattccagta  3660
gaaagaactt tcatctttcc ctcattttg ttgttttaaa acatctatct ggaggcagga  3720
caagtatggt cgttaaaag atgcaggcag aaggcatata ttggctcagt caaagtgggg  3780
aactttggtg ggtcgacgta gataagtagc atggcgggtt aatcattaac tacaaggaac  3840
ccctagtgat ggagttggcc actccctctc tgccgcgctcg ctcgctcact gaggccgggc  3900
gaccaaaggt cgcccgacgc ccgggctttg cccgggcggc ctcagtgagc gagcgagcgc  3960
gccagctggc gtaatagcga agaggcccgc accgatcgcc cttcccaaca gttgcgcagc  4020
ctgaatgcg aatggcgatt ccgttgcaat ggctggccgt aatattgttc tggatattac  4080
cagcaaggcc gatagtttga gttcttctac tcaggcaagt gatgttatta ctaatcaaag  4140
aagtattgcg acaacggtta atttgcgtga tggacagact ctttactcg gtggcctcac  4200
tgattataaa aacacttctc aggattctgg cgtaccgttc ctgtctaaaa tccctttaat  4260
cggcctcctg tttagctccc gctctgattc taacgaggaa agcacgttat acgtgctcgt  4320
caaagcaacc atagtacgcg ccctgtagcg cgcattaag cgcgcgggt gtggtggtta  4380
cgcgcagcgt gaccgctaca cttgccacgc ccctagcgcc cgctcctttc gctttcttcc  4440
cttccttcct cgccacgttc gccggctttc ccgtcaagc tctaaatcgg gggctcccctt  4500
tagggttccg atttagtgct ttacggcacc tcgaccccaa aaaacttgat taggtgatg  4560
gttcacgtag tgggccatcg ccctgataga cggtttttcg ccctttgacg ttggagtcca  4620
cgttctttaa tagtggactc ttgttccaaa ctggaacaac actcaaccct atctcggtct  4680
attctttga tttataaggg attttgccga tttcggccta ttggttaaaa aatgagctga  4740
tttaacaaaa attaacgcg aattttaaca aaatattaac gttacaatt taaatatttg  4800
cttatacaat cttcctgttt ttggggcttt tctgattatc aaccggggta catatgattg  4860
acatgctagt tttacgatta ccgttcatcg atttctttgt ttgctccaga ctctcaggca  4920
atgacctgat agcctttgta gagacctctc aaaaatagct accctctccg gcatgaattt  4980
atcagctaga acggttgaat atcatattga tggtgatttg actgtctccg gccttttca  5040
cccgtttgaa tctttaccta cacattactc aggcattgca tttaaaatat atgagggttc  5100
taaaaatttt tatccttgcg ttgaaataaa ggcttctccc gcaaaagtat tacagggtca  5160
taatgttttt ggtacaaccg atttagcttt atgctctgag gctttattgc ttaatttgc  5220
taattcttg ccttgcctgt atgatttatt ggatgttgga atcgcctgat gcggtatttc  5280
ctccttacgc atctgtgcgg tatttcacac cgcatatggt gcactctcag tacaatctgc  5340
tctgatgccg catagttaag ccagccccga caccgccaa caccgctga cgcgccctga  5400
cgggcttgtc tgctcccggc atccgcttac agacaagctg tgaccgtctc cgggagctgc  5460
atgtgtcaga ggttttcacc gtcatcaccg aaacgcgcga gacgaaaggg cctcgtgata  5520
cgcctattt tataggttaa tgtcatgata ataatggttt cttagacgtc aggtggcact  5580
tttcggggaa atgtgcgcgg aaccccctatt tgtttattt tctaaataca ttcaaatatg  5640
tatccgctca tgagacaata accctgataa atgcttcaat aatattgaaa aggaagagt  5700
atgagtattc aacatttccg tgtcgccctt attccctttt ttgcggcatt ttgccttcct  5760
gtttttgctc acccagaaac gctggtgaaa gtaaaagatg ctgaagatca gttgggtgca  5820
cgagtgggtt acatcgaact ggatctcaac agcggtaaga tccttgagag ttttcgcccc  5880
gaagaacgtt ttccaatgat gagcactttt aaagttctgc tatgtggcgc ggtattatcc  5940
cgtattgacg ccgggcaaga gcaactcggt cgccgcatac actattctca gaatgacttg  6000
gttgagtact caccagtcac agaaaagcat cttacggatg gcatgacagt aagagaatta  6060
tgcagtgctg ccataaccat gagtgataac actgcggcca acttacttct gacaacgatc  6120
ggaggaccga aggagctaac cgcttttttg cacaacatgg gggatcatgt aactcgcctt  6180
gatcgttggg aaccggagct gaatgaagcc ataccaaacg acgagcgtga ccacacgatg  6240
cctgtagcaa tggcaacaac gttgcgcaaa ctattaactg gcgaactact tactctagct  6300
tcccggcaac aattaataga ctggatgagg cggataaagt tgcaggacc acttctgcgc  6360
tcggccttcc cggctggctg gtttattgct gataaatctg gagccggtga gcgtgggtct  6420
cgcggtatca ttgcagcact ggggccagat ggtaagccct cccgtatcgt agttatctac  6480
acgacgggga gtcaggcaac tatgatgaa cgaaatagac agatcgctga ataggtgcc  6540
tcactgatta agcattggta actgtcagac caagtttact catatatact ttagattgat  6600
ttaaaacttc atttttaatt taaaaggatc taggtgaaga tccttttga taatctcatg  6660
accaaaatcc cttaacgtga gttttcgttc cactgagcgt cagacccgt agaaaagatc  6720
```

```
aaaggatctt cttgagatcc ttttttttctg cgcgtaatct gctgcttgca aacaaaaaaa 6780
ccaccgctac cagcggtggt ttgtttgccg gatcaagagc taccaactct ttttccgaag 6840
gtaactggct tcagcagagc gcagatacca aatactgtcc ttctagtgta gccgtagtta 6900
ggccaccact tcaagaactc tgtagcaccg cctacatacc tcgctctgct aatcctgtta 6960
ccagtggctg ctgccagtgg cgataagtcg tgtcttaccg ggttggactc aagacgatag 7020
ttaccggata aggcgcagcg gtcgggctga acggggggtt cgtgcacaca gcccagcttg 7080
gagcgaacga cctacaccga actgagatac ctacagcgtg agctatgaga aagcgccacg 7140
cttcccgaag ggagaaaggc ggacaggtat ccggtaagcg gcagggtcgg aacaggagag 7200
cgcacgaggg agcttccagg gggaaacgcc tggtatcttt atagtcctgt cgggtttcgc 7260
cacctctgac ttgagcgtcg atttttgtga tgctcgtcag gggggcggag cctatggaaa 7320
aacgccagca acgcggcctt tttacggttc ctggccttt gctggccttt tgctcacatg 7380
ttctttcctg cgttatcccc tgattctgtg ataaccgta ttaccgcctt tgagtgagct 7440
gataccgctc gccgcagccg aacgaccgag cgcagcgagt cagtgagcga ggaagcggaa 7500
gagcgcccaa tacgcaaacc gcctctcccc gcgcgttggc cgattcatta atg 7553

SEQ ID NO: 45        moltype = DNA   length = 7252
FEATURE              Location/Qualifiers
source               1..7252
                     mol_type = other DNA
                     organism = Synthetic construct
SEQUENCE: 45
cagctgcgcg ctcgctcgct cactgaggcc gcccgggcaa agcccggcg tcggcgacc   60
tttggtcgcc cggcctcagt gagcgagcga gcgcgcagag agggagtggc caactccatc  120
actaggggtt ccttgtagtt aatgattaac ccgccatgct acttatctac acgcgtagat  180
ctagaaaattg ttttcactgc actattgaga aattaagaga taatggcaaa agtcacaaag  240
agtatattca aaaagaagta tagcactttt tccttagaaa ccactgctaa ctgaaagaga  300
ctaagatttg tcccgtcaaa aatcctggac ctatgcctaa aacacatttc acaatccctg  360
aacttttcaa aaattggtac atgctttagc tttaaactac aggcctcact ggagctagag  420
acaagaaggt aaaaaacggc tgacaaagaa agtcctggta tcctctatga tgggagaagg  480
aaactagcta aagggaagaa taaattagag aaaaactgaa atgactgaat cggaacaagg  540
caaaggctat aaaaaaaatt agcagtatcc tcttgggggc ccttccca cactatctca  600
atgcaaatat ctgtctgaaa cggtcctgg ctaaactcca cccatgggtt ggccagcctt  660
gccttgacca atagccttga caaggcaaac ttgaccaata gtcttagagt atccagtgag  720
gccaggggcc ggcggctggc tagggatgaa gaataaaagg aagcacccctt cagcagttcc  780
acccgcggga acagagaaac aggagaatat gggccaaaca ggatatctgt ggtaagcagt  840
tcctgccccg gctcagggcc aagaacagtt ggaacagcag aatatgggcc aaacaggata  900
tctgtggtaa gcagttcctg ccccggctca gggccaagaa cagatggtcc ccagatgcgg  960
tcccgccctc agcagtttct agagaaccat cagatgtttc caggggtgccc caaggacctg 1020
aaatgaccct gtgccttatt tgaactaacc aatcagttcg cttctcgctt ctgttcgcgc 1080
gcttctgctc cccgagctct atataagcag agctcgttta gtgaaccgtc agatcgcctg 1140
gagacgccat ccacgctgtt ttgacttcca tagaaggcgg ccgcgccgcc accatggtga 1200
gcaagggcga ggagctgttc accggggtgg tgcccatcct ggtcgagctg gacggcgacg 1260
taaacggcca caagttcagc gtgtccggcg agggcgaggg cgatgccacc tacggcaagc 1320
tgaccctgaa gttcatctgc accaccggca agctgcccgt gccctggccc accctcgtga 1380
ccaccctgac ctacggcgtg cagtgcttca gccgctaccc cgaccacatg aagcagcacg 1440
acttcttcaa gtccgccatg cccgaaggct acgtccagga gcgcaccatc ttcttcaagg 1500
acgacggcaa ctacaagacc cgcgccgagg tgaagttcga gggcgacacc ctggtgaacc 1560
gcatcgagct gaagggcatc gacttcaagg aggacggcaa catcctgggg cacaagctgg 1620
agtacaacta caacagccac aacgtctata tcatggccga caagcagaag aacggcatca 1680
aggtgaactt caagatccgc cacaacatcg aggacggcag cgtgcagctc gccgaccact 1740
accagcagaa caccccatc ggcgacggcc ccgtgctgct gcccgacaac cactacctga 1800
gcacccagtc cgccctgagc aaagacccca acgagaagcg cgatcacatg gtcctgctgg 1860
agttcgtgac cgccgccggg atcactctcg gcatgacga gctgtacaag taacctgcag 1920
ggataatcaa cctctggatt acaaaatttg tgaaagattg actggtattc ttaactatgt 1980
tgctccttttt acgctatgtg gatacgctgc tttaatgcct ttgtatcatg ctattgcttc 2040
ccgtatggct ttcattttct cctccttgta taaatcctgg ttagttcttg ccacggcgga 2100
actcatcgcc gcctgccttg cccgctgctg gacaggggct cggctgttgg gcactgacaa 2160
ttccgtggtg ttttatttgtg aaatttgtga tgctattgct ttatttgtaa ccattctagc 2220
tttatttgtg aaatttgtga tgctattgct ttatttgtaa ccattataag ctgcaataaa 2280
caagttaaca acaacaattg cattcatttt atgtttcagg ttcaggggga gatgtgggag 2340
gttttttaaa gcgaattctc tggaacctat cagggaccac agtcagccag gcaagcacat 2400
ctgcccaagc caagggtgga ggcatgcagc tgtgggggtc tgtgaaaaca cttgagggag 2460
cagataactg ggccaaccat gactcagtgc ttctggaggc caacaggact gctgagtcat 2520
cctgtggggg tggaggtggg acaagggaaa gggtgaagt gtactgctga ttacaacctc 2580
tggtgctgcc tccccctcct gtttatctga gaggctagcg taaatacact tgcaaaggag 2640
gatgttttta gtagcaattt gtactgatgg tatgggccaa agatatatat cttagaggga 2700
gggctgaggg tttgaagtcc aactcctaag ccagtgccag aagagccaag acaggtacg 2760
gctgtcatca cttagccctc accctgtgga gccacactcc agggttggcc aatctactcc 2820
caggagcagga gagggcagga gccagggctg ggcataaaag tcaggcaga gccatctatt 2880
gcttacactc gcttctggaa cgtctgaggt tatcaataag ctcctagtcc agacgccatg 2940
ggtcatttca cagaggagga caaggctact atcacaagcc tgtggggcaa ggtgaatgtg 3000
gaagatgctg gaggagaaac cctgggaagg taggctctgg tgaccaggac aagggaggga 3060
aggaaggacc ctgtgcctgg caaaagtcca ggtcgcttct caggatttgt ggcaccttct 3120
gactgtcaaa tcgttcttgt caatctcaca ggctcctggt tgtcacccca tggacccaga 3180
ggttcttttga cagctttggc aacctgtcct ctgcctctgc catcatgggc aaccccaaag 3240
tcaaggcaca tggcaagaag gtgctgactt ccttgggaga tgccacaaag cacctggatg 3300
atctcaaggg cacctttgcc cagctgagtg aactgcactg tgacaagctg catgtggatc 3360
ctgagaactt caaggtgagt ccaggagatg tttcagccct gttgcctta gtctcgaggc 3420
aacttagaca acggagtatt gatctgagca cagcagggtg tgagctgttt gaagatactg 3480
```

```
gggtctcgag gtcgacgtag ataagtagca tggcgggtta atcattaact acaaggaacc  3540
cctagtgatg gagttggcca ctccctctct gcgcgctcgc tcgctcactg aggccgggcg  3600
accaaaggtc gcccgacgcc cgggctttgc ccgggcggcc tcagtgagcg agcgagcgcg  3660
ccagctggcg taatagcgaa gaggcccgca ccgatcgccc ttcccaacag ttgcgcagcc  3720
tgaatggcga atggcgattc cgttgcaatg gctggcggta atattgttct ggatattacc  3780
agcaaggccg atagtttgag ttcttctact caggcaagtg atgttattac taatcaaaga  3840
agtattgcga caacggttaa tttgcgtgat ggacagactc ttttactcgg tggcctcact  3900
gattataaaa acacttctca ggattctggc gtaccgttcc tgtctaaaat cccttttaatc 3960
ggcctcctgt ttagctcccg ctctgattct aacgaggaaa gcacgttata cgtgctcgtc  4020
aaagcaacca tagtacgcgc cctgtagcgg cgcattaagc gcggcgggtg tggtggttac  4080
gcgcagcgtg accgctacac ttgccagcgc cctagcgccc gctcctttcg ctttcttccc  4140
ttcctttctc gccacgttcg ccggctttcc ccgtcaagct ctaaatcggg gctcccttt   4200
agggttccga tttagtgctt tacggcacct cgaccccaaa aaacttgatt agggtgatgg  4260
ttcacgtagt gggccatcgc cctgatagac ggttttcgc cctttgacgt tggagtccac   4320
gttctttaat agtggactct tgttccaaac tggaacaaca ctcaaccccta tctcggtcta  4380
ttcttttgat ttataaggga ttttgccgat ttcggcctat tggttaaaaa atgagctgat  4440
ttaacaaaaa tttaacgcga attttaacaa aatattaacg tttacaattt aaatatttgc  4500
ttatacaatc ttcctgtttt tggggctttt ctgattatca accggggtac atatgattga  4560
catgctagtt ttacgattac cgttcatcga ttctcttgtt tgctccagac tctcaggcaa  4620
tgacctgata gcctttgtag agacctctca aaaatagcta ccctctccgg catgaattta  4680
tcagctagaa cggttgaata tcatattgat ggtgatttga ctgtctccgg cctttctcac  4740
ccgtttgaat cttttacctac acattactca ggcattgcat ttaaaatata tgagggttct  4800
aaaaattttt atccttgcgt tgaaataaag gcttctcccg caaaagtatt acagggtcat  4860
aatgttttg gtacaaccga tttagcttta tgctctgagg ctttattgct taattttgct  4920
aattctttgc cttgcctgta tgatttattg gatgttggaa tcgcctgatg cggtattttc  4980
tccttacgca tctgtgcggt attttcacacc gcatatggtg cactctcagt acaatctgct  5040
ctgatgccgc atagttaagc cagccccgac acccgccaac acccgctgac gcgccctgac  5100
gggcttgtct gctcccggca tccgcttaca gacaagctgt gaccgtctcc gggagctgca  5160
tgtgtcagag gttttcaccg tcatcaccga aacgcgcgag acgaaagggc ctcgtgatac  5220
gcctattttt ataggttaat gtcatgataa taatggtttc ttagacgtca ggtggcactt  5280
ttcggggaaa tgtgcgcgga acccctattt gtttattttt ctaaatacat tcaaatatgt  5340
atccgctcat gagacaataa ccctgataaa tgcttcaata atattgaaaa aggaagagta  5400
tgagtattca acatttccgt gtcgccctta ttccctttt  tgcggcattt tgccttcctg  5460
ttttgctca cccagaaacg ctggtgaaag taaaagatgc tgaagatcag ttgggtgcac  5520
gagtgggtta catcgaactg gatctcaaca gcggtaagat ccttgagagt tttcgccccg  5580
aagaacgttt tccaatgatg agcactttta aagttctgct atgtggcgcg gtattatccc  5640
gtattgacgc cgggcaagag caactcggtc gccgcataca ctattctcag aatgacttgg  5700
ttgagtactc accagtcaca gaaaagcatc ttacggatgg catgacagta agagaattat  5760
gcagtgctgc cataaccatg agtgataaac tgcggccaa cttacttctg acaacgatcg  5820
gaggaccgaa ggagctaacc gcttttttgc acaacatggg ggtcatgta  actcgccttg  5880
atcgttggga accggagctg aatgaagcca taccaaacga cgagcgtgac accacgatgc  5940
ctgtagcaat ggcaacaacg ttgcgcaaac tattaactgg cgaactactt actctagctt  6000
cccggcaaca attaatagac tggatggagg cggataagtt gcaggacca cttctgcgct  6060
cggcccttcc ggctggctgg tttattgctg ataaatctgg agccggtgag cgtgggtctc  6120
gcggtatcat tgcagcactg gggccagatg gtaagccctc ccgtatcgta gttatctaca  6180
cgacgggag tcaggcaact atggatgaac gaaatagaca gatcgctgag ataggtgcct  6240
cactgattaa gcattggtaa ctgtcagacc aagtttactc atatatactt tagattgatt  6300
taaaacttca ttttaatttt aaaaggatct aggtgaagat cctttttgat aatctcatga  6360
ccaaaatccc ttaacgtgag ttttcgttcc actgagcgtc agacccgta gaaaagatca  6420
aaggatcttc ttgagatcct ttttttctgc gcgtaatctg ctgcttgcaa acaaaaaaac  6480
caccgctacc agcggtggtt tgtttgccgg atcaagagct accaactctt tttccgaagg  6540
taactggctt cagcagagcg cagataccaa atactgtcct tctagtgtag ccgtagttag  6600
gccaccactt caagaactct gtagcaccgc ctacatacct cgctctgcta atcctgttac  6660
cagtggctgc tgccagtggc gataagtcgt gtcttaccgg gttggactca agacgatagt  6720
taccggataa ggcgcagcgg tcgggctgaa cggggggttc gtgcacacag cccagcttgg  6780
agcgaacgac ctacaccgaa ctgagatacc tacagcgtga gctatgagaa agcgccacgc  6840
ttcccgaagg gagaaaggcg gacaggtatc cggtaagcgg cagggtcgga acaggagagc  6900
gcacgaggga gcttccaggg ggaaacgcct ggtatcttta tagtcctgtc gggtttcgcc  6960
acctctgact tgagcgtcga ttttttgtgat gctcgtcagg ggggcggagc ctatggaaaa  7020
acgccagcaa cgcggccttt ttacggttcc tggccttttg ctggcctttt gctcacatgt  7080
tctttcctgc gttatcccct gattctgtgg ataaccgtat taccgccttt gagtgagctg  7140
ataccgctcg ccgcagccga acgaccgagc gcagcgagtc agtgagcgag gaagcggaag  7200
agcgcccaat acgcaaaccg cctctccccg cgcgttggcc gattcattaa tg           7252
```

SEQ ID NO: 46   moltype = DNA  length = 6991
FEATURE      Location/Qualifiers
source       1..6991
          mol_type = other DNA
          organism = Synthetic construct
SEQUENCE: 46

```
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt ccttgtagtt aatgattaac cgccatgct acttatctac acgcgtagat  180
ctagaaattg ttttcactgc ctattgaga aattaagag taatggcaaa agtcacaaag   240
agtatattca aaaagaagta tagcactttt tccttagaaa ccactgctaa ctgaaagaga  300
ctaagatttg tcccgtcaaa aatcctggac ctatgcctaa aacacatttc acaatccctg  360
aactttcaa aaattggtac atgctttagc tttaaactac aggcctcact ggagctagag   420
acaagaaggt aaaaaacggc tgacaaaaga agtcctggta tcctctatga tgggagaagg  480
aaactagcta aagggaagaa taaattagag aaaaactgga atgactgaat cggaacaagg  540
```

-continued

```
caaaggctat aaaaaaaatt agcagtatcc tcttggggc cccttcccca cactatctca    600
atgcaaatat ctgtctgaaa cggtccctgg ctaaactcca cccatgggtt ggccagcctt    660
gccttgacca atagccttga caaggcaaac ttgaccaata gtcttagagt atccagtgag    720
gccaggggcc ggcggctggc tagggatgaa gaataaaagg aagcacccct cagcagttcc    780
acccgcggga acagagaaac aggagaatat gggccaaaca ggatatctgt ggtaagcagt    840
tcctgccccg gctcagggcc aagaacagtt ggaacagcag aatatgggcc aaacaggata    900
tctgtggtaa gcagttcctg ccccggctca gggccaagaa cagatggtcc ccagatgcgg    960
tcccgccctc agcagtttct agagaaccat cagatgtttc cagggtgccc caaggacctg   1020
aaatgaccct gtgccttatt tgaactaacc aatcagttcg cttctcgctt ctgttcgcgt   1080
gcttctgctc cccgagctct atataagcag agctcgttta gtgaaccgtc agatcgcctg   1140
gagacgccat ccacgctgtt ttgacttcca tagaaggcgg ccgcgccgcc accatggtga   1200
gcaagggcga ggagctgttc accggggtgg tgcccatcct ggtcgagctg gacggcgacg   1260
taaacgccca caagttcagc gtgtccggcg agggcgaggg cgatgccacc tacggcaagc   1320
tgacccctgaa gttcatctgc accaccggca agctgcccgt gccctggccc accctcgtga   1380
ccaccctgac ctacggcgtg cagtgcttca gccgctaccc cgaccacatg aagcagcacg   1440
acttcttcaa gtccgccatg cccgaaggct acgtccagga gcgcaccatc ttcttcaagg   1500
acgacggcaa ctacaagacc cgcgccgagg tgaagttcga gggcgacacc ctggtgaacc   1560
gcatcgagct gaagggcatc gacttcaagg aggacggcaa catcctgggg cacaagctgg   1620
agtacaacta caacagccac aacgtctata tcatggccga caagcagaag aacggcatca   1680
aggtgaactt caagatccgc cacaacatcg aggacggcgc cgtgcagctc gccgaccact   1740
accagcagaa cacccccatc ggcgacggcc ccgtgctgct gcccgacaac cactacctga   1800
gcacccagtc cgccctgagc aaagacccca acgagaagcg cgatcactgg gtcctgctgg   1860
agttcgtgac cgccgccggg atcactctcg gcatggacga gctgtacaag taacctgcag   1920
ggataatcaa cctctggatt acaaaatttg tgaaagattg actggtattc ttaactatgt   1980
tgctcctttt acgctatgtg gatacgctgc tttaatgcct ttgtatcatg ctattgcttc   2040
ccgtatggct ttcatttttct cctccttgta taaatcctgg ttagttcttg ccacggcgga   2100
actcatcgcc gcctgccttg cccgctgctg gacaggggcc cggctgttgg gcactgacaa   2160
ttccgtggtg tttatttgtg aaatttgtga tgctattgct ttatttgtaa ccattctagc   2220
tttatttgtg aaatttgtga tgctattgct ttatttgtaa ccattataag ctgcaataaa   2280
caagttaaca acaacaattg cattcatttt atgtttcagg ttcagggga gatgtgggag   2340
gttttttaaa gcgaattcgt aaatacactt gcaaggagg atgttttag tagcaatttg   2400
tactgatggt atgggccaa gagatatatc ttagagggag ggctgagggt ttgaagtcca   2460
actcctaagc cagtgccaga agagccaagg acaggtacgg ctgtcatcac ttagacctca   2520
ccctgtggag ccacaccct gggttggcca atctactccc aggacaggg agggcaggag   2580
ccagggctgg gcataaaagt cagggcagag ccatctattg cttacactcg cttctggaac   2640
gtctgaggtt atcaataagc tcctagtcca gacgccatgg gtcatttcac agaggaggac   2700
aaggctacta tcacaagcct gtggggcaag gtgaatgtgg aagatgctgg aggagaaacc   2760
ctgggaaggt aggctctggt gaccaggaca agggagggaa ggaaggaccc tgtgcctggc   2820
aaaagtccag gtcgcttctc aggatttgtg gcaccttctg actgtcaaac tgttctttgtc   2880
aatctcacag gctcctggtt gtctacccat ggacccagag gttctttgac agctttggca   2940
acctgtcctc tgcctctgcc atcatgggca accccaaagt caaggcacat ggcaagaagg   3000
tgctgacttc cttgggagat gccacaaagc acctggatga tctcaagggc acctttgccc   3060
agctgagtga actgcactgt gacaagctgc atgtggatcc tgagaacttc aaggtgatgc   3120
caggagatgt ttcagccctg ttgccttag tctcgaggca acttagacaa cggagttattg   3180
atctgagcac agcagggtgt gagctgtttg aagatactgg ggtctcgagg tcgacgtaga   3240
taagtagcat ggcgggttaa tcattaacta caaggaaccc ctagtgatgg agttggccac   3300
tccctctctg cgcgctcgct cgctcactga ggccggcgca ccaaaggtcg cccgacgccc   3360
gggcttttgcc cggcggcct cagtgagcga gcgagcgcgc cagctggcgt aatagcgaag   3420
aggcccgcac cgatcgccct tcccaacagt tgcgcagcct gaatggcgaa tggcgattcc   3480
gttgcaatgg ctggcggtaa tattgttctg gatattacca gcaaggccga tagttttgagt   3540
tcttctactc aggcaagtga tgttattact aatcaaagaa attgcgac aacggttaat   3600
ttgcgtgatg gacagactct tttactcggt ggcctcactg attataaaaa cacttctcag   3660
gattctggcg taccgttcct gtctaaaatc cctttaatcg gcctcctgtt tagctcccgc   3720
tctgattcta acgaggaaag cacgttatac gtgctcgtca aagcaaccat agtacgcgcc   3780
ctgtagcagc gcattaagcg cggcgggtgt ggtggttacg gcagcgtga ccgctacact   3840
tgccagcgcc ctagcgcccg ctcctttcgc tttcttccct tcctttctcg ccacgttcgc   3900
cggctttccc cgtcaagctc taaatcgggg gctcccttta gggttccgat ttagtgcttt   3960
acggcacctc gaccccaaaa aacttgatta gggtgatggt tcacgtagtg gccatcgcc   4020
ctgatagacg gtttttcgcc ctttgacgtt ggagtccacg ttctttaata gtggactctt   4080
gttccaaact ggaacaacac tcaaccctat ctcggtctat tcttttgatt tataagggat   4140
tttgccgatt tcggcctatt ggttaaaaaa tgagctgatt taacaaaaat ttaacgcgaa   4200
ttttaacaaa atattaacgt ttacaattta aatatttgct tatacaatct tcctgttttt   4260
ggggcttttc tgattatcaa ccggggtaca tatgattgac atgctagttt tacgattacc   4320
gttcatcgat tctcttgtt gctccagact ccaggcaat gacctgatag cctttgtaga   4380
gacctctcaa aaatagctac cctctccggc atgaatttaat cagctagaac ggttgaatat   4440
catattgatg gtgatttgac tgtctccggc ctttctcacc cgtttgaatc tttacctaca   4500
cattactcag gcattgcatt taaaatatat gagggttcta aaaattttta tccttgcgtt   4560
gaaataaagg cttctcccgc aaaagtatta caggtgtcta atgttttttgg tacaaccgat   4620
ttagcttttat gctctgaggc tttattgctt aattttgtca attctttgtc ttgcctgtat   4680
gatttattgg atgttggaat cgcctgatgc ggtattttct ccttacgcat ctgtgcggta   4740
tttcacaccg catatggtgc actctcagta caatctgctc tgatgccgca gttaagcc    4800
agccccgaca cccgccaaca cccgctgacg cgccctgacg gcttgtctg ctcccggcat   4860
ccgcttacag acaagctgtg accgtctccg ggagctgcat gtgtcagagg ttttcaccgt   4920
catcaccgaa acgcgcgaga cgaaagggcc tcgtgatacg cctatttttta taggttaatg   4980
tcatgataat aatggtttct tagacgtcag gtggcacttt tcggggaaat gtgcgcggaa   5040
cccctatttg tttatttttc taaatacatt caaatatgta tccgctcatg agacaataac   5100
cctgataaat gcttcaataa tattgaaaaa ggaagagtat gagtattcaa catttccgtg   5160
tcgcccttat tccctttttt gcggcatttt gccttcctgt ttttgctcac ccagaaacgc   5220
tggtgaaagt aaaagatgct gaagatcagt tgggtgcacg agtgggttac atcgaactgg   5280
```

```
atctcaacag cggtaagatc cttgagagtt ttcgcccega agaacgtttt ccaatgatga  5340
gcacttttaa agttctgcta tgtggcgcgg tattatcccg tattgacgcc gggcaagagc  5400
aactcggtcg ccgcatacac tattctcaga atgacttggt tgagtactca ccagtcacag  5460
aaaagcatct tacggatggc atgacagtaa gagaattatg cagtgctgcc ataaccatga  5520
gtgataacac tgcggccaac ttacttctga caacgatcgg aggaccgaag gagctaaccg  5580
cttttttgca caacatgggg gatcatgtaa ctcgccttga tcgttgggaa ccggagctga  5640
atgaagccat accaaacgac gagcgtgaca ccacgatgcc tgtagcaatg caacaacgt  5700
tgcgcaaact attaactggc gaactactta ctctagcttc ccggcaacaa ttaatagact  5760
ggatggaggc ggataaagtt gcaggaccac ttctgcgctc ggcccttccg gctggctggt  5820
ttattgctga taaatctgga gccggtgagc gtgggtctcg cggtatcatt gcagcactgg  5880
ggccagatgg taagccctcc cgtatcgtag ttatctacac gacggggagt caggcaacta  5940
tggatgaacg aaatagacag atcgctgaga taggtgcctc actgattaag cattggtaac  6000
tgtcagacca agtttactca tatatacttt agattgattt aaaacttcat ttttaattta  6060
aaaggatcta ggtgaagatc cttttttgata atctcatgac caaaatccct taacgtgagt  6120
tttcgttcca ctgagcgtca gaccccgtag aaaagatcaa aggatcttct tgagatcctt  6180
ttttttctgcg cgtaatctgc tgcttgcaaa caaaaaaacc accgctacca gcggtggttt  6240
gtttgccgga tcaagagcta ccaactcttt tccgaaggt aactggcttc agcagagcgc  6300
agataccaaa tactgtcctt ctagtgtagc cgtagttagg ccaccacttc aagaactctg  6360
tagcaccgcc tacatacctc gctctgctaa tcctgttacc agtggctgct gccagtggcg  6420
ataagtcgtg tcttaccggg ttggactcaa gacgatagtt accggataag gcgcagcggt  6480
cgggctgaac ggggggttcg tgcacacagc ccagcttgga gcgaacgacc tacaccgaac  6540
tgagataccct acagcgtgag ctatgagaaa gcgccacgct tcccgaaggg agaaaggcgg  6600
acaggtatcc ggtaagcggc agggtcgaa caggagagcg cacgagggag cttccagggg  6660
gaaacgcctg gtatctttat agtcctgtcg ggtttcgcca cctctgactt gagcgtcgat  6720
ttttgtgatg ctcgtcaggg gggcggagcc tatgaaaaaa cgccagcaac gcggcctttt  6780
tacggttcct ggccttttgc tggccttttg ctcacatgtt ctttcctgcg ttatccctg  6840
attctgtgga taaccgtatt accgcctttg agtgagctga taccgctcgc cgcagccgaa  6900
cgaccgagcg cagcgagtca gtgagcgagg aagcggaaga gcgcccaata cgcaaaccgc  6960
ctctccccgc gcgttggccg attcattaat g                                 6991

SEQ ID NO: 47         moltype = DNA   length = 7825
FEATURE               Location/Qualifiers
source                1..7825
                      mol_type = other DNA
                      organism = Synthetic construct
SEQUENCE: 47
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt ccttgtagtt aatgattaac ccgccatgct acttatctac acgcgtagat  180
ctagaaattg ttttcactgc actattgaga aattaagaga taatggcaaa agtcacaaag  240
agtatattca aaagaagta tagcactttt tccttagaaa ccactgctaa ctgaaagaga  300
ctaagatttg tcccgtcaaa aatcctggac ctatgcctaa aacacatttc acaatccctg  360
aacttttcaa aaattggtac atgctttagc tttaaactac aggcctcact ggagctagag  420
acaagaaggt aaaaacggc tgacaaaaga agtcctggta tcctctatga tgggagaagg  480
aaactagcta aagggaagaa taaattagag aaaaactgga atgactgaat cggaacaagg  540
caaaggctat aaaaaaaatt agcagtatcc tcttgggggc cccttcccca cactatctca  600
atgcaaatat ctgtctgaaa cggtcctgc ctaaactcca ccgcggaa cagagaaaca   660
ggagaatatg ggccaaacag gatatctgtg gtaagcagtt cctgcccgg ctcagggcca   720
agaacagttg gaacagcaga atatgggcca acaggatat ctgtggtaag cagttcctgc   780
cccggctcag ggccaagaac agatggtccc cagatgcggt cccgccctca gcagtttcta  840
gagaaccatc gatgtttcc agggtgcccc aaggacctga aatgaccctg tgccttattt   900
gaactaacca atcagttcgc ttctcgcttc tgttcgcgcg cttctgctcc ccgagctcta   960
tataagcaga gctcgtttag tgaaccgtca gatcgcctgg agacgccatc cacgctgttt  1020
tgacttccat agaaggcggc cgcgccgcca ccatggtgag caaggcgag gagctgttca  1080
ccggggtggt gcccatcctg gtcgagctgg acggcgacgt aaacggccac aagttcagcg  1140
tgtccggcga gggcgagggc gatgccacct acggcaagct gaccctgaag ttcatctgca  1200
ccaccggcaa gctgcccgtg ccctggccca ccctcgtgac caccctgacc tacggcgtgc  1260
agtgcttcag ccgctacccc gaccacatga gcagcacga cttcttcaag tccgccatgc  1320
ccgaaggcta cgtccaggag cgcaccatct tcttcaagga cgacggcaac tacaagaccc  1380
gcgccgaggt gaagttcgag ggcgacaccc tggtgaaccg catcgagctg aagggcatcg  1440
acttcaagga ggacggcaac atcctggggc acaagctgga gtacaactac aacagccaca  1500
acgtctatat catggccgac aagcagaaga acggcatcaa ggtgaacttc aagatccgcc  1560
acaacatcga ggacggcagc gtgcagctcg ccgaccacta ccagcagaac ccccccatcg  1620
gcgacggccc cgtgctgctg cccgacaacc actacctgag cacccagtcc gccctgagca  1680
aagaccccaa cgagaagcgc gatcacatgg tcctgctgga gttcgtgacc gccgccggga  1740
tcactctcgg catggacgag ctgtacaagt aacctgcagg gataatcaac ctctggatta  1800
caaaatttgt gaaagattga ctggtattct taactatgtt gctcctttta cgctatgtgg  1860
atacgctgct ttaatgcctt tgtatcatgc tattgcttcc cgtatggctt tcattttctc  1920
ctccttgtat aaatcctggt tagttcttgc cacggcggaa ctcatcgccg cctgccttgc  1980
ccgctgctgg acaggggctc ggctgttggg cactgacaat tccgtggtgt ttatttgtga  2040
aatttgtgat gctattgctt tatttgtaac cattctagct ttatttgtga aatttgtgat  2100
gctattgctt tatttgtaac cattataagc tgcaataaac aagttaacaa caacaattgc  2160
attcatttta tgttttcaggt tcaggggag atgtgggagg tttttttaaag cgaattccga  2220
gatcgagacc atcctggcta acacaagtaa atacccgtca tactaaaaaa atacaaaaaa  2280
ttagccgggc ttggtggcgg gtgcctgtag tcccagctac tatggagget gaggcgggag  2340
aatgcgtga acgcgggggg cggagcttgc agtgagcaga gatcagggc cactgcactc  2400
cagcctgggc gacagagaga gactctgtct caaaaaaaag aaaaaaaaaa tttagtagac  2460
tagctaaaaa aatccagaga tagttattga tgcatatgta aaagtcttcc aatatttaca  2520
agtacaatga aaaaaaaata accttgaatt aagtgtagaa ctcattgaca atgtttcaaa  2580
```

```
ggatgtgagg gataaactaa aatttgggca gtacatgctg ttcctgtgta cttggaacag   2640
agggagaaaa tctgggctgg aaatattgtt ataggagtta gcacatgaag gtgacaacta   2700
aattatttgg agtagatgga gtcaccagca catgtgaata gttttagaat gaaatgaccc   2760
aagatagaac tttggagagc ccccaaattt aaataaaatc agtataagag aagaggaaga   2820
aaccaaatgg tatactagtc taaattgttt cttagtgaca aaagaataac ctgaatatta   2880
gattagctgc ctatatgctc tctgaatcaa tttcattcaa catgcaacag ttctggaacc   2940
tatcagggac cacagtcagc caggcaagca catctgccca agccaagggt ggaggcatgc   3000
agctgtgggg gtctgtgaaa acacttgagg gagcagataa ctgggccaac catgactcag   3060
tgcttctgga ggccaacagg actgctgagt catcctgtgg gggtggaggt gggacaaggg   3120
aaagggtga atggtactgc tgattacaac ctctggtgct gcctcccct cctgtttatc    3180
tgagaggcta gcgtaaatac acttgcaaag gaggatgttt ttagtagcaa tttgtactga   3240
tggtatgggg ccaagagata tatcttagag ggagggctga gggtttgaag tccaactcct   3300
aagccagtgc cagaagagcc aaggacaggt acggctgtca tcacttagac ctcaccctgt   3360
ggagccacac cctagggttg gccaatctac tcccaggagc agggaggcg ggagccaggg    3420
ctgggcataa aagtcagggc agagccatct attgcttaca ctcgcttctg gaacgtctga   3480
ggttatcaat aagctcctag tccagacgcc atgggtcatt tcacagagga ggacaaggct   3540
actatcacaa gcctgtgggg caaggtgaat gtggaagatg ctggaggaga aaccctggga   3600
aggtaggctc tggtgaccag gacaagggag ggaaggaagg accctgtgcc tggcaaaagt   3660
ccaggtcgct tctcaggatt tgtggcacct tctgactgtc aaactgttct tgtcaatctc   3720
acaggctcct ggttgtctac ccatggaccc agaggttctt tgacagcttt ggcaacctgt   3780
cctctgcctc tgccatcatg ggcaacccca aagtcaaggc acatggcaag aaggtgctga   3840
cttccttggg agatgccaca aagcacctgg atgatctcaa gggcaccttt gccagctga   3900
gtgaactgca ctgtgacaag ctgcatgtgg atcctgagaa cttcaaggtg agtccaggag   3960
atgtttcagc cctgttgcct ttagtctcga ggcaacttag acaacggagt attgatctga   4020
gcacagcagg gtgtgagctg tttgaagata ctggggtctc gaggtcgacg tagataagta   4080
gcatggggta ttaatcatta actacaagga accccctagg atggagttgg ccactccctc   4140
tctgcgcgct cgctcgctca ctgaggccgg gcgaccaaag gtcgcccgac gcccgggctt   4200
tgcccgggcg gcctcagtga gcgagcgagc gcgcagctg gcgtaatagc gaagaggccc    4260
gcaccgatcg cccttcccaa cagttgcgca gcctgaatgg cgaatggcga ttccgttgca   4320
atggctgcg gtaatattgt tctgatatt accagcagcc cgatagttt gagttcttct      4380
actcaggcaa gtgatgttat tactaatcaa agaagtattg cgacaacggt taatttgcgt   4440
gatggacaga ctcttttact cggtggcctc actgattata aaaacacttc tcaggattct   4500
ggcgtaccgt tcctgtctaa aatccccttta atcggcctcc tgtttagctc ccgctctgat   4560
tctaacgagg aaagcacgtt atacgtgctc gtcaaagcaa ccatagtacg cgccctgtag   4620
cggcgcatta agcgcggcgg gtgtggtggt tacgcgcagc gtgaccgcta cacttgccag   4680
cgccctagcg cccgctcctt tcgctttctt cccttccttt ctcgccacgt tcgccggctt   4740
tccccgtcaa gctctaaatc gggggctccc tttagggttc cgatttagtg ctttacggca   4800
cctcgacccc aaaaaacttg attagggtga tggttcacgt agtgggccat cgccctgata   4860
gacggttttt cgccctttga cgttggagtc cacgttcttt aatagtggac tcttgttcca   4920
aactggaaca acactcaacc ctatctcggt ctattctttt gatttataag gattttgcc    4980
gatttcggcc tattggttaa aaaatgagct gatttaacaa aaatttaacg cgaattttaa   5040
caaaatatta acgtttacaa tttaaatatt tgcttataca atcttcctgt ttttgggct    5100
tttctgatta tcaaccgggg tacatatgat tgacatgcta gttttacgat taccgttcat   5160
cgattctctt gtttgctcca gactctcagg caatgacctg atagcctttg tagagacctc   5220
tcaaaaatag ctaccctctc cggcatgaat ttatcagcta gaacgttga atatcatatt    5280
gatggtgatt tgactgtctc cggcctttct cacccgtttg aatctttacc tacacattac   5340
tcaggcattg catttaaaat atatgagggt tctaaaaatt tttatcttg cgttgaaata    5400
aaggcttctc ccgcaaaagt attacagggt cataatgttt ttggtacaac cgatttagct   5460
ttatgctctg aggctttatt gcttaatttt gctaattctt tgccttgcct gtatgattta   5520
ttggatgttg aatcgcctg atgcggtatt ttctccttac gcatctgtgc ggtatttcac    5580
accgcatatg gtgcactctc agtacaatct gctctgatgc cgcatagtta agccagcccc   5640
gacacccgcc aacacccgct gacgcgccct gacgggcttg tctgctcccg gcatccgctt   5700
acagacaagc tgtgaccgtc tccgggagct gcatgtgtca gaggttttca ccgtcatcac   5760
cgaaacgcgc gagacgaaag ggcctcgtga tacgcctatt tttataggtt aatgtcatga   5820
taataatggt ttcttagacg tcaggtggca cttttcgggg aaatgtgcgc ggaacccta    5880
tttgtttatt tttctaaata cattcaaata tgtatccgct catgagacaa taaccctgat   5940
aaatgcttca ataatattga aaaggaaga gtatgagtat tcaacatttc cgtgtcgccc   6000
ttattccctt ttttgcggca ttttgccttc ctgtttttgc tcacccagaa acgctggtga   6060
aagtaaaaga tgctgaagat cagttgggtg cacgagtggg ttacatcgaa ctggatctca   6120
acagcggtaa gatccttgag agttttcgcc ccgaagaacg ttttccaatg atgagcactt   6180
ttaaagttct gctatgtggc gcggtattat cccgtattga cgccgggcaa gagcaactcg   6240
gtcgccgcat acactattct cagaatgact tggttgagta ctcaccagtc acagaaaagc   6300
atcttacgga tggcatgaca gtaagagaat tatgcagtgc tgccataacc atgagtgata   6360
acactgcggc caacttactt ctgacaacga tcggaggacc gaaggagcta accgcttttt   6420
tgcacaacat gggggatcat gtaactcgcc ttgatcgttg ggaaccggag ctgaatgaag   6480
ccataccaaa cgacgagcgt gacaccacga tgcctgtagc aatggcaaca acgttgcgca   6540
aactattaac tggcgaacta cttactctag cttcccggca acaattaata gactggatgg   6600
aggcggataa agttgcagga ccacttctgc gctcggccct tccggctggc tggtttattg   6660
ctgataaatc tggagccggt gagcgtgggt ctcgcggtat cattgcagca ctggggccag   6720
atggtaagcc ctcccgtatc gtagttatct acacgacggg gagtcaggca actatggatg   6780
aacgaaatag acagatcgct gagataggtg cctcactgat taagcattgg taactgtcag   6840
accaagttta ctcatatata ctttagattg atttaaaact tcatttttaa tttaaaagga   6900
tctaggtgaa gatcctttt gataatctca tgaccaaaat cccttaacgt gagttttcgt     6960
tccactgagc gtcagacccc gtagaaaaga tcaaaggatc ttcttgagat cctttttttc   7020
tgcgcgtaat ctgctgcttg caaacaaaaa aaccaccgct accagcggtg gtttgtttgc   7080
cggatcaaga gctaccaact ctttttccga aggtaactgg cttcagcaga gcgcagatac   7140
caaatactgt ccttctagtg tagccgtagt taggccacca cttcaagaac tctgtagcac   7200
cgcctacata cctcgctctg ctaatcctgt taccagtggc tgctgccagt ggcgataagt   7260
cgtgtcttac cgggttggac tcaagacgat agttaccgga taaggcgcag cggtcgggct   7320
```

```
gaacgggggg ttcgtgcaca cagcccagct tggagcgaac gacctacacc gaactgagat 7380
acctacagcg tgagctatga gaaagcgcca cgcttcccga agggagaaag gcggacaggt 7440
atccggtaag cggcagggtc ggaacaggag agcgcacgag ggagcttcca gggggaaacg 7500
cctggtatct ttatagtcct gtcgggtttc gccacctctg acttgagcgt cgattttgt 7560
gatgctcgtc aggggggcgg agcctatgga aaaacgccaa caacgcggcc tttttacggt 7620
tcctggcctt ttgctggcct tttgctcaca tgttctttcc tgcgttatcc cctgattctg 7680
tggataaccg tattaccgcc tttgagtgag ctgataccgc tcgccgcagc cgaacgaccg 7740
agcgcagcga gtcagtgagc gaggaagcgg aagagcgccc aatacgcaaa ccgcctctcc 7800
ccgcgcgttg gccgattcat taatg                                       7825

SEQ ID NO: 48           moltype = DNA   length = 7111
FEATURE                 Location/Qualifiers
source                  1..7111
                        mol_type = other DNA
                        organism = Synthetic construct
SEQUENCE: 48
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc   120
actaggggtt ccttgtagtt aatgattaac ccgccatgct acttatctac acgcgtagat   180
ctagaaattg ttttcactgc actattgaga aattaagaga taatggcaaa agtcacaaag   240
agtatattca aaagaagta tagcactttt tccttagaaa ccactgctaa ctgaaagaga   300
ctaagatttg tcccgtcaaa aatcctggac ctatgcctaa aacacatttc acaatccctg   360
aacttttcaa aaattggtac atgctttagc tttaaactac aggcctcact ggagctagag   420
acaagaaggt aaaaaacggc tgacaaaaga agtcctggta tcctctatga tgggagaagg   480
aaactagcta aagggaagaa taattagag aaaaactgga atgactgaat cggaacaagg   540
caaaggctat aaaaaaaatt agcagtatcc tcttgggagg cccttcccca cactatctca   600
atgcaaatat ctgtctgaaa cggtccctgg ctaaactcca cccgcgggaa cagagaaaca   660
ggagaatatg ggccaaacag gatatctgtg gtaagcagtt cctgccccgg ctcagggcca   720
agaacagttg aacagcagag atatgggcca aacaggatat ctgtggtaag cagttcctgc   780
cccggctcag ggccaagaac agatggtccc cagatgcggt cccgccctca gcagtttcta   840
gagaaccatc agatgtttcc agggtgcccc aaggacctga aatgaccctg tgccttattt   900
gaactaacca atcagttcgc ttctcgcttc tgttcgcgcg cttctgctcc ccgagctcta   960
tataagcaga gctcgtttag tgaaccgtca gatcgcctgg agacgccatc cacgctgttt  1020
tgacttccat agaaggcggc cgcgccgcca ccatggtgag caagggcgag gagctgttca  1080
ccggggtggt gcccatcctg gtcgagctgg acggcgacgt aaacggccac aagttcagcg  1140
tgtccggcga gggcgagggc gatgccacct acggcaagct gaccctgaag ttcatctgca  1200
ccaccggcaa gctgcccgtg ccctggccca cccctcgtgac caccctgacc tacggcgtgc  1260
agtgcttcag ccgctacccc gaccacatga agcagcacga cttcttcaag tccgccatgc  1320
ccgaaggcta cgtccaggag cgcaccatct tcttcaagga cgacggcaac tacaagaccc  1380
gcgccgaggt gaagttcgag ggcgacaccc tggtgaaccg catcgagctg aagggcatcg  1440
acttcaagga ggacggcaac atcctggggc acaagctgga gtacaactac aacagccaca  1500
acgtctatat catggccgac aagcagaaga acggcatcaa ggtgaacttc aagatccgcc  1560
acaacatcga ggacggcagc gtgcagctcg ccgaccacta ccagcagaac cccccactg  1620
gcgacggccc cgtgctgctg cccgacaacc actacctgag cacccagtcc gccctgagca  1680
aagaccccaa cgagaagcgc gatcacatgg tcctgctgga gttcgtgacc gccgccggga  1740
tcactctcgg catggacgag ctgtacaagt aacctgcagg gataatcaac ctctggatta  1800
caaaatttgt gaaagattga ctggtattct taactatgtt gctcctttta cgctatgtgg  1860
atacgctgct ttaatgcctt tgtatcatgc tattgcttcc cgtatggctt tcattttctc  1920
ctccttgtat aaatcctggt tagttcttgc cacggcggaa ctcatcgccg cctgccttgc  1980
ccgctgctgg acagggggctc ggctgttggg cactgacaat tccgtggtgt ttatttgtga  2040
aatttgtgat gctattgctt tatttgtaac cattatctgt tcataaaac aagttaacaa  2100
gctattgctt tatttgtaac cattataagc tgcaataaac aagttaacaa caacaattgc  2160
attcatttta tgtttcaggt tcaggggag atgtgggagg ttttttaaag cgaattctct  2220
ggaacctatc agggaccaca gtcagccagg caagcacatc tgcccaagcc aagggtggag  2280
gcatgcagct gtgggggtct gtgaaaacac ttgagggagc agataactgg gccaacatg  2340
actcagtgct tctggaggcc aacaggactg ctgagtcatc ctgtggggt ggaggtggga  2400
caagggaaag gggtgaatgg tactgctgat tacaacctct ggtgctgcct cccctcctg  2460
tttatctgag aggctagcgt aaatacactt gcaaggagg atgttttag tagcaatttg  2520
tactgatggt atggggccaa gagatatatc ttagagggag ggctgagggt ttgaagtcaa  2580
actcctaagc cagtgccaga agagccaagg acaggtacgg ctgtcatcac ttagacctca  2640
ccctgtggag ccacacccta gggttggcca atcactccc aggagcaggg agggcaggag  2700
ccagggctgg gcataaaagt cagggcagag ccatctattg cttacactcg cttctggaac  2760
gtctgaggtt atcaataagc tcctagtcca gacgccatgg tcatttcac agaggaggac  2820
aaggctacta tcacaagcct gtggggcaag gtgaatgtgg aggaaatgct aggagaaacc  2880
ctgggaaggt aggctctggt gaccaggaca agggaggaa ggaaggaccc tgtgcctggc  2940
aaaagtccag gtcgcttctc aggatttgtg gcacttctg actgtcaaac tgttcttgtc  3000
aatctcacag gctcctggtt gtctacccat ggacccagag gttctttgac agctttggca  3060
acctgtcctc tgcctctgcc atcatgggca accccaaagt caaggcacat gggcaagaagg  3120
tgctgactttc cttgggagat gccacaaagc acctggtgta tctcaaggc acctttgccc  3180
agctgagtga actgcactgt gacaagctgc atgtggatcc tgagaacttc aaggtgagtc  3240
caggagatgt ttcagccctg ttgcctttag tctcgaggca acttagacaa cggagtattg  3300
atctgagcac agcagggtgt gagctgtttg aagatactgg ggtctcgagg tcgacgtaga  3360
taagtagcat ggcgggttaa tcattaacta caaggaaccc ctagtgatgg agttggccac  3420
tccctctctg cgcgctcgct cgctcactga gcgggcgca caaggggt cccgacgccc  3480
gggctttgcc cgggcggcct cagtgagcga gcgagcgcgc cagctggcgt aatagcgaag  3540
aggcccgcac cgatcgccct tcccaacagt tgcgcagcct gaatggcgaa tggcgattcc  3600
gttgcaatgg ctggcggtaa tattgttctg gatattacca gcaaggccga tagtttgagt  3660
tcttctactc aggcaagtga tgttattact aatcaaagaa gtattgcgac aacggttaat  3720
ttgcgtgatg gacagactct tttactcggt ggcctcactg attataaaaa cacttctcag  3780
```

```
gattctggcg taccgttcct gtctaaaatc cctttaatcg gcctcctgtt tagctcccgc 3840
tctgattcta acgaggaaag cacgttatac gtgctcgtca aagcaaccat agtacgcgcc 3900
ctgtagcggc gcattaagcg cggcgggtgt ggtggttacg cgcagcgtga ccgctacact 3960
tgccagcgcc ctagcgcccg ctcctttcgc tttcttccct tccttctcg ccacgttcgc 4020
cggcctttccc cgtcaagctc taaatcgggg gctcccttta gggttccgat ttagtgcttt 4080
acggcacctc gaccccaaaa aacttgatta gggtgatggt tcacgtagtg ggccatcgcc 4140
ctgatagacg gttttttcgcc cttttgacgtt ggagtccacg ttctttaata gtggactctt 4200
gttccaaact ggaacaacac tcaacccat ctcggtctat tcttttgatt tataagggat 4260
tttgccgatt tcggcctatt ggttaaaaaa tgagctgatt taacaaaaat ttaacgcgaa 4320
ttttaacaaa atattaacgt ttacaattta aatattgct tatacaatct tcctgttttt 4380
ggggcttttc tgattatcaa ccggggtaca tatgattgac atgctagttt tacgattacc 4440
gttcatcgat tctcttgttt gctccagact ctcaggcaat gacctgatag cctttgtaga 4500
gacctctcaa aaatagctac cctctccggc atgaatttat cagctagaac ggttgaatat 4560
catattgatg gtgatttgac tgtctccggc ctttctcacc cgtttgaatc tttacctaca 4620
cattactcag gcattgcatt taaaatatat gagggttcta aaaattttta tccttgcgtt 4680
gaaataaagg cttctcccgc aaaagtatta cagggtcata atgttttggg tacaaccgat 4740
ttagctttat gctctgaggc tttattgctt aattttgcta attctttgcc ttgcctgtat 4800
gatttattgg atgttggaat cgcctgatgc ggtattttct ccttacgcat ctgtgcggta 4860
tttcacaccg catatggtgc actctcagta caatctgctc tgatgccgca tagttaagcc 4920
agccccgaca cccgccaaca cccgctgacg cgccctgacg ggcttgtctg ctcccggcat 4980
ccgcttacag acaagctgtg accgtctccg ggagctgcat gtgtcagagg ttttcaccgt 5040
catcaccgaa acgcgcgaga cgaaagggcc tcgtgatacg cctatttttta taggttaatg 5100
tcatgataat aatggtttct tagacgtcag gtggcacttt tcggggaaat gtgcgcggaa 5160
cccctatttg tttatttttc taaatacatt caaatatgta tccgctcatg agacaataac 5220
cctgataaat gcttcaataa tattgaaaaa ggaagagtat gagtattcaa catttccgtg 5280
tcgcccttat tcccttttttt gcggcatttt gccttcctgt ttttgctcac ccagaaacgc 5340
tggtgaaagt aaaagatgct gaagatcagt tgggtgcacg agtgggttac atcgaactgg 5400
atctcaacag cggtaagatc cttgagagtt ttcgccccga agaacgtttt ccaatgatga 5460
gcacttttaa agttctgcta tgtggcgcgg tattatcccg tattgacgcc gggcaagagc 5520
aactcggtcg ccgcatacac tattctcaga atgacttggt tgagtactca cagtcacag 5580
aaaagcatct tacgatggc atgacagtaa gagaattatg cagtgctgcc ataaccatga 5640
gtgataacac tgcggccaac ttacttctga caacgatcgg aggaccgaag gagctaaccg 5700
cttttttgca caacatgggg gatcatgtaa ctcgccttga tcgttgggaa ccggagctga 5760
atgaagccat accaaacgac gagcgtgaca ccacgatgcc tgtagcaatg gcaacaacgt 5820
tgcgcaaact attaactggc gaactactta ctctagcttc ccggcaacaa ttaatagact 5880
ggatggaggc ggataaagtt gcaggaccac ttctgcgctc ggcccttccg gctggctggt 5940
ttattgctga taaatctgga gccggtgagc gtgggtctcg cggtatcatt gcagcactgg 6000
ggccagatgg taagccctcc cgtatcgtag ttatctacac gacggggagt caggcaacta 6060
tggatgaacg aaatagacag atcgctgaga taggtgcctc actgattaag cattggtaac 6120
tgtcagacca agtttactca tatatacttt agattgattt aaaacttcat ttttaattta 6180
aaaggatcta ggtgaagatc ctttttgata atctcatgac caaaatccct taacgtgagt 6240
tttcgttcca ctgagcgtca gaccccgtag aaaagatcaa aggatcttct tgagatcctt 6300
tttttctgcg cgtaatctgc tgcttgcaaa caaaaaaacc accgctacca gcggtggttt 6360
gtttgccgga tcaagagcta ccaactcttt tccgaaggt aactggcttc agcagagcgc 6420
agataccaaa tactgtcctt ctagtgtagc cgtagttagg ccaccacttc aagaactctg 6480
tagcaccgcc tacatacctc gctctgctaa tcctgttacc agtggctgct gccagtggcg 6540
ataagtcgtg tcttaccggg ttggactcaa gacgatagtt accggataag gcgcagcggt 6600
cgggctgaac ggggggttcg tgcacacagc ccagcttgga gcgaacgacc tacaccgaac 6660
tgagatacct acagcgtgag ctatgagaaa gcgccacgct tcccgaaggg agaaaggcgg 6720
acaggtatcc ggtaagcggc agggtcgaa caggagagcg cacgagggag cttccagggg 6780
gaaacgcctg gtatctttat agtcctgtcg ggtttcgcca cctctgactt gagcgtcgat 6840
ttttgtgatg ctcgtcaggg gggcggagcc tatggaaaaa cgccagcaac gcggcctttt 6900
tacggttcct ggccttttgc tggccttttg ctcacatgtt ctttcctgcg ttatcccctg 6960
attctgtgga taaccgtatt accgcctttg agtgagctga taccgctcgc cgcagccgaa 7020
cgaccgagcg cagcgagtca gtgagcgagg aagcggaaga gcgcccaata cgcaaaccgc 7080
ctctccccgc gcgttggccg attcattaat g                           7111
SEQ ID NO: 49           moltype = DNA   length = 8293
FEATURE                 Location/Qualifiers
source                  1..8293
                        mol_type = other DNA
                        organism = Synthetic construct
SEQUENCE: 49
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt cctacgcgta gatctggtgt atacatacat acctgaatat ggaatcaaat 180
atttttctaa gatgaaacag tcatgattta tttcaaatag gtacggataa gtagatattg 240
aggtaagcat taggtcttat attatgtaac actaatctat tactgcgctg aaactgtggc 300
tttataagaa ttgttttcac tgcactattg agaaattaag agataatgac aaaagtcaaa 360
aagagtatat tcaaaaagaa gtatagcact ttttccttag aaaccactgc taactgaaag 420
agactaagat ttgtcccgtc aaaaatcctg gacctatgcc taaaacacat tcacaatcc 480
ctgaactttt caaaaattgg tacatgcttt agctttaaac tacaggcctc actgagctaa 540
gagacaagaa ggtaaaaaac ggctgacaaa agaagtcctg gtatcctcta tgatgggaga 600
aggaaactag ctaaagggaa gaataaatta gagaaaaact tgaagaacta aatcgaaca 660
aggcaaaggc tataaaaaaa attaagcagc agtatcctct tggggggccc ttccccacac 720
tatctcaatg caaatatctg tctgaaacgg tccctggcta aactccaccc atgggttggc 780
cagccttgcc ttgacgctag cgtaaataca cttgcaagg aggatgtttt tagtagcaat 840
ttgtactgat ggtatgggc caagagatat atcttagagg gagggctgag ggtttgaagt 900
ccaactccta agccagtgcc agaagagcca aggacaggta cggctgtcat cacttagacc 960
```

```
tcaccctgtg gagccacacc ctagggttgg ccaatctact cccaggagca gggagggcag    1020
gagccagggc tgggcataaa agtcagggca gagccatcta ttgcttacat ttgcttctga    1080
cacaactgtg ttcactagca acctcaaaca gacaccatgg tgcacctgac tcctgaggag    1140
aagtctgccg ttactgccct gtggggcaag gtgaacgtgg atgaagttgg tggtgaggcc    1200
ctgggcaggt tggtatcaag gttacaagac aggtttaagg agaccaatag aaactgggca    1260
tgtggagaca gagaagactc ttgggtttct gataggcact gactctctct gcctattggt    1320
ctattttccc acccttaggc tgctggtggt ctacccttgg acccagaggt tctttgagtc    1380
ctttggggat ctgtccactc ctgatgctgt tatgggcaac cctaaggtga aggctcatgg    1440
caagaaagtg ctcggtgcct ttagtgatgg cctggctcac ctggacaacc tcaagggcac    1500
ctttgcccag ctgagtgagc tgcactgtga caagctgcac gtggatcctg agaacttcag    1560
ggtgagtcta tgggacccct gatgttttct ttcccccttct tttctatggt taagttcatg    1620
tcataggaag gggagaagta acagggtaca catattgacc aaatcagggt aattttgcat    1680
ttgtaattttt aaaaaatgct ttcttctttt aatatacttt tttgtttatc ttatttctaa    1740
ttcttccct aatctctttc tttcagggca ataatgatac aatgtatcat gcctcttttgc    1800
accattctaa agaataacag tgataatttc tgggttaagg caatagcaat atttctgcat    1860
ataaatattt ctgcatataa attgtaactg atgtaagagg tttcatattg ctaatagcag    1920
ctacaatcca gctaccattc tgcttttatt ttatggttgg gataaggctg gattattctg    1980
agtccaagct aggcccttt gctaatcatg ttcatacctc ttatcttcct cccacagctc    2040
ctgggcaacg tgctggtctg tgtgctggcc catcactttg gcaaagaatt caccccacca    2100
gtgcaggctg cctatcagaa agtggtggct ggtgtggcta atgccctggc ccacaagtat    2160
cactaagctc gctttcttgc tgtccaattt ctattaaagg ttcctttgtt ccctaagtcc    2220
aactactaaa ctgggggata ttatgaaggg ccttgagcat cctgaggattctg cctaataaaa    2280
aacatttatt ttcattgcaa tgatgtatt aaattatttc tgaatatttt actaaaaagg    2340
gaatgtggga ggttcagtg ctagtctccc ggaactatca ctctttcaca gtctgctttg    2400
gaaggactgg gcttagtatg aaaagttagg actgagaaga atttgaaagg gggcttttg    2460
tagcttgata ttcactactg tcttattacc ctatcatagg cccaccccaa atggaagtcc    2520
cattcttcct caggatgttt aagattagca ttcaggaaga gatcagaggt ctgctggctc    2580
ccttatcatg tccctatgg tgcttctggc tctgcaccgc ggccacgggg ttggggttgc    2640
gccttttcca aggcagccct gggtttgcgc agggacgcgg ctgctctggg cgtggttccg    2700
ggaaacgcag cggcgccgac cctgggtctc gcacattctt cacgtccgtt cgcagcgctc    2760
cccggatctt cgccgctacc cttgtgggcc cccggcgac gcttcctgct ccgcccctaa    2820
gtcgggaagg ttccttgcgg ttcgcggcgt gccggacgtg acaaacgaaa gccgcacgtc    2880
tcactagtac cctcgcagac ggacagcgcc agggagcaat ggcagcgcgc cgaccgcgat    2940
gggctgtggc caatagcggc tgctcagcgg ggcgcgccga gagcagcggc cggaaggggg    3000
cggtgcggga ggcggggtgt gggcggtag tgtgggccct gttcctgccc gcgcggtgtt    3060
ccgcattctg caagcctccg gagcgcacgt cggcagtcgg ctccctcgtt gaccgaatca    3120
ccgacctctc tccccagcgg ccgcgccgcc accatggaca aggattgtga aatgaaacgc    3180
accacactgg acagcccttt ggggaagctg gagctgtctg ttgtgagca gggtctgcac    3240
gaaataaagc tcctgggcaa ggggacgtct gcagctgatg ccgtggaggt cccagccccc    3300
gctgcggttc tcgaggtcc ggagcccctg atgcagtgca cagcctggct gaatgccat    3360
ttccaccagc ccgaggctat cgaagagttc ccgtgccgg ctcttcacca tcccgttttc    3420
cagcaagagt cgttcaccag acaggtgtta tggaagctgc tgaaggttgt gaaattcgga    3480
gaagtgattt cttaccagca attagcagcc ctggcagca accccaaagc cgcgcagca    3540
gtgggaggag caatgagagg caatcctgtc aaaatcctca tcccgtgcca cagagtggtc    3600
tgcagcagcg gagccgtggg caactactcc ggaggactgg ccgtgaagga atggcttctg    3660
gcccatgaag gccaccggtt ggggaagcca ggcttgggag ggagctcagg tctggcaggg    3720
gcctggctca agggagcggg agctacctcg ggctcccgc ctgctggccg aaactaagct    3780
ttatttgtga aatttgtgat gctattgctt tatttgtaac cattataagc tgcaataaac    3840
aagttaacaa caacaattgc attcatttta tgtttcaggt tcaggggag atgtggagg    3900
ttttttaaag ccctgcaggc aatagccttg acaaggcaaa cttgaccaat agtcttagag    3960
tatccagtga ggcagggc cggcggctgg ctagggatga agaataaaag gaagcaccct    4020
tcagcagttc cacacactcg cttctggaac gtctgaggtt atcaataagc tcctagtcca    4080
gacgccatgg gtcatttcac agaggaggac aagctactac tcacaagcct gtggggcaag    4140
gtgaatgtgg aagatgctgg aggagaaacc ctggaaggt aggctctggt gaccaggaca    4200
aggagggaa ggaaggaccc tgtgcctggc aaaagtccag gtcgcttctc aggatttgtg    4260
gcaccttctg actgtcaaac tgttcttgtc aatctcacag gctcctggtt gtctacccat    4320
ggacccagag gttctttgac agctttggca acctgtcctc tgcctgtgcc atcatgggca    4380
accccaaagt caaggcacat ggcaagaagg tgctgacttc cttgggagat gccacaaagc    4440
acctggatga tctcaagggc accttttgcc agctgagtga actgcactgt gacaagctgc    4500
atgtggatcc tgagaacttc aaggtgagtc caggagatgt ttcagccctg ttgcctttag    4560
tctcgaggcg tcgacaggaa ccccagtga tggagttggc cactccctct ctgcgcgctc    4620
gctcgctcac tgaggccggg cgaccaaagg tcgcccgacg cccgggcttt gcccgggcgg    4680
cctcagtgag cgagcgagcg cgcagctggc gtaatagcga gaggcccgc accgatcgcc    4740
cttcccaaca gttgcgcagc ctgaatgcg aatggcgatt ccgttgcaat ggctggcggt    4800
aatattgttc tggatattac cagcaaggcc gatagtttga gttcttctac tcaggcaagt    4860
gatgttatta ctaatcaaag aagtattgcg acaacggtta atttgcgtga tggacagact    4920
cttttactcg gtgccctcac tgattataaa aacacttctc aggattctgg cgtaccgttc    4980
ctgtctaaaa tccctttaat cggcctcctg tttagctccc gctctgattc taacgaggaa    5040
agcacgttat acgtgctcgt caaagcaacc atagtacgcg ccctgtagcg cgcattaag    5100
cgcggcggt gtggtggtta cgcgcagcgt gaccgctaca cttgccagcg ccctagcgcc    5160
cgctcctttc gctttcttcc cttcctttct cgccacgttc gccggctttc cccgtcaagc    5220
tctaaatcgg gggctccctt tagggttccg atttagtgct ttacggcacc tcgaccccaa    5280
aaaacttgat tagggtgatg gttcacgtag tgggccatcg ccctgataga cggtttttcg    5340
ccctttgacg ttggagtcca cgttctttaa tagtggactc ttgttccaaa ctggaacaac    5400
actcaaccct atctcggtct attcttttga tttataaggg attttgccga tttcggccta    5460
ttggttaaaa aatgagctga tttaacaaaa atttaacgcg aatttaaca aaatattaac    5520
gtttacaatt taaatatttg cttatacaat cttcctgttt ttggggcttt tctgattatc    5580
aaccgggggta catatgattg acatgctagt tttacgatta ccgttcatcg attctcttgt    5640
ttgctccaga ctctcaggca atgacctgat agcctttgta gagacctctc aaaaatagct    5700
```

```
acctctccg gcatgaattt atcagctaga acggttgaat atcatattga tggtgatttg   5760
actgtctccg gcctttctca cccgtttgaa tctttaccta cacattactc aggcattgca   5820
tttaaaatat atgagggttc taaaaatttt tatccttgcg ttgaaataaa ggcttctccc   5880
gcaaaagtat tacagggtca taatgttttt ggtacaaccg atttagcttt atgctctgag   5940
gctttattgc ttaattttgc taattctttg ccttgcctgt atgatttatt ggatgttgaa   6000
atcgcctgat gcggtatttt ctccttacgc atctgtgcgg tatttcacac cgcatatggt   6060
gcactctcag tacaatctgc tctgatgccg catagttaag ccagcccga cacccgccaa    6120
cacccgctga cgcgccctga cgggcttgtc tgctcccggc atccgcttac agacaagctg   6180
tgaccgtctc cgggagctgc atgtgtcaga ggttttcacc gtcatcaccg aaacgcgtga   6240
gacgaaaggg cctcgtgata cgcctatttt tataggttaa tgtcatgata ataatggttt   6300
cttagacgtc aggtggcact tttcggggaa atgtgcgcgg aaccctatt  tgtttatttt   6360
tctaaataca ttcaaatatg tatccgctca tgagacaata accctgataa atgcttcaat   6420
aatattgaaa aaggaagagt atgagtattc aacatttccg tgtcgccctt attcccttt    6480
ttgcggcatt ttgccttcct gttttgctc acccagaaac gctggtgaaa gtaaaagatg   6540
ctgaagatca gttgggtgca cgagtgggtt acatcgaact ggatctcaac agcggtaaga   6600
tccttgagag tttcgcccc  gaagaacgtt ttccaatgat gagcactttt aaagttctgc   6660
tatgtggcgc ggtattatcc cgtattgacg ccgggcaaga gcaactcggt cgccgcatac   6720
actattctca gaatgacttg gttgagtact caccagtcac agaaaagcat cttacggatg   6780
gcatgacagt aagagaatta tgcagtgctg ccataaccat gagtgataac actgcggcca   6840
acttacttct gacaacgatc ggaggaccga aggagctaac cgctttttg  cacaacatgg   6900
gggatcatgt aactcgcctt gatcgttggg aaccggagct gaatgaagcc ataccaaacg   6960
acgagcgtga ccacgatgc  cctgtagcaa tggcaacaac gttgcgcaaa ctattaactg   7020
gcgaactact tactctagct tcccggcaac aattaataga ctggatggag gcggataaag   7080
ttgcaggacc acttctgcgc tcggcccttc cggctggctg gtttattgct gataaatctg   7140
gagccggtga gcgtgggtct cgcggtatca ttgcagcact ggggccagat ggtaagccct   7200
cccgtatcgt agttatctac acgacgggga gtcaggcaac tatggatgaa cgaaatagac   7260
agatcgctga gataggtgcc tcactgatta gcattggta  actgtcagac caagtttact   7320
catatatact ttagattgat ttaaaacttc atttttaatt taaaaggatc taggtgaaga   7380
tccttttga  taatctcatg accaaaatcc cttaacgtga gttttcgttc cactgagcgt   7440
cagacccgt  agaaaagatc aaaggatctt cttgagatcc ttttttctg  cgcgtaatct   7500
gctgcttgca aacaaaaaaa ccaccgctac cagcggtggt ttgtttgccg gatcaagagc   7560
taccaactct ttttccgaag gtaactggct tcagcagagc gcagatacca aatactgtcc   7620
ttctagtgta gccgtagtta ggccaccact tcaagaactc tgtagcaccg cctacatacc   7680
tcgctctgct aatcctgtta ccagtggctg ctgccagtgg cgataagtcg tgtcttaccg   7740
ggttggactc aagacgatag ttaccggata aggcgcagcg gtcgggctga acggggggt   7800
cgtgcacaca gcccagcttg gagcgaacga cctacaccga actgagatac ctacagcgtg   7860
agctatgaga aagcgccacg cttcccgaag ggagaaaggc ggacaggtat ccggtaagcg   7920
gcagggtcgg aacaggagag cgcacgaggg agcttccagg gggaaacgcc tggtatcttt   7980
atagtcctgt cgggtttcgc cacctctgac ttgagcgtca ttttttgtga tgctcgtcag   8040
ggggcggag  cctatggaaa aacgccagca acgcggcctt tttacggttc ctggcctttt   8100
gctggccttt tgctcacatg ttctttcctg cgttatcccc tgattctgtg ataaccgta    8160
ttaccgcctt tgagtgagct gataccgctc gccgcagccg aacgaccgag cgcagcgagt   8220
cagtgagcga ggaagcggaa gagcgcccaa tacgcaaacc gcctctcccc gcgcgttggc   8280
cgattcatta atg                                                     8293
SEQ ID NO: 50           moltype = DNA   length = 8290
FEATURE                 Location/Qualifiers
source                  1..8290
                        mol_type = other DNA
                        organism = Synthetic construct
SEQUENCE: 50
cagctgcgcg ctcgctcgct cactgaggcc gcccgggcaa agcccgggcg tcggcgacc    60
tttggtcgcc cggcctcagt gagcgagcga gcgcgcagag agggagtggc caactccatc   120
actagggggt cctacgcgta gatctgtggc tttatagaaa ttgttttcac tgcactattg   180
agaaattaag agataatggc aaaagtcaca aagagtactt tcaaaaagaa gtatagcact   240
ttttccttag aaaccactgc taactgaaag agactaagat tgtcccgtc  aaaaatcctg   300
gacctatgcc taaaacacat ttcacaatcc ctgaactttt caaaaattgg tacatgcttt   360
agctttaaac tacaggcctc actggagcta gagacaagaa ggtaaaaaac ggctgacaaa   420
agaagtcctg gtatcctcta tgatgggaga aggaaactag ctaaagggaa gaataaatta   480
gagaaaaact ggaatgactg aatcggaaca aggcaaaggc tataaaaaaa attaagcagc   540
agtatcctct tgggggcccc ttccccacac tatctcaatg caaatatctg tctgaaacgg   600
tccctggcta aactccaccc atgggttggc cagccttgcc ttgacgctag cgtaaataca   660
cttgcaaagg aggatgtttt tagtagcaat ttgtactgat ggtatgggc  caagagatat   720
atcttagagg gagggctgag ggtttgaagt ccaactccta agccagtgcc agaagagcca   780
aggacaggta cggctgtcat cacttagacc tcaccctgtg gagccacacc ctagggttgg   840
ccaatctact cccaggagca gggagggcag gagccagggc tgggcataaa agtcagggca   900
gagccatcta ttgcttacat ttgcttctga cacaactgtg ttcactagca acctcaaaca   960
gacaccatgg tgcaccctga cctctgagga agtctgccg  ttactgcctt gtggggcaag  1020
gtgaacgtgg atgaagttgg tggtgaggcc ctgggcaggt tggtatcaag gttacaagac  1080
aggtttaagg agaccaatag aaactgggca tgtggagaca gagaagactc ttgggtttct  1140
gataggcact gactctctct gcctattggt ctatttccc  accctaggc  tgctggtggt  1200
ctacccttgg acccagaggt tctttgagtc ctttggggat ctgtccactc ctgatgctgt  1260
tatgggcaac cctaaggtga aggctcatgg caagaaagtg ctcggtgcct ttagtgatgg  1320
cctggctcac ctggacaacc tcaagggcac ctttgccaca ctgagtgagc tgcactgtga  1380
caagctgcac gtggatcctg agaacttcag ggtgagtcta tgggaccctt gatgttttct  1440
ttccccttct tttctatggt taagttcatg tcataggaag ggagaagta  acagggtaca  1500
catattgacc aaatcagggt aattttgcat ttgtaatttt aaaaaatgct tcttcttttt  1560
aatatacttt ttgttttatc ttatttctaa tactttccct aatctctttc tttcagggca  1620
ataatgatac aatgtatcat gcctctttgc accattctaa agaataacag tgataatttc  1680
```

```
tgggttaagg caatagcaat atttctgcat ataaatattt ctgcatataa attgtaactg 1740
atgtaagagg tttcatattg ctaatagcag ctacaatcca gctaccattc tgcttttatt 1800
ttatggttgg gataaggctg gattattctg agtccaagct aggcccttttt gctaatcatg 1860
ttcataccctc ttatcttcct cccacagctc ctgggcaacg tgctggtctg tgtgctggcc 1920
catcactttg gcaaagaatt caccccacca gtgcaggctg cctatcagaa agtggtggct 1980
ggtgtggcta atgccctggc ccacaagtat cactaagctc gctttcttgc tgtccaattt 2040
ctattaaagg ttcccttgtt ccctaagtcc aactactaaa ctgggggata ttatgaaggg 2100
ccttgagcat ctggattctg cctaataaaa aacatttatt ttcattgcaa tgatgtattt 2160
aaattatttc tgaatatttt actaaaaagg gaatgtggga ggttgcagtg ctagtctcat 2220
ggaactatca ctctttcaca gtctgcttct gaaggactgg gcttagtatg aaaagttagg 2280
actgagaaga atttgaaagg gggctttttg tagcttgata ttcactactg tcttattacc 2340
ctatcatagg cccaccccaa atggaagtcc cattcttcct caggatgttt aagattagca 2400
ttcaggaaga gatcagaggt ctgctggctc ccttatcatg tcccttatgg tgcttctggc 2460
tctgcaccgc ggccacgggg ttggggttgc gccttttcca aggcagccct gggtttgcgc 2520
agggacgcgg ctgctctggg cgtggttccg ggaaacgcag cggcgccgac cctgggtctc 2580
gcacattctt cacgtccgtt cgcagcgtca cccggatctt cgccgctacc cttgtgggcc 2640
ccccggcgac gcttcctgct ccgccctaa gtcgggaagg ttccttgcgg ttcgcggcgt 2700
gccggacgtg acaaacggaa gccgcacgtc tcactagtac cctcgcagac ggacagcgcc 2760
agggagcaat ggcagcgcgc cgaccgcgat gggctgtggc caatagcggc tgctcagcgg 2820
ggcgcgccga gagcagcggc cgggaagggg cggtgcggga ggcggggtgt ggggcggtag 2880
tgtgggccct gttcctgccc gcgcggtgtt ccgcattctg caagcctccg gagcgcacgt 2940
cggcagtcgg ctccctcgtt gaccgaatca ccgacctctc tccccagcgg ccgcgccgcc 3000
accatggaca aggattgtga aatgaaacgc accacactgg acagcccttt ggggaagctg 3060
gagctgtctg gttgtgagca gggtctgcac gaaataaagc tcctgggcaa ggggacgtct 3120
gcagctgatg ccgtggaggt cccagccccc gctgcggttc tcgaggtcc ggagccctg 3180
atgcagtgca cagcctggct gaatgcctat ttccaccagc ccgaggctat cgaagagttc 3240
cccgtgccgg ctcttcacca tcccgttttc cagcaagagt cgttcaccag acaggtgtta 3300
tggaagctgc tgaaggttgt gaaattcgga gaagtgattt cttaccagca attagcagcc 3360
ctggcaggca acccccaaagc cgcgcgagca gtgggaggag caatgagagg caatcctgtc 3420
aaaatcctca tcccgtgcca cagagtggtc tgcagcaggg agccgtggtg caactactcc 3480
ggaggactgg ccgtgaagga atggcttctg gcccatgaag ccaccggtt ggggaagcca 3540
ggcttgggag ggagctcagg tctgcaggg gcctggctca agggagcggg agctacctcg 3600
ggctccccgc ctgctggccg aaactaagat aatcaacctc tggattacaa aatttgtgaa 3660
agattgactg gtattcttaa ctatgttgct ccttttacgc tatgtggata cgctgctttta 3720
atgcctttgt atcatgctat tgcttcccgt atggcttttca ttttctcctc cttgtataaa 3780
tcctggttag ttcttgccac ggcggaactc atcgccgcct gccttgcccg ctgctggaca 3840
ggggctcggc tgttgggcac tgacaattcc gtggtgttta tttgtgaaat ttgtgatgct 3900
attgctttat ttgtaaccat tctagcttta tttgtgaaat ttgtgatgct attgctttat 3960
ttgtaaccat tataagctgc aataaacaag ttaacaacaa caattgcatt cattttatgt 4020
ttcaggttca gggggaatg tgggaggttt ttaaagccc tgcaggcaat agccttgaca 4080
aggcaaactt gaccaatagt cttagagtat ccagtgagc cagggggcg cggctggcta 4140
gggatgaaga ataaaaggaa gcacccttca gcagttccac acactcgctt ctggaacgtc 4200
tgaggttatc aataagctcc tagtccagac gccatggctc atttcacaga aggagacaag 4260
gctactatca caagcctgtg gggcaaggtg aatgtggaag atgctggagg agaaaccctg 4320
ggaaggtagg ctctggtgac caggacaagg gagggaagga aggaccctgt gcctggcaaa 4380
agtccaggtc gcttctcagg atttgtgca ccttctgact gtcaaactgt tcttgtcaat 4440
ctcacaggct cctggttgtc tacccatgga cccagagttt ctttgacagc tttggcaacc 4500
tgtcctctgc ctctgccatc atgggcaacc caaagtcaa ggcacatggc aagaaggtgc 4560
tgacttgtcg acaggaaccc ctagtgatgg agttggccac tccctctctg cgcgctcgct 4620
cgctcactga ggccgggcga ccaaaggtcg cccgacgccc gggctttgcc cggcggcct 4680
cagtgagcga gcgagcgcgc agctggcgta atagcgaaga gcccgcgcc gatcgccctt 4740
cccaacagtt gcgcagcctg aatggcgaat ggcgattccg ttgcaatggc tgcggtaat 4800
attgttctgg atattaccag caaggccgat agtttgagtt cttctactca ggcaagtgat 4860
gttattacta atcaaagaag tattgcgaca acggttaatt tgcgtgatgg acagactctt 4920
ttactcggtg gcctcactga ttataaaaac acttctcagg attctggcgt accgttcctg 4980
tctaaaatcc ctttaatcgg cctcctgttt agctcccgct ctgattctaa cgaggaaagc 5040
acgttatacg tgctcgtcaa agcaaccata gtacgcgccc tgtagcggcg cattaagcgc 5100
ggcgggtgtg gtggttacgc gcagcgtgac cgctacactt gccagcgccc tagcgcccgc 5160
tcctttcgct ttcttccctt cctttctcgc cacgttcgcc ggctttccc gtcaagctct 5220
aaatcgggg ctcccttag ggttccgatt tagtgcttta cggcacctcg acccccaaaa 5280
acttgattag ggtgatggtt cacgtagtgg gccatcgccc tgatagacgg ttttttcgccc 5340
tttgacgttg gagtccacgt tctttaatag tggactcttg ttccaaactg gaacaacact 5400
caaccctatc tcggtctatt cttttgattt ataaggatt ttgccgattt cggcctattg 5460
gttaaaaaat gagctgattt aacaaaaatt taacgcgaa tttaacaaaa tattaagctt 5520
tacaatttaa atatttgctt atacaatctt cctgttttg gggcttttct gattatcaac 5580
cggggtacat atgattgaca tgctagtttt acgattaccg ttcatcgatt ctcttgtttg 5640
ctccagactc tcaggcaatg acctgatagc ctttgtagag acctctcaaa aatagctacc 5700
ctctccggca tgaatttatc agctaagacg gttgaatatc atattgatgg tgatttgact 5760
gtctccggcc tttctcaccc gtttgaatct ttacctacac attactcaga cattgcattt 5820
aaaatatatg agggttctaa aaattttat ccttgcgttg aaataaaggc ttctcccgca 5880
aaagtattac agggtcataa tgtttttggt acaaccgatt tagctttatg ctctgaggct 5940
ttattgctta attttgctaa ttctttgcct tgcctgtatg atttattgga tgttggaatc 6000
gcctgatgcg gtatttttctc cttacgcatc tgtgcggtat ttcacaccgc atatggtgca 6060
ctctcagtac aatctgctct gatgccgcat agttaagcca gtatacactc cgctagcgct 6120
ccgctgacgc gccctgacgg gcttgtctgc tcccggcatc cgcttacaga caagctgtga 6180
ccgtctccgg gagctgcatg tgtcagaggt tttcaccgtc atcaccgaaa cgcgcgagac 6240
gaaagggcct cgtgatacgc ctatttttat aggttaatgt catgataata atggtttctt 6300
agacgtcagg tggcactttt cggggaaatg tgcgcggaac ccctatttgt ttattttctct 6360
aaatacattc aaatatgtat ccgctcatga gacaataacc ctgataaatg cttcaataat 6420
```

```
attgaaaaag gaagagtatg agtattcaac atttccgtgt cgcccttatt ccctttttg   6480
cggcattttg ccttcctgtt tttgctcacc cagaaacgct ggtgaaagta aaagatgctg   6540
aagatcagtt gggtgcacga gtgggttaca tcgaactgga tctcaacagc ggtaagatcc   6600
ttgagagttt tcgccccgaa gaacgttttc caatgatgag cacttttaaa gttctgctat   6660
gtggcgcggt attatcccgt attgacgccg ggcaagagca actcggtcgc cgcatacact   6720
attctcagaa tgacttggtt gagtactcac cagtcacaga aaagcatctt acggatggca   6780
tgacagtaag agaattatgc agtgctgcca taaccatgag tgataacact gcggccaact   6840
tacttctgac aacgatcgga ggaccgaagg agctaaccgc ttttttgcac aacatggggg   6900
atcatgtaac tcgccttgat cgttgggaac cggagctgaa tgaagccata ccaaacgacg   6960
agcgtgacac cacgatgcct gtagcaatgg caacaacgtt gcgcaaacta ttaactggcg   7020
aactacttac tctagcttcc cggcaacaat taatagactg gatggaggcg gataaagttg   7080
caggaccact tctgcgctcg gcccttccgg ctggctggtt tattgctgat aaatctggag   7140
ccggtgagcg tgggtctcgc ggtatcattg cagcactggg gccagatggt aagccctccc   7200
gtatcgtagt tatctacacg acggggagtc aggcaactat ggatgaacga aatagacaga   7260
tcgctgagat aggtgcctca ctgattaagc attggtaact gtcagaccaa gtttactcat   7320
atatacttta gattgattta aaacttcatt tttaatttaa aaggatctag gtgaagatcc   7380
tttttgataa tctcatgacc aaaatccctt aacgtgagtt ttcgttccac tgagcgtcag   7440
accccgtaga aaagatcaaa ggatcttctt gagatccttt ttttctgcgc gtaatctgct   7500
gcttgcaaac aaaaaaacca ccgctaccag cggtggtttg tttgccggat caagagctac   7560
caactctttt tccgaaggta actggcttca gcagagcgca gataccaaat actgtccttc   7620
tagtgtagcc gtagttaggc caccacttca agaactctgt agcaccgcct acatacctcg   7680
ctctgctaat cctgttacca gtggctgctg ccagtggcga taagtcgtgt cttaccgggt   7740
tggactcaag acgatagtta ccggataagg cgcagcggtc gggctgaacg ggggggttcgt   7800
gcacacagcc cagcttggag cgaacgacct acaccgaact gagatacctac agcgtgagc   7860
tatgagaaag cgccacgctt cccgaaggga gaaaggcgga caggtatccg gtaagcggca   7920
gggtcggaac aggagagcgc acgagggagc ttccaggga aaacgcctgg tatctttata   7980
gtcctgtcgg gtttcgccac ctctgacttg agcgtcgatt tttgtgatgc tcgtcagggg   8040
ggcggagcct atgaaaaac gccagcaacg cggccttttt acggttcctg gccttttgct   8100
ggccttttgc tcacatgttc tttcctgcgt tatcccctga ttctgtggat aaccgtatta   8160
ccgcctttga gtgagctgat accgctcgcc gcagccgaac gaccgagcgc agcgagtcag   8220
tgagcgagga agcggaagag cgcccaatac gcaaaccgcc tctccccgcg cgttggccga   8280
ttcattaatg                                                          8290

SEQ ID NO: 51          moltype = DNA  length = 8222
FEATURE                Location/Qualifiers
source                 1..8222
                       mol_type = other DNA
                       organism = Synthetic construct
SEQUENCE: 51
cagctgcgcg ctcgctcgct cactgaggcc gcccgggcaa agcccgggcg tcggcgacc    60
tttggtcgcc cggcctcagt gagcgagcga gcgcgcagag agggagtggc caactccatc   120
actagggggtt cctacgcgta gatctggtgt atacatacat acctgaatat ggaatcaaat   180
attttctcaa gatgaaacag tcatgattta tttcaaatag gtacggataa gtagatattg   240
aggtaagcat taggtcttat attatgtaac actaatctat tactgcgctg aaactgtggc   300
tttatagaaa ttgttttcac tgcactattg agaaattaag agataatggc aaaagtcaca   360
aagagtatat tcaaaagaa gtatagcact ttttccttag aaaccactgc taactgaaag   420
agactaagat ttgtcccgtc aaaaatcctg gacctatgcc aaaacacat ttcacaatcc   480
ctgaacttt caaaaattgg tacatgcttt agctttaaac tacaggcctc actggagcta   540
gagacaagaa ggtaaaaaac ggctgacaaa agaagtcctg gtatcctcta tgatgggaga   600
aggaaactag ctaaagggaa gaataaatta gagaaaact ggaatgactg aatcggaaca   660
aggcaagtgc tataaaaaaa attaagcagc agtatcctct tgggggcccc ttcccccac   720
tatctcaatg caaatatctg tctgaaacg tccctggcta aactccaccc atgggttggc   780
cagccttgcc ttgacgctag cgtaaataca cttgcaaagg aggatgtttt tagtagcaat   840
ttgtactgat ggtatgggc caagagatat atcttagagg gagggctgag ggttttgaagt   900
ccaactccta agcccagtgcc agaagagcca aggacagtca cgctgtcat cacttagacc   960
tcacctgtg gagccacacc ctaggggttgg ccaatctact cccaggagca ggagagggcag   1020
gagccagggc tgggcataaa agtcagggca gagccatca ttgcttacat ttgcttctga   1080
cacaactgtg ttcactagca acctcaaaca gacaccatgg tgcacctgac tcctgaggag   1140
aagtctgccg ttactgccct gtggggcaag gtgaacgtgg atgaagttgg tggtgaggcc   1200
ctgggcaggt tggtatcaag gttacaagac aggtttaagg agaccaatag aaactgggca   1260
tgtggagaca gagaagactc ttgggtttct gataggcact gactctctct gcctattggt   1320
ctatttcccc acccttaggc tgctggtggt ctacccttgg acccagaggt tctttgagtc   1380
cttttggggat ctgtccactc ctgatgctgt tatgggcaac cctaaggtga aggctcatgg   1440
caagaaagtg ctcggtgcct ttagtgatgg cctggctcac ctggacaacc tcaaggcgac   1500
ctttgcccag ctgagtgagc tgcactgtga caagctgcac gtggatcctg agaacttcag   1560
ggtgagtcta tgggacccct tgatgttttct ttccccttct tttctatggt taagttcatg   1620
tcataggaag gggagaagta acagggtaca catattgacc aaatcagggt aattttgcat   1680
ttgtaattttt aaaaaatgct ttcttctttt aatatacttt tttgtttatc ttatttctaa   1740
tactttccct aatctctttc tttcagggca ataatgatac aatgtatcat gcctctttgc   1800
accattctaa agaataacag tgataatttc tgggttaagg caatagcaat atttctgcat   1860
ataaatattt ctgcatataa attgtaactg atgtaagagg tttcatattg ctaatagcag   1920
ctacaatcca gctaccattc tgcttttatt ttatggttgg gataagctg gattattctg   1980
agtccaagct aggcccttt gctaatcatg ttcataccttc ttatcttcct cccacagctc   2040
ctgggcaacg tgctggtctg tgtgctggcc catcactttg gcaaagaatt caccccacca   2100
gtgcaggctg cctatcagaa agtggtggct ggtgtggcta atgccctggc ccacaagtat   2160
cactaagctc gctttcttgc tgtccaattt ctattaaagg ttcctttgtt ccctaagtcc   2220
aactactaaa ctgggggata ttatgaaggg ccttgagcat ctggattctg cctaataaaa   2280
aacatttatt ttcattgcaa tgatgtattt aaattatttc tgaatatttt actaaaaagg   2340
gaatgtggga ggttgcagtg ctagtctccc ggaactatca ctctttcaca gtctgctttg   2400
```

```
gaaggactgg gcttagtatg aaaagttagg actgagaaga atttgaaagg gggcttttg    2460
tagcttgata ttcactactg tcttattacc ctatcatagg cccacccaa atggaagtcc     2520
cattcttcct caggatgttt aagattagca ttcaggaaga gatcagaggt ctgctggctc    2580
ccttatcatg tcccttatgg tgcttctggc tctgcaccgc gggaacagag aaacaggaga    2640
atatgggcca aacaggatat ctgtggtaag cagttcctgc cccggctcag ggccaagaac    2700
agttggaaca gcagaatatg ggccaaacag gatatctgtg gtaagcagtt cctgccccgg    2760
ctcagggcca agaacagatg gtccccagat gcggtcccgc cctcagcagt ttctagagaa    2820
ccatcagatg tttccagggt gccccaagga cctgaaatga ccctgtgcct tatttgaact    2880
aaccaatcag ttcgcttctc gcttctgttc gcgcgctcct gctccccgag ctctatataa    2940
gcagagctcg tttagtgaac cgtcagatcg cggccgcgcc gccaccatgg tgagcaaggg    3000
cgaggagctg ttcaccgggg tggtgcccat cctggtcgag ctggacggcg acgtaaacgg    3060
ccacaagttc agcgtgtccg gcgagggcga gggcgatgcc acctacggca agctgaccct    3120
gaagttcatc tgcaccaccg gcaagctgcc cgtgccctgg cccaccctcg tgaccaccct    3180
gacctacggc gtgcagtgct tcagccgcta ccccgaccac atgaagcagc acgacttctt    3240
caagtccgcc atgcccgaag gctacgtcca ggagcgcacc atcttcttca aggacgacgg    3300
caactacaag acccgcgccg aggtgaagtt cgagggcgac accctggtga accgcatcga    3360
gctgaagggc atcgacttca aggaggacgg caacatcctg gggcacaagc tggagtacaa    3420
ctacaacagc cacaacgtct atatcatggc cgacaagcag aagaacggca tcaaggtgaa    3480
cttcaagatc cgccacaaca tcgaggacgg cagcgtgcag ctcgccgacc actaccagca    3540
gaacaccccc atcggcgacg gccccgtgct gctgcccgac aaccactacc tgagcaccca    3600
gtccgccctg agcaaagacc ccaacgagaa gcgcgatcac atggtcctgc tggagttcgt    3660
gaccgccgcc gggatcactc tcggcatgga cgagctgtac aagtaagctt tatttgtgaa    3720
atttgtgatg ctattgcttt atttgtaacc attataagct gcaataaaca agttaacaac    3780
aacaattgca ttcattttat gtttcaggtt caggggaga tgtgggaggt tttttaaagc     3840
cctgcaggca atagccttga caaggcaaac ttgaccaata gtcttagagt atccagtgag    3900
gccagggcc ggcggctggc tagggatgaa gaataaaagg aagcacccct cagcagttcc     3960
acacactcgc ttctggaacg tctgaggtta tcaataagct cctagtccag acgccatggg    4020
tcatttcaca gaggaggaca aggctactat cacaagcctg tggggcaagg tgaatgtgga    4080
agatgctgga ggagaaaccc tgggaaggta ggctctggtg accaggacaa gggagggaag    4140
gaaggaccct gtgcctggca aaagtccagg tcgcttctca ggatttgtgg caccttctga    4200
ctgtcaaaact gttcttgtca atctcacagg ctcctggttg tctacccatg gacccagagg    4260
ttctttgaca gctttggcaa cctgtcctct gcctctgcca tcatgggcaa ccccaaagtc    4320
aaggcacatg gcaagaaggt gctgacttcc ttgggagatg ccacaaagca cctggatgat    4380
ctcaagggca cctttgccca gctgagtgaa ctgcactgtg acaagctgca tgtggatcct    4440
gagaacttca aggtgagtcc aggagatgtt tcagcctgt tgcctttagt ctcgaggcgt     4500
cgacaggaac ccctagtgat ggagttggcc actccctctc tgcgcgctcg ctcgctcact    4560
gaggccgggc gaccaaggt cgcccgacgc ccgggctttg cccgggcggc ctcagtgagc     4620
gagcgagcgc gcagctggcg taatagcgaa gaggcccgca ccgatcgccc ttcccaacag    4680
ttgcgcagcc tgaatggcga atggcgattc cgttgcaagt gctggcggta atattgttca    4740
ggatattacc agcaaggccg atagtttgag ttcttctact caggcaagtg atgttattac    4800
taatcaaaga agtattgcga caacggttaa tttgcgtgat ggacagactc ttttactcgg    4860
tggcctcact gattataaaa acacttctca ggattctggc gtaccgttcc tgtctaaaat    4920
ccctttaatc ggcctcctgt ttagctcccg tctgattct aacgaggaaa gcacgttata    4980
cgtgctcgtc aaagcaacca tagtacgcgc cctgtagcgg cgcattaagc gcggcgggtg    5040
tggtggttac gcgcagcgtg accgctacac ttgccagcgc cctagcgccc gctcctttcg    5100
cttcttccc ttcttctc gccacgttcg ccggcttc ccgtcaagct ctaaatcggg         5160
ggctcccttt aggtccga tttagtgctt tacggcacct cgaccccaaa aaacttgatt      5220
agggtgatgg ttcacgtagt gggccatcgc cctgatagac ggtttttcgc cctttgacgt    5280
tggagtccac gttctttaat agtggactct tgttccaaac tggaacaaca ctcaaccctta   5340
tctcggtcta ttcttttgat ttataaggga ttttgccgat ttcggcctat tggttaaaaa    5400
atgagctgat ttaacaaaaa tttaacgcga attttaacaa aatattaacg tttacaattt    5460
aaatatttgc ttatacaatc ttcctgtttt tggggcttt ctgattatca accggggtac     5520
atatgattga catgctagtt ttacgattac cgttcatcga ttctcttgtt tgctccagac    5580
tctcaggcaa tgacctgata gcctttgtag agacctctca aaaatagcta ccctctccgg    5640
catgaattta tcagctagaa cggttgaata tcatattgat ggtgatttga ctgtctccgg    5700
cctttctcac ccgttgaat ctttacctac acattactca ggcattgcat ttaaaatata    5760
tgagggttct aaaaattttt atccttgcgt tgaaataaag gcttctcccg caaaagtatt    5820
acagggtcat aatgttttg gtacaaccga tttagcttta tgctctgagg ctttattgct     5880
taattttgct aattctttgc cttgcctgta tgatttattg gatgttggaa tcgcctgatg    5940
cggtattttc tccttacgca tctgtgcggt atttcacacc gcatatggtg cactctcagt    6000
acaatctgct ctgatgccgc atagttaagc cagccccgac acccgccaac acccgctgac    6060
gcgccctgac gggcttgtct gctcccggca tccgcttaca gacaagctgt gaccgtctcc    6120
gggagctgca tgtgtcagag gttttcaccg tcatcaccga aacgcgcgag acgaaagggc    6180
ctcgtgatac gcctattttt ataggttaat gtcatgataa taatggtttc ttagacgtca    6240
ggtggcactt ttcggggaaa tgtgcgcgga acccctattt gtttattttt ctaaatacat    6300
tcaaatatgt atccgctcat gagacaataa ccctgataaa tgcttcaata atattgaaaa    6360
aggaagagta tgagtattca acatttccgt gtcgccctta ttcccttttt tgcggcattt    6420
tgccttcctg ttttgctca cccagaaacg ctggtgaaag taaaagatgc tgaagatcag    6480
ttgggtgcac gagtgggtta catcgaactg gatctcaaca gcggtaagat cttgagagt     6540
tttcgccccg aagaacgttt tccaatgatg agcactttta aagttctgct atgtggcgcg    6600
gtattatccc gtattgacgc cgggcaagag caactcggtc gccgcataca ctattctcag    6660
aatgacttgg ttgagtactc accagtcaca gaaaagcatc ttacgatgg catgacagta    6720
agagaattat gcagtgctgc cataaccatg agtgataaca ctgcggccaa cttacttctg    6780
acaacgatcg gaggaccgaa ggagctaacc gcttttttgc acaacatggg ggatcatgta    6840
actcgccttg atcgttggga accggagctg aatgaagcca taccaaacga cgagcgtgac    6900
accacgatgc ctgtagcaat ggcaacaacg ttgcgcaaac tattaactgg cgaactactt    6960
actctagctt cccggcaaca attaatagac tggatggagg cggataaagt tgcaggacca    7020
cttctgcgct cggcccttcc ggctggctgg tttattgctg ataaatctgg agccggtgag    7080
cgtgggtctc gcggtatcat tgcagcactg gggccagatg gtaagccctc ccgtatcgta    7140
```

```
gttatctaca cgacggggag tcaggcaact atggatgaac gaaatagaca gatcgctgag    7200
ataggtgcct cactgattaa gcattggtaa ctgtcagacc aagtttactc atatatactt    7260
tagattgatt taaaacttca tttttaattt aaaaggatct aggtgaagat ccttttttgat   7320
aatctcatga ccaaaatccc ttaacgtgag ttttcgttcc actgagcgtc agaccccgta    7380
gaaaagatca aaggatcttc ttgagatcct ttttttctgc gcgtaatctg ctgcttgcaa    7440
acaaaaaaac caccgctacc agcggtggtt tgtttgccgg atcaagagct accaactctt    7500
tttccgaagg taactggctt cagcagagcg cagataccaa atactgtcct tctagtgtag    7560
ccgtagttag gccaccactt caagaactct gtagcaccgc ctacatacct cgctctgcta    7620
atcctgttac cagtggctgc tgccagtggc gataagtcgt gtcttaccgg gttggactca    7680
agacgatagt taccggataa ggcgcagcgg tcgggctgaa cggggggttc gtgcacacag    7740
cccagcttgg agcgaacgac ctacaccgaa ctgagatacc tacagcgtga gctatgagaa    7800
agcgccacgc ttcccgaagg gagaaaggcg gacaggtatc cggtaagcgg cagggtcgga    7860
acaggagagc gcacgaggga gcttccaggg ggaaacgcct ggtatcttta tagtcctgtc    7920
gggtttcgcc acctctgact tgagcgtcga tttttgtgat gctcgtcagg gggcggagc     7980
ctatggaaaa acgccagcaa cgcggccttt ttacggttcc tggccttttg ctggccttt     8040
gctcacatgt tctttcctgc gttatcccct gattctgtgg ataaccgtat taccgccttt    8100
gagtgagctg ataccgctcg ccgcagccga acgaccgagc gcagcgagtc agtgagcgag    8160
gaagcggaag agcgcccaat acgcaaaccg cctctccccg cgcgttggcc gattcattaa    8220
tg                                                                   8222

SEQ ID NO: 52           moltype = DNA  length = 8126
FEATURE                 Location/Qualifiers
source                  1..8126
                        mol_type = other DNA
                        organism = Synthetic construct
SEQUENCE: 52
cagctgcgcg ctcgctcgct cactgaggcc gcccgggcaa agcccgggcg tcggcgacc      60
tttggtcgcc cggcctcagt gagcgagcga gcgcgcagag agggagtggc caactccatc    120
actgggggtt cctacgcgta gatctggtgt atacatacat acctgaatat ggaatcaaat    180
atttttctaa gatgaaacag tcatgattta tttcaaatag gtacggataa gtagatattg    240
aggtaagcat taggtcttat attatgtaac actaatctat tactgcgctg aaactgtggc    300
tttatagaaa ttgttttcac tgcactattg agaaattaag agataatggc aaaagtcaca    360
aagagtatat tcaaaagaa gtatagcact ttttccttag aaaccactgc taactgaaag     420
agactaagat ttgtcccgtc aaaaatcctg gacctatgcc taaaacacat ttcacaatcc    480
ctgaactttt caaaaattgg tacatgcttt agctttaaac tacaggcctc actggagcta    540
gagacaagaa ggtaaaaaac ggctgacaaa agaagtcctg gtatcctcta tgatgggaga    600
aggaaactag ctaaagggaa gaataaatta gagaaaaact ggaatgactg aatcggaaca    660
aggcaaaggc tataaaaaaa attaagcagc agtatcctct tgggggcccc ttccccacac    720
tatctcaatg caaatatctg tctgaaacgt tccctgacta aactccaccc atgggttgcc    780
cagccttgcc ttgacaaggc aaacttgacc aatagtctta gagtatccag tgaggccagg    840
ggccggcggc tggctaggga tgaagaataa aaggaagcac ccttcagcag ttccacacac    900
tcgcttctgg aacgtctgag gttatcaata agctcctagt ccagacgcca tggtgcacct    960
gactcctgag gagaagtctg ccgttactgc cctgtgggga aaggtgaacg tggatgaagt   1020
tggtggtgag gccctgggca ggttggtatc aaggttacaa gacaggttta aggagaccaa   1080
tagaaactgg gcatgtggag acagagaaga ctcttgggtt tctgataggc actgactctc   1140
tctgcctatt ggtctatttt cccaccctta ggctgctggt ggtctaccct ggacccaga    1200
ggttctttga gtcctttggg gatctgtcca ctcctgatgc tgttatgggc aaccctaagg   1260
tgaaggctca tggcaagaaa gtgctcggtg cctttagtga tggcctggct cacctggaca   1320
acctcaaggg cacctttgcc cagctgagtg agctgcactg tgacaagctg cacgtggatc   1380
ctgagaactt cagggtgagt ctatgggacc cttgatgttt tctttcccct tcttttctat   1440
ggttagttc atgtcatagg aaggggagaa gtaacagagt acacatattg accaaatcag   1500
ggtaattttg catttgtaat tttaaaaaat gctttcttct tttaatatac ttttttgttt   1560
atcttatttc taatactttc cctaatctct tcctttcagg gcaataatga tacaatgtat   1620
catgcctctt tgcaccattc taaagaataa cagtgataat ttctgggtta aggcaatagc   1680
aatattttctg catataaata tttctgcata taaattgtaa ctgatgtaag aggtttcata   1740
ttgctaatag cagctacaat ccagctacca ttctgctttt attttatggt tgggataagg   1800
ctggattatt ctgagtccaa gctaggccct tttgctaatc atgttcatac ctcttatctt   1860
cctcccacag ctcctgggca acgtgctggt ctgtgtgctg gcccatcact ttggcaaaga   1920
attcacccca ccagtgcagg ctgcctatca gaaagtggtg gctggtgtgg ctaatgccct   1980
ggcccacaag tatcactaag ctcgctttct tgctgtccaa tttctattaa aggttccttt   2040
gttccctaag tccaactact aaactggggg atattatgaa gggccttgag catctggatt   2100
ctgcctaata aaaaacattt atttcattg caatgatgta tttaaattat ttctgaatat    2160
tttactaaaa agggaatgtg ggaggttcta gtgctagtct cccggaacta tcactctttc   2220
acagtctgct ttgaaggac tgggcttagt atgaaaagtt aggactgaga agatttgaa    2280
aggggctttt ttgtagcttg atattcacta ctgtcttatt accctatcat aggcccaccc   2340
caaatggaag tccattcttt ctcaggatgt ttaagatta gcatttcagga agagatcaga   2400
ggtctgctgg ctccttatc atgtccctta tggtgcttct ggctctgcac gcggccacg    2460
gggttgggggt tgcgccttt ccaaggcagc cctgggttttg cgcgggacg cggctgctct   2520
gggcgttggtt ccgggaacg cagcggcgcc gacctgtcgc tcgcacatt cttcacgtcc    2580
gttcgcagcg tcaccggat cttcgccgct acccttgtgg gccccggc gacgcttcct    2640
gctccgcccc taagtcggga aggttccttg cggttcgcgg cgtgccggac gtgacaaacg   2700
gaagccgcac gtctcactag taccctcgca gacgacagc gccagggagc aatgcagcg     2760
cgccgaccgc gatgggctgt ggccaatagc ggctgctcag cggggcgcgc cgagagcagc   2820
ggcgggaag gggggtgcg ggaggcgggg tgtgggcgg tagtgtggc cctgttcctg    2880
cccgcgcggg gttccgcatt ctgcaagcct ccgagcgca cgtcggcagt cggctccctc    2940
gttgaccgaa tcaccgacct ctctccccag cggccgcgcc gccaccatgg acaaggattg   3000
tgaaatgaaa cgcaccacac tggacagccc tttgggggaag ctggagctgt ctggttgtga   3060
gcagggtctg cacgaaataa agctcctggg caaggggacg tctgcagctg atgccgtgga   3120
ggtcccagcc ccgctgcgg ttctcggagg tccggagccc ctgatgcagt gcacagcctg   3180
```

```
gctgaatgcc tatttccacc agcccgaggc tatcgaagag ttccccgtgc cggctcttca   3240
ccatcccgtt ttccagcaag agtcgttcac cagacaggtg ttatggaagc tgctgaaggt   3300
tgtgaaattc ggagaagtga tttcttacca gcaattagca gccctggcag gcaaccccaa   3360
agccgcgcga gcagtgggag gagcaatgag aggcaatcct gtcaaaatcc tcatcccgtg   3420
ccacagagtg gtctgcagca gcggagccgt gggcaactac tccggaggac tggccgtgaa   3480
ggaatggctt ctggcccatg aaggccaccg gttggggaag ccaggcttgg gagggagctc   3540
aggtctggca ggggcctggc tcaagggagc gggagctacc tcgggctccc cgcctgctgg   3600
ccgaaactaa gctttatttg tgaaatttgt gatgctattg ctttatttgt aaccattata   3660
agctgcaata aacaagttaa caacaacaat tgcattcatt ttatgtttca ggttcagggg   3720
gagatgtggg aggttttttta aagccctgca ggcaatagcc ttgacaaggc aaacttgacc   3780
aatagtctta gagtatccag tgaggccagg ggccggcggc tggctaggga tgaagaataa   3840
aaggaagcac ccttcagcag ttccacacac tcgcttctgg aacgtctgag gttatcaata   3900
agctcctagt ccagacgcca tgggtcattt cacagaggag gacaaggcta ctatcacaag   3960
cctgtgggc aaggtgaatg tggaagatgc tggaggagaa accctgggaa ggtaggctct   4020
ggtgaccagg acaagggagg gaaggaagga ccctgtgcct ggcaaaagtc caggtcgctt   4080
ctcaggattt gtggcacctt ctgactgtca aactgttctt gtcaatctca caggctcctg   4140
gttgtctacc catggaccca gaggttcttt gacagctttg gcaacctgtc ctctgcctct   4200
gccatcatgg gcaacccaa agtcaaggca catggcaaga aggtgctgac ttccttggga   4260
gatgccacaa agcacctgga tgatctcaag ggcacctttg cccagctgag tgaactgcac   4320
tgtgacaagc tgcatgtgga tcctgagaac ttcaaggtga gtccaggaga tgtttcagcc   4380
ctgttgcctt tagtctcgag gcgtcgacag gaaccctag tgatggagtt ggccactccc   4440
tctctgcgcg ctcgctcgct cactgaggcc gggcgaccaa aggtcgcccg acgcccggcg   4500
tttgcccggg cggcctcagt gagcgagcga gcgcgcagct ggcgtaatag cgaagaggcc   4560
cgcaccgatc gcccttccca acagttgcgc agcctgaatg gcgaatggcg attccgttgc   4620
aatgctggc ggtaatattg ttctggatat taccagcaag gccgatagtt tgagttcttc   4680
tactcaggca agtgatgtta ttactaatca aagaagtatt gcgacaacgg ttaatttgcg   4740
tgatggacag actcttttac tcggtggcct cactgattat aaaaacactt ctcaggattc   4800
tggcgtaccg ttcctgtcta aaatcccttt aatcggcctc ctgtttagct cccgctctga   4860
ttctaacgag gaaagcacgt tatacgtgct cgtcaaagca accatagtac gcgccctgta   4920
gcggcgcatt aagcgcggcg ggtgtggtgg ttacgcgcag cgtgaccgct acacttgcca   4980
gcgccctagc gcccgctcct ttcgctttct tcccttcctt tctcgccacg ttcgccggct   5040
ttccccgtca agctctaaat cggggggctcc ctttagggtt ccgatttagt gctttacggc   5100
acctcgaccc caaaaaactt gattagggtg atggttcacg tagtgggcca tcgccctgat   5160
agacggtttt tcgccctttg acgttggagt ccacgttctt taatagtgga ctcttgttcc   5220
aaactggaac aacactcaac cctatctcgg tctattcttt tgatttataa gggattttgc   5280
cgatttcggc ctattggtta aaaaatgagc tgatttaaca aaaatttaac gcgaatttta   5340
acaaaatatt aacgtttaca atttaaatat ttgcttatac aatcttcctg ttttggggc   5400
ttttctgatt atcaaccggg gtacatatga ttgacatgct agttttacga ttaccgttca   5460
tcgattctct tgtttgctcc agactctcag gcaatgacct gatagcctttt gtagagacct   5520
ctcaaaaata gctaccctct ccggcatgaa tttatcagct agaacggttg aatatatcat   5580
tgatggtgat ttgactgtct ccggcctttc tcacccgttt gaatcttac ctacacatta   5640
ctcaggcatt gcatttaaaa tatatgaggg ttctaaaaat tttatccttt gcgttgaaat   5700
aaaggcttct cccgcaaaag tattacaggg tcataatgtt tttggtacaa ccgatttagc   5760
tttatgctct gaggctttat tgcttaattt tgctaattct ttgccttgcc tgtatgattt   5820
attggatgtt ggaatcgcct gatgcggtat ttttctcctta cgcatctgtg cggtatttca   5880
caccgcatat ggtgcactct cagtacaatc tgctctgatg ccgcatagtt aagccagccc   5940
cgacacccgc caacacccgc tgacgcgccc tgacgggctt gtctgctccc ggcatccgct   6000
tacagacaag ctgtgaccgt ctccgggagc tgcatgtgtc agaggttttc accgtcatca   6060
ccgaaacgcg cgagacgaaa gggcctcgtg atacgcctat ttttataggt taatgtcatg   6120
ataataatgg tttcttagac gtcaggtggc acttttcggg gaaatgtgcg cggaaccccct   6180
atttgtttat ttttctaaat acattcaaat atgtatccgc tcatgagaca ataaccctga   6240
taaatgcttc aataatattg aaaaaggaag agtatgagta ttcaacattt ccgtgtcgcc   6300
cttattccct tttttgcggc attttgcctt cctgtttttg ctcacccaga aacgctggtg   6360
aaagtaaaag atgctgaaga tcagttgggt gcacgagtgg gttacatcga actggatctc   6420
aacagcggta agatcttga gagtttttcgc cccgaagaac gttttccaat gatgagcact   6480
tttaaagttc tgctatgtgg cgcggtatta tcccgtattg acgccgggca agagcaactc   6540
ggtcgccgca tacactattc tcagaatgac ttggttgagt actcaccagt cacagaaaag   6600
catcttacgg atggcatgac agtaagagaa ttatgcagtg ctgccataac catgagtgat   6660
aacactgcgg ccaacttact tctgacaacg atcggaggac cgaaggagct aaccgcttt   6720
ttgcacaaca tgggggatca tgtaactcgc cttgatcgtt gggaaccgga gctgaatgaa   6780
gccataccaa acgacgagcg tgacaccacg atgcctgtag caatggcaac aacgttgcgc   6840
aaactattaa ctggcgaact acttactcta gcttcccggc aacaattaat agactggatg   6900
gaggcggata aagttgcagg accacttctg cgctcggccc ttccggctgg ctggtttatt   6960
gctgataaat ctggagccgg tgagcgtggg tctcgcggta tcattgcagc actggggcca   7020
gatggtaagc cctcccgtat cgtagttatc tacacgacgg ggagtcaggc aactatggat   7080
gaacgaaata gacagatcgc tgagataggt gcctcactga ttaagcattg gtaactgtca   7140
gaccaagttt actcatatat actttagatt gatttaaaac ttcatttta atttaaaagg   7200
atctaggtga agatcctttt tgataatctc atgaccaaaa tcccttaacg tgagttttcg   7260
ttccactgag cgtcagaccc cgtagaaaag atcaaaggat cttcttgaga tccttttttt   7320
ctgcgcgtaa tctgctgctt gcaaacaaaa aaaccaccgc taccagcggt ggtttgtttg   7380
ccggatcaag agctaccaac tcttttttccg aaggtaactg gcttcagcag agcgcagata   7440
ccaaatactg tccttctagt gtagccgtag ttaggccacc acttcaagaa ctctgtagca   7500
ccgcctacat acctcgctct gctaatcctg ttaccagtgg ctgctgccag tggcgataag   7560
tcgtgtctta ccgggttgga ctcaagacga tagttaccgg ataaggcgca gcggtcgggc   7620
tgaacggggg gttcgtgcac acagcccagc ttggagcgaa cgacctacac cgaactgaga   7680
tacctacagc gtgagctatg agaaagcgcc acgcttcccg aagggagaaa ggcggacagg   7740
tatccggtaa gcggcagggt cggaacagga gagcgcacga gggagcttcc agggggaaac   7800
gcctggtatc tttatagtcc tgtcgggttt cgccacctct gacttgagcg tcgatttttg   7860
tgatgctcgt cagggggggcg gagcctatgg aaaaacgcca gcaacgcggc cttttacgg   7920
```

|  |  |  |  |  |  |
|---|---|---|---|---|---|
| ttcctggcct | tttgctggcc | ttttgctcac | atgttctttc | ctgcgttatc | ccctgattct | 7980 |
| gtggataacc | gtattaccgc | ctttgagtga | gctgataccg | ctcgccgcag | ccgaacgacc | 8040 |
| gagcgcagcg | agtcagtgag | cgaggaagcg | gaagagcgcc | caatacgcaa | accgcctctc | 8100 |
| cccgcgcgtt | ggccgattca | ttaatg |  |  |  | 8126 |

| SEQ ID NO: 53 | moltype = DNA length = 8168 |
|---|---|
| FEATURE | Location/Qualifiers |
| source | 1..8168 |
|  | mol_type = other DNA |
|  | organism = Synthetic construct |

SEQUENCE: 53

|  |  |  |  |  |  |  |
|---|---|---|---|---|---|---|
| cagctgcgcg | ctcgctcgct | cactgaggcc | gcccgggcaa | agcccgggcg | tcgggcgacc | 60 |
| tttggtcgcc | cggcctcagt | gagcgagcga | gcgcgcagag | agggagtggc | caactccatc | 120 |
| actagggggtt | cctgcggccg | cgatgtgagg | acacagtggg | aagtcagcca | cctgcaaccc | 180 |
| aggaagagag | ccctgaccag | gaaccagcag | aaaagtgaga | aaaaatcctg | ttgttgaagt | 240 |
| cacccagtct | atgctatttt | gttatagcac | cttgcactaa | gtaaggcaga | tgaagaaaga | 300 |
| gaaaaaaata | agcttcggtg | ttcagtggat | tagaaaccat | gtttatctca | ggtttacaaa | 360 |
| tctccacttg | tcctctgtgt | ttcagaataa | aataccaact | ctactactct | catctgtaag | 420 |
| atgcaaatag | taagcctgag | cccttctgtc | taactttgaa | ttctattttt | tcttcaacgt | 480 |
| actttaggct | tgtaatgtgt | ttatatacag | tgaaatgtca | agttcttttct | ttatatttct | 540 |
| ttctttcttt | tttttcctca | gcctcagagt | tttccacatg | cccttcctac | tttcaggaac | 600 |
| ttctttctcc | aaacgtcttc | tgcctggctc | catcaaatca | taaggaccc | acttcaaatg | 660 |
| ccatcactca | ctaccatttc | acaattcgca | ctttctttct | ttgtcctttt | ttttttttagt | 720 |
| aaaacaagtt | tataaaaaat | tgaaggaata | aatgaatggc | tacttcatag | gcagagtaga | 780 |
| cgcaagggct | actggttgcc | gattttttatt | gttattttttc | aatagtatgc | taaacaaggg | 840 |
| gtagattatt | tatgctgccc | attttttagac | cataaaagat | aacttcctga | tgttgccatg | 900 |
| gcattttttttt | cctttttaatt | ttatttcatt | tcatttttaat | ttcgaaggta | catgtgcagg | 960 |
| atgtgcaggc | ttgttacatg | ggtaaatgtg | tgtcttctg | gccttttagc | catctgtatc | 1020 |
| aatgagcaga | tataagcttt | acacaggatc | atgaaggatg | aaagaatttc | accaatatta | 1080 |
| taattaatttc | aatcaacctg | atagcttagg | ggataaaata | atttgaagat | acagcttgcc | 1140 |
| tccgataagc | cagaattcca | gagcttctgg | cattataatc | tagcaaggtt | agagatcatg | 1200 |
| gatcactttc | agagaaaaac | aaaaacaaac | taaccaaaag | caaaacagaa | ccaaaaaacc | 1260 |
| accataaata | cttcctaccc | tgttaatggt | ccaatatgtc | agaaacagca | ctgtgttaga | 1320 |
| aataaagctg | tctaaagtac | actaatattc | gagttataat | agtgtgtgga | ctattagtca | 1380 |
| ataaaaaacaa | cccttgcctc | tttagagttg | tttttcatgt | acacgcacat | cttatgtctt | 1440 |
| agagtaagat | tccctgagaa | gtgaacctag | cattttataca | agataattaa | ttctaatcca | 1500 |
| cagtacctgc | caaagaacat | tctaccatca | tctttactga | gcatagaaga | gctacgccaa | 1560 |
| aaccctgggt | catcagccag | cacacacact | tatccagtgg | taaatacaca | tcatctggtg | 1620 |
| tatacataca | tacctgaata | tggaatcaaa | tattttttca | agatgaaaca | gtcatgattt | 1680 |
| atttcaaata | ggtacggata | agtagatatt | gaggtaagca | ttaggtctta | tattatgtaa | 1740 |
| cactaatcta | ttactgcgct | gaaactgtgg | ctttatagaa | attgttttca | ctgcactatt | 1800 |
| gagaaattaa | gagataatgg | caaagtcac | aaagagtata | ttcaaaaaga | agtatagcac | 1860 |
| tttttcctta | gaaaccactg | ctaactgaaa | gagactaaga | tttgtcccgt | caaaaatcct | 1920 |
| ggacctatgc | ctaaaacaca | tttcacaatc | cctgaacttt | tcaaaaattg | gtacatgctt | 1980 |
| tagctttaaa | ctacaggcct | cactggagct | agagacaaga | aggtaaaaaa | cggctgacaa | 2040 |
| aagaagtcct | ggtatcctct | atgatgggag | aaggaaacta | gctaaaggga | agaataaatt | 2100 |
| agagaaaaac | tggaatgact | gaatcggaac | aaggcaaagg | ctataaaaaa | aattagcagt | 2160 |
| atcctcttgg | gggccccttc | cccacactat | ctcaatgcaa | atatctgtct | gaaacggtcc | 2220 |
| ctggctaaac | tccaccatg | ggttggccag | ccttgccttg | acaaggcaaa | cttgaccaat | 2280 |
| agtcttagag | tatccagtga | ggccagggc | cggcggctgg | ctaggatga | agaataaaag | 2340 |
| gaagcaccct | tcagcagttc | cacacactcg | ctttctgagg | gtctgaggtt | atcaataagc | 2400 |
| tcctagtcca | gacgccatgg | gtcatttcac | agaggaggac | aaggctacta | tcacaagcct | 2460 |
| gtggggcaag | gtgaatgtgg | aagatgctgg | aggagaaacc | ctgggaaggt | aggctctggt | 2520 |
| gaccaggaca | agggagggaa | ggaaggaccc | tgtgcctggc | aaaagtccag | gtcgcttctc | 2580 |
| aggattttgtg | gcaccttctg | actgtcaaac | tgttcttgtc | aatctcacag | gctcctggtt | 2640 |
| gtctacccat | ggaccagag | gttctttgac | agctttggca | acctgtcctc | tgcctctgcc | 2700 |
| atcatgggca | accccaaagt | caaggcacat | ggcaagaagg | tgctgacttc | cttgggagat | 2760 |
| gccacaaagc | cctggatga | tctcaaggc | cctttgccc | agctgagtga | actgcactgt | 2820 |
| gacaagctgc | atgtggatcc | tgagaacttc | aaggtgagtc | caggagatgt | ttcagccctg | 2880 |
| ttgcctttag | tctcgaggca | acttagacaa | cggagtattg | atctgagcac | agcagggtgt | 2940 |
| gagctgtttg | aagatactgg | ggttgggggt | gaagaaactg | cagaggacta | actgggctga | 3000 |
| gacccagtga | taatgttta | gggcctaagg | agtgcctcta | aaaatctaga | tggacaattt | 3060 |
| tgactttgag | aaaagagagg | tggaaatgag | gaaaatgact | tttctttatt | agattccagt | 3120 |
| agaaagaact | ttcatctttc | cctcatttttt | gttgttttaa | aactctatc | tggaggcagg | 3180 |
| acaagtatgg | tcgttaaaaa | gatgcaggca | gaaggcatat | attggctcag | tcaaagtggg | 3240 |
| gaactttggt | ggccaaacat | acattgctaa | ggctattcct | atatcagctg | gacacatata | 3300 |
| aaatgctgct | aatgcttcat | tacaaactta | tatccttaa | ttccagatgg | gggcaaagta | 3360 |
| tgtccagggg | tgaggaacaa | ttgaaacatt | tgggctggag | tagattttga | aagtcagctc | 3420 |
| tgtgtgtgtg | tgtgtgtgtg | cgcgcgcgcg | tgtgtgtgtc | tgtgtcagcg | tgtgttttct | 3480 |
| ttaacgtctt | cagcctacaa | catacagggt | tcatggtggc | aagaagatag | caagatttaa | 3540 |
| attatgccca | gtgactagtg | cttcaagggg | aacaactacc | tgcatttaat | gggaaggcaa | 3600 |
| aatctcaggc | tttgagggaa | gttaacatag | gcttgattct | gggtgaaagc | ttggtgtgta | 3660 |
| gttatctgga | ggcaggctg | gagctctcag | ctcactatgg | gttcatcttt | attgtctcct | 3720 |
| ttcatctcaa | cagctcctcgg | gaaatgct | ggtgaccgtt | ttggcaatcc | atttccgtaa | 3780 |
| agaattcacc | cctgaggtgc | aggcttcctg | gcagaagatg | gtgactcag | tggccagtgc | 3840 |
| cctgcctcc | agataccact | gagctcactg | cccatgattc | agagcttca | aggataggct | 3900 |
| ttattctgca | agcaatacaa | ataataaatc | tattctgctg | agagatcaca | catgattttc | 3960 |
| tcagctctt | tttttttacat | cttttttaaat | atatgagcca | caaggggttt | atattgaggg | 4020 |
| aagtgtgtat | gtgtatttct | gcatgcctgt | ttgtgtttgt | ggtgtgtgca | tgctcctcat | 4080 |

```
ttattttttat atgagatgtg cattttgatg agcaaataaa agcagtaaag acacttgtac   4140
acgggagttc tgcaagtggg agtaaatggt gtaggagaaa tccggtggga agaaagacct   4200
ctataggaca ggacttctca gaaacagatg ttttggaaga gatgggaaaa ggttcagtga   4260
agacctgggg gctggattga ttgcagctga gtagcaagga tggttcttaa ggaagggaaa   4320
gtgttccaag ctttaggaat tcaaggttta gtcaggtgta gcaattctat ttttattagga  4380
ggaatactat ttctaatggc acttagcttt tcacagccct tgtggatgcc taaatcggat   4440
ccctgcagg aggaacccct agtgatggag ttggccactc cctctctgcg cgctcgctcg   4500
ctcactgagg ccgggcgacc aaaggtcgcc cgacgcccgg gctttgcccg gcggcctca   4560
gtgagcgagc gagcgcgcag ctggcgtaat agcgaagagg cccgcaccga tcgcccttcc   4620
caacagttgc gcagcctgaa tggcgaatgg cgattccgtt gcaatggctg gcggtaatat   4680
tgttctggat attaccagca aggccgatag tttgagttct tctactcagg caagtgatgt   4740
tattactaat caaagaagta ttgcgacaac ggttaatttg cgtgatggac agactctttt   4800
actcggtggc ctcactgatt ataaaaacac ttctcaggat tctggcgtac cgttcctgtc   4860
taaaatccct ttaatcggcc tcctgtttag ctcccgctct gattctaacg aggaaagcac   4920
gttatacgtg ctcgtcaaag caaccatagt acgcgccctg tagcggcgca ttaagcgcgg   4980
cgggtgtggt ggttacgcgc agcgtgaccg ctacacttgc cagcgcccta gcgcccgctc   5040
ctttcgcttt cttcccttcc tttctcgcca cgttcgccgg ctttccccgt caagctctaa   5100
atcggggct ccctttaggg ttccgattta gtgctttacg gcacctcgac cccaaaaaac   5160
ttgattaggg tgatggttca cgtagtgggc catcgccctg atagacggtt tttcgccctt   5220
tgacgttgga gtccacgttc tttaatagtg actcttgtt ccaaactgga caacactca   5280
accctatctc ggtctattct tttgatttat aagggatttt gccgatttcg gcctattggt   5340
taaaaaatga gctgatttaa caaaaattta acgcgaattt taacaaaata ttaacgttta   5400
caatttaaat atttgcttat acaatcttcc tgttttggg gcttttctga ttatcaaccg   5460
gggtacatat gattgacatg ctagttttac gattaccgtt catcgattct cttgtttgct   5520
ccagactctc aggcaatgac ctgatagcct ttgtagagac ctctcaaaaa tagctaccct   5580
ctccgcatg aatttatcag ctagaacggt tgaatatcat attgatggtg atttgactgt   5640
ctccggcctt tctcacccgt ttgaatcttt acctacacat tactcaggca ttgcatttaa   5700
aatatatgag ggttctaaaa attttttatcc ttgcgttgaa ataaaggctt ctcccgcaaa   5760
agtattacag ggtcataatg ttttttggtac aaccgattta gctttatgct ctgaggcttt   5820
attgcttaat tttgctaatt ctttgccttg cctgtatgat ttattggatg ttggaatcgc   5880
ctgatgcggt atttttctcct tacgcatctg tgcggtattt cacaccgcat atggtgcact   5940
ctcagtacaa tctgctctga tgccgcatag ttaagccagc cccgacaccc gccaacaccc   6000
gctgacgcgc cctgacgggc ttgtctgctc ccggcatccg cttacagaca agctgtgacc   6060
gtctccggga gctgcatgtg tcagaggttt tcaccgtcat caccgaaacg cgcgaggcag   6120
aagggcctcg tgatacgcct atttttatag gttaatgtca tgataataat ggtttcttag   6180
acgtcaggtg gcacttttcg gggaaatgtg cgcggaaccc ctatttgttt attttttctaa   6240
atacattcaa atatgtatcc gctcatgaga caataaccct gataaatgct tcaataatat   6300
tgaaaaagga agagtatgag tattcaacat ttccgtgtcg cccttattcc cttttttgcg   6360
gcattttgcc ttcctgtttt tgctcaccca gaaacgctgg tgaaagtaaa agatgctgaa   6420
gatcagttgg gtgcacgagt gggttacatc gaactggatc tcaacagcgg taagatcctt   6480
gagagttttc gccccgaaga acgttttcca atgatgagca cttttaaagt tctgctatgt   6540
ggcgcggtat tatcccgtat tgacgccggg caagagcaac tcggtcgccg catacactat   6600
tctcagaatg acttggttga gtactcacca gtcacagaaa agcatcttac ggatggcatg   6660
acagtaagag aattatgcag tgctgccata accatgagtg ataacactgc ggccaactta   6720
cttctgacaa cgatcggagg accgaaggag ctaaccgctt ttttgcacaa catgggggat   6780
catgtaactc gccttgatcg ttgggaaccg gagctgaatg aagccatacc aaacgacgag   6840
cgtgacacca cgatgcctgt agcaatggca acaacgttgc gcaaactatt aactggcgaa   6900
ctacttactc tagcttcccg gcaacaatta atagactgga tggaggcgga taaagttgca   6960
ggaccacttc tgcgctcggc ccttccggct ggctggttta ttgctgataa atctggagcc   7020
ggtgagcgtg ggtctcgcgg tatcattgca gcactggggc cagatggtaa gccctcccgt   7080
atcgtagtta tctacacgac ggggagtcag gcaactatgg atgaacgaaa tagacagatc   7140
gctgagatag gtgcctcact gattaagcat tggtaactgt cagaccaagt ttactcatat   7200
atactttaga ttgatttaaa acttcatttt taatttaaaa ggatctaggt gaagatcctt   7260
tttgataatc tcatgaccaa aatcccttaa cgtgagtttt cgttccactg agcgtcagac   7320
cccgtagaaa agatcaaagg atcttcttga gatcctttt tctgcgcgt aatctgctgc   7380
ttgcaaacaa aaaaaccacc gctaccagcg gtggtttgtt tgccggatca gagctacca   7440
actcttttc cgaaggtaac tggcttcagc agagcgcaga taccaaatac tgtccttcta   7500
gtgtagccgt agttaggcca ccacttcaag aactctgtag caccgcctac atacctcgct   7560
ctgctaatcc tgttaccagt ggctgctgcc agtggcgata agtcgtgtct taccgggttg   7620
gactcaagac gatagttacc ggataaggcg cagcggtcgg gctgaacggg gggttcgtgc   7680
acacagccca gcttggagcg aacgacctac accgaactga gatacctaca gcgtgagcta   7740
tgagaaagcg ccacgcttcc cgaagggaga aaggcggaca ggtatccggt aagcggcagg   7800
gtcggaacag gagagcgcac gagggagctt ccaggggga acgcctggta tctttatagt   7860
cctgtcgggt ttcgccacct ctgacttgag cgtcgatttt tgtgatgctc gtcaggggggc   7920
cggagcctat ggaaaaacgc cagcaacgcg gccttttac ggttcctggc ctttgctgtg   7980
ccttttgctc acatgttctt tcctgcgtta tcccctgatt ctgtggataa ccgtattacc   8040
gcctttgagt gagctgatac cgctcgccgc agccgaacga ccgagcgcag cgagtcagtg   8100
agcgaggaag cggaagagcg cccaatacgc aaaccgcctc tccccgcgcg ttggccgatt   8160
cattaatg                                                            8168
```

SEQ ID NO: 54      moltype = DNA   length = 7556
FEATURE            Location/Qualifiers
source             1..7556
                   mol_type = other DNA
                   organism = Synthetic construct
SEQUENCE: 54
cagctgcgcg ctcgctcgct cactgaggcc gcccgggcaa agcccgggcg tcgggcgacc    60
tttggtcgcc cggcctcagt gagcgagcga gcgcgcagag gggagtggc caactccatc   120
actaggggtt ccttgtagtt aatgattaac ccgccatgct acttatctac acgcgtagat   180

```
cttaagtata gcacaatgct tactaaatga gactaagact tgtcccatcg aaaatcctgg   240
acctatgcct aaaacacgtg tcacaatccc cgaacttttc aaaaattggt acatgcttta   300
actttaatct ccaggcctca ctggagctag agacaagaag gtaaaaaaag gctgacaaaa   360
gaagtcctgg tatcttctat ggtgggagaa ggaaactagc taaagggaag aataaattag   420
agaaaaattg gaatgattga atcggaacaa ggcaaaggct ataaaaaaat taagcagcag   480
tatcctcttg ggggcccctt ccccacacta tctcaatgca aatatctgtc tgaaacggtc   540
cctggctaaa ctccacccat gggttggcca gtcttgcctt gacaaggcaa ccttgaccaa   600
tagtcttaga gtatcaggtg aggccagggg ccggcggctg gctagggatg aagaataaaa   660
ggaagcaccc tccagcagtt ccacacactc gcttctggca cggctgagat tatcaataag   720
ctcctagtcc agacgccatg gtgcacctga ctcctgagga gaagtctgcc gttactgccc   780
tgtggggcaa ggtgaacgtg gatgaagttg gtggtgaggc cctgggcagg ttggtatcaa   840
ggttacaaga caggtttaag gagaccaata gaaactgggc atgtggagac agagaagact   900
cttgggtttc tgataggcac tgactctctc tgcctattgg tctattttcc cacccttagg   960
ctgctggtgg tctacccttg gacccagagg ttctttgagt cctttgggga tctgtccact  1020
cctgatgctg ttatgggcaa ccctaaggtg aaggctcatg gcaagaaagt gctcggtgcc  1080
tttagtgatg gcctggctca cctggacaac ctcaagggca cctttgccca gctgagtgag  1140
ctgcactgtg acaagctgca cgtggatcct gagaacttca gggtgagtct atgggaccct  1200
tgatgttttc tttccccttc ttttctatgg ttaagttcat gtcataggaa ggggagaagt  1260
aacagggtac acatattgac caaatcaggg taattttgca tttgtaattt taaaaaatgc  1320
tttcttcttt taatatactt ttttgtttat cttatttcta atactttccc taatctcttt  1380
ctttcagggc aataatgata caatgtatca tgcctctttg caccattcta aagaataaca  1440
gtgataattt ctgggttaag gcaatagcaa tatttcgtca tataaatatt tctgcatata  1500
aattgtaact gatgtaagag gtttcatatt gctaatagca gctacaatcc agctaccatt  1560
ctgcttttat tttatggttg ggataaggct ggattattct gagtccaagc taggcccttt  1620
tgctaatcat gttcatacct cttatcttcc tcccacagcc cctgggcaac gtgctggtct  1680
gtgtgctggc ccatcacttt ggcaaagaat tcacccccac agtgcaggct gcctatcaga  1740
aagtggtggc tggtgtggct aatgccctgg cccacaagta tcactaagct cgcttttctt  1800
ctgtccaatt tctattaaag gttcctttgt tccctaagtc caactactaa actgggggat  1860
attatgaagg gccttgagca tctggattct gcctaataaa aaacatttat tttcattgca  1920
atgatgtatt taaattattt ctgaatattt tactaaaaag ggaatgtggg aggttgcagt  1980
gctagtctcc cggaactatc actctttcac agtctgcttt ggaaggactg ggcttagtat  2040
gaaaagttag gactgagaag aatttgaaag ggggctttt gtagcttgat attcactact  2100
gtcttattac cctatcatag gcccacccca aatggaagtc ccattcttcc tcaggatgtt  2160
taagattagc attcaggaag agatcagagg tctgctggct cccttatcat gtcccttatg  2220
gtgcttctgg ctctgcaccg cgggaacaga gaaacaggag aatatgggcc aaacaggata  2280
tctgtggtaa gcagttcctg ccccggctca gggccaagaa cagttggaac agcagaatat  2340
gggccaaaca ggatatctgt ggtaagcagt tcctgccccg gctcagggcc aagaacagat  2400
ggtccccaga tgcggtcccg ccctcagcag tttctagaga accatcagat gtttccaggg  2460
tgccccaagg acctgaaatg accctgtgcc ttatttgaac taaccaatca gttcgcttct  2520
cgcttctgtt cgcgcgcttc tgctccccga gctctatata agcagagctc gtttagtgaa  2580
ccgtcagatc gcggccgcgc cgccaccatg gtgagcaagg gcgaggagct gttcaccggg  2640
gtggtgccca tcctggtcga gctggacggc gacgtaaacg gccacaagtt cagcgtgtcc  2700
ggcgagggcg agggcgatgc cacctacggg aagctgaccc tgaagttcat ctgcaccacc  2760
ggcaagctgc ccgtgccctg gcccaccctc gtgaccaccc tgacctacgg cgtgcagtgc  2820
ttcagccgct accccgacca catgaagcag cacgacttct tcaagtccgc catgcccgaa  2880
ggctacgtcc aggagcgcac catcttcttc aaggacgacg gcaactacaa gacccgcgcc  2940
gaggtgaagt tcgagggcga caccctggtg aaccgcatcg agctgaaggg catcgacttc  3000
aaggaggacg gcaacatcct ggggcacaag ctggagtaca actacaacag ccacaacgtc  3060
tatatcatgg ccgacaagca gaagaacggc atcaaggtga acttcaagat ccgccacaac  3120
atcgaggacg gcagcgtgca gctcgccgac cactaccagc agaacacccc catcggcgac  3180
ggccccgtgc tgctgcccga caaccactac ctgagcaccc agtccgccct gagcaaagac  3240
cccaacgaga gcgcgatca catggtcctg ctggagttcg tgaccgccgc gggatcact  3300
ctcggcatgg acgagctgta caaggagggc agaggaagtc ttctaacatg cggtgacgtg  3360
gaggagaatc cgggcccccc tgcaggaact tcagggtgag tccaggagtt tcagcagttt  3420
cagagttcag tctcaaggca acttagacaa ctgagtattg atctgaggac agtcgaatct  3480
acctgctggg tgtgagctat ttgaagatac tgggggttggg agtgaagaaa ctgcagagga  3540
ctaactgggc tgagaccgaa tggtaatgtt ttagggccta aggagtgcct ctaaaaatct  3600
agacggacaa ttttgacatt gacaaaagag aggtggaaat gaggaaaatg acttttcttt  3660
attagattcc ggtagaaaga actttcatct ttccctcatt tttgttattt gtttttaaac  3720
atctatctgg aggcaggaca agtatggtca ttaaaaagat gcaggcagaa ggcatatatt  3780
ggcccagtca aagtgtcgac gtagataagt agcatggcgg gttaatcatt aactacaagg  3840
aaccccctagt gatggagttg gccactccct ctctgcgcgc tcgctcgctc actgaggccg  3900
ggcgaccaaa ggtcgcccga cgcccgggct tgcccgggg gcctcagtg agcgagcgag  3960
cgcgccagct ggcgtaatag cgaagaggcc cgcaccgatc gcccttccca acagttgcgc  4020
agcctgaatg gcgaatggcg attccgttgc aatggctggc ggtaatattg ttctggatat  4080
taccagcaag gccgatagtt tgagttcttc tactcaggca agtgatgtta ttactaatca  4140
aagaagtatt gcgacaacgg ttaatttgcg tgatggacag actcttttac tcggtggcct  4200
cactgattat aaaaacactt ctcaaggatt ctggcgtaca ttcctgtcta aaatcccttt  4260
aatcggcctc ctgtttagct cccgctctga ttctaacgag gaaagcacgt tatacgtgct  4320
cgtcaaagca accatagtac gcgccctgta gcggcgcatt aagcgcggcg ggtgtggtgg  4380
ttacgcgcag cgtgaccgct acacttgcca gcgccctagc gcccgctcct ttcgctttct  4440
tcccttcctt tctcgccacg ttcgccggct ttccccgtca gctctaaat cggggggctcc  4500
ctttagggtt ccgatttagt gctttacggc acctcgaccc caaaaaactt gattagggtg  4560
atggttcacg tagtgggcca tcgccctgat agacggtttt tcgccctttg acgttggagt  4620
ccacgttctt taatagtgga ctcttgttcc aaactggaac aacactcaac cctatctcgg  4680
tctattcttt tgatttataa gggattttgc cgatttcggc ctattggtta aaaaatgagc  4740
tgatttaaca aaaatttaac gcgaatttta acaaaatatt aacgtttaca atttaaatat  4800
ttgcttatac aatcttcctg ttttttgggc ttttctgatt atcaacccgg gtacatatga  4860
ttgacatgct agttttacga ttaccgttca tcgattctct tgtttgctcc agactctcag  4920
```

```
gcaatgacct gatagccttt gtagagacct ctcaaaaata gctaccctct ccggcatgaa   4980
tttatcagct agaacggttg aatatcatat tgatggtgat ttgactgtct ccggcctttc   5040
tcacccgttt gaatctttac ctacacatta ctcaggcatt gcatttaaaa tatatgaggg   5100
ttctaaaaat ttttatcctt gcgttgaaat aaaggcttct cccgcaaaag tattacaggg   5160
tcataatgtt tttggtacaa ccgatttagc tttatgctct gaggctttat tgcttaattt   5220
tgctaattct ttgccttgcc tgtatgattt attggatgtt ggaatcgcct gatgcggtat   5280
tttctcctta cgcatctgtg cggtatttca caccgcatat ggtgcactct cagtacaatc   5340
tgctctgatg ccgcatagtt aagccagccc cgacacccgc caacacccgc tgacgcgccc   5400
tgacgggctt gtctgctccc ggcatccgct tacagacaag ctgtgaccgt ctccgggag   5460
tgcatgtgtc agaggttttc accgtcatca ccgaaacgcg cgagacgaaa gggcctcgtg   5520
atacgcctat ttttataggt taatgtcatg ataataatgg tttcttagac gtcaggtggc   5580
acttttcggg gaaatgtgcg cggaacccct atttgtttat ttttctaaat acattcaaat   5640
atgtatccgc tcatgagaca ataacccctga taaatgcttc aataatattg aaaaaggaag   5700
agtatgagta ttcaacattt ccgtgtcgcc cttattccct tttttgcggc attttgcctt   5760
cctgtttttg ctcacccaga aacgctggtg aaagtaaaag atgctgaaga tcagttgggt   5820
gcacgagtgg gttacatcga actggatctc aacagcggta agatccttga gttttcgc    5880
cccgaagaac gttttccaat gatgagcact tttaaagttc tgctatgtgg cgcggtatta   5940
tcccgtattg acgccgggca agagcaactc ggtcgccgca tacactattc tcagaatgac   6000
ttggttgagt actcaccagt cacagaaaag catcttacgg atggcatgac agtaagagaa   6060
ttatgcagtg ctgccataac catgagtgat aacactgcgg ccaacttact tctgacaacg   6120
atcggaggac cgaaggagct aaccgctttt ttgcacaaca tgggggatca tgtaactcgc   6180
cttgatcgtt gggaaccgga gctgaatgaa gccataccaa acgacgagcg tgacaccacg   6240
atgcctgtag caatggcaac aacgttgcgc aaactattaa ctggcgaact acttactcta   6300
gcttcccggc aacaattaat agactggatg gaggcggata agttgcagg accacttctg    6360
cgctcggccc ttccggctgg ctggtttatt gctgataaat ctggagccgg tgagcgtggg   6420
tctcgcggta tcattgcagc actggggcca gatggtaagc cctcccgtat cgtagttatc   6480
tacacgacgg ggagtcaggc aactatggat gaacgaaata gacagatcgc tgagataggt   6540
gcctcactga ttaagcattg gtaactgtca gaccaagttt actcatatat actttagatt   6600
gatttaaaac ttcattttta atttaaaagg atctaggtga agatccttt tgataatctc   6660
atgaccaaaa tcccttaacg tgagttttcg ttccactgag cgtcagaccc cgtagaaaag   6720
atcaaaggat cttcttgaga tcctttttt ctgcgcgtaa tctgctgctt gcaaacaaaa   6780
aaaccaccgc taccagcggt ggtttgtttg ccggatcaag agctaccaac tcttttccg    6840
aaggtaactg gcttcagcag agcgcagata ccaaatactg tccttctagt gtagccgtag   6900
ttaggccacc acttcaagaa ctctgtagca ccgcctacat acctcgctct gctaatcctg   6960
ttaccagtgg ctgctgccag tggcgataag tcgtgtctta ccgggttgga ctcaagacga   7020
tagttaccgg ataagcgca gcggtcgggc tgaacggggg gttcgtgcac acagcccagc    7080
ttggagcgaa cgacctacac cgaactgaga tacctacagc gtgagctatg agaaagcgcc   7140
acgcttcccg aagggagaaa ggcggacagg tatccggtaa gcggcagggt cggaacagga   7200
gagcgcacga gggagcttcc aggggggaaac gcctggtatc tttatagtcc tgtcgggttt   7260
cgccaccctct gacttgagcg tcgatttttt tgatgctcgt caggggggcg agcctatgg   7320
aaaaacgcca gcaacgcggc cttttacgg ttcctggcct tttgctggcc ttttgctcac    7380
atgttctttc ctgcgttatc ccctgattct gtggataacc gtattaccgc ctttgagtga   7440
gctgataccg ctcgccgcag ccgaacgacc gagcgcagcg agtcagtgag cgaggaagcg   7500
aagagcgcc caatacgcaa accgcctctc cccgcgcgtt ggccgattca ttaatg         7556
SEQ ID NO: 55            moltype = DNA   length = 7635
FEATURE                  Location/Qualifiers
source                   1..7635
                         mol_type = other DNA
                         organism = Synthetic construct
SEQUENCE: 55
cagctgcgcg ctcgctcgct cactgaggcc gcccgggcaa agcccgggcg tcggcgacc     60
tttggtcgcc cggcctcagt gagcgagcga gcgcgcagag agggagtggc caactccatc    120
actagggggt ccttgtagtt aatgattaac ccgccatgct acttatctac acgcgtagat    180
cttccaact gtcacagtgt gtgcctatt agtcaattaa agcagtccct gcctctttag    240
agttgttttc catgcaatta catgtcttat gtcttagaat aagattccct gagaactgaa    300
cctagcattt atacaagata attaattcta agccatagta cctgcaaaag aacattctac    360
tatcatcttt actgaacaca gaagagctac caccaaaaacc tgggtcatca gccagcacac    420
acacttatcc agtgataaat atacatcatc gggtgcctac atacataccta gaataagaaa    480
aaaaaatacc tttgctgaga tgaaacacac atgatttatt tcaaataggt acagagaagt    540
agatactgaa gtaaggatta agtattatat tatattcat aacattaatc tattcctgca    600
ctgaaaccgt tgctttatat gattttttt ttcactacac taatgagaac ttaagagata    660
atggcctaaa accacagaga gtattttcaa agataagtat agcacaatgc ttactaaatg    720
agactaagac ttgtcccatc gaaaatcctg gacctatgcc tcacacacg gtcacacacg    780
ccgaactttt caaaaattgg tacatgcttt aactttaatc tccaggcctc actggagcta    840
gagacaagaa ggtaaaaaaa ggctgacaaa agaagtcctg gtatcttcta tggtgggaga    900
aggaaactag ctaaagggaa gaataaatta gagaaaaatt ggaatgattg aatcggaaca    960
aggcaaaggc tataaaaaaa ttaagcagca gtatcctctt gggggccccc tccccacact   1020
atctcaatgc aaaatatctgt ctgaaacggt ccctggctaa actccaccccg cgggaacaga  1080
gaaacaggag aatatgggcc aaacaggata tctgtggtaa gcagttcctg ccccggctca   1140
gggcaagaa cagttggaac agcagaatat gggccaaaca ggatatcgt ggtaagcagt   1200
tcctgccccg gctcagggcc aagaacagat ggtcccaga tgcggtcccg ccctcagcag   1260
tttctagaga accatcagat gttccaggg tgccccaagg acctgaaatg accctgtgcc   1320
ttattgaac taaccaatca gttcgcttct cgcttctgt cgcgcgcttc tgctcccga    1380
gctctatata agcagagctc gtttagtgaa ccgtcagatc gcctggagac gccatccacg   1440
ctgtttgac ttccatagaa ggcggcgcg ccgccaccat ggtgagcaag ggcgaggagc   1500
tgttcaccgg ggtggtgccc atcctggtcg agctggacgg cgacgtaaac ggccacaagt   1560
tcagcgtgtc cggcgagggc gagggcgatg ccacctacgg caagctgacc ctgaagttca   1620
tctgcaccac cggcaagctg cccgtgccct ggcccaccct cgtgaccacc ctgacctacg   1680
```

```
gcgtgcagtg cttcagccgc taccccgacc acatgaagca gcacgacttc ttcaagtccg   1740
ccatgcccga aggctacgtc caggagcgca ccatcttctt caaggacgac ggcaactaca   1800
agacccgcgc cgaggtgaag ttcgagggcg acaccctggt gaaccgcatc gagctgaagg   1860
gcatcgactt caaggaggac ggcaacatcc tggggcacaa gctggagtac aactacaaca   1920
gccacaacgt ctatatcatg gccgacaagc agaagaacgg catcaaggtg aacttcaaga   1980
tccgccacaa catcgaggac ggcagcgtgc agctcgccga ccactaccag cagaacaccc   2040
ccatcggcga cggccccgtg ctgctgcccg acaaccacta cctgagcacc cagtccgccc   2100
tgagcaaaga ccccaacgag aagcgcgatc acatggtcct gctggagttc gtgaccgccg   2160
ccgggatcac tctcggcatg gacgagctgt acaagtaacc tgcagggata atcaacctct   2220
ggattacaaa atttgtgaaa gattgactgg tattcttaac tatgttgctc cttttacgct   2280
atgtggatac gctgctttaa tgcctttgta tcatgctatt gcttcccgta tggctttcat   2340
tttctcctcc ttgtataaat cctggttagt tcttgccacg gcggaactca tcgccgcctg   2400
ccttgccgc tgctggacag gggctcggct gttgggcact gacaattccg tggtgtttat   2460
ttgtgaaatt tgtgatgcta ttgctttatt tgtaaccatt ctagctttat ttgtgaaatt   2520
tgtgatgcta ttgctttatt tgtaaccatt ataagctgca ataaacaagt taacaacaac   2580
aattgcattc attttatgtt tcaggttcag ggggagatgt gggaggtttt ttaaagcgaa   2640
ttcgtaaata cacttgcaaa ggaggatgtt tttagtagca atttgtactg atggtatggg   2700
gccaagagat atatccttaga gggaggctg agggtttgaa gtccaactcc taagccagtg   2760
ccagaagagc caaggacagg tacggctgtc atcacttaga cctcaccctg tggagccaca   2820
ccctagggtt ggccaatcta ctcccaggag cagggagggc aggagccagg ctgggcata   2880
aaaagtcaggg cagagccatc tattgcttac actcgcttct ggaacggctg agattatcaa   2940
taagctccta gtccagacgc catggtcat ttccacagag aggacaaggc tactatcaca   3000
agcctgtggg gcaaggtgaa tgtggaagat gctggaggag aaaccctggg aaggtaggct   3060
ctggtgacca ggacaaggaa gggaaggaag gaccctgtgc ctggcaaaag tccaggccac   3120
ttctcaggat ttgtggcact ttctgactgt caaactgctc ttgttcaatc tcacaggctc   3180
ctggttgtct acccatggac ccagaggttc tttgacagct tggcaacct gtcctctgcc   3240
tctgccatca tgggcaaccc caaggtcaag gcacacggca agaaggtgct gacttccttg   3300
ggagatgcca taaagaacct ggatgatctc aagggcacct tgcccagct gagtgagctg   3360
cactgtgaca agctgcatgt ggatcctgag aacttcaggg tgagtccagg agtttcagca   3420
gtttcagagt tcagtctcaa ggcaacttag acaactgagt attgatctga ggacagtcga   3480
atctacctgc tgggtgtgag ctatttgaag atactggggt tgggagtgaa gaaactgcag   3540
aggactaact gggctgagac cgaatggtaa tgtttaggg cctaaggagt gcctctaaaa   3600
atctagacgg acaattttga cattgacaaa agagaggtgg aaatgaggaa aatgactttt   3660
ctttattaga ttccggtaga aagaactttc atctttcct cattttttgtt atttgttta   3720
aaacatctat ctggaggcag gacaagtatg gtcattaaaa agatgcaggc agaaggcata   3780
tattggccca gtcaaagtgg gaactctgg tgaccaaaca gagtctgagg ctattcctat   3840
atcagctgga cacatacaaa atgccgcctc gaggtcgacg tagataagta gcatggcggg   3900
ttaatcatta actacaagga accccctagt atggagttgg ccactccctc tctgcgcgct   3960
cgctcgctca ctgaggccgg gcgaccaaag gtcgcccgac gcccgggctt tgcccgggcg   4020
gcctcagtga gcgagcgagc gcgccagctg gcgtaatagc gaagaggccc gcaccgatcg   4080
cccttcccaa cagttgcgca gcctgaatgg cgaatgcga ttcgttgca atggctggcg   4140
gtaatattgt tctggatatt accagcaagg ccgatagttt gagttcttct actcaggcaa   4200
gtgatgtta tactaatcaa agaagtattg cgacaaccgt taatttgcgt gatggacaga   4260
ctctttttact cggtgcctc actgattata aaaacactcc tcaggattct ggcgtaccgt   4320
tcctgtctaa aatcccttta atcggcctcc tgtttagctc ccgctctgat tctaacgagg   4380
aaaagcacgtt atacgtgctc gtcaaagcaa ccatagtacg cgcccgtag cggcgcatta   4440
agcgcggcgg gtgtggtggt tacgcgcagc gtgaccgcta cacttgccag cgccctagcg   4500
cccgctcctt tcgctttctt cccttcctt ctcgccacgt tcgccggctt tccccgtcaa   4560
gctctaaatc gggggctccc tttagggttc cgatttagtg ctttacggca cctcgacccc   4620
aaaaaacttg attagggtga tggttcacgt agtgggccat cgccctgata cggttttt   4680
cgcccttttga cgttggagtc cacgttcttt aatagtagac tcttgttcca aactgcaaca   4740
acactcaacc ctatctcggt ctattctttt gatttataag ggattttgcc gatttcggcc   4800
tattggttaa aaaatgagct gatttaacaa aaatttaacg cgaattttaa caaaatatta   4860
acgtttacaa tttaaatatt tgcttataca atcttcctgt ttttgggct tttctgatta   4920
tcaaccgggg tacatatgat tgacatgcta gttttacgat taccgttcat cgattctctt   4980
gtttgctcca gactctcagg caatgacctg atagcctttg tagagacctc tcaaaaatag   5040
ctaccctctc cggcatgaat ttatcagcta gaacggttga atatcatatt gatggtgatt   5100
tgactgtctc cggcctttct cacccgtttg aatcttacc tacacattac tcaggcattg   5160
catttaaaat atatgagggt tctaaaaatt tttatccttg cgttgaaata aaggcttctc   5220
ccgcaaaagt attacaggt cataatgttt ttggtacaac cgatttagct ttatgctctg   5280
aggctttatt gcttaatttt gctaattctt tgccttgcct gtatgattta ttggatgttg   5340
gaatcgcctg atgcggtatt ttctccttac gcatctgtgc ggtatttcac accgcatatg   5400
gtgcactctc agtacaatct gctctgatgc cgcatagtta agccagcccc gacacccgcc   5460
aacacccgct gacgcgccct gacgggcttg tctgctcccg gcatccgctt acagacaagc   5520
tgtgaccgtc tccgggagct gcatgtgtca gaggttttca ccgtcatcac cgaaacgcgc   5580
gagacgaaag gcctcgtgat acgcctattt ttataggtt aatgtcatga taataatggt   5640
ttcttagacg tcaggtggca cttttcgggg aaatgtgcgc ggaaccccta tttgtttatt   5700
tttctaaata cattcaaata tgtatccgct catgagacaa taaccctgat aaatgcttca   5760
ataatattga aaaggaaga gtatgagtat tcaacatttc cgtgtcgccc ttattccctt   5820
ttttgcggca ttttgccttc ctgttttgc tcacccagaa acgctggtga agtaaaaga   5880
tgctgaagat cagttgggtg cacgagtggg ttacatcgaa ctggatctca acagcggtaa   5940
gatccttgag agttttcgcc ccgaagaacg ttttccaatg atgagcactt ttaaagttct   6000
gctatgtggc gcggtattat cccgtattga cgccgggcaa gagcaactcg gtcgccgcat   6060
acactattct cagaatgact tggttgagta ctcaccagtc acagaaaagc atcttacgga   6120
tggcatgaca gtaagagaat atgcagtgc tgccataacc atgagtgata acactgcggc   6180
caacttactt ctgacaacga tcggaggacc gaaggagcta accgcttttt tgcacaacat   6240
gggggatcat gtaactcgcc ttgatcgttg ggaaccggag ctgaatgaag ccataccaaa   6300
cgacgagcgt gacaccacga tgcctgtagc aatggcaaca acgttgcgca aactattaac   6360
tggcgaacta cttactctag cttcccggca acaattaata gactggatgg aggcggataa   6420
```

```
agttgcagga ccacttctgc gctcggccct tccggctggc tggtttattg ctgataaatc   6480
tggagccggt gagcgtgggt ctcgcggtat cattgcagca ctggggccag atggtaagcc   6540
ctcccgtatc gtagttatct acacgacggg gagtcaggca actatggatg aacgaaatag   6600
acagatcgct gagataggtg cctcactgat taagcattgg taactgtcag accaagttta   6660
ctcatatata ctttagattg atttaaaact tcatttttaa tttaaaagga tctaggtgaa   6720
gatcctttt gataatctca tgaccaaaat cccttaacgt gagttttcgt tccactgagc    6780
gtcagacccc gtagaaaaga tcaaaggatc ttcttgagat cctttttttc tgcgcgtaat   6840
ctgctgcttg caaacaaaaa aaccaccgct accagcggtg gtttgtttgc cggatcaaga   6900
gctaccaact cttttccga aggtaactgg cttcagcaga gcgcagatac caaatactgt    6960
ccttctagtg tagccgtagt taggccacca cttcaagaac tctgtagcac cgcctacata   7020
cctcgctctg ctaatcctgt taccagtggc tgctgccagt ggcgataagt cgtgtcttac   7080
cgggttggac tcaagacgat agttaccgga taaggcgcag cggtcgggct gaacggggggg  7140
ttcgtgcaca cagcccagct tggagcgaac gacctacacc gaactgagat acctacagcg   7200
tgagctatga gaaagcgcca cgcttcccga agggagaaag gcggacaggt atccggtaag   7260
cggcagggtc ggaacaggag agcgcacgag ggagcttcca gggggaaacg cctggtatct   7320
ttatagtcct gtcgggtttc gccacctctg acttgagcgt cgatttttgt gatgctcgtc   7380
aggggggcgg agcctatgga aaaacgccag caacgcggcc ttttacggt tcctggcctt    7440
ttgctggcct tttgctcaca tgttctttcc tgcgttatcc cctgattctg tggataaccg   7500
tattaccgcc tttgagtgag ctgataccgc tcgccgcagc cgaacgaccg agcgcagcga   7560
gtcagtgagc gaggaagcgg aagagcgccc aatacgcaaa ccgcctctcc ccgcgcgttg   7620
gccgattcat taatg                                                   7635

SEQ ID NO: 56           moltype = DNA   length = 8285
FEATURE                 Location/Qualifiers
source                  1..8285
                        mol_type = other DNA
                        organism = Synthetic construct
SEQUENCE: 56
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc   120
actaggggtt cctacgcgta gatctggtgc ctacatacat acctgaataa gaaaaaaaaa   180
tacctttgct gagatgaaac acacatgatt tatttcaaat aggtacagag aagtagatac   240
tgaagtaagg attaagtatt atattatatt acataacatt aatctattcc tgcactgaaa   300
ccgttgcttt atatgattt tttttcact acactaatga gaacttaaga gataatggcc    360
taaaaccaca gagagtattt tcaaagataa gtatagcaca atgcttacta aatgagacta   420
agacttgtcc catcgaaaat cctggaccta tgcctaaaac acgtgtcaca atccccgaac   480
ttttcaaaaa ttggtacatg ctttaacttt aatctccagg cctcactgga gctagagaca   540
agaaggtaaa aaaaggctga caaaagaagt cctggtatct tctatggtgg gagaaggaaa   600
ctagctaaag ggaagaataa attagagaaa aattgaaatg attgaatcgg aacaaggcaa   660
aggctataaa aaaattaagc agcagtatcc tcttgggggc cccttcccca cactatctca   720
atgcaaatat ctgtctgaaa cggtcccgtg ctaaactcca cccatggggtt ggccagtctt   780
gccttgacgc tagcgtaaat acacttgcaa aggaggatgt ttttagtagc aatttgtact   840
gatggtatgg ggccaagaga tatatcttag agggaggggt gagggttga agtccaactc    900
ctaagccagt gccagaagag ccaaggacag gtacggctgt catcacttag acctcaccct   960
gtggagccac accctagggt tggccaatct actcccagga gcagggaggg caggagccag   1020
ggctgggcat aaaagtcagg gcagagccat ctattgctta catttgcttc tgacacaact   1080
gtgttcacta gcaacctcaa acagacacca tggtgcacct gactcctgag gagaagtctg   1140
ccgttactgc cctgtggggc aaggtgaacg tggatgaagt tggtggtgag gccctgggca   1200
ggttggtatc aaggttacaa gacaggttta aggagaccaa tagaaactgg gcatgtggag   1260
acagagaaga ctcttgggtt tctgataggc actgactctc tctgcctatt ggtctatttt   1320
cccacccgtta ggctgctggt ggtctacccct tggacccaga ggttctttga gtcctttggg   1380
gatctgtcca ctcctgatgc tgttatgggc aaccctaagg tgaaggctca tggcaagaaa   1440
gtgctcggtg cctttagtga tggcctggct cacctggaca acctcaaggg caccttgcc    1500
cagctgagtg agctgcactg tgacaagctg cacgtggatc ctgagaactt cagggtgagt   1560
ctatgggacc cttgatgttt tctttccct tcttttctat ggttaagttc atgtcatagg    1620
aaggggagaa gtaacagggt acacatattg accaaatcag ggtaattttg catttgtaat   1680
tttaaaaaat gctttcttct tttaatatac ttttttgttt atcttatttc taatactttc   1740
cctaatctct ttctttcagg gcaataatga tacaatgtat catgcctctt tgcaccattc   1800
taaagaataa cagtgataat ttctgggtta aggcaatagc aatatttctg catataaata   1860
tttctgcata taaattgtaa ctgatgtaag aggtttcata ttgctaatag cagctacaat   1920
ccagctacca ttctgctttt attttatggt tgggataagg ctggattatt ctgagtccaa   1980
gctaggccct tttgctaatc atgttcatac ctcttatctt cctcccacag ctcctgggca   2040
acgtgctggt ctgtgtgctg gcccatcact ttggcaaaga attcacccca ccagtgcagg   2100
ctgcctatca gaaagtggtg gctggtgtgg ctaatgccct ggcccacaag tatcactaag   2160
ctcgctttct tgctgtccaa tttctattaa aggttccttt gttccctaag tccaactact   2220
aaactggggg atattatgaa gggccttgag catctggatt ctgcctaata aaaaacattt   2280
attttcattg caatgatgta tttaaattat ttctgaatat tttactaaaa agggaatgtg   2340
ggaggttgca gtgctagtct cccggaacta tcactctttc acagtctgct ttggaaggac   2400
tgggcttagt atgaaaagtt aggactgaga agaatttgaa aggggcttt ttgtagctgg    2460
atattcacta ctgtcttatt accctatcat aggcccaccc caaatggaag tccattctt    2520
cctcaggatg tttaagatta gcattcagga agagatcaga ggtctgctgg ctcccttatc   2580
atgtccctta tggtgcttct ggctctgcac cgcggccacg ggttggggt tgcgccttt     2640
ccaaggcagc cctgggtttg cgcagggacg cggctgctct gggcgtggtt ccgggaaacg   2700
cagcggcgtc gacctgggt ctcgcacatt cttcacgtcg gttccgacg agtccaaggt     2760
cttcgccgct acccttgtgg gccccccggc gacgcttcct gctccgcccc taagtcggga   2820
aggttccttg cggttcgcgg cgtgccggac gtgacaaacg gaagccgcac gtctcactag   2880
taccctcgca gacggacagc gccagggagc aatggcagcg cgccgaccgc gatgggctgt   2940
ggccaatagc ggctgctcag cggggcgcgc cgagagcagc ggccgggaag gggcggtgcg   3000
ggaggcgggg tgtggggcgg tagtgtgggc cctgttcctg cccgcgcggt gttccgcatt   3060
```

```
ctgcaagcct ccggagcgca cgtcggcagt cggctccctc gttgaccgaa tcaccgacct   3120
ctctccccag cggccgcgcc gccaccatga caaggattg tgaaatgaaa cgcaccacac    3180
tggacagccc tttggggaag ctggagctgt ctggttgtga gcagggtctg cacgaaataa   3240
agctcctggg caaggggacg tctgcagctg atgccgtgga ggtcccagcc cccgctgcgg   3300
ttctcggagg tccggagccc ctgatgcagt gcacagccctg gctgaatgct ctatttccacc  3360
agcccgaggc tatcgaagag ttccccgtgc cggctcttca ccatcccgtt ttccagcaag    3420
agtcgttcac cagacaggtg ttatggaagc tgctgaaggt tgtgaaattc ggagaagtga    3480
tttcttacca gcaattagca gccctggcag gcaaccccaa agccgcgcga gcagtgggag    3540
gagcaatgag aggcaatcct gtcaaaatcc tcatcccgtg ccacagagtg gtctgcagca    3600
gcggagccgt gggcaactac tccggaggac tggccgtgaa ggaatggctt ctggcccatg    3660
aaggccaccg gttggggaag ccaggcttgg gagggagctc aggtctggca ggggcctggc    3720
tcaagggagc gggagctacc tcgggctccc cgcctgctgg ccgaaactaa gctttatttg    3780
tgaaatttgt gatgctattg ctttatttgt aaccattata agctgcaata aacaagttaa    3840
caacaacaat tgcattcatt ttatgtttca ggttcagggg gagatgtggg aggttttta     3900
aagccctgca ggcaatagcc ttgacaaggc aaccttgacc aatagtctta gagtatcagg    3960
tgaggccagg ggccggcggc tggctaggga tgaagaataa aaggaagcac cctccagcag    4020
ttccacacac tcgcttctgg aacggctgag attatcaata agctcctagt ccagacgcca    4080
tgggtcattt cacagaggag gacaaggcta ctatcacaag cctgtgggc aaggtgaatg     4140
tggaagatgc tggaggagaa accctgggaa ggtaggctct ggtgaccagg acaaggaagg    4200
gaaggaagga ccctgtgcct ggcaaaagtc caggccactt ctcaggattt gtggcacttt    4260
ctgactgtca aactgctctt gttcaatctc acaggctcct ggttgtctac ccatggaccc    4320
agaggttctt tgacagcttt ggcaacctgt cctctgcctc tgccatcatg ggcaaccca    4380
aggtcaaggc acacggcaag aaggtgctga cttcctggg agatgccata aagaacctgg     4440
atgatctcaa gggcaccttt gcccagctga gtgagctgca ctgtgacaag ctgcatgtgg    4500
atcctgaaga cttcaggggtg agtccaggag tttcagcagt ttcagagttc agtctcaagg   4560
cgtcgacagg aacccctagt gatggagttg gccactccct ctctgcgcgc tcgctcgctc   4620
actgaggccg ggcgaccaaa ggtcgcccga cgccccgcct ttgcccgggc ggcctcagtg    4680
agcgagcgag cgcgcagctg gcgtaatagc gaagaggccc gcaccgatcg cccttcccaa    4740
cagttgcgca gcctgaatgg cgaatggcga ttccgttgca atggctggcg gtaatattgt    4800
tctggatatt accagcaagg ccgatagttt gagttcttct actcaggcaa gtgatgttat    4860
tactaatcaa agaagtattg cgacaacggt taatttgcgt gatggacaga ctcttttact    4920
cggtggcctc actgattata aaaacacttc tcaggattct ggcgtaccgt tcctgtctaa    4980
aatcccttta atcggcctcc tgtttagctc ccgctctgat ctaacgagg aaagcacgtt    5040
atacgtgctc gtcaaagcaa ccatagtacg cgccctgtag cggcgcatta gcgcggcgg    5100
gtgtggtggt tacgcgcagc gtgaccgcta cacttgccag cgccctagcg cccgctcctt    5160
tcgctttctt cccttccttt ctcgccacgt tcgccggctt tccccgtcaa gctctaaatc    5220
gggggctccc tttagggttc cgatttagtg ctttacggca cctcgacccc aaaaaacttg    5280
attagggtga tggttcacgt agtgggccat cgccctgata gacggttttt cgccctttga    5340
cgttggagtc cacgttcttt aatagtggac tcttgttcca aactggaaca acactcaacc    5400
ctatctcggt ctattctttt gatttataag gattttgcc gatttcggcc tattggttaa     5460
aaaatgagct gatttaacaa aaatttaacg cgaattttaa caaaatatta cgtttacaa     5520
tttaaatatt tgcttataca atcttcctgt ttttgggct tttctgatta tcaaccgggg     5580
tacatatgat tgacatgcta gttttacgat taccgttcat cgattctctt gtttgctcca    5640
gactctcagg caatgacctg atagcctttg tagagacctc tcaaaaatag ctaccctctc    5700
cggcatgaat ttatcagcta gaacggttga atatcatatt gatggtgatt tgactgtctc    5760
cggccttttct caccccgtttg aatctttacc tacacattac tcaggcattg catttaaaat   5820
atatgaggt tctaaaaatt tttatccttg cgttgaaata aggcttctc ccgcaaaagt      5880
attcagggt cataatgttt ttggtacaac cgatttagct ttatgctctg aggctttatt     5940
gcttaatttt gctaattctt tgccttgcct gtatgattta ttggatgttg aatcgcctg     6000
atgcggtatt ttctccttac gcatctgtgc ggtatttcac accgcatatg gtgcactctc     6060
agtacaatct gctctgatgc cgcatagtta agccagcccc gacacccgcc aacacccgct    6120
gacgcgccct gacgggcttg tctgctcccg gcatccgctt acagacaagc tgtgaccgtc    6180
tccgggagct gcatgtgtca gaggttttca ccgtcatcac cgaaacgcgc gagacgaaag    6240
ggcctcgtga tacgcctatt tttataggtt aatgtcatga taataatggt ttcttagacg    6300
tcaggtggca cttttcgggg aaatgtgcgc ggaacccta tttgtttatt tttctaaata    6360
cattcaaata tgtatccgct catgagacaa taaccctgat aaatgcttca ataattatta    6420
aaaaggaaga gtatgagtat tcaacatttc cgtgtcgccc ttattccctt ttttgcggca    6480
ttttgccttc ctgtttttgc tcacccagaa acgctggtga agtaaaaaga tgctgaagat    6540
cagttgggtg cacgagtggg ttacatcgaa ctggatctca acagcggtaa gatccttgag    6600
agttttcgcc ccgaagaacg ttttccaatg atgagcactt ttaaagttct gctatgtggc    6660
gcggtattat cccgtattga cgccgggcaa gagcaactcg gtcgccgcat acactattct    6720
cagaatgact tggttgagta ctcaccagtc acagaaaagc atcttacgga tggcatgaca    6780
gtaagagaat tatgcagtgc tgccataacc atgagtgata acactgcggc caacttactt    6840
ctgacaacga tcggaggacc gaaggagcta accgcttttt tgcacaacat ggggatcatg    6900
gtaactcgcc ttgatcgttg ggaaccggag ctgaatgaag ccataccaaa cgacgagcgt    6960
gacaccacga tgcctgtagc aatggcaaca acgttgcgca aactattaac tggcgaacta    7020
cttactctag cttcccggca acaattaata gactggatgg aggcggataa agttgcagga    7080
ccacttctgc gctcggccct tccggctggc tggtttattg ctgataaatc tggagccggt    7140
gagcgtgggt ctcgcggtat cattgcagca ctgggggcca gatggtaagc ctcccgtatc    7200
gtagttatct acacgacggg gagtcaggca actatggatg aacgaaatag acagatcgct    7260
gagataggtg cctcactgat taagcattgg taactgtcag accaagttta ctcatatata    7320
ctttagattg atttaaaact tcattttttaa tttaaaagga tctaggtgaa gatcctttt    7380
gataatctca tgaccaaaat cccttaacgt gagttttcgt tccactgagc gtcagacccc    7440
gtagaaaaga tcaaaggatc ttcttgagat ccttttttt tctgcgcgtaa tctgctgcttg   7500
caaacaaaaa aaccaccgct accagcggtg gtttgtttgc cggatcaaga gctaccaact    7560
cttttttccga aggtaactgg cttcagcaga gcgcagatac caaatactgt ccttctagtg   7620
tagccgtagt taggccacca cttcaagaac tctgtagcac cgcctacata cctcgctctg    7680
ctaatcctgt taccagtggc tgctgccagt ggcgataagt cgtgtcttac cgggttggac    7740
tcaagacgat agttaccgga taaggcgcag cggtcgggct gaacggggg ttcgtgcaca     7800
```

```
cagcccagct tggagcgaac gacctacacc gaactgagat acctacagcg tgagctatga  7860
gaaagcgcca cgcttcccga agggagaaag gcggacaggt atccggtaag cggcagggtc  7920
ggaacaggag agcgcacgag ggagcttcca gggggaaacg cctggtatct ttatagtcct  7980
gtcgggtttc gccacctctg acttgagcgt cgattttgt gatgctcgtc agggggggcgg  8040
agcctatgga aaaacgccag caacgcggcc tttttacggt tcctggcctt ttgctggcct  8100
tttgctcaca tgttctttcc tgcgttatcc cctgattctg tggataaccg tattaccgcc  8160
tttgagtgag ctgataccgc tcgccgcagc cgaacgaccg agcgcagcga gtcagtgagc  8220
gaggaagcgg aagagcgccc aatacgcaaa ccgcctctcc ccgcgcgttg gccgattcat  8280
taatg                                                              8285

SEQ ID NO: 57          moltype = DNA  length = 8214
FEATURE                Location/Qualifiers
source                 1..8214
                       mol_type = other DNA
                       organism = Synthetic construct
SEQUENCE: 57
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt cctacgcgta gatcggtgc ctacatacat acctgaataa gaaaaaaaaa  180
tacctttgct gagatgaaac acacatgatt tatttcaaat aggtacagag aagtagatac  240
tgaagtaagg attaagtatt atattatatt acataacatt aatctattcc tgcactgaaa  300
ccgttgcttt atatgatttt ttttttcact acactaatga gaacttaaga gataatgacc  360
taaaaccaca gagagtattt tcaaagataa gtatagcaca atgcttacta aatgagacta  420
agacttgtcc catcgaaaat cctgaccta tgcctaaaac acgtgtcaca atccccgaac  480
tttttcaaaaa ttggtacatg ctttaacttt aatctccagg cctcactgga gctagagaca  540
agaaggtaaa aaaaggctga caaaagaagt cctggtatct tctatggtgg gagaaggaaa  600
ctagctaaag ggaagaataa attagagaaa aattggaatg attgaatcgg aacaaggcaa  660
aggctataaa aaaattaagc agcagtatcc tcttgggggc ccttccccca cactatctca  720
atgcaaatat ctgtctgaaa cggtccctgg ctaaactcca cccatgggtt ggccagtctt  780
gccttgacgc tagcgtaaat acacttgcaa aggaggatgt ttttagtagc aatttgtact  840
gatggtatgg ggccaagaga tatattctag agggaggggt gagggtttga agtccaactc  900
ctaagccagt gccagaagag ccaaggacag gtaccggctgt catcacttag acctcaccct  960
gtggagccac accctagggt tggccaatct actcccagga gcagggaggg caggagccag 1020
ggctgggcat aaaagtcagg gcagagccat ctattgctta catttgcttc tgacacaact 1080
gtgttcacta gcaaccctcaa acagacacca tggtgcacct gactcctgag gagaagtctg 1140
ccgttactgc cctgtgggc aaggtgaacg tggatgaagt tggtggtgag gccctgggca 1200
ggttggtatc aaggttacaa gacaggttta aggagaccaa tagaaactgg gcatgtggag 1260
acagagaaga ctcttgggtt tctgataggc actgactctc tctgcctatt ggtctatttt 1320
cccaccctta ggctgctggt ggtctaccct tggacccaga ggttctttga gtcctttggg 1380
gatctgtcca ctcctgatgc tgttatgggc aaccctaagg tgaaggctca tggcaagaaa 1440
gtgctcggtg cctttagtga tggcctggct cacctggaca acctcaaggg cacctttgcc 1500
cagctgagtg agctgcactg tgacaagctg cacgtggatc ctgagaactt cagggtgagt 1560
ctatggaccc cttgatgttt tctttcccct gttaagttc atgtcatagg 1620
aaggggagaa gtaacagggt acacatattg accaaatcag ggtaattttg catttgtaat 1680
tttaaaaaat gctttcttct tttaatatac tttttgttt atcttatttc taatactttc 1740
cctaatctct ttctttcagg gcaataatga tacaatgtat catgcctctt tgcaccattc 1800
taaagaataa cagtgataat ttctgggtta aggcaatagc aatatttctg catataaata 1860
tttctgcata taaattgtaa ctgatgtaag aggtttcata ttgctaatag cagctacaat 1920
ccagctacca ttctgctttt attttatggt tgggataagg ctggattatt ctgagtccaa 1980
gctaggccct tttgctaatc atgttcatac ctcttatctt cctcccacag ctcctgggca 2040
acgtgctggt ctgtgtgctg gcccatcact ttggcaaaga attcacccca ccagtgcagg 2100
ctgcctatca gaaagtggtg gctggtgtgg ctaatgccct ggcccacaag tatcactaag 2160
ctcgcttttct tgctgtccaa tttctattaa aggttccttt gttccctaag tccaactact 2220
aaactggggg atattatgaa gggccttgag catctggatt ctgcctaata aaaaacattt 2280
attttcattg caatgatgta tttaaattat ttctgaatat tttactaaaa agggaatgtg 2340
ggaggttgca gtgctagtct cccggaacta tcactctttc acagtctgct ttggaaggac 2400
tgggcttagt atgaaaagtt aggactgaga agaatttgaa aggggctttt tgtagcttg 2460
atattcacta ctgtctattt accctatcat aggcccaccc caaatggaag tcccattctt 2520
cctcaggatg tttaagatta gcattcagga agatgatcaga ggtctgctgg ctcccttatc 2580
atgtccctta tggtgcttct ggctctgcac cgcgggaaca gagaaacagg agaatatgag 2640
ccaaacagga tatctgtggt aagcagttcc tgccccggct cagggccaag aacagttgga 2700
acagcagaat atgggccaaa caggatatct gtggtaagca gttcctgccc cggctcaggg 2760
ccaagaacag atggtcccca gatgcggtcc cgccctcagc agtttctaga gaaccatcag 2820
atgtttccag ggtgccccaa ggacctgaaa tgaccctgtc cctatttga actaaccaat 2880
cagttcgctt ctcgcttctg ttcgcgcgct tctgctcccc gagctctata aagcagagc 2940
tcgtttagtg aaccgtcaga tcgcggccga gccgccacca tggtgagcaa gggcgaggag 3000
ctgttcaccg gggtggtgcc catcctggtc gagctggacg gcgacgtaaa cggccacaag 3060
ttcagcgtgt ccggcgaggg cgaggcgat gccacctggg acaagctgac cctgaagttc 3120
atctgcacca ccggcaagct gcccgtgccc tggcccaccc tcgtgaccac cctgacctac 3180
ggcgtgcagt gcttcagccg ctaccccgac cacatgaagc agcacgactt cttcaagtcc 3240
gccatgcccg aaggctacgt ccaggagcgc accatcttct tcaaggacga cggcaactac 3300
aagacccgcg ccgaggtgaa gttcgagggc gacaccctgg tgaaccgcat cgagctgaag 3360
ggcatcgact tcaaggagga cggcaacatc ctggggcaca gctggagta caactacaac 3420
agccacaacg tctatatcat ggccgacaag cagaagaacg gcatcaaggt gaacttcaag 3480
atccgccaca acatcgagga ggcagcgtg cagctcgccg accactacca gcagaacacc 3540
cccatcggcg acgcccccgt gctgctgccc gacaaccact acctgagcac ccagtccgcc 3600
ctgagcaaag ccccaacga gaagcgcgat cacatggtcc tgctggagtt cgtgaccgcc 3660
gccgggatca ctctcggcat ggacgagctg tacaagtaag ctttatttgt gaaatttgtg 3720
atgctattgc tttatttgta accattataa gctgcaataa acaagttaac aacaacaatt 3780
```

```
gcattcattt tatgtttcag gttcagggg agatgtggga ggttttttaa agccctgcag   3840
gcaatagcct tgacaaggca accttgacca atagtcttag agtatcaggt gaggccaggg   3900
gccggcggct ggctagggat gaagaataaa aggaagcacc ctccagcagt tccacacact   3960
cgcttctgga acggctgaga ttatcaataa gctcctagtc cagacgccat gggtcatttc   4020
acagaggagg acaaggctac tatcacaagc ctgtggggca aggtgaatgt ggaagatgct   4080
ggaggagaaa ccctgggaag gtaggctctg gtgaccagga caaggaaggg aaggaaggac   4140
cctgtgcctg gcaaaagtcc aggccacttc tcaggatttg tggcactttc tgactgtcaa   4200
actgctcttg ttcaatctca caggctcctg gttgtctacc catggaccca gaggttcttt   4260
gacagctttg gcaacctgtc ctctgcctct gccatcatgg gcaaccccaa ggtcaaggca   4320
cacggcaaga aggtgctgac ttccttggga gatgccataa agaacctgga tgatctcaag   4380
ggcacctttg cccagctgag tgagctgcac tgtgacaagc tgcatgtgga tcctgagaac   4440
ttcagggtga gtccaggagt ttcagcagtt tcagagttca gtctcaaggc gtcgacagga   4500
accctagtg atggagttgg ccactccctc tctgcgcgct cgctcgctca ctgaggccgg   4560
gcgaccaaag gtcgcccgac gcccgggctt tgcccgggcg gcctcagtga gcgagcgagc   4620
gcgcagctgg cgtaatagcg aagaggcccg caccgatcgc ccttcccaac agttgcgcag   4680
cctgaatggc gaatggcgat tccgttgcaa tggctggcgg taatattgtt ctggatatta   4740
ccagcaaggc cgatagtttg agttcttcta ctcaggcaag tgatgttatt actaatcaaa   4800
gaagtattgc gacaacggtt aatttgcgtg atggacaagt tcttttactc ggtgcctca   4860
ctgattataa aaacacttct caggattctg gcgtaccgtt cctgtctaaa atccctttaa   4920
tcggcctcct gtttagctcc cgctctgatt ctaacgagga agcacgtta tacgtgctcg   4980
tcaaagcaac catagtacgc gccctgtagc ggcgcattaa gcgcggcggg tgtggtggtt   5040
acgcgcagcg tgaccgctac acttgccagc gccctagcgc ccgctccttt cgctttcttc   5100
ccttcctttc tcgccacgtt cgccggcttt cccgtcaag ctctaaatcg ggggctccct   5160
ttagggttcc gatttagtgc tttacggcac ctcgacccca aaaaacttga ttagggtgat   5220
ggttcacgta gtgggccatc gccctgatag acggtttttc gccctttgac gttggagtcc   5280
acgttcttta atagtggact cttgttccaa actggaacaa cactcaaccc tatctcggtc   5340
tattctttg atttataagg gattttgccg atttcggcct attggttaaa aaatgagctg   5400
atttaacaaa aatttaacgc gaattttaac aaaatattaa cgtttacaat ttaaatattt   5460
gcttatacaa tcttcctgtt tttggggctt ttctgattat caaccggggt acatatgatt   5520
gacatgctag ttttacgatt accgttcatc gattctcttg tttgctccag actctcaggc   5580
aatgacctga tagcctttgt agagacctct caaaaatagc tacccctctcc ggcatgaatt   5640
tatcagctag aacggttgaa tatcatattg atggtgattt gactgtctcc ggcctttctc   5700
acccgtttga atctttacct acacattact caggcattgc atttaaaata tatgagggtt   5760
ctaaaaattt ttatccttgc gttgaaataa aggcttctcc cgcaaaagta ttacagggtc   5820
ataatgtttt tggtacaacc gatttagctt tatgctctga ggctttattg cttaattttg   5880
ctaattcttt gccttgcctg tatgatttat tggatgttgg aatcgcctga tgcggtattt   5940
tctccttacg catctgtgcg gtatttcaca ccgcatatgg tgcactctca gtacaatctg   6000
ctctgatgcc gcatagttaa gccagccccg acacccgcca cacccgctg acgcgccctg   6060
acgggcttgt ctgctcccgg catccgctta cagacaagct gtgaccgtct ccgggagctg   6120
catgtgtcag aggttttcac cgtcatcacc gaaacgcgcg agacgaaagg gcctcgtgat   6180
acgcctattt tataggtta atgtcatgat aataatggtt tcttagacgt caggtggcac   6240
ttttcgggga aatgtgcgcg gaaccccctat tgtttattt tctaaatac attcaaatat   6300
gtatccgctc atgagacaat aaccctgata aatgcttcaa taatattgaa aaaggaagag   6360
tatgagtatt caaactttcc gtgtcgccct tattccctttt tttgcggcat tttgccttcc   6420
tgttttgct cacccagaaa cgctggtgaa agtaaaagat gctgaagatc agttgggtgc   6480
acgagtggg tacatcgaac tggatctcaa cagcggtaag atccttgaga gttttcgccc   6540
cgaagaacgt tttccaatga tgagcacttt taaagttctg ctatgtggcg cggtattatc   6600
ccgtattgac gccgggcaag agcaactcgg tcgccgcata cactattctc agaatgactt   6660
ggttgagtac tcaccagtca cagaaaagca tcttacggat ggcatgacag taagagaatt   6720
atgcagtgct gccataacca tgagtgataa cactgcggcc aacttacttc tgacaacgat   6780
cggaggaccg aaggagctaa ccgcttttt gcacaacatg gggatcatg taactcgcct   6840
tgatcgttgg gaaccggagc tgaatgaagc cataccaaac gacgagcgtg acaccacgat   6900
gcctgtagca atggcaacaa cgttgcgcaa actattaact ggcgaactac ttactctagc   6960
ttcccggcaa caattaatag actggatgga ggcggataaa gttgcaggac cacttctgcg   7020
ctcggccctt ccggctggct ggtttattgc tgataaatct ggagccggtg agcgtgggtc   7080
tcgcggtatc attgcagcac tggggccaga tggtaagccc tcccgtatcg tagttatcta   7140
cacgacgggg agtcaggcaa ctatggatga acgaaataga cagatcgctg agataggtgc   7200
ctcactgatt aagcattggt aactgtcaga ccaagtttac tcatatatac tttagattga   7260
tttaaaacttt cattttttaat ttaaaaggat ctaggtgaag atccttttg ataatctcat   7320
gaccaaaatc ccttaacgtg agttttcgtt ccactgagcg tcagaccccg tagaaaagat   7380
caaaggatct tcttgagatc ctttttttct gcgcgtaatc tgctgcttgc aaacaaaaaa   7440
accaccgcta ccagcggtgg tttgtttgcc ggatcaagag ctaccaactc tttttccgaa   7500
ggtaactggc ttcagcagag cgcagatacc aaatactgtc cttctagtgt agccgtagtt   7560
aggccaccac ttcaagaact ctgtagcacc gcctacatac ctcgctctgc taatcctgtt   7620
accagtggct gctgccagtg gcgataagtc gtgtcttacc gggttggact caagacgata   7680
gttaccggat aaggcgcagc ggtcgggctg aacggggggt tcgtgcacac agcccagctt   7740
ggagcgaacg acctacaccg aactgagata cctacagcgt gagctatgag aaagcgccac   7800
gcttcccgaa gggagaaagg cggacaggta tccggtaagc ggcagggtcg gaacaggaga   7860
gcgcacgagg gagcttccag gggggaacgc ctggtatctt tatagtcctg tcgggtttcg   7920
ccacctctga cttgagcgtc gatttttgtg atgctcgtca gggggggcgga gcctatgaaa   7980
aaacgccagc aacgcggcct ttttacggtt cctggccttt tgctggcctt ttgctcacat   8040
gttctttcct gcgttatccc ctgattctgt ggataaccgt attaccgcct ttgagtgagc   8100
tgataccgct cgccgcagcc gaacgaccga gcgcagcgag tcagtgagcg aggaagcgga   8160
agagcgccca atacgcaaac cgcctctccc cgcgcgttgg ccgattcatt aatg          8214
```

SEQ ID NO: 58        moltype = DNA   length = 15824
FEATURE               Location/Qualifiers
source                1..15824
                        mol_type = other DNA

```
                         organism = Synthetic construct
SEQUENCE: 58
gcgtataatg gactattgtg tgctgataag gagaacataa gcgcagaaca atatgtatct    60
attccggtgt tgtgttcctt tgttattctg ctattatgtt ctcttatagt gtgacgaaag   120
cagcataatt aatcgccact tgttctttga ttgtgttacg atatccagag acttagaaac   180
gggggaaccg ggatgagcaa ggtaaaaatc ggtgagttga tcaacacgct tgtgaatgag   240
gtagaggcaa ttgatgcctc agaccgccca caaggcgaca aaacgaagag aattaaagcc   300
gcagccgcac ggtataagaa cgcgttattt aatgataaaa gaaagttccg tgggaaagga   360
ttgcagaaaa gaataaccgc gaatacttt aacgcctata tgacgcgggc aagaaagcgg   420
tttgatgata aattcatca tagctttgat aaaaatatta ataaattatc ggaaaagtat   480
cctctttaca gcgaagaatt atcttcatgg ctttctatgc ctacggctaa tattcgccag   540
cacatgtcat cgttacaatc taaattgaaa gaataatgc cgcttgccga agagttatca   600
aatgtaagaa taggctctaa aggcagtgat gcaaaaatag caagactaat aaaaaaatat   660
ccagattgga gttttgctct tagtgattta aacagtagt attggaagga gcgccgtgac   720
tatctttata agttattcca acaaggctct gcgttgttag aagaactaca ccagctcaag   780
gtcaaccatg aggttctgta ccatctgcag ctaagccctg cggagcgtac atctatacag   840
caacgatggg ccgatgttct gcgcgagaag aagcgtaatg ttgtggttat tgactaccca   900
acatacatgc agtctatcta tgatattttg aataatccgt cgactttatt tagtttaaac   960
actcgttctg gaatggcacc tttgcccttt gctctggctg cggtatcagg gcgaagaatg  1020
attgagataa tgtttcaggg tgaatttgcc gtttcaggaa agtatacggt taatttctca  1080
gggcaagcta aaaacgctc tgaagataaa agcgtaacca gaacgattta tctttatgc  1140
gaagcaaaat tattcgttga attattaaca gaattgcctc cttgctctgc tgcatctgat  1200
ttcgatgagg ttgttaaagg atatggaaag gatgatacaa ggtctgagaa cggcaggata  1260
aatgctattt tagcaaaagc atttaacct tgggttaaat cattttttcgg cgatgaccgt  1320
cgtgtttata agatagccg cgctatttac gctcgcatcg cttatgagat gttcttccgc  1380
gtcatccac ggtggaaaaa cgtcgacgag gatgtgttct tcatggagat tctcggacac  1440
gacgatgaga acacccagct gcactataag cagttcaagc tggccaactt ctccagaacc  1500
tggcgacctg aagttgggga tgaaaacacc aggctggtgg ctctgcagaa actgacgat  1560
gaaatgccag gctttgccag aggtgacgct ggcgtccgtc tgcatgaaac cgttaagcag  1620
ctggtggagc aggacccatc agcaaaaata accaacagca ctctccggac ctttaaattt  1680
agcccgacga tgattagccg gtacctggag tttgccgctg atgcattggg gcagttcgtt  1740
ggcgagaacg ggcagtggca gctgaagata gagacacctg caatcgtcct gcctgatgaa  1800
gaatccgttg aaaccatcga cgaaccggat gatgagtccc aagacgacga gctggatgaa  1860
gatgaaattg agctcgacga gggtggcggc gatgaaccaa ccgaagagga agggccagaa  1920
gaacatcagc caactgctct aaaaacccgtc ttcaagcctg caaaaaataa cggggacgga  1980
acgtacaaga tagagtttga atacgatgga aagcattatg cctggtccgg ccccgccgat  2040
agccctatgc ccgcaatgcg atccgcatgg gaaacgtact acagctaaaa gaaaagccac  2100
cggtgttaat cggtggcttt tttattgagg cctgtcccta cccatcccct gcaagggacg  2160
gaaggattag gcggaaactg cagctgcaac tacggacatc gccgtcccga ctgcagggac  2220
ttccccgcgt aaagcggggc ttaaattcgg gctggccaac cctattttc tgcaatcgct  2280
ggcgatgtta gtttcgtgga tagcgtttcc agcttttcaa tggccagctc aaaatgtgct  2340
ggcagcacct tctccagttc cgtatcaata tcggtgatcg gcagctctcc acaagacata  2400
ctccggcgac cgccacgaac tacatcgcgc agcagctccc gttcgtagac acgcatgttg  2460
cccagagccg tttctgcagc cgttaatatc cggcgcagct cggcgatgat tgccgggaga  2520
tcatccacgt ttattgggtt cggtgatggg ttcctgcagg cgcggcggag agccatccag  2580
acgccgctaa cccatgcgtt acggtactga aaactttgtg ctatgtcgtt tatcaggccc  2640
cgaagttctt ctttctgccg ccagtccagt ggttcaccgg cgttcttagg ctcaggctcg  2700
acaaaagcat actcgccgtt tttccggata gctggcagaa cctcgttcgt cacccacttg  2760
cggaaccgcc aggctgtcgt cccctgtttc accgcgtcgc ggcagcggag gattatggtg  2820
tagaggccag attccgatac cacatttact tccctggcca tccgatcaag tttttgtgcc  2880
tcggttaaac cgagggtcaa tttttcatca tgatccagct tacgcaatgc atcagaaggg  2940
ttggctatat tcaatgcagc acagatatcc agcgccacaa accacgggtc accaccgaca  3000
agaaccaccc gtatagggtg gcttttcctga aatgaaaaga cggagagagc cttcattgcg  3060
cctccccgga tttcagctgc tcagaaaggg acagggagca gccgcgagct tcctgcgtga  3120
gttcgcgcgc gacctgcaga agttccgcag cttcctgcaa atacagcggg gcctcataac  3180
tggagatagt gcggtgagca gagcccacaa gcgcttcaac ctgcagcagg cgttcctcaa  3240
tcgtcttcag caggccctgg gcgtttaact gaatctggtt catgcgatca cctcgctgac  3300
cgggatacgg gctgacagaa cgaggacaaa acggctggcg aactggcgac gagcttctcg  3360
ctcggatgat gcagtggtgg aaaggcggtg gatatgggat tttttgtccg tcgggacgac  3420
agctgcaaat ttgaatttga acatggtatg cattcctatc ttgtataggg tgctaccacc  3480
agagttgaga atctctatag gggtggtagc ccagacaggg ttctcaacac cggtacaaga  3540
agaaccggc ccaaccgaag ttggcccat ctgagccacc ataattcagg tatgcgcaga  3600
tttaacacac aaaaaaacac gctggcgcgt gttgtgcgct tcttgtcatt cggggttgag  3660
aggccggct acagattttg ctgcagcggg gtaactctac cgccaaagca gaacgcacgt  3720
caataattta ggtggatatt ttaccccgtg accagtcacg tgcacaggtg tttttatagt  3780
ttgctttact gactgatcag aacctgatca gttattggag tccggtaatc ttattgatga  3840
ccgcagccac cttagatgtt gtctcaaacc ccatacggcc acgaatgagc cactggaacg  3900
gaatagtcag caggtacagc ggaacgaacc acaaacggtt cagcagctgc agaacgtcg  3960
catcacgacg ttccatccat tcggtattgt cgacgacctg gtaagcgtat tgtcctggca  4020
tttttgctgc ttccgagtag caatcctctt caccacaaag aaagttactt atctgcttcc  4080
agttttcgaa cccttcttct ttgagccgct tttccagctc attcctccac aaaacaggca  4140
cccatcctct gcgataaatc atgattattt gtccttaaa taaggctgta gaactgcaaa  4200
atcgctctcg ttcacatgct gtacgtgat gcgtagcaaa ttgccgttcc atccctgtaa  4260
tccaccttct ttggaaagat cgtccttgac ctcacgaaga acttatcca atagccctga  4320
ggcacaagaa attgcctgct ctggatcagc aaattcatat tgattaatag gtgattgcca  4380
cacaccaaaa acaggaatca tctttttcggc taaacgcctc tcctgttctt tcttaatctc  4440
aagttgtaag cggaccagct caccatccat catttttttgt agatcatgcg ccactattca  4500
cccccactgg ccatcagcaa ataaagcttc atactcggac accggcaggc ggcttccacg  4560
gattgaaagg tcaagccaac cacgtccaga tgggtcagcc ttatccgatt cttcccaccg  4620
```

```
ttctgcagct gtagcaacca ggcattctac cgccttcatg tagtcttctg tacggaacca    4680
gccgtagtta atgccaccat cagtaactgc ccaggccatc ttttctctt cggcctcaat     4740
agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgtgcg caatgcagca ataaactgtc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attacccctc cggttatatc gccacgcgtt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt      5340
tggatcgagg gttaccatgt atatctatat ttagatccaa atcgcgatcc acttcgatgg     5400
tggttttttc caccttacgt gcgtgaattg ataaaccggc ctcgcggcgc ttctccacga    5460
tattcatgag gaactcgacc gagtccgggt caatgaacg catcgtgggg cgtgcatcgc       5520
catctctggc gcgtctggtc ttactggata gccccataga ctcaggatg cctatgcaga      5580
ggtctgcagg cgctttcttc ttgcctttct ctgtgttgaa gccgccgatg cgtaaaacgt    5640
tgtttagcag atcgccgt tccggcgtga gcaggttatc tctggcgcgt ttgagggcga      5700
ccatgtctgc ttcaccttcc aggtttttg gatcgatacc gcagtcgcgg aagtactgct      5760
gcagcgtcgc cgatttgagg gtgtagaaac cacgcatgcc tatctcaaca gcaggggtcg    5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact tttttcaggc cgccgtcgaa atagaatttt aacgccacct    6060
cgtcgacatc cagctgcagc tccttttcga tgtcccagcg gaccagctgg gcctgctcat    6120
ccaggacag ggtgcgtttt tttatcaact catcgtgttc atcgcggtca ggagtatcga      6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagcgtgc atgaatgaag agttagccac gccgagtgaa attcggtcac    6420
cgtcaaagac aacgtctgtc agcagcccgg agtggccagc cgtttcgagc aaggcctgca    6480
cgtaggcgcg tttgattttt tccggatcgg tttcacgttt accgcgaagc ttgtcgaaac    6540
cgataatgta ttcctgagct gtacggtcgc ggcgcagcat ctggatgcg tcgctgggga     6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt     6840
cggtggccaa catgattcgt tcgccgcgtt gcactgcagc gataacctcg gtcatgatcc    6900
gattttctc ggtataaaat acgcggatag gcttgttggt ttcgcggttg cgaacgtcga    6960
ccgggagttc aatcacgtga atttgcagcc aggcaggtag gccgcagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gcctttccct tcggtcatca tttcatgcag gccgcctatc agggatacgc    7380
ggtgcgac ggaaacgcca cgcgtggact gcagcatcag tggacgcagg aggcctgtcg       7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg cacggcatt     7620
tgcgattcaa ccggcgcgta atgtgatctt taacgacgtc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacagatcg gttgcacggc    7860
tcagatgatt tctcgttaac tggcgagcga cttccttcag cccctctcag ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat tgcgcagcc gggtacatgt     8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaatttt tgcgcccct gcaggtcgcc aataacaaag catgcaccga      8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcgagcggg cgtgcttcag     8640
cctggcgctc catgcgtgca cgttcttctt ccggctgagc gaccacggcg gcaccattcc    8700
gttgctgttc acggcggatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggccttaa ggctcttctg cagagcttcc ggggaggaat       8880
tattgtaggg ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacgatcg ctgccaaagc gctccgcgta gaattcttgt aaggtcattt      9060
tttagccttt ccatgcgaat tagcattttt tcggttgaa aaaatccgca ggagcagcca      9120
caataaacgc actatctttc tgaaggacgt atctgcgtta tcgtggctac ttcctgaaaa    9180
aggcccgagt tgccgactc ggttttttt tcgtctttt tcggctgcta cggtctggtt        9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
```

```
ttgaagatca ctttatcat ggataacccg ttgagagtta gcactatcaa ggtagtaatg   9420
ctgctcgtca taacgggcta atcgttgaat tgtgatctcg ccgttattat cacaaaccag   9480
tacatcctca cccggtacaa gcgtaagtga agaatcgacc aggataacat ctcccggctg   9540
gtagtttcgc tgaatctggt tcccgaccgt cagtgcgtaa acggtgttcc gttgactcac   9600
gaacggcagg aatcgctctg tgttggcagg ttctccaggc tgccagtctc tatccggtcc  9660
tgtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgttcgc ctcgtgtttt   9900
catacccctta atcataaatg atctctttat agctggctat aatttttata aattatacct   9960
agctttaatt ttcacttatt gattataata atccccatga aacccgaaga acttgtgcgc  10020
catttcggcg atgtgaaaaa agcagcggtt ggcgtgggcg tgacacccgg cgcagtctat  10080
caatggctgc aagctgggga gattccacct ctacgacaaa gcgatataga ggtccgtacc  10140
gcgtacaaat taaagagtga tttcacctct cagcgcatgg gtaaggaagg gcataacaag  10200
gggatcctct agacgcagaa aggcccaccc gaaggtgagc cagtgtgatt acatttgcgg  10260
cctaactgtg gccagtccag ttacgctgga gtcactagtg cggccgcgac aacttgtcta  10320
gggcccaatg gcccatacac ttagtgtaat acgactcact ataggagag cggccgcttt   10380
ttcagcaaga ttaagccgcc accatggcgc cgcggcctcc taagaagaag cggaaagtcg  10440
aattcgtgga tctgcgaaca ctgggctata gccagcagca gcaggagaag atcaaaccca  10500
aggtgaggtc cacagtcgca cagcaccatg aagcccggtg gggccacggg ttcactcacg  10560
ctcatattgt cgcactgtct cagcatccag ccgctctggg aaccgtggca gtcacatacc  10620
agcacatcat tactgccctg cccgaggctc ccatgaaga gatgaccgga gtcggcaaac  10680
agtggagcgg cgcacgggcc ctggaggctc tgctgaccga cgcaggggaa ctgagaggac  10740
cccctctgca gctggataca gggcagctgg tgaagattgc taagaggga ggggtgacag   10800
caatggaagc cgtccacgca agcaggaacg cactgacagg gcccccctg aacctgaccc   10860
cggaccaagt ggtggctatc gccagcaatc acggcgctc gaaacggtg gcagcggctg   10920
agcggctgtt gccggtgctg tgccaggacc atggcctgac cccggaccaa gtggtggcta  10980
tcgccagcaa tcacggcggc aagcaagcgc tcgaaacggt gcagcggctg ttgccggtgc  11040
tgtgccagga ccatggcctg accccggacc aagtggtggc tatcgccagc aatcacggcg  11100
gcaagcaagc gctcgaaacg gtgcagcggc tgttgccggt gctgtgccag gaccatggcc  11160
tgaccccgga ccaagtggtg gctatcgcca gcaacggtgg cggcaagcaa gcgctcgaaa  11220
cggtgcagcg gctgttgccg gtgctgtgcc aggaccatgg cctgaccccg gaccaagtgg  11280
tggctatcgc cagcaacggt ggcggcaagc aagcgctcga aacggtgcag cggctgttgc  11340
cggtgctgtg ccaggaccat ggcctgaccc cggaccaagt ggtggctatc gccagcaatc  11400
acggcggaaa acaggccctt gaaacggtgc agcggctgtt gccggtgctg tgccaggacc  11460
atggcctgac cccggaccaa gtggtggcta tcgccagcaa tcacggcggc aagcaagcgc  11520
tcgaaacggt gcagcggctg ttgccggtgc tgtgccagga ccatgcctg actccggacc  11580
aagtggtggc tatcgccagc cacgatgcg gcaagcaagc gctcgaaacg gtgcagcggc  11640
tgttgccggt gctgtgccag gaccatggcc tgactccgga ccaagtggtg gctatcgcca  11700
gccacgatgg cggcaagcaa gcgctcgaaa cggtgcagcg gctgttgccg gtgctgtgcc  11760
aggaccatgg cctgaccccg gaccaagtgg tggctatcgc cagcaacatt ggcggcaagc  11820
aagcgctcga aacggtgcag cggctgttgc cggtgctgtg ccaggaccat ggcctgaccc  11880
cggaccaagt ggtggctatc gccagcaatc acggcggcaa gcaagcgctc gaaacggtgc  11940
agcggctgtt gccggtgctg tgccaggacc atggcctgac tccggaccaa gtggtggcta  12000
tcgccagcca cgatgcggc aagcaagcgc tcgaaacggt gcagcggctg ttgccggtgc   12060
tgtgccagga ccatggcctg actccggacc aagtggtggc tatcgccagc cacgatggcg  12120
gcaagcaagc gctcgaaacg gtgcagcggc tgttgccggt gctgtgccag gaccatggcc  12180
tgaccccgga ccaagtggtg gctatcgcca gcaacggtgg cggcaagcaa gcgctcgaaa  12240
cggtgcagcg gctgttgccg gtgctgtgcc aggaccatgg cctgaccccg gaccaagtgg  12300
tggctatcgc cagcaacggt ggcggcaagc aagcgctcga aacggtgcag cggctgttgc  12360
cggtgctgtg ccaggaccat ggcctgaccc cggaccaagt ggtggctatc gccagcaatc  12420
acggcggcaa gcaagcgctc gaaagcattg gcccagct gagccggcct gatccggcgt   12480
tggccgcgtt gaccaacgac cacctggtcg ctctggcttg cctgggagga cgccctgcta  12540
tggacgctgt gaagaaagga ctgccccacg cacccgaact gattagacgg gtgaaccgga  12600
gaatcggcga gagaacatcc catagggtgg caatctctag aactcagctg gtcaagagtg  12660
aactgaggag aaaagaaatca gagctgcgc acaagctgaa atacgtgcct catgagtata  12720
tcgaactgat cgagattgct cgcaattcaa cccaggaccg gatcctggaa atgaaagtga  12780
tggagttctt tatgaaagtc tacggatatc gggggaaaca cctgggaggg agcagaaagc  12840
cagatgggc catctacaca gtgggatccc ccatcgacta tggcgtgatt gtcgataca  12900
aagcctacag cggaggctat aacctgccta tcggccaggc tgacgagatg cagagatacg  12960
tggaggaaaa ccagacccgc aataagcata ttaaccccaa tgaatggtgg aaagtgtatc  13020
ctagctccgt cacagagttc aagttctctg tcgtgagcgg acactttaag ggcaactaca  13080
aagcacagct gactaggctg aatcatatca ccaactgcaa tggagccgtg ctgtctgtcg  13140
aggaactgct gatcggggga gagatgatta aggctggcac cgtgcaatgg tttgactcca  13200
cagagcgctg tgtctctgg gaggaagtga ggcgcaagtt caacaatggg gaaatcaact  13260
tctaacctgc aggatgataa gctagccccg ggcgtacgga aaaaaaaaaa aaaaaaaaaa  13320
aaaaaaaaaa aaaaaaaaaa aaaaaaaaaa aaaaaaaaaa aaaaaaaaaa aaaaaaaaaa  13380
aaaaaaaaaa aaaaaaaaaa aaaaaaaaaa aaaaaaaaaa aaaaaaaaaa aaaaaaaaaa  13440
aaaaaaaaaa aaaaaaaaaa aaaaaaaaaa aaaaaaaaaa aaaaaaaaaa aaaaaaaaaa  13500
aaaaaaaaaa aaaaaaaaaa aaaaaaaaaa aaaaaaaaaa aaaaaaaaaa aaaaaaaaaa  13560
aaaaaaaaaa aaaaaaaaaa aaaaaaaaaa aaaacgagac cttagggcca ttagacttga  13620
agtcaagcgg ccgcttacaa ctggaccttg ctggtacata gaactgatta actgaccatt  13680
taaatcatac caacatggtc aaataaaacg aaaggctcag tcgaaagact gggcctttcg  13740
ttttatctg atcggcacgt aagaggttcc aactttcacc ataatgaaat aagatcacta  13800
ccgggcgtat tttgagttat cgagattttc aggagctaag gaagctaaaa tgagccatat  13860
tcaacgggaa acgtcttgct cgaggccgcg attaaattcc aacatggatg ctgatttata  13920
tgggtataaa tgggctcgcg ataatgtcgg gcaatcaggt gcgacaatct atcgattgta  13980
tgggaagccc gatgcgccag agttgtttct gaaacatggc aaaggtagcg ttgccaatga  14040
tgttacagat gagatggtca ggctaaactg gctgacggaa tttatgcctc ttccgaccat  14100
```

```
caagcattt  atccgtactc  ctgatgatgc  atggttactc  accactgcga  tcccagggaa  14160
aacagcattc  caggtattag  aagaatatcc  tgattcaggt  gaaaatattg  ttgatgcgct  14220
ggcagtgttc  ctgcgccggt  tgcattcgat  tcctgtttgt  aattgtcctt  ttaacggcga  14280
tcgcgtattt  cgtctggctc  aggcgcaatc  acgaatgaat  aacggtttgg  ttggtgcgag  14340
tgattttgat  gacgagcgta  atggctggcc  tgttgaacaa  gtctggaaag  aaatgcataa  14400
acttttgcca  ttctcaccgg  attcagtcgt  cactcatggt  gatttctcac  ttgataacct  14460
tattttgac  gaggggaaat  taataggttg  tattgatgtt  ggacgagtcg  gaatcgcaga  14520
ccgataccag  gatcttgcca  tcctatggaa  ctgcctcggt  gagttttctc  cttcattaca  14580
gaaacggctt  tttcaaaaat  atggtattga  taatcctgat  atgaataaat  tgcagtttca  14640
cttgatgctc  gatgagtttt  tctaacctag  gtgacagaag  tcaaaagcct  ccggtcggag  14700
gcttttgact  ttctgctaga  tctgtttcaa  tgccggtgaag  ggccaggcag  ctggggatta  14760
tgtccagacc  cggccagcat  gttggtttta  tcgcatattc  agcgttgtcg  cgtttaccca  14820
ggtaaaatgg  aagcagtgta  tcgtctgcgt  gaatgtgcaa  atcaggaacg  taaccgtggt  14880
acatagatgc  agtcccttgc  gggtcgttcc  cttcaacgag  taggacgcgg  tgcccttgca  14940
aggctaacca  ttgcgcctgg  tgtactgcag  atgaggtttt  ataaaccctc  cccttgtgtg  15000
acataacgga  aagtacaacc  gggtttttat  cgtcaggtct  ttggtttggg  ttaccaaaca  15060
cactccgcat  atggctaatt  tggtcaattg  tgtagccagc  gcgacgttct  actcggccc   15120
tcatctcaaa  atcaggagcc  ggtagacgac  cagcttttc   cgcatctctg  atagcctgcg  15180
gtgttacgcc  gatcaggtct  gcaacttctg  ttataccca   gcggcgagta  atacgacgcg  15240
cttccgggct  gtcatcgccg  aactgtgcga  tggcaatagc  gcgcgtcatt  tcctgaccgc  15300
gattgataca  gtctttcagc  aaattaatta  acgacatcct  gtttcctctc  aaacatgccc  15360
ttatctttgt  gttttttcatc  atacttacg   ttttaaagc   aaagcaacat  aaaaaaagca  15420
aagtgactta  gaaaacgcaa  agttaaggtt  caaatcaatt  ttttgatgcg  ctacagaagc  15480
tatttagctt  catctaagcg  caacggtatt  acttacgttg  gtatatttaa  aacctaactt  15540
aatgatttta  aatgataata  aatcatacca  attgctatca  aaagttaagc  gaacatgctg  15600
attttcacgc  tgtttataca  ctttgaggca  tctctatctc  ttctgtctct  atattgaaac  15660
acaatcaaag  aacatcaatc  catgtgacat  cccccactat  ctaagaacac  cataacagaa  15720
cacaacatag  gaatgcaaca  ttaatgtatc  aataattcgg  aacatatgca  ctatatcata  15780
tctcaattac  ggaacatatc  agcacacaat  tgcccattat  acgc                    15824
```

SEQ ID NO: 59            moltype = DNA   length = 16028
FEATURE                  Location/Qualifiers
source                   1..16028
                         mol_type = other DNA
                         organism = Synthetic construct
SEQUENCE: 59
```
gcgtataatg  gactattgtg  tgctgataag  gagaacataa  gcgcagaaca  atatgtatct  60
attccggtgt  tgtgttcctt  tgttattctg  ctattatgtt  ctcttatagt  gtgacgaaag  120
cagcataatt  aatcgccact  tgttctttga  ttgtgttacg  atatccagag  acttagaaac  180
gggggaaccg  ggatgagcaa  ggtaaaaatc  ggtgagttga  tcaacacgct  tgtgaatgag  240
gtagaggcaa  ttgatgcctc  agaccgccca  caaggcgaca  aaacgaagag  aattaaagcc  300
gcagccgcac  ggtataagaa  cgcgttattt  aatgataaaa  gaaagttccg  tgggaaagga  360
ttgcagaaaa  gaataaccgc  gaatacttt   aacgcctata  tgagcagggc  aagaaagcgg  420
tttgatgata  aattacatca  tagctttgat  aaaaatatta  ataaattatc  ggaaaagtat  480
cctctttaca  gcgaagaatt  atcttcatgg  ctttctatgc  ctacggctaa  tattcgccag  540
cacatgtcat  cgttacaatc  taaattgaaa  gaaataatgc  cgcttgccga  agagttatca  600
aatgtaagaa  taggctctaa  aggcagtgat  gcaaaaatag  cagactaat   aaaaaaaatat  660
ccagattgga  gttttgctct  tagtgattta  aacagtgatg  attggaagga  gcgccgtgac  720
tatcttata   agttattcca  acaaggctct  gcgttgttag  aagaactaca  ccagctcaag  780
gtcaaccatg  aggttctgta  ccatctgcag  ctaagccctg  cggagcgtac  atctatacag  840
caacgagggg  ccgatgttct  gcgcgagaag  aagcgtaaga  ttgtggttat  tgactaccca  900
acatacatgc  agtctatcta  tgatatttgt  aataatcctg  cgactttatt  tagtttaaac  960
actcgttctg  gaatggcacc  tttggccttt  gctctggctg  cggtatcagg  gcgaagaatg  1020
attgagataa  tgtttcaggg  tgaatttgcc  gtttcaggaa  agtatacggt  taatttctca  1080
gggcaagcta  aaaaacgctc  tgaagataaa  agcgtaacca  gaacgattta  tacttttatgc  1140
gaagcaaaat  tattcgttga  attattaaca  gaattgcgtt  cttgctctgc  tgcatctgat  1200
ttcgatgagg  ttgttaaagg  atatggaaag  gatgatacaa  ggtctgagaa  cggcaggata  1260
aatgctattt  tagcaaaagc  atttaacccct  tgggttaaat  cattttttcg  cgatgaccgt  1320
cgtgtttata  aagatagccg  cgctatttac  gctcgcatcg  cttatgagat  gttcttccgc  1380
gtcgatccac  ggtggaaaaa  cgtcgacgag  gatgcgttct  tcatggagat  tctcggacac  1440
gacgatgaga  acacccagct  gcactataag  cagttcaagc  tggccaactt  ctccagaacc  1500
tggcgacctg  aagttgggga  tgaaaacacc  aggctggtgg  ctctgcagaa  actggacgat  1560
gaaatgccag  gctttgccag  aggtgacgct  ggcgtccgtc  tgcatgaaac  cgtttaagcag  1620
ctggtgggagc  aggaccatc   agcaaaaata  accaacagca  ctctccgggc  ctttaaattt  1680
agcccgacga  tgattagccg  gtacctggaa  tttgccgctg  atgcattggg  gcagttcgtt  1740
ggcgagaacg  ggcagtggca  gctgaagata  gagacacctg  caatcgtcct  gcctgatgaa  1800
gaatccgttg  aaaccatcga  cgaaccggat  gatgagtccc  aagacgacga  gctggatgaa  1860
gatgaaattg  agctcgacga  gggtggcgg   gatgaaccaa  ccgaagagga  agggccaaga  1920
gaacatcagc  caactgctct  aaaaacccgtc  ttcaagcctg  caaaaaataa  cgggggacgga  1980
acgtacaaga  tagagtttga  atacgatgga  aagcattatg  cctggtccgg  ccccgccgat  2040
agccctatgg  ccgcaatgcg  atccgcatgg  gaaacgtact  acagctaaaa  gaaaagccac  2100
cggtgttaat  cggtggcttt  tttattgagg  cctgtcccta  cccatcccct  gcaagggacg  2160
gaaggattag  gcggaaactg  cagctgcaac  tacggacatc  gccgtcccga  ctgcagggac  2220
ttcccccgct  aaagcggggc  ttaaattcgg  gctggccaac  cctattttc   tgcaatcgct  2280
ggcgatgtta  gtttcgtgga  tagcgttccc  agcttttcaa  tggccagctc  aaaatgtgct  2340
ggcagcacct  tctccagttc  cgtatcaata  tcggtgatcg  gcagctctcc  acaagacata  2400
ctccggcgac  cgcacgaac   tacatcgcgc  agcagctccc  gttcgtagac  acgcatgttg  2460
cccagagccg  tttctgcagc  cgttaatatc  cggcgcagct  cggcgatgat  tgccgggaga  2520
tcatccacgg  ttattgggtt  cggtgatggg  ttcctgcagg  cgcggcggag  agccatccag  2580
```

```
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagaggccag attccgatac cacatttact ccctgacgaa tccgatcaag ttttttgtgcc   2880
tcggttaaac cgagggtcaa ttttttcatca tgatccagct tacgcaatgc atcagaaggg   2940
ttggctatat tcaatgcagc acagatatcc agcgccacaa accacgggtc accaccgaca   3000
agaaccaccc gtatagggtg gctttcctga aatgaaaaga cggagagagc cttcattgcg   3060
cctccccgga tttcagctgc tcagaaaggg acagggagca gccgcgagct tcctgcgtga   3120
gttcgcgcgc gacctgcaga agttccgcag cttcctgcaa atacagcgtg gcctcataac   3180
tggagatagt gcggtgagca gagcccacaa cgcttcaac ctgcagcagg cgttcctcaa    3240
tcgtcttcag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcagtggtgg aaaggcggtg gatatgggat ttttttgtccg tgcggacgac   3420
agctgcaaat ttgaatttga acatggtatg cattcctatc ttgtataggg tgctaccacc   3480
agagttgaga atctctatag gggtggtagc ccagacaggg ttctcaacac cggtacaaga   3540
agaaaccggc ccaaccgaag ttggcccat ctgagccacc ataattcagg tatgcgcaga    3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
ccgcagccac cttagatgtt gtctcaaacc ccatacggcc acgaatgac cactggaacg    3900
gaatagtcag caggtacagc ggaacgaacc acaaacggtt cagcgctgc cagaacgtcg    3960
catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtccttttaaa taaggctgta gaactgcaaa   4200
atcgctctcg ttcacatgct gtacgtagat gcgtagcaaa ttgccgttcc atccctgtaa   4260
tccacctttc ttggaaagat cgtccttgac ctcacgaaga actttatcca atagccctgc   4320
ggcacaagaa aattgcctgct ctggatcagc aaattcatat tgattaatag gtgattgcca   4380
cacaccaaaa acaggaatca tctttttcggc taaacgcctc tcctgttctt tcttaatctc   4440
aagttgtaag cggaccagct caccatccat cattttttgt agatcatgcg ccactattca   4500
cccccactgg ccatcagcaa ataaagcttc atactcggac accggcaggc ggcttccacg   4560
gattgaaagg tcaagccaac cacgtccaga tgggtcagcc ttatccgatt cttcccaccg   4620
ttctgcagct gtagcaacca ggcattctac cgccttcatg tagtccttctg tacggaacca   4680
gccgtagtta atgccaccat cagtaactgc ccaggccatc ttttttctctt cggcctcaat   4740
agcccggatg cggttatcgc acagctgcgc acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctcg caatgcagca ataaactccc   4920
tcactatctg agaacccgtt catccgaatg atcgtgaatg gaagttcccg gccagttta    4980
taatcgctat agcttgtcgc gtcgtggctg accttgacca cataagggtc gtagccctcc   5040
acgatgacaa ggcattcccg ttgttttccc attacccctc cggttatatc gccacggctt   5100
gccgcttggc tagaaacgct ttcagcagcc ttatttcgcg tactgaatgac aggtcctaa    5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtgggc gtccggaacg tgctctgttt    5340
tggatcgagg gttaccatgt atatctatat ttagatccaa atcgcgatcc acttcgatgg   5400
tggttttttc caccttacgt gcgtgaattg ataaaccggc ctcgcggcgc ttctccacga   5460
tattcatgag gaactcgacc gagtccgggt caatggaacg catcgtgggg cgtgcatcgc   5520
catctctggc gcgtctggtc ttactggata gccccataga ctccaggatg cctatgcaga   5580
ggtctgcagg cgctttcttc ttgccttttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggttttttg gatcgatacc gcagtcgcgg aagtactgct   5760
gcagcgtcgc cgatttgagg gtgtagaaac cacgcatgcc tatctcaaca gcagggggtcg   5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact ttttttcaggc cgccgtcgaa atagaatttt aacgccacct   6060
cgtcgacatc cagctgcagc tcctttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgaccttga tagccatcat   6300
catgcatgat gcaaatcatg ttgctggcat aatcatttct ggccgatgcc tcgagcgcgg   6360
cggctttaat tttgagctgc atgaatgaag agttagccac ggcgagtgca attcggtcac   6420
cgtcaaagac aacgtctgtc agcagcccgg agtggccagc cgtttcgagc aaggcctgcg   6480
cgtaggcgcg tttgattttt tccggatcgg tttcacgtttt accgcgaagc ttgtcgaaac   6540
cgataatgta ttcctgagct gtacggtcgc ggcgcagcat ctggatgcg tcgctgggga    6600
ccacttcgcc gcagaacatg ccgaaatggc ggtggaagtg ttttccctca atcgatacac   6660
ctgaagatat cgacgggctg tagatgaggc cgtcatattt tttcaccatc actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga attctgcagc aggcaggtga gccagcctcc tcgcgtcgt    7020
tcatcgccag ttcagccagg tcaacaagca gatcttggc atcggcatcc accataatgg    7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttccagc agcctttaag tatggagttg atgcaaatag    7260
tcagcttgtt ggcatatggc gccattccct gatagccggg atcctgataa tgcagaatgt   7320
```

```
cggctttcgc gcctttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccggcgcgta atgtgatctt taacggtacc gttataaatt tctgcgatac   7680
ccatatcccg cagcgtgctg ctgaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacagatcg gttgcacggc   7860
tcagatgatt tctcgttaac tggcgagcga cttccttcag ccctctcagg ctgtgcaggt   7920
cgttaaaatc gctgcattcc agctcagggt catcctcaaa agttgggtaa acacatttga   7980
cgccggaaaa cttctccatg atgtcgaatc cggtgcggag gcctgtgttg ccttttcctt   8040
cagctgagga tttgcggtcg ttatcgagag cgcaagtgat ttgcgcagcc gggtacatgt   8100
tcaccagctg ctcgacaacg tgaatcatgt tgttagcgca aaccgcaatg actaccgcgt   8160
caaagcgttt tttcgggtcg tttctggtcg ccagccagat ggatgccccg gtggcgaaac   8220
cctctgcagt cgcaattttt tgcgcccccct gcaggtcgcc aataacaaag catgcaccga   8280
cgaaatcacc gttagtgatg gcgctggtct ggaacttgcc accattcaga tcgatacgtt   8340
gccagccaac aatccgcccg tcttttcttc cgtccaggtg ggacagaggt atcgccatgt   8400
aagttgttgg tccacggctc catttcgcac tgtcgtgact ggtcacgcga cgtatatcac   8460
aagcgccaaa tacgtcacga attcccttt ttaccgcata aggccaggag ccatcttcag   8520
ctggcgaatg ttcccaggcg cgatggaaag ccaaccatcc aagcaggcgt tcctgctcca   8580
tctgattgtt tttaaatca ttaacgcgtt gttgttcagc tcggaggcgg cgtgcttcag   8640
cctggcgctc catgcgtgca cgttcttctt ccggctgagc gaccacggtc gcaccattcc   8700
gttgctgttc acgcgatac tccgaaaaca ggaatgaaaa gccactccag gagccagcgt   8760
catgcgcttt ttcaacgaag ttaacgaaag gataactgat gccatccttg ctctgctcaa   8820
ggcgtgaata gatttccaca cggccttta ggctcttctg cagagcttcc ggggaggaat   8880
tattgtaggt ggtatagcgc tctacaccac cgcgcggatt gagctgaatc ttatcagcac   8940
acgcaggcca gttgataccg gccatcttcg ccagctcagt cagctcatca cgtgccgcgt   9000
caagcagtga aaacggatcg ctgccaaagc gctccgcgta gaattcttgt aaggtcattt   9060
tttagccttt ccatgcgaat tagcattttt tcgggttgaa aaaatccgca ggagcagcca   9120
caataaacgc actatctttc tgaaggacgt atctgcgtta tcgtggctac ttcctgaaaa   9180
aggcccgagt tgccgactcc ggttttttttt tcgtctttt tcggctgcta cggtctggtt   9240
caaccccgac aaagtataga tcggattaaa ccagaattat agtcagcaat aaaccctgtt   9300
attgtatcat ctaccctcaa ccatgaacga tttgatcgta ccgatcactt ggtgactaaa   9360
ttgaagatca cttttatcat ggataacccg ttgagagtta gcactatcaa ggtagtaatg   9420
ctgctcgtca taacgggcta atcgttgaat tgtgatctcg ccgttattat cacaaaccag   9480
tacatcctca cccggtacaa gcgtaagtga agaatcgacc aggataacat ctcccggctg   9540
gtagtttcgc tgaatctggt tcccgaccgt cagtgcgtaa acggtgttcc gttgactcac   9600
gaacggcagg aatcgctctg tgttggcagg ttctccaggc tgccagtctc tatccggtcc   9660
tgtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgtttcgc ctcgtgtttt   9900
catacccctta atcataaatg atctctttat agctggctat aattttttata aattatacct   9960
agctttaatt ttcacttatt gattataata atccccatga aacccgaaga acttgtgcgc  10020
catttcggcg atgtggaaaa agcagcggtt ggcgtgggcg tgacacccgg cgcagtctat  10080
caatgcgtgc aagctgggga gattccacct ctacgacaaa gcgatataga ggtccgtacc  10140
gcgtacaaat taaagagtga tttcacctct cagcgcatgg gtaaggaagg gcataacaag  10200
gggatcctct agacgcagaa aggcccaccc gaaggtgagc cagtgtgatt acatttgcgg  10260
cctaactgtg gccagtccag ttacgctgga gtcactagtg cggccgcgac aacttgtcta  10320
gggcccaatg gcccatacac ttagtgtaat acgactcact ataggggagg cggccgctch  10380
ttcagcaaga ttaagccgcc accatggcgc gcggcctcc taagaagaag cggaaagtcg  10440
aattcgtgga tctgcgaaca ctgggctata gccagcagca gcaggagaag atcaaaccca  10500
aggtgaggtc cacagtcgca cagcaccatg aagccctggt gggccacggg ttcactcacg  10560
ctcatattgt cgcactgtct cagcatccag ccgctctgag aaccgtggca gtcacataac  10620
agcacatcat tactgccctg cccgaggcta cccatgaaga catcgtggga gtcggcaaac  10680
agtggagcgg cgcacgggcc ctggaggctc tgctgaccga cgcaggggaa ctgagaggac  10740
cccctctgca gctggataca gggcagctgg tgaagattgc taagagggga ggggtgacag  10800
caatggaagc cgtccacgca agcaggaacg cactgacagg ggcccccctg aacctgaccc  10860
cggaccaagt ggtggctatc gccagcaatc acggcggcaa gcaagcgctc gaaacggtgc  10920
agcggctgtt gccggtgctg tgccaggacc atggcctgac cccggaccaa gtggtggcta  10980
tcgccagcaa tcacggcggc aagcaagcgc tcgaaacggt gcagcggctg ttgccggtgc  11040
tgtgccagga ccatggcctg accccggacc aagtggtggc tatcgccagc aacggtggcg  11100
gcaagcaagc gctcgaaacg gtgcagcggc tgttgccggt gctgtgccag gaccatggcc  11160
tgactccgga ccaagtggtg gctatcgcca gccacgatgg cggcaagcaa gcgctcgaaa  11220
cggtgcagcg gctgttgccg gtgctgtgcc aggaccatgg cctgaccccg gaccaagtgg  11280
tggctatcgc cagcaacatt ggcggcaagc aagcgctcga acggtgcag cggctgttgc  11340
cggtgctgtg ccaggaccat ggcctgaccc cggaccaagt ggtggctatc gccagcaaca  11400
ttggtggaaa acaggccgtt gaaacggtgc agcggctgct gccgtgctgc tgccaggacc  11460
atggcctgac cccggaccaa gtggtggcta tcgccagcaa tcacggcggc aagcaagcgc  11520
tcgaaacggt gcagcggctg ttgccggtgc tgtgccagga ccatggcctg accccggacc  11580
aagtggtggc tatcgccagc aacggtggcg gcaagcaagc gctcgaaacg gtgcagcggc  11640
tgttgccggt gctgtgccag gaccatggcc tgaccccgga ccaagtggtg gctatcgcca  11700
gcaacggtgg cggcaagcaa gcgctcgaaa cggtgcagcg gctgttgccg gtgctgtgcc  11760
aggaccatgg cctgaccccg gaccaagtgg tggctatcgc cagcaacggt ggcggcaagc  11820
aagcgctcga acggtgcag cggctgttgc cggtgctgtg ccaggaccat ggcctgaccc  11880
cggaccaagt ggtggctatc gccagcaatc acggcggcaa gcaagcgctc gaaacggtgc  11940
agcggctgtt gccggtgctg tgccaggacc atggcctgac cccggaccaa gtggtggcta  12000
tcgccagcca cgatggcggc aagcaagcgc tcgaaacggt gcagcggctg ttgccggtgc  12060
```

```
tgtgccagga ccatggcctg actccggacc aagtggtggc tatcgccagc cacgatggcg  12120
gcaagcaagc gctcgaaacg gtgcagcggc tgttgccggt gctgtgccag gaccatggcc  12180
tgaccccgga ccaagtggtg gctatcgcca gcaacggtgg cggcaagcaa gcgctcgaaa  12240
cggtgcagcg gctgttgccg gtgctgtgcc aggaccatgg cctgaccccg gaccaagtgg  12300
tggctatcgc cagcaacggt ggcggcaagc aagcgctcga aacggtgcag cggctgttgc  12360
cggtgctgtg ccaggaccat ggcctgaccc cggaccaagt ggtggctatc gccagcaatc  12420
acggcggcaa gcaagcgctc gaaacggtgc agcggctgtt gccggtgctg tgccaggacc  12480
atggcctgac cccggaccaa gtggtggcta tcgccagcaa cggtggcggc aagcaagcgc  12540
tcgaaacggt gcagcggctg ttgccggtgc tgtgccagga ccatggcctg accccggacc  12600
aagtggtggc tatcgccagc cacggtggcg gcaagcaagc gctcgaaagc attgtggccc  12660
agctgagccg gcctgatccg gcgttggccg cgttgaccaa cgaccacctg gtcgctctgg  12720
cttgcctggg aggacgccct gctatggacg ctgtgaagaa aggactgccc cacgcacccg  12780
aactgattag acgggtgaac cggagaatcg gcgagagaac atcccatagg gtggcaatgc  12840
ctagaactca gctggtcaag agtgaactgg aggaaaagaa atcagagctg cgccacaagc  12900
tgaaatacgt gcctcatgag tatatcgaac tgatcgagat tgctcgcaat tcaaccccagg  12960
accggatcct ggaaatgaaa gtgatggagt tctttatgaa agtctacgga tatcgggggga  13020
aacacctggg agggagcaga aagccagatg gggccatcta cacagtggga tcccccatcg  13080
actatggcgt gattgtcgat actaaagcct acagcgagg ctataacctg cctatcggcc  13140
aggctgacga gatgcagaga tacgtggagg aaaaccagac cgcaataag catattaacc  13200
ccaatgaatg gtggaaagtg tatcctagct ccgtcacaga gttcaagttt ctgttcgtga  13260
gcggacactt aagggcaac tacaaagcac agctgactag gctgaatcat atcaccaact  13320
gcaatggagc cgtgctgtct gtcgaggaac tgctgatcgg gggagagtg attaaggctg  13380
gcacactgac tctggaggaa gtgaggcgca agttcaacaa tggggaaatc aacttctaac  13440
ctgcaggatg ataagctagc cccgggcgta cggaaaaaaa aaaaaaaaaa aaaaaaaaaa  13500
aaaaaaaaaa aaaaaaaaaa aaaaaaaaaa aaaaaaaaaa aaaaaaaaaa aaaaaaaaaa  13560
aaaaaaaaaa aaaaaaaaaa aaaaaaaaaa aaaaaaaaaa aaaaaaaaaa aaaaaaaaaa  13620
aaaaaaaaaa aaaaaaaaaa aaaaaaaaaa aaaaaaaaaa aaaaaaaaaa aaaaaaaaaa  13680
aaaaaaaaaa aaaaaaaaaa aaaaaaaaaa aaaaaaaaaa aaaaaaaaaa aaaaaaaaaa  13740
aaaaaaaaaa aaaaaaaaaa aaaaaaaaaa aaaaaaaaaa aaaaaaaaaa aaaaaaacg   13800
agaccttagg gccattagac ttgaagtcaa gcggccgctt acaactggac cttgctggta  13860
catagaactg attaactgac catttaaatc ataccaacat ggtcaaataa aacgaaaggc  13920
tcagtcgaaa gactgggcct ttcgttttaa tctgatcggc acgtaagagg ttccaacttt  13980
caccataatg aaataagatc actaccgggc gtattttgag ttatcgagat tttcaggagc  14040
taaggaagct aaaatgagcc atattcaacg ggaaacgtct tgctcgaggc cgcgattaaa  14100
ttccaacatg gatgctgatt tatatgggta taaatgggct cgcgataatg tcgggcaatc  14160
aggtgcgaca atctatcgat tgtatgggaa gcccgatgcg ccagagttgt ttctgaaaca  14220
tggcaaaggt agcgttgcca atgatgttac agatgagatg gtcaggctaa actggctgac  14280
ggaatttatg cctcttccga ccatcaagca ttttatccgt actcctgatg atgcatggtt  14340
actcaccact gcgatcccag ggaaaacagc attccaggta ttagaagaat atcctgattc  14400
aggtgaaaat attgttgatg cgctggcagt gttcctgcgc cggttgcatt cgattcctgt  14460
ttgtaattgt cctttaacg gcgatcgcgt atttcgtctg gctcaggcgc aatcacgaat  14520
gaataacggt ttggttggtg cgagtgattt tgatgacgag cgtaatggct ggcctgttga  14580
acaagtctgg aaagaaatgc ataaacttt gccattctca ccggattcag tcgtcactca  14640
tggtgatttc tcacttgata accttatttt tgacgagggg aaattaatag gttgtattga  14700
tgttggacga gtcggaatcg cagaccgata ccaggatctt gccatcctat ggaactgcct  14760
cggtgagttt tctccttcat tacagaaacg ctttttcaa aaatatggta ttgataatcc  14820
tgatatgaat aaattgcagt ttcacttgat gctcgatgag ttttttctaac ctaggtgaca  14880
gaagtcaaaa gcctccggtc ggaggctttt gactttctgc tagatctgtt tcaatgcggt  14940
gaagggccag gcagctgggg attatgtcca gacccggcca gcatgttggt tttatcgcat  15000
attcagcgtt gtcgcgttta cccaggtaaa atggaagcag tgtatcgtct gcgtgaatgt  15060
gcaaatcagg aacgtaaccg tggtacatag atgcagtccg ttgcgggtcg ttcccttcaa  15120
cgagtaggac gcggtgccct tgcaaggcta accattgcgc ctggtgtact gcagatgagg  15180
ttttataaac ccctcccttg tgtgacataa cggaaagtac aaccgggttt ttatcgtcag  15240
gtctttggtt tgggttacca aacacactcc gcatatggct aatttggtca attgtgtagc  15300
cagcgcgacg ttctactcgg cccctcatct caaaatcagg agccgtgaa cgaccagctt  15360
tttccgcatc tctgatagcc tgcggtgtta cgccgatcag gtctgcaact tctgttatac  15420
cccagcggcg agtaatacga cgcgcttccg ggctgtcatc gccgaactgt gcgatggcaa  15480
tagcgcgcgt catttcctga ccgcgattga tacagtcttt cagcaaatta attaacgaca  15540
tcctgtttcc tctcaaacat gcccttatct ttgtgttttt catcatactt tacgttttta  15600
aagcaaagca acataaaaaa agcaaagtaa cttagaaaac gcaaagttaa ggttcaaatc  15660
aatttttttga tgcgctacag aagctattta gcttcatcta agcgcaacgg tattacttac  15720
gttggtatat ttaaaaccta acttaatgat tttaaatgat aataaatcat accaattgct  15780
atcaaaagtt aagcgaacat gctgattttc acgctgtttta tacactttga ggcatctcta  15840
tctcttctgt ctctatattg aaacacaatc aaagaacatc aatccatgg acatccccca  15900
ctatctaaga acaccataac agaacacaac ataggaatgc aacattaatg tatcaataat  15960
tcggaacata tgcactatat catatctcaa ttacggaaca tatcagcaca caattgccca  16020
ttatacgc                                                          16028
```

SEQ ID NO: 60          moltype = AA  length = 19
FEATURE                Location/Qualifiers
source                 1..19
                       mol_type = protein
                       organism = Synthetic construct
SEQUENCE: 60
LLNFDLLKLA GDVESNPGP                                                19

SEQ ID NO: 61          moltype = AA  length = 19
FEATURE                Location/Qualifiers
source                 1..19

```
SEQUENCE: 61
TLNFDLLKLA GDVESNPGP                                                    19

SEQ ID NO: 62          moltype = AA   length = 14
FEATURE                Location/Qualifiers
source                 1..14
                       mol_type = protein
                       organism = Synthetic construct
SEQUENCE: 62
LLKLAGDVES NPGP                                                         14

SEQ ID NO: 63          moltype = AA   length = 17
FEATURE                Location/Qualifiers
source                 1..17
                       mol_type = protein
                       organism = Synthetic construct
SEQUENCE: 63
NFDLLKLAGD VESNPGP                                                      17

SEQ ID NO: 64          moltype = AA   length = 20
FEATURE                Location/Qualifiers
source                 1..20
                       mol_type = protein
                       organism = Synthetic construct
SEQUENCE: 64
QLLNFDLLKL AGDVESNPGP                                                   20

SEQ ID NO: 65          moltype = AA   length = 24
FEATURE                Location/Qualifiers
source                 1..24
                       mol_type = protein
                       organism = Synthetic construct
SEQUENCE: 65
APVKQTLNFD LLKLAGDVES NPGP                                              24

SEQ ID NO: 66          moltype = AA   length = 40
FEATURE                Location/Qualifiers
source                 1..40
                       mol_type = protein
                       organism = Synthetic construct
SEQUENCE: 66
VTELLYRMKR AETYCPRPLL AIHPTEARHK QKIVAPVKQT                              40

SEQ ID NO: 67          moltype = AA   length = 18
FEATURE                Location/Qualifiers
source                 1..18
                       mol_type = protein
                       organism = Synthetic construct
SEQUENCE: 67
LNFDLLKLAG DVESNPGP                                                     18

SEQ ID NO: 68          moltype = AA   length = 40
FEATURE                Location/Qualifiers
source                 1..40
                       mol_type = protein
                       organism = Synthetic construct
SEQUENCE: 68
LLAIHPTEAR HKQKIVAPVK QTLNFDLLKL AGDVESNPGP                              40

SEQ ID NO: 69          moltype = AA   length = 33
FEATURE                Location/Qualifiers
source                 1..33
                       mol_type = protein
                       organism = Synthetic construct
SEQUENCE: 69
EARHKQKIVA PVKQTLNFDL LKLAGDVESN PGP                                    33

SEQ ID NO: 70          moltype =      length =
SEQUENCE: 70
000

SEQ ID NO: 71          moltype = AA   length = 5
FEATURE                Location/Qualifiers
source                 1..5
                       mol_type = protein
                       organism = Synthetic construct
SEQUENCE: 71
```

DGGGS                                                                                    5

SEQ ID NO: 72           moltype = AA  length = 5
FEATURE                 Location/Qualifiers
source                  1..5
                        mol_type = protein
                        organism = Synthetic construct
SEQUENCE: 72
TGEKP                                                                                    5

SEQ ID NO: 73           moltype = AA  length = 4
FEATURE                 Location/Qualifiers
source                  1..4
                        mol_type = protein
                        organism = Synthetic construct
SEQUENCE: 73
GGRR                                                                                     4

SEQ ID NO: 74           moltype = AA  length = 5
FEATURE                 Location/Qualifiers
source                  1..5
                        mol_type = protein
                        organism = Synthetic construct
SEQUENCE: 74
GGGGS                                                                                    5

SEQ ID NO: 75           moltype = AA  length = 14
FEATURE                 Location/Qualifiers
source                  1..14
                        mol_type = protein
                        organism = Synthetic construct
SEQUENCE: 75
EGKSSGSGSE SKVD                                                                         14

SEQ ID NO: 76           moltype = AA  length = 18
FEATURE                 Location/Qualifiers
source                  1..18
                        mol_type = protein
                        organism = Synthetic construct
SEQUENCE: 76
KESGSVSSEQ LAQFRSLD                                                                     18

SEQ ID NO: 77           moltype = AA  length = 8
FEATURE                 Location/Qualifiers
source                  1..8
                        mol_type = protein
                        organism = Synthetic construct
SEQUENCE: 77
GGRRGGGS                                                                                 8

SEQ ID NO: 78           moltype = AA  length = 9
FEATURE                 Location/Qualifiers
source                  1..9
                        mol_type = protein
                        organism = Synthetic construct
SEQUENCE: 78
LRQRDGERP                                                                                9

SEQ ID NO: 79           moltype = AA  length = 12
FEATURE                 Location/Qualifiers
source                  1..12
                        mol_type = protein
                        organism = Synthetic construct
SEQUENCE: 79
LRQKDGGGSE RP                                                                           12

SEQ ID NO: 80           moltype = AA  length = 16
FEATURE                 Location/Qualifiers
source                  1..16
                        mol_type = protein
                        organism = Synthetic construct
SEQUENCE: 80
LRQKDGGGSG GGSERP                                                                       16

SEQ ID NO: 81           moltype = AA  length = 10
FEATURE                 Location/Qualifiers
source                  1..10
                        mol_type = protein
                        organism = Synthetic construct -continued

```
SEQUENCE: 81
GGGGSGGGGS                                                                10

SEQ ID NO: 82          moltype = AA  length = 15
FEATURE                Location/Qualifiers
source                 1..15
                       mol_type = protein
                       organism = Synthetic construct
SEQUENCE: 82
GGGGSGGGGS GGGGS                                                          15

SEQ ID NO: 83          moltype = AA  length = 20
FEATURE                Location/Qualifiers
source                 1..20
                       mol_type = protein
                       organism = Synthetic construct
SEQUENCE: 83
GGGGSGGGGS GGGGSGGGGS                                                     20

SEQ ID NO: 84          moltype = AA  length = 25
FEATURE                Location/Qualifiers
source                 1..25
                       mol_type = protein
                       organism = Synthetic construct
SEQUENCE: 84
GGGGSGGGGS GGGGSGGGGS GGGGS                                               25
```

HOMOLOGY DIRECTED REPAIR COMPOSITIONS FOR THE TREATMENT OF HEMOGLOBINOPATHIES

RELATED APPLICATIONS

This application is a continuation of U.S. patent application Ser. No. 16/608,182, filed on Oct. 24, 2019, which is a national stage filing under 35 U.S.C. 371 of International Application No. PCT/US2018/029235, filed Apr. 24, 2018, which claims the benefit of U.S. Provisional Application No. 62/488,927, filed on Apr. 24, 2017. The entire teachings of the above applications are incorporated herein by reference.

GOVERNMENT SUPPORT

This invention was made with government support under HL136135 awarded by the National Institutes of Health. The government has certain rights in the invention.

BACKGROUND

Technical Field

The present disclosure relates to improved compositions for use in homology directed repair of the human globin locus. More particularly, the disclosure relates to improved donor repair templates for editing the human globin locus for the prevention, treatment, or amelioration of at least one symptom of a hemoglobinopathy.

Description of the Related Art

Hemoglobinopathies are a diverse group of inherited monogenetic blood disorders that result from variations in the structure and/or synthesis of hemoglobin. The most common hemoglobinopathies are sickle cell disease (SCD), α-thalassemia, and β-thalassemia. Approximately 5% of the world's population carries a globin gene mutation. The World Health Organization estimates that more than 300,000 infants are born each year with major hemoglobin disorders. Hemoglobinopathies manifest highly variable clinical manifestations that range from mild hypochromic anemia to moderate hematological disease to severe, lifelong, transfusion-dependent anemia with multiorgan involvement.

The only potentially curative treatment available for hemoglobinopathies is allogeneic hematopoietic stem cell transplantation. However, it is estimated that HLA-compatible HSC transplants are available to less than 20% of affected individuals and long term toxicities are substantial. In addition, HSC transplants are also associated with significant mortality and morbidity in subjects that have SCD or severe thalassemias. The significant mortality and morbidity is due in part to pre-HSC transplantation transfusion-related iron overload, graft-versus-host disease (GVHD), and high doses of chemotherapy/radiation required for pre-transplant conditioning of the subject, among others.

Supportive treatments for hemoglobinopathies include periodic blood transfusions for life, combined with iron chelation, and in some cases splenectomy. Additional treatments for SCD include analgesics, antibiotics, ACE inhibitors, and hydroxyurea. However, the side effects associated with hydroxyurea treatment include cytopenia, hyperpigmentation, weight gain, opportunistic infections, azoospermia, hypomagnesemia, and cancer.

At best, patients treated with existing methods have a projected lifespan of 50 to 60 years.

BRIEF SUMMARY

The present disclosure generally relates, in part, to improved donor repair templates used for editing a human γ-globin gene.

In particular embodiments, a DNA donor repair template is contemplated comprising: a 5' homology arm and a 3' homology arm, wherein the donor repair template comprises a polynucleotide sequence within at least about 1 kb, at least about 1.5 kb, or at least about 2 kb upstream of the transcription start site of a human gamma globin gene and further comprises a deletion of Chr11: 5249959-5249971.

In particular embodiments, a DNA donor repair template is contemplated comprising: a 5' homology arm; a selection cassette; an erythroid expression control sequence; and a 3' homology arm.

In certain embodiments, the length of the 5' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 5' homology arm comprises a polynucleotide sequence within at least about 1 kb, at least about 1.5 kb, or at least about 2 kb upstream of the transcription start site of a human gamma globin gene.

In some embodiments, the 5' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 5' homology arm comprises a polynucleotide sequence within 1 kb upstream of the transcription start site of a human gamma globin gene and the 5' homology arm comprises a deletion in the region of Chr11: 5249957-5249977.

In certain embodiments, the deletion in the region of Chr11: 5249957-5249977 is a deletion associated with hereditary persistence of fetal hemoglobin.

In some embodiments, the deletion in the region of Chr11: 5249957-5249977 is a deletion associated with derepression of gamma globin expression.

In particular embodiments, the deletion in the region of Chr11: 5249957-5249977, comprises a deletion of the polynucleotide sequence of any one of SEQ ID NOs: 1-6.

In particular embodiments, the deletion in the region of Chr11: 5249957-5249977, comprises a deletion of the polynucleotide sequence of Chr11: 5249959-5249971.

In further embodiments, the selection cassette comprises a ubiquitous promoter, a constitutive promoter, an inducible promoter, or hematopoietic stem cell promoter, operably linked to a polynucleotide sequence encoding a selectable marker, and one or more post-transcription regulatory elements.

In certain embodiments, the promoter is selected from the group consisting of: a cytomegalovirus (CMV) immediate early promoter, a viral simian virus 40 (SV40) promoter, a Moloney murine leukemia virus (MoMLV) LTR promoter, a Rous sarcoma virus (RSV) LTR promoter, a herpes simplex virus (HSV) (thymidine kinase) promoter, a H5, P7.5, or P11 vaccinia virus promoter, a short elongation factor 1-alpha (EF1a-short) promoter, a long elongation factor 1-alpha (EF1a-long) promoter, an early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, a human ROSA 26 promoter, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter.

In particular embodiments, the selectable marker is selected from the group consisting of: a hygromycin-B phosphotransferase (HPH) gene, an amino 3'-glycosyl phosphotransferase (NEO) gene, a dihydrofolate reductase (DHFR) gene, an adenosine deaminase (ADA) gene, a multi-drug resistance (MDR) gene, an $O^6$-methylguanine-DNA-methyltransferase (MGMT) gene, a bleomycin (BLE) gene, and a blasticidin-S deaminase (BSR) gene.

In certain embodiments, the one or more post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence.

In some embodiments, the polyadenylation sequence is selected from the group consisting of: an ideal poly(A) sequence, an SV40 poly(A) sequence, a bovine growth hormone (BGH) poly(A) sequence, and a rabbit β-globin poly(A) sequence.

In some embodiments, the erythroid expression control sequence comprises a human β-globin LCR responsive promoter.

In particular embodiments, the erythroid expression control sequence comprises an ankyrin gene promoter, an α-spectrin gene promoter, a β-spectrin gene promoter, or a β-globin gene promoter, optionally in combination with an HPFH-2 enhancer, an HS40 enhancer, or a β-globin gene 3' enhancer.

In further embodiments, the erythroid expression control sequence is positioned to be operably linked to an endogenous gamma globin gene when the DNA donor repair template is integrated into the human genome.

In certain embodiments, the endogenous gamma globin gene is the A-gamma globin gene (HBGA; HBG1).

In further embodiments, the endogenous gamma globin gene is the G-gamma globin gene (HBGG; HBG2).

In additional embodiments, DNA donor repair template is integrated into the human genome at both the HBG1 locus and the HBG2 locus and the erythroid expression control sequence of the DNA donor repair template integrated at the HBG1 locus is positioned to be operably linked to the endogenous HBG1 gene and the erythroid expression control sequence of the DNA donor repair template integrated at the HBG2 locus is positioned to be operably linked to the endogenous HBG2 gene.

In particular embodiments, the length of the 3' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 3' homology arm comprises a polynucleotide sequence downstream of the 5' homology arm and upstream of the start codon of the human gamma globin gene.

In particular embodiments, a DNA donor repair template is contemplated comprising: a 5' homology arm; a polynucleotide encoding a therapeutic globin and one or more post-transcriptional control elements; a selection cassette; and a 3' homology arm.

In particular embodiments, the length of the 5' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 5' homology arm comprises a polynucleotide sequence within 1 kb upstream of the transcription start site of a human gamma globin gene and the 5' homology arm comprises a deletion in the region of Chr11: 5249957-5249977.

In some embodiments, the deletion in the region of Chr11: 5249957-5249977 is a deletion associated with hereditary persistence of fetal hemoglobin.

In certain embodiments, the deletion in the region of Chr11: 5249957-5249977 is a deletion associated with derepression of gamma globin expression.

In some embodiments, the deletion in the region of Chr11: 5249957-5249977, comprises a deletion of the polynucleotide sequence of any one of SEQ ID NOs: 1-6.

In particular embodiments, the deletion in the region of Chr11: 5249957-5249977, comprises a deletion of the polynucleotide sequence of Chr11: 5249959-5249971.

In further embodiments, the endogenous gamma globin promoter is operably linked to the polynucleotide encoding the therapeutic globin.

In particular embodiments, the therapeutic globin is γ-globin, β-globin, δ-globin, or an anti-sickling β-globin.

In certain embodiments, the anti-sickling β-globin is selected from the group consisting of: β-globin$^{A-T87Q}$, β-globin$^{A-T87Q/K120E/K95E}$, and β-globin$^{A-T87Q/G16D/E22A}$.

In additional embodiments, the one or more post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence.

In particular embodiments, the polyadenylation sequence is selected from the group consisting of: an ideal poly(A) sequence, an SV40 poly(A) sequence, a bovine growth hormone (BGH) poly(A) sequence, and a rabbit β-globin poly(A) sequence.

In particular embodiments, the DNA donor repair template further comprises an erythroid enhancer that enhances the expression of the polynucleotide encoding the therapeutic globin.

In certain embodiments, the erythroid enhancer is selected from an HPFH-2 enhancer, an HS40 enhancer, or a β-globin gene 3' enhancer.

In some embodiments, the selection cassette comprises a ubiquitous promoter, a constitutive promoter, an inducible promoter, or hematopoietic stem cell promoter, operably linked to a polynucleotide sequence encoding a selectable marker, and optionally one or more post-transcription regulatory elements.

In some embodiments, the promoter is selected from the group consisting of: a cytomegalovirus (CMV) immediate early promoter, a viral simian virus 40 (SV40) promoter, a Moloney murine leukemia virus (MoMLV) LTR promoter, a Rous sarcoma virus (RSV) LTR promoter, a herpes simplex virus (HSV) (thymidine kinase) promoter, a H5, P7.5, or P11 vaccinia virus promoter, a short elongation factor 1-alpha (EF1a-short) promoter, a long elongation factor 1-alpha (EF1a-long) promoter, an early growth response 1 (EGR1) promoter, a ferritin H (FerH) promoter, a ferritin L (FerL)

promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, a human ROSA 26 promoter, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter.

In particular embodiments, the selectable marker is selected from the group consisting of: a hygromycin-B phosphotransferase (HPH) gene, an amino 3-glycosyl phosphotransferase (NEO) gene, a dihydrofolate reductase (DHFR) gene, an adenosine deaminase (ADA) gene, a multi-drug resistance (MDR) gene, an $O^6$-methylguanine-DNA-methyltransferase (MGMT) gene, a bleomycin (BLE) gene, and a blasticidin-S deaminase (BSR) gene.

In certain embodiments, the one or more post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence.

In some embodiments, the polyadenylation sequence is selected from the group consisting of: an ideal poly(A) sequence, an SV40 poly(A) sequence, a bovine growth hormone (BGH) poly(A) sequence, and a rabbit β-globin poly(A) sequence.

In particular embodiments, the selection cassette comprises a ubiquitous promoter, a constitutive promoter, an inducible promoter, or hematopoietic stem cell promoter, operably linked to a polynucleotide sequence encoding a selectable marker, and a ribosomal skipping sequence or viral self-cleaving peptide.

In certain embodiments, the length of the 3' homology arm is at least about 100 bp, at least about 200 bp, at least about 300 bp, at least about 400 bp, at least about 500 bp, at least about 600 bp, at least about 700 bp, at least about 800 bp, at least about 900 bp, or at least about 1000 bp and wherein the 3' homology arm comprises a polynucleotide sequence downstream of the start codon of the gamma globin gene.

In certain embodiments, the gamma globin gene is the A-gamma globin gene (HBGA; HBG1).

In various embodiments, a viral vector comprises a DNA donor repair template contemplated herein.

In particular embodiments, the viral vector is a recombinant adeno-associated viral vector (rAAV) or a retrovirus.

In some embodiments, the rAAV has one or more ITRs from AAV2.

In further embodiments, the rAAV has a serotype selected from the group consisting of: AAV1, AAV2, AAV3, AAV4, AAV5, AAV6, AAV7, AAV8, AAV9, and AAV10.

In certain embodiments, the rAAV has an AAV6 serotype.

In additional embodiments, the retrovirus is a lentivirus.

In particular embodiments, the lentivirus is an integrase deficient lentivirus.

In some embodiments, a cell comprises a DNA donor repair template or a viral vector contemplated herein.

In some embodiments, the DNA donor repair template has been inserted into a human gamma globin gene target site by homology directed repair.

In further embodiments, the target site is an engineered nuclease target site set forth in SEQ ID NO: 7 or SEQ ID NO: 8.

In particular embodiments, the cell is a hematopoietic cell.

In certain embodiments, the cell is $CD34^+$ cell.

In particular embodiments, the cell is $CD133^+$ cell.

In various embodiments, a method for increasing gamma globin expression in a hematopoietic stem or progenitor cell comprising introducing one or more engineered nucleases that cleave a target site set forth in SEQ ID NO: 9 and a DNA donor repair template contemplated herein into the cell, whereby the DNA donor repair template is inserted into the cell genome by homology directed repair at a double strand break introduced by the one or more engineered nucleases.

In particular embodiments, a method for increasing therapeutic globin expression in a hematopoietic stem or progenitor cell comprises introducing one or more engineered nucleases that cleave a target site set forth in SEQ ID NO: 7 or SEQ ID NO: 8 and a DNA donor repair template contemplated herein into the cell, whereby the DNA donor repair template is inserted into the cell genome by homology directed repair at a double strand break introduced by the one or more engineered nucleases.

In some embodiments, a genome edited cell produced by a HDR with a donor repair template contemplated herein is provided.

In various embodiments, a composition comprises a DNA donor repair template, a viral vector, or a cell contemplated herein.

In various embodiments, a composition comprises a physiologically acceptable excipient and a DNA donor repair template, a viral vector, or a cell contemplated herein.

In further embodiments, a method of treating a hemoglobinopathy in a subject comprises administering the subject a cell or composition contemplated herein.

In various embodiments, a method of ameliorating at least one symptom, of a hemoglobinopathy in a subject comprises administering the subject a cell or composition contemplated herein.

In particular embodiments, the β-globin alleles of the subject are $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$, or $\beta^S/\beta^S$.

In additional embodiments, a method of treating a thalassemia in a subject comprises administering the subject an effective amount of a cell or composition contemplated herein.

In certain embodiments, the thalassemia is a β-thalassemia.

In particular embodiments, the β-globin alleles of the subject are $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In certain embodiments, a method of treating sickle cell disease in a subject comprises administering the subject an effective amount of a cell or composition contemplated herein.

In particular embodiments, the β-globin alleles of the subject are $\beta^E/\beta^S$, $\beta^0/\beta^S$, $\beta^C/\beta^S$, $\beta^+/\beta^S$ or $\beta^S/\beta^S$.

In some embodiments, a method of treating a β-thalassemia in a subject comprises administering the subject an effective amount of a cell or composition contemplated herein.

In particular embodiments, the β-globin alleles of the subject are $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

BRIEF DESCRIPTION OF SEVERAL VIEWS OF THE DRAWINGS

FIG. 4A shows a diagram of the human β hemoglobin locus on Chromosome 11 highlighting the Aγ(HBG1) promoter structure. FIG. 4B provides a schematic of repressive elements that bind the γ-hemoglobin promoter including the CCAAT Displacement Protein (CDP/CUX1), DRED Complex (in conjunction with COUP-TFII), BCL11a (associated with the NURD complex which also partners with LRF) and the NF-Y binding sites. Negative transcription factors are shown in red. Positive transcriptions factors are shown in green. The putative BCL11a binding sequence (TGACCA) is underlined in red. The distal and proximal CCAAT boxes are underlined in green. Green * indicate the location of published HPFH SNPs. The bracketed green line highlights the 13 bp HPFH deletion as labeled. FIG. 4C shows TALENs selected in silico and tested. Blue boxes represent Repeat Variable Diresidues (RVDs) and their corresponding nucleotide is listed below. Scissors represent FokI endonuclease and the dotted line and indicated bp numbers represent the spacer length between the TALEN pairs.

FIG. 5A provides an experimental timeline for TALEN transfection of hPBSCs. FIG. 5B shows cell viability (right axis) and total cell number (left axis) assessed at two recovery temperatures (37° C. and 30° C.) and over increasing TALEN mRNA doses measured at 24 hours post transfection. (n=6/condition, p-values *<0.05, <0.005, *<0.0005)). TALEN mRNA doses higher than 1 ug had a significant negative impact on transfected cells and the effect was more pronounced with a 30° C. recovery step. FIG. 5C provides schematic of a novel ddPCR fall off assay designed to detect NHEJ events at both the HBG1 and HBG2 promoters. A common set of primers (green) are used to amplify the HBG1 and HGB2 alleles. A common NHEJ ddPCR Probe linked to HEX bind over the TALEN target cut site and is designed to fall off if single base insertion or deletion is present in the binding region. Unique HBG1 and HBG2 Ref ddPCR Probes linked to FAM bind to a region with three unique nucleotides allowing for editing of HBG1 and HBG2 to be assessed independently. FIG. 5D shows ddPCR results for hPBSCs edited with TALEN mRNA at increasing concentrations and two recovery temperatures. All cells transfected with TALEN mRNA result in significant indel generation. 30° C. recovery results in significantly higher rates of NHEJ than 37° C. but decreases with doses of TALEN mRNA over 1 ug. HBG1 NHEJ editing rates detected by this assay are roughly 50% of HBG2 due to the presence of large intergenic deletions. FIG. 5E shows rates of NHEJ following 1 ug mRNA transfection and detected by ddPCR do not vary by donor (n=3 donors). FIG. 5F shows NHEJ assessment by Next Gen Sequencing (Illumina MiSeq) detects editing rates lower than the ddPCR assay but demonstrate a consistent doubling in editing following 30° C. recovery. FIG. 5G shows indel frequency by size (bp) demonstrating higher editing rates following 30° C. recovery (bottom, blue) also result in higher rates of 13 bp deletion as well as an increased frequency of larger (5-8 bp) deletions than 37° C. (above, black) recovery where 1 bp deletions predominate. Solid bars represent HBG1, Outlined bars represent HBG2.

FIGS. 6A-6D demonstrate TALEN-induced ds breaks drive fetal hemoglobin expression in differentiated hPBSCs. FIG. 6A provides an experimental timeline for erythroid differentiation following transfection. FIG. 6B shows representative flow at 14 days of differentiation comparing the erythroid progeny of mock and TALEN edited hPBSCs. The left panel demonstrates that the overall CD235a+ staining profile is nearly identical between mock (82.5%, blue) and TALEN edited cells (88.5%, orange). Isotype control is shown in brown. The right panel shows HbF expression is significantly higher in TALEN edited cells (61.1%) compared to mock (27.4%). FIG. 6C shows combined analysis of HbF expression at increasing doses of TALEN mRNA and at different recovery temperatures demonstrating a significant increase in HbF expression in all TALEN transfected cells compared to mock (p<0.0005) and a greater increase seen at 30° C. recovery (outlined blue circles) compared to 37° C. (filled black circles). Cells transfected with 1 ug TALEN result in significantly more HbF expression with 37° C. recovery resulting in 44±3% HbF and 30° C. recovery resulting in 57±3% HbF compared to mock HbF expression of 24±2 (30° C.) or 24±5 (37° C.). FIG. 6D shows hemoglobin protein expression detected by HPLC demonstrates a significant increase in overall HbF expression at 1 ug TALEN mRNA. There is a 2.4 fold increase (26±3% total HbF protein) seen with 37° C. culture following 1 ug transfection. 30° C. cold shock treatment resulted in a 4.6 fold increase in HbF protein expression to 41±8% when transfected with 1 ug mRNA (p<0.005).

FIGS. 7A-7H demonstrates sustained multi-lineage engraftment of TALEN edited hPBSCs in recipient W41 mice. FIG. 7A provides experimental timeline for editing of hPBSCs followed by both primary and secondary transplants. FIG. 7B shows human engraftment (% hCD45 positive) at sac for both the primary and secondary transplants. Shapes correspond to experimental cohorts. Primary and secondary transplant average engraftment was not significantly different following TALEN editing (Primary: mock 67±3% n=4, TALEN 71±8% n=9. Secondary: mock 3.6±1.9% n=2, TALEN 2.8±1.4% n=5). FIG. 7C provides summary of FACS analysis of primary transplants at sac (Transplant 1 at 16 weeks, Transplant 2 at 24 weeks) with multilineage engraftment in mice transfused with either mock or TALEN edited cells. CD19+ engraftment is more robust at 24 weeks with population profiles otherwise similar. FIG. 7D shows NHEJ rates detected by ddPCR at sac for both the primary and secondary transplants. Transplant 1 had a higher input editing rate (HBG1=56%, HBG2=46%) than transplant 2 (HBG1=20%, HBG2=28%). Editing rates drop by approximately 50% post transplant but are maintained following secondary transplant. FIG. 7E shows indel frequency measured by Next Gen Sequencing demonstrates the edits maintained post transplant tend to be in the 2-7 bp range with a relative decrease in the 13 bp HPFH deletion. FIG. 7F shows comparison of percent modification (deletion) seen at each nucleotide indicates that the majority of deletions occur over the BCL11a binding site (red line) and distal CCAAT box (green line) with a relative decrease in retained deletions post transplant of the 3' end of the 13 bp HPFH deletion. FIG. 7G shows flow analysis at the time of harvest shows that human HbF is significantly upregulated in mice that receive TALEN edited hPBSCs (Mock=21±1%, TALEN 33±15%). FIG. 7H shows flow analysis following ex vivo liquid differentiation demonstrates significantly higher HbF in animals that received TALEN edited hPBSCs (Mock=59±2%, TALEN=70±6%).

FIG. 9 provides templates that rely on large genomic deletions to induce fetal hemoglobin.

FIG. 10 provides templates designed to express T87Q using the HBG1 promoter or drive the endogenous HBG1 gene using the d13 HPFH promoter or the HBB promoter.

FIG. 11 provides 'Round 3' repair templates designed to express T87Q using the HBG1 promoter or drive the endogenous HBG1 gene using the d13 HPFH promoter or the HBB promoter and some containing an MGMT chemo selection cassette.

FIG. 12 provides a summary of Rhesus related constructs.

FIG. 27 demonstrates Construct 1345 is a rAAV construct that can drive homology-dependent repair into the HBG1 locus. The donor template introduces a HBB promoter that drives T87Q globin.

FIG. 30 demonstrates Construct 1343 is a rAAV construct that can drive homology-dependent repair into the human HBG1 locus. The donor template introduces a HBB promoter that drives T87Q globin expression and allows for chemo therapeutic selection, as it has a PGK-promoter driving P140K MGMT expression. Construct 1346 is a rAAV construct that can drive homology-dependent repair into the human HBG1 locus. The donor template introduces a HBG1 d13 promoter that drives T87Q globin expression and allows for chemo therapeutic selection, as it has a PGK-promoter driving P140K MGMT expression.

FIG. 46 provides a transplants summary for various animals tested.

FIG. 47A shows recapitulation of 13-nucleotide HPFH deletion by CRISPR/Cas9 gene editing. FIG. 47B shows immunophenotypic separation of HSPC subsets from bone marrow enriched-CD34+ cells (A17117) by surface antibody staining. FIG. 47C shows HbG gene editing efficiency measured at 24 h post CRISPR RNPs electroporation in sorted HSPCs subset. Results are means and standard deviations from 2 donors. FIG. 47D shows proportion of 13-nt HPFH deletion relative to all other deletions in reactions from FIG. 47C. * denotes statistically significant decrease (t-test, $P<0.05$) in 13-nt deletion in CD90+ subset as compared to CD34+ cells. FIG. 47E shows colony-forming cells in CD34+ and HSPC subsets plated on methylcellulose media at 24 h post mock electroporation. FIG. 47F shows colony-forming cells in CD34+ and HSPC subsets plated on methylcellulose media at 24 h post CRISPR/Cas9 RNPs electroporation. Results are from the same donor. FIG. 47G shows deletion profile in CD34+-edited cells (A17117) at 4 days post electroporation. Each color box shows deletion with a frequency higher than 1% and the white portion at the bottom shows combined deletions that contributes less than 1%. FIG. 47H provides sequences of the most common deletions (color-coded) from FIG. 47G. FIG. 47I shows in vitro HbF expression (defined as ratio of HbF/HbA measured by flow cytometry) in differentiated erythroblast as function of HbG editing levels (measured by TIDE). Results are from 4 different donors and HbF/HbA ratio was normalized to mock-treated samples in each donor for comparison.

FIGS. 48A-48D show hematopoietic recovery in all transplanted animals by measuring neutrophil count (cells per μL) (FIG. 48A), platelet count (cells per μL) (FIG. 48B), lymphocyte count (cells per μL) (FIG. 48C), and monocyte count (cells per μL) (FIG. 48D) in view of days post transplantation.

FIG. 49A shows HbG editing efficiency by Miseq analysis measured over days post transplantation. FIG. 49B shows percent HPFH 13-nt deletion by Miseq analysis measured over days post transplantation. FIGS. 49C-49D show mutant frequency for animals A17114 and A17116.

FIGS. 50A-50E show fetal hemoglobin production in all transplanted animals. Percent F-cells (flow cytometry) (FIG. 50A) and percent γ-globin relative to β-like globin (HPLC) (FIG. 50B) was measured over days post transplantation for all transplanted animals. Percent F-cells (flow cytometry) was measured in view of percent γ-globin (HPLC) for four of the transplanted animals (FIG. 50B). Percent γ-globin and percent F-cells were then measured in view of HbG editing (measured by TIDE) (FIG. 50D). For four animal models the percent total of gamma-1, gamma-2, beta, alpha-2, and alpha-1 was measured over days post transplantation.

FIGS. 51A-51G shows multilineage engraftment of CRISPR/Cas9-edited HSPCs in bone marrow of transplanted animals at 6 months post infusion. FIGS. 51A-51B show immunophenotypic separation of HSPC subsets from bone marrow enriched-CD34+ cells by surface antibody staining, as well as showing colony-forming cells in CD34+ and HSPC subsets for animal models A17114 (FIG. 51A) and A17116 (FIG. 51B). FIG. 51C shows HbG editing efficiency (measured by TIDE) for three animal models measuring CD34+ cells, CD45RA+ cells, CD50− cells, and CD90+ cells. FIGS. 51D and 51E provide flow cytometry sorting of HSPCs subsets. FIG. 51F shows HbG editing efficiency (measured by TIDE) for three animal models measuring T cells, B cells, Gran cells, mono cells, 71+ erythroid cells. FIG. 51G shows mutant frequency for animal model A17114 in multiple cell types.

FIG. 52 provides quantification of large deletion events and off-target sites.

FIGS. 53A-53F show HbG editing efficiency in different HSPC subsets. FIG. 53A shows titration of molar ratios of Cas9 protein to gRNA for optimization of HbG editing efficiency (determined by Surveyor assay). Circles show individual data points and bar shows mean. Results are from 3 different NHP donors. FIG. 53B shows size distribution of HbG deletions in edited NHP CD34+ cells 4 days post treatment. Results are from Miseq analysis using 1 donor and deletion frequency was normalized to 100%. FIG. 53C shows flow cytometry sorting of HSPCs subsets from A17114 after CD34+ enrichment. FIG. 53D shows HbG editing efficiency in HSPCs sorted subsets from FIG. 53C determined by Miseq analysis. FIG. 53E shows flow cytometry sorting of HSPCs subsets from A17117 after CD34+ enrichment. FIG. 53F shows HbG editing efficiency in HSPCs sorted subsets from FIG. 53E determined by Miseq analysis.

FIGS. 54A-54D show results pre-editing and post-editing, including flow cytometry sorting (FIG. 54A), showing colony forming cells (FIG. 54B), measuring percent indels by Miseq analysis (FIG. 54C), and measuring HbG editing efficiency (measured by TIDE) (FIG. 54D).

FIGS. 61A-61B shows. FIG. 61A shows longitudinal analysis of gamma globin (HbG) editing in peripheral blood of transplanted animals as determined by TIDE analysis. FIG. 61B shows frequency of circulating F-cells in transplanted animals as compared to control transplants (grey) and to an untransplanted control (black).

FIG. 62A provides a schematic of targeted integration strategy using combination of CRISPR/Cas9 and AAV donor delivery. FIG. 62B shows HDR time course experiment in rhesus CD34+ cells treated with or without CRISPR/Cas9 RNPs and with 2 different doses of AAV donor. FIG. 62C provides representative flow plots of treated cells (day 7) showing GFP positive cells as surrogate for HDR events.

BRIEF DESCRIPTION OF THE SEQUENCE IDENTIFIERS

Figure 1:
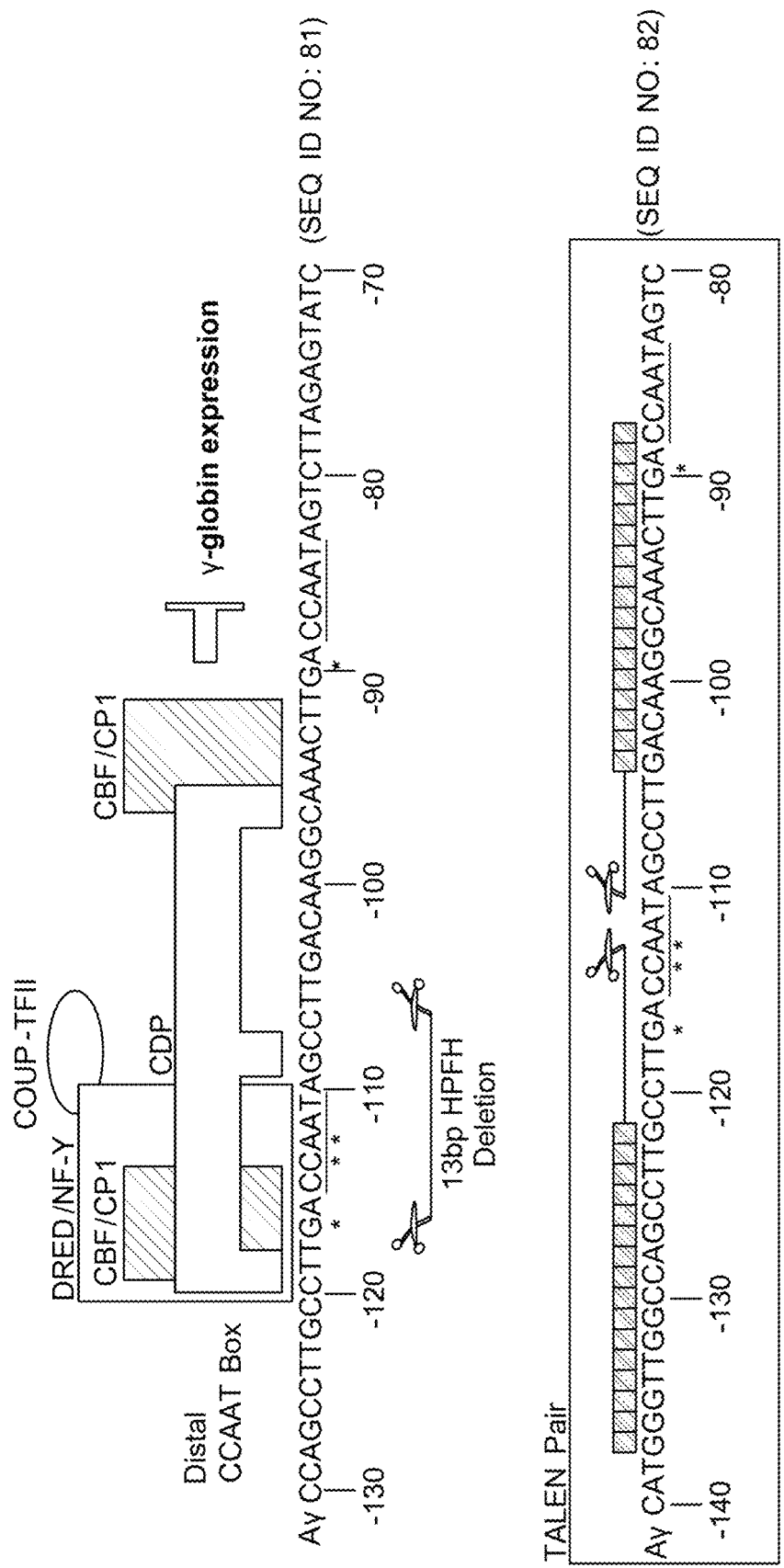
FIG. 1 shows an upstream region of the γ-globin promoter, including the 13 bp sequence responsible for repression of γ-globin gene expression (top panel) and a nuclease target site strategy for disruption of the 13 bp sequence.

SEQ ID NOs: 1-6 set forth polynucleotide sequences in the human γ-globin promoter, that when disrupted, are associated with HPFH.

SEQ ID NOs: 7-8 set forth polynucleotide sequence of the human γ-globin gene and its reverse complement, both of which can be used to target donor repair templates contemplated herein.

SEQ ID NO: 9 sets forth a polynucleotide sequence of 1 kb upstream of the transcriptional start site of the human γ-globin gene.

SEQ ID NOs: 10-57 set forth various AAV donor templates.

SEQ ID NOs: 58-59 set forth TALEN plasmid sequences.

SEQ ID NOs: 60-69 set forth polynucleotide sequences for exemplary 2A sites.

SEQ ID NOs: 70-80 set forth linker sequences.

DETAILED DESCRIPTION

A. Overview

The present disclosure generally relates to, in part, improved genome editing compositions for use in homology directed repair (HDR). Without wishing to be bound by any particular theory, the DNA donor repair templates contemplated herein are used to increase the amount of a therapeutic globin in a cell and to select the cells. The therapeutic cells can be used to treat, prevent, or ameliorate at least one symptom associated with a hemoglobinopathy.

Normal adult hemoglobin comprises a tetrameric complex of two alpha-(α) globin proteins and two beta-(β-) globin proteins. In development, the fetus produces fetal hemoglobin (HbF), which comprises two gamma-(γ) globin proteins instead of the two β-globin proteins. At some point during perinatal development, a "globin switch" occurs; erythrocytes down-regulate γ-globin expression and switch to predominantly producing β-globin. This switch results primarily from decreased transcription of the γ-globin genes and increased transcription of β-globin genes.

There is a segment of the human population that has deletions in various regions of the globin locus that lead to a condition known as Hereditary Persistence of Fetal Hemoglobin (HPFH). The deletions associated with HPFH are associated with increases in HbF in adulthood and are referred to herein collectively as HPFH deletions, a number of which are described herein, and others that are known in the art. HPFH is not associated with any significant clinical manifestations, even when 100% of the individual's hemoglobin is HbF. Thus, individuals that have a hemoglobinopathy that also have HPFH, have increased HbF expression, which can lessen the severity of the disease.

In particular preferred embodiments, the genome editing compositions contemplated herein are used to engineer the globin locus to phenocopy a 13 bp deletion in the γ-globin promoter associated with HPFH (Gilman et al. *Nucleic Acids Res.* 1988 Nov. 25; 16(22): 10635-10642). Without wishing to be bound by any particular theory, it is contemplated that the DNA donor repair templates contemplated herein can be used to derepress the γ-globin locus to drive expression of a therapeutic globin gene and to select genome edited cells. The DNA donor repair templates contemplated herein are also advantageous because they can be designed to alter both the A-γ-globin gene and the G-γ-globin gene. A further advantage is that the engineered nuclease(s) used to introduce a DSB into the locus to facilitate HDR in the presence of a DNA donor repair template, can still lead to therapeutic editing in the absence of a DNA donor repair template because cleavage of the 13 bp target sequence will be repaired by NHEJ, thereby producing indels at the target site, disrupting the repressive function of the intact 13 bp sequence, and derepressing γ-globin expression.

In other particular preferred embodiments, the genome edited compositions contemplated herein are used to increase expression of endogenous γ-globin and select for edited cells. Without wishing to be bound by any particular theory, it is contemplated that the DNA donor repair templates contemplated herein can be used for selection and to introduce a β-globin LCR responsive promoter in operable linkage to an endogenous γ-globin gene to drive expression of endogenous γ-globin. The DNA donor repair templates contemplated herein are also advantageous because they can be designed to alter both the A-γ-globin gene and the G-γ-globin gene. A further advantage is that the engineered nuclease(s) used to introduce a DSB into the locus to facilitate HDR in the presence of a DNA donor repair template, can still lead to therapeutic editing in the absence of a DNA donor repair template because cleavage of the 13 bp target sequence will be repaired by NHEJ, thereby producing indels at the target site, disrupting the repressive function of the intact 13 bp sequence, and derepressing γ-globin expression.

The engineered nucleases contemplated herein can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

Genome edited cells engineered by HDR with a DNA donor repair template and one or more engineered nucleases are contemplated in particular embodiments.

Genome edited cells and compositions comprising the same are also contemplated for use in the treatment, prevention, and/or amelioration of at least one symptom of a hemoglobinopathy.

Accordingly, the methods and compositions contemplated herein represent a quantum improvement compared to existing gene editing strategies for the treatment of hemoglobinopathies.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined and in some cases elaborated on below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a DNA donor repair template, genome editing composition, or genome edited cell contemplated herein to produce, elicit, or cause a greater response (i.e., physiological response) compared to the response caused by either vehicle or control. A measurable response may include an increase in γ-globin expression, HbF expression, and/or an increase in transfusion independence, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By "decrease" or "lower" or "lessen" or "reduce" or "abate" or "ablate" or "inhibit" or "dampen" refers generally to the ability of a DNA donor repair template, genome editing composition, or genome edited cell contemplated herein to produce, elicit, or cause a lesser response (i.e., physiological response) compared to the response caused by either vehicle or control. A measurable response may include a decrease in endogenous β-globin, transfusion dependence, RBC sickling, and the like. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By "maintain," or "preserve," or "maintenance," or "no change," or "no substantial change," or "no substantial decrease" refers generally to the ability of a DNA donor repair template, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurably different from the reference response.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO that references only one strand of a target site or target sequence, it would be understood that the target site or target sequence bound and/or cleaved by a nuclease variant is double-stranded and comprises the reference sequence and its complement. In a preferred embodiment, the target site is a sequence in the human gamma globin gene that when disrupted, is associated with an HPFH phenotype.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may bias repair towards an altNHEJ pathway.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins, for example, endogenous globins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., SEQ ID NOs: 1-9), typically where the variant maintains at least one biological activity of the reference sequence. In various illustrative embodiments, viral vector and transfer plasmid polynucleotide sequences and compositions comprising the same are contemplated. In particular embodiments, polynucleotides encoding one or more therapeutic polypeptides and/or other genes of interest are contemplated.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material, e.g., a polynucleotide, a polypeptide, a cell, that is substantially or essentially free from components that normally accompany it in its native state. In particular embodiments, the term "obtained" or "derived" is used synonymously with isolated. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., Current Protocols in Molecular Biology, John Wiley & Sons Inc., 1994-1998, Chapter 15.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express a polynucleotide. In one embodiment, the nucleic acid cassette contains a polynucleotide(s)-of-interest. In another embodiment, the nucleic acid cassette contains one or more expression control sequences, e.g., a promoter, enhancer, post-transcriptional regulatory element, poly(A) sequence, and a polynucleotide(s)-of-interest. Vectors may comprise one, two, three, four, five or more nucleic acid cassettes. The nucleic acid cassette is positionally and sequentially oriented within the vector such that the nucleic acid in the cassette can be transcribed into RNA. Preferably, the cassette has its 3' and 5' ends adapted for ready insertion into a vector, e.g., it has restriction endonuclease sites at each end. In a preferred embodiment, the nucleic acid cassette one or more expression control sequences operably linked to a polynucleotide encoding a therapeutic RNA, e.g., a shmiR, and/or a polypeptide, that can be used to treat, prevent, or ameliorate a genetic disorder. The cassette can be removed and inserted into a plasmid or viral vector as a single unit.

As used herein, the term "polynucleotide(s)-of-interest" refers to one or more polynucleotides, e.g., a polynucleotide encoding a polypeptide (i.e., a polypeptide-of-interest), inserted into an expression vector that is desired to be expressed. In preferred embodiments, polynucleotides comprise one or more polynucleotides-of-interest that encode one or more therapeutic globins. In particular embodiments, the polynucleotide-of-interest is a transgene that encodes a polypeptide that provides a therapeutic function for the treatment of a hemoglobinopathy, e.g., α-globin, β-globin, β-globin$^{A-T87Q}$, anti-sickling globins, γ-globin, and δ globin.

Polynucleotides, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "expression control sequence" refers to a polynucleotide sequence that comprises one or more promoters, enhancers, or other transcriptional control elements or combinations thereof that are capable of directing, increasing, regulating, or controlling the transcription or expression of an operatively linked polynucleotide. In particular embodiments, vectors of the invention comprise one or more expression control sequences that are specific to particular erythroid cells, erythroid cell types, or erythroid cell lineages. In preferred embodiments, vectors comprise one or more expression control sequences specific to erythroid cells, e.g., an erythroid specific expression control sequence.

An "endogenous" expression control sequence is one which is naturally linked to a given gene in the genome. An "exogenous" expression control sequence is one which is placed in juxtaposition to a gene by means of genetic manipulation (i.e., molecular biological techniques) such that transcription of that gene is directed by the linked enhancer/promoter. A "heterologous" expression control sequence is an exogenous sequence that is from a different species than the cell being genetically manipulated. A "synthetic" expression control sequence may comprise elements of one or more endogenous and/or exogenous sequences, and/or sequences determined in vitro or in silico that provide optimal promoter and/or enhancer activity for the particular gene therapy. In particular embodiments, a vector comprises exogenous, endogenous, or heterologous expression control sequences such as promoters and/or enhancers.

The term "promoter" as used herein refers to an expression control sequence that comprises a recognition site of a polynucleotide (DNA or RNA) to which an RNA polymerase binds. The term "enhancer" refers to an expression control sequence that comprises a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer or other expression control sequence) and a second polynucleotide sequence, e.g., a polynucleotide-of-interest, wherein the expression control sequence directs transcription of the nucleic acid corresponding to the second sequence.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Illustrative examples of polypeptides include, but are not limited to globin polypeptides, suitable for use in the compositions and methods of particular embodiments. Also, see, e.g., U.S. Pat. Nos. 6,051,402; 7,901,671; and 9,068,199, the full disclosure and claims of which are specifically incorporated herein by reference in their entireties.

Particular embodiments contemplated herein, also include polypeptide "variants." The recitation polypeptide "variant" refers to polypeptides that are distinguished from a reference polypeptide by the addition, deletion, truncations, modifications, and/or substitution of at least one amino acid residue, and that retain a biological activity. In certain embodiments, a polypeptide variant is distinguished from a reference polypeptide by one or more substitutions, which may be conservative or non-conservative, as known in the art. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, amino acid additions or deletions occur at the C-terminal end and/or the N-terminal end of the reference polypeptide.

Polypeptides contemplated in particular embodiments include fusion polypeptides. "Fusion polypeptides" or "fusion proteins" refer to a polypeptide having at least two, three, four, five, six, seven, eight, nine, or ten polypeptide segments, including, but not limited to one or more linker and/or self-cleaving polypeptides.

A peptide "linker" sequence refers to a polypeptide sequence that may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between. Exemplary linkers include, but are not limited to the following amino acid sequences: glycine polymers (G)n; glycine-serine polymers (G1-5S1-5)n, where n is an integer of at least one, two, three, four, or five; glycine-alanine polymers; alanine-serine polymers; GGG (SEQ ID NO: 70); DGGGS (SEQ ID NO: 71); TGEKP (SEQ ID NO: 72) (see e.g., Liu et al., PNAS 5525-5530 (1997)); GGRR (SEQ ID NO: 73) (Pomerantz et al. 1995, supra); (GGGGS)n wherein n=1, 2, 3, 4 or 5 (SEQ ID NO: 74) (Kim et al., PNAS 93, 1156-1160 (1996);

EGKSSGSGSESKVD (SEQ ID NO: 75) (Chaudhary et al., 1990, Proc. Natl. Acad. Sci. U.S.A. 87:1066-1070); KES-GSVSSEQLAQFRSLD (SEQ ID NO: 76) (Bird et al., 1988, Science 242:423-426), GGRRGGGS (SEQ ID NO: 77); LRQRDGERP (SEQ ID NO: 78); LRQKDGGGSERP (SEQ ID NO: 79); LRQKD(GGGS)2ERP (SEQ ID NO: 80). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods.

C. Engineered Nucleases

In particular embodiments, HDR at target sites comprises introducing one or more double strand breaks (DSB) at a target site using one or more engineered nucleases in the presence of a DNA donor repair template contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence. The nuclease variant may be designed and/or modified from a naturally occurring nuclease or from a previous nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerase or template-independent DNA polymerase activity.

Illustrative examples of nucleases that may be engineered to bind and cleave a target sequence include, but are not limited to homing endonucleases (meganucleases), mega-TALs, transcription activator-like effector nucleases (TALENs), zinc finger nucleases (ZFNs), and clustered regularly-interspaced short palindromic repeats (CRISPR)/Cas nuclease systems.

1. Homing Endonucleases/Meganucleases

In various embodiments, a plurality of homing endonucleases or meganucleases are introduced into a cell and engineered to bind to, and to introduce single-stranded nicks or double-strand breaks (DSBs) at a target site in a human γ-globin gene, e.g., a polynucleotide sequence as set for the in any one of SEQ ID NOs: 1-9. "Homing endonuclease" and "meganuclease" are used interchangeably and refer to naturally-occurring nucleases or engineered meganucleases that recognize 12-45 base-pair cleavage sites and are commonly grouped into five families based on sequence and structure motifs: LAGLIDADG, GIY-YIG, HNH, His-Cys box, and PD-(D/E)XK.

Engineered HEs do not exist in nature and can be obtained by recombinant DNA technology or by random mutagenesis. Engineered HEs may be obtained by making one or more amino acid alterations, e.g., mutating, substituting, adding, or deleting one or more amino acids, in a naturally occurring HE or previously engineered HE. In particular embodiments, an engineered HE comprises one or more amino acid alterations to the DNA recognition interface.

Engineered HEs contemplated in particular embodiments may further comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, engineered HEs are introduced into a hematopoietic cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The HE and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or engineered HE. By way of non-limiting example, an engineered HE contemplated in particular embodiments may be derived by constructing libraries of HE variants in which one or more amino acid residues localized in the DNA recognition interface of the natural HE (or a previously engineered HE) are varied. The libraries may be screened for target cleavage activity against each predicted target site using cleavage assays (see e.g., Jarjour et al., 2009. *Nuc. Acids Res.* 37(20): 6871-6880).

LAGLIDADG homing endonucleases (LHE) are the most well studied family of meganucleases, are primarily encoded in archaea and in organellar DNA in green algae and fungi, and display the highest overall DNA recognition specificity. LHEs comprise one or two LAGLIDADG catalytic motifs per protein chain and function as homodimers or single chain monomers, respectively. Structural studies of LAGLI-DADG proteins identified a highly conserved core structure (Stoddard 2005), characterized by an αββαββα fold, with the LAGLIDADG motif belonging to the first helix of this fold. The highly efficient and specific cleavage of LHE's represent a protein scaffold to derive novel, highly specific endonucleases. However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

Illustrative examples of LHEs from which engineered LHEs may be designed include, but are not limited to I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-Ncrl, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

Other illustrative examples of LHEs from which engineered LHEs may be designed include, but are not limited to I-CreI and I-SceI.

In one embodiment, the engineered LHE is selected from the group consisting of: I-CpaMI, I-HjeMI, I-OnuI, I-PanMI, and SmaMI.

In one embodiment, the engineered LHE is I-OnuI.

In a particular embodiment, the engineered I-OnuI LHE comprises one or more amino acid substitutions in the DNA recognition interface. In particular embodiments, the I-OnuI LHE comprises at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the DNA recognition interface of I-OnuI (Taekuchi et al. 2011. *Proc Natl Acad Sci U.S.A.* 2011 Aug. 9; 108(32): 13077-13082) or an engineered variant of I-OnuI.

In one embodiment, the I-OnuI LHE comprises at least 70%, more preferably at least 80%, more preferably at least 85%, more preferably at least 90%, more preferably at least 95%, more preferably at least 97%, more preferably at least 99% sequence identity with the DNA recognition interface of I-OnuI (Taekuchi et al. 2011. *Proc Natl Acad Sci U.S.A.* 2011 Aug. 9; 108(32): 13077-13082) or an engineered variant of I-OnuI.

In a particular embodiment, an engineered I-OnuI LHE comprises one or more amino acid substitutions or modifications in the DNA recognition interface, particularly in the subdomains situated from positions 24-50, 68 to 82, 180 to 203 and 223 to 240 of I-OnuI.

In one embodiment, an engineered I-OnuI LHE comprises one or more amino acid substitutions or modifications at additional positions situated anywhere within the entire I-OnuI sequence. The residues which may be substituted and/or modified include but are not limited to amino acids that contact the nucleic acid target or that interact with the nucleic acid backbone or with the nucleotide bases, directly or via a water molecule. In one non-limiting example an engineered I-OnuI LHE contemplated herein comprises one or more substitutions and/or modifications, preferably at least 5, preferably at least 10, preferably at least 15, more preferably at least 20, even more preferably at least 25 in at least one position selected from the position group consisting of positions: 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, 240 of I-OnuI.

2. MegaTALs

In various embodiments, one or more megaTALs are introduced into a hematopoietic cell and engineered to bind and introduce DSBs at a target site in a human γ-globin gene, e.g., a polynucleotide sequence as set for the in any one of SEQ ID NOs: 1-9. A "megaTAL" refers to an engineered nuclease comprising an engineered TALE DNA binding domain and an engineered meganuclease, and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a megaTAL can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. *Science* 318:648-651). TALE DNA binding domains contemplated in particular embodiments are engineered de novo or from naturally occurring TALEs, e.g., AvrBs3 from *Xanthomonas campestris* pv. *vesicatoria*, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S* for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-16 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-13.5 repeat units, more preferably 7.5-12.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises an "N-terminal domain (NTD)" polypeptide, one or more TALE repeat domains/units, a "C-terminal domain (CTD)" polypeptide, and an engineered meganuclease.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids +1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids +1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids –20 to –1 of a *Xanthomonas* TALE protein (–20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids –20 to –1 of a *Ralstonia* TALE protein (–20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a meganuclease engineered to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to an engineered meganuclease. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the meganuclease. In this way, the megaTALs contemplated herein, increase the specificity and efficiency of genome editing.

In particular embodiments, a megaTAL contemplated herein, comprises one or more TALE DNA binding repeat units and an engineered LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD, one or more TALE DNA binding repeat units, a CTD, and an engineered LHE selected from the group consisting of I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD, about 9.5 to about 15.5 TALE DNA binding repeat units, and an engineered I-OnuI LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an engineered I-OnuI LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

3. Talens

In various embodiments, a plurality of transcription activator-like effector nucleases (TALENs) are introduced into a cell and engineered to bind to, and to introduce single-stranded nicks or double-strand breaks (DSBs) at a target site in a human γ-globin gene, e.g., a polynucleotide sequence as set forth in any one of SEQ ID NOs: 1-9. A "TALEN" refers to an engineered nuclease comprising an engineered TALE DNA binding domain contemplated elsewhere herein and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a TALEN can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The TALEN and 3' processing enzyme may be introduced separately, e.g., in different vectors or separate mRNAs, or together, e.g., as a fusion protein, or in a polycistronic construct separated by a viral self-cleaving peptide or an IRES element.

In one embodiment, targeted double-stranded cleavage is achieved with two TALENs, each comprising an endonuclease half-domain can be used to reconstitute a catalytically active cleavage domain. In another embodiment, targeted double-stranded cleavage is achieved using a single polypeptide comprising a TALE DNA binding domain and two endonuclease half-domains.

TALENs contemplated in particular embodiments comprise an NTD, a TALE DNA binding domain comprising about 3 to 30 repeat units, e.g., about 3, 4, 5, 6, 7, 8, 9, 10, 11, 12, 13, 14, 15, 16, 17, 18, 19, 20, 21, 22, 23, 24, 25, 26, 27, 28, 29, or 30 repeat units, and an endonuclease domain or half-domain.

TALENs contemplated in particular embodiments comprise an NTD, a TALE DNA binding domain comprising about 3.5 to 30.5 repeat units, e.g., about 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 repeat units, a CTD, and an endonuclease domain or half-domain.

TALENs contemplated in particular embodiments comprise an NTD of about 121 amino acids to about 137 amino acids as disclosed elsewhere herein, a TALE DNA binding domain comprising about 9.5 to about 15.5 repeat units (i.e., about 9.5, about 10.5, about 11.5, about 12.5, about 13.5, about 14.5, or about 15.5 repeat units), a CTD of about 20 amino acids to about 85 amino acids, and an endonuclease domain or half domain.

In particular embodiments, a TALEN comprises an endonuclease domain of a type restriction endonuclease. Restriction endonucleases (restriction enzymes) are present in many species and are capable of sequence-specific binding to DNA (at a recognition site), and cleaving DNA at or near the site of binding. Certain restriction enzymes (e.g., Type-IIS) cleave DNA at sites removed from the recognition site and have separable binding and endonuclease domains. In one embodiment, TALENs comprise the endonuclease domain (or endonuclease half-domain) from at least one Type-IIS restriction enzyme and one or more TALE DNA-binding domains contemplated elsewhere herein.

Illustrative examples of Type-IIS restriction endonuclease domains suitable for use in TALENs contemplated in particular embodiments include endonuclease domains of the at least 1633 Type-IIS restriction endonucleases disclosed at "rebase.neb.com/cgi-bin/sublist?S."

Additional illustrative examples of Type-IIS restriction endonuclease domains suitable for use in TALENs contemplated in particular embodiments include those of endonucleases selected from the group consisting of Aar I, Ace III, Aci I, Alo I, Alw26 I, Bae I, Bbr7 I, Bbv I, Bbv II, BbvC I, Bcc I, Bce83 I, BceA I, Bcef I, Bcg I, BciV I, Bfi I, Bin I, Bmg I, Bpu10 I, BsaX I, Bsb I, BscA I, BscG I, BseR I, BseY I, Bsi I, Bsm I, BsmA I, BsmF I, Bsp24 I, BspG I, BspM I, BspNC I, Bsr I, BsrB I, BsrD I, BstF5 I, Btr I, Bts I, Cdi I, CjeP I, Drd II, EarI, Eci I, Eco31 I, Eco57 I, Eco57M I, Esp3 I, Fau I, Fin I, Fok I, Gdi II, Gsu I, Hga I, Hin4 II, Hph I, Ksp632 I, Mbo II, Mly I, Mme I, Mnl I, Pfl1108, I Ple I, Ppi I Psr I, RleA I, Sap I, SfaN I, Sim I, SspD5 I, Sth132 I, Sts I, TspDT I, TspGW I, Tth111 II, UbaP I, Bsa I, and BsmB I.

In one embodiment, a TALEN contemplated herein comprises an endonuclease domain of the Fok I Type-IIS restriction endonuclease.

In one embodiment, a TALEN contemplated herein comprises a TALE DNA binding domain and an endonuclease half-domain from at least one Type-IIS restriction endonuclease to enhance cleavage specificity, optionally wherein the endonuclease half-domain comprises one or more amino acid substitutions or modifications that minimize or prevent homodimerization.

Illustrative examples of cleavage half-domains suitable for use in particular embodiments contemplated in particular embodiments include those disclosed in U.S. Patent Publication Nos. 20050064474; 20060188987, 20080131962, 20090311787; 20090305346; 20110014616, and 20110201055, each of which are incorporated by reference herein in its entirety.

4. Zinc Finger Nucleases

In various embodiments, a plurality of zinc finger nucleases (ZFNs) are introduced into a cell and engineered to bind to, and to introduce single-stranded nicks or double-strand breaks (DSBs) at a target site in a human γ-globin gene, e.g., a polynucleotide sequence as set for the in any one of SEQ ID NOs: 1-9. A "ZFN" refers to an engineered nuclease comprising one or more zinc finger DNA binding domains and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a ZFN can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The ZFN and 3' processing enzyme may be introduced separately, e.g., in different vectors or separate mRNAs, or together, e.g., as a fusion protein, or in a polycistronic construct separated by a viral self-cleaving peptide or an IRES element.

In one embodiment, targeted double-stranded cleavage is achieved using two ZFNs, each comprising an endonuclease half-domain can be used to reconstitute a catalytically active cleavage domain. In another embodiment, targeted double-stranded cleavage is achieved with a single polypeptide comprising one or more zinc finger DNA binding domains and two endonuclease half-domains.

In one embodiment, a ZNF comprises a TALE DNA binding domain contemplated elsewhere herein, a zinc finger DNA binding domain, and an endonuclease domain (or endonuclease half-domain) contemplated elsewhere herein.

In one embodiment, a ZNF comprises a zinc finger DNA binding domain, and a meganuclease contemplated elsewhere herein.

In particular embodiments, the ZFN comprises a zinc finger DNA binding domain that has one, two, three, four, five, six, seven, or eight or more zinc finger motifs and an endonuclease domain (or endonuclease half-domain). Typically, a single zinc finger motif is about 30 amino acids in length. Zinc fingers motifs include both canonical $C_2H_2$ zinc fingers, and non-canonical zinc fingers such as, for example, $C_3H$ zinc fingers and $C_4$ zinc fingers.

Zinc finger binding domains can be engineered to bind any DNA sequence. Candidate zinc finger DNA binding domains for a given 3 bp DNA target sequence have been identified and modular assembly strategies have been devised for linking a plurality of the domains into a multi-finger peptide targeted to the corresponding composite DNA target sequence. Other suitable methods known in the art can also be used to design and construct nucleic acids encoding zinc finger DNA binding domains, e.g., phage display, random mutagenesis, combinatorial libraries, computer/rational design, affinity selection, PCR, cloning from cDNA or genomic libraries, synthetic construction and the like. (See, e.g., U.S. Pat. No. 5,786,538; Wu et al., *PNAS* 92:344-348 (1995); Jamieson et al., *Biochemistry* 33:5689-5695 (1994); Rebar & Pabo, *Science* 263:671-673 (1994); Choo & Klug, *PNAS* 91:11163-11167 (1994); Choo & Klug, *PNAS* 91: 11168-11172 (1994); Desjarlais & Berg, *PNAS* 90:2256-2260 (1993); Desjarlais & Berg, *PNAS* 89:7345-7349 (1992); Pomerantz et al., *Science* 267:93-96 (1995); Pomerantz et al., *PNAS* 92:9752-9756 (1995); Liu et al., *PNAS* 94:5525-5530 (1997); Griesman & Pabo, *Science* 275:657-661 (1997); Desjarlais & Berg, *PNAS* 91:11-99-11103 (1994)).

Individual zinc finger motifs bind to a three or four nucleotide sequence. The length of a sequence to which a zinc finger binding domain is engineered to bind (e.g., a target sequence) will determine the number of zinc finger motifs in an engineered zinc finger binding domain. For example, for ZFNs in which the zinc finger motifs do not bind to overlapping subsites, a six-nucleotide target sequence is bound by a two-finger binding domain; a nine-nucleotide target sequence is bound by a three-finger binding domain, etc. In particular embodiments, DNA binding sites for individual zinc fingers motifs in a target site need not be contiguous, but can be separated by one or several nucleotides, depending on the length and nature of the linker sequences between the zinc finger motifs in a multi-finger binding domain.

In particular embodiments, ZNFs contemplated herein comprise, a zinc finger DNA binding domain comprising two, three, four, five, six, seven or eight or more zinc finger motifs, and an endonuclease domain or half-domain from at least one Type-IIS restriction enzyme and one or more TALE DNA-binding domains contemplated elsewhere herein.

In particular embodiments, ZNFs contemplated herein comprise, a zinc finger DNA binding domain comprising three, four, five, six, seven or eight or more zinc finger motifs, and an endonuclease domain or half-domain from at least one Type-IIS restriction enzyme selected from the group consisting of: Aar I, Ace III, Aci I, Alo I, Alw26 I, Bae I, Bbr7 I, Bbv I, Bbv II, BbvC I, Bcc I, Bce83 I, BceA I, Bcef I, Bcg I, BciV I, Bfi I, Bin I, Bmg I, Bpu10 I, BsaX I, Bsb I, BscA I, BscG I, BseR I, BseY I, Bsi I, Bsm I, BsmA I, BsmF I, Bsp24 I, BspG I, BspM I, BspNC I, Bsr I, BsrB I, BsrD I, BstF5 I, Btr I, Bts I, Cdi I, CjeP I, Drd II, EarI, Eci I, Eco31 I, Eco57 I, Eco57M I, Esp3 I, Fau I, Fin I, Fok I, Gdi II, Gsu I, Hga I, Hin4 II, Hph I, Ksp632 I, Mbo II, Mly I, Mme I, Mnl I, Pfl1108, I Ple I, Ppi I Psr I, RleA I, Sap I, SfaN I, Sim I, SspD5 I, Sth132 I, Sts I, TspDT I, TspGW I, Tth111 II, UbaP I, Bsa I, and BsmB I.

In particular embodiments, ZNFs contemplated herein comprise, a zinc finger DNA binding domain comprising three, four, five, six, seven or eight or more zinc finger motifs, and an endonuclease domain or half-domain from the Fok I Type-IIS restriction endonuclease.

In one embodiment, a ZFN contemplated herein comprises a zinc finger DNA binding domain and an endonuclease half-domain from at least one Type-IIS restriction endonuclease to enhance cleavage specificity, optionally wherein the endonuclease half-domain comprises one or more amino acid substitutions or modifications that minimize or prevent homodimerization.

5. CRISPR/Cas Nuclease System

In various embodiments, a CRISPR (Clustered Regularly Interspaced Short Palindromic Repeats)/Cas (CRISPR Associated) nuclease system is introduced into a cell and engineered to bind to, and to introduce single-stranded nicks or double-strand breaks (DSBs) at a target site in a human γ-globin gene, e.g., a polynucleotide sequence as set forth in any one of SEQ ID NOs: 1-9. The CRISPR/Cas nuclease system is an engineered nuclease system based on a bacterial system that can be used for mammalian genome engineering. See, e.g., Jinek et al. (2012) *Science* 337:816-821; Cong et al. (2013) *Science* 339:819-823; Mali et al. (2013) *Science* 339:823-826; Qi et al. (2013) *Cell* 152:1173-1183; Jinek et al. (2013), *eLife* 2:e00471; David Segal (2013) *eLife* 2:e00563; Ran et al. (2013) *Nature Protocols* 8(11):2281-2308; Zetsche et al. (2015) *Cell* 163(3):759-771, each of which is incorporated herein by reference in its entirety.

In one embodiment, the CRISPR/Cas nuclease system comprises Cas nuclease and one or more RNAs that recruit the Cas nuclease to the target site, e.g., a transactivating cRNA (tracrRNA) and a CRISPR RNA (crRNA), or a single guide RNA (sgRNA). crRNA and tracrRNA can engineered into one polynucleotide sequence referred to herein as a "single guide RNA" or "sgRNA."

In one embodiment, the Cas nuclease is engineered as a double-stranded DNA endonuclease or a nickase or catalytically dead Cas, and forms a target complex with a crRNA and a tracrRNA, or sgRNA, for site specific DNA recognition and site-specific cleavage of the protospacer target sequence located within one or more target sites in a human γ-globin gene, e.g., a polynucleotide sequence as set forth in any one of SEQ ID NOs: 1-9. The protospacer motif abuts a short protospacer adjacent motif (PAM), which plays a role in recruiting a Cas/RNA complex. Cas polypeptides recognize PAM motifs specific to the Cas polypeptide. Accordingly, the CRISPR/Cas system can be used to target and cleave either or both strands of a double-stranded polynucleotide sequence flanked by particular 3' PAM sequences specific to a particular Cas polypeptide. PAMs may be identified using bioinformatics or using experimental approaches. Esvelt et al., 2013, *Nature Methods*. 10(11): 1116-1121, which is hereby incorporated by reference in its entirety.

In one embodiment, the Cas nuclease comprises one or more heterologous DNA binding domains, e.g., a TALE DNA binding domain or zinc finger DNA binding domain. Fusion of the Cas nuclease to TALE or zinc finger DNA binding domains increases the DNA cleavage efficiency and specificity. In a particular embodiment, a Cas nuclease optionally comprises one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity. In particular embodiments, a Cas nuclease can be introduced into a T cell with an end-processing enzyme that exhibits 5-3' exonuclease, 5-3' alkaline exonuclease, 3-5'exonuclease (e.g., Trex2), 5' flap endonuclease, helicase or template-independent DNA polymerases activity. The Cas nuclease and 3' processing enzyme may be introduced separately, e.g., in different vectors or separate mRNAs, or together, e.g., as a fusion protein, or in a polycistronic construct separated by a viral self-cleaving peptide or an IRES element.

In various embodiments, the Cas nuclease is Cas9 or Cpf1.

Illustrative examples of Cas9 polypeptides suitable for use in particular embodiments contemplated in particular embodiments may be obtained from bacterial species including, but not limited to: *Enterococcus faecium, Enterococcus italicus, Listeria innocua, Listeria monocytogenes, Listeria seeligeri, Listeria ivanovii, Streptococcus agalactiae, Streptococcus anginosus, Streptococcus bovis, Streptococcus dysgalactiae, Streptococcus equinus, Streptococcus gallolyticus, Streptococcus macacae, Streptococcus mutans, Streptococcus pseudoporcinus, Streptococcus pyogenes, Streptococcus thermophilus, Streptococcus gordonii, Streptococcus infantarius, Streptococcus macedonicus, Streptococcus mitis, Streptococcus pasteurianus, Streptococcus suis, Streptococcus vestibularis, Streptococcus sanguinis, Streptococcus downei, Neisseria bacilliformis, Neisseria cinerea, Neisseria flavescens, Neisseria lactamica, Neisseria meningitidis, Neisseria subflava, Lactobacillus brevis, Lactobacillus buchneri, Lactobacillus casei, Lactobacillus paracasei, Lactobacillus fermentum, Lactobacillus gasseri, Lactobacillus jensenii, Lactobacillus johnsonii, Lactobacillus rhamnosus, Lactobacillus ruminis, Lactobacillus salivarius, Lactobacillus sanfranciscensis, Corynebacterium accolens, Corynebacterium diphtheriae, Corynebacterium matruchotii, Campylobacter jejuni, Clostridium perfringens, Treponema vincentii, Treponema phagedenis,* and *Treponema denticola.*

Illustrative examples of Cpf1 polypeptides suitable for use in particular embodiments contemplated in particular embodiments may be obtained from bacterial species including, but not limited to: *Francisella* spp., *Acidaminococcus* spp., *Prevotella* spp., *Lachnospiraceae* spp., among others.

Conserved regions of Cas9 orthologs include a central HNH endonuclease domain and a split RuvC/RNase H domain. Cpf1 orthologs possess a RuvC/RNase H domain but no discernable HNH domain. The HNH and RuvC-like domains are each responsible for cleaving one strand of the double-stranded DNA target sequence. The HNH domain of the Cas9 nuclease polypeptide cleaves the DNA strand complementary to the tracrRNA:crRNA or sgRNA. The RuvC-like domain of the Cas9 nuclease cleaves the DNA strand that is not-complementary to the tracrRNA:crRNA or sgRNA. Cpf1 is predicted to act as a dimer wherein each RuvC-like domain of Cpf1 cleaves either the complementary or non-complementary strand of the target site. In particular embodiments, a Cas9 nuclease variant (e.g., Cas9 nickase) is contemplated comprising one or more amino acids additions, deletions, mutations, or substitutions in the HNH or RuvC-like endonuclease domains that decreases or eliminates the nuclease activity of the variant domain.

Illustrative examples of Cas9 HNH mutations that decrease or eliminate the nuclease activity in the domain include, but are not limited to: *S. pyogenes* (D10A); *S. thermophilus* (D9A); *T. denticola* (D13A); and *N. meningitidis* (D16A).

Illustrative examples of Cas9 RuvC-like domain mutations that decrease or eliminate the nuclease activity in the domain include, but are not limited to: *S. pyogenes* (D839A, H840A, or N863A); *S. thermophilus* (D598A, H599A, or N622A); *T. denticola* (D878A, H879A, or N902A); and *N. meningitidis* (D587A, H588A, or N611A).

6. End-Processing Enzymes

Genome editing compositions and methods contemplated in particular embodiments comprise editing cellular genomes using a nuclease variant and an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a homing endonuclease variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antarctic Phosphatase, Alkaline Phosphatase, Poly nucleotide Kinase (PNK), ApeI, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a homing endonuclease variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, *E. coli* ExoI, hTREX2, mouse TREX2, rat TREX2, hTREX1, mouse TREX1, rat TREX1, and Rat TREX1.

In particular embodiments, the DNA end-processing enzyme is a 3' or 5' exonuclease, preferably Trex 1 or Trex2, more preferably Trex2, and even more preferably human or mouse Trex2.

D. Target Sites

The engineered nucleases contemplated herein are designed to bind to any suitable target sequence and can have a novel binding specificity, compared to a naturally-occurring nuclease. In particular embodiments, the target site is a regulatory region of a γ-globin gene including, but not limited to transcription factor binding sites. In particular embodiments, the nuclease target site is in a polynucleotide sequence that when deleted or disrupted is associated with HPFH, e.g., at position −120 to −102 relative to the transcriptional start site of a γ-globin gene; preferably the nuclease target site is at, or disrupts or deletes, a 13 bp polynucleotide sequence in a γ-globin gene associated with HPFH (SEQ ID NO: 3); more preferably the nuclease target site is at, or disrupts or deletes, a CCAAT polynucleotide sequence at position −115 to −111 (relative to the transcriptional start site) of the promoter of the HBG1 gene; and even more preferably the nuclease target site is at, or disrupts or deletes, a CAAT polynucleotide sequence at position −114 to −111 (relative to the transcriptional start site) of the HBG1 gene.

In particular embodiments, the nuclease target site is in, or near, the region of Chr11: 5249957-5249977.

In particular embodiments, the nuclease target site is in, or near, the polynucleotide sequence of any one of SEQ ID NOs: 1-6 in the region of Chr11: 5249957-5249977.

In particular embodiments, the nuclease target site is in, or near, the region of Chr11: 5249959-5249971 (in the HBG1 gene).

In particular embodiments, the engineered nucleases introduce a DSB in, near, or flanking the 5' and/or 3' sequences of a 13 bp polynucleotide sequence in a γ-globin gene associated with HPFH (SEQ ID NO: 3), so that in the event that a DNA donor repair template is not inserted into the target site, the target site will still be disrupted by NHEJ in the absence of a DNA donor repair template, and thus, either HDR or NHEJ events at the target site will lead to derepression of γ-globin gene expression and/or therapeutic globin expression (either endogenous γ-globin expression or heterologous expression of another therapeutic globin, including but not limited to, γ-globin, β-globin, or an anti-sickling form of β-globin.

In a preferred embodiment, an engineered nuclease cleaves double-stranded DNA and introduces a DSB into the polynucleotide sequence set forth in any one of SEQ ID NOs: 1-9, more preferably, in the human HBG1 and/or HBG2 gene.

E. Donor Repair Templates

In preferred embodiments, one or more engineered nucleases are used to introduce a DSB in a target sequence in the presence of a donor repair template. The donor repair template may comprise single-stranded or double-stranded DNA or RNA. In the presence of a donor repair template the DSB may be repaired through homology directed repair (HDR) mechanisms.

In particular embodiments, a donor repair template comprises a pair of homology arms, a selection cassette and an erythroid expression control sequence. In preferred embodiments, the donor repair template is inserted into a γ-globin gene and the erythroid expression control sequence is positioned such that it is operably linked to the endogenous polynucleotide sequence encoding a γ-globin.

In particular embodiments, a donor repair template comprises a pair of homology arms, a polynucleotide encoding a therapeutic globin and one or more post-transcriptional control elements; and a selection cassette. In preferred embodiments, the donor repair template is inserted into a γ-globin gene at a site that derepresses the γ-globin promoter, thereby operably linking a derepressed γ-globin promoter to the polynucleotide encoding a therapeutic globin. In other preferred embodiments, the 5' homology arm encodes a deletion in a site that derepresses the γ-globin promoter thereby operably linking a derepressed γ-globin promoter to the polynucleotide encoding a therapeutic globin.

A "pair of homology arms" refers to a group of two homology arms. In particular embodiments a pair of homology arms comprises a 5' homology arm and a 3' homology arm. A "5' homology arm" refers to a polynucleotide sequence that is identical, or nearly identical, or homologous to a DNA sequence 5' of a target site (e.g., double strand break site). A "3' homology arm" refers to a polynucleotide sequence that is identical, or nearly identical, or homologous to a DNA sequence 3' of the target site. In particular embodiments, a pair of homology arms comprises a homology arm comprising a polynucleotide sequence that includes a target site for a double strand break with a mutation in the target site to minimize recleavage of the target site. In particular preferred embodiments, the 5' homology arm comprises a polynucleotide sequence within 1 kb upstream of a γ-globin transcriptional start site (SEQ ID NO: 9). In more particular preferred embodiments, the 5' homology arm comprises a polynucleotide sequence within 1 kb upstream of a γ-globin transcriptional start site and further comprises a deletion of, or lacks the polynucleotide sequence set forth in any one of SEQ ID NOs: 1-6.

In some embodiments, where the donor repair template is designed to derepress a γ-globin promoter and operably link the derepressed promoter to a polynucleotide encoding a therapeutic globin, the 5' homology arm comprises a polynucleotide sequence within 1 kb upstream of a γ-globin transcriptional start site and further comprises a deletion of, or lacks the polynucleotide sequence set forth in any one of SEQ ID NOs: 1-6 and the 3' homology arm comprises a sequence downstream of the 5' homology arm. In some embodiments, the donor repair template disrupts endogenous γ-globin gene expression, optionally through deletion of genomic sequence encoding γ-globin.

In some embodiments, where the donor repair template is designed to operably link a β-globin LCR responsive expression control sequence to an endogenous genomic sequence encoding a γ-globin, the 5' homology arm comprises a polynucleotide sequence within 1 kb upstream of a γ-globin transcriptional start site and may further comprise a deletion of, or lack the polynucleotide sequence set forth in any one of SEQ ID NOs: 1-6 and the 3' homology arm comprises a sequence downstream of the 5' homology arm, but upstream of a γ-globin gene transcription start site.

In particular embodiments, either one of, or both, homology arms in a pair of homology arms is independently located about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, from the target site, including all intervening distances from the target site.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 600 bp, about 100 bp to about 500 bp, about 100 bp to about 400 bp, about 100 bp to about 300 bp, about 100 bp to about 200 bp, about 200 bp to about 600 bp, about 200 bp to about 500 bp, about 200 bp to about 400 bp, about 200 bp to about 300 bp, about 300 bp to about 600 bp, about 300 bp to about 500 bp, about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of any 5' and 3' homology arms present in a DNA donor repair template are independently selected from about 100 bp, about 200 bp, about 300 bp, about 400 bp, about 500 bp, or about 600 bp. In one embodiment, a 5'homology arm is about 300 bp and a 3' homology arm is about 300 bp.

Donor repair templates contemplated herein comprise a selection cassette. As used herein, the term "selection cassette" refers to an expression cassette that comprises one or more expression control sequences operably linked to a polynucleotide sequence encoding a selectable marker and one or more post-transcriptional elements or a ribosomal skipping polypeptide.

Illustrative examples of expression control sequences suitable for use in selection cassettes contemplated herein include but are not limited to: a constitutive promoter, a conditional promoter, or hematopoietic stem cell promoter. As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) promoter, a Moloney murine leukemia virus (MoMLV) LTR promoter, a Rous sarcoma virus (RSV) LTR promoter, a herpes simplex virus (HSV) (thymidine kinase) promoter, a H5, P7.5, or P11 vaccinia virus promoter, a short elongation factor 1-alpha (EF1a-short) promoter, a long elongation factor 1-alpha (EF1a-long) promoter, an early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90BT) promoter, a heat shock protein 70 kDa (HSP70) promoter, a β-kinesin (β-KIN) promoter, a human ROSA 26 promoter, a Ubiquitin C promoter (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., *J Virol*. 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

Illustrative examples of tissue specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fins-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-β) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), an interferon beta (IFN-β) promoter (hematopoietic cell expression), an α-spectrin promoter (erythroid cell expression), a β-spectrin promoter (erythroid cell expression), a β-globin LCR (erythroid cell expression), a γ-globin promoter (erythroid cell expression), a β-globin promoter (erythroid cell expression), an α-globin HS40 enhancer (erythroid cell expression), an ankyrin-1 promoter (erythroid cell expression), and a Wiskott-Aldrich syndrome protein (WASP) promoter (hematopoietic cell expression).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

In particular embodiments, a selection cassette comprises an EF1α promoter or an MND promoter operably linked to a polynucleotide encoding a selectable marker.

Illustrative examples of selectable markers suitable for use in selection cassettes contemplated herein include, but are not limited to: hygromycin-B phosphotransferase (HPH) which may be positively selected for with hygromycin B; amino 3'-glycosyl phosphotransferase (NEO), which may be positively selected for with G418; dihydrofolate reductase (DHFR), which may be positively selected for with methotrexate; adenosine deaminase (ADA), which may be positively selected for with 2'-deoxycoformycin; multi-drug resistance protein (MDR), which may be positively selected for by anti-cancer drugs including, but not limited to vinca alkaloids, taxanes, anthracyclines, epipodophyllotoxins, colchicine, doxorubicin, and actinomycin D; $O^6$-methylguanine-DNA-methyltransferase (MGMT), which may be selected for by $O^6$-benzylguanine/1,3-bis(2-chloroethyl)-1-nitrosourea (BG/BCNU); Sh ble (BLE), which may be positively selected for with bleocin or zeocin; and blasticidin-S deaminase (BSR), which may be positively selected for with blastocidin.

In particular embodiments, a selection cassette comprises a ubiquitous promoter operably linked to a polynucleotide encoding MGMT.

Illustrative examples of post-transcriptional control sequences for use in selection cassettes include, but are not limited to: woodchuck hepatitis virus post-transcriptional response element (WPRE) or variant thereof, a hepatitis B virus post-transcriptional response element (HPRE) or variant thereof, and a polyadenylation sequence.

As used herein, the terms "post-transcriptional control sequences," "posttranscriptional regulatory element" or "PRE" refer to a cis-acting element that regulates expression at the mRNA level by, for example, regulating capping, splicing, poly(A) tail addition, and mRNA stability. Illustrative examples of PTE include, but are not limited to, woodchuck hepatitis virus posttranscriptional regulatory element (WPRE; Zufferey et al., 1999, J. Virol., 73:2886); the posttranscriptional regulatory element present in hepatitis B virus (HPRE) (Huang and Yen, 1995, Mol. Cell. Biol., 5:3864); and the like (Liu et al., 1995, Genes Dev., 9:1766).

The term "poly(A) site" or "poly(A) sequence" as used herein denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is a synthetic poly(A) sequence (e.g., AATAAA, ATTAAA, AGTAAA). Illustrative examples of poly(A) sequences include, but are not limited to an SV40 poly(A) sequence, a bovine growth hormone poly(A) sequence (BGHpA), a rabbit β-globin poly(A) sequence (rβgpA), or another suitable heterologous or endogenous poly(A) sequence known in the art.

In particular embodiments, the polynucleotide encoding the selectable marker is fused to a polynucleotide encoding a viral self-cleaving peptide or ribosomal skipping sequence.

Illustrative examples of ribosomal skipping sequences include, but are not limited to: a 2A or 2A-like site, sequence or domain (Donnelly et al., 2001. J. Gen. Virol. 82:1027-

1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a *Thosea asigna* virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 1.

TABLE 1

Exemplary 2A sites include the following sequences:

| | |
|---|---|
| SEQ ID NO: 60 | LLNFDLLKLAGDVESNPGP |
| SEQ ID NO: 61 | TLNFDLLKLAGDVESNPGP |
| SEQ ID NO: 62 | LLKLAGDVESNPGP |
| SEQ ID NO: 63 | NFDLLKLAGDVESNPGP |
| SEQ ID NO: 64 | QLLNFDLLKLAGDVESNPGP |
| SEQ ID NO: 65 | APVKQTLNFDLLKLAGDVESNPGP |
| SEQ ID NO: 66 | VTELLYRMKRAETYCPRPLLAIHPTEARHKQKIVAPVKQT |
| SEQ ID NO: 67 | LNFDLLKLAGDVESNPGP |
| SEQ ID NO: 68 | LLAIHPTEARHKQKIVAPVKQTLNFDLLKLAGDVESNPGP |
| SEQ ID NO: 69 | EARHKQKIVAPVKQTLNFDLLKLAGDVESNPGP |

In some embodiments, where the donor repair template is designed to derepress a γ-globin promoter and operably link the derepressed promoter to a polynucleotide encoding a therapeutic globin.

The term "globin" as used herein refers to proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. The term excludes hemocyanins. Examples of globins include α-globin or variant thereof, β-globin or variant thereof, a γ-globin or a variant thereof, and δ-globin or a variant thereof.

In particular embodiments, the therapeutic globin or antisickling variant thereof includes, but is not limited to: β-globin, δ-globin, γ-globin, β-globinA-T87Q, β-globinA-T87Q/K120E/K95E, or β-globinA-T87Q/G16D/E22A.

In some embodiments, the expression of the therapeutic globin is enhanced or improved by including one or more post-transcriptional elements and/or erythroid enhancers.

Illustrative examples of post-transcriptional elements and/or erythroid enhancers suitable for use in particular embodiments of donor repair templates contemplated herein include, but are not limited to: post-transcription regulatory elements are selected from the group consisting of: a woodchuck hepatitis virus post-transcriptional response element (WPRE) or variant thereof, a hepatitis B virus post-transcriptional response element (HPRE) or variant thereof, and a polyadenylation sequence and an erythroid enhancer selected from the group consisting of: an HPFH-2 enhancer, an HS40 enhancer, and a β-globin gene 3' enhancer.

In particular embodiments, a donor repair template is designed to operably link an erythroid expression control sequence to an endogenous genomic sequence encoding a γ-globin.

Illustrative examples of erythroid expression control sequences include, but are not limited to: a human β-globin LCR responsive promoter, an ankyrin gene promoter, an α-spectrin gene promoter, a β-spectrin gene promoter, or a β-globin gene promoter, optionally in combination with an HPFH-2 enhancer, an HS40 enhancer, and a β-globin gene 3' enhancer.

In particular embodiments, a donor repair template is inserted into a γ-globin locus to both derepress a γ-globin promoter to enable erythroid expression of a therapeutic globin and to select for genetically modified cells comprising the donor repair template. Derepression of the γ-globin promoter may occur through selection of the nuclease target sites or through engineering a deletion into one of the homology arms of the donor repair template. In particular embodiments, it is advantageous to engineer the nuclease to cleave at a transcription factor binding site associated with repression of a γ-globin gene, that way, derepression can occur by HDR; or in absence of HDR, the repressive site can still be disrupted by NHEJ, which also leads to derepression of the γ-globin gene. In preferred embodiments, the nuclease target site is designed to delete or disrupt a polynucleotide sequence associated with HPFH, e.g., at position −120 to −102 relative to the transcriptional start site of a γ-globin gene (see SEQ ID NOs: 1-6); preferably, a 13 bp polynucleotide sequence in a γ-globin gene associated with HPFH (SEQ ID NO: 3); more preferably a CCAAT polynucleotide sequence at position −115 to −111 (relative to the transcriptional start site of a γ-globin gene); and even more preferably the nuclease target site is at, or disrupts or deletes, a CAAT polynucleotide sequence at position −114 to −111 (relative to the transcriptional start site) of the HBG1 gene. In some embodiments, the donor repair template is also designed to disrupt endogenous γ-globin expression in favor of expressing the therapeutic globin of the donor repair template.

In other particular embodiments, a donor repair template is inserted into a γ-globin locus to derepress a γ-globin promoter, to enable selection of genetically modified cells comprising the template, and to enable erythroid expression of endogenous γ-globin. Derepression of the γ-globin promoter may occur through selection of the nuclease target sites or through engineering a deletion into one of the homology arms of the donor repair template. In particular embodiments, it is advantageous to engineer the nuclease to cleave at a transcription factor binding site associated with repression of a γ-globin gene, that way, γ-globin expression can occur by through HDR; or through NHEJ and derepression of the γ-globin gene. In preferred embodiments, the nuclease target site is designed to delete or disrupt a polynucleotide sequence associated with HPFH, e.g., at position −120 to −102 relative to the transcriptional start site of a γ-globin gene (see SEQ ID NOs: 1-6); preferably, a 13 bp polynucleotide sequence in a γ-globin gene associated with HPFH (SEQ ID NO: 3); more preferably a CCAAT polynucleotide sequence at position −115 to −111 (relative to the transcriptional start site of a γ-globin gene); and even more preferably the nuclease target site is at, or disrupts or deletes, a CAAT polynucleotide sequence at position −114 to −111 (relative to the transcriptional start site) of the HBG1 gene.

In various embodiments, an engineered nuclease is introduced into a hematopoietic cell, e.g., a hematopoietic stem or progenitor cell, or CD34+ cell, using non-viral or viral based methods and a donor repair template is introduced into a hematopoietic cell using viral methods by transducing the cell with an adeno-associated virus (AAV), retrovirus, e.g., lentivirus, IDLV, etc., herpes simplex virus, adenovirus, or vaccinia virus vector comprising the donor repair template.

In particular embodiments, delivery of one or more polynucleotides encoding nucleases and/or donor repair templates may be provided by the same method or by different methods, and/or by the same vector or by different vectors.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) Gene Therapy. 10:180-187; and Balazs et al. (2011) Journal of Drug Delivery. 2011:1-12. Antibody-targeted, bacterially derived, non-living nanocell-based delivery is also contemplated in particular embodiments.

Illustrative examples of viral vector systems suitable for use in particular embodiments contemplated herein include, but are not limited to adeno-associated virus (AAV), retrovirus, herpes simplex virus, adenovirus, and vaccinia virus vectors.

In various embodiments, one or more polynucleotides encoding a nuclease variant and/or donor repair template are introduced into a hematopoietic cell, e.g., a hematopoietic stem or progenitor cell, or CD34+ cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding a nuclease variant and/or donor repair template are introduced into a hematopoietic cell, e.g., a hematopoietic stem or progenitor cell, or CD34+ cell, by transducing the cell with a retrovirus, e.g., lentivirus, comprising the one or more polynucleotides. In one embodiment, a nuclease variant and/or donor repair template are introduced into a hematopoietic cell, e.g., a hematopoietic stem or progenitor cell, or CD34+ cell, by transducing the cell with an integrase deficient lentivirus.

As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D116I, D116A, E152G, or E152A mutation; D64V, D116I, and E152G mutations; or D64V, D116A, and E152A mutations.

In one embodiment, the HIV-1 integrase deficient pol gene comprises a D64V mutation.

F. Genome Edited Cells

The genome edited cells manufactured by the methods contemplated in particular embodiments provide improved cell-based therapeutics for the treatment of hemoglobinopathies. Without wishing to be bound to any particular theory, it is believed that the compositions and methods contemplated herein enable therapeutic globin expression and more robust selection of genome edited cells that may be used to treat, and in some embodiments potentially cure, hemoglobinopathies.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

Illustrative examples of cell types whose genome can be edited using the compositions and methods contemplated herein include, but are not limited to, cell lines, primary cells, stem cells, progenitor cells, and differentiated cells.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells. "Proliferation" or "expansion" of cells refers to symmetrically dividing cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

In particular embodiments, the cell is a primary cell. The term "primary cell" as used herein is known in the art to refer to a cell that has been isolated from a tissue and has been established for growth in vitro or ex vivo. Corresponding cells have undergone very few, if any, population doublings and are therefore more representative of the main functional component of the tissue from which they are derived in comparison to continuous cell lines, thus representing a more representative model to the in vivo state. Methods to obtain samples from various tissues and methods to establish primary cell lines are well-known in the art (see, e.g., Jones and Wise, Methods Mol Biol. 1997). Primary cells for use in the methods contemplated herein are derived from umbilical cord blood, placental blood, mobilized peripheral blood and bone marrow. In one embodiment, the primary cell is a hematopoietic stem or progenitor cell.

In one embodiment, the genome edited cell is an embryonic stem cell.

In one embodiment, the genome edited cell is an adult stem or progenitor cell.

In one embodiment, the genome edited cell is primary cell.

In a preferred embodiment, the genome edited cell is a hematopoietic cell, e.g., hematopoietic stem cell, hematopoietic progenitor cell, an erythroid cell, or cell population comprising hematopoietic cells.

As used herein, the term "population of cells" refers to a plurality of cells that may be made up of any number and/or combination of homogenous or heterogeneous cell types, as described elsewhere herein. For example, for transduction of hematopoietic stem or progenitor cells, a population of cells may be isolated or obtained from umbilical cord blood, placental blood, bone marrow, or mobilized peripheral blood. A population of cells may comprise about 10%, about 20%, about 30%, about 40%, about 50%, about 60%, about 70%, about 80%, about 90%, or about 100% of the target cell type to be edited. In certain embodiments, hematopoietic stem or progenitor cells may be isolated or purified from a population of heterogeneous cells using methods known in the art.

Illustrative sources to obtain hematopoietic cells include, but are not limited to: cord blood, bone marrow or mobilized peripheral blood.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Additional illustrative examples of hematopoietic stem or progenitor cells suitable for use with the methods and compositions contemplated herein include hematopoietic cells that are $CD34^+CD38^{Lo}CD90^+CD45^{RA-}$, hematopoietic cells that are $CD34^+$, $CD59^+$, Thy1/$CD90^+$, $CD38^{Lo/-}$, C-kit/$CD117^+$, and $Lin^{(-)}$, and hematopoietic cells that are $CD133^+$.

Various methods exist to characterize hematopoietic hierarchy. One method of characterization is the SLAM code. The SLAM (Signaling lymphocyte activation molecule) family is a group of >10 molecules whose genes are located mostly tandemly in a single locus on chromosome 1 (mouse), all belonging to a subset of immunoglobulin gene superfamily, and originally thought to be involved in T-cell stimulation. This family includes CD48, CD150, CD244, etc., CD150 being the founding member, and, thus, also called slamF1, i.e., SLAM family member 1. The signature SLAM code for the hematopoietic hierarchy is hematopoietic stem cells (HSC)—$CD150^+CD48^-CD244^-$; multipotent progenitor cells (MPPs)—$CD150^-CD48^-CD244^+$; lineage-restricted progenitor cells (LRPs)—$CD150^-CD48^+CD244^+$; common myeloid progenitor (CMP)—$lin^-SCA\text{-}1\text{-}c\text{-}kit^+CD34^+CD16/32^{mid}$; granulocyte-macrophage progenitor (GMP)—$lin^-SCA\text{-}1\text{-}c\text{-}kit^+CD34^+CD16/32^{hi}$; and megakaryocyte-erythroid progenitor (MEP)—$lin^-SCA\text{-}1\text{-}c\text{-}kit^+CD34^-CD16/32^{low}$.

Preferred target cell types edited with the compositions and methods contemplated herein include, hematopoietic cells, preferably human hematopoietic cells, more preferably human hematopoietic stem and progenitor cells, and even more preferably $CD34^+$ human hematopoietic stem cells. The term "CD34+ cell," as used herein refers to a cell expressing the CD34 protein on its cell surface. "CD34," as used herein refers to a cell surface glycoprotein (e.g., sialomucin protein) that often acts as a cell-cell adhesion factor. CD34+ is a cell surface marker of both hematopoietic stem and progenitor cells.

In one embodiment, the genome edited hematopoietic cells are $CD150^+CD48^-$ $CD244^-$ cells.

In one embodiment, the genome edited hematopoietic cells are $CD34^+CD133^+$ cells.

In one embodiment, the genome edited hematopoietic cells are CD133+ cells.

In one embodiment, the genome edited hematopoietic cells are CD34+ cells.

In particular embodiments, a population of hematopoietic cells comprising hematopoietic stem and progenitor cells (HSPCs) comprises an edited γ-globin gene, wherein the edit is a DSB preferably repaired by HDR in the presence of a donor repair template that derepresses the γ-globin promoter, and enables therapeutic globin expression and cell selection, but where a DSB repaired by NHEJ may also be advantageous in derepressing the γ-globin promoter in certain embodiments.

In particular embodiments, the genome edited cells comprise erythroid cells.

In particular embodiments, the genome edited cells comprise one or more mutations in a β-globin gene. In one embodiment, the β-globin alleles of the subject are selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, the genome edited cells comprise one or more one or more mutations in a β-globin gene that result in a thalassemia. In one embodiment, the thalassemia is an α-thalassemia. In one embodiment, the thalassemia is a β-thalassemia. In one embodiment, the β-globin alleles of the subject are selected from the group consisting of: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, the genome edited cells comprise one or more one or more mutations in a β-globin gene that result in sickle cell disease. In one embodiment, the β-globin alleles of the subject are selected from the group consisting of: $\beta^E/\beta^S$, $\beta^0/\beta^S$, $\beta^C/\beta^S$, $\beta^+/\beta^S$ or $\beta^S/\beta^S$.

G. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in a human γ-globin gene in a cell or a population of cells. In preferred embodiments, the cell is a hematopoietic cell, e.g., a hematopoietic stem or progenitor cell, or a CD34+ cell.

In particular embodiments, the compositions contemplated herein comprise a population of cells, an engineered nuclease, and a donor repair template. In particular embodiments, the compositions contemplated herein comprise a population of cells, an engineered nuclease, an end-processing enzyme, and a donor repair template.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified hematopoietic stem and/or progenitor cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g. pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited hematopoietic stem and/or progenitor cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited cells, e.g., hematopoietic stem and progenitor cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions include, but are not limited to QBSF-60 (Quality Biological, Inc.), StemPro-34 (Life Technologies), and X-VIVO 10.

In a preferred embodiment, the compositions comprising genome edited hematopoietic stem and/or progenitor cells are formulated in PlasmaLyte.

In various embodiments, compositions comprising hematopoietic stem and/or progenitor cells are formulated in a cryopreservation medium. For example, cryopreservation media with cryopreservation agents may be used to maintain a high cell viability outcome post-thaw. Illustrative examples of cryopreservation media used in particular compositions include, but are not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of mycoplasma, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contains about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intraarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22$^{nd}$ Edition. Edited by Loyd V. Allen Jr. Philadelphia, PA: Pharmaceutical Press; 2012, which is incorporated by reference herein, in its entirety.

H. Genome Edited Cell Therapies

The genome edited cells manufactured by the methods contemplated in particular embodiments provide improved drug products for use in the prevention, treatment, and amelioration of a hemoglobinopathy or for preventing, treating, or ameliorating at least one symptom associated with a hemoglobinopathy or a subject having a hemoglobinopathic mutation in a β-globin gene. As used herein, the term "drug product" refers to genetically modified cells produced using the compositions and methods contemplated herein. In particular embodiments, the drug product comprises genetically modified hematopoietic stem or progenitor cells, e.g., CD34⁻ cells. The genetically modified hematopoietic stem or progenitor cells can be selected through positive selection in vitro, ex vivo or in vivo and give rise to adult erythroid cells with increased γ-globin gene expression and allow treatment of subjects having no or minimal expression of the γ-globin gene in vivo, thereby significantly expanding the opportunity to bring genome edited cell therapies to subjects for which this type of treatment was not previously a viable treatment option.

In particular embodiments, genome edited hematopoietic stem or progenitor cells comprise a selection cassette and a mechanism to express a therapeutic globin through derepression of a γ-globin promoter or through operably linking an erythroid expression control sequence to an endogenous γ-globin coding sequence. The genetically modified cells may be positively selected for a selectable marker in a donor repair template through in vitro or ex vivo culture with the appropriate drug, or though in vivo selection by administration of the drug to a subject that has been administered a population of cells comprising the genetically modified cells that comprise the donor repair template. Drug-based selection, including dose and dosing schedule may be determined using methods known in the art.

In particular embodiments, genome edited hematopoietic stem or progenitor cells provide a curative, preventative, or ameliorative therapy to a subject diagnosed with or that is suspected of having a hemoglobinopathy.

As used herein, "hematopoiesis," refers to the formation and development of blood cells from progenitor cells, as well as formation of progenitor cells from stem cells. Blood cells include but are not limited to erythrocytes or red blood cells (RBCs), reticulocytes, monocytes, neutrophils, megakaryocytes, eosinophils, basophils, B-cells, macrophages, granulocytes, mast cells, thrombocytes, and leukocytes.

As used herein, the term "hemoglobinopathy" or "hemoglobinopathic condition" refers to a diverse group of inherited blood disorders that involve the presence of abnormal hemoglobin molecules resulting from alterations in the structure and/or synthesis of hemoglobin. Normally, hemoglobin consists of four protein subunits: two subunits of β-globin and two subunits of α-globin. Each of these protein subunits is attached (bound) to an iron-containing molecule called heme; each heme contains an iron molecule in its center that can bind to one oxygen molecule. Hemoglobin within red blood cells binds to oxygen molecules in the lungs. These cells then travel through the bloodstream and deliver oxygen to tissues throughout the body.

Hemoglobin A (HbA) is the designation for the normal hemoglobin that exists after birth. Hemoglobin A is a tetramer with two alpha chains and two beta chains ($\alpha_2\beta_2$). Hemoglobin A2 is a minor component of the hemoglobin found in red cells after birth and consists of two alpha chains and two delta chains ($\alpha_2\delta_2$). Hemoglobin A2 generally comprises less than 3% of the total red cell hemoglobin. Hemoglobin F (HbF) is the predominant hemoglobin during fetal development. The molecule is a tetramer of two alpha chains and two gamma chains ($\alpha_2\gamma_2$). In preferred embodiments, subjects are administered genome edited hematopoietic stem or progenitor cells that give rise to erythroid cells that have increased γ-globin gene expression and/or decreased hemoglobinopathic β-globin gene expression, thereby increasing the amount of HbF in the subject.

The most common hemoglobinopathies include sickle cell disease, β-thalassemia, and α-thalassemia.

In particular embodiments, the compositions and methods contemplated herein provide genome edited cell therapies for subjects having a sickle cell disease. The term "sickle cell anemia" or "sickle cell disease" is defined herein to include any symptomatic anemic condition which results from sickling of red blood cells. Sickle cell anemia $\beta^S/\beta^S$, a common form of sickle cell disease (SCD), is caused by Hemoglobin S (HbS). HbS is generated by replacement of glutamic acid (E) with valine (V) at position 6 in β-globin, noted as Glu6Val or E6V. Replacing glutamic acid with valine causes the abnormal HbS subunits to stick together and form long, rigid molecules that bend red blood cells into a sickle (crescent) shape. The sickle-shaped cells die prematurely, which can lead to a shortage of red blood cells (anemia). In addition, the sickle-shaped cells are rigid and can block small blood vessels, causing severe pain and organ damage.

Additional mutations in the β-globin gene can also cause other abnormalities in β-globin, leading to other types of sickle cell disease. These abnormal forms of β-globin are often designated by letters of the alphabet or sometimes by a name. In these other types of sickle cell disease, one β-globin subunit is replaced with HbS and the other β-globin subunit is replaced with a different abnormal variant, such as hemoglobin C (HbC; β-globin allele noted as $\beta^C$) or hemoglobin E (HbE; β-globin allele noted as $\beta^E$).

In hemoglobin SC (HbSC) disease, the β-globin subunits are replaced by HbS and HbC. HbC results from a mutation in the β-globin gene and is the predominant hemoglobin found in people with HbC disease ($\alpha_2\beta^C_2$). HbC results when the amino acid lysine replaces the amino acid glutamic acid at position 6 in β-globin, noted as Glu6Lys or E6K. HbC disease is relatively benign, producing a mild hemolytic anemia and splenomegaly. The severity of HbSC disease is variable, but it can be as severe as sickle cell anemia.

HbE is caused when the amino acid glutamic acid is replaced with the amino acid lysine at position 26 in β-globin, noted as Glu26Lys or E26K. People with HbE disease have a mild hemolytic anemia and mild splenomegaly. HbE is extremely common in Southeast Asia and in some areas equals hemoglobin A in frequency. In some cases, the HbE mutation is present with HbS. In these cases, a person may have more severe signs and symptoms associated with sickle cell anemia, such as episodes of pain, anemia, and abnormal spleen function.

Other conditions, known as hemoglobin sickle-β-thalassemias (HbSBetaThal), are caused when mutations that produce hemoglobin S and β-thalassemia occur together. Mutations that combine sickle cell disease with beta-zero ($\beta^0$; gene mutations that prevent β-globin production) thalassemia lead to severe disease, while sickle cell disease combined with beta-plus ($\beta^+$; gene mutations that decrease β-globin production) thalassemia is milder.

As used herein, "thalassemia" refers to a hereditary disorder characterized by defective production of hemoglobin. Examples of thalassemias include α- and β-thalassemia.

In particular embodiments, the compositions and methods contemplated herein provide genome edited cell therapies for subjects having a β-thalassemia. β-thalassemias are caused by a mutation in the β-globin chain, and can occur in a major or minor form. Nearly 400 mutations in the β-globin gene have been found to cause β-thalassemia. Most of the mutations involve a change in a single DNA building block (nucleotide) within or near the β-globin gene. Other mutations insert or delete a small number of nucleotides in the β-globin gene. As noted above, β-globin gene mutations that decrease β-globin production result in a type of the condition called beta-plus (β$^+$) thalassemia. Mutations that prevent cells from producing any beta-globin result in beta-zero (β$^0$) thalassemia. In the major form of β-thalassemia, children are normal at birth, but develop anemia during the first year of life. The minor form of β-thalassemia produces small red blood cells. Thalassemia minor occurs if you receive the defective gene from only one parent. Persons with this form of the disorder are carriers of the disease and usually do not have symptoms.

HbE/β-thalassemia results from combination of HbE and β-thalassemia (β$^E$/β$^0$, β$^E$/β$^+$) and produces a condition more severe than is seen with either HbE trait or β-thalassemia trait. The disorder manifests as a moderately severe thalassemia that falls into the category of thalassemia intermedia. HbE/β-thalassemia is most common in people of Southeast Asian background.

In a preferred embodiment, genome edited cell therapies contemplated herein are used to treat, prevent, or ameliorate a hemoglobinopathy is selected from the group consisting of hemoglobin C disease, hemoglobin E disease, sickle cell anemia, sickle cell disease (SCD), thalassemia, β-thalassemia, thalassemia major, thalassemia intermedia, hemoglobin Bart syndrome and hemoglobin H disease.

In various embodiments, the genome editing compositions are administered by direct injection to a cell, tissue, or organ of a subject in need of gene therapy, in vivo, e.g., bone marrow. In various other embodiments, cells are edited in vitro or ex vivo, and optionally selected and expanded ex vivo. The genome edited cells are then administered to a subject in need of therapy. In certain embodiments, the cells are edited in vitro or ex vivo and selected in vivo after administration to a subject in need of therapy.

Preferred cells for use in the genome editing methods contemplated herein include autologous/autogeneic ("self") cells, preferably hematopoietic cells, more preferably hematopoietic stem or progenitor cell, and even more preferably CD34$^+$ cells.

As used herein, the terms "individual" and "subject" are often used interchangeably and refer to any animal that exhibits a symptom of a hemoglobinopathy that can be treated with the reprogrammed nucleases, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having a hemoglobinopathy.

As used herein, the term "patient" refers to a subject that has been diagnosed with hemoglobinopathy that can be treated with the reprogrammed nucleases, genome editing compositions, gene therapy vectors, genome editing vectors, genome edited cells, and methods contemplated elsewhere herein.

As used herein "treatment" or "treating," includes any beneficial or desirable effect on the symptoms or pathology of a hemoglobinopathy or hemoglobinopathic condition, and may include even minimal reductions in one or more measurable markers of the hemoglobinopathy or hemoglobinopathic condition. Treatment can optionally involve delaying of the progression of the hemoglobinopathy or hemoglobinopathic condition. "Treatment" does not necessarily indicate complete eradication or cure of the hemoglobinopathy or hemoglobinopathic condition, or associated symptoms thereof.

As used herein, "prevent," and similar words such as "prevention," "prevented," "preventing" etc., indicate an approach for preventing, inhibiting, or reducing the likelihood of the occurrence or recurrence of, hemoglobinopathy or hemoglobinopathic condition. It also refers to delaying the onset or recurrence of a hemoglobinopathy or hemoglobinopathic condition or delaying the occurrence or recurrence of the symptoms of hemoglobinopathy or hemoglobinopathic condition. As used herein, "prevention" and similar words also includes reducing the intensity, effect, symptoms and/or burden of a hemoglobinopathy or hemoglobinopathic condition prior to its onset or recurrence.

As used herein, the phrase "ameliorating at least one symptom of" refers to decreasing one or more symptoms of the hemoglobinopathy or hemoglobinopathic condition for which the subject is being treated, e.g., thalassemia, sickle cell disease, etc. In particular embodiments, the hemoglobinopathy or hemoglobinopathic condition being treated is β-thalassemia, wherein the one or more symptoms ameliorated include, but are not limited to, weakness, fatigue, pale appearance, jaundice, facial bone deformities, slow growth, abdominal swelling, dark urine, iron deficiency (in the absence of transfusion), requirement for frequent transfusions. In particular embodiments, the hemoglobinopathy or hemoglobinopathic condition being treated is sickle cell disease (SCD) wherein the one or more symptoms ameliorated include, but are not limited to, anemia; unexplained episodes of pain, such as pain in the abdomen, chest, bones or joints; swelling in the hands or feet; abdominal swelling; fever; frequent infections; pale skin or nail beds; jaundice; delayed growth; vision problems; signs or symptoms of stroke; iron deficiency (in the absence of transfusion), requirement for frequent transfusions.

As used herein, the term "amount" refers to "an amount effective" or "an effective amount" of a nuclease variant, genome editing composition, or genome edited cell sufficient to achieve a beneficial or desired prophylactic or therapeutic result, including clinical results.

A "prophylactically effective amount" refers to an amount of a nuclease variant, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

The genome edited cells may be administered as part of a bone marrow or cord blood transplant in an individual that has or has not undergone bone marrow ablative therapy. In one embodiment, genome edited cells contemplated herein are administered in a bone marrow transplant to an individual that has undergone chemoablative or radioablative bone marrow therapy.

In one embodiment, a dose of genome edited cells is delivered to a subject intravenously. In preferred embodiments, genome edited hematopoietic stem cells are intravenously administered to a subject.

In one illustrative embodiment, the effective amount of genome edited cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of genome edited cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of genome edited cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

Some variation in dosage will necessarily occur depending on the condition of the subject being treated. The person responsible for administration will, in any event, determine the appropriate dose for the individual subject.

In particular embodiments, a genome edited cell therapy is used to treat, prevent, or ameliorate a hemoglobinopathy, or condition associated therewith, comprising administering to subject having a β-globin genotype selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$, a therapeutically effective amount of the genome edited cells contemplated herein.

In particular embodiments, genome edited cell therapies contemplated herein are used to treat, prevent, or ameliorate a thalassemia, or condition associated therewith. Thalassemias treatable with the genome edited cell contemplated herein include, but are not limited to α-thalassemias and β-thalassemias. In particular embodiments, a genome edited cell therapy is used to treat, prevent, or ameliorate a β-thalassemia, or condition associated therewith, comprising administering to subject having a β-globin genotype selected from the group consisting of: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$, a therapeutically effective amount of the genome edited cells contemplated herein.

In particular embodiments, genome edited cell therapies contemplated herein are used to treat, prevent, or ameliorate a sickle cell disease or condition associated therewith. In particular embodiments, a genome edited cell therapy is used to treat, prevent, or ameliorate a sickle cell disease or condition associated therewith, comprising administering to subject having a β-globin genotype selected from the group consisting of: $\beta^E/\beta^S$, $\beta^0/\beta^S$, $\beta^C/\beta^S$, $\beta^+/\beta^S$ or $\beta^S/\beta^S$, a therapeutically effective amount of the genome edited cells contemplated herein.

One of ordinary skill in the art would be able to use routine methods in order to determine the appropriate route of administration and the correct dosage of an effective amount of a composition comprising genome edited cells contemplated herein. It would also be known to those having ordinary skill in the art to recognize that in certain therapies, multiple administrations of pharmaceutical compositions contemplated herein may be required to effect therapy.

One of the prime methods used to treat subjects amenable to treatment with genome edited hematopoietic stem and progenitor cell therapies is blood transfusion. Thus, one of the chief goals of the compositions and methods contemplated herein is to reduce the number of, or eliminate the need for, transfusions.

In particular embodiments, the drug product is administered once.

In certain embodiments, the drug product is administered 1, 2, 3, 4, 5, 6, 7, 8, 9, or 10 or more times over a span of 1 year, 2 years, 5, years, 10 years, or more.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Genome Editing Strategies for Treatment of Hemoglobinopathies

Figure 2:
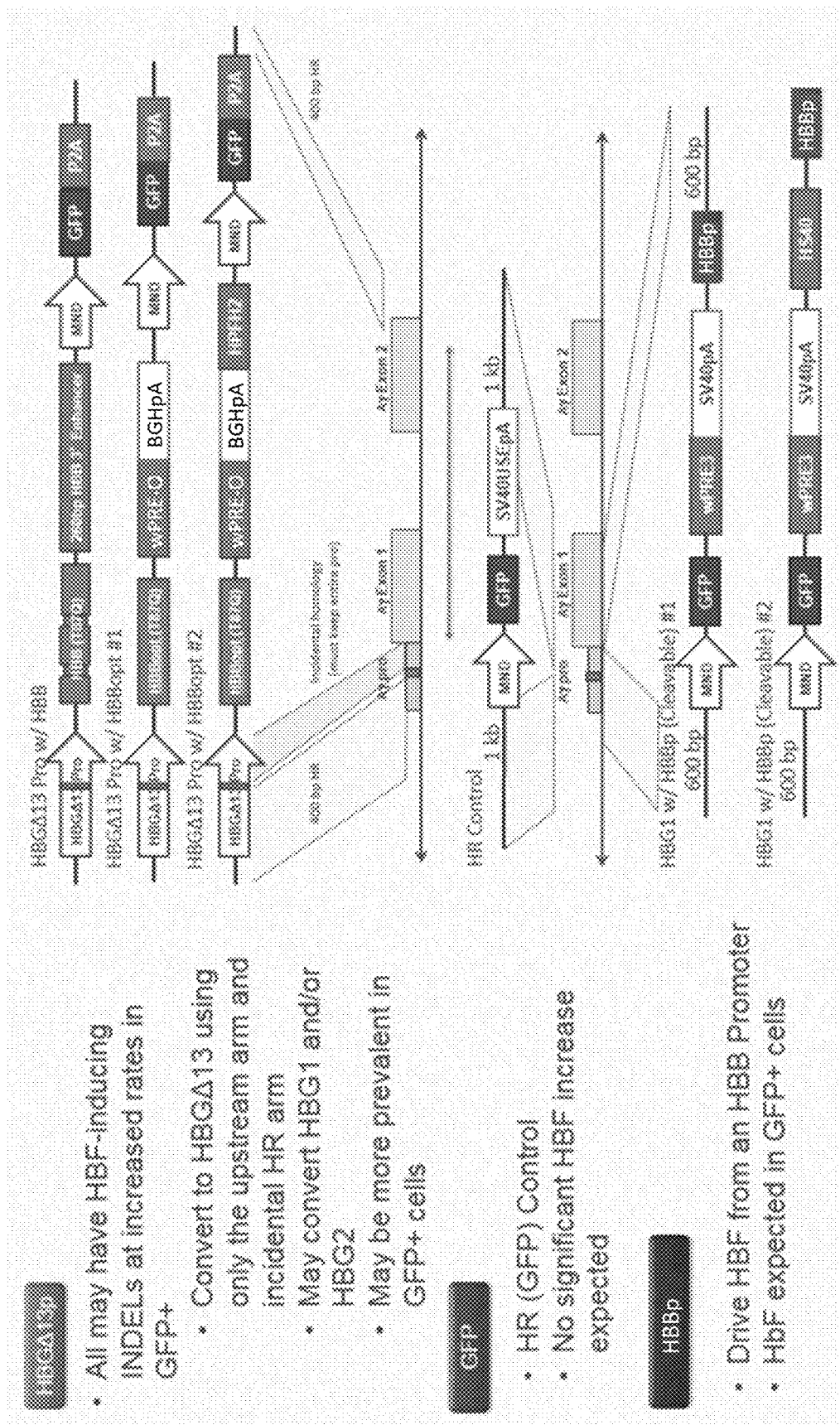
FIG. 2 shows a diagram of the various illustrative donor repair templates that were integrated into the γ-globin locus by homology directed repair.
Figure 3:
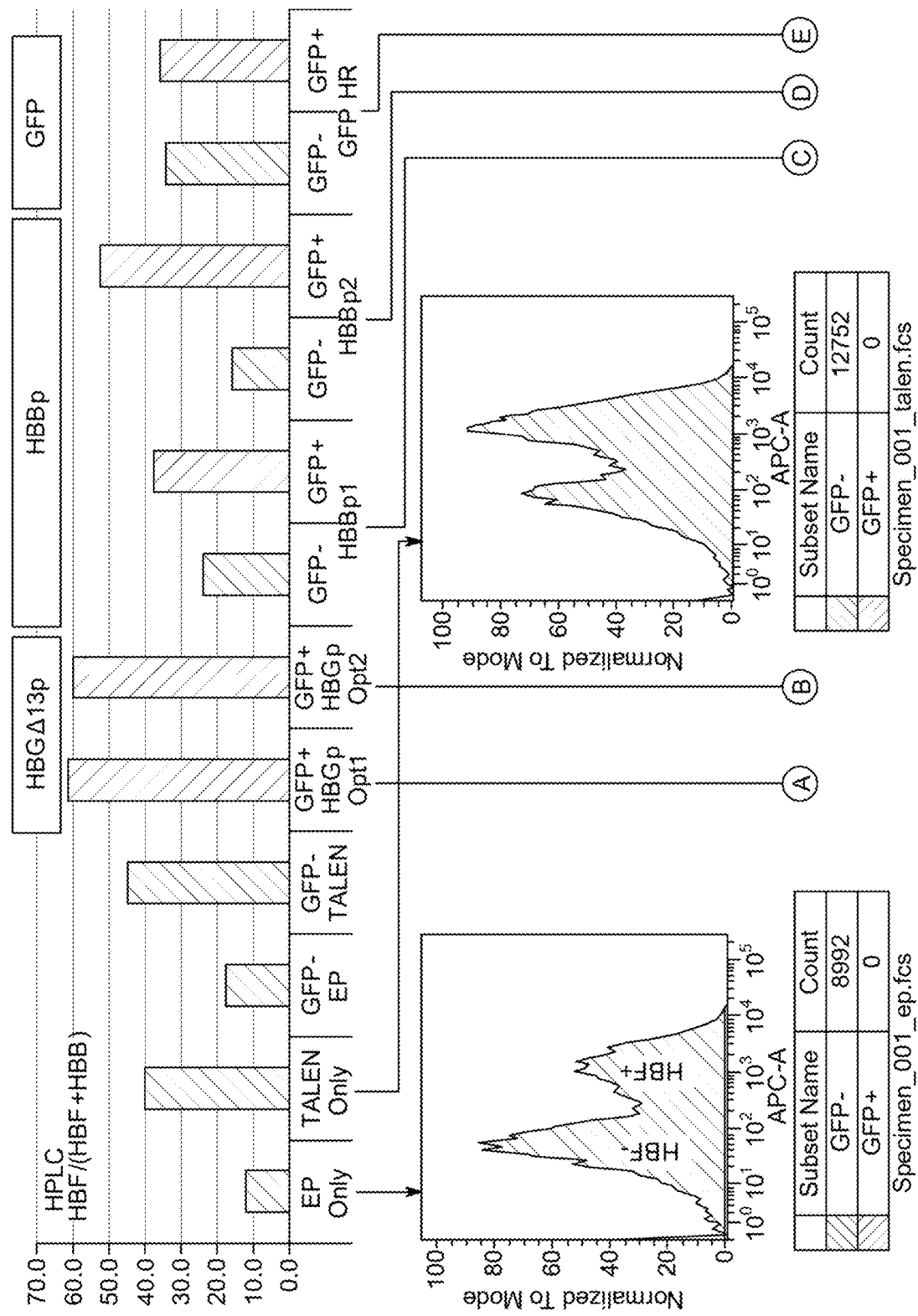
FIG. 3 shows the flow cytometric analysis of HbF expression by HPLC following erythroid differentiation.
Figure 3:
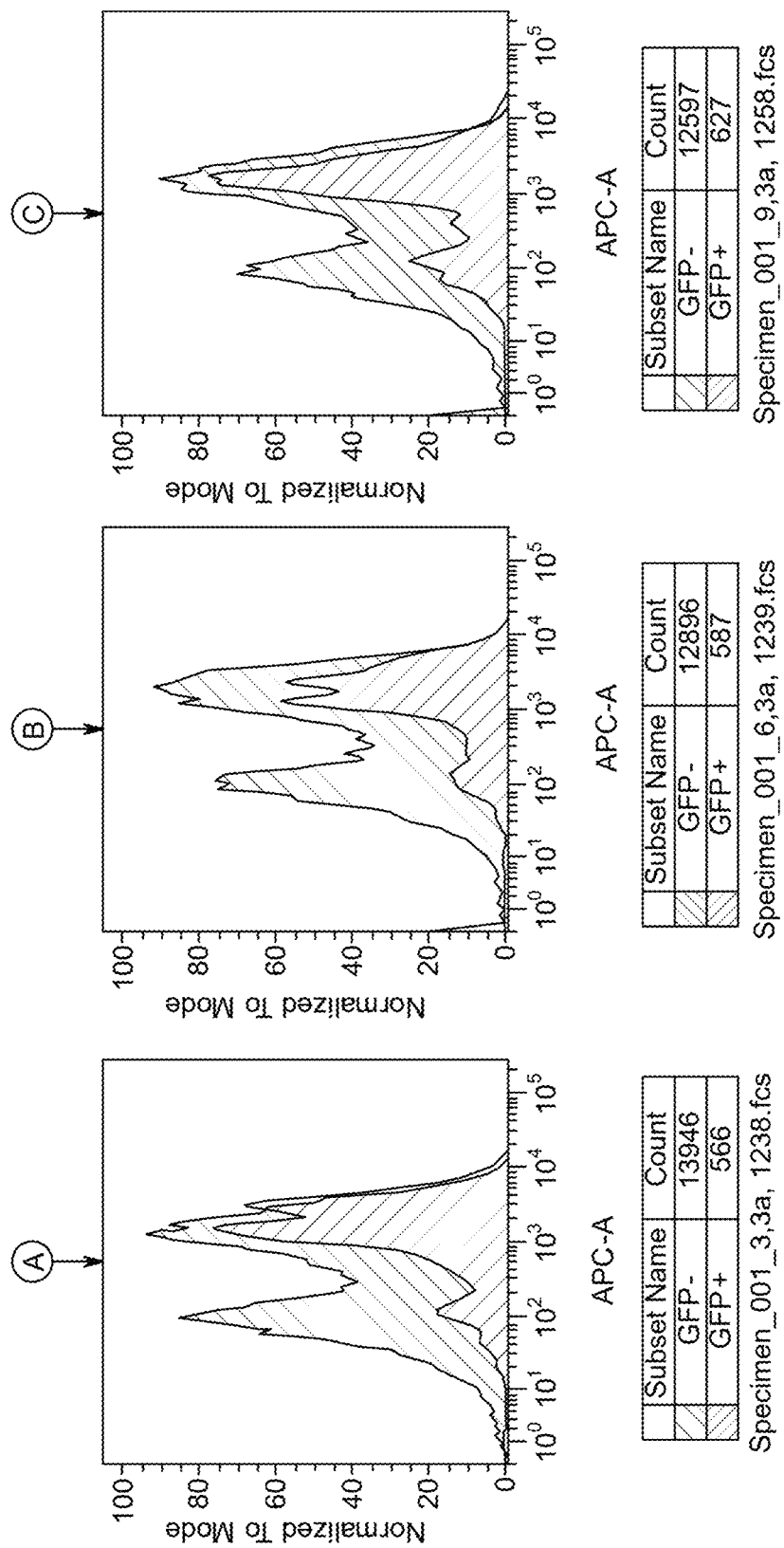
Figure 3:
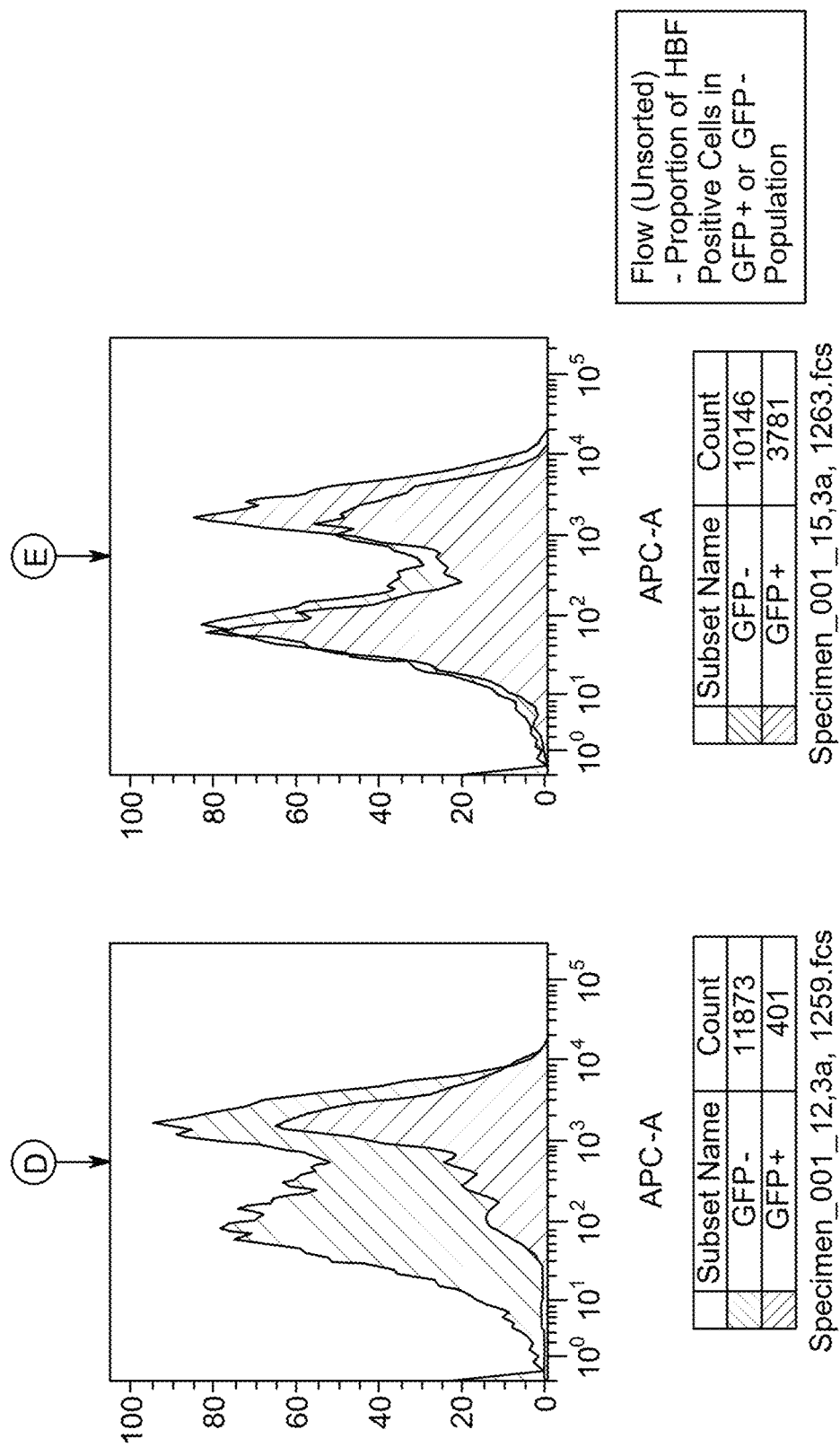

Human CD34+ hematopoietic stem and progenitor cells were selected and cultured for 48-72 hours in growth medium containing SCF, TPO, and FLT3. The hCD34+ cells were then centrifuged, re-suspended in electroporation media, and electroporated with a polynucleotide encoding a nuclease. In this particular example, hCD34+ cells were electroporated with an mRNA encoding TALENs nucleases that target a 13 base pair region (SEQ ID NO: 3) in the γ-globin promoter (e.g., SEQ ID NO: 9), that when deleted, has shown to be associated with HPFH. FIG. 1. The electroporated hCD34+ cells were cultured for 4 hours and were then transduced with AAV vectors (packaged with AAV6 capsid) comprising the cassettes schematized in FIG. 2. The transduced hCD34+ cells were then cultured in methylcellulose to assess CFU potential and flow cytometric analysis of fetal globin expression following erythroid differentiation. FIG. 3.

The γ-globin locus was targeted by HDR using the illustrative donor repair templates and TALENs nucleases and resulted in upregulation of fetal globin (HbF) expression ($2^{nd}$, and $4^{th}$ bars), and was also detectable when a GFP selection cassette was used ($11^{th}$ and $12^{th}$ bars). Analysis of erythroid-differentiated colonies in CFU assays from cells targeted with the GFP-vector showed GFP expression, thereby demonstrating that integration of a donor repair template comprising a selection cassette into this region of the γ-globin gene did not disrupt γ-globin expression or erythroid differentiation. HbF expression was further increased when the nuclease was co-transfected with donor repair templates that comprised a 13 bp deletion in the γ-globin promoter associated with HPFH or the β-globin promoter (see bars 5/6, and 7-10 respectively).

Example 2

Approach

A gene editing strategy was developed with TALEN's or Crispr/Cas9 ribonucleoprotein (RNP) delivery to create clinically useful deletions, including a naturally occurring 13 bp deletion, at the HBG1 and HBG2 promoter region that drives increased fetal hemoglobin expression. The deletions created by these designer nucleases eliminate suppressive elements that function to block fetal globin expression. Upon editing this region at the HBG1 or HBG2 loci, fetal hemoglobin is induced. Re-induction of fetal hemoglobin can be therapeutic in sickle-cell and β-thalassemia patients and potentially curative to alleviate symptoms. In parallel with generation of clinically useful indels/deletions, we have developed AAV gene delivery cassettes that, following introduction by homology-directed-repair (HDR), will mediate expression of functional hemoglobin based upon a series of alternative strategies described below. This overall approach thereby effectively partners: a) deletional events that promote fetal hemoglobin induction with b) additional HDR-mediated gene expression events that drive therapeutic hemoglobin production, that together, synergize to provide increased overall therapeutic benefit.

Strategies

Multiple strategies have been optimized for inducing hemoglobin at the HBG1 and HBG2 loci:
1. Nucleases (TALEN's and Crispr/Cas9) that edit at HBG1 and HBG2 loci and drive indels and re-induce both G1 and G2 globin.
2. Early parental constructs that integrate at the HBG1 locus and test expression of globin.
3. Optimized homology-directed repair templates that integrate at the HBG1 locus and drive: (A) HBG1 expression or (B) $β^{T87Q}$ expression in human or non-human primate cells.
4. Optimized homology-directed repair templates that integrate at the HBG1 locus and drive HBG1 expression or $β^{T87Q}$ expression and, in parallel, allow for chemo-therapeutic selection of HDR-edited human or non-human primate cells.

Strategy 1: Nucleases (TALEN's and Crispr/Cas9) that Edit at HBG1 and HBG2 Loci in Mobilized Primary Human CD34+ HSC Cells Drive Indels and Re-Induce Both G1 and G2 Globin.

Figure 4A:
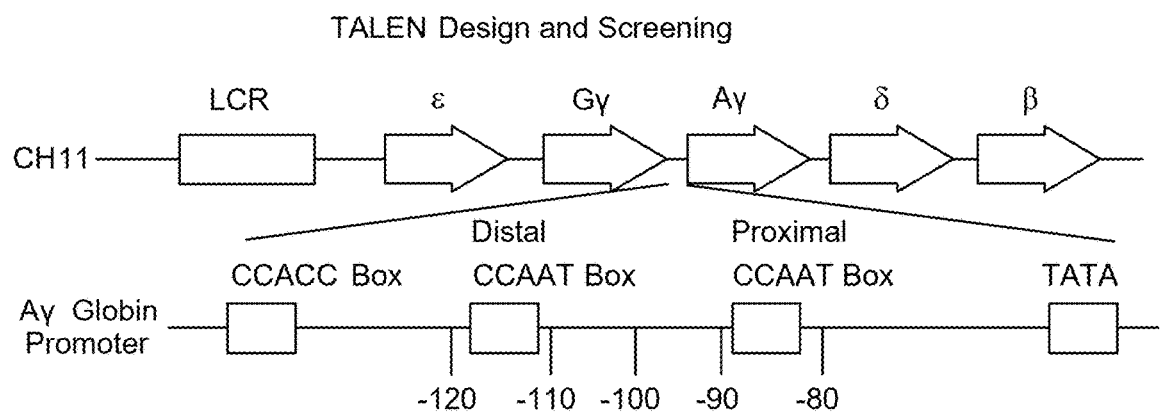
FIGS. 4A-4C show TALEN design and screening.
Figure 4B:
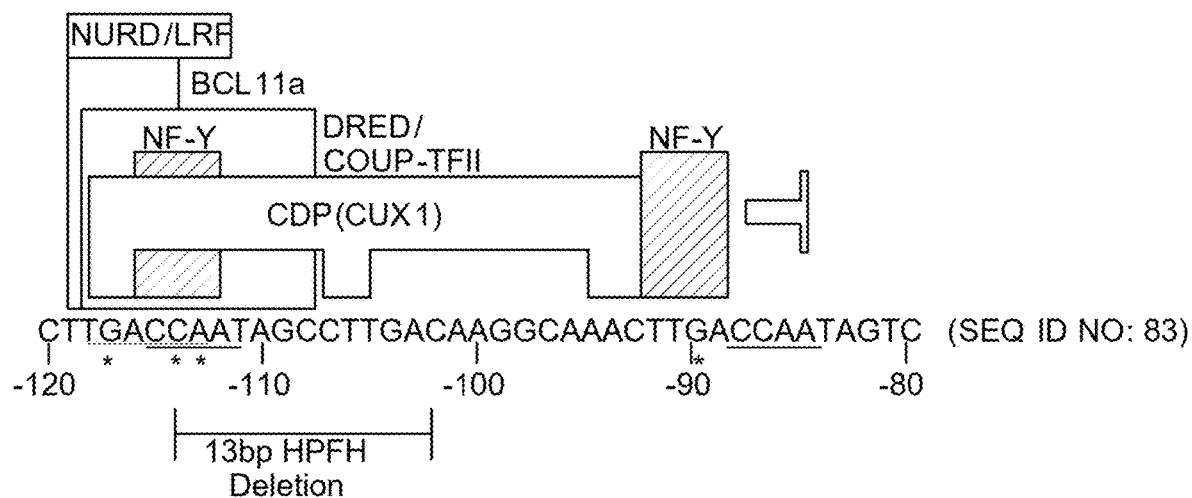
Figure 4C:
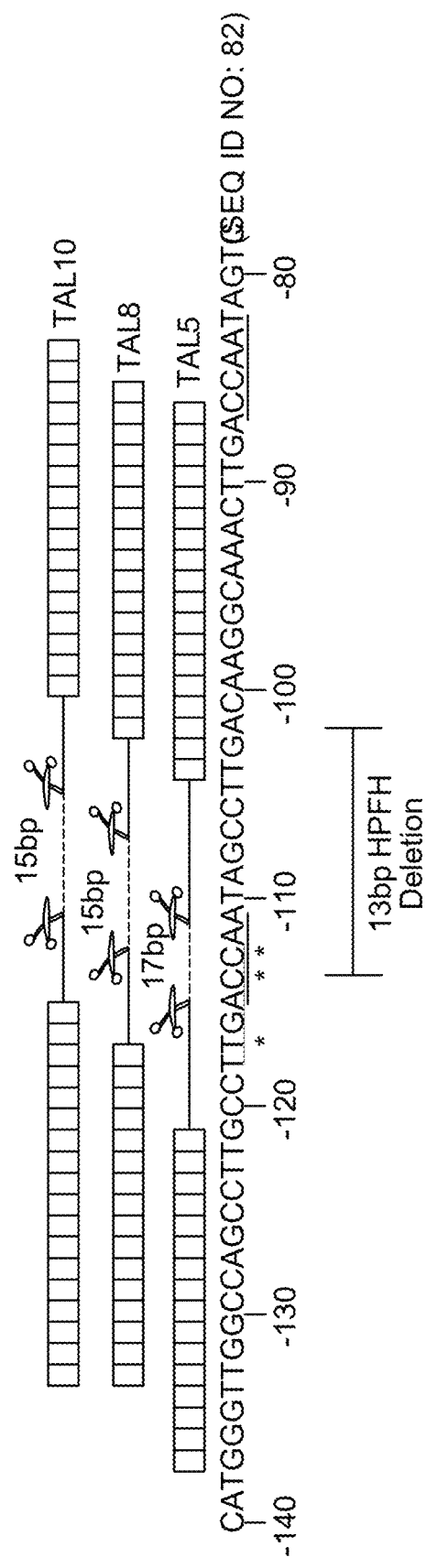
Figure 5A:
FIGS. 5A-5G demonstrate optimizing TALEN editing conditions to maximize efficiency.
Figure 5B:
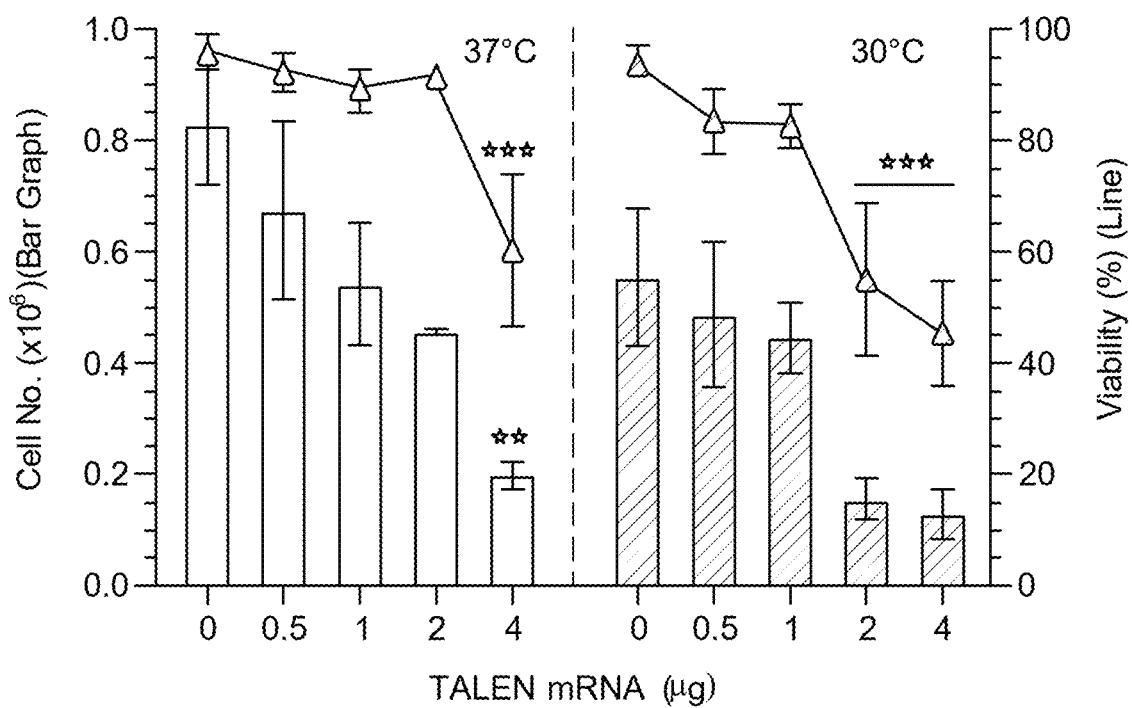
Figure 5C:
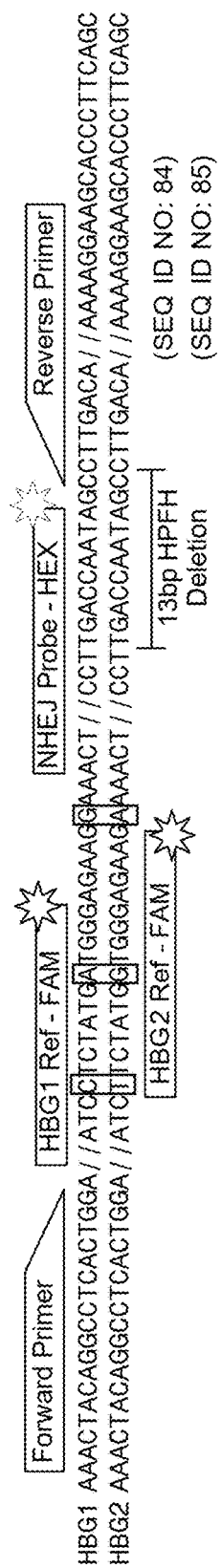
Figure 5D:
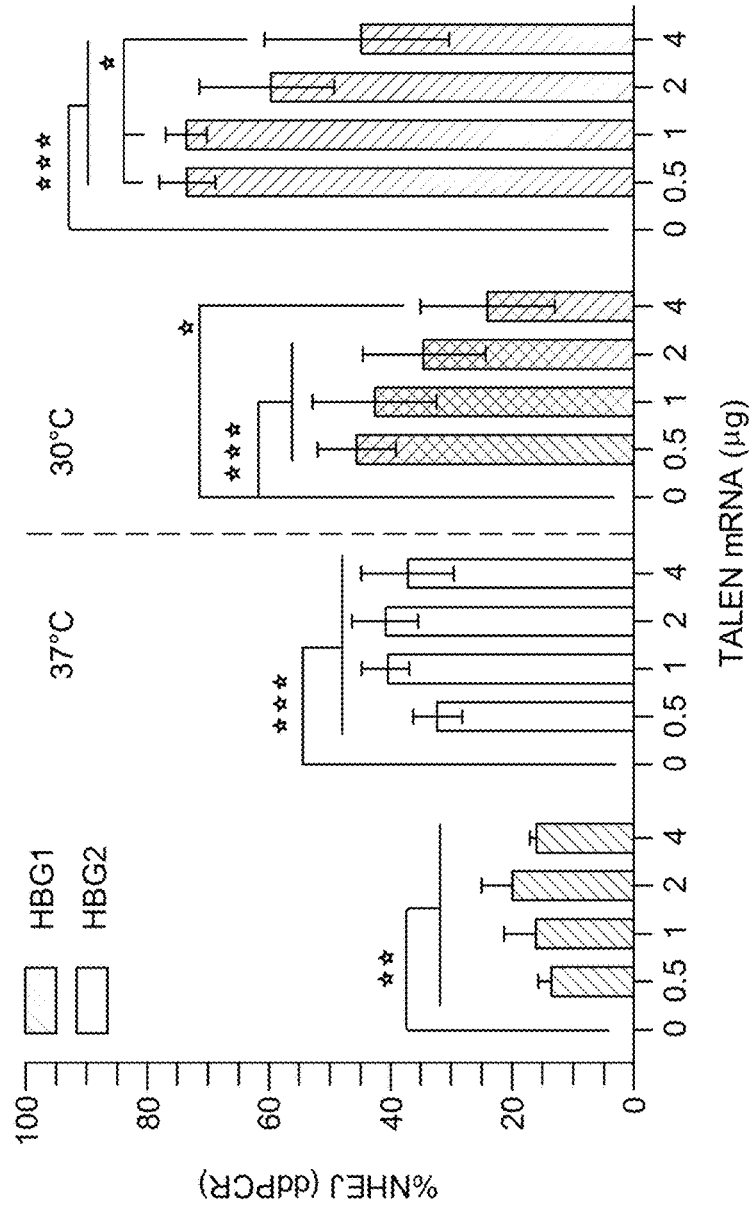
Figure 5E:
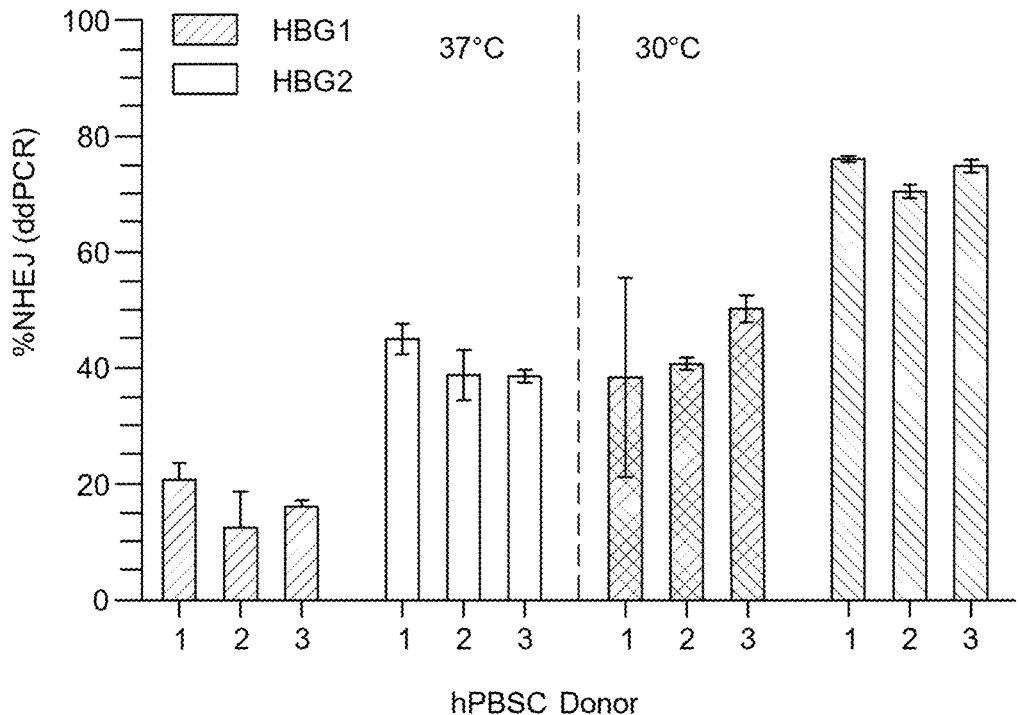
Figure 5F:
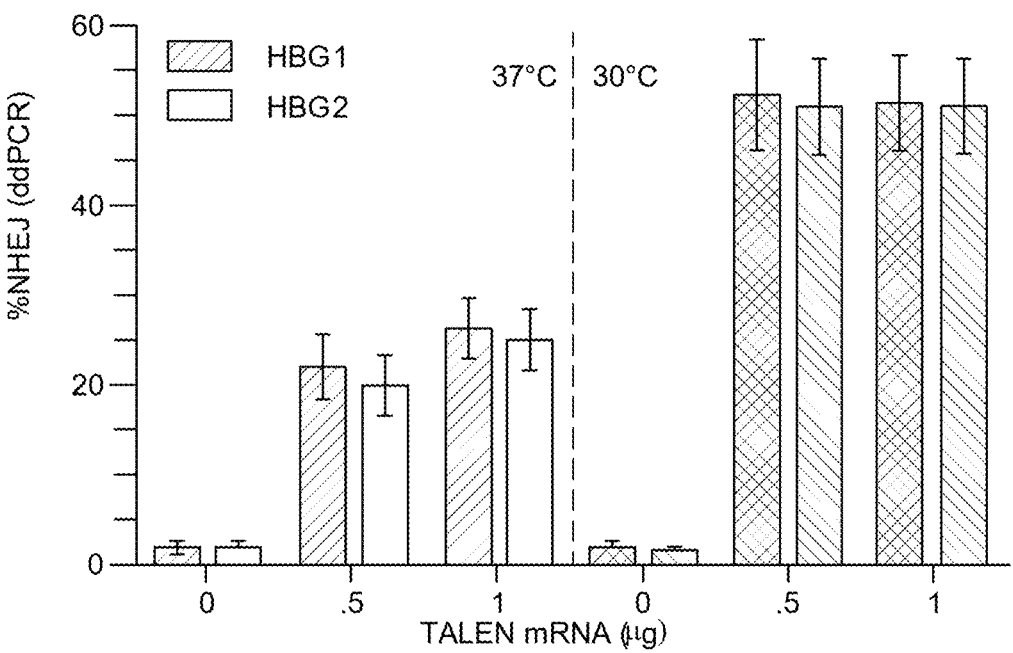
Figure 5G:
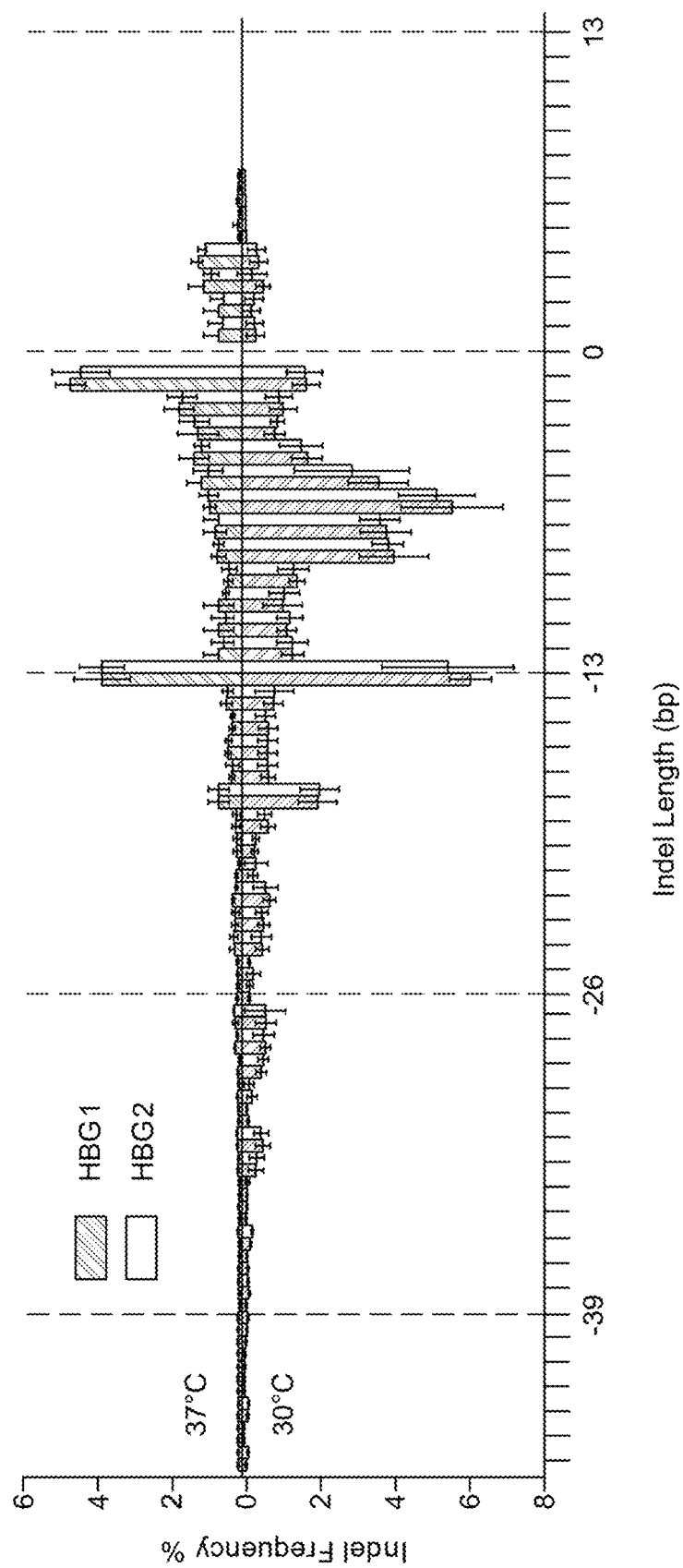
Figure 7D:
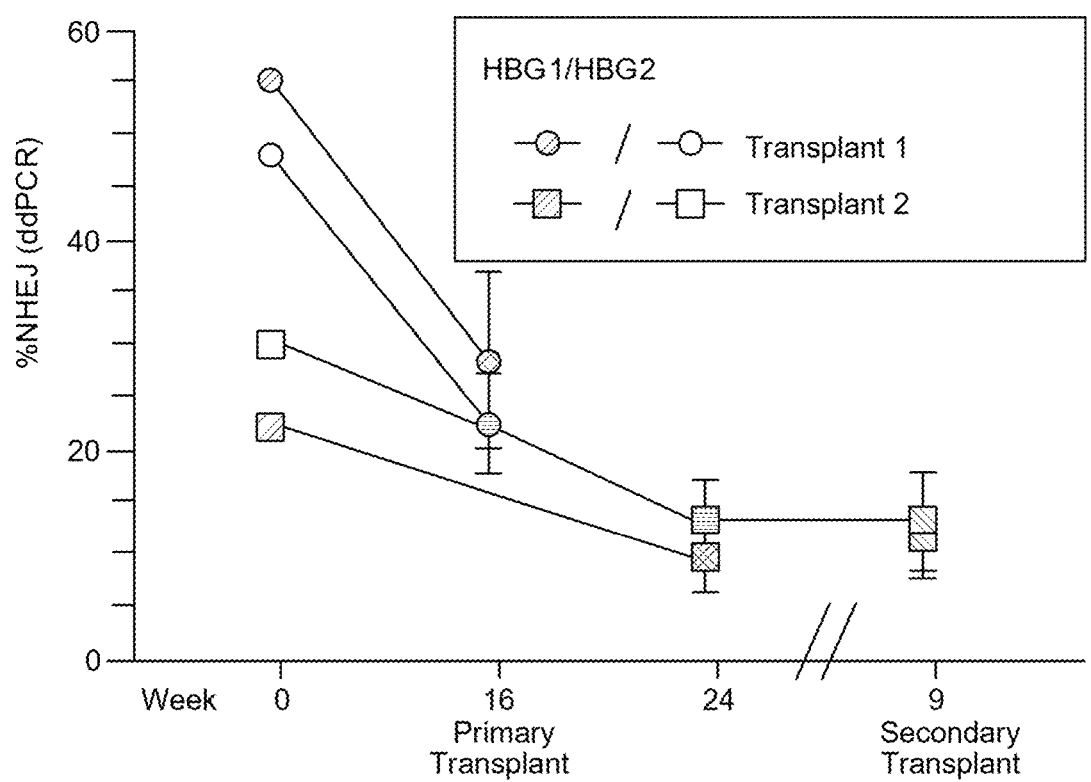
Figure 7E:
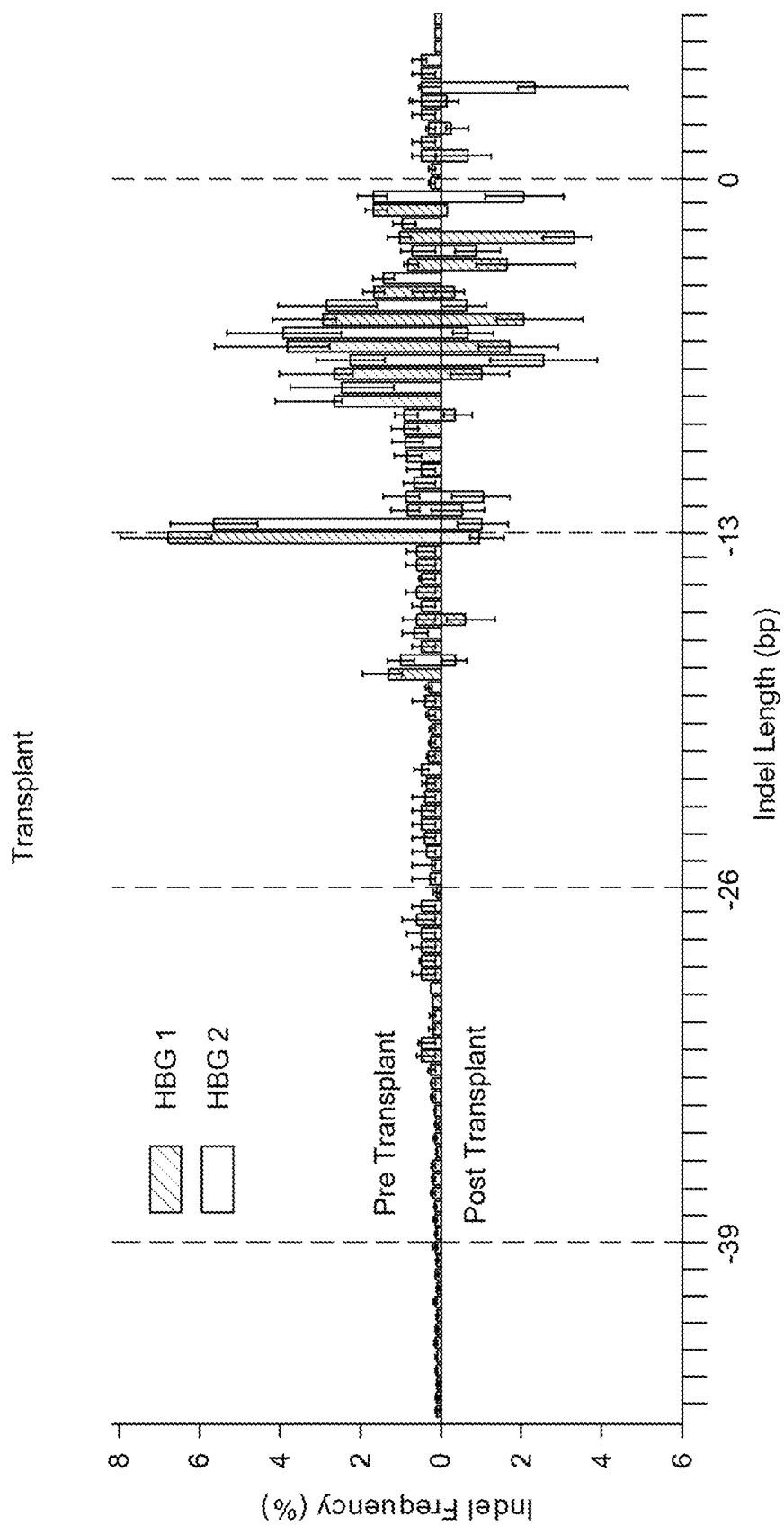
Figure 7F:
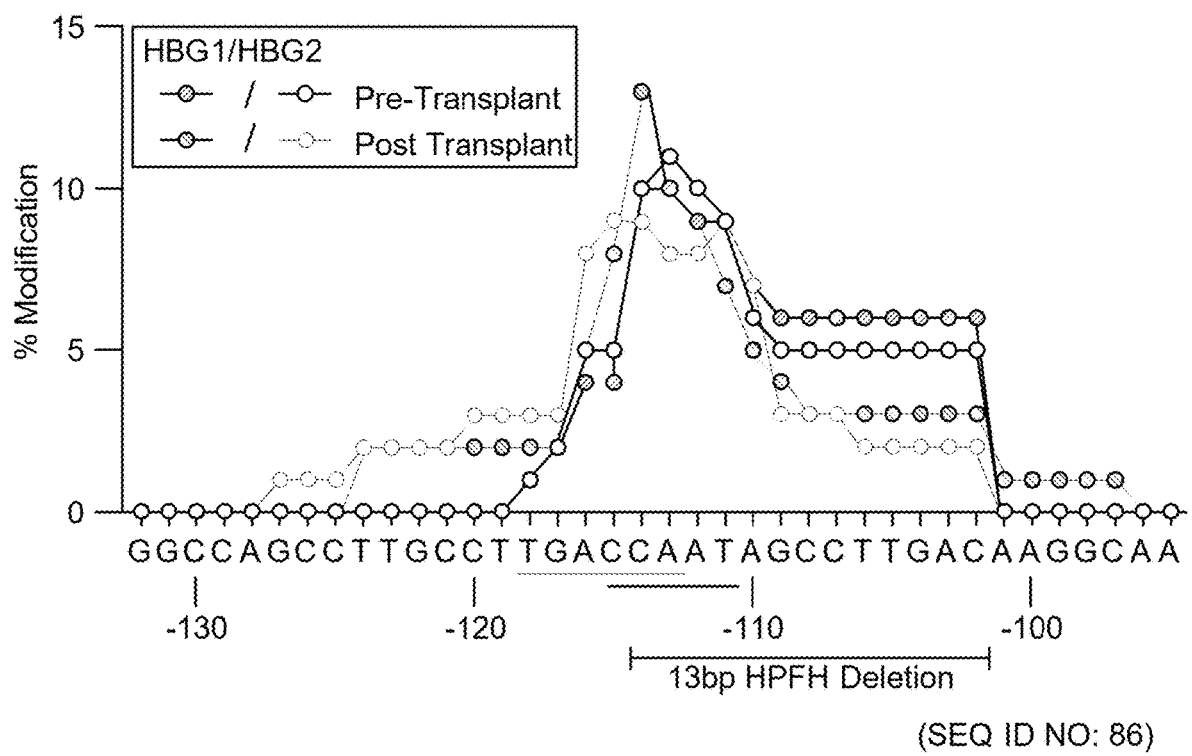
Figure 7G:
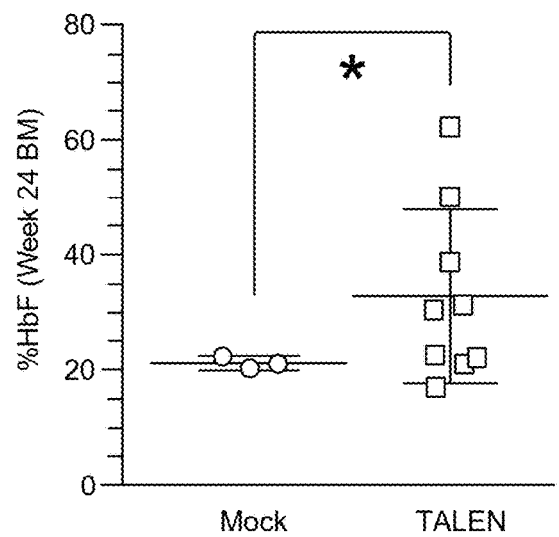
Figure 7H:
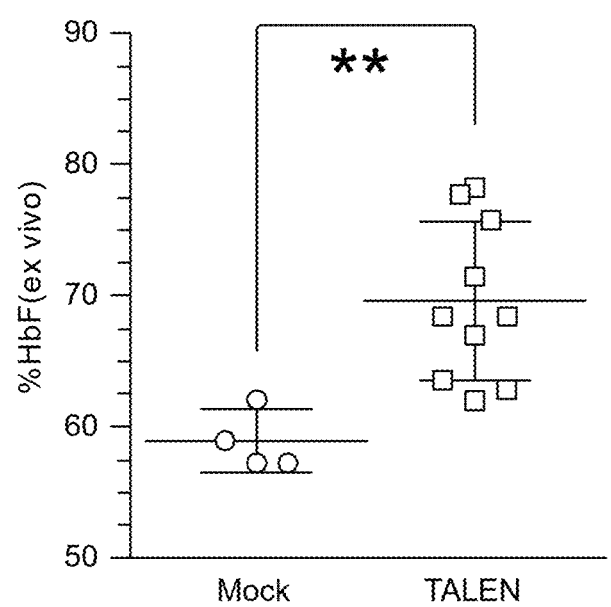

1A. 13 bp deletion drives fetal hemoglobin expression in gene edited mobilized primary human CD34+ HSC cells. (FIGS. 4-6) TALEN and RNP nucleases drive non-homologus end joining (NHEJ) mediated re-creation of 13 bp deletion and other useful deletions at the HBG1 and HBG2 loci. These deletions obliterate the distal CCAAT box along with sites that bind multiple transcription factors including the BCL11A binding site TGACCA and results in the induction of both HBG1 and HBG2 fetal hemoglobin.

Figure 8:
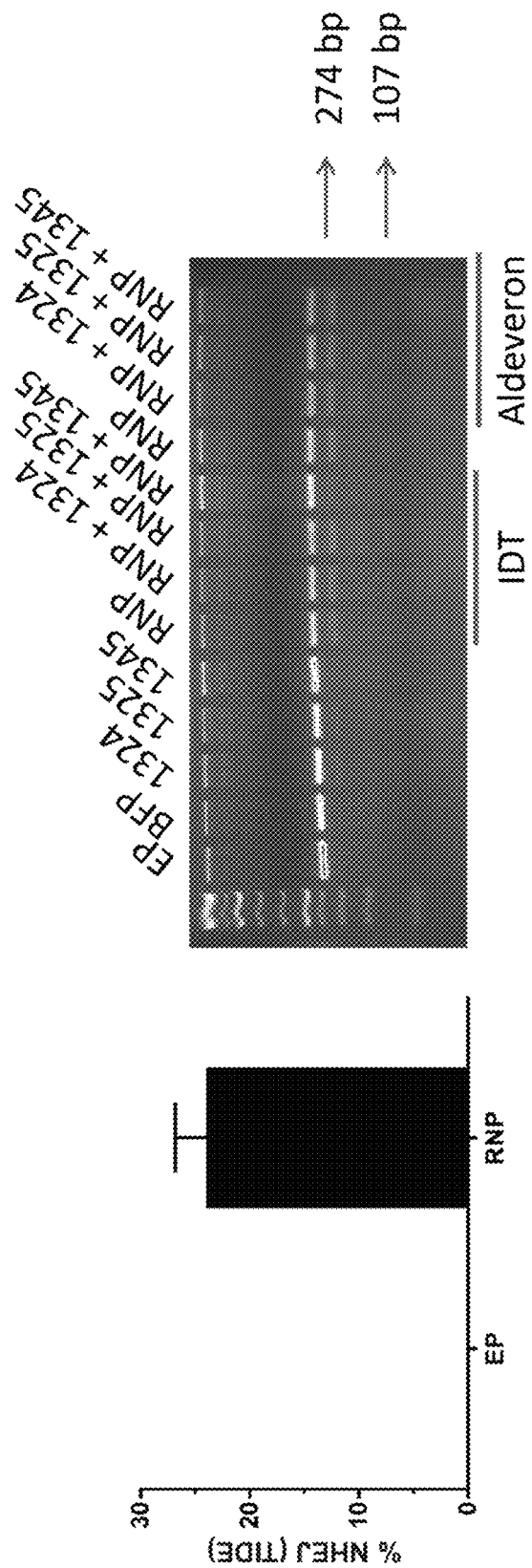
FIG. 8 demonstrates ribonucleoprotein delivery with Cas9 and sgRNA has been optimized for editing at the HBG1 and G2 loci. The panel on the left shows ~26% overall editing at the HbG1 and HbG2 loci by TIDE analysis. The panel on the right shows a T7 endonuclease assay that shows, no Indels in the electroporation only samples and the presence of Indels in the RNP and RNP+AAV samples.
Figure 13:
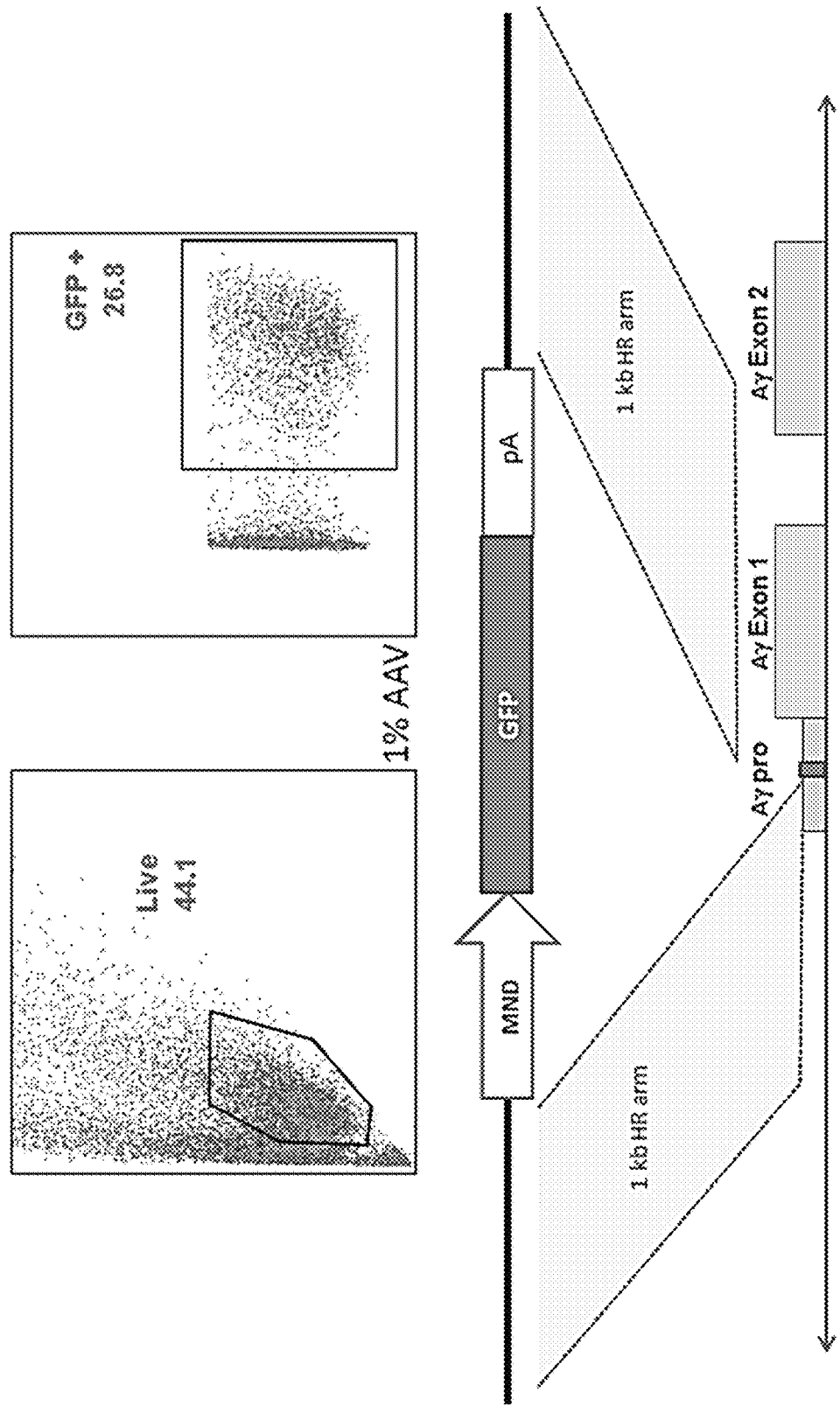
FIG. 13 shows construct 1263—GFP Control repair template. This template is used to assess HDR rates at the HGB1 locus. The data demonstrates efficient HDR within this locus. The HDR rates are comparable to our own and others published results at other genetic loci in human CD34+ HSC. This construct is used to compare to other HDR constructs that create deletions and/or have smaller HR arms, etc, and this acts as a benchmark for editing.
Figure 14:
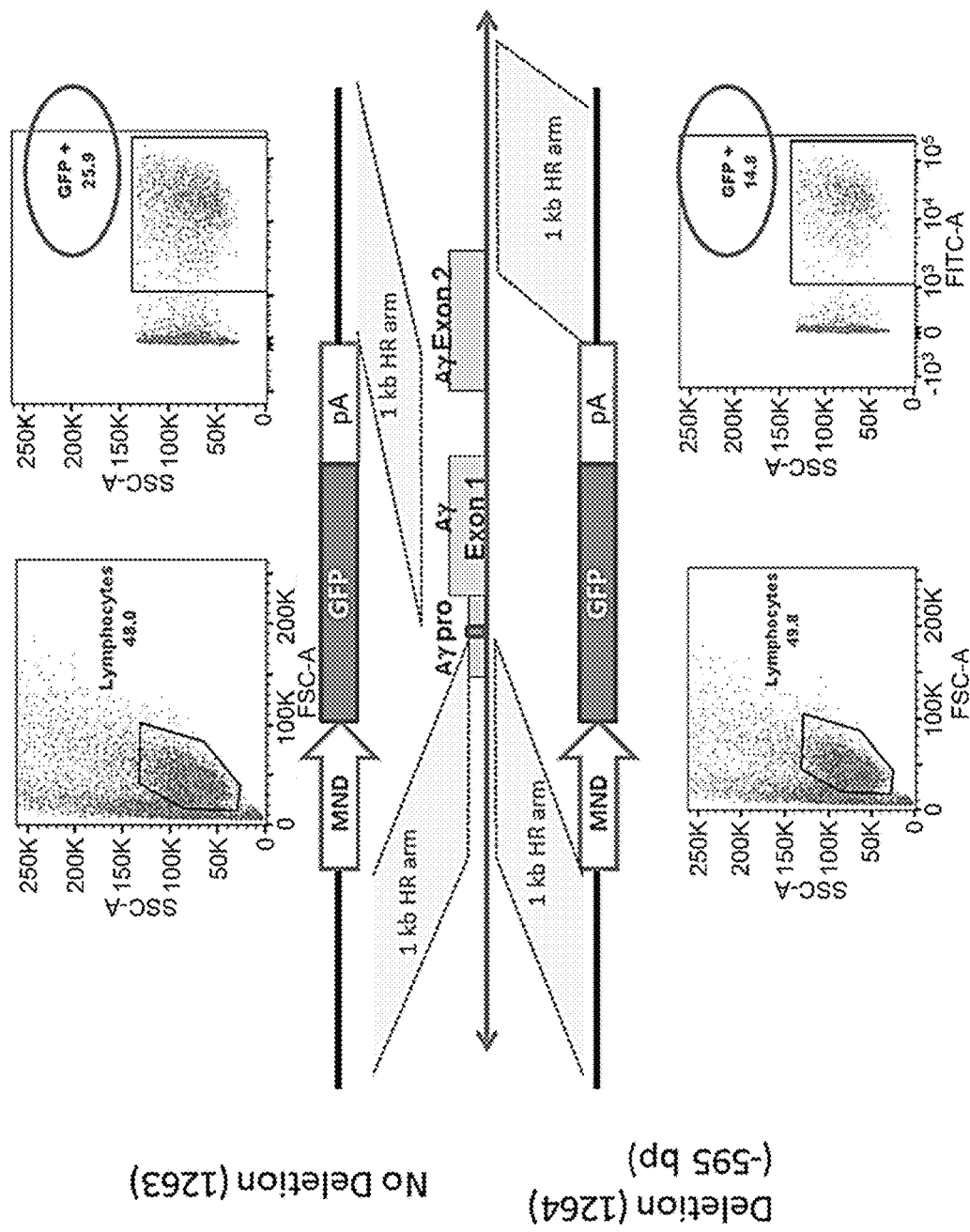
FIG. 14 shows when HR arms bind to sequences distant from each other in the genome, they require a deletion event to occur and decrease HR efficiency.
Figure 15:
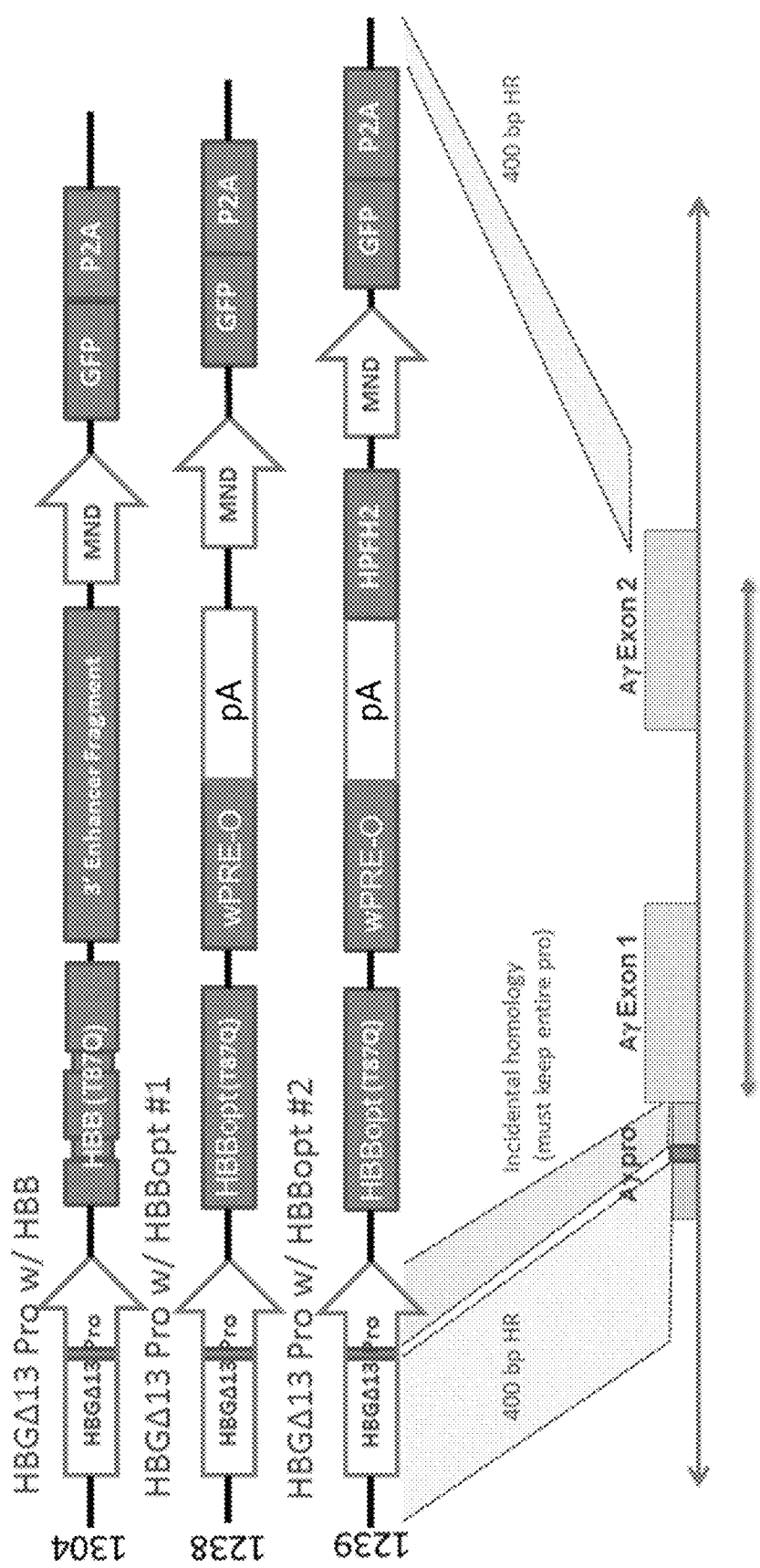
FIG. 15 provides alternative constructs using the HBGd13 Promoter driving HBB T87Q anti-sickling globin.

1B. Edited mobilized primary human CD34+ HSC cells engraft and retain deletions in the gamma hemoglobin promoter (including the 13 bp and other useful deletions) in their LT-HSC population (FIG. 7) which allows for the de-repression of fetal hemoglobin. TALEN-edited cells were engrafted into W41 NSG mice and the data supports that the edited cells robustly drive multi-lineage engraftment. The edits remain in the erythroid population up to 24 weeks and are sustained across multiple animals in three independent transplant experiments. Edits remain detectable in LT-HSC populations that engraft and re-populate the bone marrow in primary and secondary transplant recipients. These data prove that creating deletions in the gamma hemoglobin promoter that drive fetal hemoglobin (including the 13 bp deletion) may be an effective long-term therapeutic approach. FIG. 8 shows use of RNPs to efficiently target the same region in HBG1 and 2 in mobilized primary human CD34+ HSC cells.

Strategy 2: Development and Testing of Initial/Parental Constructs for HDR Based Editing of the HBG1 Locus (FIGS. 9-18).

The initial constructs tested various elements including alternative promoters, enhancers, polyA tails, introns, varying homology arm lengths, deletional versus non-deletional constructs to identify the best design to maximize globin expression. Various constructs were designed and tested to identify the best regulatory regions to promote maximal globin expression. The data supports the following:
- HBB and HBG1-d13 promoters work equally well with respect to globin expression.
- Tissue-specific enhancers like HS-40, HPFH-2 produce the maximum protein expression from the donor templates.
- wPRE-3, wPRE-O elements work well and enhance stability of the mRNA and therefore globin expression.
- Longer HR arms mediated higher rates of HDR using AAV donor templates.
- Deletional templates (e.g. ones that had deletions near the nuclease cleavage site) yielded lower HR rates than non-deletional templates.

The early designs helped identify that HBG1 locus is amenable to HDR and with a positive control AAV delivering GFP, a 30% HR rate was observed at the HBG1 locus.

The basic function of elements described in the naming conventions of the described templates are as follows:
- HPFH2 Enhancer—used in HBG1 cassettes to enhance promoter activity;
- d13HBG1 Promoter—HBG1 promoter with 13 bp HPFH deletion that promotes HBG1 expression;
- HBBpro—utilizes the endogenous HBB promoter to drive HBG1 expression;
- HS40 Enhancer—used in combination with HBBpro and HBG1pro to enhance the promoter activity;
- T2A—used in constructs to use the exons and polyA from the native gene;
- wPRE3.SV40USE.pA—"minimal" wPRE and modified SV40 polyA;
- MND—denotes MND-CMV1 short version promoter;
- T87Q—Anti-sickling hemoglobin gene;
- MGMT—Anti-sickling P140K mutant MGMT for chemoselection; and
- GFP—Green Fluorescent Protein.

Data optimizing HDR templates with GFP include control templates expressing only GFP (Constructs 1263 and 1264);

templates inducing G1 globin (Constructs 1324 and 1325); and templates driving $\beta^{T87Q}$ (Construct 1345).

Strategy 3: Homology-Directed Repair Templates that Integrate at the HBG1 Locus and Drive: (A) HBG1 Expression or (B) $\beta^{T87Q}$ Expression in Mobilized Primary Human CD34+ HSC Cells and Non-Human Primate BM CD34+ Cells (FIGS. 19-27).

rAAV-6 and rAAV-5 delivery of HDR templates have been designed and optimized for delivery of donor templates into human and Rhesus cells, respectively.

3A. Homology-directed repair templates that integrate at the HBG1 locus and drive HBG1 expression. Constructs 1324 and 1325 (FIGS. 19-20) are donor templates with optimized promoters (HBG1, HBB, PGK) and enhancers (HS-40, HPFH2), poly-A tail (SV-40) with varying homology arm lengths (400-1000 bp) and drive insertion at the HBG1 promoter region and recapitulates the 13 bp deletion that drives HBG1 native promoter-mediated induction of Gamma 1 globin. Data shown demonstrates results following co-delivery of these templates with AAV and RNP in mobilized primary human CD34+ HSC cells.

Figure 28:
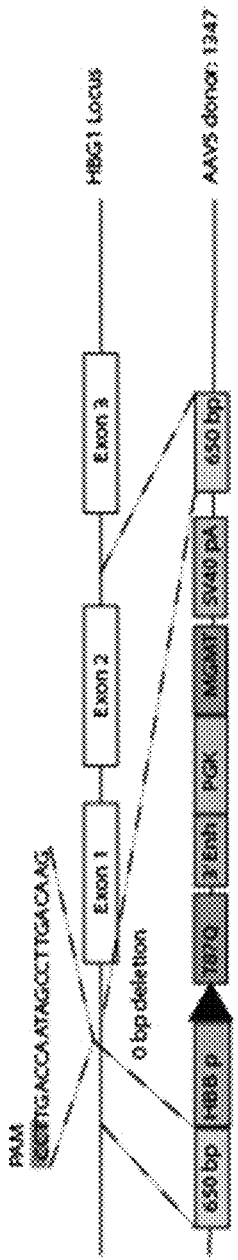
FIG. 28 demonstrates Construct 1347 is a rAAV construct that can drive homology-dependent repair into the Rhesus HBG1 locus. The donor template introduces a HBB promoter that drives T87Q globin.
Figure 29:
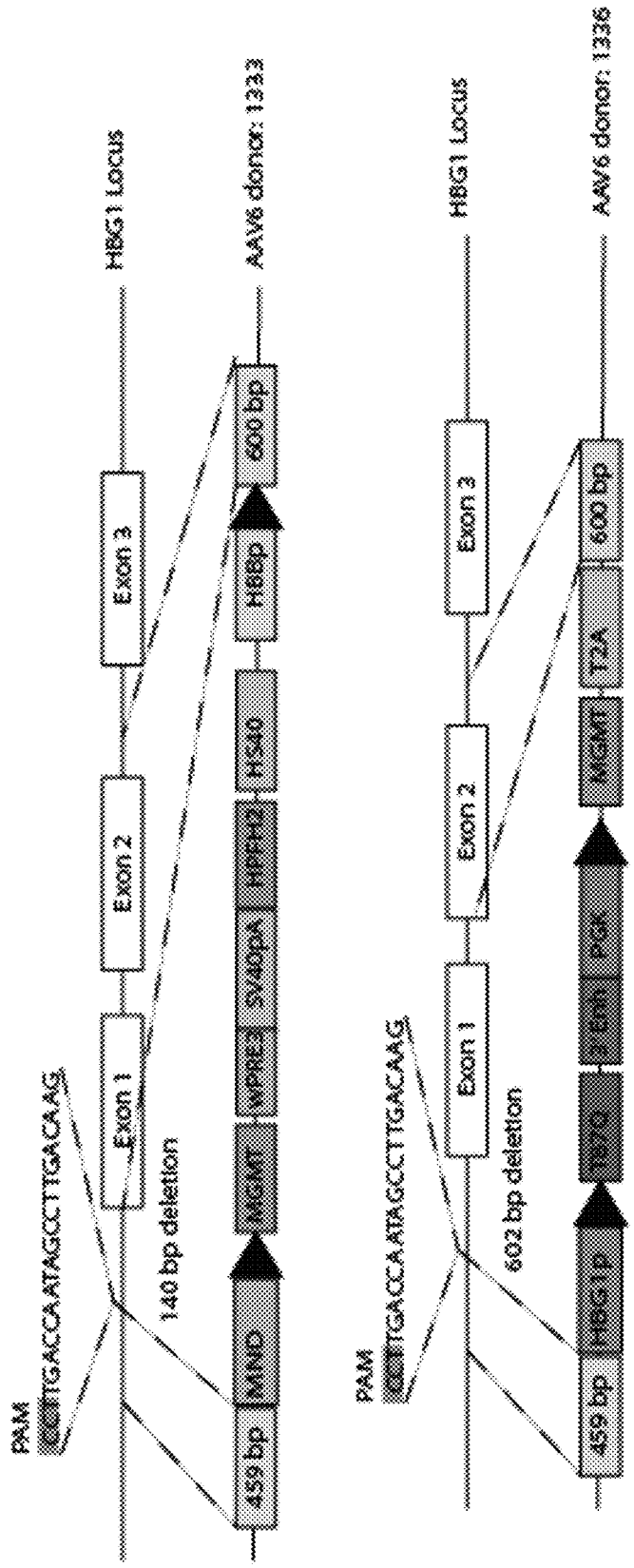
FIG. 29 demonstrates Construct 1333 is a rAAV construct that can drive homology-dependent repair into the human HBG1 locus. The donor template introduces a HBB promoter that drives Gamma globin expression and allows for chemo therapeutic selection, as it has a MND-promoter driving P140K MGMT expression. Construct 1336 is a rAAV construct that can drive homology-dependent repair into the human HBG1 locus. The donor template introduces a HBG1 d13 promoter that drives T87Q globin expression and allows for chemo therapeutic selection, as it has a PGK-promoter driving P140K MGMT expression.
Figure 31:
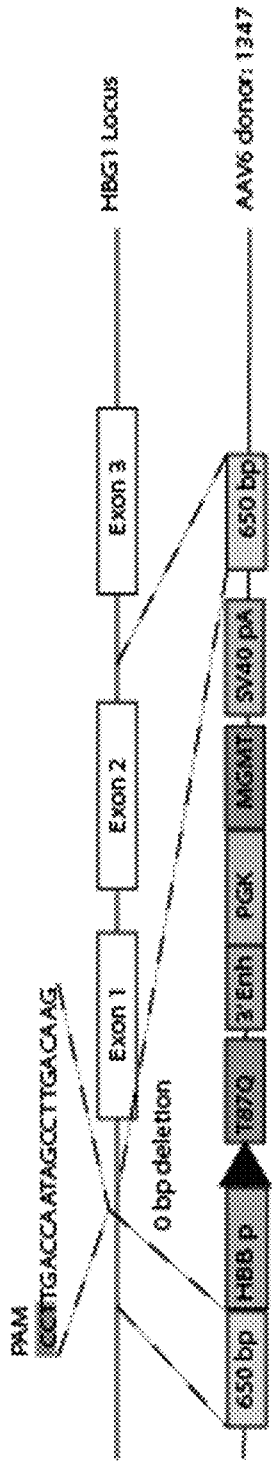
FIG. 31 demonstrates Construct 1347 is a rAAV construct that can drive homology-dependent repair into the human HBG1 locus. The donor template introduces a HBB promoter that drives T87Q globin expression and allows for chemo therapeutic selection, as it has a PGK-promoter driving P140K MGMT expression.
Figure 32:
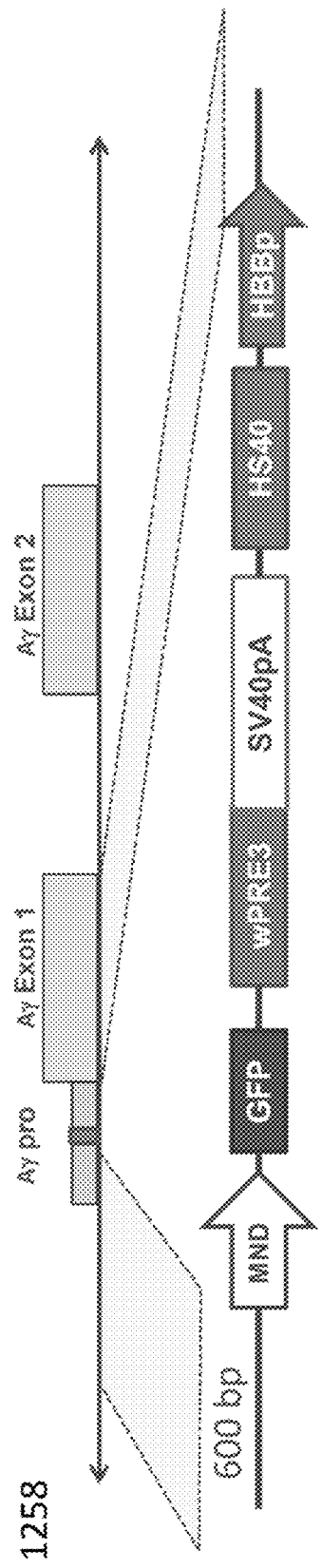
FIG. 32 provides an example of an HBB promoter driving HBG1 expression.
Figure 33:
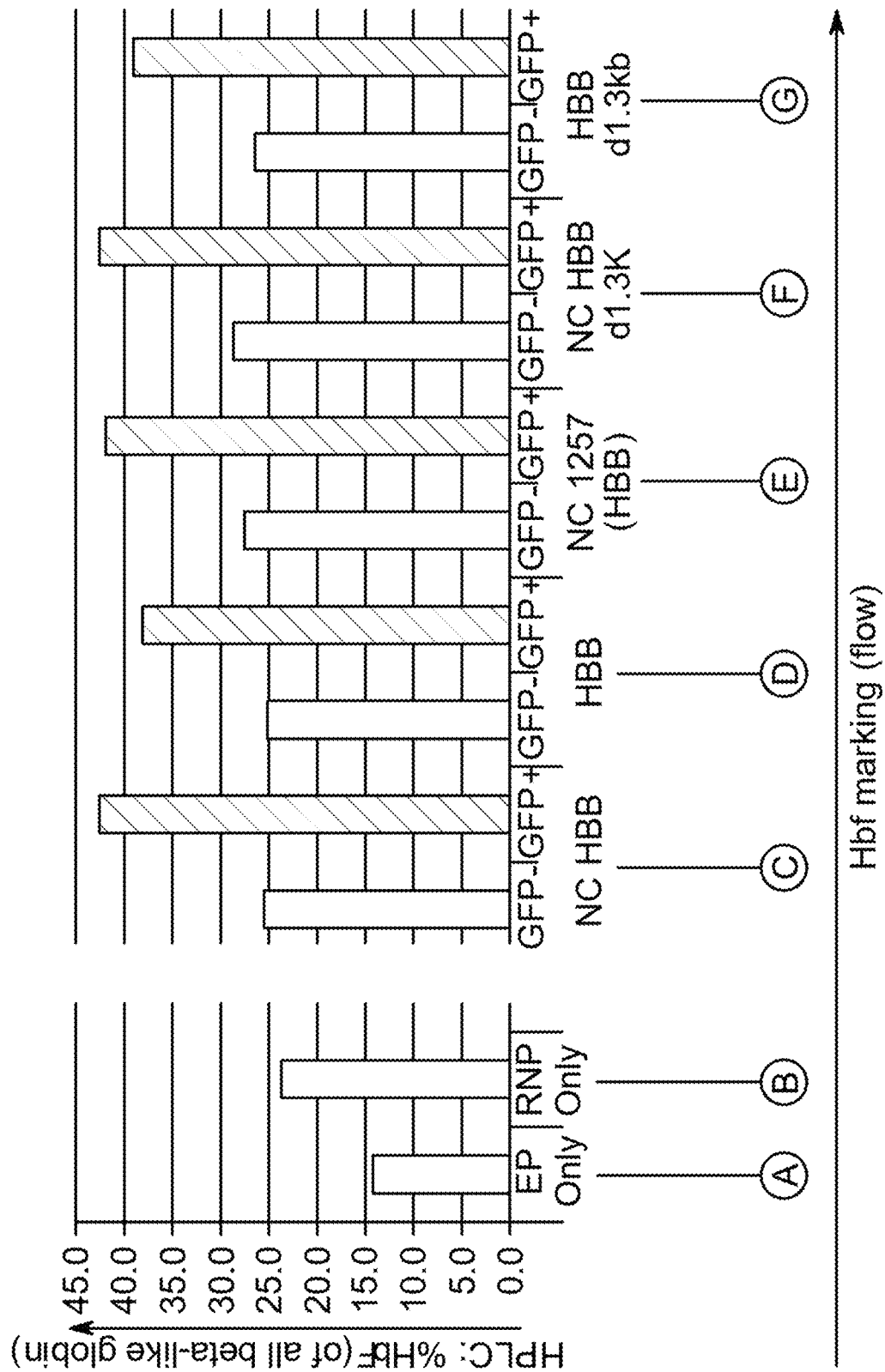
FIG. 33 demonstrates use of multiple HDR templates (numbers listed under flow plots) and TALEN co-delivery demonstrating increased HbF expression in GFP+ cells.
Figure 33:
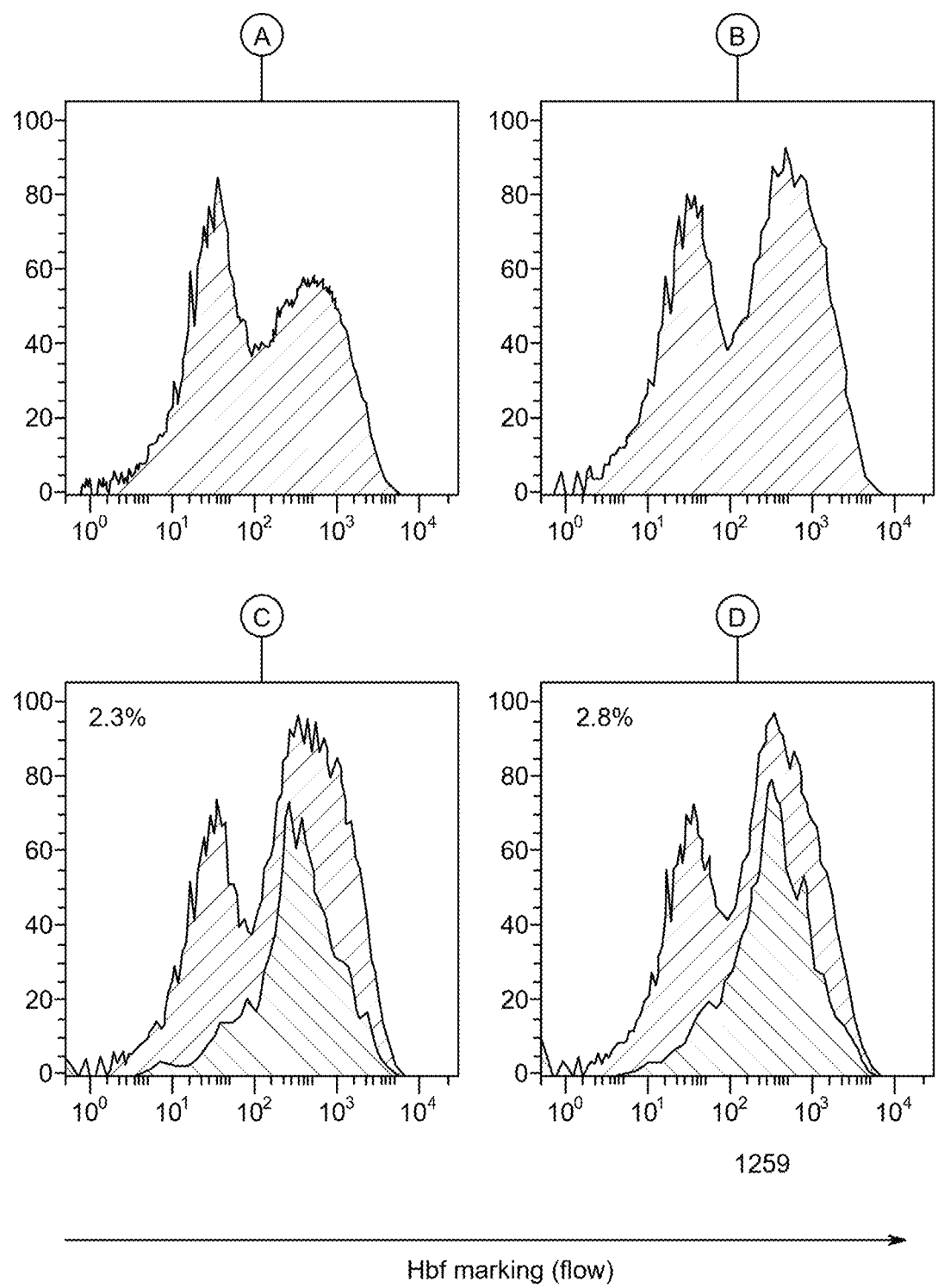
Figure 33:
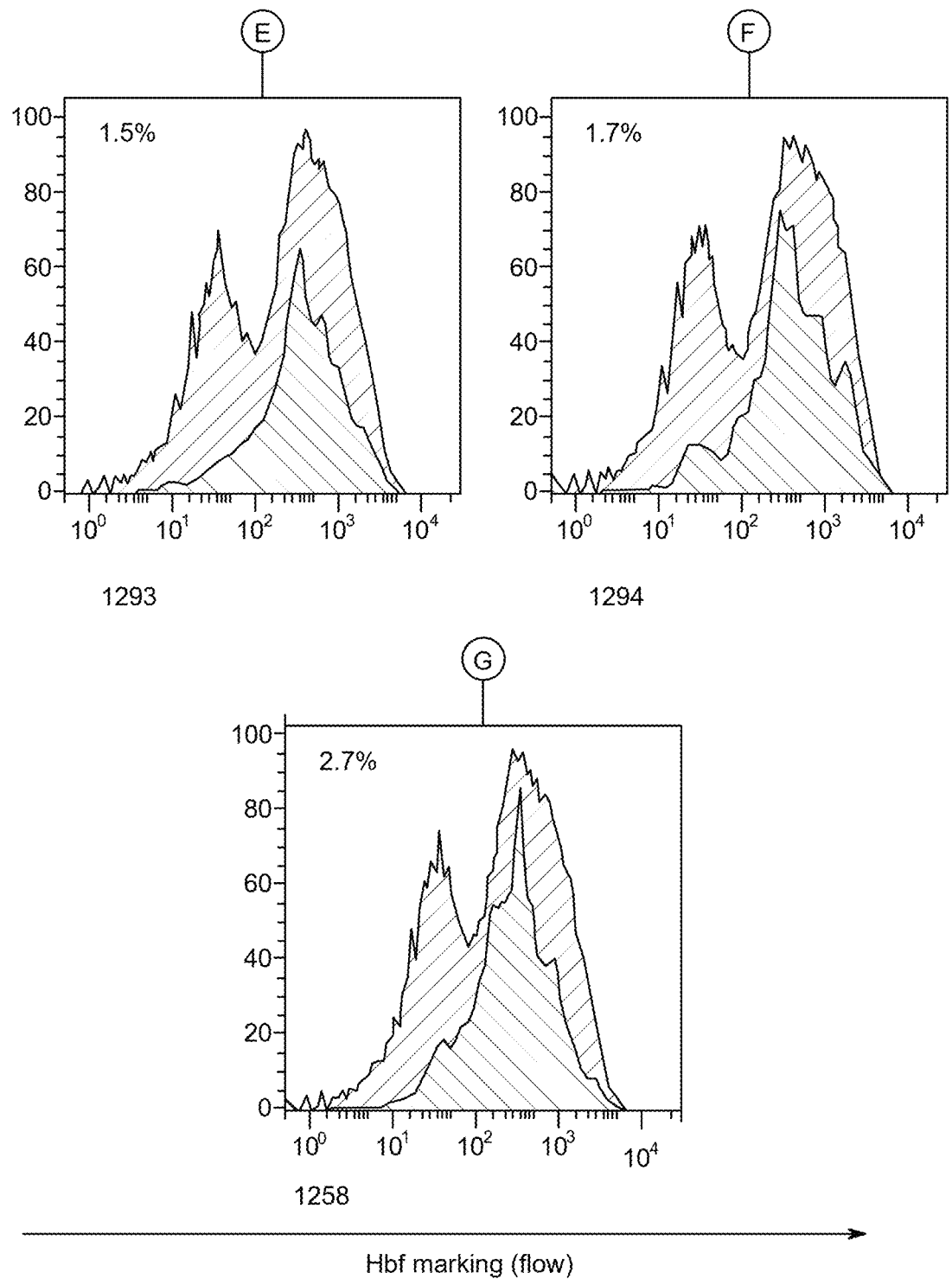
Figure 34:
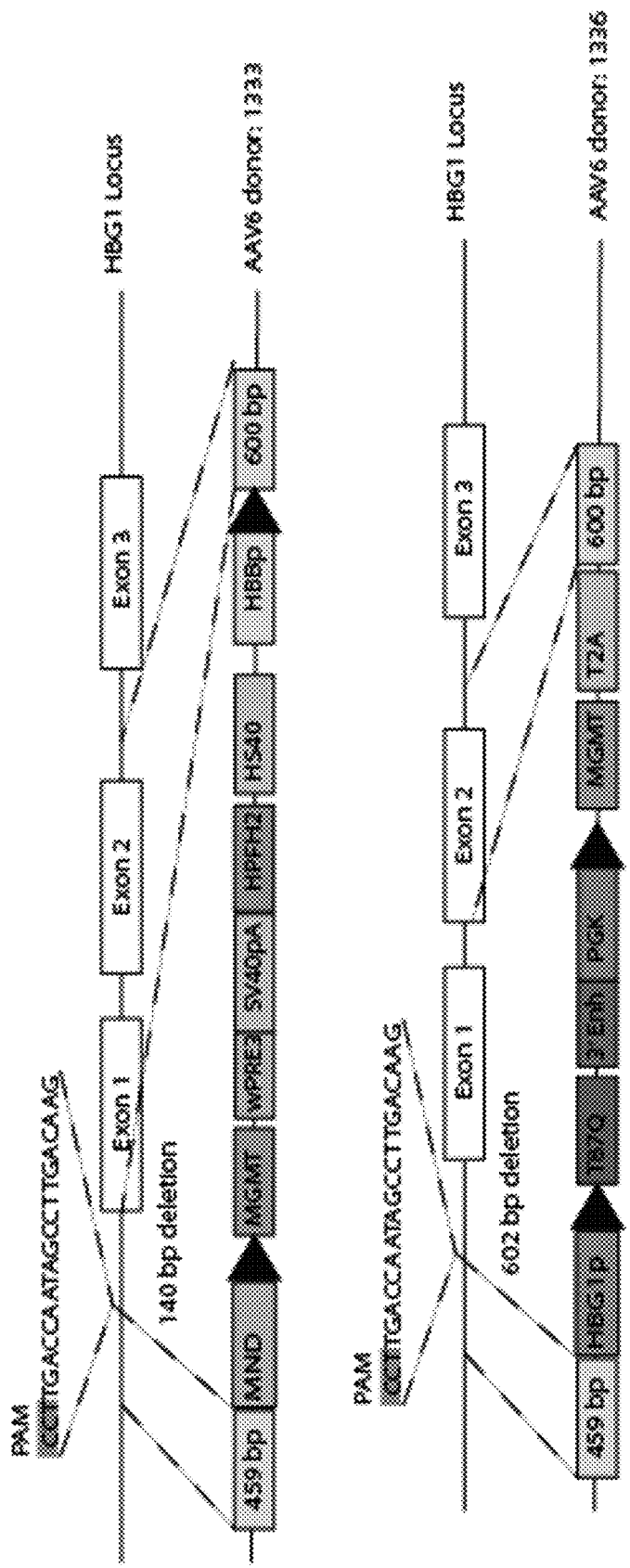
FIG. 34 demonstrates MGMT chemoselection HDR-cassettes (Constructs 1333, 1336) are designed to drive fetal hemoglobin expression as well as the ability to expand engrafted cells pre- or post-transplant via chemoselection.
Figure 35:
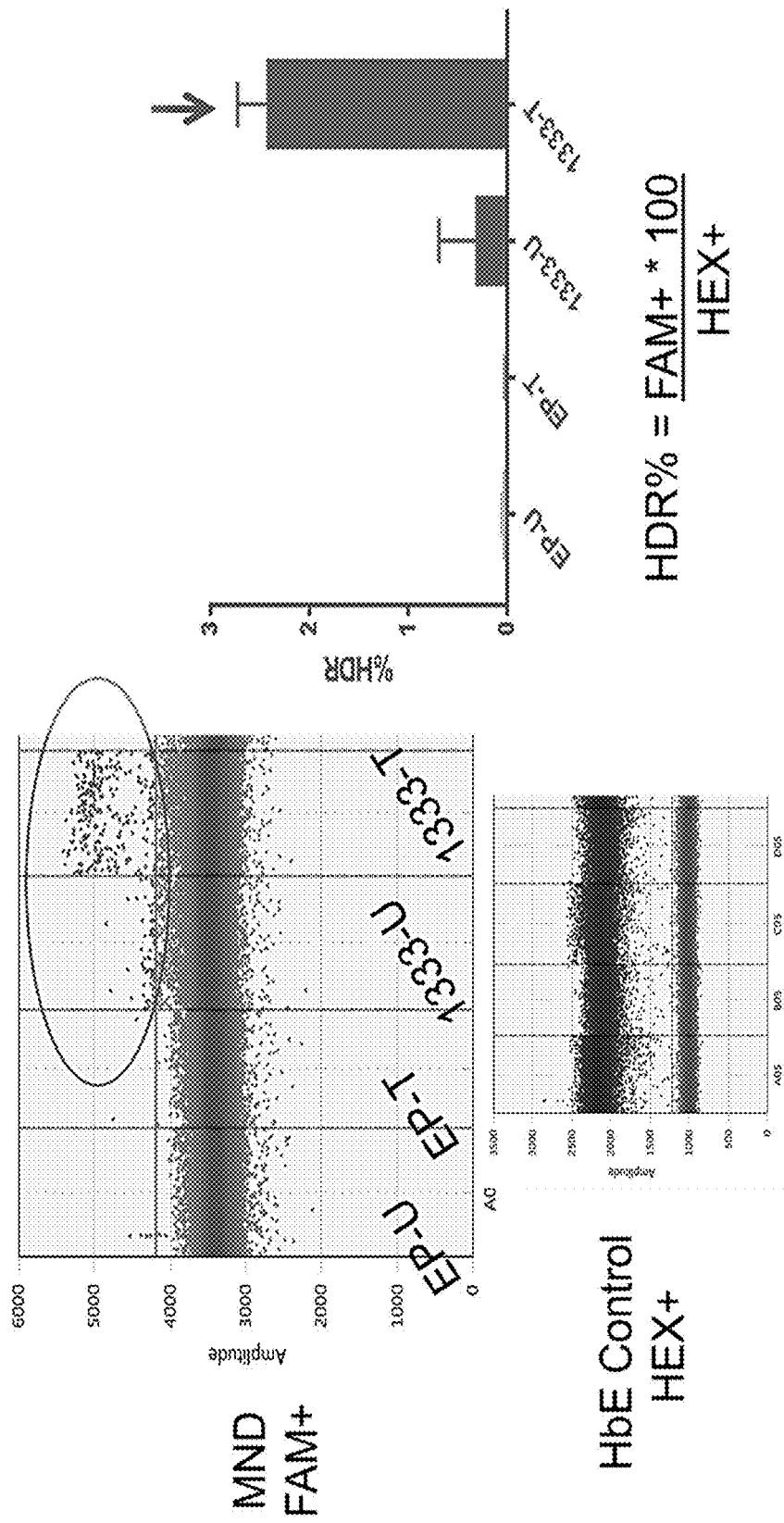
FIG. 35 demonstrates HDR editing and chemoselection using 1333 MGMT HDR donor cassette. Following HDR-editing of CD34+ HSC, chemoselection in vitro allows for 5-fold expansion of the edited population over non-edited cells. Edited cells are tracked using ddPCR based assay.
Figure 36:
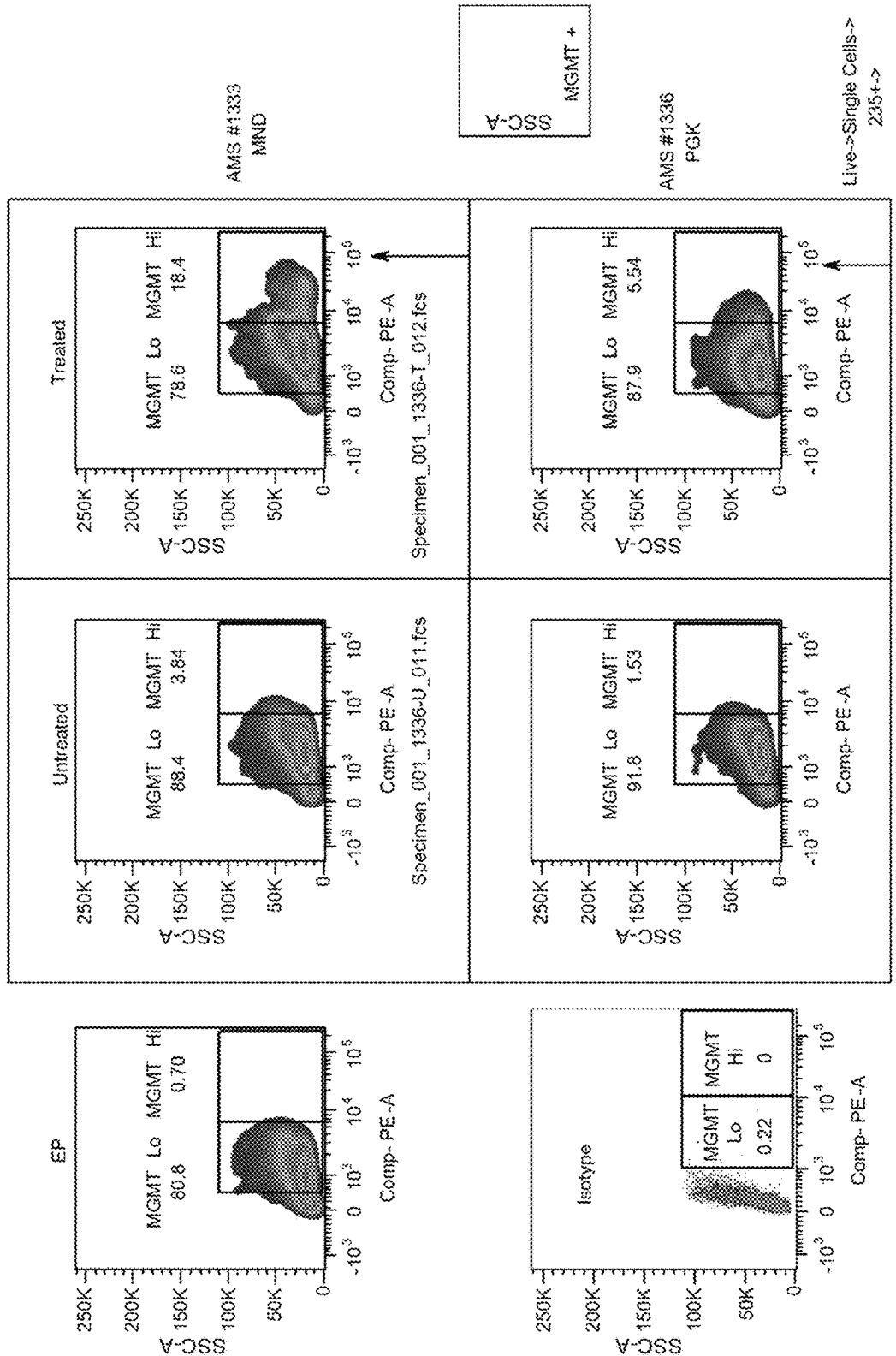
FIG. 36 demonstrates HDR editing and chemoselection using 1333 MGMT HDR donor cassette. Cells edited with an MGMT cassette are able to be chemoselected as shown here by flow cytometry expansion of MGMT Hi cells post selection.

3B. Homology-directed repair templates that integrate at the HBG1 locus and drive $\beta^{T87Q}$ expression. Constructs 1345 (FIG. 27) is a donor template with optimized promoters (HBG1, HBB, PGK) and enhancers (HS-40, HPFH2), poly-A tail (SV-40) with varying homology arm lengths (400-1000 bp) that drive insertion at the HBG1 promoter region and drives HBB promoter-mediated induction of $\beta^{T87Q}$ globin (anti-sickling globin) at the HBG1 locus. (Rhesus version of this construct: 1348 is shown on FIG. 28). Data shown demonstrates results following co-delivery of these templates as AAV and RNP in mobilized primary human CD34+ HSC cells.

Strategy 4: Homology-Directed Repair Templates that Integrate at the HBG1 Locus and Drive HBG1 Expression or $\beta^{T87Q}$ Expression and have a P140K MGMT Cassette that Allows for Chemo-Therapeutic Selection of Edited Human or Non-Human Primate CD34+ Cells (FIGS. 28-31; 34-36).

4A. Homology-directed repair templates that integrate at the HBG1 locus and drive HBG1 expression and allows for chemo-selection. Construct 1333 is a donor template with optimized promoters (HBG1, HBB, PGK) and enhancers (HS-40, HPFH2), poly-A tail (SV-40) with varying homology arm lengths (400-1000 bp) and drive insertion at the HBG1 promoter region and induces HBG1 native promoter-mediated induction of G1 globin and has the P140K MGMT cassette that allows for enrichment of edited cells ex vivo before transplant or in vivo in the patient following infusion of edited cells.

4B. Homology-directed repair templates that integrate at the HBG1 locus and drive $\beta^{T87Q}$ expression. Constructs 1336, 1346, 1343, 1344: These are donor templates with optimized promoters (HBG1, HBB, PGK) and enhancers (HS-40, HPFH2), poly-A tail (SV-40) with varying homology arm lengths (400-1000 bp) that drive insertion at the HBG1 promoter region and drives HBB promoter-mediated induction of T87Q globin (anti-sickling globin) at the HBG1 locus. All constructs also have a P140K MGMT cassette that allows for enrichment of edited cells ex vivo before transplant or in vivo following infusion of edited cells. (Rhesus version: Construct 1348).

Conclusions

1. The data proves the idea that creating deletions using TALEN or RNP nuclease delivery in the promoter of gamma hemoglobin including re-creating the 13 bp deletion at the HBG1 and/or HBG2 loci drive fetal hemoglobin expression.
2. TALEN's as well as Crispr/Cas9 nucleases can create deletions in the promoter including re-creating the 13 bp deletion as well as a range of other useful deletions.
3. Edited mobilized human CD34+ HSC engraft and retain their multi-lineage engraftment potential in primary and secondary recipient mice.
4. Edits are sustained in the LT-HSC population and are able to re-populate the bone marrow in the scenario of a primary and secondary transplant and to continue to facilitate fetal hemoglobin production.
5. The HBG1 locus is amenable to HDR. Construct 1263 drives HDR rates of ~30% as assessed by GFP+ cells following co-delivery of TALEN and 1263 and confirms that the locus supports HDR.
6. Constructs 1324, 1325, and 1345 drive HDR following co-delivery of RNP+AAV donors. Construct 1345 produces 3.5% HDR in RNP+1345 treated cells.
7. AAV HDR-donor cassettes promote gamma globin or T87Q globin expression following HDR depending on the respective cassette.
8. MGMT donor templates are effective in permitting selection for HDR-edited cells. There is 5-fold enrichment of HDR edited cells when chemo-selection is used in vitro in CD34+ cells containing the MGMT cassettes.

The data confirms that the d13 deletion and related useful deletions can be used effectively as a therapeutic approach for treating sickle cell anemia and thalassemia. Most importantly, its shown that HDR cassettes can be delivered to HBG1 locus following nuclease cleavage at this site. The approach is useful and novel as both NHEJ and HDR outcomes will drive a functional response that is desirable. This combined strategy is unique as all edited cells (including HDR and NHEJ edited outcomes) have a therapeutic benefit and these combined events are more likely to provide a curative approach in sickle or β-thalassemia patients.

Example 3

Talen Mediated Therapeutic Gene Editing Strategy for β-Hemoglobinopathies

Hemoglobinopathies including sickle cell disease (SCD) and β-thalassemia are the most common single-gene disorders in the world and represent a major global public health concern. The unifying principle of this heterogeneous mix of gene mutations is the decreased production of wild type hemoglobin molecules either due to structural defects in the case of SCD or insufficient production of β-globin subunits.

Patients who carry both a mutation causing a hemoglobinopathy as well as increased expression of fetal hemoglobin (HPFH) tend to exhibit a milder phenotype. These mutations range from large deletions to single nucleotide polymorphisms. The focus of this Example is on a unique naturally occurring 13 bp deletion in the γ-hemoglobin promoter that has been shown to induce high levels of fetal hemoglobin expression.

The 13 bp deletion site offers a unique target for therapeutic gene editing in the treatment of hemoglobinopathies. The sequence specific introduction of double strand breaks using targeted nucleases, such as TALENs or RNPs, has the potential to generate a HPFH phenotype by NHEJ (via disruption of the distal CCAAT box) but also allows for the integration of therapeutic repair templates and selection elements via HDR.

Methods:

TALEN Design & Testing—Multiple TALEN pairs were designed, Golden Gate assembled into a novel expression vector with an encoded poly-A tail, mRNA was generated by CellScript IVT. mRNA was transfected into human mobilized peripheral blood CD34 cells using the Neon Transfection System.

Editing Efficiency—INDEL generation detected by T7 Assay following globin specific nested PCR. Colony sequencing and next generation sequencing were carried out to determine specific sequence variants. A globin specific ddPCR assay was developed to detect INDEL generation.

Erythroid Differentiation—Following TALEN editing, CD34 cells are moved to erythroid differentiation media and cultured for 7-10 days. HbF expression is assessed by flow and HPLC.

Murine Transplants—1e6 CD34 cells (Control & TALEN transfected) were injected by tail vein into W41 mice following minimal radiation (150rad) 18 hours post electroporation. Marrow was harvested and sort/analyzed 24 weeks post transplant. Secondary animals were transplanted with 50% of the primary harvested cells and were subsequently harvested at 9 weeks.

HR Template Testing—HR Templates were designed and synthesized, packaged into AAV6 constructs and introduced to the CD34 cells at the time of TALEN transfection. Cells were differentiated and analyzed by flow and HPLC.

Results (In Vitro)

An experimental timeline (shown below) provided for neon transfection of human mobilized peripheral blood CD34 cells.

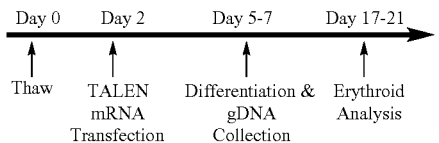

Figure 16:
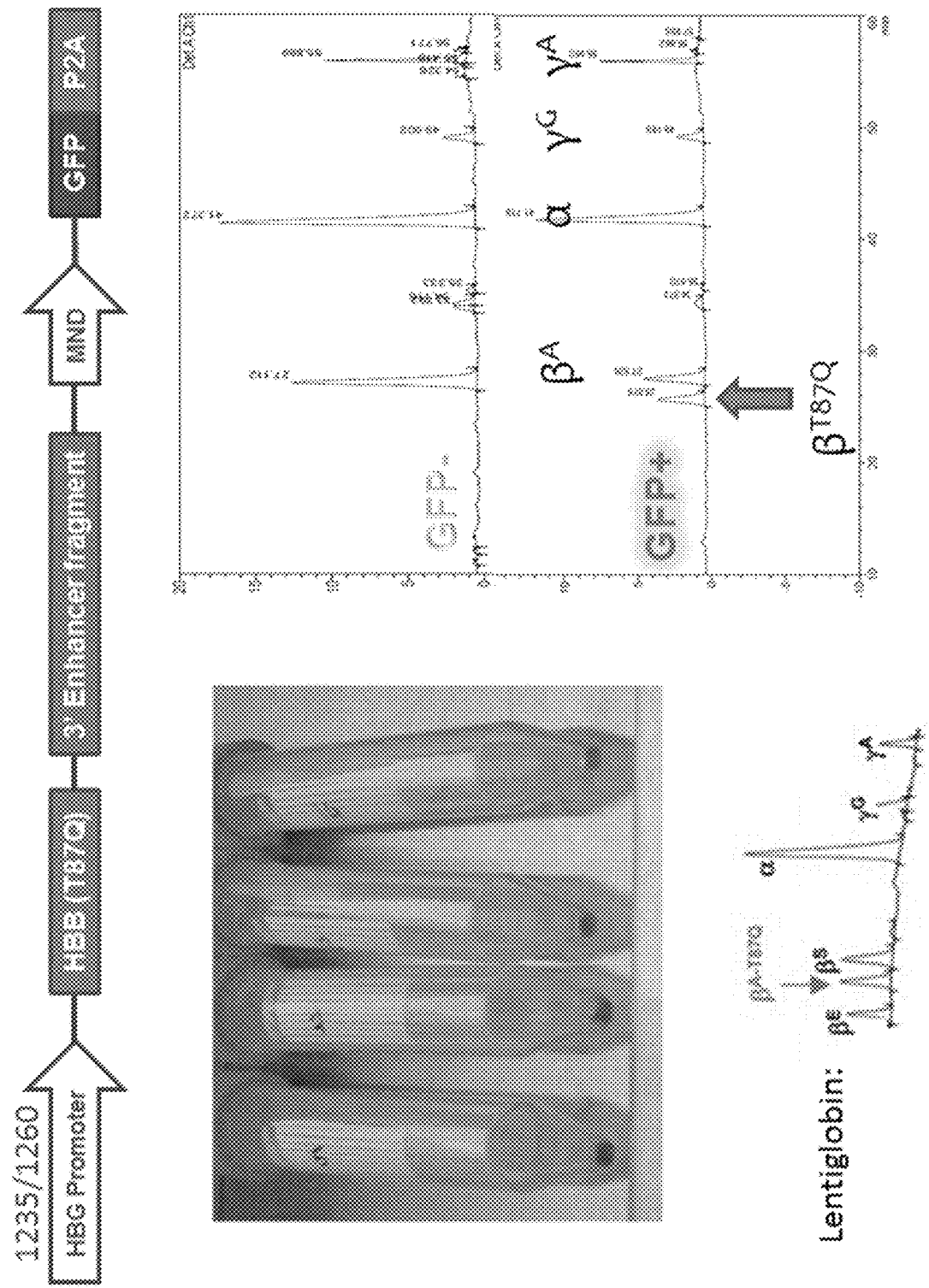
FIG. 16 demonstrates GFP Positive cells generated using construct 1235/60 also express T87Q as well as increased levels of HBF.
Figure 17:
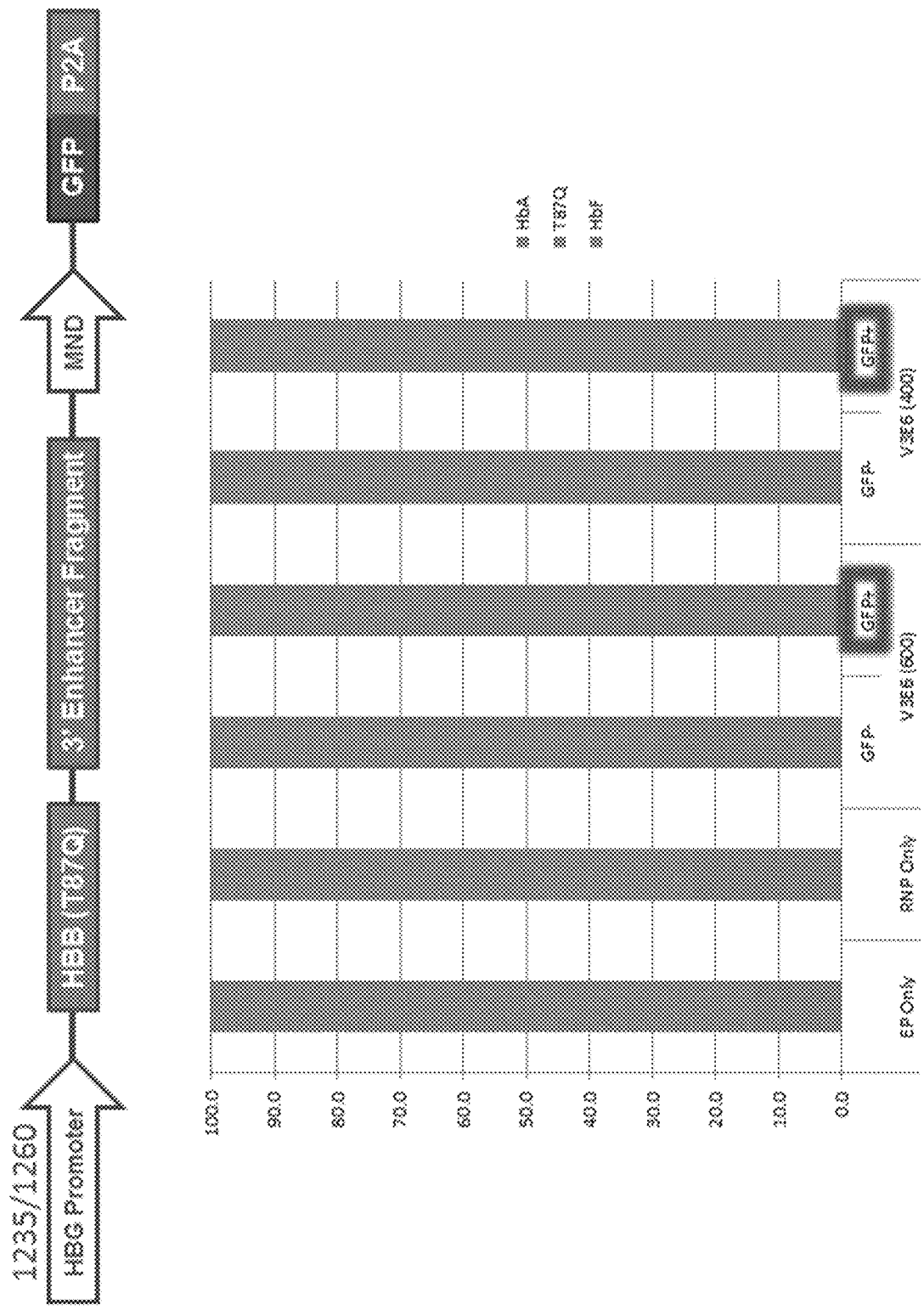
FIG. 17 demonstrates GFP Positive cells express both T87Q as well as increased levels of HBF FIG. 18 demonstrates the HDR templates V3E6 (with either 600 or 400 bp homology arms) are capable of expressing T87Q following HDR-editing. Fetal hemoglobin also increases in these cells likely due to NHEJ events in other alleles.
Figure 18:
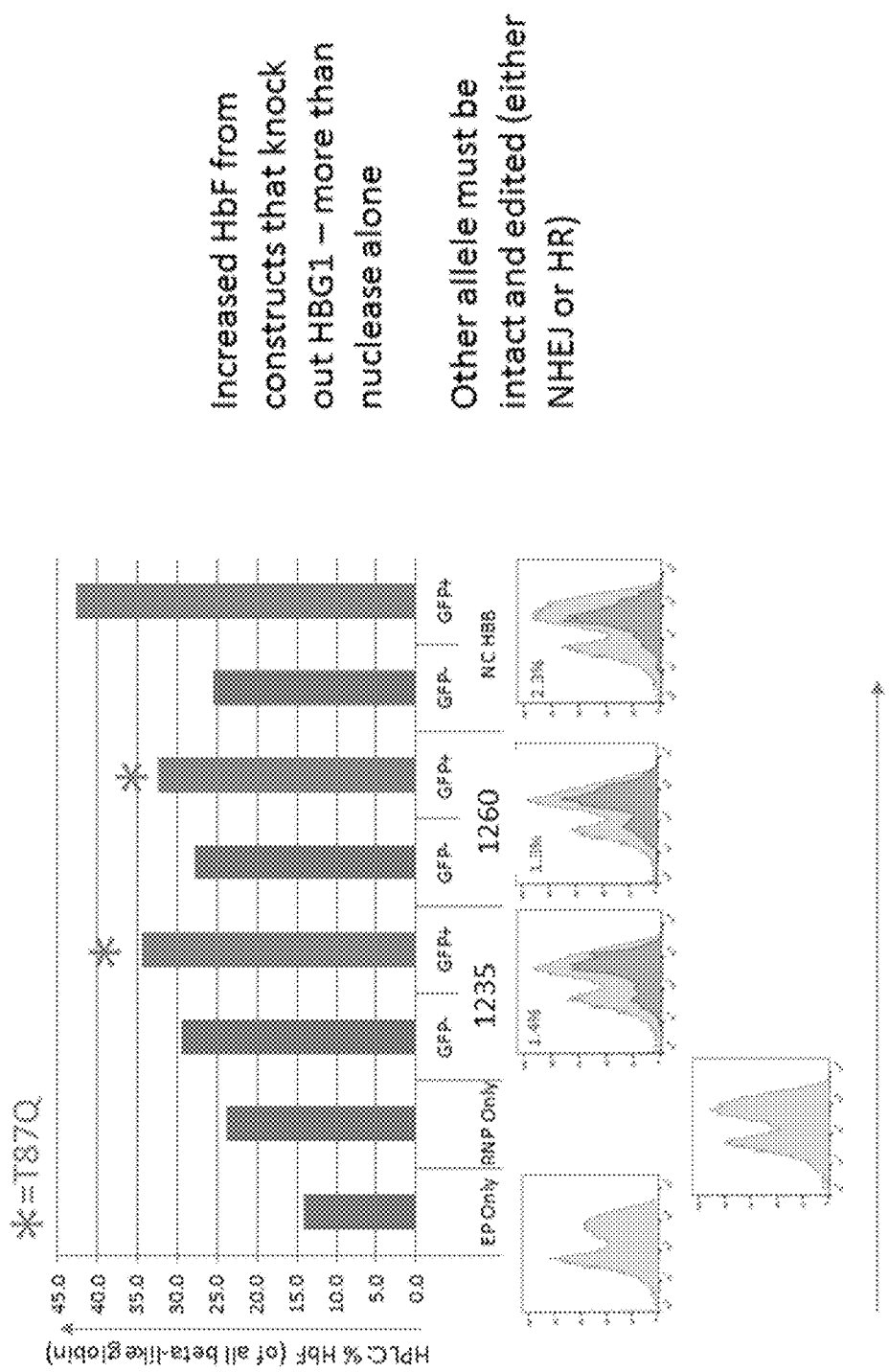
Figure 19:
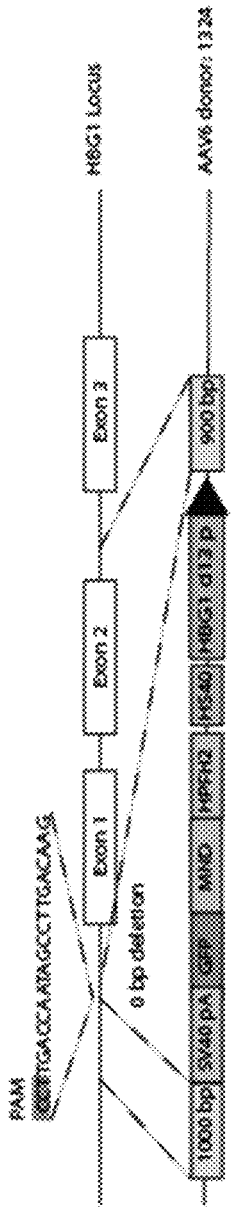
FIG. 19 demonstrates Construct 1324 is a rAAV construct that can drive homology-dependent repair into the HBG1 locus. The donor template introduces a d13 promoter that drives gamma-1 globin. MND-GFP is in the reverse orientation. It has an alternate HDR site due to incidental homology.
Figure 20:
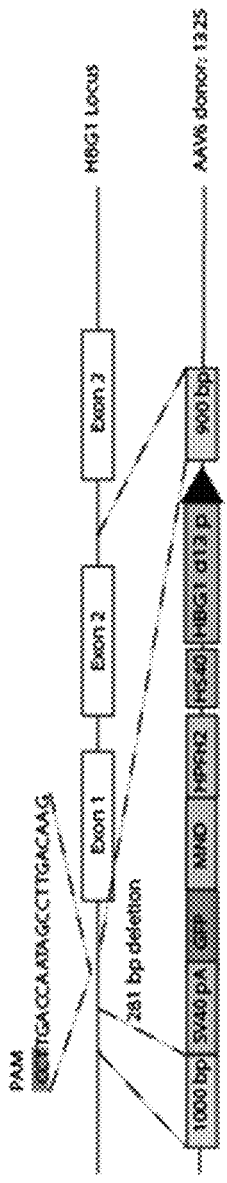
FIG. 20 demonstrates Construct 1325 is a rAAV construct that can drive homology-dependent repair into the HBG1 locus. The donor template introduces a d13 promoter that drives gamma-1 globin. This is a deletional construct that has a 240 bp deletion that may lower HDR rates. MND-GFP is in the reverse orientation.
Figure 21:
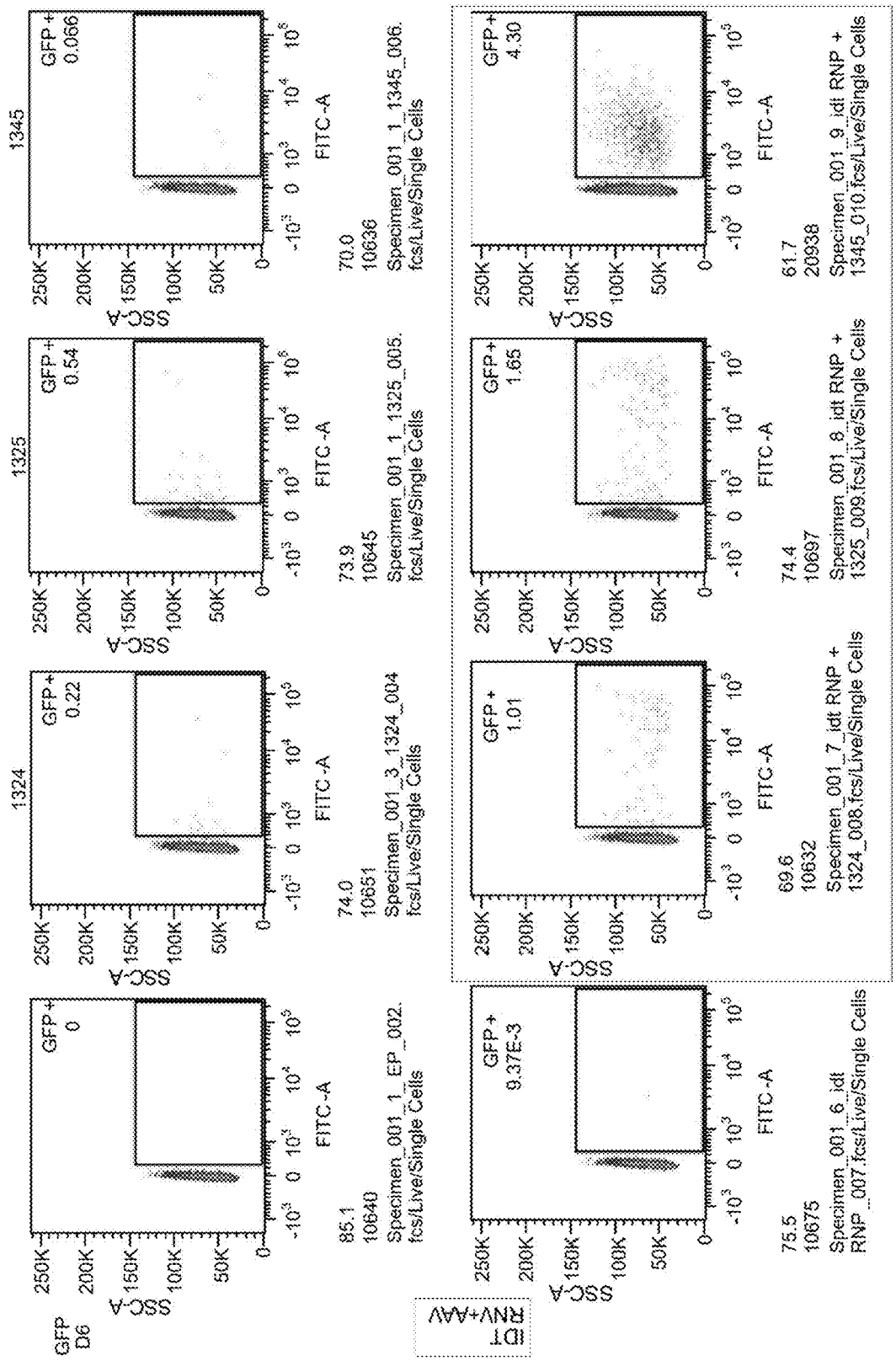
FIG. 21 shows that HDR occurs at HBG1 locus following with co-delivery of RNP and indicated AAV donor. The GFP+ population seen in the boxes are from day 6 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples. Construct 1345 is shown on FIG. 27.
Figure 21:
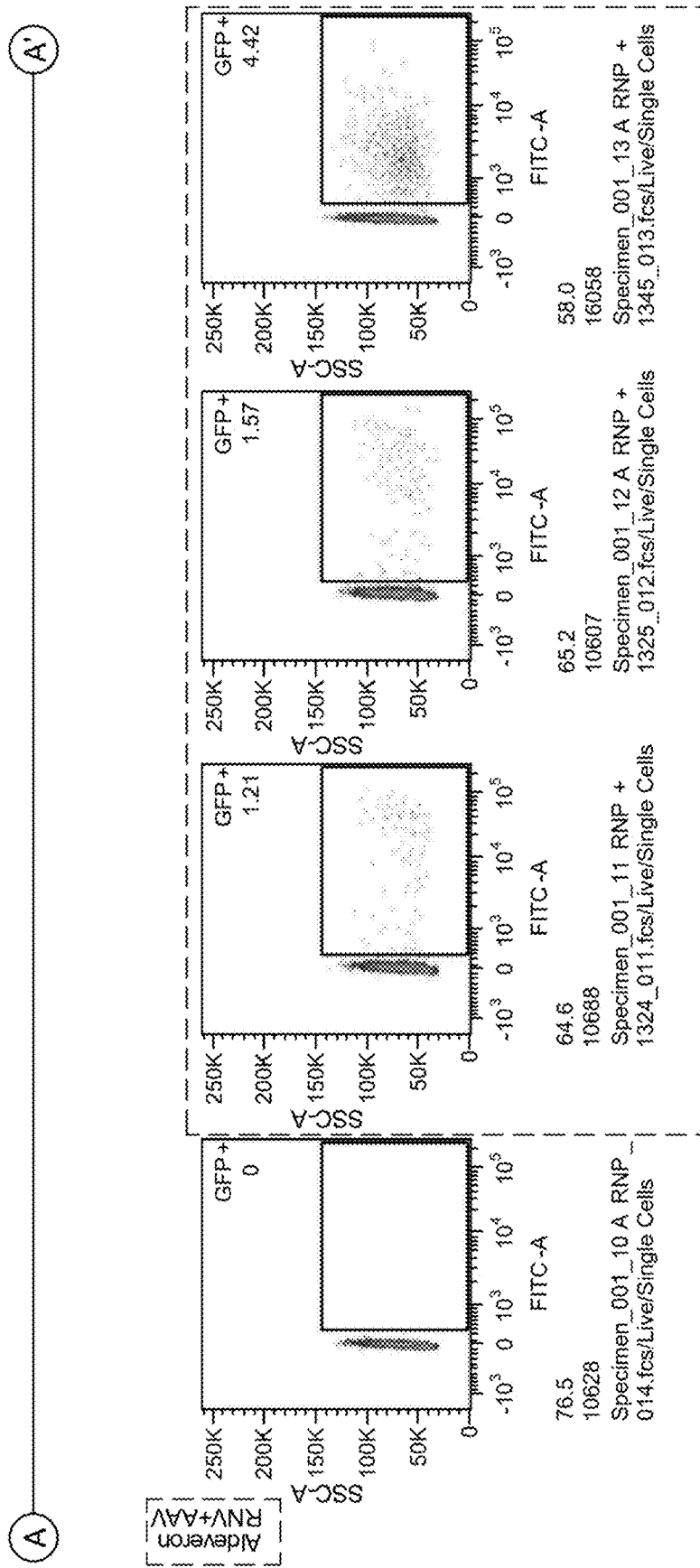
Figure 22:
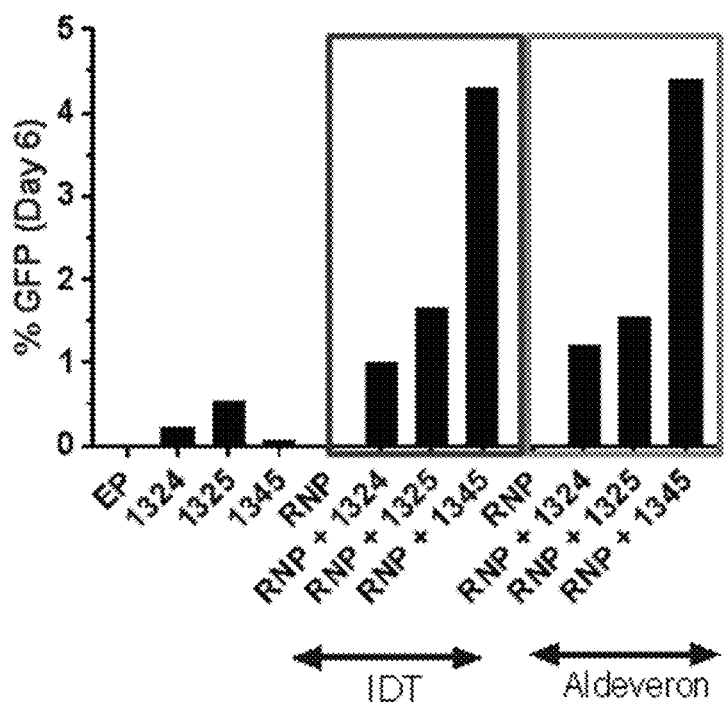
FIG. 22 shows that HDR occurs at HBG1 locus following with co-delivery of RNP and indicated AAV donor. The GFP+ population are from day 6 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples.
Figure 23:
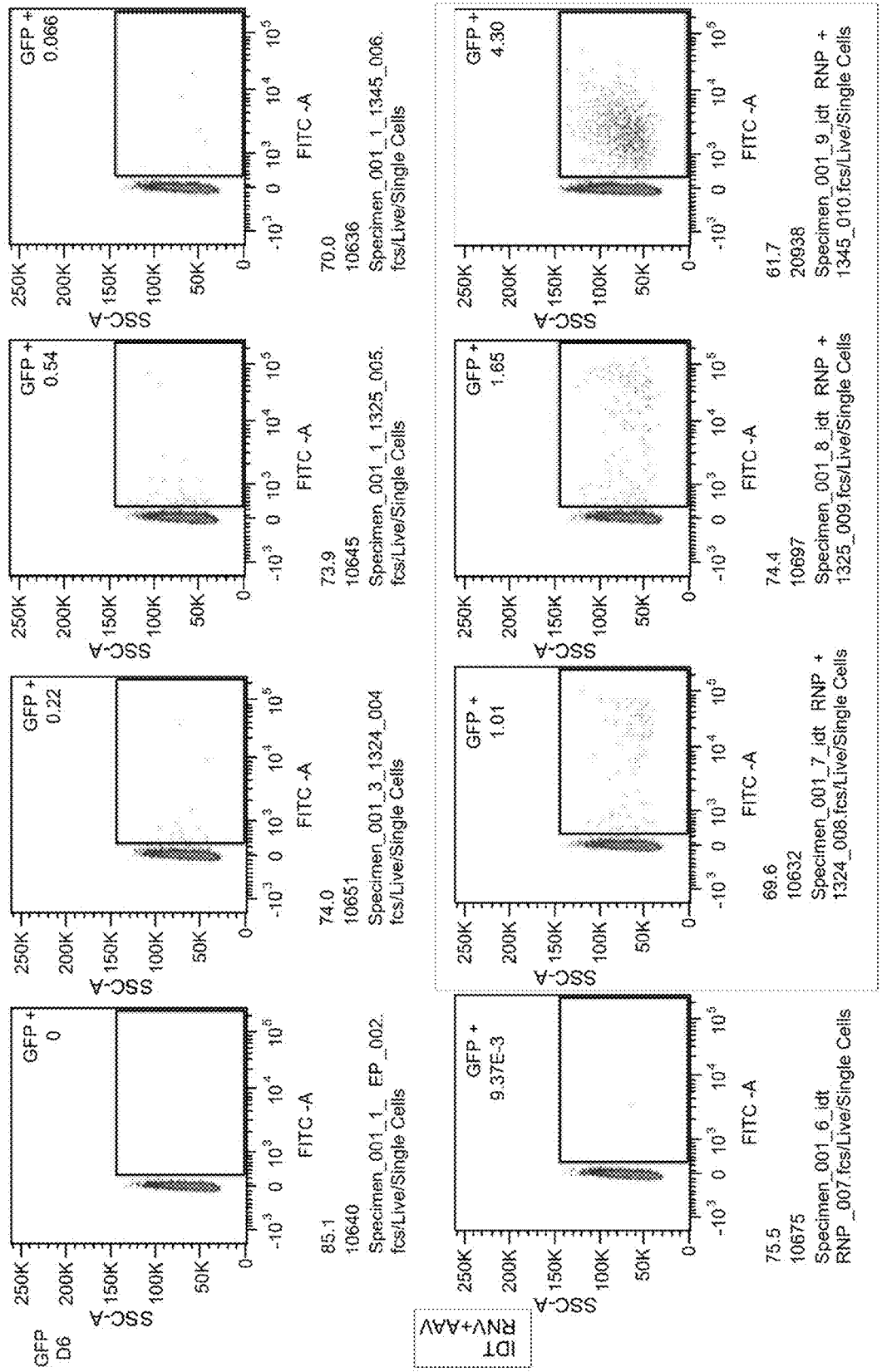
FIG. 23 shows that HDR occurs at HBG1 locus following with co-delivery of RNP and indicated AAV donor. The GFP+ population seen in the boxes are from day 13 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples.
Figure 23:
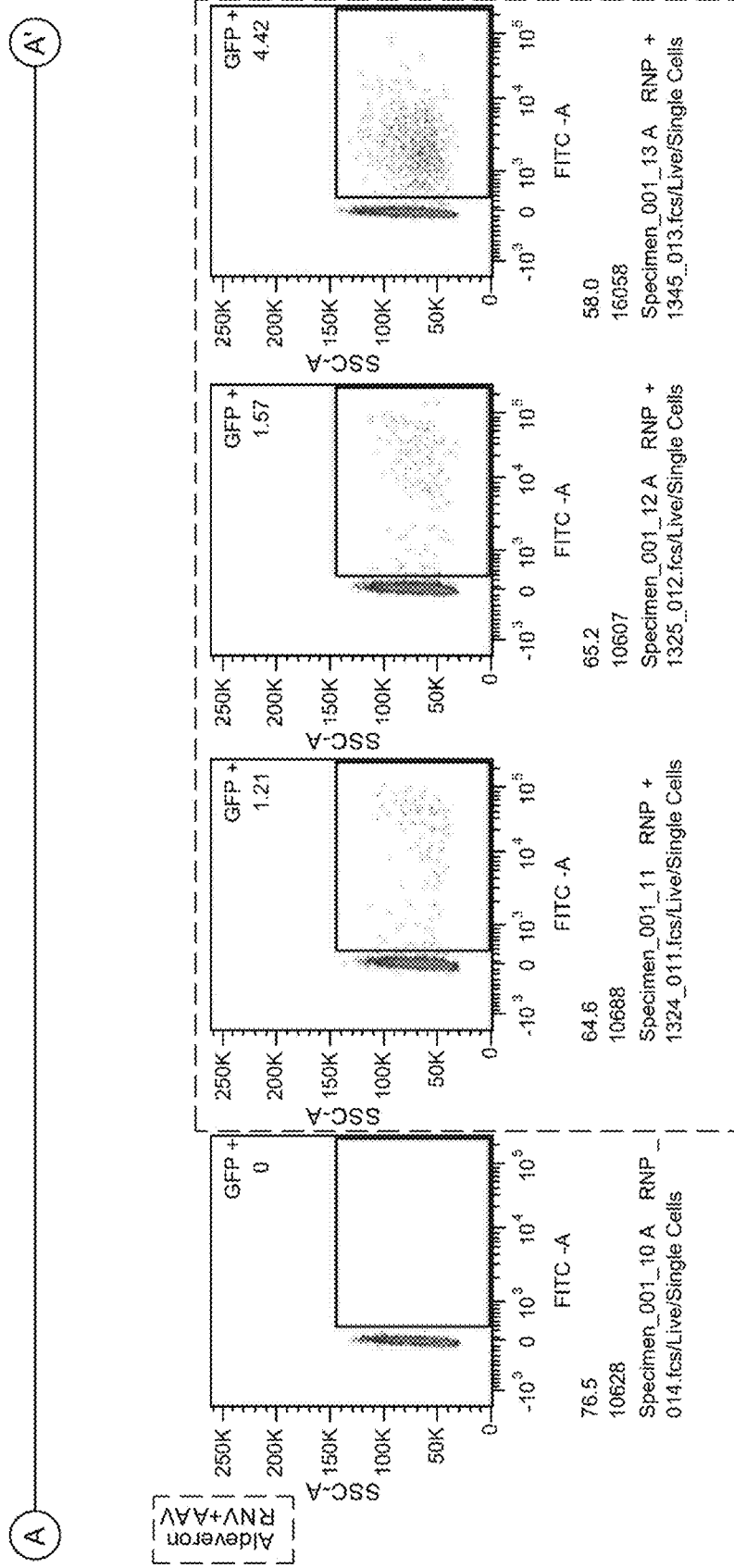
Figure 24:
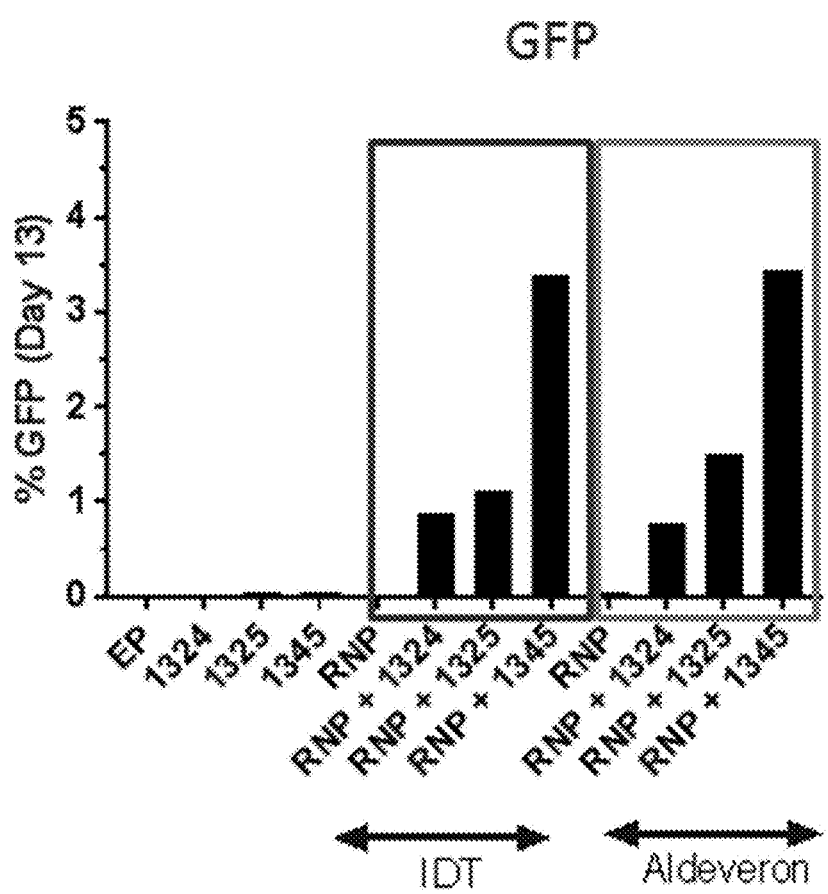
FIG. 24 shows that HDR occurs at HBG1 locus following with co-delivery of RNP and indicated AAV donor. The GFP+ population are from day 13 post-editing and shows that all 3 AAV donors support HDR-based editing of HBG1 locus in RNP+1324, RNP+1325, RNP+1345 samples. Irrespective of the Cas9 vendor used there is integration of AAV into the HBG1 locus in RNP+1324, RNP+1325, RNP+1345 samples.
Figure 25:
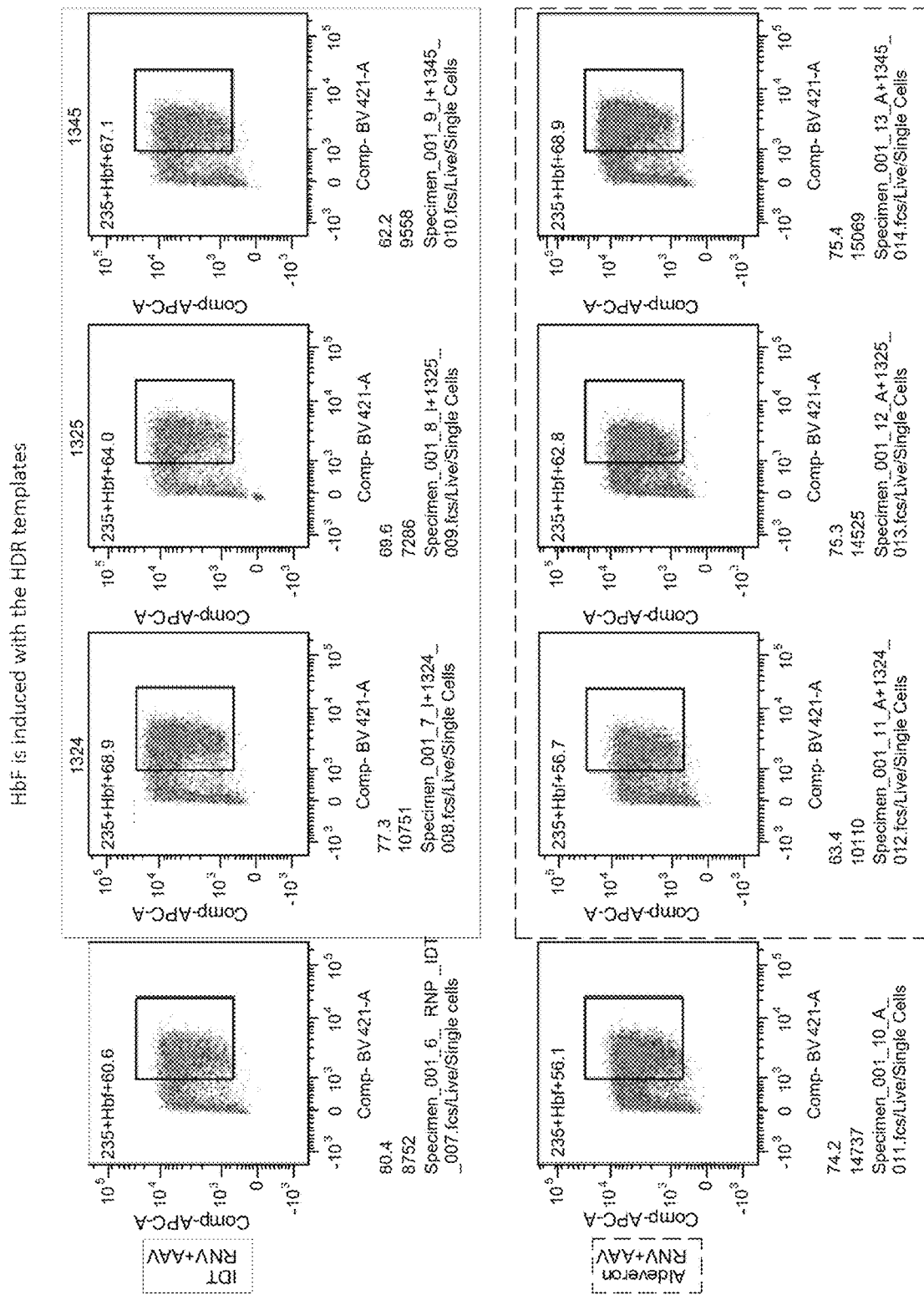
FIG. 25 shows that HDR drives increase in fetal hemoglobin induction in erythroid cells. All 3 AAV donors support HDR-based editing and lead to increased fetal hemoglobin induction following integration into the HBG1 locus in RNP+1324, RNP+1325, RNP+1345 samples. Irrespective of the Cas9 vendor used there is increased fetal hemoglobin induction with integration of AAV into the HBG1 locus in RNP+1324, RNP+1325, RNP+1345 samples.
Figure 26:
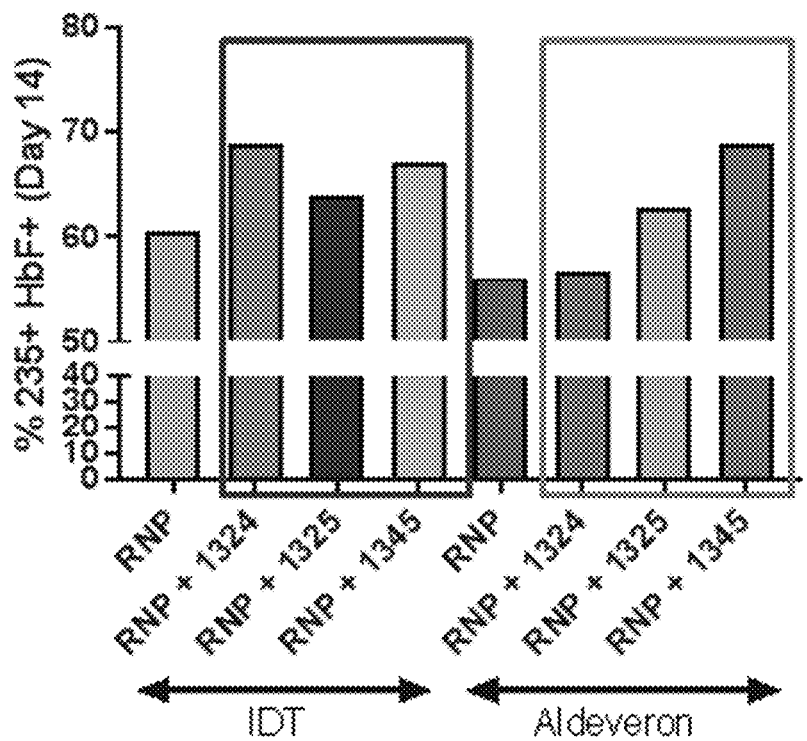
FIG. 26 shows that HDR drives increase in fetal hemoglobin induction in erythroid cells. All 3 AAV donors support HDR-based editing and lead to increased fetal hemoglobin induction following integration into the HBG1 locus in RNP+1324, RNP+1325, RNP+1345 samples. Irrespective of the Cas9 vendor used there is increased fetal hemoglobin induction with integration of AAV into the HBG1 locus in RNP+1324, RNP+1325, RNP+1345 samples.
Figure 38:
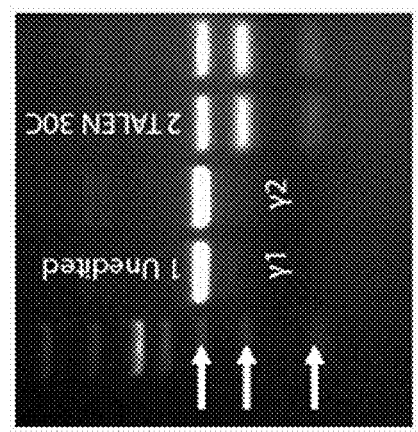
FIG. 38 provides a T7 analysis showing del13 TALEN pair transfection induces INDELs in human CD34 cells at both the γ1 (HBG1) and γ2 (HBG2) locus.
Figure 37:
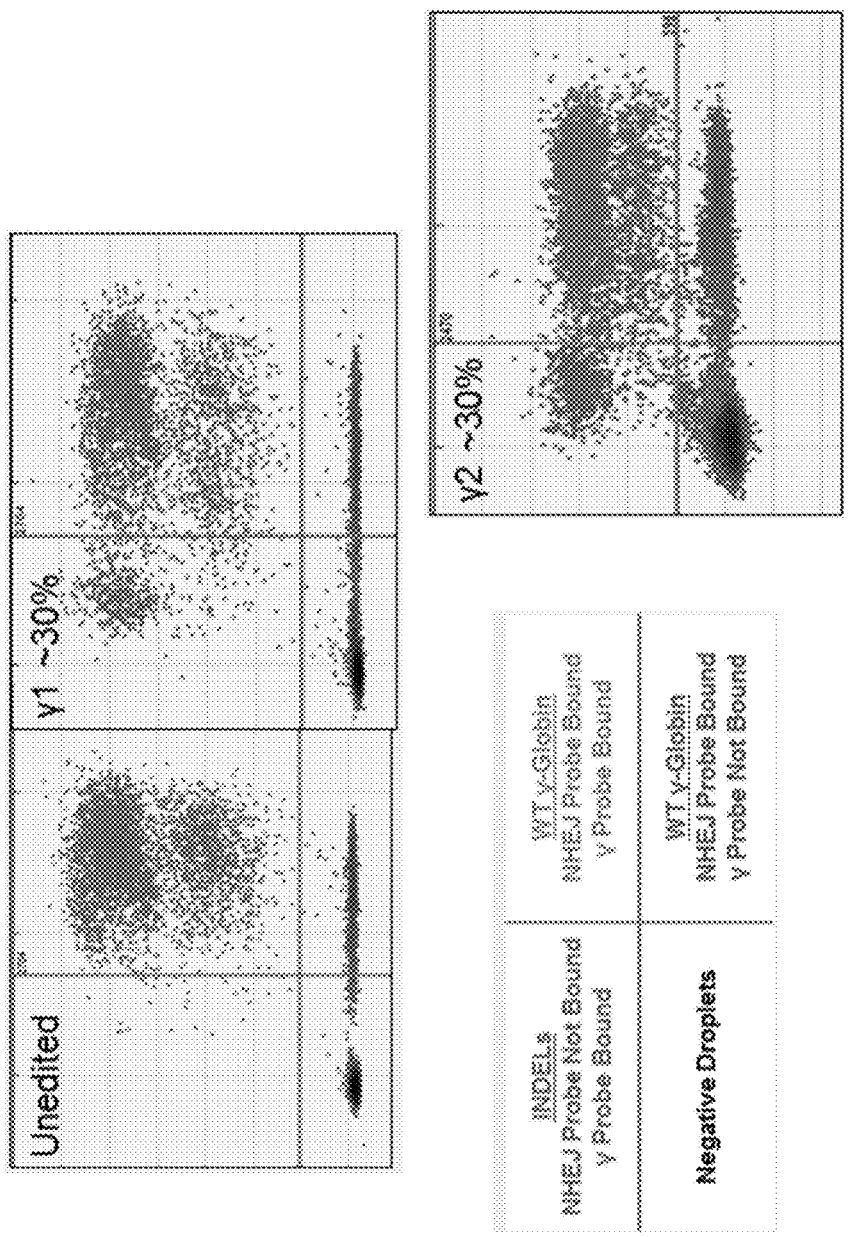
FIG. 37 demonstrates 20-30% INDEL rate at both loci using γ1 (HBG1) and γ2 (HBG2) specific probes with ddPCR. This increases to 50% with a 30 C recovery step.
Figure 39:
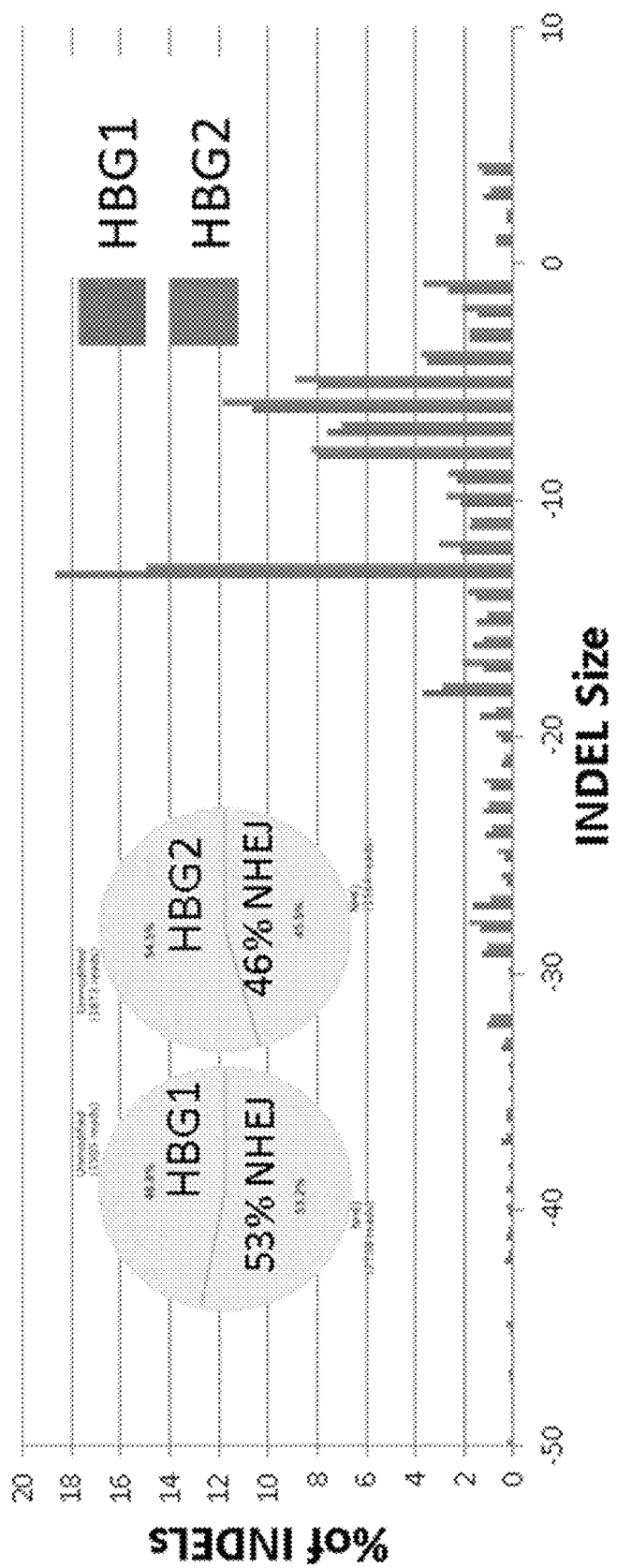
FIG. 39 shows confirmed editing rates (50% in this example) via Next Gen Sequencing. There is an overrepresentation of the 13 bp deletion likely the result of microhomology in the region.
Figure 40:
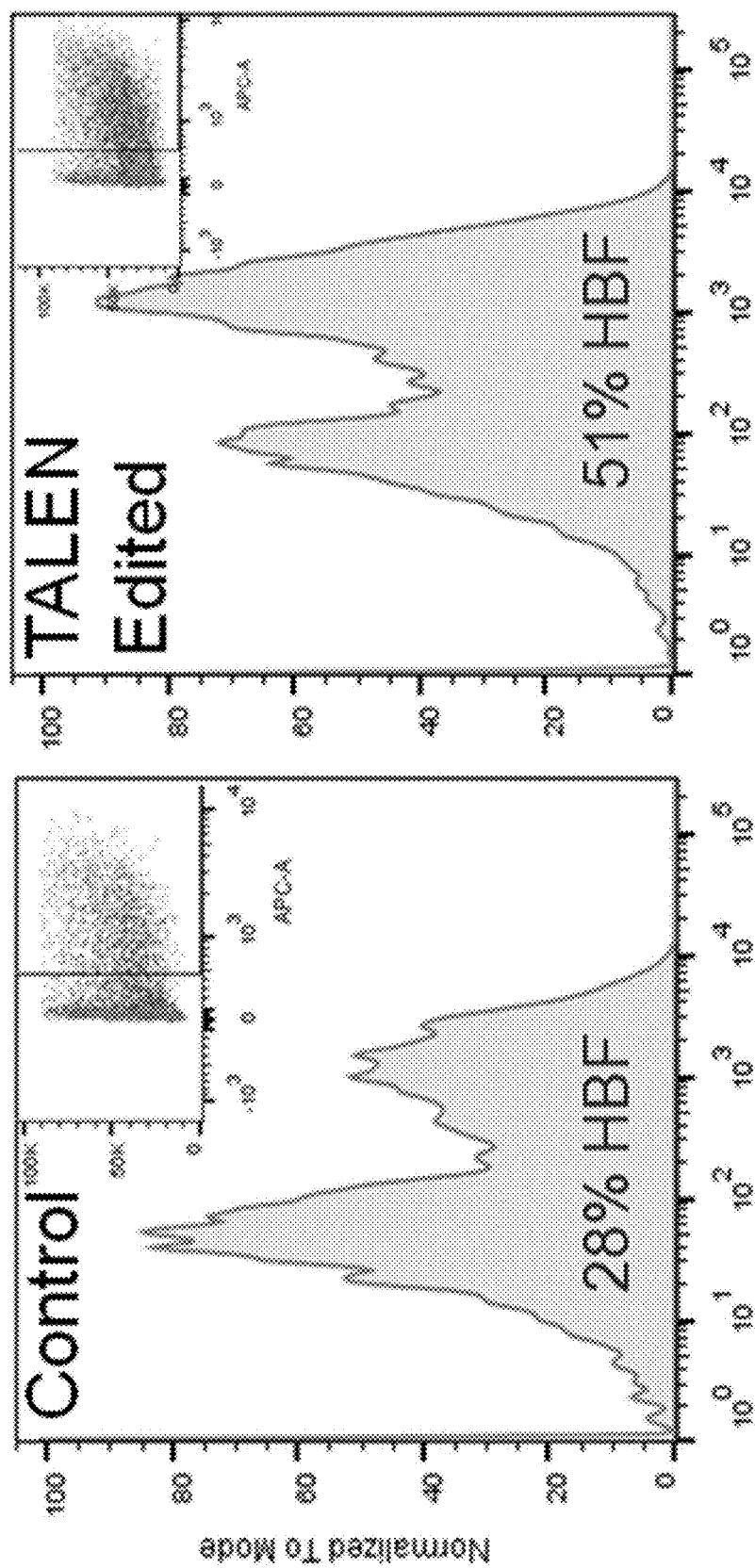
FIG. 40 shows results of HbF induction by flow cytometry. TALEN editing of peripheral blood CD34 cells followed by erythroid differentiation results in significantly increased number of F-cells.
Figure 41:
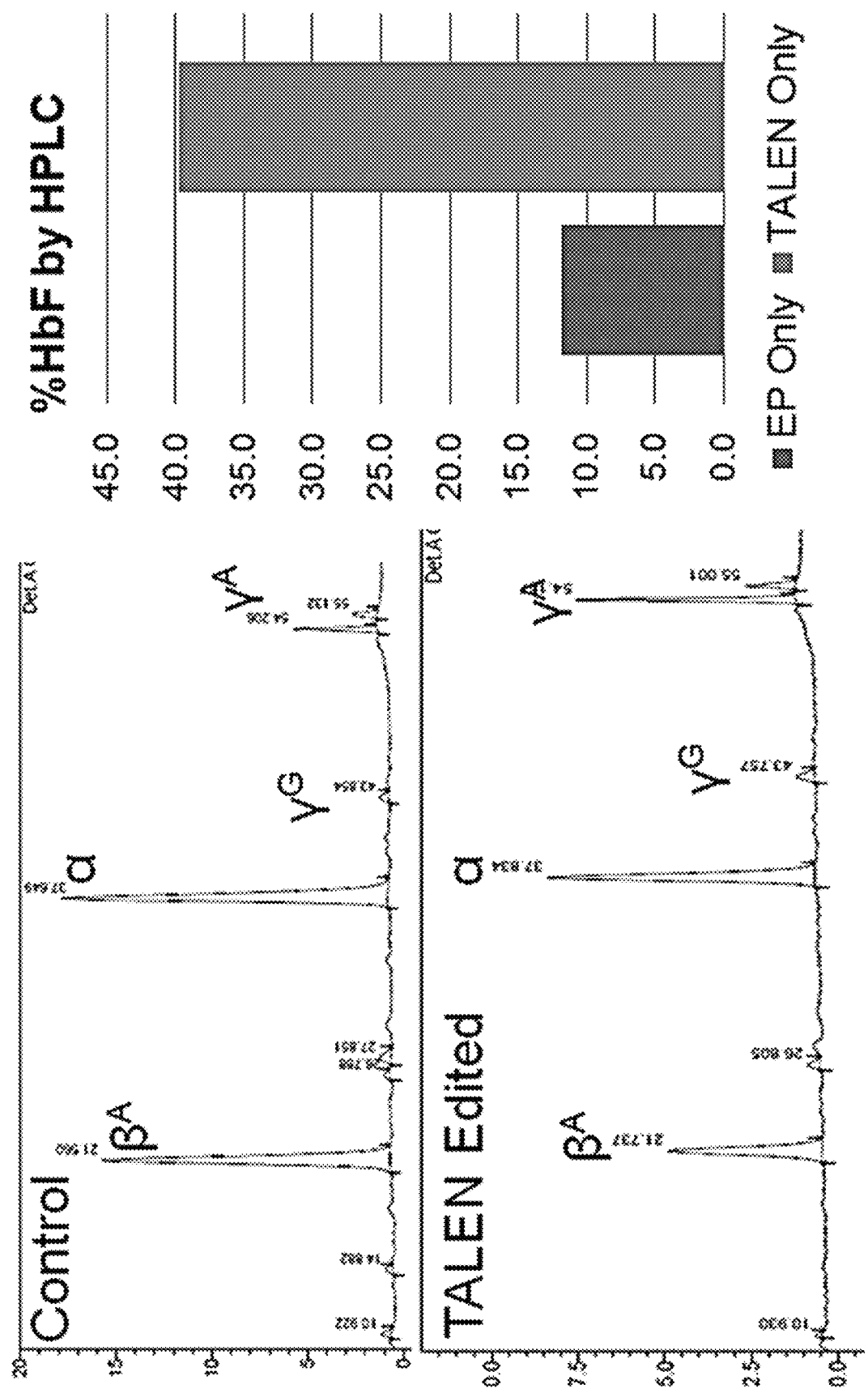
FIG. 41 shows results of HbF induction by HPLC. TALEN editing of peripheral blood CD34 cells followed by erythroid differentiation results in significantly increased HbF protein expression. The difference in protein expression is greater than the percent F-cells suggesting that the increased F-cells express higher levels of HbF than control F-cells.

T7 Analysis showed that del13 TALEN pair transfection induces INDELs in human CD34 cells at both the γ1(HBG1) and γ2(HBG2) locus (FIG. 38). ddPCR showed 20-30% INDEL rate at both loci using γ1(HBG1) and γ2(HBG2) specific probes. This increased to 50% with a 30 C recovery step (FIG. 37). Next gen sequencing then provided confirmed editing rates (50% in this example). There was an overrepresentation of the 13 bp deletion, which was likely the result of microhomology in the region (FIG. 39). HbF induction by flow cytometry demonstrated TALEN editing of peripheral blood CD34 cells followed by erythroid differentiation, which resulted in significantly increased number of F-cells (FIG. 40). HbF induction by HPLC demonstrated TALEN editing of peripheral blood CD34 cells followed by erythroid differentiation, which resulted in significantly increased HbF protein expression (FIG. 41). The difference in protein expression was greater than the percent F-cells suggesting that the increased F-cells expressed higher levels of HbF than control F-cells. HR template integration yielded HbF induction and anti-sickling T87Q expression (FIGS. 16-17). Combined, over 60% of the globin expressed in edited cells is potentially clinically beneficial.

Results (In Vivo)

An experimental timeline (shown below) provided for neon transfected human CD34 cells transplanted by tail vein injection in W41 mice.

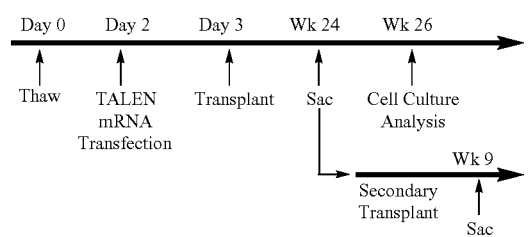

Figure 42:
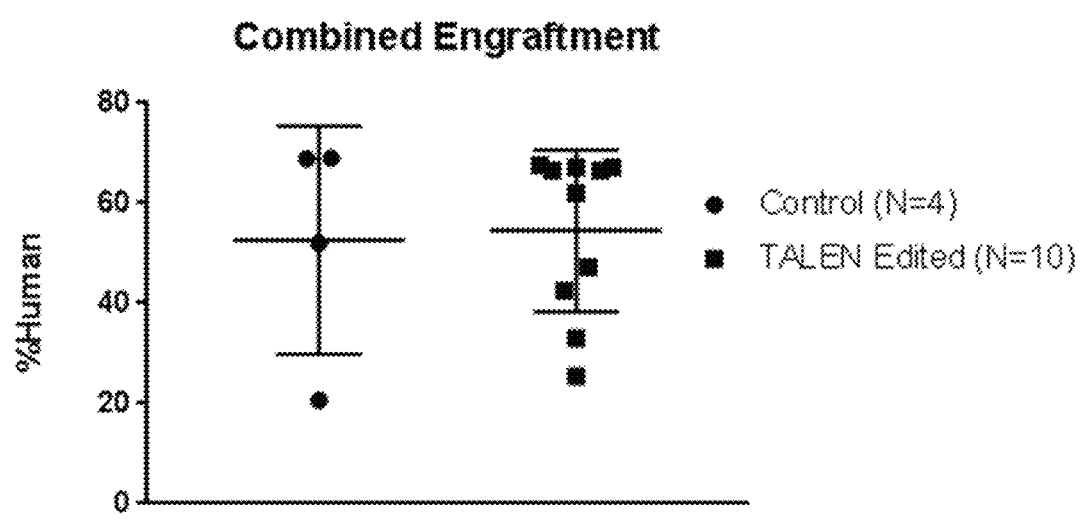
FIG. 42 shows results of human engraftment at week 24. No significant difference in percent human engraftment between control and edited cells is seen.
Figure 43:
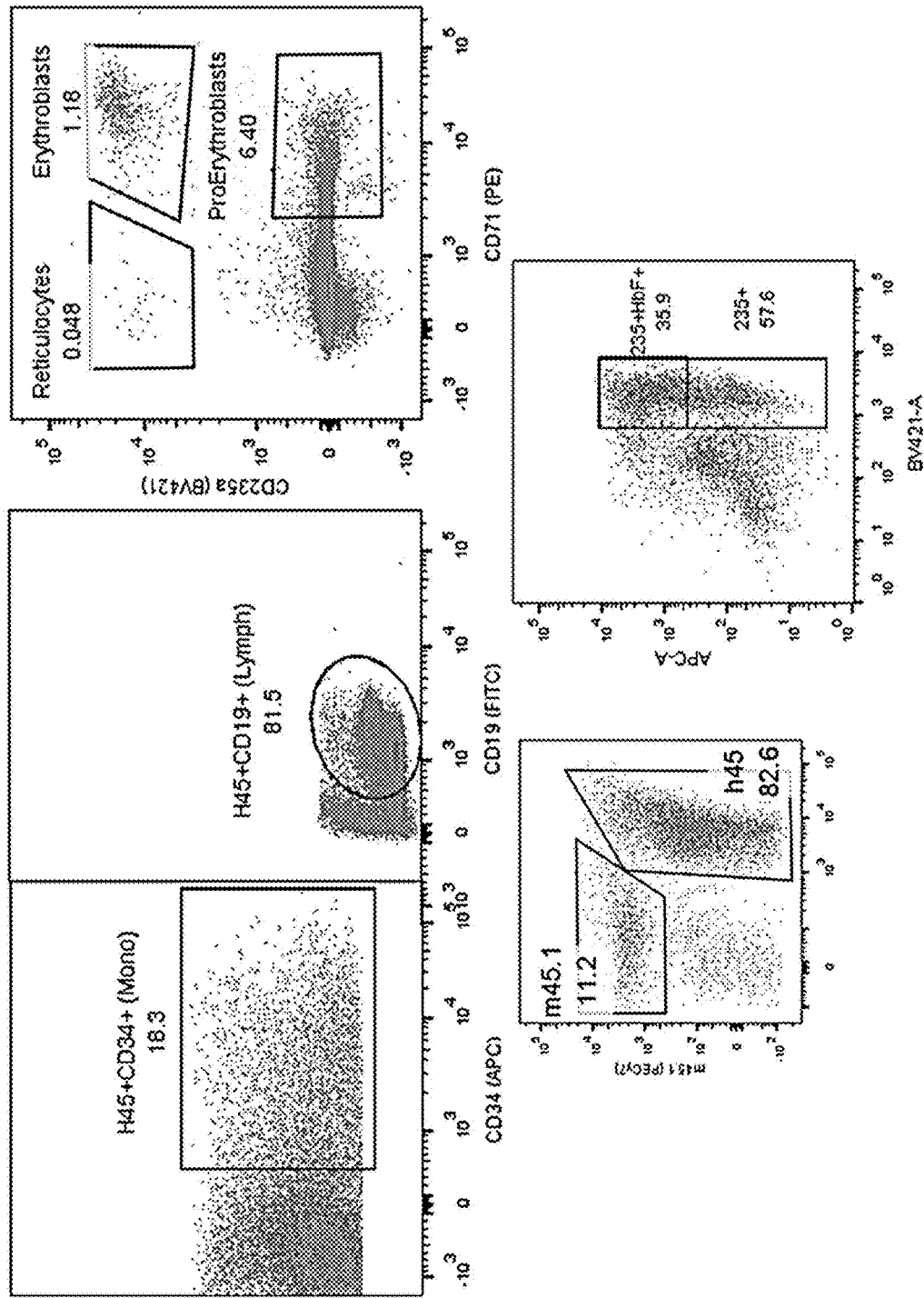
FIG. 43 shows engrafted edited CD34 cells generate all human hematopoietic lineages. Human erythroid, CD34+ Lymphoid and Myeloid, and CD19+ cells were all identified and sorted from harvested marrows following transplant (W24).
Figure 44:
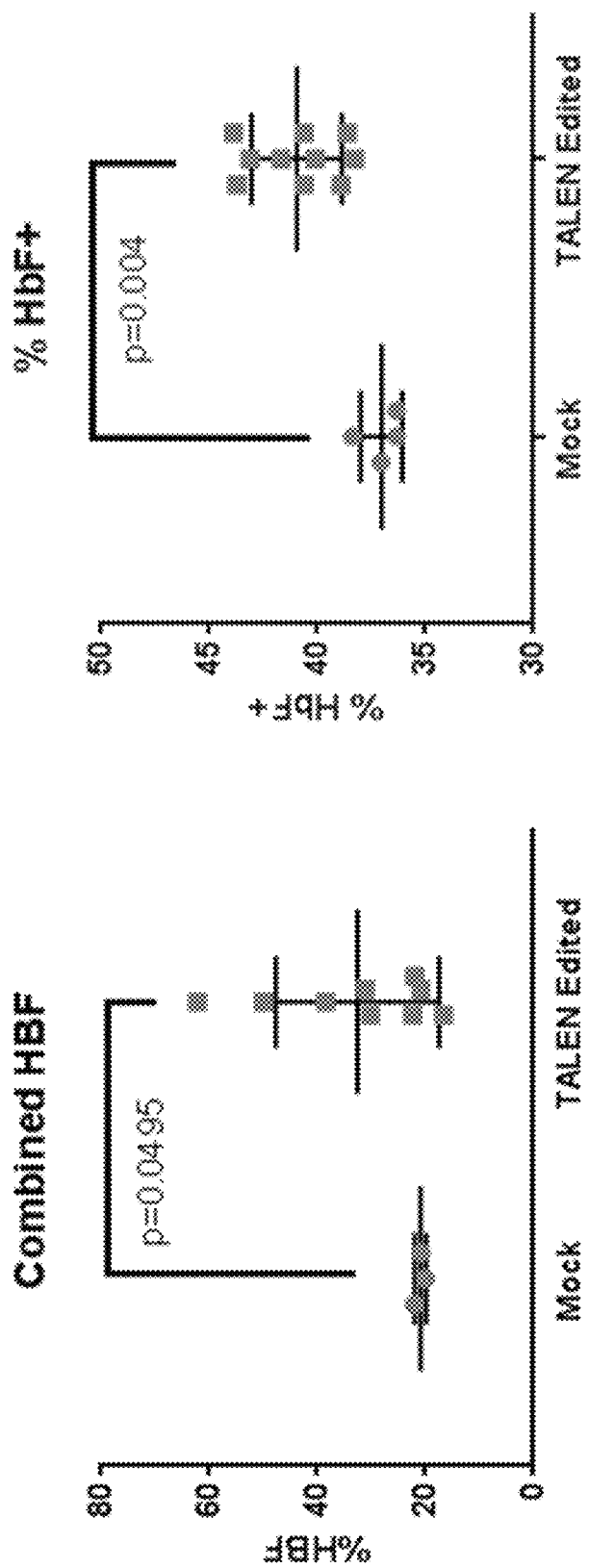
FIG. 44 shows TALEN edited CD34 cells produce more F-cells. At sac (A) there is a significantly higher rate of human F-Cells detected in the marrow. Differentiated CD34 cells from the marrow produce more F-Cells (B).
Figure 45:
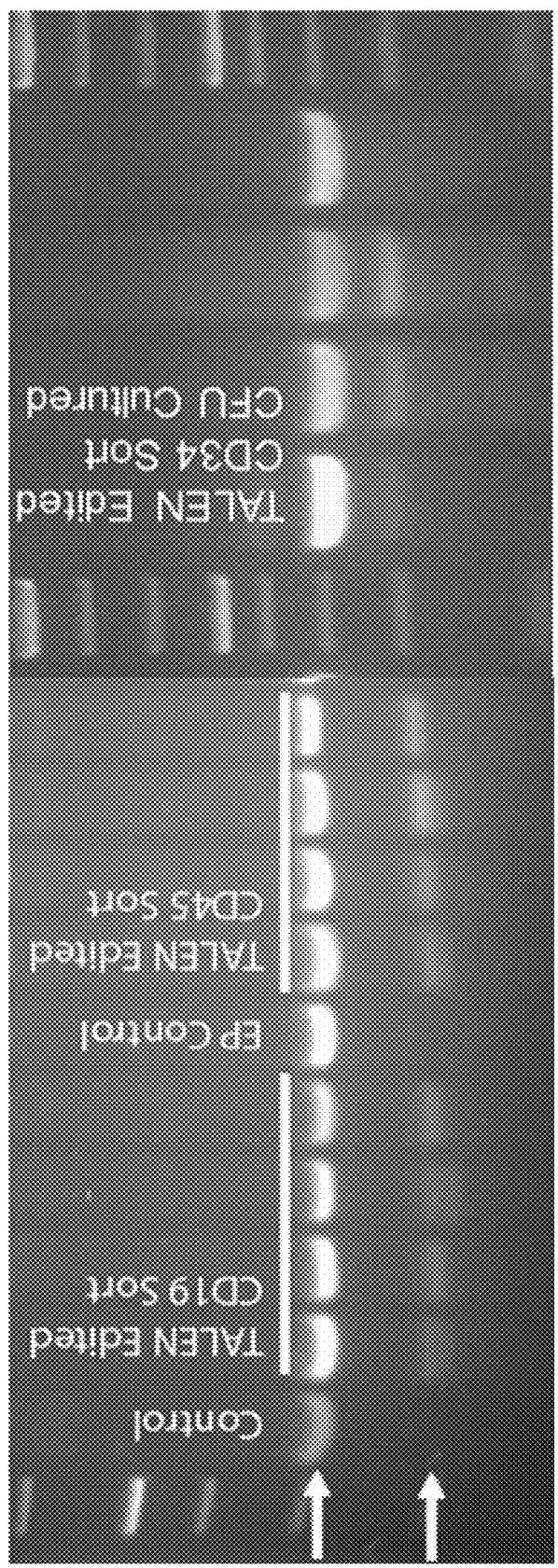
FIG. 45 shows sorted cells from all lineages retain INDELs from TALEN editing. T7 Analysis demonstrating INDELS are present in vitro.
Figure 47A:
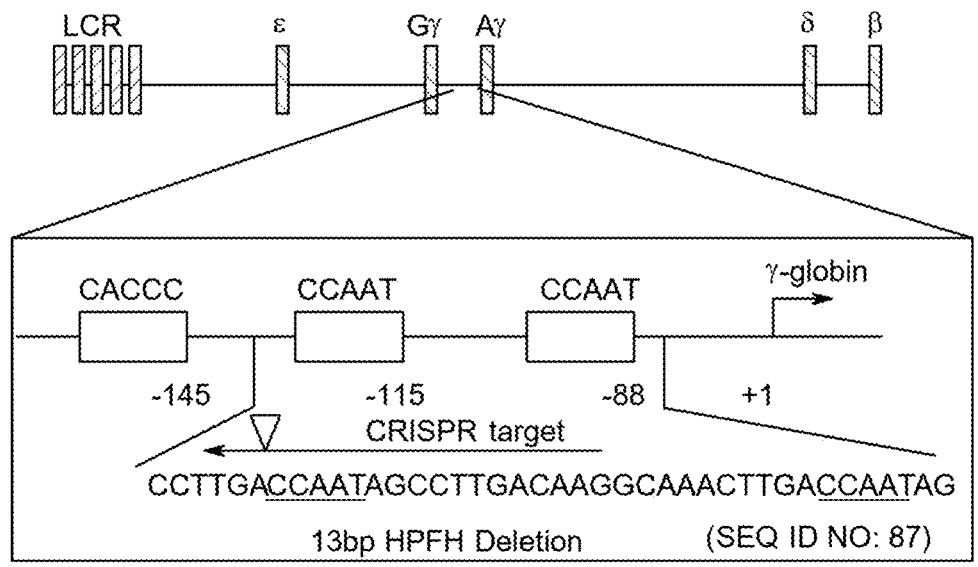
FIGS. 47A-47I show results of recapitulating the 13-nucleotide HPFH deletion by CRISPR/Cas9 gene editing.
Figure 47B:
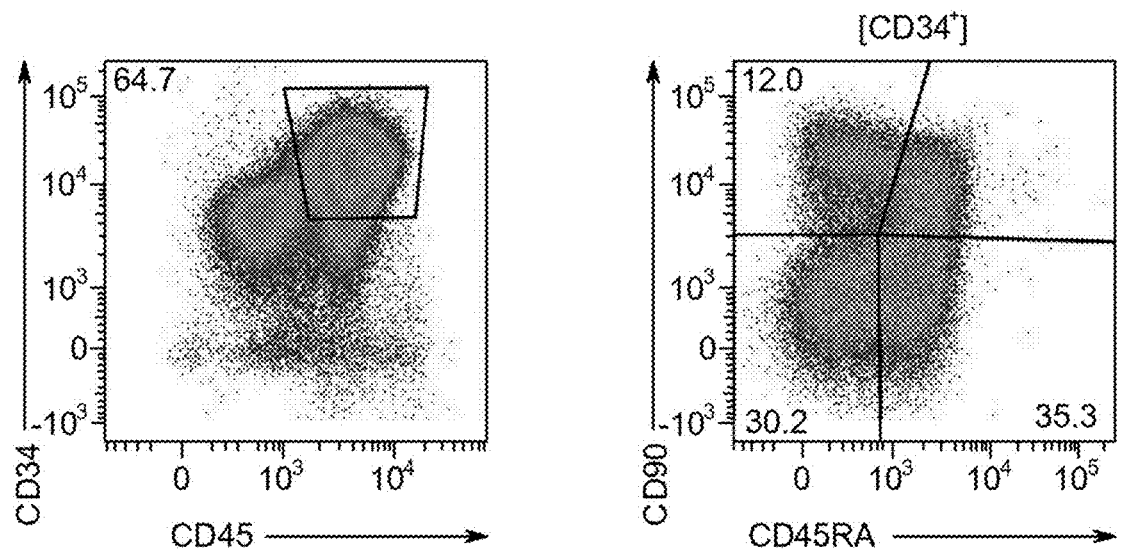
Figure 47C:
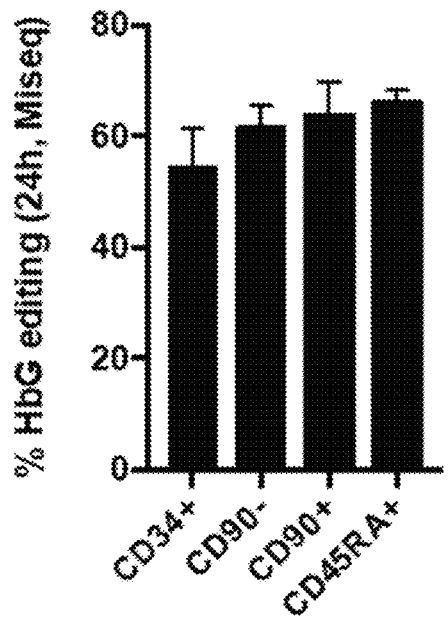
Figure 47D:
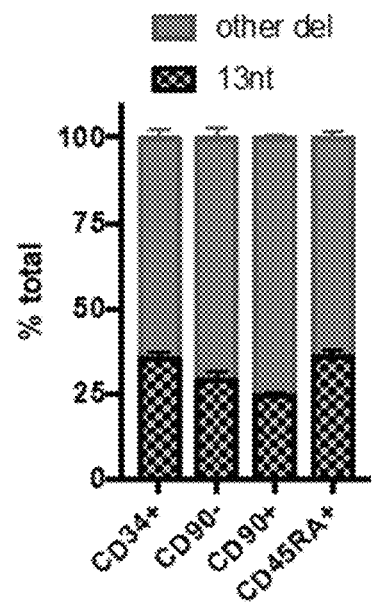
Figure 47E:
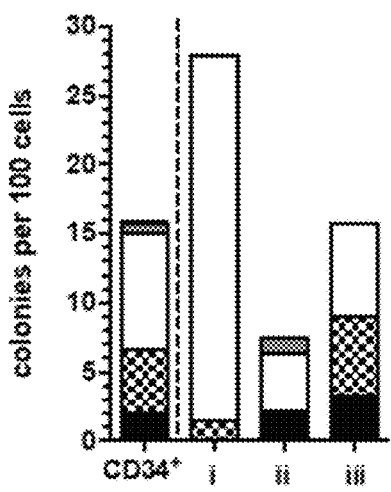
Figure 47F:
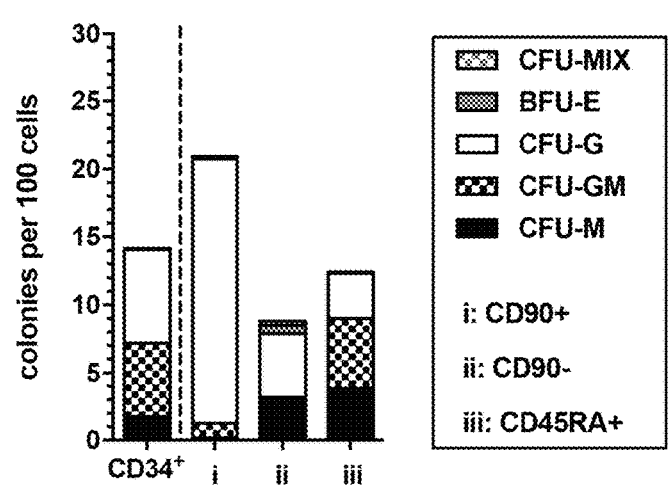
Figure 47H:
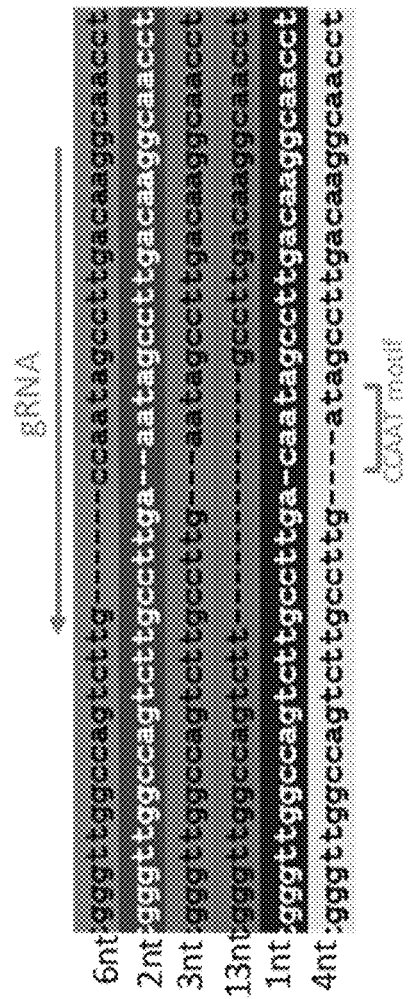
Figure 47I:
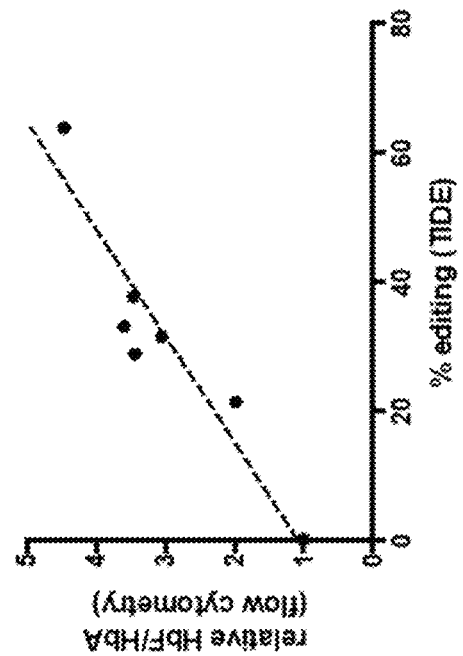
Figure 47G:
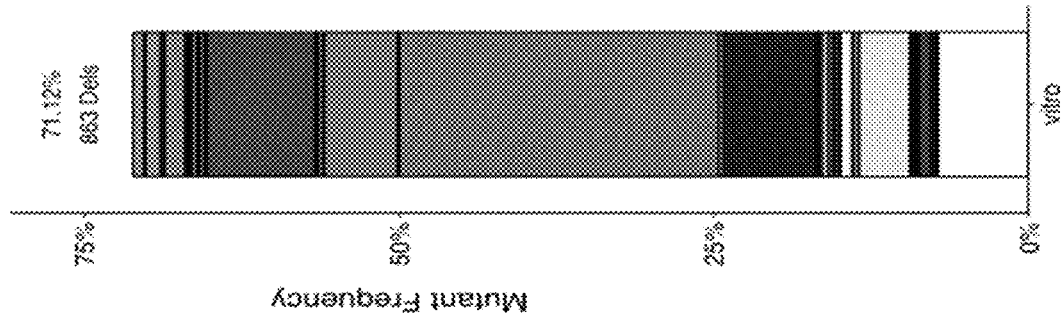
Figure 49A:
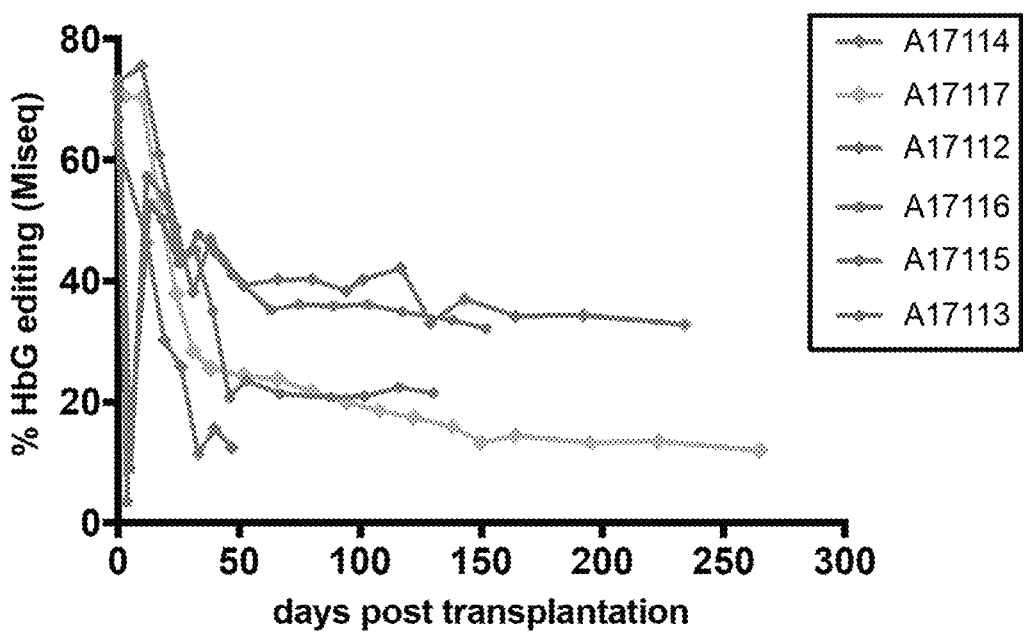
FIGS. 49A-49D show tracking of HbG editing in vivo in all transplanted animals.
Figure 49B:
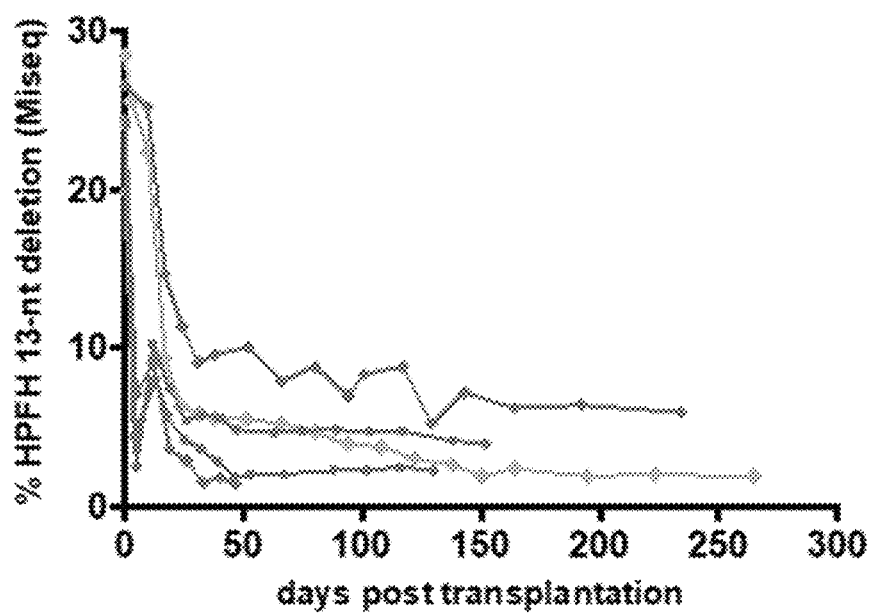
Figure 49C:
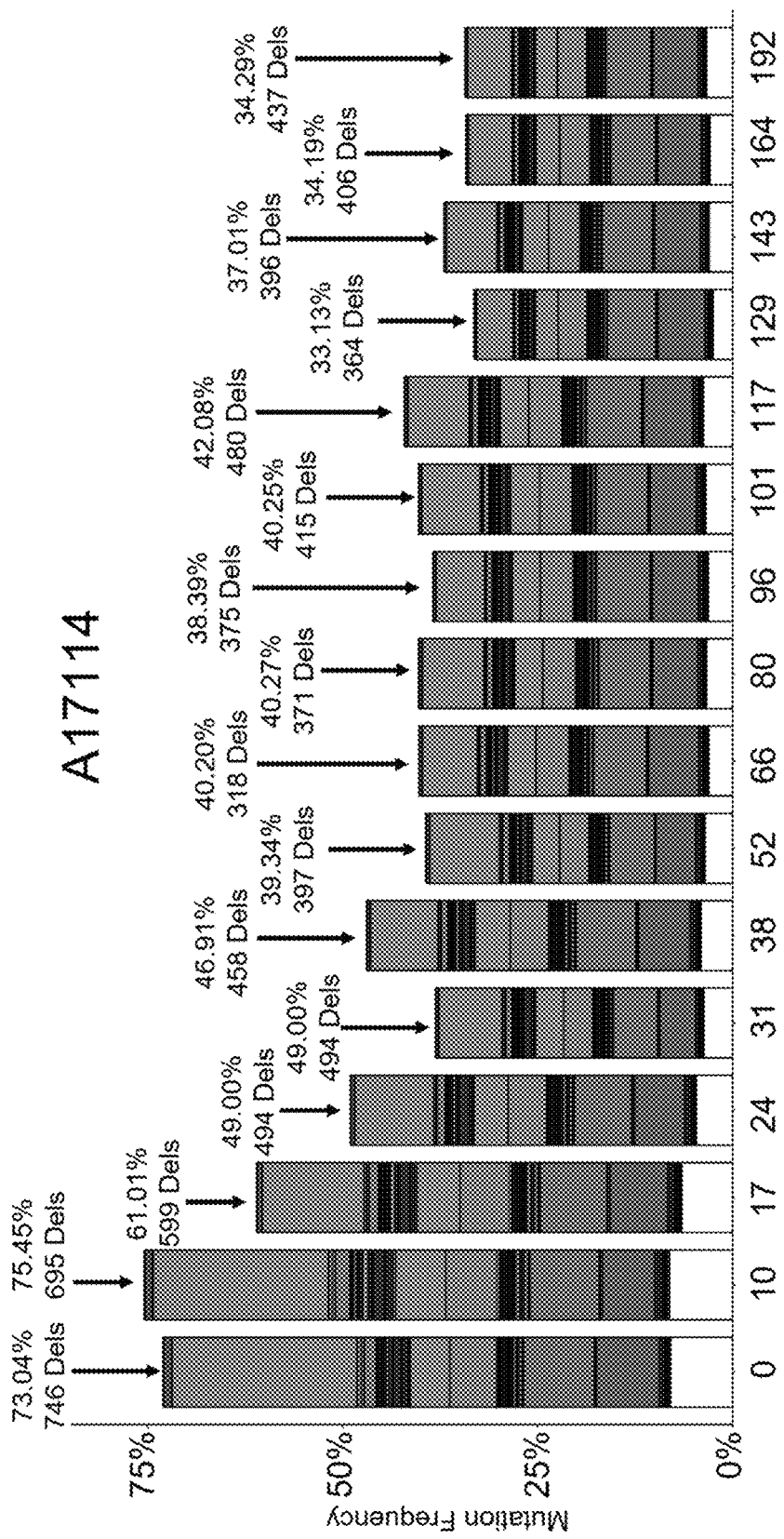
Figure 49D:
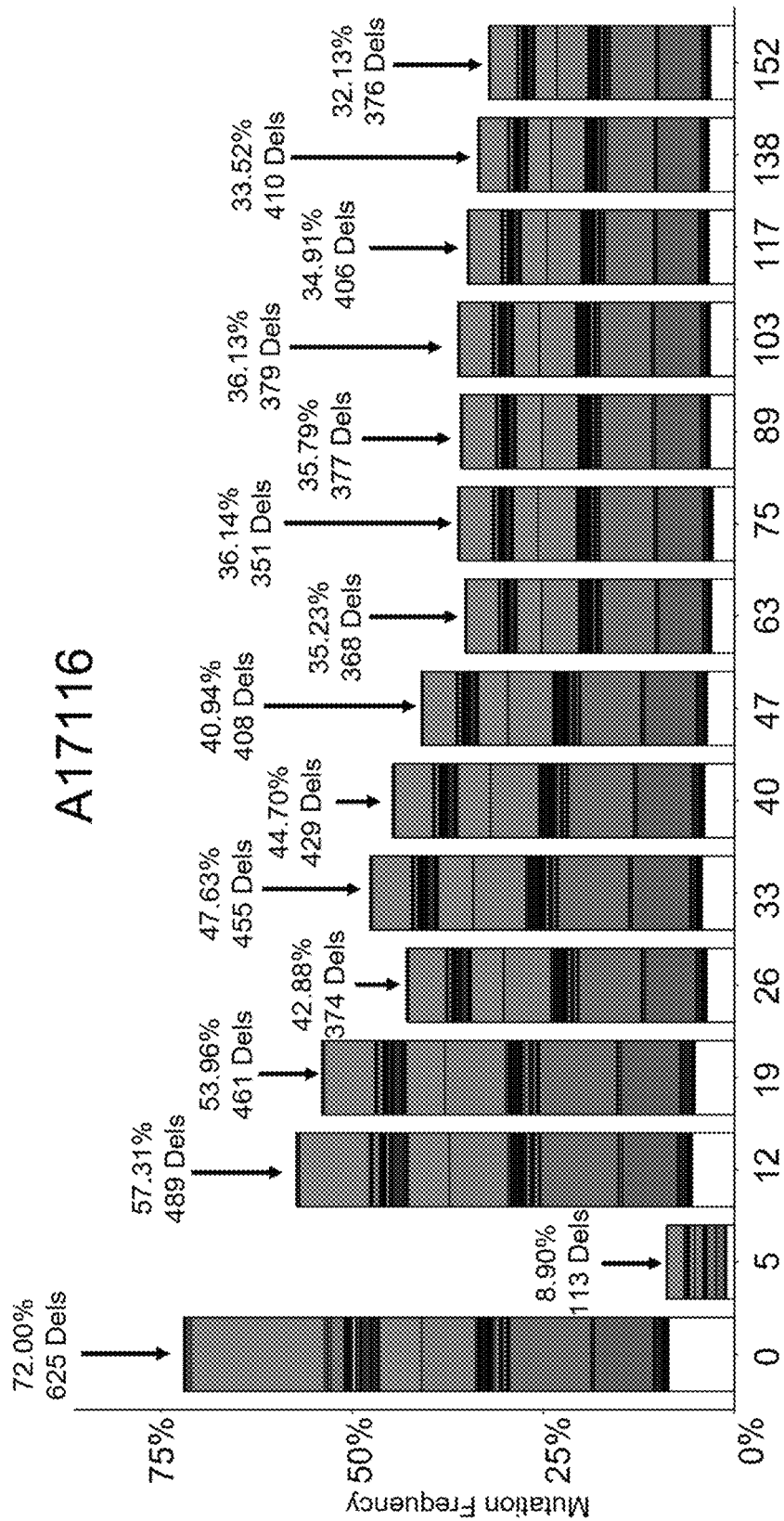
Figure 50E:
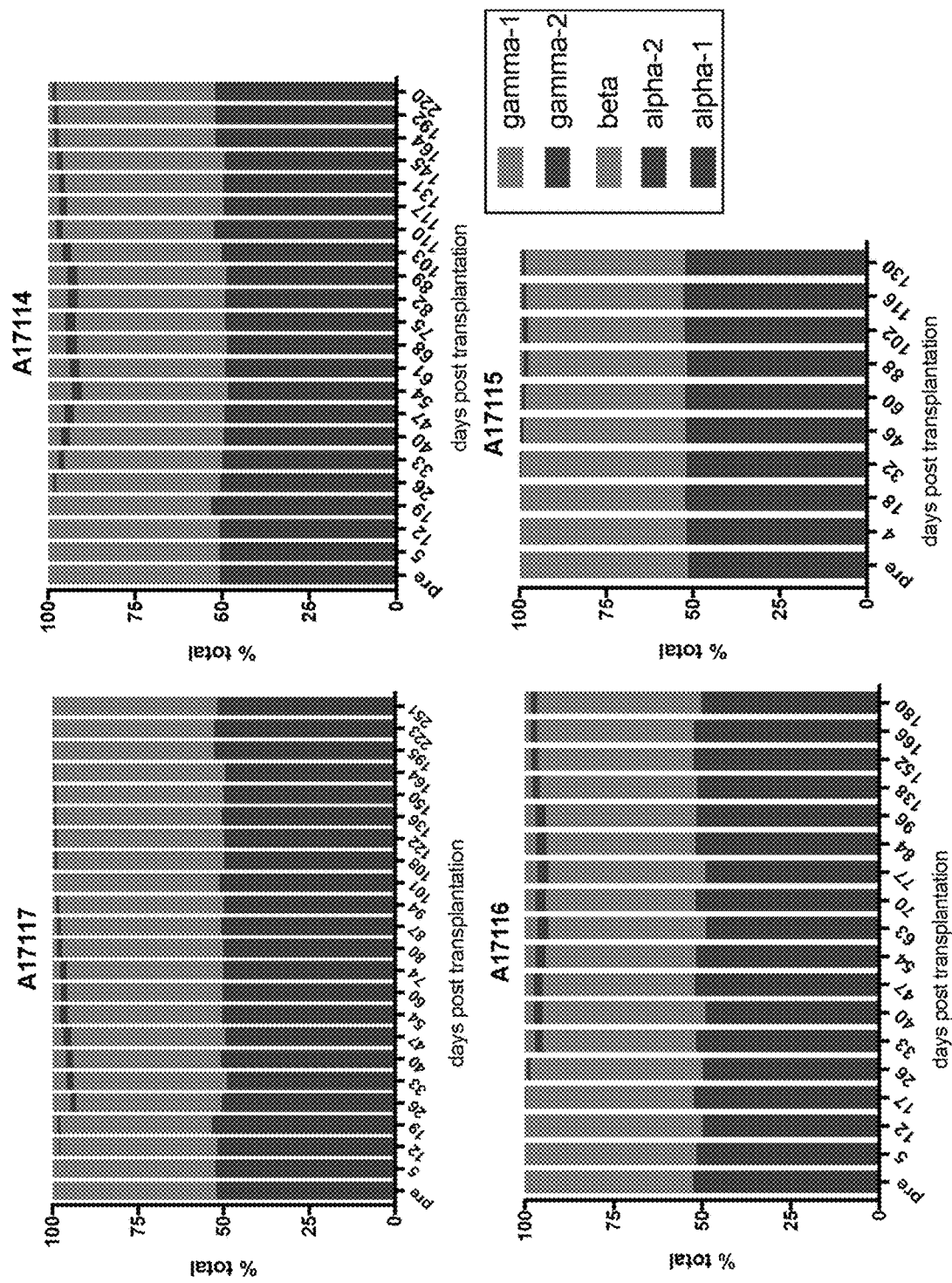
Figure 51D:
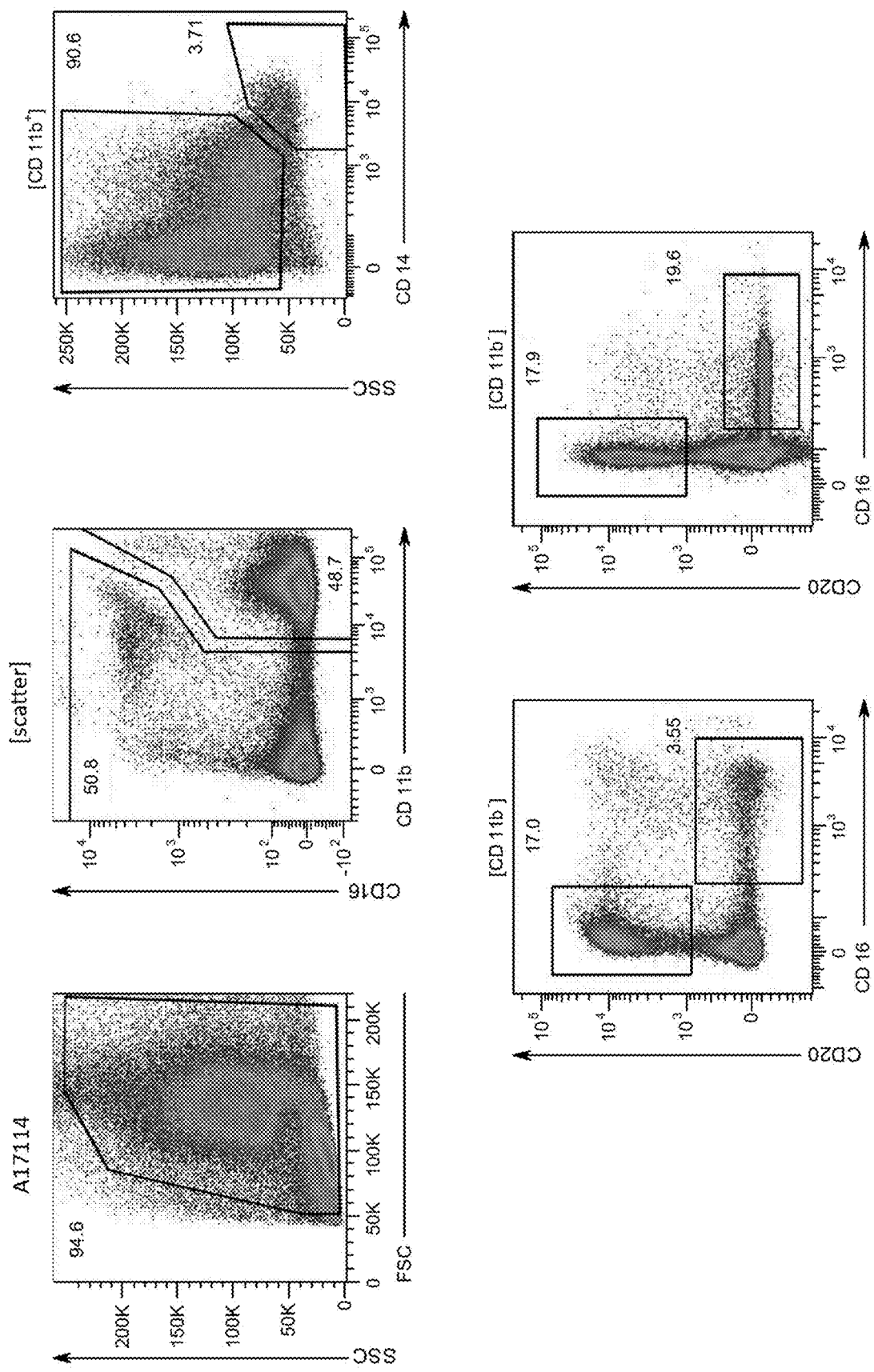
Figure 51E:
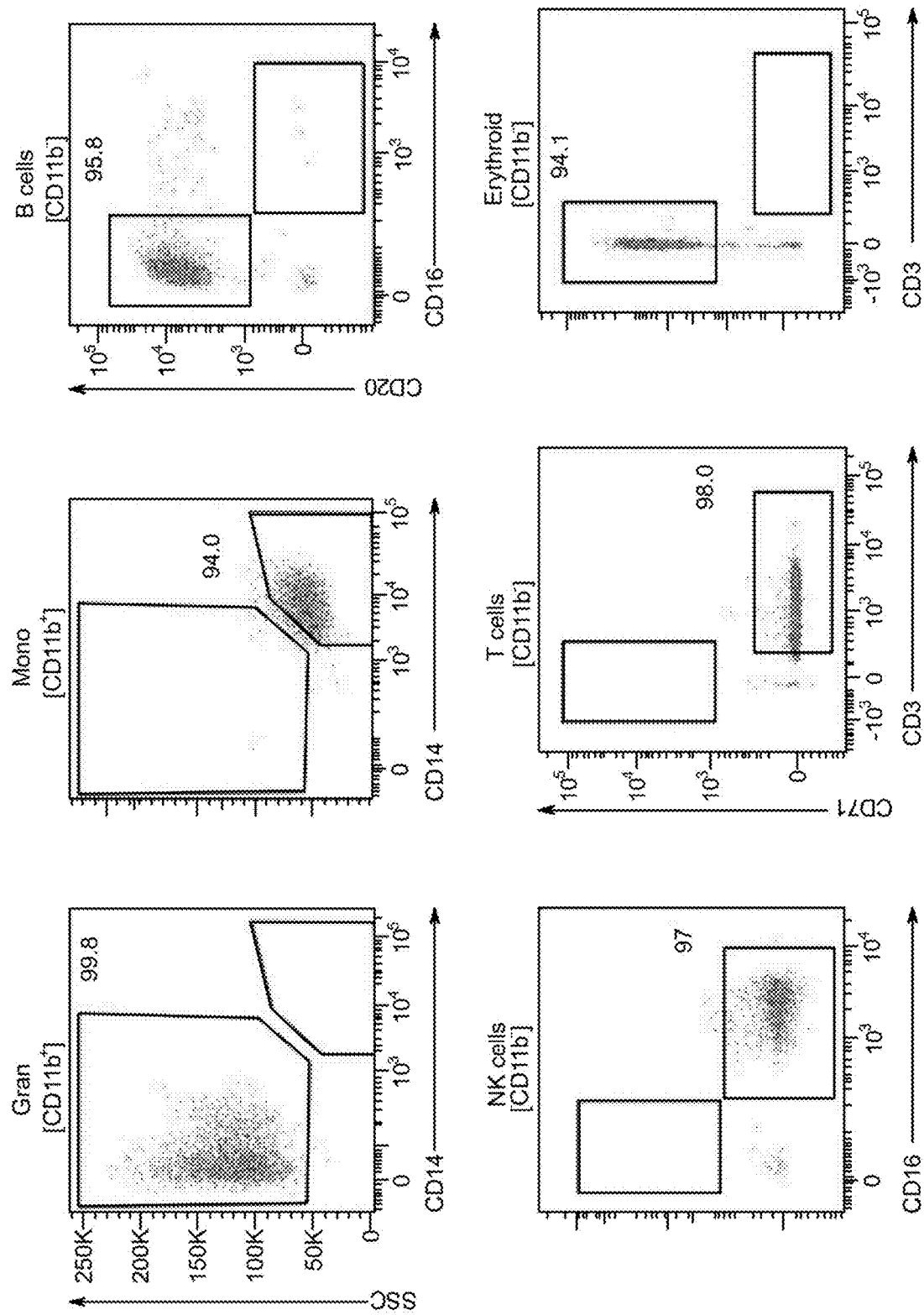
Figure 51F:
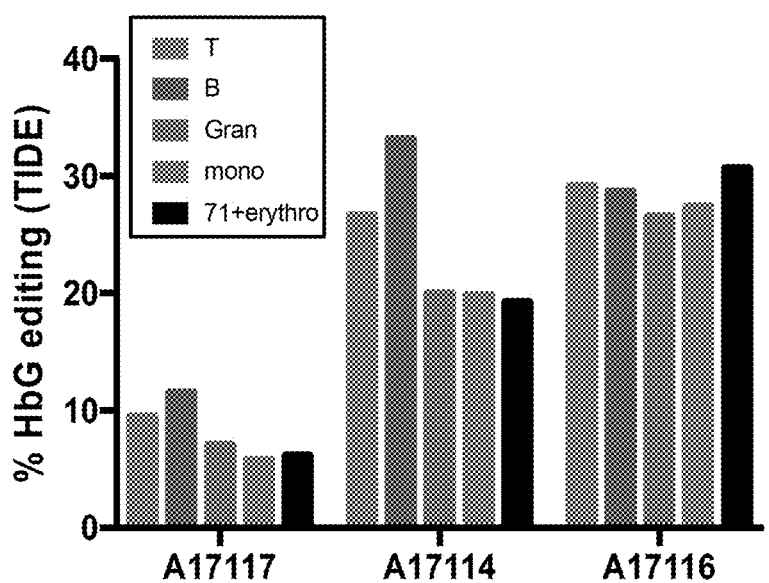
Figure 51G:
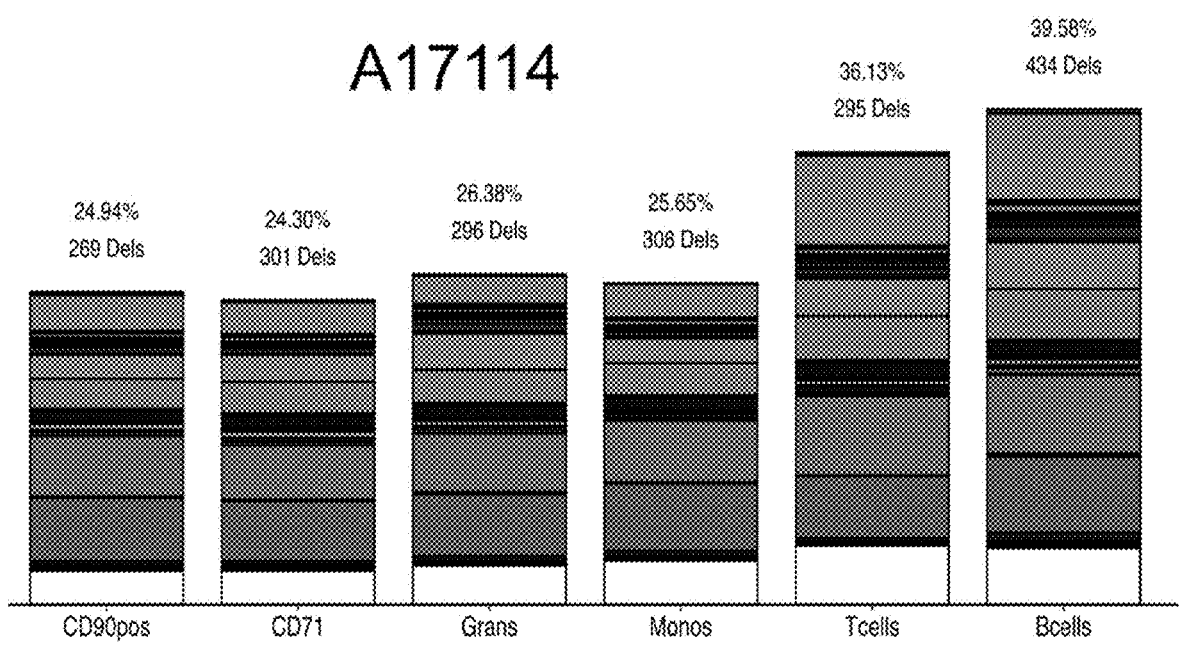
Figure 54A:
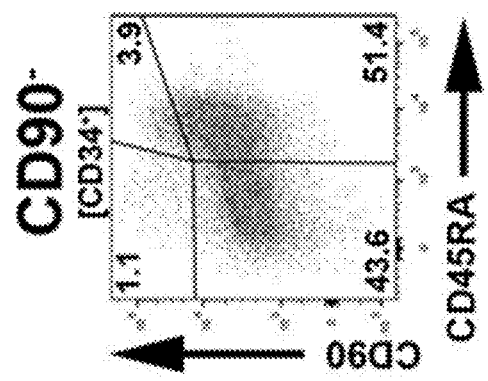
FIGS. 54A-54D demonstrates validation of CD90+ editing approach.
Figure 53F:
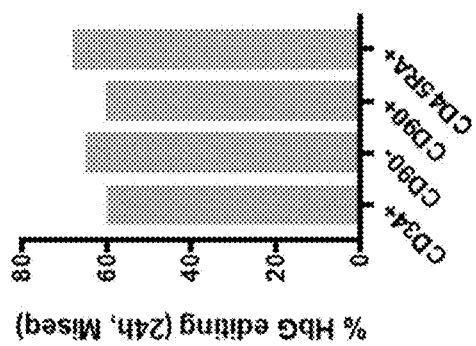
Figure 54B:
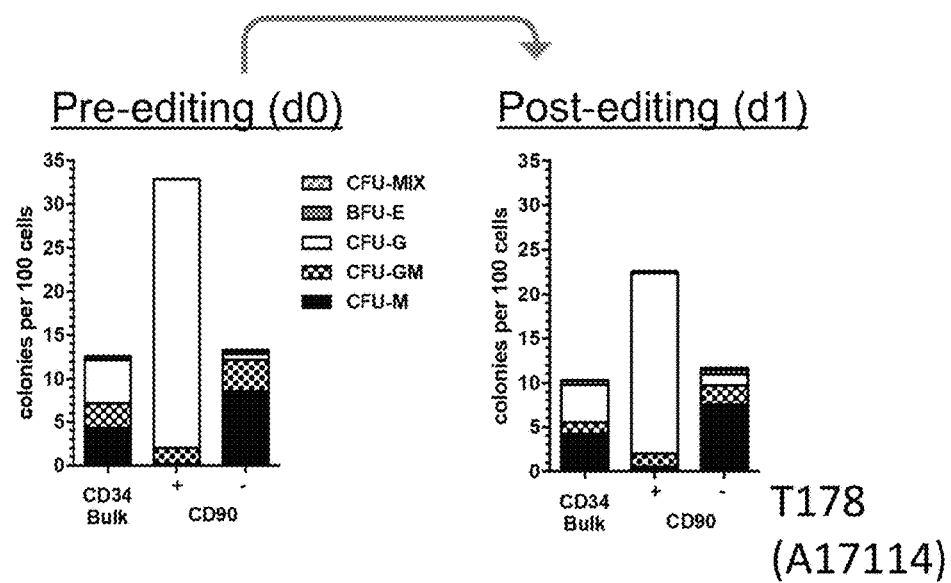
Figures 54C, 54D:
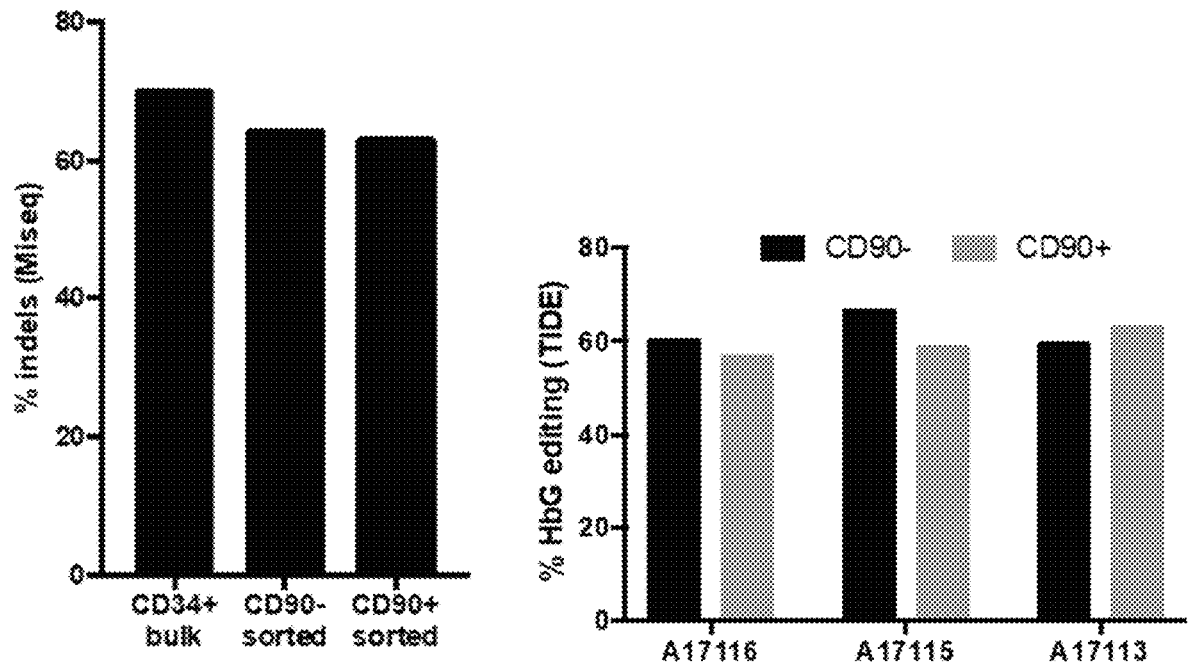
Figure 55A:
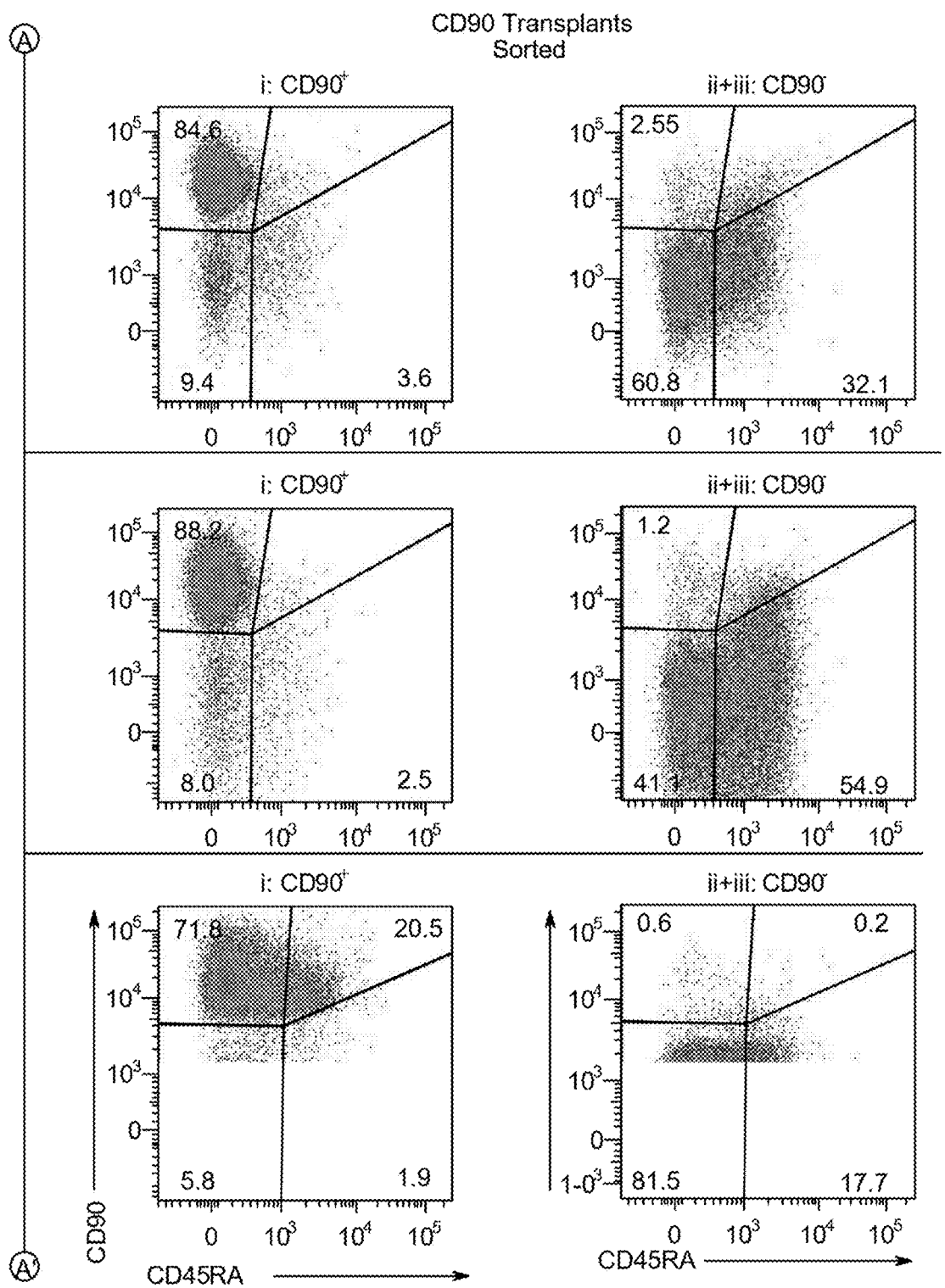
FIGS. 55A-55B provide flow cytometry analysis of infusion product pre- (FIG. 55A) and post- (FIG. 55B) CRISPR/Cas9 editing.
Figure 55A:
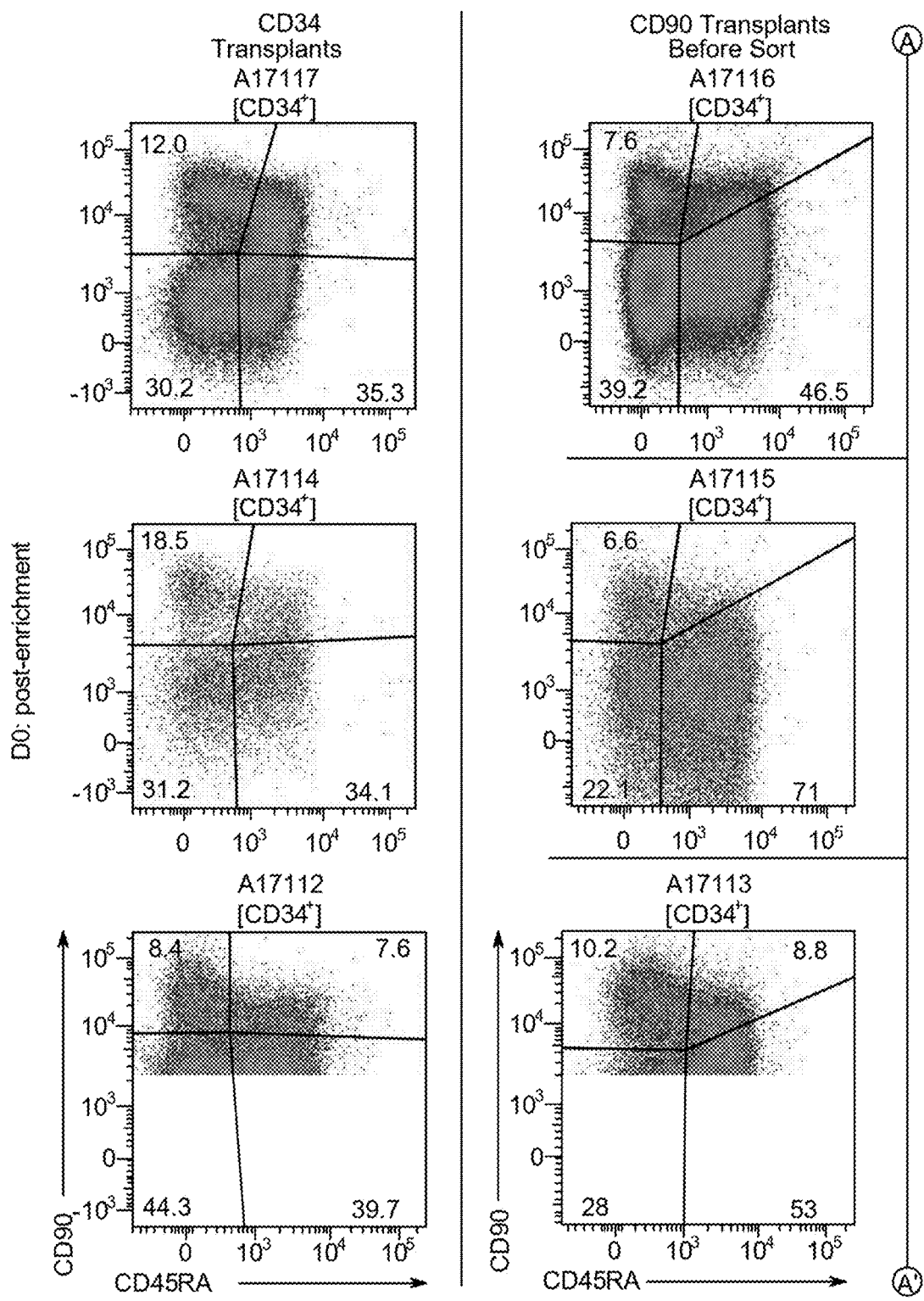
Figure 55B:
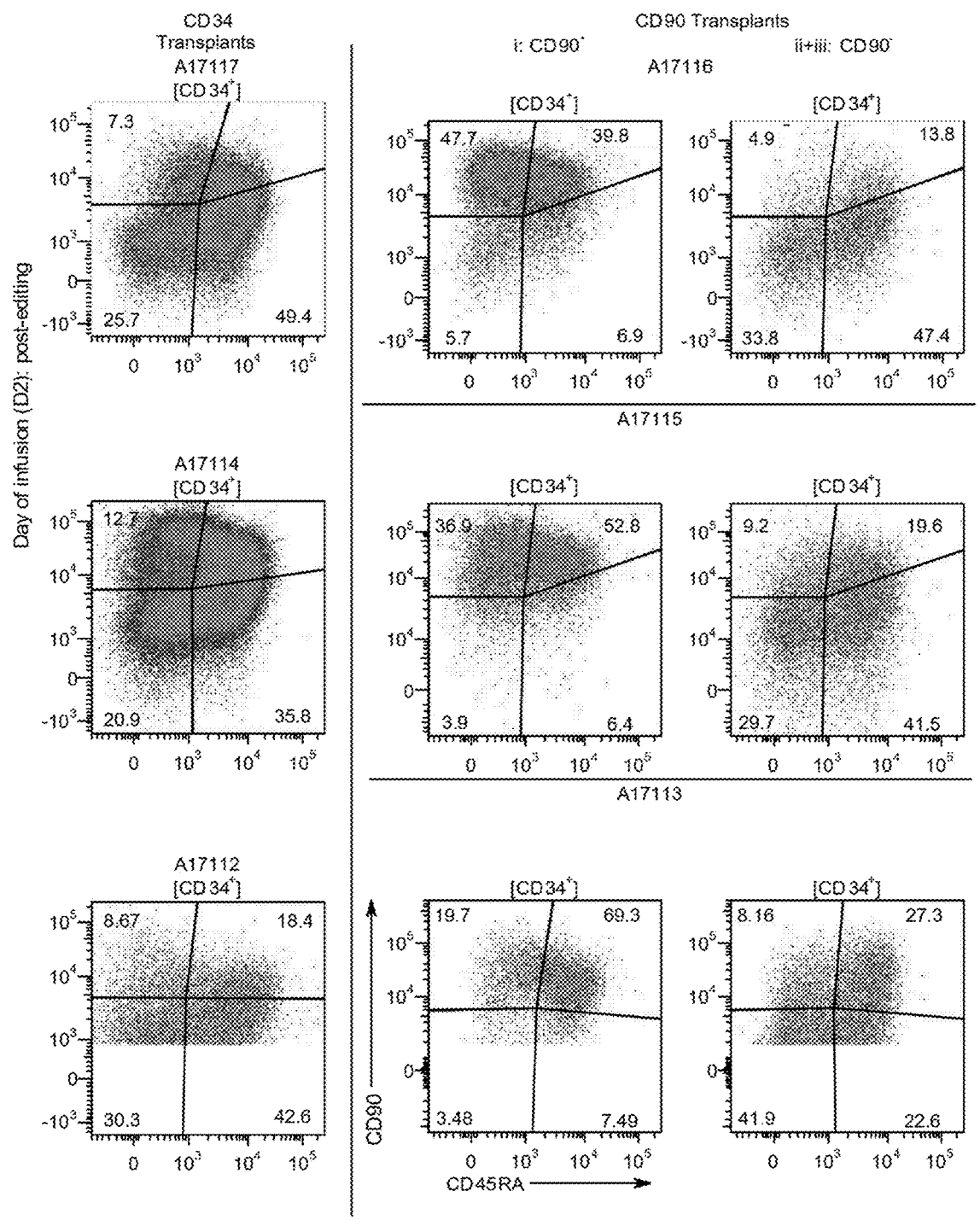
Figure 55B:
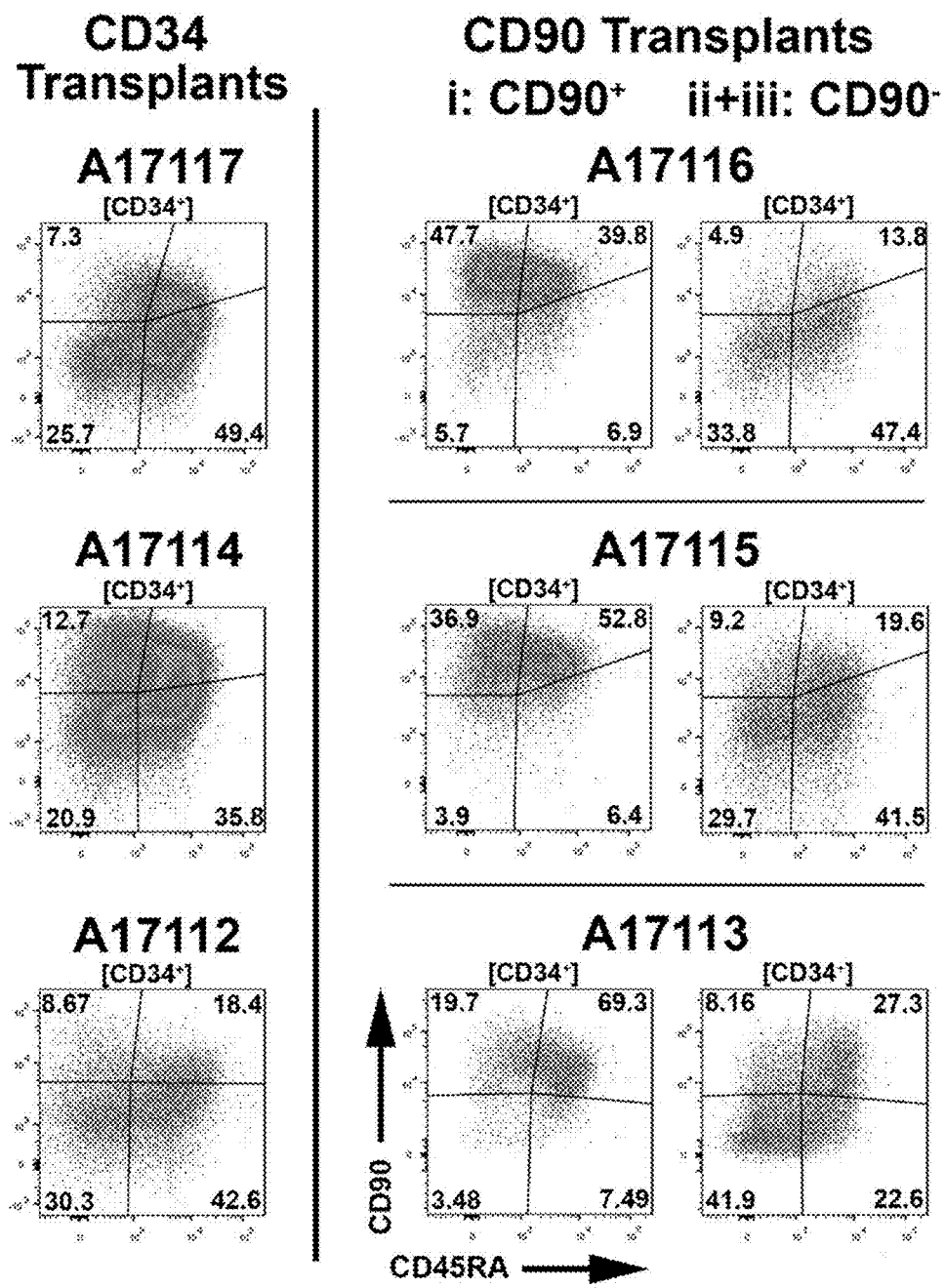
Figure 56A:
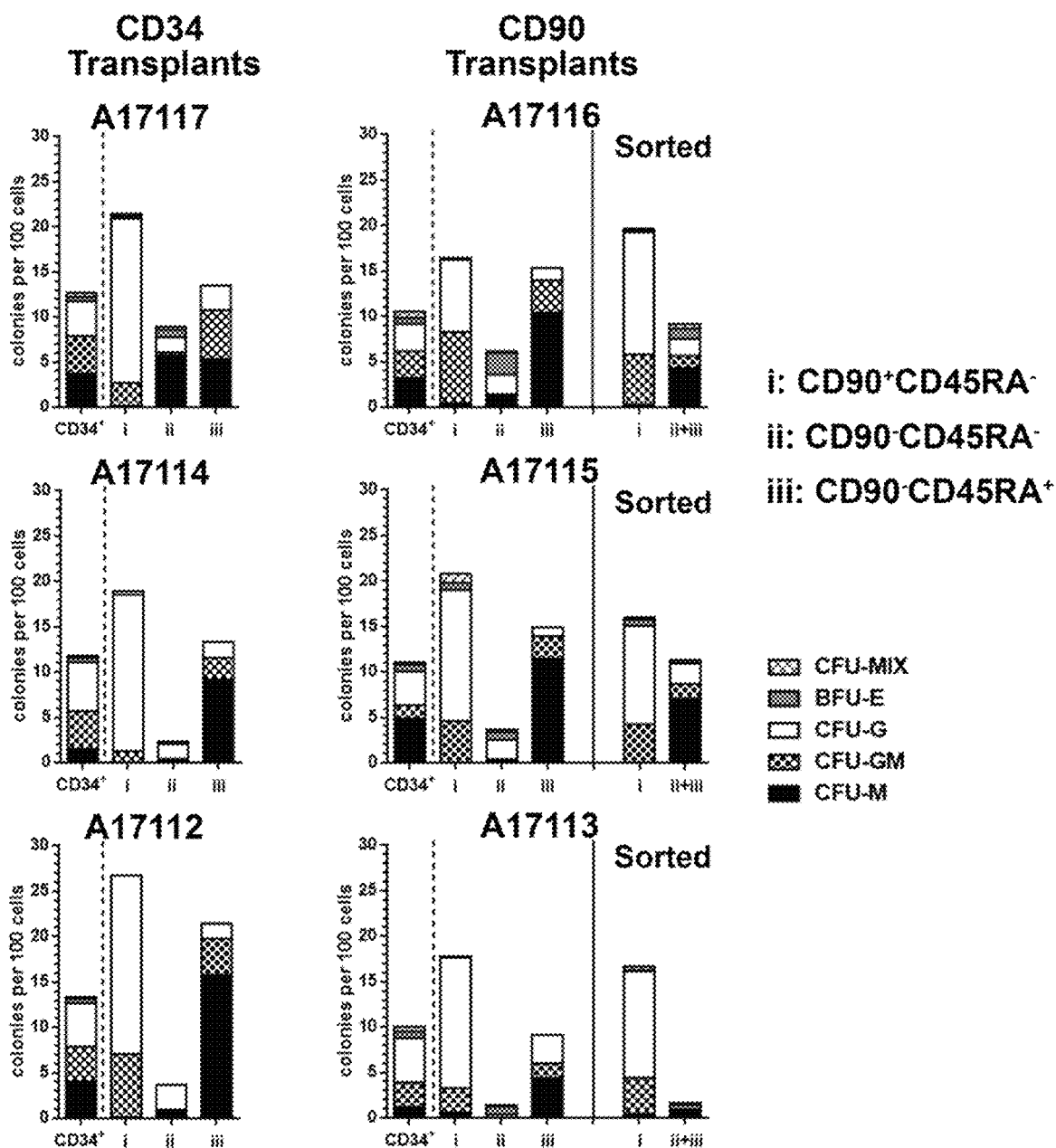
FIGS. 56A-56B provides colony-forming assays of infusion product pre- (FIG. 56A) and post- (FIG. 56B) editing.
Figure 56B:
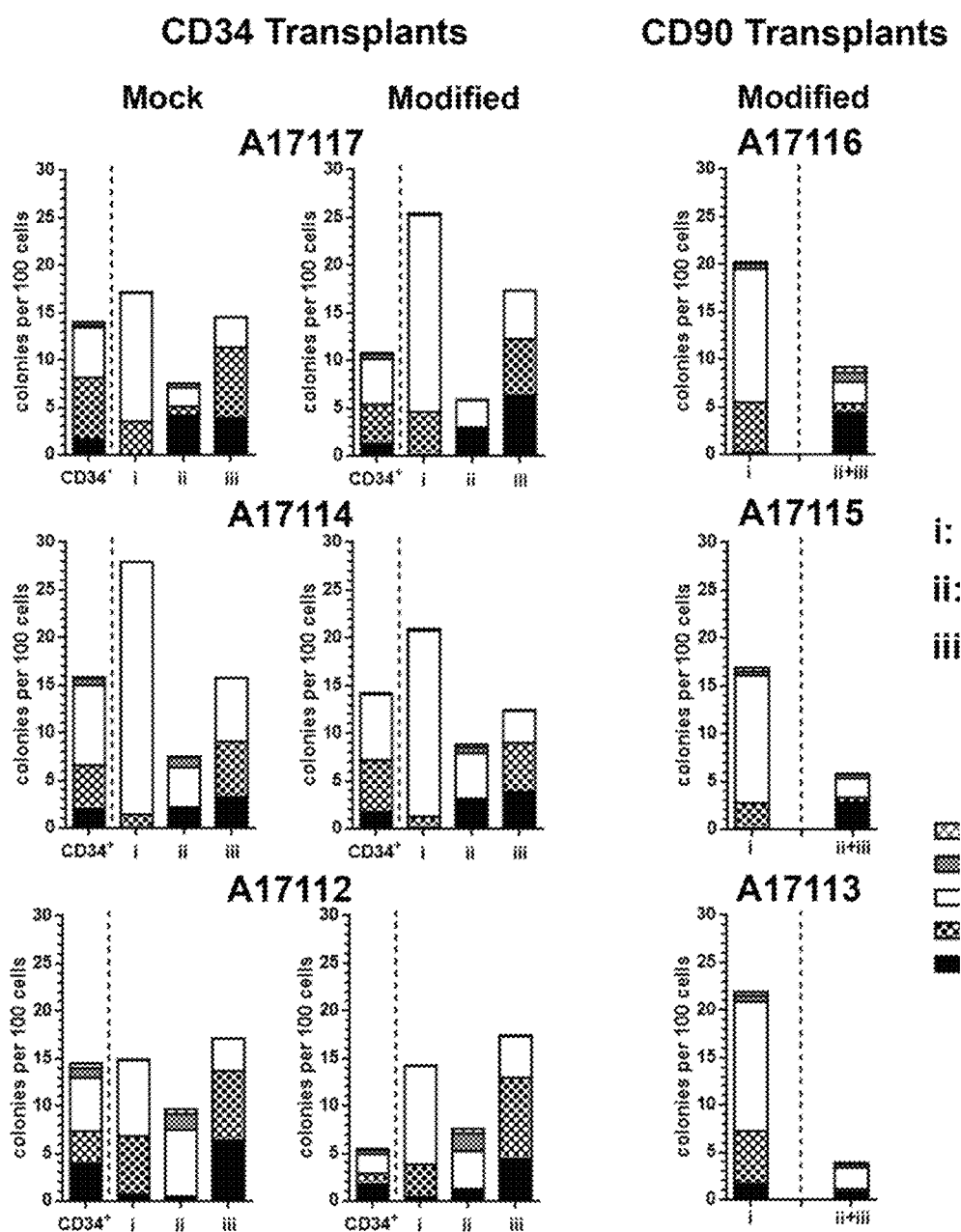
Figure 57:
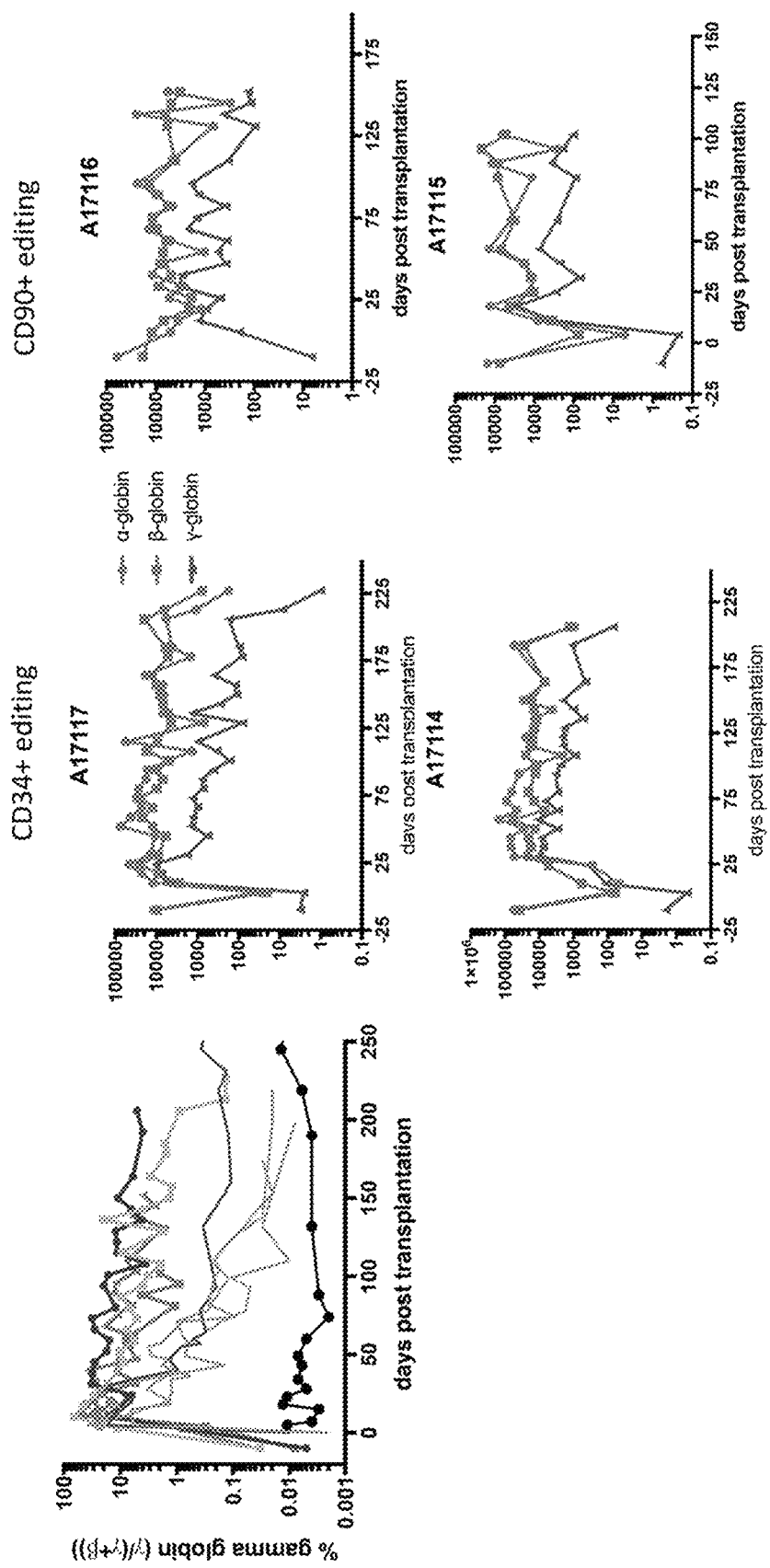
FIG. 57 shows quantitative PCR measurement of hemoglobin expression in peripheral blood of transplanted animals.
Figure 58:
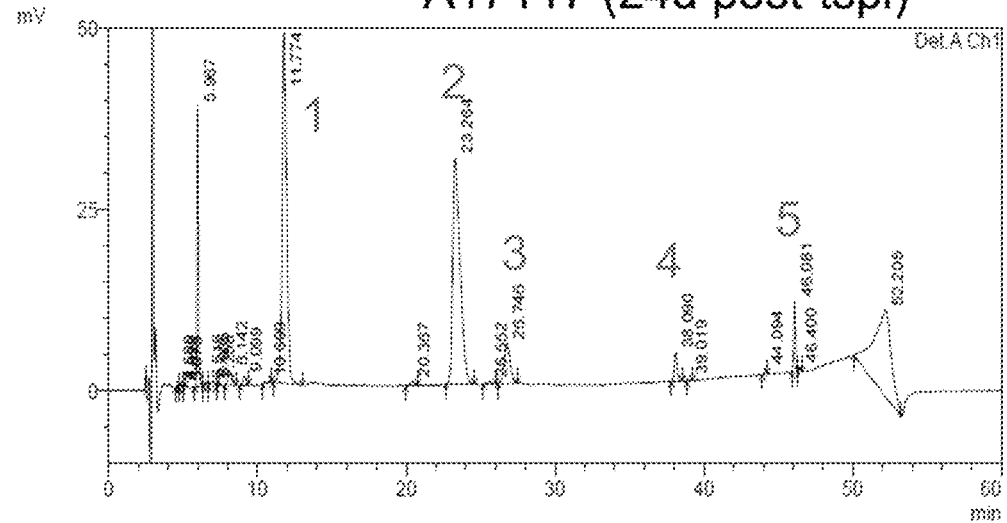
FIG. 58 shows validation of RP-HPLC approach for analysis of hemoglobin expression from NHP peripheral blood.
Figure 58:
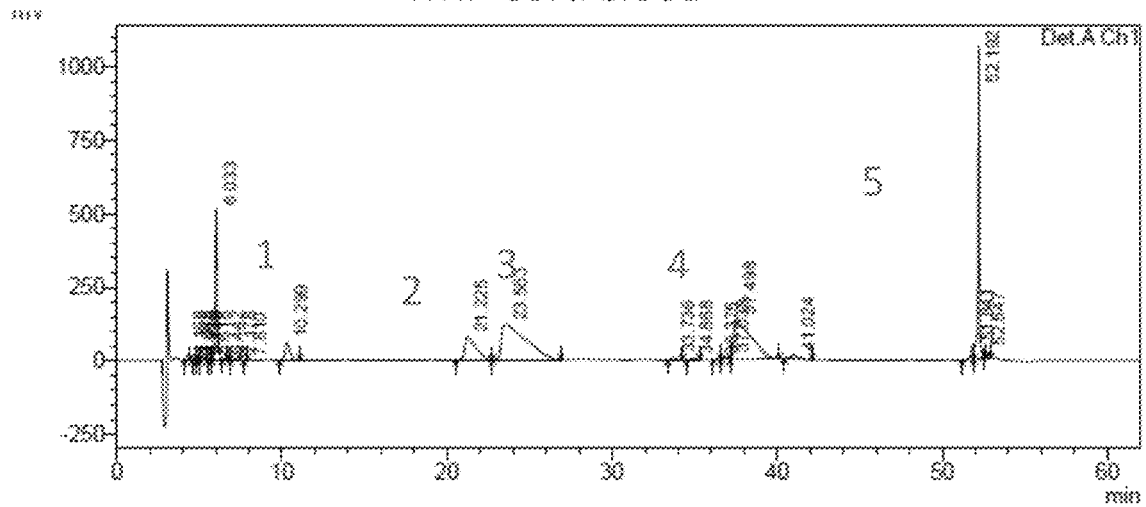
Figure 59:
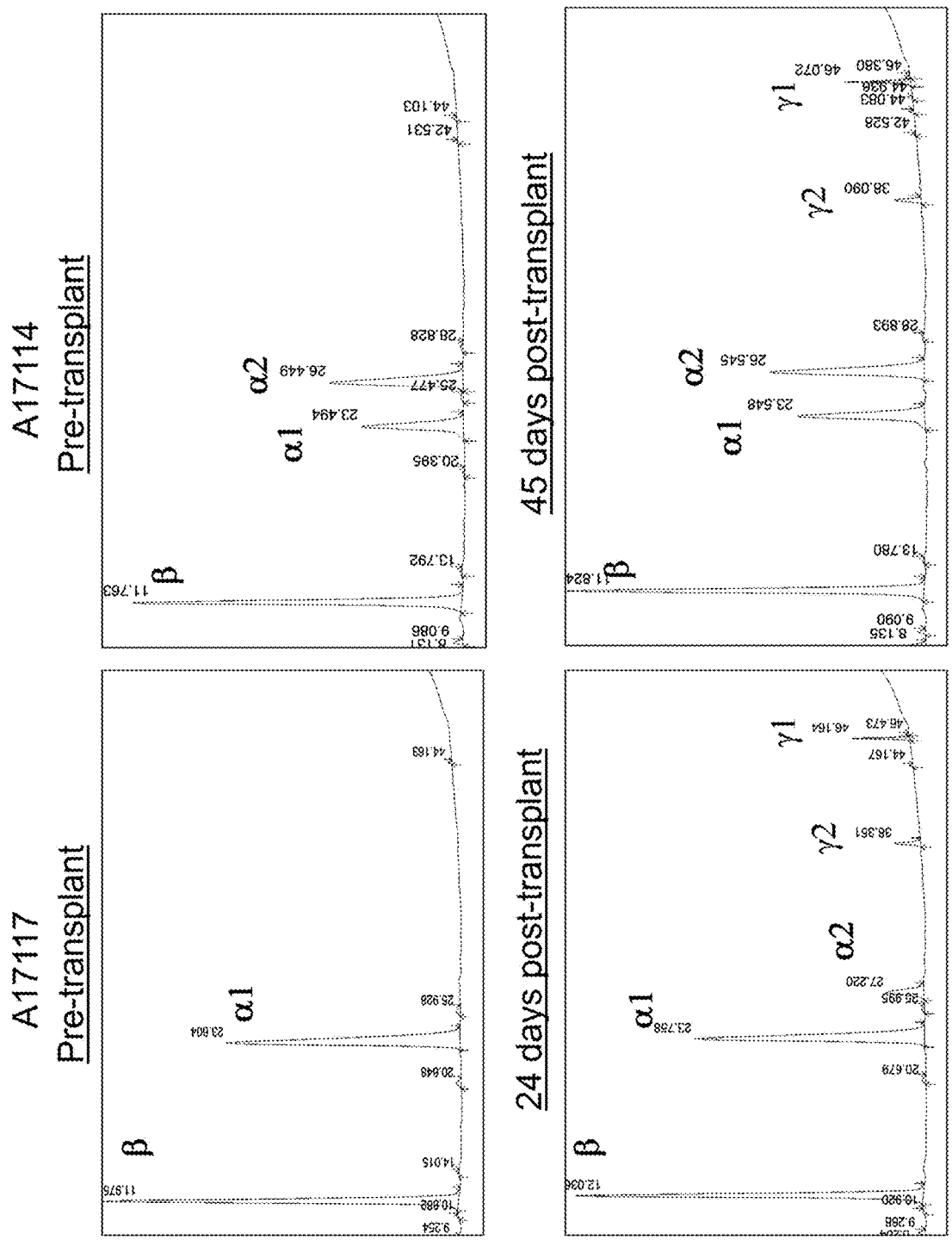
FIG. 59 shows representative HPLC profiles of peripheral blood from experimental animals pre- and post-transplant.
Figure 59:
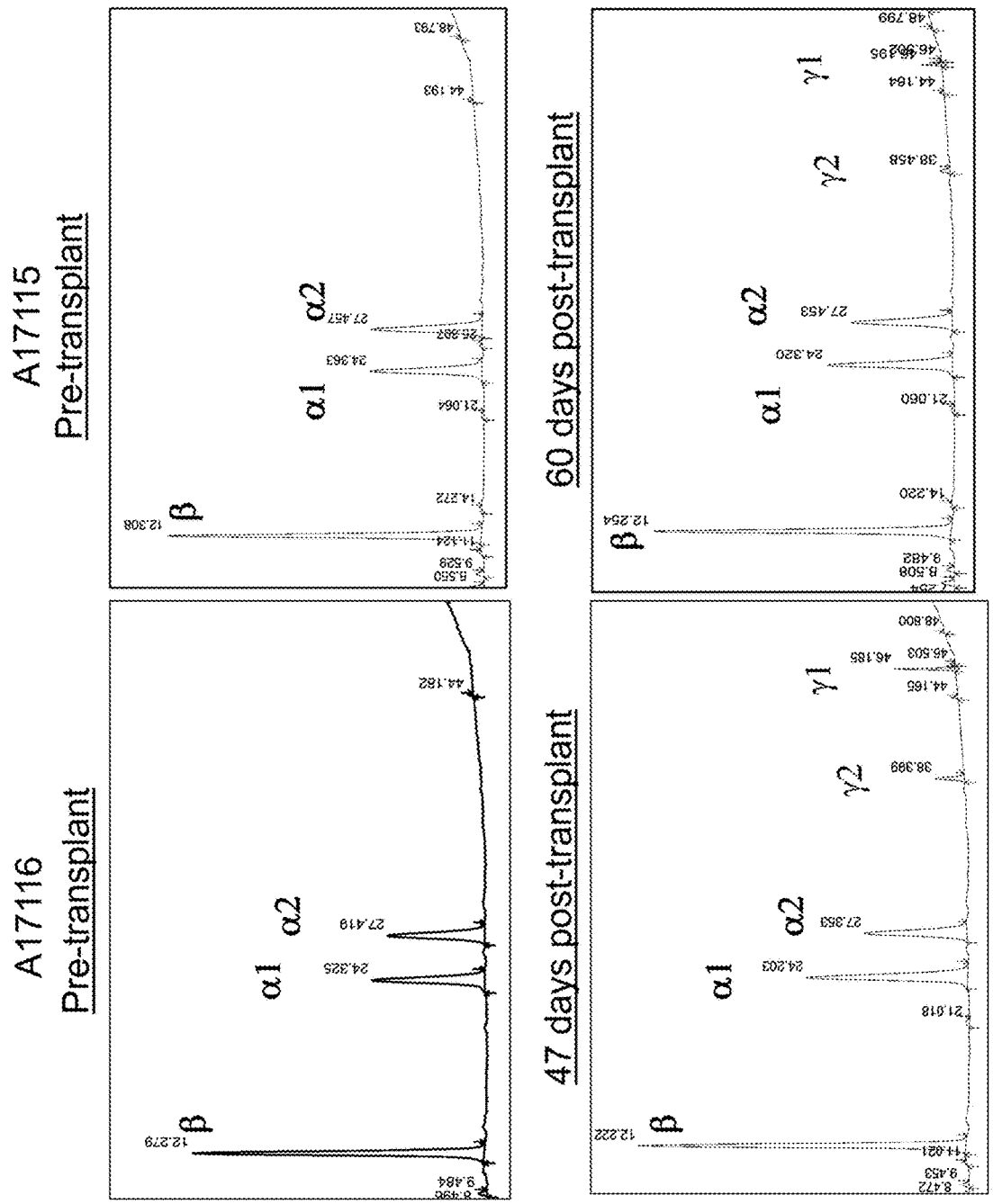

Week 24 human engraftment showed no significant differences in percent human engraftment between control and edited cells (FIG. 42). Engrafted edited CD34 cells generated all human hematopoietic lineages. Human erythroid, CD34+ Lymphoid and Myeloid, and CD19+ cells were all identified and sorted from harvested marrows following transplant (W24) (FIG. 43). The TALEN edited CD34 cells produced more F-Cells. At sac (A) there was a significantly higher rate of human F-Cells detected in the marrow, while differentiated CD34 cells from the marrow produced more F-Cells (B) (FIG. 44). Sorted cells from all lineages retained INDELs from TALEN editing. T7 Analysis demonstrated INDELS are present in vitro (FIG. 45). Secondary mice engraftments and marrow cells retained edits made; human engraftment at 9 weeks was low (<2%) but present and marrow cells retained edits at both loci.

Conclusions

It was demonstrated that TALEN mRNA mediated disruption of repressive elements in the promoters of the γ-hemoglobin genes HBG1 and HBG2 can result in the induction of fetal hemoglobin expression. These cells retain the ability to engraft in W41 mice and differentiate into multiple lineages while retaining the TALEN induced gene edits. The successful engraftment of hematopoietic cells in secondary mice suggests that at least a portion of the edited peripheral blood CD34 cells represent hematopoietic stem cells. A homologous repair template was successfully integrated at the cut site using the same TALEN mRNA to generate the double strand break resulting in the expression of both anti-sickling T87Q hemoglobin as well as increased levels of fetal hemoglobin. Additional repair templates allow for further exploration of controlling hemoglobin expression at this locus.

Example 4

CRISPR/Cas9-Edited Hematopoietic Stem and Progenitor Cells for the Reactivation of Fetal Hemoglobin A promising therapeutic strategy for hemoglobinopathies consists in the genome engineering of patients' hematopoietic stem and progenitor cells (HSPCs) to reactivate fetal hemoglobin (HbF) production, which can serve as substitute for defective or absent adult hemoglobin molecules. Here, the nonhuman primate (NHP) large animal transplantation model was used to address existing challenges for clinical translation of this approach to ensure efficient gene editing in scale-up conditions and optimize long-term engraftment of gene-edited cells.

The CRISPR/Cas9 nuclease platform was employed to recapitulate a 13-nucleotide (nt) deletion in the gamma globin gene promoter identified in individuals with hereditary persistence of fetal hemoglobin (HPFH). Two rhesus macaques were transplanted with bone marrow-derived CD34+ cells edited ex vivo by CRISPR/Cas9 ribonucleoprotein electroporation. 70% editing efficiency was detected in the infusion product, with over 25% of cells containing the 13-nt deletion. Both animals showed rapid hematopoietic recovery and peripheral blood gene editing levels stabilized at 15% and 30%, respectively, at 6 months post transplantation (FIG. 61A). HbF production, as determined by peripheral blood F-cells staining (FIG. 61B) and quantitative PCR, was substantially increased in both animals as compared to controls and correlated with in vivo editing levels.

Figure 60A:
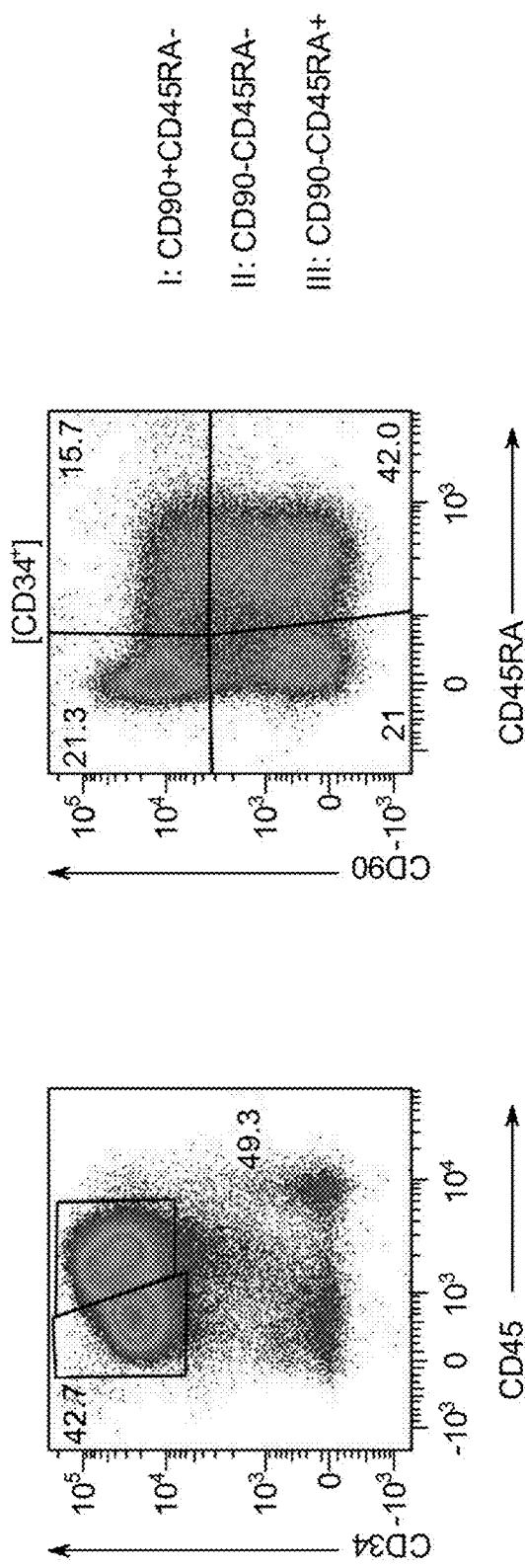
FIGS. 60A-60F provides validation of sorting approach from bone marrow analysis of animal models A17114 and A17116.
Figure 60B:
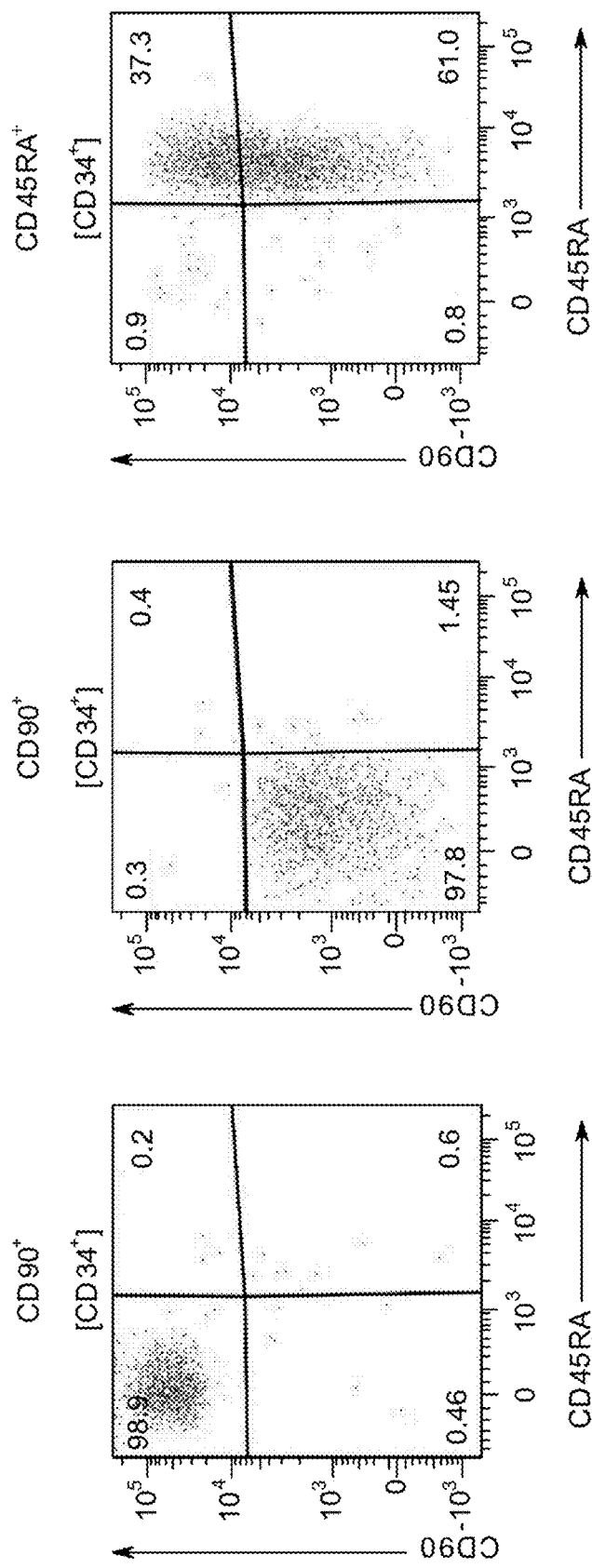
Figure 60C:
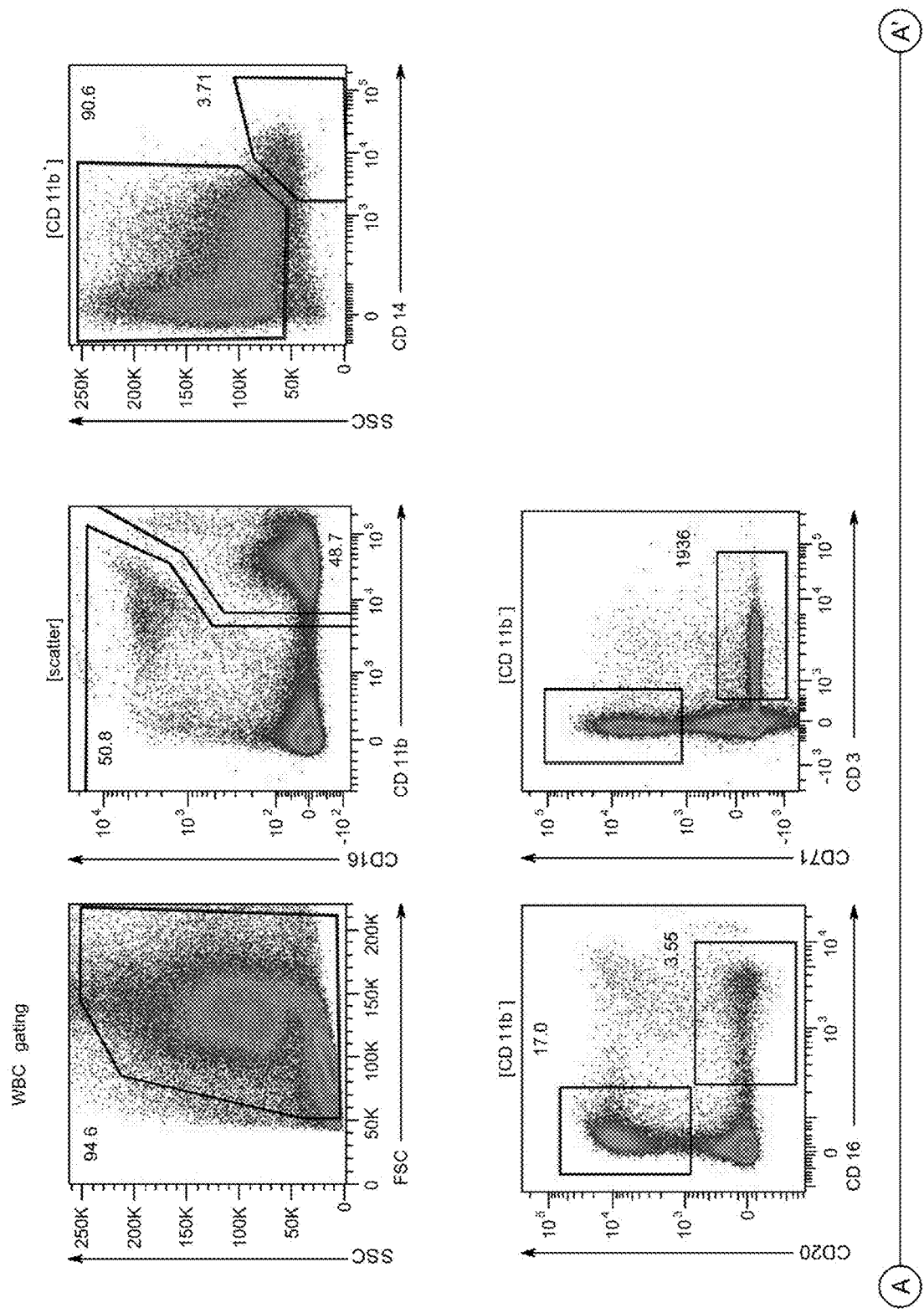
Figure 60C:
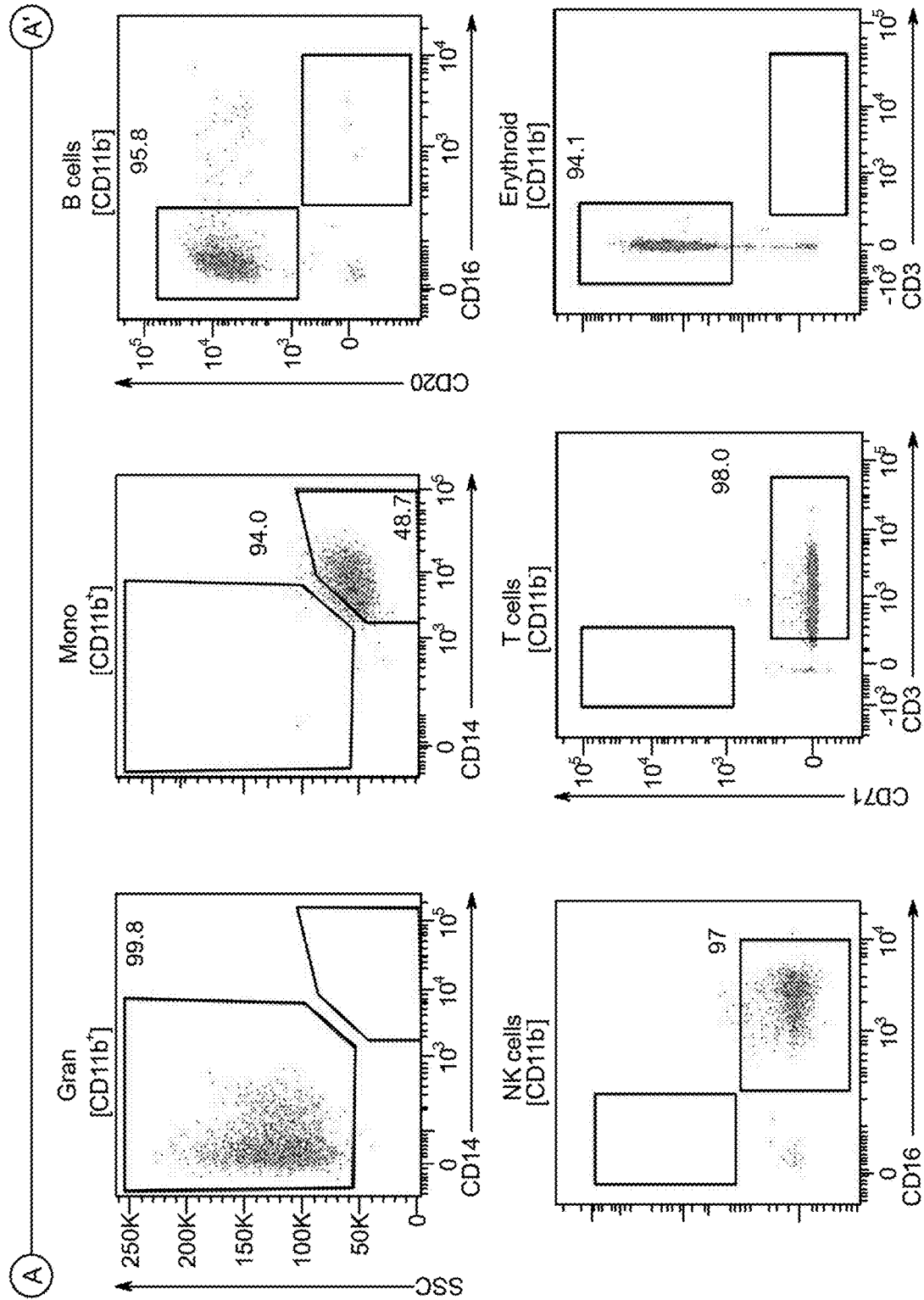
Figure 60D:
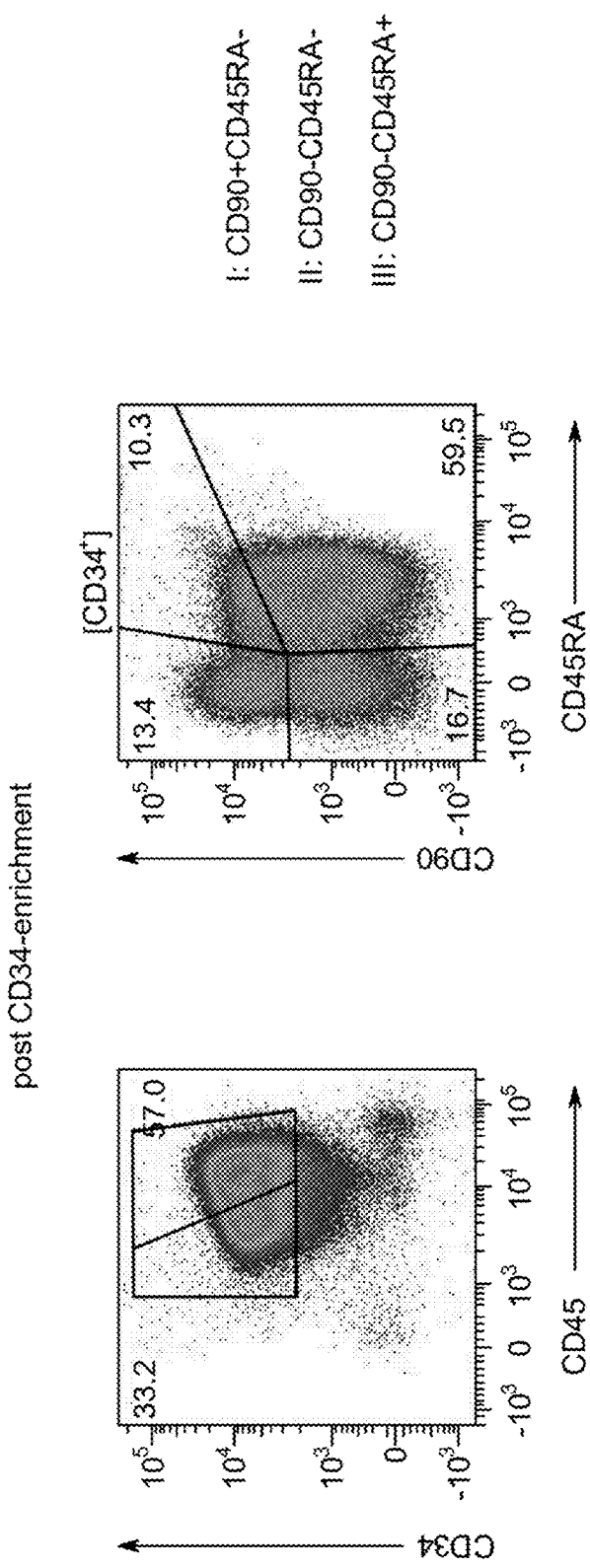
Figure 60E:
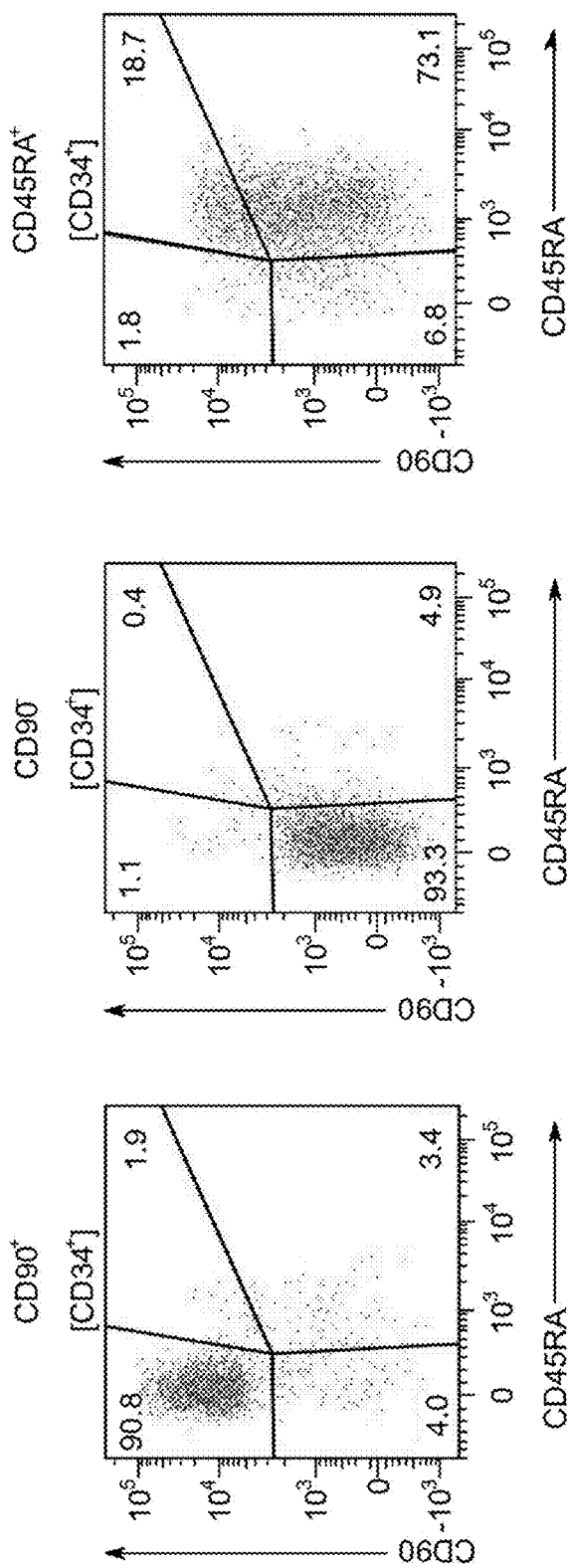
Figure 60F:
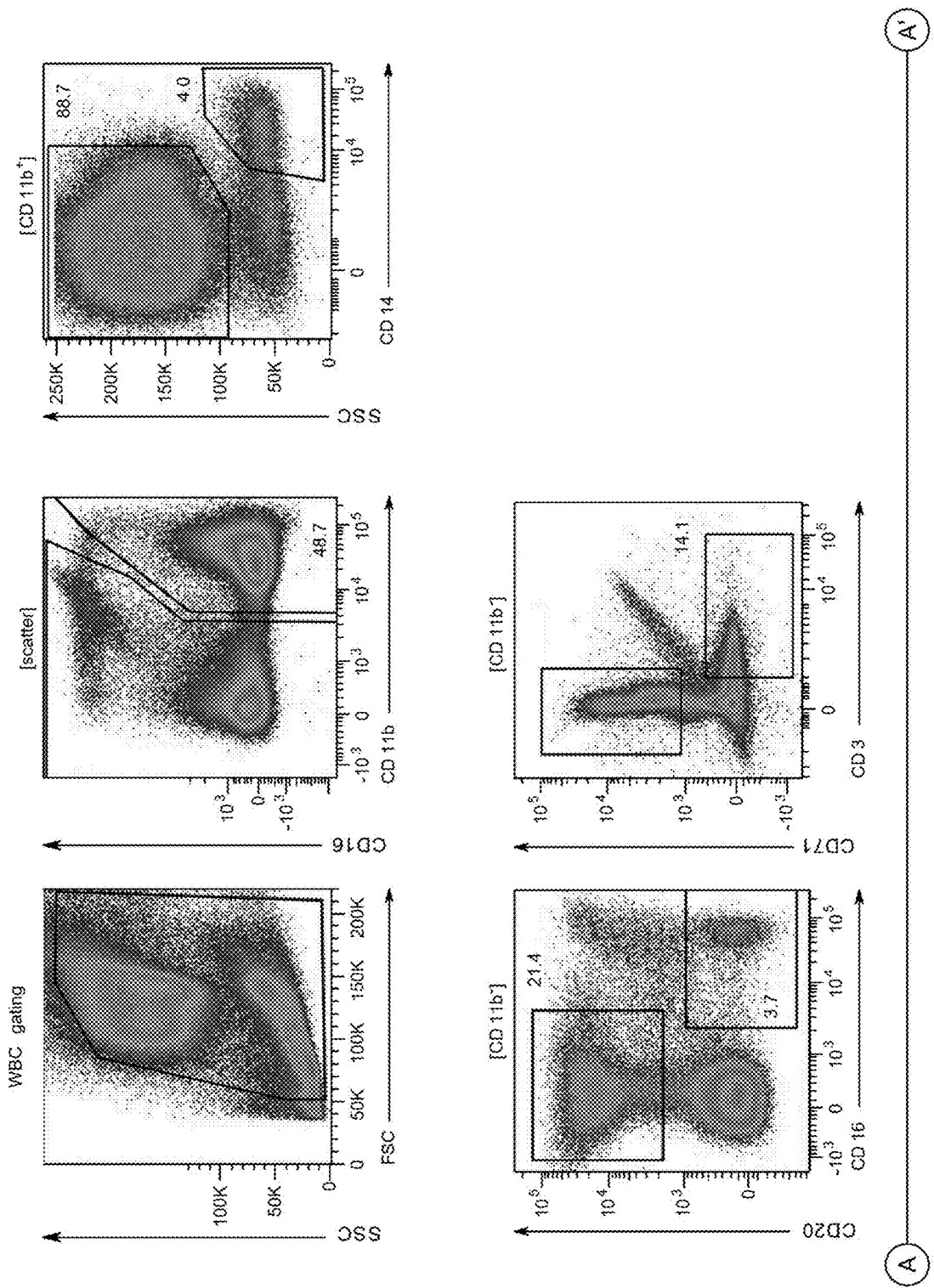
Figure 60F:
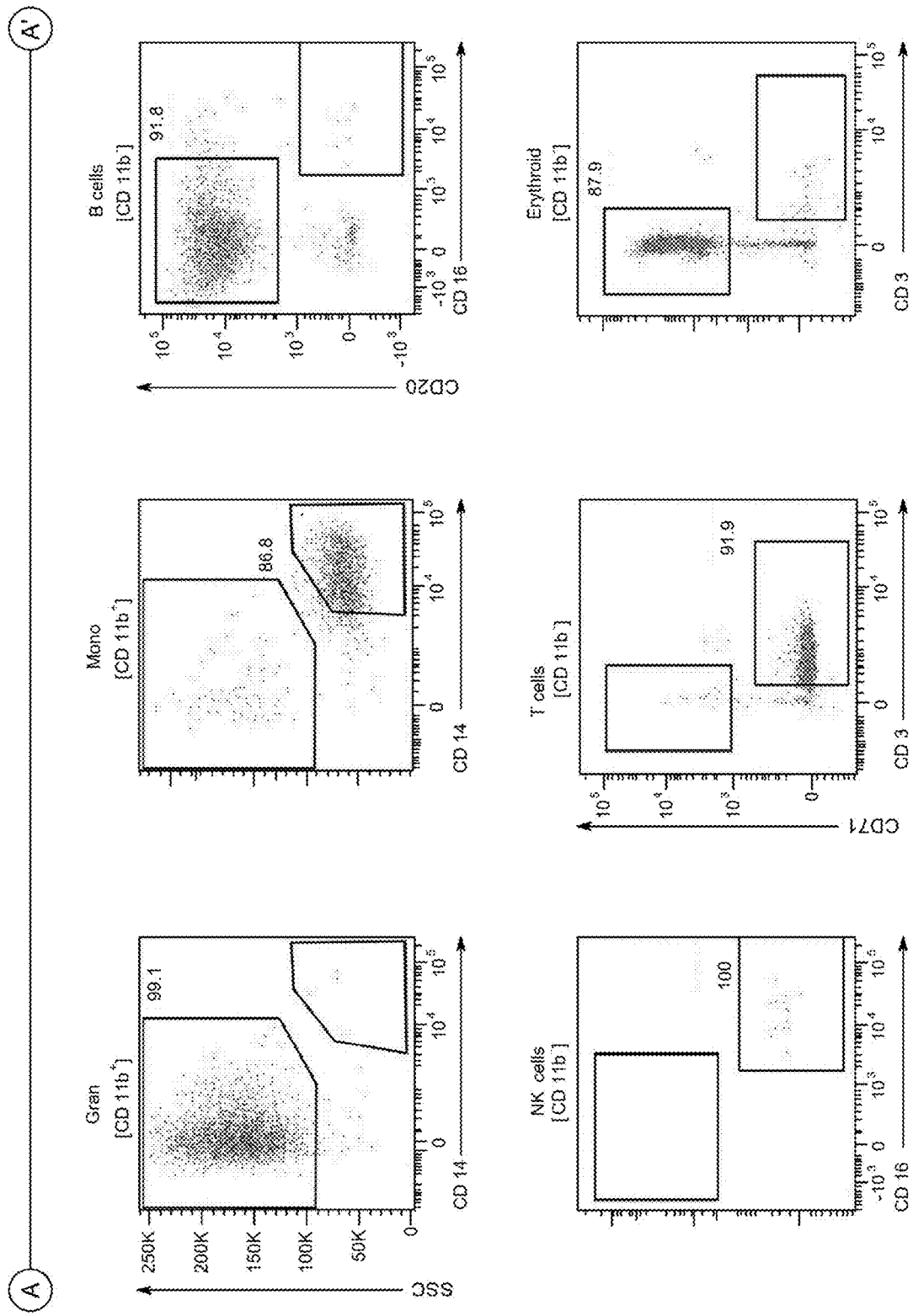
Figure 62A:
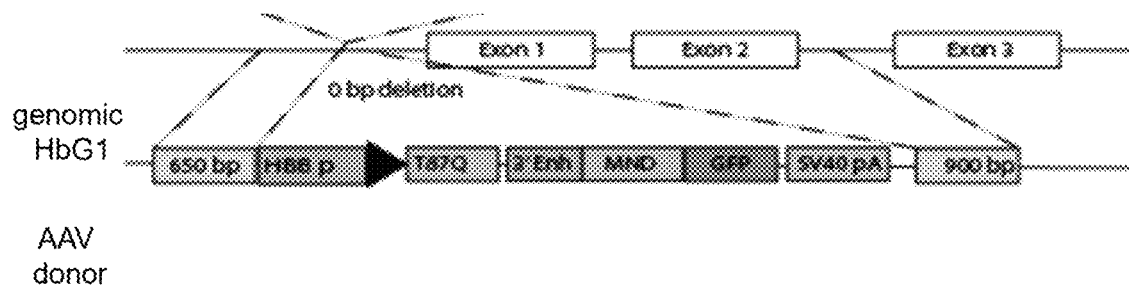
FIGS. 62A-62C demonstrate targeted integration of Globin T87Q/GFP donor cassette by HDR in Rhesus CD34+ HSPCs.
Figure 62B:
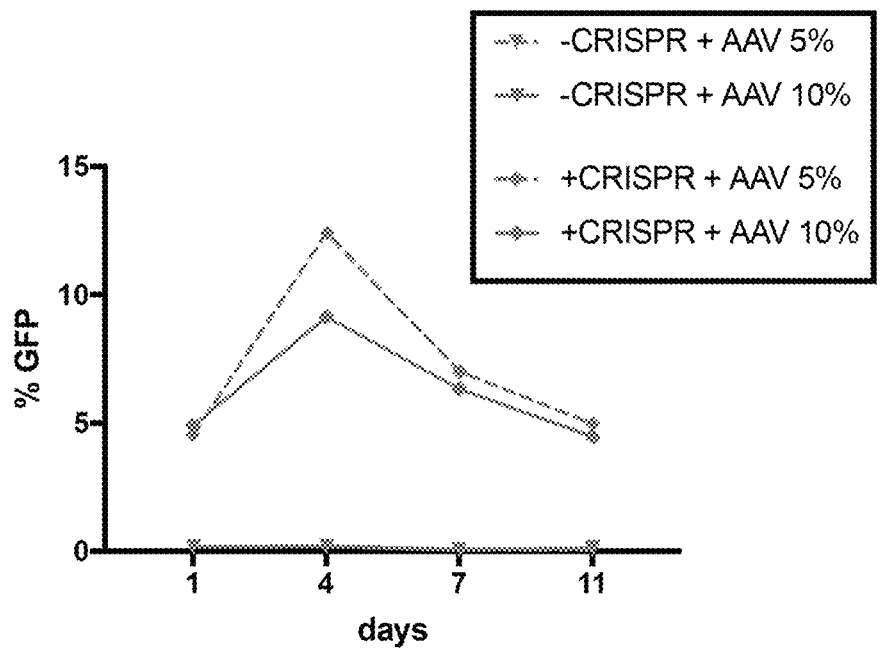
Figure 62C:
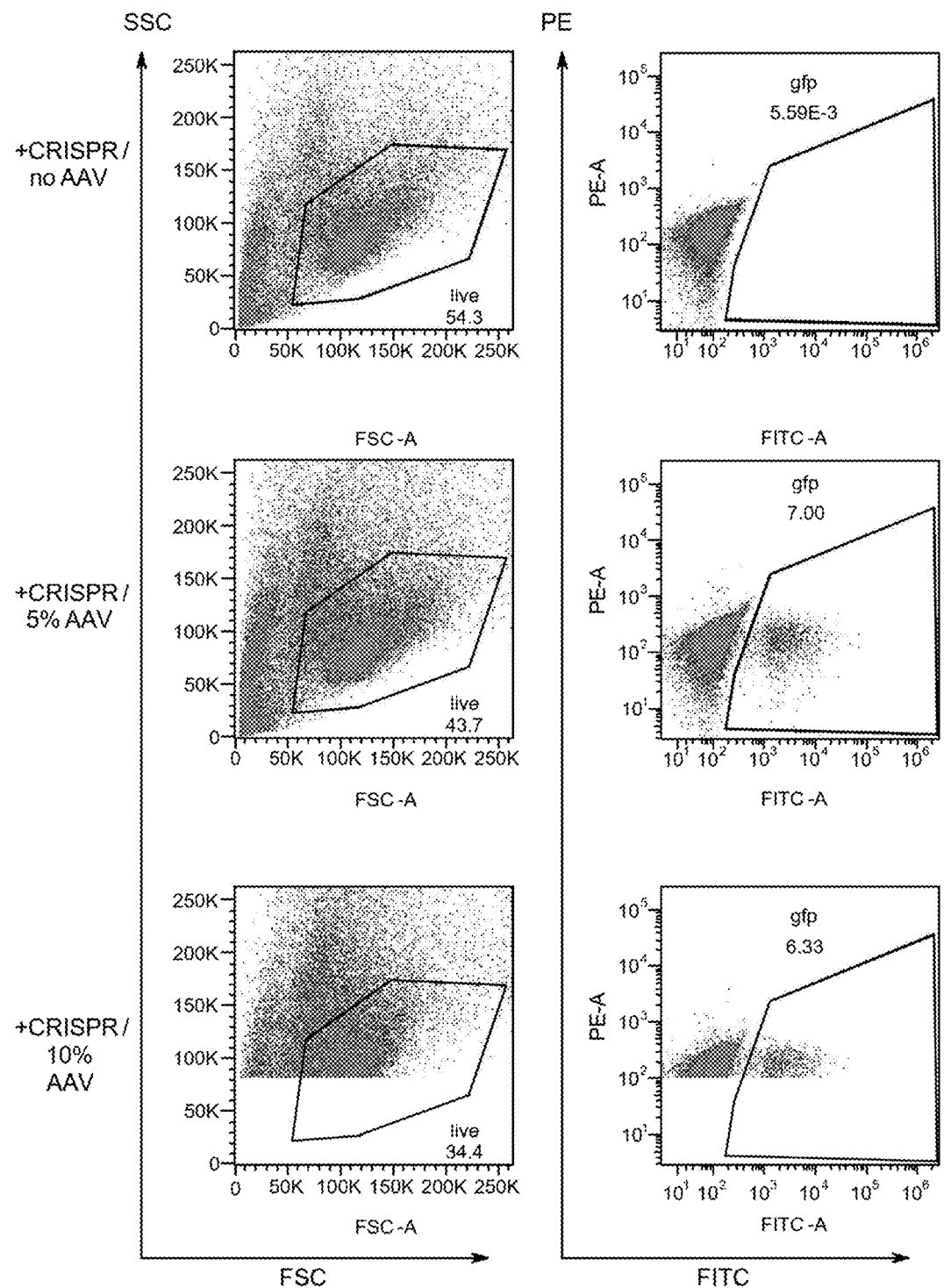

To circumvent challenges associated with scale up and cost of editing reagents, the transplantation protocol was further optimized by purifying a refined and more highly enriched target cell population (CD34$^+$CD45RA$^-$CD90$^+$) (described in PCT Application No. WO2017/218948, which is incorporated herein by reference in its entirety), and capable of both rapid short-term and as durable multilineage hematopoietic reconstitution. Two rhesus macaques were co-infused with this CRISPR/Cas9-edited subset (comprising only 5-7% of total CD34+ cells) along with the remaining un-edited cells. In vivo gene-editing levels started at less than 5% but rapidly increased to 50% within a week, and persisted at efficiencies comparable to animals receiving edited CD34+ cells, consistent with this refined cell subset as major contributor to hematopoietic recovery (FIG. 60A).

Taken together, these data demonstrate robust engraftment of CRISPR/Cas9-edited HSPCs following targeting of the 13 nt-HPFH site in the NHP model leading to high levels of HbF production. In addition, efficient editing and engraftment of the CD90+ cell subset is shown, an approach that reduces the required amount of editing reagents by 95%, circumvents challenges associated with scale up, without compromising editing or engraftment efficiencies, and thereby facilitating clinical translation of gene editing for the treatment of hemoglobinopathies.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Lengthy table referenced here

US12385070-20250812-T00001

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US12385070B2). An electronic copy of the table will also be available from the USPTO upon request and payment of the fee set forth in 37 CFR 1.19(b)(3).

What is claimed is:

1. A DNA donor repair template comprising: a 5' homology arm, a selection cassette, an erythroid expression control sequence, and a 3' homology arm, wherein the DNA donor repair template has a sequence with at least 95% sequence identity to SEQ ID NOs: 17, 18, 19, 20, or 21.

2. The DNA donor repair template of claim 1, wherein the DNA donor repair template comprises a sequence having at least 95% sequence identity to the sequence as set forth in SEQ ID NO: 17.

3. The DNA donor repair template of claim 1, wherein the DNA donor repair template has a sequence as set forth in SEQ ID NO: 17.

4. The DNA donor repair template of claim 1, wherein the DNA donor repair template comprises a sequence having at least 95% sequence identity to the sequence as set forth in SEQ ID NO: 18.

5. The DNA donor repair template of claim 1, wherein the DNA donor repair template has a sequence as set forth in SEQ ID NO: 18.

6. The DNA donor repair template of claim 1, wherein the DNA donor repair template comprises a sequence having at least 95% sequence identity to the sequence as set forth in SEQ ID NO: 19.

7. The DNA donor repair template of claim 1, wherein the DNA donor repair template has a sequence as set forth in SEQ ID NO: 19.

8. The DNA donor repair template of claim 1, wherein the DNA donor repair template comprises a sequence having at least 95% sequence identity to the sequence as set forth in SEQ ID NO: 20.

9. The DNA donor repair template of claim 1, wherein the DNA donor repair template has a sequence as set forth in SEQ ID NO: 20.

10. The DNA donor repair template of claim 1, wherein the DNA donor repair template comprises a sequence having at least 95% sequence identity to the sequence as set forth in SEQ ID NO: 21.

11. The DNA donor repair template of claim 1, wherein the DNA donor repair template has a sequence as set forth in SEQ ID NO: 21.

12. A viral vector comprising the DNA donor repair template of claim 1.

13. The viral vector of claim 12, wherein the viral vector is a recombinant adeno-associated viral vector (rAAV) or a retrovirus.

14. The viral vector of claim 13, wherein the rAAV has one or more ITRs from AAV2.

15. The viral vector of claim 13, wherein the rAAV has a serotype selected from the group consisting of: AAV1, AAV2, AAV3, AAV4, AAV5, AAV6, AAV7, AAV8, AAV9, and AAV10.

16. The viral vector of claim 13, wherein the rAAV has an AAV6 serotype.

17. The viral vector of claim 13, wherein the retrovirus is a lentivirus.

18. The viral vector of claim 17, wherein the lentivirus is an integrase deficient lentivirus.

19. A cell comprising the DNA donor repair template of claim 1.

20. The cell of claim 19, wherein the DNA donor repair template has been inserted into a human gamma globin gene target site by homology directed repair.

21. The cell of claim 20, wherein the target site is an engineered nuclease target site set forth in SEQ ID NO: 7 or SEQ ID NO: 8.

22. The cell of claim 19, wherein the cell is a hematopoietic cell.

23. The cell of claim 19, wherein the cell is CD34+ cell.

24. The cell of claim 19, wherein the cell is CD133+ cell.

25. A cell comprising the viral vector of claim 12.

26. A composition comprising the DNA donor repair template of claim 1 and a physiologically acceptable excipient.

27. A composition comprising a cell of claim 19 and a physiologically acceptable excipient.

* * * * *

UNITED STATES PATENT AND TRADEMARK OFFICE
CERTIFICATE OF CORRECTION

Page 1 of 1

PATENT NO. : 12,385,070 B2
APPLICATION NO. : 18/344732
DATED : August 12, 2025
INVENTOR(S) : Andrew Scharenberg et al.

It is certified that error appears in the above-identified patent and that said Letters Patent is hereby corrected as shown below:

On the Title Page

Item (71), please change "Seattle Children's Hospital" to "Seattle Children's Hospital d/b/a Seattle Children's Research Institute".

Item (73), please change "Seattle Children's Hospital" to "Seattle Children's Hospital d/b/a Seattle Children's Research Institute".

Signed and Sealed this
Ninth Day of September, 2025

Coke Morgan Stewart
*Acting Director of the United States Patent and Trademark Office*